US010683357B2

(12) United States Patent
Cai et al.

(10) Patent No.: US 10,683,357 B2
(45) Date of Patent: Jun. 16, 2020

(54) ANTIBODIES AGAINST OX40 AND USES THEREOF

(71) Applicant: BRISTOL-MYERS SQUIBB COMPANY, Princeton, NJ (US)

(72) Inventors: Zhehong Cai, Sunnyvale, CA (US); Indrani Chakraborty, Fremont, CA (US); Marie-Michelle Navarro Garcia, San Jose, CA (US); Thomas D. Kempe, Sunnyvale, CA (US); Alan J. Korman, Piedmont, CA (US); Alexander T. Kozhich, Princeton, NJ (US); Hadia Lemar, Tracy, CA (US); Mark Maurer, Seattle, WA (US); Christina Maria Milburn, Santa Cruz, CA (US); Michael Quigley, Ambler, PA (US); Xiang Shao, Milpitas, CA (US); Mohan Srinivasan, Cupertino, CA (US); Kent Thudium, Oakland, CA (US); Susan Chien-Szu Wong, Fremont, CA (US); Jochem Gokemeijer, Wayland, MA (US); Xi-Tao Wang, Wellesley, MA (US); Han Chang, West Windsor, NJ (US); Patrick Guirnalda, Framingham, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 311 days.

(21) Appl. No.: 15/474,731

(22) Filed: Mar. 30, 2017

(65) Prior Publication Data

US 2017/0306035 A1 Oct. 26, 2017

Related U.S. Application Data

(62) Division of application No. 15/166,114, filed on May 26, 2016, now Pat. No. 9,644,032.

(60) Provisional application No. 62/333,556, filed on May 9, 2016, provisional application No. 62/327,140, filed on Apr. 25, 2016, provisional application No. 62/264,691, filed on Dec. 8, 2015, provisional application No. 62/239,574, filed on Oct. 9, 2015, (Continued)

(51) Int. Cl.
| | |
|---|---|
| *C07H 21/04* | (2006.01) |
| *C12P 21/06* | (2006.01) |
| *C12N 15/87* | (2006.01) |
| *C12N 1/20* | (2006.01) |
| *C12N 5/20* | (2006.01) |
| *C12N 15/00* | (2006.01) |
| *C07K 16/28* | (2006.01) |
| *C07K 16/30* | (2006.01) |
| *A61P 35/00* | (2006.01) |
| *A61K 39/395* | (2006.01) |
| *G01N 33/574* | (2006.01) |
| *A61K 39/00* | (2006.01) |

(52) U.S. Cl.
CPC ...... *C07K 16/2878* (2013.01); *A61K 39/3955* (2013.01); *A61P 35/00* (2018.01); *C07K 16/30* (2013.01); *C07K 16/3023* (2013.01); *C07K 16/3038* (2013.01); *C07K 16/3069* (2013.01); *G01N 33/574* (2013.01); *A61K 2039/505* (2013.01); *A61K 2039/507* (2013.01); *C07K 16/2818* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/52* (2013.01); *C07K 2317/56* (2013.01); *C07K 2317/565* (2013.01); *C07K 2317/567* (2013.01); *C07K 2317/73* (2013.01); *C07K 2317/74* (2013.01); *C07K 2317/75* (2013.01); *C07K 2317/76* (2013.01); *C07K 2317/92* (2013.01); *C07K 2317/94* (2013.01); *G01N 2333/70514* (2013.01)

(58) Field of Classification Search
None
See application file for complete search history.

(56) References Cited

U.S. PATENT DOCUMENTS

| | | | |
|---|---|---|---|
| 5,759,546 A | 6/1998 | Weinberg et al. | |
| 5,821,332 A | 10/1998 | Godfrey et al. | |
| 6,156,878 A | 12/2000 | Godfrey et al. | |

(Continued)

FOREIGN PATENT DOCUMENTS

| | | | |
|---|---|---|---|
| EP | 0726952 B1 | 1/2007 | |
| EP | 1525223 B1 | 11/2007 | |

(Continued)

OTHER PUBLICATIONS

Stamatopoulos et al. Immunoglobulin light chain repertoire in chronic lymphocytic leukemia. Blood 106 (10), 3575-3583 (Year: 2005).*

(Continued)

*Primary Examiner* — Maher M Haddad
(74) *Attorney, Agent, or Firm* — Sterne, Kessler, Goldstein & Fox P.L.L.C.

(57) ABSTRACT

Provided herein are antibodies, or antigen binding portions thereof, that bind to OX40. Also provided are uses of these proteins in therapeutic applications, such as in the treatment of cancer. Further provided are cells that produce the antibodies, polynucleotides encoding the heavy and/or light chain variable region of the antibodies, and vectors comprising the polynucleotides encoding the heavy and/or light chain variable region of the antibodies.

19 Claims, 88 Drawing Sheets

Specification includes a Sequence Listing.

Related U.S. Application Data provisional application No. 62/168,377, filed on May 29, 2015.

(56) References Cited

U.S. PATENT DOCUMENTS

| | | |
|---|---|---|
| 6,277,962 B1 | 8/2001 | Godfrey et al. |
| 6,413,744 B1 | 7/2002 | Morris et al. |
| 6,566,082 B1 | 5/2003 | Weinberg et al. |
| 6,897,040 B2 | 5/2005 | Morris et al. |
| 7,166,445 B2 | 1/2007 | Morris et al. |
| 7,364,733 B2 | 4/2008 | Godfrey et al. |
| 7,504,101 B2 | 3/2009 | Weinberg |
| 7,550,140 B2 | 6/2009 | Bakker et al. |
| 7,879,976 B2 | 2/2011 | Friess et al. |
| 7,960,515 B2 | 6/2011 | Min et al. |
| 8,133,983 B2 | 3/2012 | Bakker et al. |
| 8,153,765 B2 | 4/2012 | Park et al. |
| 8,236,930 B2 | 8/2012 | Min et al. |
| 9,212,495 B2 | 12/2015 | Nakamura et al. |
| 9,644,032 B2 | 5/2017 | Cai et al. |
| 2005/0002916 A1 | 1/2005 | Jooss et al. |
| 2005/0069869 A1* | 3/2005 | Ambrosino .......... A61K 39/215 435/5 |
| 2010/0034826 A1* | 2/2010 | Terrett .................. C07K 16/30 424/142.1 |
| 2010/0136030 A1 | 6/2010 | Salah-Eddine et al. |
| 2010/0196359 A1 | 8/2010 | Kato et al. |
| 2010/0254978 A1 | 10/2010 | Lawson et al. |
| 2011/0182889 A1 | 7/2011 | Fong et al. |
| 2011/0206681 A1 | 8/2011 | Min et al. |
| 2012/0128687 A1 | 5/2012 | Adler et al. |
| 2015/0190506 A1 | 7/2015 | Cheung et al. |
| 2015/0210769 A1 | 7/2015 | Freeman et al. |
| 2015/0210772 A1 | 7/2015 | Kim |
| 2015/0307617 A1 | 10/2015 | Du et al. |
| 2016/0108123 A1 | 4/2016 | Freeman et al. |
| 2016/0137740 A1 | 5/2016 | Hammond et al. |
| 2016/0152720 A1 | 6/2016 | Kim et al. |
| 2016/0166685 A1 | 6/2016 | Cheung et al. |
| 2016/0347849 A1 | 12/2016 | Cai et al. |

FOREIGN PATENT DOCUMENTS

| | | |
|---|---|---|
| EP | 2364716 A2 | 9/2011 |
| EP | 1060247 B2 | 10/2011 |
| EP | 2242771 B1 | 7/2013 |
| JP | 2014240412 A | 12/2014 |
| WO | 9512673 A1 | 5/1995 |
| WO | 9521915 A1 | 8/1995 |
| WO | 9942585 A1 | 8/1999 |
| WO | 0114529 A1 | 3/2001 |
| WO | 0175166 A2 | 10/2001 |
| WO | 03106498 A2 | 12/2003 |
| WO | 04093831 A2 | 11/2004 |
| WO | 04112706 A2 | 12/2004 |
| WO | 2005/079479 A2 | 9/2005 |
| WO | 2006/029459 A1 | 3/2006 |
| WO | 07062245 A2 | 5/2007 |
| WO | 07084559 A2 | 7/2007 |
| WO | 07149880 A2 | 12/2007 |
| WO | 08047242 A2 | 4/2008 |
| WO | 08051424 A2 | 5/2008 |
| WO | WO-2008076379 A2 | 6/2008 |
| WO | 08106116 A2 | 9/2008 |
| WO | 08135380 A1 | 11/2008 |
| WO | 2009/079335 A1 | 6/2009 |
| WO | 09079335 A1 | 6/2009 |
| WO | 2009/126688 A2 | 10/2009 |
| WO | 10096418 A2 | 8/2010 |
| WO | 11071871 A1 | 6/2011 |
| WO | 11095506 A1 | 8/2011 |
| WO | 12027328 A2 | 3/2012 |
| WO | 2013027328 A1 | 2/2013 |
| WO | 13038191 A2 | 3/2013 |
| WO | 2013/119202 A1 | 8/2013 |
| WO | 2014/089113 A1 | 6/2014 |
| WO | 2014/116846 A2 | 7/2014 |
| WO | 14148895 A1 | 9/2014 |
| WO | 2015/009856 A2 | 1/2015 |
| WO | 15095423 A2 | 6/2015 |
| WO | 2015/112900 A1 | 7/2015 |
| WO | 2015/131176 A1 | 9/2015 |
| WO | 2015/153513 A1 | 10/2015 |
| WO | 2015/153514 A1 | 10/2015 |
| WO | 16004875 A1 | 1/2016 |
| WO | 16004876 A1 | 1/2016 |
| WO | 16034085 A1 | 3/2016 |
| WO | 2016/054555 A2 | 4/2016 |
| WO | 16057667 A1 | 4/2016 |
| WO | 16061142 A1 | 4/2016 |
| WO | 16065330 A1 | 4/2016 |
| WO | 2016/073282 A1 | 5/2016 |
| WO | 16073380 A1 | 5/2016 |
| WO | 16073759 A1 | 5/2016 |
| WO | 16100882 A1 | 6/2016 |

OTHER PUBLICATIONS

U.S. Appl. No. 15/166,114, filed May 26, 2016, Zhehong Cai.
U.S. Appl. No. 15/166,114, filed Jan. 4, 2017, I. Ouspenski.
U.S. Appl. No. 15/166,114, filed Nov. 28, 2016, I. Ouspenski.
U.S. Appl. No. 15/166,114, filed Aug. 19, 2016, I. Ouspenski.
Al-Shamkhani, A. et al., "OX40 is differentially expressed on activated rat and mouse T cells and is the sole receptor for the OX40 ligand," Eur. J. Immunol., vol. 26: 1695-1699 (1996).
Aspeslagh, S. et al., "Rationale for anti-OX40 cancer immunotherapy," European Journal of Cancer, vol. 52: 50-66 (2016).
Bremer, E., et al., "Targeting of the Tumor Necrosis Factor Receptor Superfamily for Cancer Immunotherapy," ISRN Oncology, Hindawi Publishing Corporation, vol. 2013, Article ID 371854, 25 pages (2013).
Calderhead, D.M., "Cloning of mouse OX40 a T cell activation marker that may mediate T-B cell interactions," J Immunol., vol. 151:5261-5271 (1993).
Dumitriu, I.E. et al., Tumor Necrosis Factor Receptor Superfamily Member 4 Precursor Homo sapiens)NCBI Reference Sequence: NP_003318.1, 5 pages, May 30, 2012.
Godfrey, W. et al., "Identification of a Human OX-40 Ligand, a Costimulator of CD4+ T Cells with Homology to Tumor Necrosis," J. Exp. Med., vol. 180: 757-762 (1994).
Guo, Z. et al., "PD-1 Blockade and OX40 Triggering Synergistically Protects against Tumor Growth in a Murine Model of Ovarian Cancer," PLOS One, vol. 9(2):1-10 (2014).
Hellmann, MD. et al., "Combinatorial Cancer Immunotherapies," Advances in Immunology, vol. 130(25):251-277 (2016).
Houot, R. et al., "Therapeutic effect of CD137 immunomodulation in lymphoma and its enhancement by Treg depletion," Blood, vol. 114(16):3431-3438 (2009).
International Search Report and Written Opinion for International Application No. PCT/US2015/058087, dated Apr. 8, 2016., 20 pages.
Jensen, S. et al., "Signaling through OX40 Enhances Anti-tumor Immunity," Semin Oncol., vol. 37(5): 524-532. doi:10.1053/j.seminoncol.2010.09.013 (2010).
Latza, U. et al., "The human OX40 homolog: cDNA structure, expression and chromosomal assignment of the ACT35 antigen," Eur. J. Immunol., vol. 24: 677-683 (1994).
Mallett, S. et al., "Characterization of the MRC OX40 antigen of activated CD4 positive T lymphocytes—a molecule related to nerve growth factor receptor," The EMBO Journal, vol. 9(4):1063-1068 (1990).
Melero, I. et al., "Evolving synergistic combinations of targeted immunotherapies to combat cancer," Nature Reviews, vol. 15:457-472 (2015).
Morales-Kastresana, A., et al., "Combined Immunostimulatory Monoclonal Antibodies Extend Survival in an Aggressive Transgenic Hepatocellular Carcinoma Mouse Model," Clin. Can. Research, 19(22):6151-6162 (2013).

(56) References Cited

OTHER PUBLICATIONS

Morris, N. et al., "Development and Characterization of Recombinant Human Fc:OX40L fusion protein linked via a coiled-coil trimerization Domain," Mol Immunol., vol. 44(12): 3112-3121 (2007).
Piconese, S. et al., OX40 triggering blocks suppression by regulatory T cells and facilitates tumor rejection, JEM, vol. 205(4):825-839 (2008).
Press Release, Updated, GlaxoSmithKline taps MD Anderson for Cancer Immune Therapy in potential $335M deal, Special Report: 20 Major Pharma-Academic Alliances in 2012, 3 pages, Dec. 7, 2012.
Redmond, W. et al., "Combined targeting of co-stimulatory (OX40) and co-inhibitory (CTLA-4) pathways elicits potent effector T cells capable of driving robust antitumor immunity," Cancer Immunol. Res., vol. 2(2):142-153 (2014).
Study of BMS-986178 Monotherapy or in Combination with Nivolumab or Ipilimumab in Subjects with Advanced Solid Tumors.
Sugamura, K. et al., "Therapeutic Targeting of the Effector T-Cell Co-Stimulatory Molecule OX40," Nature Reviews, vol. 4: 420-431 (2004).
Weinberg, A. et al., "Anti-OX40 (CD134 Administration to Non-human Primates: Immunostimulatory Effects and Toxicokinetic Study," J. Immunother, vol. 29(6): 575-585 (2006).
Weinberg, A. et al., "Science gone translational: the OX40 agonist story," Immunological Reviews, vol. 244: 218-231 (2011).
Gyuangyong, S., et al., "Critical role of OX40 in the expansion and survival of CD4 T-cell-derived double negative T cells," Cell Death & Disease 9(6):2041-4889, Nature Publishing Group, United Kingdom (2018).

* cited by examiner

Anti-OX40 3F4 VH (hIgG1)

V segment: 1-08
D segment: 6-6
J segment: JH5b

```
         Q    V    Q    L    V    Q    S    G    A    E    V    K    K    P    G    A    S
1        CAG  GTG  CAG  CTG  GTG  CAG  TCT  GGG  GCT  GAG  GTG  AAG  AAG  CCT  GGG  GCC  TCA

_CDR1_____
         V    K    V    S    C    K    A    S    G    N    T    F    T    S    Y    D    V
52       GTG  AAG  GTC  TCC  TGC  AAG  GCT  TCT  GGA  AAC  ACC  TTC  ACC  AGT  TAT  GAT  GTC

_____                                                             _CDR2_____
         N    W    V    R    Q    A    T    G    Q    G    L    E    W    M    G    W    M
103      AAC  TGG  GTG  CGA  CAG  GCC  ACT  GGA  CAA  GGG  CTT  GAG  TGG  ATG  GGA  TGG  ATG

_____
         N    P    N    S    G    N    T    G    Y    A    P    K    F    Q    G    R    V
154      AAC  CCT  AAC  AGT  GGT  AAC  ACA  GGC  TAT  GCA  CCG  AAG  TTC  CAG  GGC  AGA  GTC

T    M    T    R    N    T    S    I    S    T    A    Y    M    E    L    S    S
205      ACC  ATG  ACC  AGG  AAC  ACC  TCC  ATA  AGC  ACA  GCC  TAC  ATG  GAG  CTG  AGC  AGC

_CDR3_____
         L    R    S    E    D    T    A    V    Y    Y    C    A    R    I    Y    S    S
256      CTG  AGA  TCT  GAG  GAC  ACG  GCC  GTT  TAT  TAC  TGT  GCG  AGA  ATA  TAT  AGC  AGC

_____
         S    Y    N    W    F    D    P    W    G    Q    G    T    L    V    T    V    S
307      TCG  TAC  AAC  TGG  TTC  GAC  CCC  TGG  GGC  CAG  GGA  ACC  CTG  GTC  ACC  GTC  TCC

S
358      TCA
```

FIG. 1A

Anti-OX40 3F4 VK (hKappa)

V segment: L6
J segment: JK4

```
        E   I   V   L   T   Q   S   P   A   T   L   S   L   S   P   G   E
1       GAA ATT GTG TTG ACA CAG TCT CCA GCC ACC CTG TCT TTG TCT CCA GGG GAA

_CDR1_____
        R   A   T   L   S   C   R   A   S   Q   S   V   S   S   Y   L   A
52      AGA GCC ACC CTC TCC TGC AGG GCC AGT CAG AGT GTT AGC AGC TAC TTA GCC

_CDR2_____
        W   Y   Q   Q   K   P   G   Q   A   P   R   L   L   I   Y   D   A
103     TGG TAC CAA CAG AAA CCT GGC CAG GCT CCC AGG CTC CTC ATC TAT GAT GCA

_____
        S   N   R   A   T   G   I   P   A   R   F   S   G   S   G   S   G
154     TCC AAC AGG GCC ACT GGC ATC CCA GCC AGG TTC AGT GGC AGT GGG TCT GGG

T   D   F   T   L   T   I   S   S   L   E   P   E   D   F   A   V
205     ACA GAC TTC ACT CTC ACC ATC AGC AGC CTA GAG CCT GAA GAT TTT GCA GTT

_CDR3_____
        Y   Y   C   Q   Q   R   S   N   W   P   L   T   F   G   G   G   T
256     TAT TAC TGT CAG CAG CGT AGC AAC TGG CCT CTC ACT TTC GGC GGA GGG ACC

K   V   E   I   K
307     AAG GTG GAG ATC AAA
```

FIG. 1B

Anti-OX40 14B6 VH (hIgG1)

V segment: 5-51
D segment: 3-9
J segment: JH2

```
           E   V   Q   L   E   Q   S   G   A   E   V   K   K   P   G   E   S
  1        GAG GTG CAG CTG GAG CAG TCT GGA GCA GAG GTG AAA AAG CCC GGG GAG TCT

_CDR1_____
           L   K   I   S   C   K   G   S   G   Y   S   F   T   S   N   W   I
 52        CTG AAG ATC TCC TGT AAG GGT TCT GGA TAC AGC TTT ACC AGC AAC TGG ATC

___                                                          _CDR2____
           G   W   V   R   Q   M   P   G   K   G   L   E   W   M   G   F   I
103        GGC TGG GTG CGC CAG ATG CCC GGG AAA GGC CTG GAG TGG ATG GGG TTC ATC

Y   P   G   D   S   D   T   R   Y   S   P   S   F   Q   G   Q   V
154        TAT CCT GGT GAC TCT GAT ACC AGG TAC AGC CCG TCC TTC CAA GGC CAG GTC

T   I   S   A   D   K   S   I   S   T   A   Y   L   Q   W   S   S
205        ACC ATC TCA GCC GAC AAG TCC ATC AGC ACC GCC TAC CTG CAG TGG AGC AGC

_CDR3_____
           L   K   A   S   D   I   A   M   Y   Y   C   A   R   Y   G   D   D
256        CTC AAG GCC TCG GAC ATC GCC ATG TAT TAC TGT GCG AGA TAT GGG GAT GAC

_____
           W   Y   F   D   L   W   G   R   G   T   L   V   T   V   S   S
           TGG TAC TTC GAT CTC TGG GGC CGT GGC ACC CTG GTC ACT GTC TCC TCA
```

FIG. 2A

Anti-OX40 14B6 VK1 (hKappa)

V segment: L6
J segment: JK5

```
        E   I   V   L   T   Q   S   P   A   T   L   S   L   S   P   G   E
  1    GAA ATT GTG TTG ACA CAG TCT CCA GCC ACC CTG TCT TTG TCT CCA GGG GAA

__CDR1_____
        R   A   T   L   S   C   R   A   S   Q   S   V   S   S   Y   L   A
 52    AGA GCC ACC CTC TCC TGC AGG GCC AGT CAG AGT GTT AGC AGC TAC TTA GCC

__CDR2_____
        W   F   Q   Q   R   P   G   Q   A   P   R   L   L   I   Y   D   A
103    TGG TTC CAA CAG AGA CCT GGC CAG GCT CCC AGG CTC CTC ATC TAT GAT GCA

S   N   R   A   T   G   I   P   A   R   F   S   G   S   G   S   G
154    TCC AAC AGG GCC ACT GGC ATC CCA GCC AGG TTC AGT GGC AGT GGG TCT GGG

T   D   F   S   L   T   I   S   S   L   E   P   E   D   F   A   V
205    ACA GAC TTC TCT CTC ACC ATC AGC AGC CTA GAG CCT GAA GAT TTT GCA GTT

__CDR3_____
        Y   Y   C   Q   Q   R   G   D   W   P   I   T   F   G   Q   G   T
256    TAT TAC TGT CAG CAG CGT GGC GAC TGG CCC ATC ACC TTC GGC CAA GGG ACA

R   L   E   I   K
307    CGA CTG GAG ATT AAA
```

FIG. 2B

Anti-OX40 14B6 VK2 (hKappa)

V segment: L15
J segment: JK5

```
         D    I    Q    M    T    Q    S    P    S    S    L    S    A    S    V    G    D
  1      GAC  ATC  CAG  ATG  ACC  CAG  TCT  CCA  TCC  TCA  CTG  TCT  GCA  TCT  GTA  GGA  GAC

_CDR1_____
         R    V    T    I    T    C    R    A    S    Q    G    I    S    S    W    L    A
  52     AGA  GTC  ACC  ATC  ACT  TGT  CGG  GCG  AGT  CAG  GGT  ATT  AGC  AGC  TGG  TTA  GCC

_CDR2_____
         W    Y    Q    Q    K    P    E    K    A    P    K    S    L    I    Y    A    A
  103    TGG  TAT  CAG  CAG  AAA  CCA  GAG  AAA  GCC  CCT  AAG  TCC  CTG  ATC  TAT  GCT  GCA

_____
         S    S    L    Q    S    G    V    P    S    R    F    S    G    S    G    S    G
  154    TCC  AGT  TTG  CAA  AGT  GGG  GTC  CCA  TCA  AGG  TTC  AGC  GGC  AGT  GGA  TCT  GGG

T    D    F    T    L    T    I    S    S    L    Q    P    E    D    F    A    T
  205    ACA  GAT  TTC  ACT  CTC  ACC  ATC  AGC  AGC  CTG  CAG  CCT  GAA  GAT  TTT  GCA  ACT

_CDR3_____
         Y    Y    C    Q    Q    Y    N    S    Y    P    R    I    T    F    G    Q    G
  256    TAT  TAC  TGC  CAA  CAG  TAT  AAT  AGT  TAC  CCT  CGG  ATC  ACC  TTC  GGC  CAA  GGG

T    R    L    E    I    K
  307    ACA  CGA  CTG  GAG  ATT  AAA
```

FIG. 2C

Anti-OX40 23H3 VH (hIgG1)

V segment: DP-44
J segment: JH4b

```
          E   V   Q   L   V   Q   S   G   G   G   L   V   H   P   G   G   S
1         GAG GTT CAG CTG GTG CAG TCT GGG GGA GGC TTG GTA CAT CCT GGG GGG TCC

_CDR1_____
          L   R   L   S   C   A   G   S   G   F   T   F   S   N   Y   A   M
52        CTG AGA CTC TCC TGT GCA GGC TCT GGA TTC ACC TTC AGT AAC TAT GCT ATG

___                                               _CDR2____
          Y   W   V   R   Q   A   P   G   K   G   L   E   W   V   S   A   I
103       TAC TGG GTT CGC CAG GCT CCA GGA AAA GGT CTG GAG TGG GTA TCA GCC ATT

_____
          G   I   G   G   D   T   F   Y   T   D   S   V   K   G   R   F   T
154       GGT ATT GGT GGT GAC ACA TTC TAT ACA GAC TCC GTG AAG GGC CGA TTC ACC

I   S   R   D   N   A   K   N   S   L   S   L   Q   M   N   S   L
205       ATC TCC AGA GAC AAT GCC AAG AAC TCC TTG TCT CTT CAA ATG AAC AGC CTG

_CDR3_____
          R   A   E   D   M   A   V   Y   Y   C   A   R   M   G   T   G   Y
256       AGA GCC GAG GAC ATG GCT GTG TAT TAC TGT GCA AGA ATG GGA ACT GGG TAC

_____
          F   F   D   Y   W   G   Q   G   T   L   V   T   V   S   S
307       TTC TTT GAC TAC TGG GGC CAG GGA ACC CTG GTC ACC GTC TCC TCA
```

FIG. 3A

Anti-OX40 23H3 VK (hKappa)

V segment: L6
J segment: JK3

```
          E   I   V   L   T   Q   S   P   A   T   L   S   L   S   P   G   E
  1       GAA ATT GTG TTG ACA CAG TCT CCA GCC ACC CTG TCT TTG TCT CCA GGG GAA
                                      _CDR1_____
          R   A   T   L   S   C   R   A   S   Q   S   V   S   S   Y   L   A
 52       AGA GCC ACC CTC TCC TGC AGG GCC AGT CAG AGT GTT AGC AGC TAC TTA GCC
                                                                  _CDR2_____
          W   Y   Q   Q   K   P   G   Q   A   P   R   L   L   I   Y   D   A
103       TGG TAC CAA CAG AAA CCT GGC CAG GCT CCC AGG CTC CTC ATC TAT GAT GCA
          _____
          S   N   R   A   T   G   I   P   A   R   F   S   G   S   G   S   G
154       TCC AAC AGG GCC ACT GGC ATC CCA GCC AGG TTC AGT GGC AGT GGG TCT GGG

T   D   F   T   L   T   I   S   S   L   E   P   E   D   F   A   V
205       ACA GAC TTC ACT CTC ACC ATC AGC AGC CTA GAG CCT GAA GAT TTT GCA GTT
                      _CDR3_____
          Y   Y   C   Q   Q   R   S   N   W   P   L   T   F   G   P   G   T
256       TAT TAC TGT CAG CAG CGT AGC AAC TGG CCT CTC ACT TTC GGC CCT GGG ACC

K   V   D   I   K
307       AAA GTG GAT ATC AAA
```

FIG. 3B

Anti-OX40 6E1 VH (hIgG1)

V segment: 3-30.3
D segment: 3-10
J segment: JH1

```
        Q   V   Q   L   V   E   S   G   G   G   V   V   Q   P   G   R   S
1       CAG GTG CAG CTG GTG GAG TCT GGG GGA GGC GTG GTC CAG CCT GGG AGG TCC

_CDR1_____
        L   R   L   S   C   A   A   S   G   F   T   F   S   S   F   A   M
52      CTG AGA CTC TCC TGT GCA GCC TCT GGA TTC ACC TTC AGT AGC TTT GCT ATG

_____                                                   _CDR2_____
        H   W   V   R   Q   A   P   G   K   G   L   E   W   V   T   V   I
103     CAC TGG GTC CGC CAG GCT CCA GGC AAG GGG CTG GAG TGG GTG ACA GTT ATT

S   Y   D   G   S   I   K   Y   Y   T   D   S   V   K   G   R   F
154     TCA TAT GAT GGA AGC ATT AAA TAC TAC ACA GAC TCC GTG AAG GGC CGA TTC

T   F   S   R   D   N   S   K   N   T   L   Y   L   Q   M   N   S
205     ACC TTC TCC AGA GAC AAT TCC AAG AAC ACT CTG TAT CTG CAA ATG AAC AGC

_CDR3_____
        L   R   A   E   D   T   A   V   Y   Y   C   T   R   D   G   N   Y
256     CTG AGA GCT GAG GAC ACG GCT GTG TAT TAC TGT ACG AGA GAT GGA AAC TAT

_____
        G   S   A   R   Y   F   Q   H   W   G   Q   G   T   L   V   T   V
307     GGT TCG GCG AGA TAC TTC CAG CAC TGG GGC CAG GGC ACC CTG GTC ACC GTC

S   S
358     TCC TCA
```

FIG. 4A

Anti-OX40 6E1 VK1 (hKappa)

V segment: L15
J segment: JK1

```
         D   I   Q   M   T   Q   S   P   S   S   L   S   A   S   V   G   D
  1      GAC ATC CAG ATG ACC CAG TCT CCA TCC TCA CTG TCT GCA TCT GTA GGA GAC

__CDR1_____
         R   V   T   I   T   C   R   A   S   Q   G   I   S   S   W   L   A
 52      AGA GTC ACC ATC ACT TGT CGG GCG AGT CAG GGT ATT AGC AGC TGG TTA GCC

_CDR2____
         W   Y   Q   Q   K   P   E   K   A   P   K   S   L   I   Y   A   A
103      TGG TAT CAG CAG AAA CCA GAG AAA GCC CCT AAG TCC CTG ATC TAT GCT GCA

_____
         S   S   L   Q   S   G   V   P   S   R   F   S   G   S   G   S   G
154      TCC AGT TTG CAA AGT GGG GTC CCA TCA AGG TTC AGC GGC AGT GGA TCT GGG

T   D   F   T   L   T   I   S   S   L   Q   P   E   D   F   A   T
205      ACA GAT TTC ACT CTC ACC ATC AGC AGC CTG CAG CCT GAA GAT TTT GCA ACT

_CDR3_____
         Y   Y   C   Q   Q   Y   N   S   Y   P   R   T   F   G   Q   G   T
256      TAT TAC TGC CAA CAG TAT AAT AGT TAC CCT CGG ACG TTC GGC CAA GGG ACC

K   V   E   I   K
307      AAG GTG GAA ATC AAA
```

FIG. 4B

Anti-OX40 6E1 VK2 (hKappa)

V segment: L6
J segment: JK2

```
         E   I   V   L   T   Q   S   P   A   T   L   S   L   S   P   G   E
  1      GAA ATT GTG TTG ACA CAG TCT CCA GCC ACC CTG TCT TTG TCT CCA GGG GAA

_CDR1_____
         R   A   T   L   S   C   R   A   S   Q   S   V   S   S   Y   L   A
 52      AGA GCC ACC CTC TCC TGC AGG GCC AGT CAG AGT GTT AGC AGC TAC TTA GCC

_CDR2____
         W   Y   Q   Q   K   P   G   Q   A   P   R   L   L   I   Y   D   A
103      TGG TAC CAA CAG AAA CCT GGC CAG GCT CCC AGG CTC CTC ATC TAT GAT GCA

_____
         S   N   R   A   T   G   I   P   A   R   F   S   G   S   G   S   G
154      TCC AAC AGG GCC ACT GGC ATC CCA GCC AGG TTC AGT GGC AGT GGG TCT GGG

T   D   F   T   L   T   I   S   S   L   E   P   E   D   F   A   V
205      ACA GAC TTC ACT CTC ACC ATC AGC AGC CTA GAG CCT GAA GAT TTT GCA GTT

_CDR3_____
         Y   Y   C   Q   Q   R   S   N   W   P   Y   T   F   G   Q   G   T
256      TAT TAC TGT CAG CAG CGT AGC AAC TGG CCG TAC ACT TTT GGC CAG GGG ACC

K   L   E   I   K
307      AAG CTG GAG ATC AAA
```

FIG. 4C

Anti-OX40 18E9 VH (hIgG1)

V segment: DP-44
D segment: 3-9
J segment: JH4b

```
         E   V   Q   L   V   Q   S   G   G   G   L   V   H   P   G   G   S
  1      GAG GTT CAG CTG GTG CAG TCT GGG GGA GGC TTG GTT CAT CCT GGG GGG TCC

_CDR1_____
         L   R   L   S   C   A   H   S   G   F   T   F   T   S   S   A   M
 52      CTG AGA CTC TCC TGT GCA CAC TCT GGA TTC ACC TTC ACT AGC TCT GCT ATG

_____                                              _CDR2_____
         H   W   V   R   Q   A   P   G   K   G   L   E   W   I   S   A   I
103      CAC TGG GTT CGC CAG GCT CCA GGA AAA GGT CTG GAA TGG ATA TCA GCT ATT

_____
         G   T   G   G   D   T   Y   Y   A   D   S   V   K   G   R   F   T
154      GGT ACT GGT GGT GAC ACA TAC TAT GCA GAC TCC GTG AAG GGC CGA TTC ACC

I   S   R   D   N   A   K   N   S   L   Y   L   Q   I   N   S   L
205      ATC TCC AGA GAC AAT GCC AAG AAC TCC TTG TAT CTT CAA ATA AAC AGC CTG

_CDR3_____
         R   A   E   D   M   A   V   Y   Y   C   A   R   D   F   Y   D   I
256      AGA GCC GAG GAC ATG GCT GTA TAT TAC TGT GCA AGA GAC TTT TAC GAT ATT

_____
         L   T   G   I   F   D   Y   W   G   Q   G   T   L   V   T   V   S
307      TTG ACT GGT ATC TTT GAC TAC TGG GGC CAG GGA ACC CTG GTC ACC GTC TCC

S
358      TCA
```

FIG. 5A

Anti-OX40 18E9 VK (hKappa)

V segment: L5
J segment: JK1

```
          D   I   Q   M   T   Q   S   P   S   S   V   S   A   S   V   G   D
1         GAC ATC CAG ATG ACC CAG TCT CCA TCT TCC GTG TCT GCA TCT GTA GGA GAC

_CDR1_____
          R   V   T   I   T   C   R   A   S   Q   G   I   S   S   W   L   A
52        AGA GTC ACC ATC ACT TGT CGG GCG AGT CAG GGT ATT AGC AGC TGG TTA GCC

_CDR2____
          W   Y   Q   H   K   P   G   K   A   P   K   L   L   I   Y   A   A
103       TGG TAT CAG CAT AAA CCA GGG AAA GCC CCT AAG CTC CTG ATC TAT GCT GCA

_____
          S   S   L   Q   S   G   V   P   S   R   F   S   G   S   G   S   G
154       TCC AGT TTG CAA AGT GGG GTC CCA TCA AGG TTC AGC GGC AGT GGA TCT GGG

T   D   F   T   L   T   I   S   S   L   Q   P   E   D   F   A   T
205       ACA GAT TTC ACT CTC ACC ATC AGC AGC CTG CAG CCT GAA GAT TTT GCA ACT

_CDR3_____
          Y   Y   C   Q   Q   A   N   S   F   P   S   T   F   G   Q   G   T
256       TAC TAT TGT CAA CAG GCT AAT AGT TTC CCT TCG ACG TTC GGC CAA GGG ACC

K   V   E   I   K
307       AAG GTG GAA ATC AAA
```

FIG. 5B

Anti-OX40 8B11 VH (hIgG1)

V segment: DP-44
J segment: JH4b

```
       E   I   Q   L   V   Q   S   G   G   G   L   V   H   P   G   G   S
  1    GAA ATT CAG CTG GTG CAG TCT GGG GGA GGC TTG GTA CAT CCT GGG GGG TCC

__CDR1_____
       L   R   L   S   C   A   G   S   G   F   T   F   S   S   D   A   M
  52   CTG AGA CTC TCC TGT GCA GGC TCT GGA TTC ACC TTC AGT AGC GAT GCT ATG

____                                                 __CDR2_____
       Y   W   V   R   Q   A   P   G   K   G   L   E   W   V   S   A   I
 103   TAC TGG GTT CGC CAG GCT CCA GGA AAA GGT CTG GAG TGG GTA TCA GCT ATT

_____
       G   I   G   G   D   T   Y   Y   T   D   S   V   M   G   R   F   T
 154   GGT ATT GGT GGT GAC ACA TAC TAT ACA GAC TCC GTG ATG GGC CGA TTC ACC

I   S   R   D   N   A   K   N   S   L   Y   L   Q   M   N   S   L
 205   ATC TCC AGA GAC AAT GCC AAG AAC TCC TTG TAT CTT CAA ATG AAC AGC CTG

__CDR3_____
       R   A   E   D   M   A   V   Y   Y   C   A   R   L   G   M   G   Y
 256   AGA GCC GAG GAC ATG GCT GTG TAT TAC TGT GCA AGG CTG GGG ATG GGG TAC

_____
       Y   F   D   Y   W   G   Q   G   T   L   V   T   V   S   S
 307   TAC TTT GAC TAC TGG GGC CAG GGA ACC CTG GTC ACC GTC TCC TCA
```

FIG. 6A

Anti-OX40 8B11 VK (hKappa)

V segment: L6
J segment: JK1

```
          E   I   V   L   T   Q   S   P   A   T   L   S   L   S   P   G   E
  1       GAA ATT GTG TTG ACA CAG TCT CCA GCC ACC CTG TCT TTG TCT CCA GGG GAA

_CDR1_____
          R   A   T   L   S   C   R   A   S   Q   S   V   S   S   Y   L   A
 52       AGA GCC ACC CTC TCC TGC AGG GCC AGT CAG AGT GTT AGC AGC TAC TTA GCC

_CDR2____
          W   Y   Q   Q   K   P   G   Q   A   P   R   L   L   I   Y   D   A
103       TGG TAC CAA CAG AAA CCT GGC CAG GCT CCC AGG CTC CTC ATC TAT GAT GCA

_____
          S   N   R   A   T   G   I   P   A   R   F   S   G   S   G   S   G
154       TCC AAC AGG GCC ACT GGC ATC CCA GCC AGG TTC AGT GGC AGT GGG TCT GGG

T   D   F   T   L   T   I   S   S   L   E   P   E   D   F   A   V
205       ACA GAC TTC ACT CTC ACC ATC AGC AGC CTA GAG CCT GAA GAT TTT GCA GTT

_CDR3_____
          Y   Y   C   Q   Q   R   S   N   W   P   P   T   F   G   Q   G   T
256       TAT TAC TGT CAG CAG CGT AGC AAC TGG CCT CCG ACG TTC GGC CAA GGG ACC

K   V   E   I   K
307       AAG GTG GAA ATC AAA
```

FIG. 6B

Anti-OX40 20B3 VH (hIgG2)

V segment: 3-13
J segment: JH4b

```
          E   V   Q   L   V   E   S   G   G   G   L   V   Q   P   G   G   S
1         GAG GTG CAG CTG GTG GAG TCT GGG GGA GGC TTG GTA CAG CCT GGG GGG TCC

_CDR1_____
          L   R   L   S   C   A   A   S   G   F   T   F   S   S   Y   D   M
52        CTG AGA CTC TCC TGT GCA GCC TCT GGA TTC ACC TTC AGT AGC TAC GAC ATG

____                                                       _CDR2____
          H   W   V   R   Q   T   T   G   K   G   L   E   W   V   S   V   I
103       CAC TGG GTC CGC CAA ACT ACA GGA AAA GGT CTG GAG TGG GTC TCA GTT ATT

G   T   A   G   D   T   Y   Y   P   G   S   V   K   G   R   F   T
154       GGT ACT GCT GGT GAC ACA TAC TAT CCA GGC TCC GTG AAG GGC CGA TTC ACC

I   S   R   E   N   A   K   N   S   L   Y   L   Q   M   N   S   L
205       ATC TCC AGA GAA AAT GCC AAG AAC TCC TTG TAT CTT CAA ATG AAC AGC CTG

_CDR3_____
          R   A   G   D   T   A   V   Y   Y   C   A   R   G   G   M   G   N
256       AGA GCC GGG GAC ACG GCT GTG TAT TAC TGT GCA AGA GGG GGG ATG GGG AAC

_____
          Y   F   D   Y   W   G   Q   G   T   L   V   T   V   S   S
307       TAC TTT GAC TAC TGG GGC CAG GGA ACC CTG GTC ACC GTC TCC TCA
```

FIG. 7A

Anti-OX40 20B3 VK (hKappa)

V segment: L6
J segment: JK4

```
         E   I   V   L   T   Q   S   P   A   T   L   S   L   S   P   G   E
  1      GAA ATT GTG TTG ACA CAG TCT CCA GCC ACC CTG TCT TTG TCT CCA GGG GAA

_CDR1_____
         R   A   T   L   S   C   R   A   S   Q   S   V   S   S   Y   L   A
  52     AGA GCC ACC CTC TCC TGC AGG GCC AGT CAG AGT GTT AGC AGC TAC TTA GCC

_CDR2_____
         W   Y   Q   Q   K   P   G   Q   A   P   R   L   L   I   Y   D   A
  103    TGG TAC CAA CAG AAA CCT GGC CAG GCT CCC AGG CTC CTC ATC TAT GAT GCA

_____
         S   N   R   A   T   G   I   P   A   R   F   S   G   S   G   S   G
  154    TCC AAC AGG GCC ACT GGC ATC CCA GCC AGG TTC AGT GGC AGT GGG TCT GGG

T   D   F   T   L   T   I   S   S   L   E   P   E   D   F   A   V
  205    ACA GAC TTC ACT CTC ACC ATC AGC AGC CTA GAG CCT GAA GAT TTT GCA GTT

_CDR3_____
         Y   Y   C   Q   Q   R   S   N   W   P   L   T   F   G   G   G   T
  256    TAT TAC TGT CAG CAG CGT AGC AAC TGG CCG CTC ACT TTC GGC GGA GGG ACC

K   V   E   I   K
  307    AAG GTG GAG ATC AAA
```

FIG. 7B

Anti-OX40 14A2 VH (hIgG1)

V segment: 3-30.3
J segment: JH5b

```
          Q   V   Q   L   V   E   S   G   G   G   V   V   Q   P   G   R   S
  1       CAG GTG CAG CTG GTG GAG TCT GGG GGA GGC GTG GTC CAG CCT GGG AGG TCC

_CDR1_____
          L   R   L   S   C   A   A   S   G   F   T   F   S   N   Y   A   L
 52       CTG AGA CTC TCC TGT GCA GCC TCT GGA TTC ACC TTC AGT AAC TAT GCT CTG

___                                                 _CDR2____
          H   W   V   R   Q   A   P   G   K   G   L   E   W   V   A   L   I
103       CAC TGG GTC CGC CAG GCT CCA GGC AAG GGG CTG GAG TGG GTG GCA CTT ATA

_____
          S   Y   D   G   S   R   K   H   Y   A   D   S   V   K   G   R   F
154       TCA TAT GAT GGA AGC AGG AAA CAC TAC GCA GAC TCC GTG AAG GGC CGA TTC

S   I   S   R   D   N   S   K   N   T   L   Y   L   Q   M   N   S
205       AGT ATC TCC AGA GAC AAT TCC AAG AAC ACA CTG TAT CTG CAA ATG AAC AGC

_CDR3_____
          L   R   A   E   D   T   A   V   Y   Y   C   A   S   L   T   M   V
256       CTG AGA GCT GAG GAC ACG GCT GTG TAT TAC TGT GCG AGT CTT ACT ATG GTT

_____
          R   E   G   G   Q   G   T   L   V   T   V   S   S
307       CGG GAG GGG GGC CAG GGA ACC CTG GTC ACC GTC TCC TCA
```

FIG. 8A

Anti-OX40 14A2 VK1 (hKappa)

V segment: A27
J segment: JK3

```
          E   I   V   L   T   Q   S   P   G   T   L   S   L   S   P   G   E
1         GAA ATT GTG TTG ACG CAG TCT CCA GGC ACC CTG TCT TTG TCT CCA GGG GAA

_CDR1_____
          R   A   T   L   S   C   R   A   S   Q   S   V   S   S   S   Y   L
52        AGA GCC ACC CTC TCC TGC AGG GCC AGT CAG AGT GTT AGC AGC AGC TAC TTA

____                                                          _CDR2
          A   W   Y   Q   Q   K   P   G   Q   A   P   R   L   L   I   Y   G
103       GCC TGG TAC CAG CAG AAA CCT GGC CAG GCT CCC AGG CTC CTC ATC TAT GGT

_____
          A   S   S   R   A   T   G   I   P   D   R   F   S   G   S   G   S
154       GCA TCC AGC AGG GCC ACT GGC ATC CCA GAC AGG TTC AGT GGC AGT GGG TCT

G   T   D   F   T   L   T   I   S   R   L   E   P   E   D   F   A
205       GGG ACA GAC TTC ACT CTC ACC ATC AGC AGA CTG GAG CCT GAA GAT TTT GCA

_CDR3_____
          V   Y   Y   C   Q   Q   Y   G   S   S   P   F   T   F   G   P   G
256       GTG TAT TAC TGT CAG CAG TAT GGT AGC TCA CCA TTC ACT TTC GGC CCT GGG

T   K   V   D   I   K
307       ACC AAA GTG GAT ATC AAA
```

FIG. 8B

Anti-OX40 14A2 VK2 (hKappa)

V segment: O14/O4
J segment: JK4

```
         D    I    Q    L    T    Q    S    P    S    S    L    S    A    S    V    G    D
1        GAC  ATC  CAG  TTG  ACC  CAG  TCT  CCA  TCC  TCC  CTG  TCT  GCA  TCT  GTA  GGA  GAC

_CDR1_____
         R    V    T    I    T    C    R    V    S    Q    G    I    S    S    Y    L    N
52       AGA  GTC  ACC  ATC  ACT  TGC  CGG  GTG  AGT  CAG  GGC  ATT  AGC  AGT  TAT  TTA  AAT

_CDR2_____
         W    Y    R    Q    K    P    G    K    V    P    K    L    L    I    Y    S    A
103      TGG  TAT  CGG  CAG  AAA  CCA  GGG  AAA  GTT  CCT  AAG  CTC  CTG  ATC  TAT  AGT  GCA

_____
         S    N    L    Q    S    G    V    P    S    R    F    S    G    S    G    S    G
154      TCC  AAT  TTG  CAA  TCT  GGA  GTC  CCA  TCT  CGG  TTC  AGT  GGC  AGT  GGA  TCT  GGG

T    D    F    T    L    T    I    S    S    L    Q    P    E    D    V    A    T
205      ACA  GAT  TTC  ACT  CTC  ACT  ATC  AGC  AGC  CTG  CAG  CCT  GAA  GAT  GTT  GCA  ACT

_CDR3_____
         Y    Y    G    Q    R    T    Y    N    A    P    Y    T    F    G    G    G    T
256      TAT  TAC  GGT  CAA  CGG  ACT  TAC  AAT  GCC  CCT  TAC  ACT  TTC  GGC  GGA  GGG  ACC

K    V    E    I    K
307      AAG  GTG  GAG  ATC  AAA
```

FIG. 8C

Anti-OX40 20C1 VH (hIgG1)

V segment: DP-44
J segment: JH4b

```
        E   A   Q   L   V   Q   S   G   G   G   L   V   H   P   G   G   S
1       GAG GCT CAG CTG GTG CAG TCT GGG GGA GGC TTG GTT CAT CCT GGG GGG TCC

_CDR1_____
        L   R   L   S   C   A   D   S   G   F   T   F   S   S   Y   A   M
52      CTG AGA CTC TCC TGT GCA GAC TCT GGA TTC ACC TTC AGT AGC TAT GCT ATG

_____                                               _CDR2_____
        Y   W   V   R   Q   A   P   G   K   G   L   E   W   V   S   A   I
103     TAC TGG GTT CGC CAG GCT CCA GGA AAA GGT CTG GAG TGG GTA TCA GCT ATT

D   T   D   G   G   T   F   Y   A   D   S   V   R   G   R   F   T
154     GAT ACT GAT GGT GGC ACA TTC TAT GCA GAC TCC GTG CGG GGC CGA TTC ACC

I   S   R   D   N   A   K   N   S   L   Y   L   Q   M   N   G   L
205     ATC TCC AGA GAC AAT GCC AAG AAC TCC TTG TAT CTT CAA ATG AAC GGC CTG

_CDR3_____
        R   A   E   D   M   A   V   Y   F   C   A   R   L   G   E   G   Y
256     AGA GCC GAG GAC ATG GCT GTG TAT TTC TGT GCA AGA CTT GGG GAA GGG TAC

_____
        F   F   D   Y   W   G   Q   G   T   L   V   T   V   S   S
307     TTC TTT GAC TAC TGG GGC CAG GGA ACC CTG GTC ACC GTC TCC TCA
```

FIG. 9A

Anti-OX40 20C1 VK (hKappa)

V segment: L6
J segment: JK4

```
          E   I   V   L   T   Q   S   P   A   T   L   S   L   S   P   G   E
1         GAA ATT GTG TTG ACA CAG TCT CCA GCC ACC CTG TCT TTG TCT CCA GGG GAA

_CDR1_____
          R   A   T   L   S   C   R   A   S   Q   S   V   S   S   Y   L   A
52        AGA GCC ACC CTC TCC TGC AGG GCC AGT CAG AGT GTT AGC AGC TAC TTA GCC

_CDR2____
          W   Y   Q   Q   K   P   G   Q   A   P   R   L   L   I   Y   D   A
103       TGG TAC CAA CAG AAA CCT GGC CAG GCT CCC AGG CTC CTC ATC TAT GAT GCA

_____
          S   N   R   A   T   G   I   P   A   R   F   S   G   S   G   S   G
154       TCC AAC AGG GCC ACT GGC ATC CCA GCC AGG TTC AGT GGC AGT GGG TCT GGG

T   D   F   T   L   T   I   S   S   L   E   P   E   D   F   A   V
205       ACA GAC TTC ACT CTC ACC ATC AGC AGC CTA GAG CCT GAA GAT TTT GCA GTT

_CDR3_____
          Y   Y   C   Q   Q   R   S   N   W   P   P   T   F   G   G   G   T
256       TAT TAC TGT CAG CAG CGT AGC AAC TGG CCT CCC ACT TTC GGC GGA GGG ACC

K   V   E   I   K
307       AAG GTG GAG ATC AAA
```

FIG. 9B

Anti-OX-40.21 VH

```
              A2V                                        H13Q
              ~~~~                                       ~~~~
                      20C1 VH
    ~~~~~~~~~~~~~~~~~~~~~~~~~~~~~~~~~~~~~~~~~~~~~~~~~~~~~~~~~~
      E   V   Q   L   V   Q   S   G   G   G   L   V   Q   P   G
  1  GAG GTT CAG CTG GTG CAG TCT GGG GGA GGC TTG GTT CAG CCT GGG
                                  D24G
                                  ~~~~
                      20C1 VH
    ~~~~~~~~~~~~~~~~~~~~~~~~~~~~~~~~~~~~~~~~~~~~~~~~~~~~~~~~~~
      G   S   L   R   L   S   C   A   G   S   G   F   T   F   S
  46 GGG TCC CTG AGA CTC TCC TGT GCA GGC TCT GGA TTC ACC TTC AGT
                      20C1 VH
    ~~~~~~~~~~~~~~~~~~~~~~~~~~~~~~~~~~~~~~~~~~~~~~~~~~~~~~~~~~
      S   Y   A   M   Y   W   V   R   Q   A   P   G   K   G   L
  91 AGC TAT GCT ATG TAC TGG GTT CGC CAG GCT CCA GGA AAA GGT CTG
                                              G55A
                                              ~~~~
                      20C1 VH
    ~~~~~~~~~~~~~~~~~~~~~~~~~~~~~~~~~~~~~~~~~~~~~~~~~~~~~~~~~~
      E   W   V   S   A   I   D   T   D   A   G   T   F   Y   A
 136 GAG TGG GTA TCA GCT ATT GAT ACT GAT GCT GGC ACA TTC TAT GCA
                      20C1 VH
    ~~~~~~~~~~~~~~~~~~~~~~~~~~~~~~~~~~~~~~~~~~~~~~~~~~~~~~~~~~
      D   S   V   R   G   R   F   T   I   S   R   D   N   A   K
 181 GAC TCC GTG CGG GGC CGA TTC ACC ATC TCC AGA GAC AAT GCC AAG
                                          G82bS              M87T
                                          ~~~~~              ~~~~
                      20C1 VH
    ~~~~~~~~~~~~~~~~~~~~~~~~~~~~~~~~~~~~~~~~~~~~~~~~~~~~~~~~~~
      N   S   L   Y   L   Q   M   N   S   L   R   A   E   D   T
 226 AAC TCC TTG TAT CTT CAA ATG AAC AGC CTG AGA GCC GAG GAC ACG
                      20C1 VH
    ~~~~~~~~~~~~~~~~~~~~~~~~~~~~~~~~~~~~~~~~~~~~~~~~~~~~~~~~~~
      A   V   Y   F   C   A   R   L   G   E   G   Y   F   F   D
 271 GCT GTG TAT TTC TGT GCA AGA CTT GGG GAA GGG TAC TTC TTT GAC
                      20C1 VH
    ~~~~~~~~~~~~~~~~~~~~~~~~~~~~~~~~~~~~~~~~~~~~~~~~~~~~~~~~~~
                                                        C gamma1
                                                      ~~~~~~~~~~
      Y   W   G   Q   G   T   L   V   T   V   S   S   A   S   T
 316 TAC TGG GGC CAG GGA ACC CTG GTC ACC GTC TCC TCA GCT AGC ACC
                                      C gamma1
    ~~~~~~~~~~~~~~~~~~~~~~~~~~~~~~~~~~~~~~~~~~~~~~~~~~~~~~~~~~
      K   G   P   S   V   F   P   L   A   P   S   S   K   S   T
 361 AAG GGC CCA TCG GTC TTC CCC CTG GCA CCC TCC TCC AAG AGC ACC
                                      C gamma1
    ~~~~~~~~~~~~~~~~~~~~~~~~~~~~~~~~~~~~~~~~~~~~~~~~~~~~~~~~~~
      S   G   G   T   A   A   L   G   C   L   V   K   D   Y   F
 406 TCT GGG GGC ACA GCG GCC CTG GGC TGC CTG GTC AAG GAC TAC TTC
                                      C gamma1
    ~~~~~~~~~~~~~~~~~~~~~~~~~~~~~~~~~~~~~~~~~~~~~~~~~~~~~~~~~~
      P   E   P   V   T   V   S   W   N   S   G   A   L   T   S
 451 CCC GAA CCG GTG ACG GTG TCG TGG AAC TCA GGC GCC CTG ACC AGC
                                      C gamma1
    ~~~~~~~~~~~~~~~~~~~~~~~~~~~~~~~~~~~~~~~~~~~~~~~~~~~~~~~~~~
      G   V   H   T   F   P   A   V   L   Q   S   S   G   L   Y
 496 GGC GTG CAC ACC TTC CCG GCT GTC CTA CAG TCC TCA GGA CTC TAC
                                      C gamma1
    ~~~~~~~~~~~~~~~~~~~~~~~~~~~~~~~~~~~~~~~~~~~~~~~~~~~~~~~~~~
```

FIG. 10A

```
           S   L   S   S   V   V   T   V   P   S   S   S   L   G   T
       541 TCC CTC AGC AGC GTG GTG ACC GTG CCC TCC AGC AGC TTG GGC ACC
                                    C gamma1
           ~~~~~~~~~~~~~~~~~~~~~~~~~~~~~~~~~~~~~~~~~~~~~~~~~~~~~~~~~~
           Q   T   Y   I   C   N   V   N   H   K   P   S   N   T   K
       586 CAG ACC TAC ATC TGC AAC GTG AAT CAC AAG CCC AGC AAC ACC AAG
                                    C gamma1
           ~~~~~~~~~~~~~~~~~~~~~~~~~~~~~~~~~~~~~~~~~~~~~~~~~~~~~~~~~~
           V   D   K   R   V   E   P   K   S   C   D   K   T   H   T
       631 GTG GAC AAG AGA GTT GAG CCC AAA TCT TGT GAC AAA ACT CAC ACA
                                    C gamma1
           ~~~~~~~~~~~~~~~~~~~~~~~~~~~~~~~~~~~~~~~~~~~~~~~~~~~~~~~~~~
           C   P   P   C   P   A   P   E   L   L   G   G   P   S   V
       676 TGC CCA CCG TGC CCA GCA CCT GAA CTC CTG GGG GGA CCG TCA GTC
                                    C gamma1
           ~~~~~~~~~~~~~~~~~~~~~~~~~~~~~~~~~~~~~~~~~~~~~~~~~~~~~~~~~~
           F   L   F   P   P   K   P   K   D   T   L   M   I   S   R
       721 TTC CTC TTC CCC CCA AAA CCC AAG GAC ACC CTC ATG ATC TCC CGG
                                    C gamma1
           ~~~~~~~~~~~~~~~~~~~~~~~~~~~~~~~~~~~~~~~~~~~~~~~~~~~~~~~~~~
           T   P   E   V   T   C   V   V   V   D   V   S   H   E   D
       766 ACC CCT GAG GTC ACA TGC GTG GTG GTG GAC GTG AGC CAC GAA GAC
                                    C gamma1
           ~~~~~~~~~~~~~~~~~~~~~~~~~~~~~~~~~~~~~~~~~~~~~~~~~~~~~~~~~~
           P   E   V   K   F   N   W   Y   V   D   G   V   E   V   H
       811 CCT GAG GTC AAG TTC AAC TGG TAC GTG GAC GGC GTG GAG GTG CAT
                                    C gamma1
           ~~~~~~~~~~~~~~~~~~~~~~~~~~~~~~~~~~~~~~~~~~~~~~~~~~~~~~~~~~
           N   A   K   T   K   P   R   E   E   Q   Y   N   S   T   Y
       856 AAT GCC AAG ACA AAG CCG CGG GAG GAG CAG TAC AAC AGC ACG TAC
                                    C gamma1
           ~~~~~~~~~~~~~~~~~~~~~~~~~~~~~~~~~~~~~~~~~~~~~~~~~~~~~~~~~~
           R   V   V   S   V   L   T   V   L   H   Q   D   W   L   N
       901 CGT GTG GTC AGC GTC CTC ACC GTC CTG CAC CAG GAC TGG CTG AAT
                                    C gamma1
           ~~~~~~~~~~~~~~~~~~~~~~~~~~~~~~~~~~~~~~~~~~~~~~~~~~~~~~~~~~
           G   K   E   Y   K   C   K   V   S   N   K   A   L   P   A
       946 GGC AAG GAG TAC AAG TGC AAG GTC TCC AAC AAA GCC CTC CCA GCC
                                    C gamma1
           ~~~~~~~~~~~~~~~~~~~~~~~~~~~~~~~~~~~~~~~~~~~~~~~~~~~~~~~~~~
           P   I   E   K   T   I   S   K   A   K   G   Q   P   R   E
       991 CCC ATC GAG AAA ACC ATC TCC AAA GCC AAA GGG CAG CCC CGA GAA
                                    C gamma1
           ~~~~~~~~~~~~~~~~~~~~~~~~~~~~~~~~~~~~~~~~~~~~~~~~~~~~~~~~~~
           P   Q   V   Y   T   L   P   P   S   R   E   E   M   T   K
      1036 CCA CAG GTG TAC ACC CTG CCC CCA TCC CGG GAG GAG ATG ACC AAG
                                    C gamma1
           ~~~~~~~~~~~~~~~~~~~~~~~~~~~~~~~~~~~~~~~~~~~~~~~~~~~~~~~~~~
           N   Q   V   S   L   T   C   L   V   K   G   F   Y   P   S
      1081 AAC CAG GTC AGC CTG ACC TGC CTG GTC AAA GGC TTC TAT CCC AGC
                                    C gamma1
           ~~~~~~~~~~~~~~~~~~~~~~~~~~~~~~~~~~~~~~~~~~~~~~~~~~~~~~~~~~
           D   I   A   V   E   W   E   S   N   G   Q   P   E   N   N
      1126 GAC ATC GCC GTG GAG TGG GAG AGC AAT GGG CAG CCG GAG AAC AAC
                                    C gamma1
           ~~~~~~~~~~~~~~~~~~~~~~~~~~~~~~~~~~~~~~~~~~~~~~~~~~~~~~~~~~
           Y   K   T   T   P   P   V   L   D   S   D   G   S   F   F
      1171 TAC AAG ACC ACG CCT CCC GTG CTG GAC TCC GAC GGC TCC TTC TTC
                                    C gamma1
           ~~~~~~~~~~~~~~~~~~~~~~~~~~~~~~~~~~~~~~~~~~~~~~~~~~~~~~~~~~
           L   Y   S   K   L   T   V   D   K   S   R   W   Q   Q   G
      1216 CTC TAT AGC AAG CTC ACC GTG GAC AAG AGC AGG TGG CAG CAG GGG
                                    C gamma1
```

FIG. 10A...continued

```
         N   V   F   S   C   S   V   M   H   E   A   L   H   N   H
     1261 AAC GTC TTC TCA TGC TCC GTG ATG CAT GAG GCT CTG CAC AAC CAC
                          C gamma1

Y   T   Q   K   S   L   S   L   S   P   G   *
     1306 TAC ACG CAG AAG AGC CTC TCC CTG TCC CCG GGT TGA
```

FIG. 10A...continued

Anti-OX-40.21 VK

```
                              20C1 VK
      ~~~~~~~~~~~~~~~~~~~~~~~~~~~~~~~~~~~~~~~~~~~~~~~~~~~~~~~~~~~~
        E   I   V   L   T   Q   S   P   A   T   L   S   L   S   P
    1 GAA ATT GTG TTG ACA CAG TCT CCA GCC ACC CTG TCT TTG TCT CCA
                              20C1 VK
      ~~~~~~~~~~~~~~~~~~~~~~~~~~~~~~~~~~~~~~~~~~~~~~~~~~~~~~~~~~~~
        G   E   R   A   T   L   S   C   R   A   S   Q   S   V   S
   46 GGG GAA AGA GCC ACC CTC TCC TGC AGG GCC AGT CAG AGT GTT AGC
                              20C1 VK
      ~~~~~~~~~~~~~~~~~~~~~~~~~~~~~~~~~~~~~~~~~~~~~~~~~~~~~~~~~~~~
        S   Y   L   A   W   Y   Q   Q   K   P   G   Q   A   P   R
   91 AGC TAC TTA GCC TGG TAC CAA CAG AAA CCT GGC CAG GCT CCC AGG
                              20C1 VK
      ~~~~~~~~~~~~~~~~~~~~~~~~~~~~~~~~~~~~~~~~~~~~~~~~~~~~~~~~~~~~
        L   L   I   Y   D   A   S   N   R   A   T   G   I   P   A
  136 CTC CTC ATC TAT GAT GCA TCC AAC AGG GCC ACT GGC ATC CCA GCC
                              20C1 VK
      ~~~~~~~~~~~~~~~~~~~~~~~~~~~~~~~~~~~~~~~~~~~~~~~~~~~~~~~~~~~~
        R   F   S   G   S   G   S   G   T   D   F   T   L   T   I
  181 AGG TTC AGT GGC AGT GGG TCT GGG ACA GAC TTC ACT CTC ACC ATC
                              20C1 VK
      ~~~~~~~~~~~~~~~~~~~~~~~~~~~~~~~~~~~~~~~~~~~~~~~~~~~~~~~~~~~~
        S   S   L   E   P   E   D   F   A   V   Y   Y   C   Q   Q
  226 AGC AGC CTA GAG CCT GAA GAT TTT GCA GTT TAT TAC TGT CAG CAG
                              20C1 VK
      ~~~~~~~~~~~~~~~~~~~~~~~~~~~~~~~~~~~~~~~~~~~~~~~~~~~~~~~~~~~~
        R   S   N   W   P   P   T   F   G   G   G   T   K   V   E
  271 CGT AGC AAC TGG CCT CCC ACT TTC GGC GGA GGG ACC AAG GTG GAG
        20C1 VK
      ~~~~~~~~~
                              C kappa
      ~~~~~~~~~~~~~~~~~~~~~~~~~~~~~~~~~~~~~~~~~~~~~~~~~~~~~~~~~~~~
        I   K   R   T   V   A   A   P   S   V   F   I   F   P   P
  316 ATC AAA CGT ACG GTG GCT GCA CCA TCT GTC TTC ATC TTC CCG CCA
                              C kappa
      ~~~~~~~~~~~~~~~~~~~~~~~~~~~~~~~~~~~~~~~~~~~~~~~~~~~~~~~~~~~~
        S   D   E   Q   L   K   S   G   T   A   S   V   V   C   L
  361 TCT GAT GAG CAG TTG AAA TCT GGA ACT GCC TCT GTT GTG TGC CTG
                              C kappa
      ~~~~~~~~~~~~~~~~~~~~~~~~~~~~~~~~~~~~~~~~~~~~~~~~~~~~~~~~~~~~
        L   N   N   F   Y   P   R   E   A   K   V   Q   W   K   V
  406 CTG AAT AAC TTC TAT CCC AGA GAG GCC AAA GTA CAG TGG AAG GTG
                              C kappa
      ~~~~~~~~~~~~~~~~~~~~~~~~~~~~~~~~~~~~~~~~~~~~~~~~~~~~~~~~~~~~
        D   N   A   L   Q   S   G   N   S   Q   E   S   V   T   E
  451 GAT AAC GCC CTC CAA TCG GGT AAC TCC CAG GAG AGT GTC ACA GAG
                              C kappa
      ~~~~~~~~~~~~~~~~~~~~~~~~~~~~~~~~~~~~~~~~~~~~~~~~~~~~~~~~~~~~
        Q   D   S   K   D   S   T   Y   S   L   S   S   T   L   T
  496 CAG GAC AGC AAG GAC AGC ACC TAC AGC CTC AGC AGC ACC CTG ACG
                              C kappa
      ~~~~~~~~~~~~~~~~~~~~~~~~~~~~~~~~~~~~~~~~~~~~~~~~~~~~~~~~~~~~
        L   S   K   A   D   Y   E   K   H   K   V   Y   A   C   E
  541 CTG AGC AAA GCA GAC TAC GAG AAA CAC AAA GTC TAC GCC TGC GAA
                              C kappa
      ~~~~~~~~~~~~~~~~~~~~~~~~~~~~~~~~~~~~~~~~~~~~~~~~~~~~~~~~~~~~
        V   T   H   Q   G   L   S   S   P   V   T   K   S   F   N
  586 GTC ACC CAT CAG GGC CTG AGC TCG CCC GTC ACA AAG AGC TTC AAC
        C kappa
      ~~~~~~~~~
```

FIG. 10B

```
               R   G   E   C   *
           631 AGG GGA GAG TGT TAG
```

FIG. 10B...continued

| | OX40.6 | OX40.8 | OX40.4 | OX40.5 | OX40.1 |
|---|---|---|---|---|---|
| EC50 | 0.857 | | | 2.669 | 1.190 |

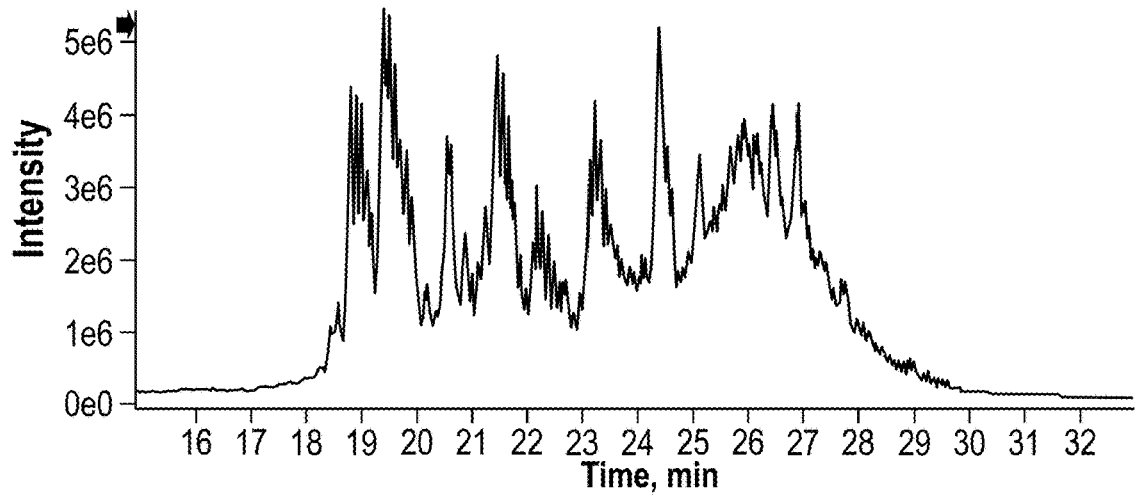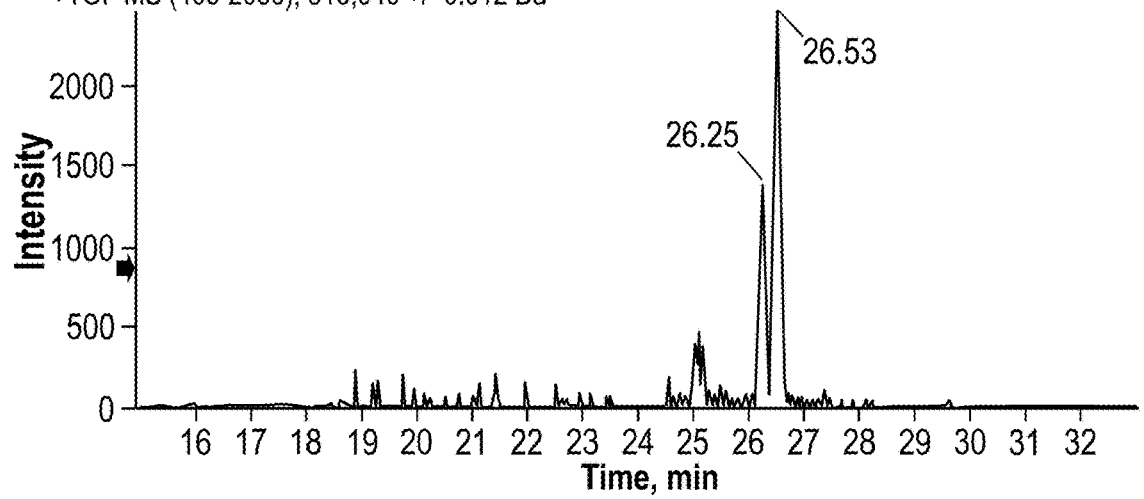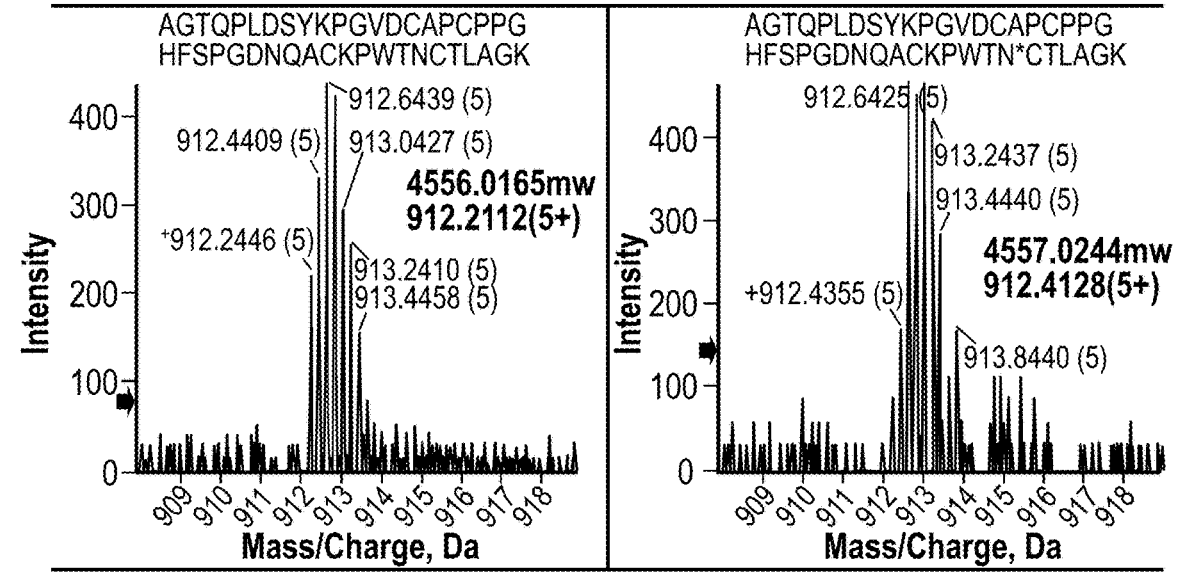
FIG. 20B

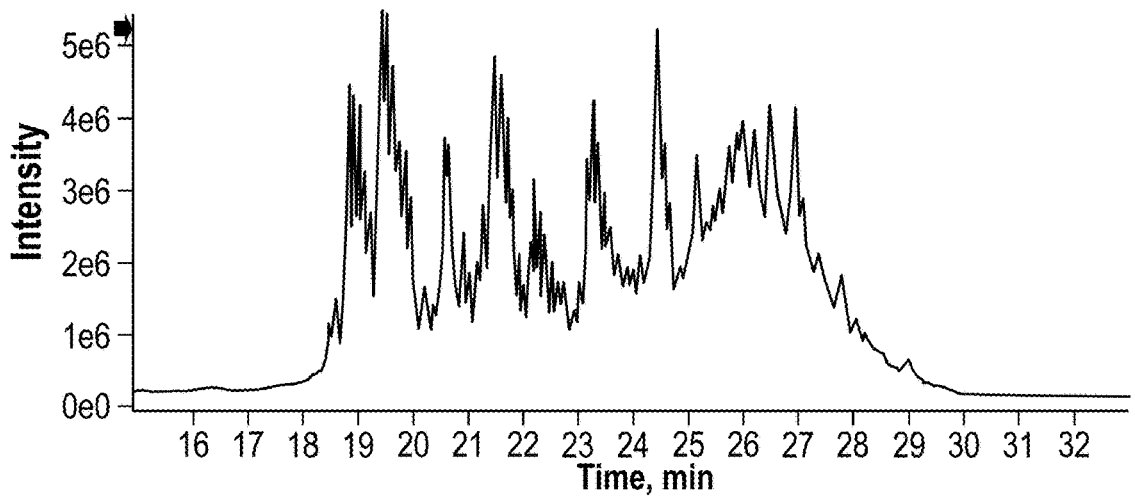
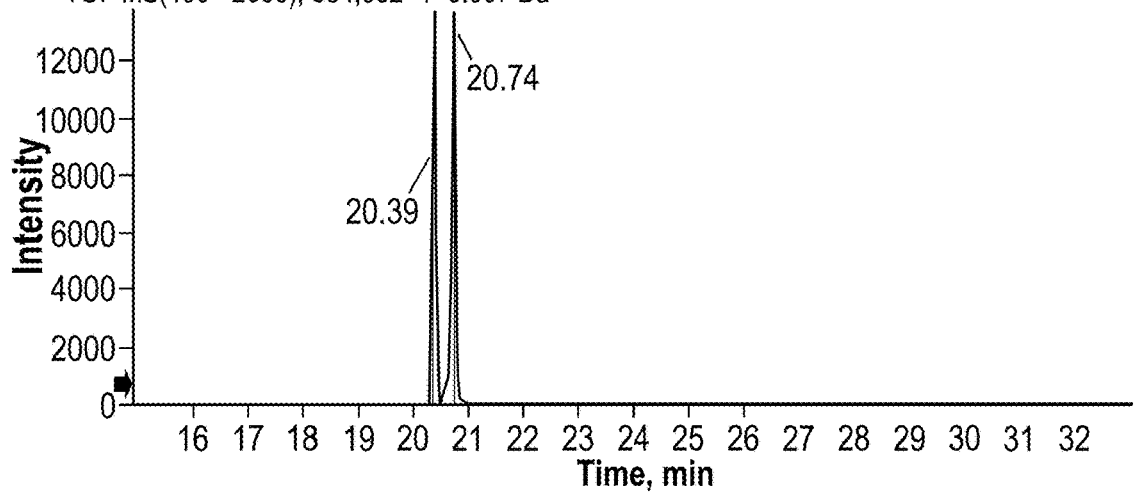
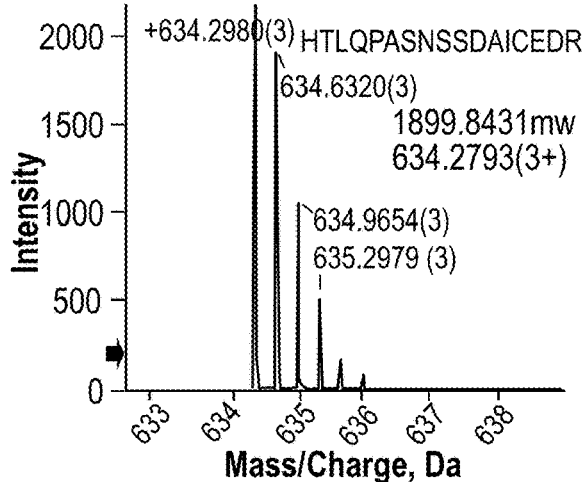
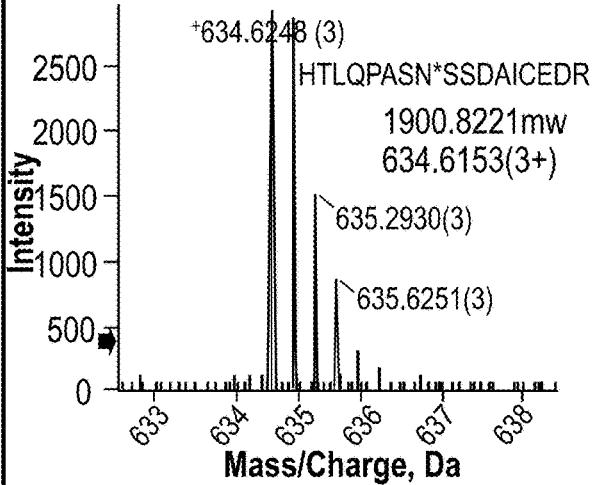
Figure 20C

SEQUENCE LISTING

<160> NUMBER OF SEQ ID NOS: 318

<210> SEQ ID NO 1
<211> LENGTH: 277
<212> TYPE: PRT
<213> ORGANISM: Homo sapiens
<220> FEATURE:
<221> NAME/KEY: misc_feature
<222> LOCATION: (1)..(277)
<223> OTHER INFORMATION: Human OX40 precursor

<400> SEQUENCE: 1

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205
```

```
Val Pro Gly Gly Arg Ala Val Ala Ala Ile Leu Gly Leu Gly Leu Val
    210                 215                 220
Leu Gly Leu Leu Gly Pro Leu Ala Ile Leu Leu Ala Leu Tyr Leu Leu
225                 230                 235                 240
Arg Arg Asp Gln Arg Leu Pro Pro Asp Ala His Lys Pro Pro Gly Gly
                245                 250                 255
Gly Ser Phe Arg Thr Pro Ile Gln Glu Glu Gln Ala Asp Ala His Ser
            260                 265                 270
Thr Leu Ala Lys Ile
            275

<210> SEQ ID NO 2
<211> LENGTH: 189
<212> TYPE: PRT
<213> ORGANISM: Homo sapiens
<220> FEATURE:
<221> NAME/KEY: misc_feature
<222> LOCATION: (1)..(189)
<223> OTHER INFORMATION: Extracellular domain of mature human OX40

<400> SEQUENCE: 2

Leu His Cys Val Gly Asp Thr Tyr Pro Ser Asn Asp Arg Cys Cys His
1               5                   10                  15
Glu Cys Arg Pro Gly Asn Gly Met Val Ser Arg Cys Ser Arg Ser Gln
            20                  25                  30
Asn Thr Val Cys Arg Pro Cys Gly Pro Gly Phe Tyr Asn Asp Val Val
        35                  40                  45
Ser Ser Lys Pro Cys Lys Pro Cys Thr Trp Cys Asn Leu Arg Ser Gly
    50                  55                  60
Ser Glu Arg Lys Gln Leu Cys Thr Ala Thr Gln Asp Thr Val Cys Arg
65                  70                  75                  80
Cys Arg Ala Gly Thr Gln Pro Leu Asp Ser Tyr Lys Pro Gly Val Asp
                85                  90                  95
Cys Ala Pro Cys Pro Pro Gly His Phe Ser Pro Gly Asp Asn Gln Ala
            100                 105                 110
Cys Lys Pro Trp Thr Asn Cys Thr Leu Ala Gly Lys His Thr Leu Gln
        115                 120                 125
Pro Ala Ser Asn Ser Ser Asp Ala Ile Cys Glu Asp Arg Asp Pro Pro
    130                 135                 140
Ala Thr Gln Pro Gln Glu Thr Gln Gly Pro Pro Ala Arg Pro Ile Thr
145                 150                 155                 160
Val Gln Pro Thr Glu Ala Trp Pro Arg Thr Ser Gln Gly Pro Ser Thr
                165                 170                 175
Arg Pro Val Glu Val Pro Gly Gly Arg Ala Val Ala Ala
            180                 185

<210> SEQ ID NO 3
<211> LENGTH: 277
<212> TYPE: PRT
<213> ORGANISM: Macaca fascicularis
<220> FEATURE:
<221> NAME/KEY: misc_feature
<222> LOCATION: (1)..(277)
<223> OTHER INFORMATION: Cynomolgus OX40

<400> SEQUENCE: 3

Met Cys Val Gly Ala Arg Arg Leu Gly Arg Gly Pro Cys Ala Ala Leu
1               5                   10                  15
```

Leu Leu Leu Gly Leu Gly Leu Ser Thr Thr Ala Lys Leu His Cys Val
            20                  25                  30

Gly Asp Thr Tyr Pro Ser Asn Asp Arg Cys Cys Gln Glu Cys Arg Pro
        35                  40                  45

Gly Asn Gly Met Val Ser Arg Cys Asn Arg Ser Gln Asn Thr Val Cys
50                      55                  60

Arg Pro Cys Gly Pro Gly Phe Tyr Asn Asp Val Val Ser Ala Lys Pro
65                  70                  75                  80

Cys Lys Ala Cys Thr Trp Cys Asn Leu Arg Ser Gly Ser Glu Arg Lys
                85                  90                  95

Gln Pro Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Thr Gln Pro
                165                 170                 175

Gln Glu Thr Gln Gly Pro Pro Ala Arg Pro Thr Thr Val Gln Pro Thr
            180                 185                 190

Glu Ala Trp Pro Arg Thr Ser Gln Arg Pro Ser Thr Arg Pro Val Glu
        195                 200                 205

Val Pro Arg Gly Pro Ala Val Ala Ala Ile Leu Gly Leu Gly Leu Ala
210                 215                 220

Leu Gly Leu Leu Gly Pro Leu Ala Met Leu Leu Ala Leu Leu Leu Leu
225                 230                 235                 240

Arg Arg Asp Gln Arg Leu Pro Pro Asp Ala Pro Lys Ala Pro Gly Gly
                245                 250                 255

Gly Ser Phe Arg Thr Pro Ile Gln Glu Glu Gln Ala Asp Ala His Ser
            260                 265                 270

Ala Leu Ala Lys Ile
        275

<210> SEQ ID NO 4
<211> LENGTH: 183
<212> TYPE: PRT
<213> ORGANISM: Homo sapiens
<220> FEATURE:
<221> NAME/KEY: misc_feature
<222> LOCATION: (1)..(183)
<223> OTHER INFORMATION: Human OX40-L

<400> SEQUENCE: 4

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Thr Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn

```
            85                  90                  95
Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
                180

<210> SEQ ID NO 5
<211> LENGTH: 329
<212> TYPE: PRT
<213> ORGANISM: Homo sapiens
<220> FEATURE:
<221> NAME/KEY: misc_feature
<222> LOCATION: (1)..(329)
<223> OTHER INFORMATION: human IgG1 constant domain

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 6
<211> LENGTH: 329
<212> TYPE: PRT
<213> ORGANISM: Homo sapiens
<220> FEATURE:
<221> NAME/KEY: misc_feature
<222> LOCATION: (1)..(329)
<223> OTHER INFORMATION: human IgG1 constant domain (allotypic variant)

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 7
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: human IgG1 kappa light chain

<400> SEQUENCE: 7

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 8
<211> LENGTH: 5
<212> TYPE: PRT
<213> ORGANISM: Artificial Sequence
<220> FEATURE:
<223> OTHER INFORMATION: Synthetic: heavy chain constant region
      alternative C-terminus

<400> SEQUENCE: 8

```
Leu Ser Pro Gly Lys
1               5
```

<210> SEQ ID NO 9
<211> LENGTH: 4
<212> TYPE: PRT
<213> ORGANISM: Artificial Sequence
<220> FEATURE:
<223> OTHER INFORMATION: Synthetic: heavy chain constant region
      alternative C-terminus

<400> SEQUENCE: 9

```
Leu Ser Pro Gly
1
```

<210> SEQ ID NO 10
<211> LENGTH: 107
<212> TYPE: PRT
<213> ORGANISM: Homo sapiens
<220> FEATURE:

```
<221> NAME/KEY: misc_feature
<222> LOCATION: (1)..(107)
<223> OTHER INFORMATION: Human IgG1 kappa light chain constant region
      (CL)

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 11
<211> LENGTH: 5
<212> TYPE: PRT
<213> ORGANISM: Artificial Sequence
<220> FEATURE:
<223> OTHER INFORMATION: Synthetic: 3F4 VH CDR1

<400> SEQUENCE: 11

Ser Tyr Asp Val Asn
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic: 3F4 VH CDR2

<400> SEQUENCE: 12

Trp Met Asn Pro Asn Ser Gly Asn Thr Gly Tyr Ala Pro Lys Phe Gln
1               5                   10                  15

Gly

<210> SEQ ID NO 13
<211> LENGTH: 11
<212> TYPE: PRT
<213> ORGANISM: Artificial Sequence
<220> FEATURE:
<223> OTHER INFORMATION: Synthetic: 3F4 VH CDR3

<400> SEQUENCE: 13

Ile Tyr Ser Ser Ser Tyr Asn Trp Phe Asp Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic: 3F4 VL CDR1

<400> SEQUENCE: 14
```

Arg Ala Ser Gln Ser Val Ser Ser Tyr Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic: 3F4 VL CDR2

<400> SEQUENCE: 15

Asp Ala Ser Asn Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic: 3F4 VL CDR3

<400> SEQUENCE: 16

Gln Gln Arg Ser Asn Trp Pro Leu Thr
1               5

<210> SEQ ID NO 17
<211> LENGTH: 120
<212> TYPE: PRT
<213> ORGANISM: Artificial Sequence
<220> FEATURE:
<223> OTHER INFORMATION: Synthetic: 3F4 VH

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Ser Tyr
                20                  25                  30

Asp Val Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Pro Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Ser Ser Ser Tyr Asn Trp Phe Asp Pro Trp Gly Gln
            100                 105                 110

Gly Thr Leu Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: Synthetic: 3F4 VL

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105
```

<210> SEQ ID NO 19
<211> LENGTH: 5
<212> TYPE: PRT
<213> ORGANISM: Artificial Sequence
<220> FEATURE:
<223> OTHER INFORMATION: Synthetic: 14B6 VH CDR1

<400> SEQUENCE: 19

```
Ser Asn Trp Ile Gly
1               5
```

<210> SEQ ID NO 20
<211> LENGTH: 17
<212> TYPE: PRT
<213> ORGANISM: Artificial Sequence
<220> FEATURE:
<223> OTHER INFORMATION: Synthetic: 14B6 VH CDR2

<400> SEQUENCE: 20

```
Phe Ile Tyr Pro Gly Asp Ser Asp Thr Arg Tyr Ser Pro Ser Phe Gln
1               5                   10                  15

Gly
```

<210> SEQ ID NO 21
<211> LENGTH: 9
<212> TYPE: PRT
<213> ORGANISM: Artificial Sequence
<220> FEATURE:
<223> OTHER INFORMATION: Synthetic: 14B6 VH CDR3

<400> SEQUENCE: 21

```
Tyr Gly Asp Asp Trp Tyr Phe Asp Leu
1               5
```

<210> SEQ ID NO 22
<211> LENGTH: 11
<212> TYPE: PRT
<213> ORGANISM: Artificial Sequence
<220> FEATURE:
<223> OTHER INFORMATION: Synthetic: 14B6 VL1 CDR1

<400> SEQUENCE: 22

```
Arg Ala Ser Gln Ser Val Ser Ser Tyr Leu Ala
1               5                   10
```

<210> SEQ ID NO 23
<211> LENGTH: 7
<212> TYPE: PRT
<213> ORGANISM: Artificial Sequence
<220> FEATURE:
<223> OTHER INFORMATION: Synthetic: 14B6 VL1 CDR2

<400> SEQUENCE: 23

-continued

Asp Ala Ser Asn Arg Ala Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic: 14B6 VL1 CDR3

<400> SEQUENCE: 24

Gln Gln Arg Gly Asp Trp Pro Ile Thr
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic: 14B6 VL2 CDR1

<400> SEQUENCE: 25

Arg Ala Ser Gln Gly Ile Ser Ser Trp Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic: 14B6 VL2 CDR2

<400> SEQUENCE: 26

Ala Ala Ser Ser Leu Gln Ser
1               5

<210> SEQ ID NO 27
<211> LENGTH: 10
<212> TYPE: PRT
<213> ORGANISM: Artificial Sequence
<220> FEATURE:
<223> OTHER INFORMATION: Synthetic: 14B6 VL2 CDR3

<400> SEQUENCE: 27

Gln Gln Tyr Asn Ser Tyr Pro Arg Ile Thr
1               5                   10

<210> SEQ ID NO 28
<211> LENGTH: 118
<212> TYPE: PRT
<213> ORGANISM: Artificial Sequence
<220> FEATURE:
<223> OTHER INFORMATION: Synthetic: 14B6 VH

<400> SEQUENCE: 28

Glu Val Gln Leu Glu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Asn
            20                  25                  30

Trp Ile Gly Trp Val Arg Gln Met Pro Gly Lys Gly Leu Glu Trp Met
        35                  40                  45

Gly Phe Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Ile Ala Met Tyr Tyr Cys
                85                  90                  95

Ala Arg Tyr Gly Asp Asp Trp Tyr Phe Asp Leu Trp Gly Arg Gly Thr
            100                 105                 110

Leu Val Thr Val Ser Ser
            115

<210> SEQ ID NO 29
<211> LENGTH: 107
<212> TYPE: PRT
<213> ORGANISM: Artificial Sequence
<220> FEATURE:
<223> OTHER INFORMATION: Synthetic: 14B6 VL1

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Phe Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Ser Leu Thr Ile Ser Ser Leu Glu Pro
65                  70                  75                  80

Glu Asp Phe Ala Val Tyr Tyr Cys Gln Gln Arg Gly Asp Trp Pro Ile
                85                  90                  95

Thr Phe Gly Gln Gly Thr Arg Leu Glu Ile Lys
            100                 105

<210> SEQ ID NO 30
<211> LENGTH: 108
<212> TYPE: PRT
<213> ORGANISM: Artificial Sequence
<220> FEATURE:
<223> OTHER INFORMATION: Synthetic: 14B6 VL2

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Ile Thr Phe Gly Gln Gly Thr Arg Leu Glu Ile Lys
            100                 105

<210> SEQ ID NO 31
<211> LENGTH: 5
<212> TYPE: PRT
<213> ORGANISM: Artificial Sequence
<220> FEATURE:
<223> OTHER INFORMATION: Synthetic: 23H3 VH CDR1
```

<400> SEQUENCE: 31

Asn Tyr Ala Met Tyr
1               5

<210> SEQ ID NO 32
<211> LENGTH: 16
<212> TYPE: PRT
<213> ORGANISM: Artificial Sequence
<220> FEATURE:
<223> OTHER INFORMATION: Synthetic: 23H3 VH CDR2

<400> SEQUENCE: 32

Ala Ile Gly Ile Gly Gly Asp Thr Phe Tyr Thr Asp Ser Val Lys Gly
1               5                   10                  15

<210> SEQ ID NO 33
<211> LENGTH: 9
<212> TYPE: PRT
<213> ORGANISM: Artificial Sequence
<220> FEATURE:
<223> OTHER INFORMATION: Synthetic: 23H3 VH CDR3

<400> SEQUENCE: 33

Met Gly Thr Gly Tyr Phe Phe Asp Tyr
1               5

<210> SEQ ID NO 34
<211> LENGTH: 11
<212> TYPE: PRT
<213> ORGANISM: Artificial Sequence
<220> FEATURE:
<223> OTHER INFORMATION: Synthetic: 23H3 VL CDR1

<400> SEQUENCE: 34

Arg Ala Ser Gln Ser Val Ser Ser Tyr Leu Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Synthetic: 23H3 VL CDR2

<400> SEQUENCE: 35

Asp Ala Ser Asn Arg Ala Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic: 23H3 VL CDR3

<400> SEQUENCE: 36

Gln Gln Arg Ser Asn Trp Pro Leu Thr
1               5

<210> SEQ ID NO 37
<211> LENGTH: 117
<212> TYPE: PRT
<213> ORGANISM: Artificial Sequence
<220> FEATURE:
<223> OTHER INFORMATION: Synthetic: 23H3 VH

```
<400> SEQUENCE: 37

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ser Ala Ile Gly Ile Gly Gly Asp Thr Phe Tyr Thr Asp Ser Val Lys
    50                  55                  60

Gly Arg Phe Thr Ile Ser Arg Asp Asn Ala Lys Asn Ser Leu Ser Leu
65                  70                  75                  80

Gln Met Asn Ser Leu Arg Ala Glu Asp Met Ala Val Tyr Tyr Cys Ala
                85                  90                  95

Arg Met Gly Thr Gly Tyr Phe Phe Asp Tyr Trp Gly Gln Gly Thr Leu
            100                 105                 110

Val Thr Val Ser Ser
        115

<210> SEQ ID NO 38
<211> LENGTH: 107
<212> TYPE: PRT
<213> ORGANISM: Artificial Sequence
<220> FEATURE:
<223> OTHER INFORMATION: Synthetic: 23H3 VL

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Pro Gly Thr Lys Val Asp Ile Lys
            100                 105

<210> SEQ ID NO 39
<211> LENGTH: 5
<212> TYPE: PRT
<213> ORGANISM: Artificial Sequence
<220> FEATURE:
<223> OTHER INFORMATION: Synthetic: 6E1 VH CDR1

<400> SEQUENCE: 39

Ser Phe Ala Met His
1               5

<210> SEQ ID NO 40
<211> LENGTH: 17
<212> TYPE: PRT
<213> ORGANISM: Artificial Sequence
<220> FEATURE:
<223> OTHER INFORMATION: Synthetic: 6E1 VH CDR2

<400> SEQUENCE: 40
```

```
Val Ile Ser Tyr Asp Gly Ser Ile Lys Tyr Tyr Thr Asp Ser Val Lys
1               5                   10                  15

Gly

<210> SEQ ID NO 41
<211> LENGTH: 12
<212> TYPE: PRT
<213> ORGANISM: Artificial Sequence
<220> FEATURE:
<223> OTHER INFORMATION: Synthetic: 6E1 VH CDR3

<400> SEQUENCE: 41

Asp Gly Asn Tyr Gly Ser Ala Arg Tyr Phe Gln His
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic: 6E1 VL1 CDR1

<400> SEQUENCE: 42

Arg Ala Ser Gln Gly Ile Ser Ser Trp Leu Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic: 6E1 VL1 CDR2

<400> SEQUENCE: 43

Ala Ala Ser Ser Leu Gln Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic: 6E1 VL1 CDR3

<400> SEQUENCE: 44

Gln Gln Tyr Asn Ser Tyr Pro Arg Thr
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic: 6E1 VL2 CDR1

<400> SEQUENCE: 45

Arg Ala Ser Gln Ser Val Ser Ser Tyr Leu Ala
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic: 6E1 VL2 CDR2
```

```
<400> SEQUENCE: 46

Asp Ala Ser Asn Arg Ala Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic: 6E1 VL2 CDR3

<400> SEQUENCE: 47

Gln Gln Arg Ser Asn Trp Pro Tyr Thr
1               5

<210> SEQ ID NO 48
<211> LENGTH: 121
<212> TYPE: PRT
<213> ORGANISM: Artificial Sequence
<220> FEATURE:
<223> OTHER INFORMATION: Synthetic: 6E1 VH

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Ala Met His Trp Val Arg Gln Ala Pro Gly Lys Gly Leu Glu Trp Val
        35                  40                  45

Thr Val Ile Ser Tyr Asp Gly Ser Ile Lys Tyr Tyr Thr Asp Ser Val
    50                  55                  60

Lys Gly Arg Phe Thr Phe Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Gly Asn Tyr Gly Ser Ala Arg Tyr Phe Gln His Trp Gly
            100                 105                 110

Gln Gly Thr Leu Val Thr Val Ser Ser
        115                 120

<210> SEQ ID NO 49
<211> LENGTH: 107
<212> TYPE: PRT
<213> ORGANISM: Artificial Sequence
<220> FEATURE:
<223> OTHER INFORMATION: Synthetic: 6E1 VL1

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95
```

```
Thr Phe Gly Gln Gly Thr Lys Val Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: Synthetic: 6E1 VL2

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Thr Phe Gly Gln Gly Thr Lys Leu Glu Ile Lys
            100                 105

<210> SEQ ID NO 51
<211> LENGTH: 5
<212> TYPE: PRT
<213> ORGANISM: Artificial Sequence
<220> FEATURE:
<223> OTHER INFORMATION: Synthetic: 18E9 VH CDR1

<400> SEQUENCE: 51

Ser Ser Ala Met His
1               5

<210> SEQ ID NO 52
<211> LENGTH: 16
<212> TYPE: PRT
<213> ORGANISM: Artificial Sequence
<220> FEATURE:
<223> OTHER INFORMATION: Synthetic: 18E9 VH CDR2

<400> SEQUENCE: 52

Ala Ile Gly Thr Gly Gly Asp Thr Tyr Tyr Ala Asp Ser Val Lys Gly
1               5                   10                  15

<210> SEQ ID NO 53
<211> LENGTH: 12
<212> TYPE: PRT
<213> ORGANISM: Artificial Sequence
<220> FEATURE:
<223> OTHER INFORMATION: Synthetic: 18E9 VH CDR3

<400> SEQUENCE: 53

Asp Phe Tyr Asp Ile Leu Thr Gly Ile Phe Asp Tyr
1               5                   10

<210> SEQ ID NO 54
<211> LENGTH: 11
<212> TYPE: PRT
<213> ORGANISM: Artificial Sequence
```

```
<220> FEATURE:
<223> OTHER INFORMATION: Synthetic: 18E9 VL CDR1

<400> SEQUENCE: 54

Arg Ala Ser Gln Gly Ile Ser Ser Trp Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic: 18E9 VL CDR2

<400> SEQUENCE: 55

Ala Ala Ser Ser Leu Gln Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic: 18E9 VL CDR3

<400> SEQUENCE: 56

Gln Gln Ala Asn Ser Phe Pro Ser Thr
1               5

<210> SEQ ID NO 57
<211> LENGTH: 120
<212> TYPE: PRT
<213> ORGANISM: Artificial Sequence
<220> FEATURE:
<223> OTHER INFORMATION: Synthetic: 18E9 VH

<400> SEQUENCE: 57

Glu Val Gln Leu Val Gln Ser Gly Gly Gly Leu Val His Pro Gly Gly
1               5                   10                  15

Ser Leu Arg Leu Ser Cys Ala His Ser Gly Phe Thr Phe Thr Ser Ser
            20                  25                  30

Ala Met His Trp Val Arg Gln Ala Pro Gly Lys Gly Leu Glu Trp Ile
        35                  40                  45

Ser Ala Ile Gly Thr Gly Gly Asp Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Ile Asn Ser Leu Arg Ala Glu Asp Met Ala Val Tyr Tyr Cys Ala
                85                  90                  95

Arg Asp Phe Tyr Asp Ile Leu Thr Gly Ile Phe Asp Tyr Trp Gly Gln
            100                 105                 110

Gly Thr Leu Val Thr Val Ser Ser
        115                 120

<210> SEQ ID NO 58
<211> LENGTH: 107
<212> TYPE: PRT
<213> ORGANISM: Artificial Sequence
<220> FEATURE:
<223> OTHER INFORMATION: Synthetic: 18E9 VL

<400> SEQUENCE: 58

Asp Ile Gln Met Thr Gln Ser Pro Ser Ser Val Ser Ala Ser Val Gly
```

```
            1               5                  10                  15
Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ser
                    85                  90                  95

Thr Phe Gly Gln Gly Thr Lys Val Glu Ile Lys
                100                 105

<210> SEQ ID NO 59
<211> LENGTH: 5
<212> TYPE: PRT
<213> ORGANISM: Artificial Sequence
<220> FEATURE:
<223> OTHER INFORMATION: Synthetic: 8B11 VH CDR1

<400> SEQUENCE: 59

Ser Asp Ala Met Tyr
1               5

<210> SEQ ID NO 60
<211> LENGTH: 16
<212> TYPE: PRT
<213> ORGANISM: Artificial Sequence
<220> FEATURE:
<223> OTHER INFORMATION: Synthetic: 8B11 VH CDR2

<400> SEQUENCE: 60

Ala Ile Gly Ile Gly Gly Asp Thr Tyr Tyr Thr Asp Ser Val Met Gly
1               5                  10                  15

<210> SEQ ID NO 61
<211> LENGTH: 9
<212> TYPE: PRT
<213> ORGANISM: Artificial Sequence
<220> FEATURE:
<223> OTHER INFORMATION: Synthetic: 8B11 VH CDR3

<400> SEQUENCE: 61

Leu Gly Met Gly Tyr Tyr Phe Asp Tyr
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic: 8B11 VL CDR1

<400> SEQUENCE: 62

Arg Ala Ser Gln Ser Val Ser Ser Tyr Leu Ala
1               5                  10

<210> SEQ ID NO 63
<211> LENGTH: 7
<212> TYPE: PRT
<213> ORGANISM: Artificial Sequence
<220> FEATURE:
<223> OTHER INFORMATION: Synthetic: 8B11 VL CDR2
```

-continued

<400> SEQUENCE: 63

Asp Ala Ser Asn Arg Ala Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic: 8B11 VL CDR3

<400> SEQUENCE: 64

Gln Gln Arg Ser Asn Trp Pro Pro Thr
1               5

<210> SEQ ID NO 65
<211> LENGTH: 136
<212> TYPE: PRT
<213> ORGANISM: Artificial Sequence
<220> FEATURE:
<223> OTHER INFORMATION: Synthetic: 8B11 VH

<400> SEQUENCE: 65

Met Glu Phe Val Leu Ser Trp Val Phe Leu Val Ala Ile Leu Lys Gly
1               5                   10                  15

Val Gln Cys Glu Ile Gln Leu Val Gln Ser Gly Gly Gly Leu Val His
            20                  25                  30

Pro Gly Gly Ser Leu Arg Leu Ser Cys Ala Gly Ser Gly Phe Thr Phe
        35                  40                  45

Ser Ser Asp Ala Met Tyr Trp Val Arg Gln Ala Pro Gly Lys Gly Leu
    50                  55                  60

Glu Trp Val Ser Ala Ile Gly Ile Gly Gly Asp Thr Tyr Tyr Thr Asp
65                  70                  75                  80

Ser Val Met Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Met Gly Tyr Tyr Phe Asp Tyr Trp Gly Gln
        115                 120                 125

Gly Thr Leu Val Thr Val Ser Ser
    130                 135

<210> SEQ ID NO 66
<211> LENGTH: 107
<212> TYPE: PRT
<213> ORGANISM: Artificial Sequence
<220> FEATURE:
<223> OTHER INFORMATION: Synthetic: 8B11 VL

<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
                65                  70                  75                  80
Glu Asp Phe Ala Val Tyr Tyr Cys Gln Gln Arg Ser Asn Trp Pro Pro
                    85                  90                  95

Thr Phe Gly Gln Gly Thr Lys Val Glu Ile Lys
            100                 105
```

<210> SEQ ID NO 67
<211> LENGTH: 5
<212> TYPE: PRT
<213> ORGANISM: Artificial Sequence
<220> FEATURE:
<223> OTHER INFORMATION: Synthetic: 20B3 VH CDR1

<400> SEQUENCE: 67

```
Ser Tyr Asp Met His
1               5
```

<210> SEQ ID NO 68
<211> LENGTH: 16
<212> TYPE: PRT
<213> ORGANISM: Artificial Sequence
<220> FEATURE:
<223> OTHER INFORMATION: Synthetic: 20B3 VH CDR2

<400> SEQUENCE: 68

```
Val Ile Gly Thr Ala Gly Asp Thr Tyr Tyr Pro Gly Ser Val Lys Gly
1               5                   10                  15
```

<210> SEQ ID NO 69
<211> LENGTH: 9
<212> TYPE: PRT
<213> ORGANISM: Artificial Sequence
<220> FEATURE:
<223> OTHER INFORMATION: Synthetic: 20B3 VH CDR3

<400> SEQUENCE: 69

```
Gly Gly Met Gly Asn Tyr Phe Asp Tyr
1               5
```

<210> SEQ ID NO 70
<211> LENGTH: 11
<212> TYPE: PRT
<213> ORGANISM: Artificial Sequence
<220> FEATURE:
<223> OTHER INFORMATION: Synthetic: 20B3 VL CDR1

<400> SEQUENCE: 70

```
Arg Ala Ser Gln Ser Val Ser Ser Tyr Leu Ala
1               5                   10
```

<210> SEQ ID NO 71
<211> LENGTH: 7
<212> TYPE: PRT
<213> ORGANISM: Artificial Sequence
<220> FEATURE:
<223> OTHER INFORMATION: Synthetic: 20B3 VL CDR2

<400> SEQUENCE: 71

```
Asp Ala Ser Asn Arg Ala Thr
1               5
```

<210> SEQ ID NO 72
<211> LENGTH: 9
<212> TYPE: PRT
<213> ORGANISM: Artificial Sequence
<220> FEATURE:

<223> OTHER INFORMATION: Synthetic: 20B3 VL CDR3

<400> SEQUENCE: 72

Gln Gln Arg Ser Asn Trp Pro Leu Thr
1               5

<210> SEQ ID NO 73
<211> LENGTH: 117
<212> TYPE: PRT
<213> ORGANISM: Artificial Sequence
<220> FEATURE:
<223> OTHER INFORMATION: Synthetic: 20B3 VH

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Thr Thr Gly Lys Gly Leu Glu Trp Val
        35                  40                  45

Ser Val Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Met Gly Asn Tyr Phe Asp Tyr Trp Gly Gln Gly Thr Leu
            100                 105                 110

Val Thr Val Ser Ser
        115

<210> SEQ ID NO 74
<211> LENGTH: 107
<212> TYPE: PRT
<213> ORGANISM: Artificial Sequence
<220> FEATURE:
<223> OTHER INFORMATION: Synthetic: 20B3 VL

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 75
<211> LENGTH: 5
<212> TYPE: PRT
<213> ORGANISM: Artificial Sequence
<220> FEATURE:
<223> OTHER INFORMATION: Synthetic: 14A2 VH CDR1

```
<400> SEQUENCE: 75

Asn Tyr Ala Leu His
1               5

<210> SEQ ID NO 76
<211> LENGTH: 17
<212> TYPE: PRT
<213> ORGANISM: Artificial Sequence
<220> FEATURE:
<223> OTHER INFORMATION: Synthetic: 14A2 VH CDR2

<400> SEQUENCE: 76

Leu Ile Ser Tyr Asp Gly Ser Arg Lys His Tyr Ala Asp Ser Val Lys
1               5                   10                  15
Gly

<210> SEQ ID NO 77
<211> LENGTH: 8
<212> TYPE: PRT
<213> ORGANISM: Artificial Sequence
<220> FEATURE:
<223> OTHER INFORMATION: Synthetic: 14A2 VH CDR3

<400> SEQUENCE: 77

Leu Thr Met Val Arg Glu Gly Gly
1               5

<210> SEQ ID NO 78
<211> LENGTH: 12
<212> TYPE: PRT
<213> ORGANISM: Artificial Sequence
<220> FEATURE:
<223> OTHER INFORMATION: Synthetic: 14A2 VL1 CDR1

<400> SEQUENCE: 78

Arg Ala Ser Gln Ser Val Ser Ser Ser Tyr Leu Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Synthetic: 14A2 VL1 CDR2

<400> SEQUENCE: 79

Gly Ala Ser Ser Arg Ala Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic: 14A2 VL1 CDR3

<400> SEQUENCE: 80

Gln Gln Tyr Gly Ser Ser Pro Phe Thr
1               5

<210> SEQ ID NO 81
<211> LENGTH: 11
<212> TYPE: PRT
<213> ORGANISM: Artificial Sequence
<220> FEATURE:
```

<223> OTHER INFORMATION: Synthetic: 14A2 VL2 CDR1

<400> SEQUENCE: 81

Arg Val Ser Gln Gly Ile Ser Ser Tyr Leu Asn
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic: 14A2 VL2 CDR2

<400> SEQUENCE: 82

Ser Ala Ser Asn Leu Gln Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic: 14A2 VL2 CDR3

<400> SEQUENCE: 83

Gln Arg Thr Tyr Asn Ala Pro Tyr Thr
1               5

<210> SEQ ID NO 84
<211> LENGTH: 115
<212> TYPE: PRT
<213> ORGANISM: Artificial Sequence
<220> FEATURE:
<223> OTHER INFORMATION: Synthetic: 14A2 VH

<400> SEQUENCE: 84

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Met Val Arg Glu Gly Gly Gln Gly Thr Leu Val Thr
            100                 105                 110

Val Ser Ser
        115

<210> SEQ ID NO 85
<211> LENGTH: 108
<212> TYPE: PRT
<213> ORGANISM: Artificial Sequence
<220> FEATURE:
<223> OTHER INFORMATION: Synthetic: 14A2 VL1

<400> SEQUENCE: 85

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Synthetic: 14A2 VL2

<400> SEQUENCE: 86

Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
            20                  25                  30

Leu Asn Trp Tyr Arg Gln Lys Pro Gly Lys Val Pro Lys Leu Leu Ile
            35                  40                  45

Tyr Ser Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro Tyr
                85                  90                  95

Thr Phe Gly Gly Gly Thr Lys Val Glu Ile Lys
            100                 105

<210> SEQ ID NO 87
<211> LENGTH: 5
<212> TYPE: PRT
<213> ORGANISM: Artificial Sequence
<220> FEATURE:
<223> OTHER INFORMATION: Synthetic: 20C1 VH CDR1

<400> SEQUENCE: 87

Ser Tyr Ala Met Tyr
1               5

<210> SEQ ID NO 88
<211> LENGTH: 16
<212> TYPE: PRT
<213> ORGANISM: Artificial Sequence
<220> FEATURE:
<223> OTHER INFORMATION: Synthetic: 20C1 VH CDR2

<400> SEQUENCE: 88

Ala Ile Asp Thr Asp Gly Gly Thr Phe Tyr Ala Asp Ser Val Arg Gly
1               5                   10                  15

<210> SEQ ID NO 89
<211> LENGTH: 9

```
<212> TYPE: PRT
<213> ORGANISM: Artificial Sequence
<220> FEATURE:
<223> OTHER INFORMATION: Synthetic: 20C1 VH CDR3

<400> SEQUENCE: 89

Leu Gly Glu Gly Tyr Phe Phe Asp Tyr
1               5

<210> SEQ ID NO 90
<211> LENGTH: 11
<212> TYPE: PRT
<213> ORGANISM: Artificial Sequence
<220> FEATURE:
<223> OTHER INFORMATION: Synthetic: 20C1 VL CDR1

<400> SEQUENCE: 90

Arg Ala Ser Gln Ser Val Ser Ser Tyr Leu Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Synthetic: 20C1 VL CDR2

<400> SEQUENCE: 91

Asp Ala Ser Asn Arg Ala Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic: 20C1 VL CDR3

<400> SEQUENCE: 92

Gln Gln Arg Ser Asn Trp Pro Pro Thr
1               5

<210> SEQ ID NO 93
<211> LENGTH: 117
<212> TYPE: PRT
<213> ORGANISM: Artificial Sequence
<220> FEATURE:
<223> OTHER INFORMATION: Synthetic: 20C1 VH

<400> SEQUENCE: 93

Glu Ala Gln Leu Val Gln Ser Gly Gly Gly Leu Val His Pro Gly Gly
1               5                   10                  15

Ser Leu Arg Leu Ser Cys Ala Asp Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Gly Gly Thr Phe Tyr Ala Asp Ser Val Arg
    50                  55                  60

Gly Arg Phe Thr Ile Ser Arg Asp Asn Ala Lys Asn Ser Leu Tyr Leu
65                  70                  75                  80

Gln Met Asn Gly Leu Arg Ala Glu Asp Met Ala Val Tyr Phe Cys Ala
                85                  90                  95

Arg Leu Gly Glu Gly Tyr Phe Phe Asp Tyr Trp Gly Gln Gly Thr Leu
            100                 105                 110
```

```
Val Thr Val Ser Ser
        115

<210> SEQ ID NO 94
<211> LENGTH: 107
<212> TYPE: PRT
<213> ORGANISM: Artificial Sequence
<220> FEATURE:
<223> OTHER INFORMATION: Synthetic: 20C1 VL

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gly Gly Thr Lys Val Glu Ile Lys
            100                 105

<210> SEQ ID NO 95
<211> LENGTH: 446
<212> TYPE: PRT
<213> ORGANISM: Artificial Sequence
<220> FEATURE:
<223> OTHER INFORMATION: Synthetic: OX40.6 heavy chain

<400> SEQUENCE: 95

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ser Ala Ile Gly Ile Gly Gly Asp Thr Phe Tyr Thr Asp Ser Val Lys
    50                  55                  60

Gly Arg Phe Thr Ile Ser Arg Asp Asn Ala Lys Asn Ser Leu Ser Leu
65                  70                  75                  80

Gln Met Asn Ser Leu Arg Ala Glu Asp Thr Ala Val Tyr Tyr Cys Ala
                85                  90                  95

Arg Met Gly Thr Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
                180                 185                 190
Leu Gly Thr Gln Thr Tyr Ile Cys Asn Val Asn His Lys Pro Ser Asn
                195                 200                 205
Thr Lys Val Asp Lys Arg Val Glu Pro Lys Ser Cys Asp Lys Thr His
                210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
                290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly
            435                 440                 445

<210> SEQ ID NO 96
<211> LENGTH: 214
<212> TYPE: PRT
<213> ORGANISM: Artificial Sequence
<220> FEATURE:
<223> OTHER INFORMATION: Synthetic: OX40.6 light chain

<400> SEQUENCE: 96

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Leu
                85                  90                  95
Thr Phe Gly Pro Gly Thr Lys Val Asp Ile Lys Arg Thr Val Ala Ala
```

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 97
<211> LENGTH: 446
<212> TYPE: PRT
<213> ORGANISM: Artificial Sequence
<220> FEATURE:
<223> OTHER INFORMATION: Synthetic: OX40.7 heavy chain

<400> SEQUENCE: 97

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ser Ala Ile Gly Ile Gly Gly Asp Thr Phe Tyr Thr Asp Ser Val Lys
    50                  55                  60

Gly Arg Phe Thr Ile Ser Arg Asp Asn Ala Lys Asn Ser Leu Ser Leu
65                  70                  75                  80

Gln Met Asn Ser Leu Arg Ala Glu Asp Thr Ala Val Tyr Tyr Cys Ala
                85                  90                  95

Arg Tyr Gly Thr Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                    245                 250                 255
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 98
<211> LENGTH: 214
<212> TYPE: PRT
<213> ORGANISM: Artificial Sequence
<220> FEATURE:
<223> OTHER INFORMATION: Synthetic: OX40.7 light chain

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 99
<211> LENGTH: 444
<212> TYPE: PRT
<213> ORGANISM: Artificial Sequence
<220> FEATURE:
<223> OTHER INFORMATION: Synthetic: OX40.8 heavy chain

<400> SEQUENCE: 99

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Met Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
                305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 100
<211> LENGTH: 215
<212> TYPE: PRT
<213> ORGANISM: Artificial Sequence
<220> FEATURE:
<223> OTHER INFORMATION: Synthetic: OX40.8 light chain

<400> SEQUENCE: 100

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
            210                 215
```

-continued

```
<210> SEQ ID NO 101
<211> LENGTH: 444
<212> TYPE: PRT
<213> ORGANISM: Artificial Sequence
<220> FEATURE:
<223> OTHER INFORMATION: Synthetic: OX40.9 heavy chain

<400> SEQUENCE: 101
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Tyr Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln

```
                 370                 375                 380
Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 102
<211> LENGTH: 215
<212> TYPE: PRT
<213> ORGANISM: Artificial Sequence
<220> FEATURE:
<223> OTHER INFORMATION: Synthetic: OX40.9 light chain

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 103
<211> LENGTH: 444
<212> TYPE: PRT
<213> ORGANISM: Artificial Sequence
<220> FEATURE:
<223> OTHER INFORMATION: Synthetic: OX40.10 heavy chain

<400> SEQUENCE: 103

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
            35                  40                  45

Ala Leu Ile Ser Tyr Ser Gly Ser Arg Lys His Tyr Ala Asp Ser Val
            50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Leu Thr Met Val Arg Glu Gly Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly

<210> SEQ ID NO 104
<211> LENGTH: 215
<212> TYPE: PRT
<213> ORGANISM: Artificial Sequence
<220> FEATURE:
<223> OTHER INFORMATION: Synthetic: OX40.10 light chain

<400> SEQUENCE: 104

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 105
<211> LENGTH: 444
<212> TYPE: PRT
<213> ORGANISM: Artificial Sequence
<220> FEATURE:
<223> OTHER INFORMATION: Synthetic: OX40.11 heavy chain

<400> SEQUENCE: 105

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Ser Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Ser Leu Thr Met Val Arg Glu Gly Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 106
<211> LENGTH: 215
<212> TYPE: PRT
<213> ORGANISM: Artificial Sequence
<220> FEATURE:
<223> OTHER INFORMATION: Synthetic: OX40.11 light chain

<400> SEQUENCE: 106
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 107
<211> LENGTH: 444
<212> TYPE: PRT
<213> ORGANISM: Artificial Sequence
<220> FEATURE:
<223> OTHER INFORMATION: Synthetic: OX40.12 heavy chain

<400> SEQUENCE: 107

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Ser Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Met Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
    435                 440

<210> SEQ ID NO 108
<211> LENGTH: 215
<212> TYPE: PRT
<213> ORGANISM: Artificial Sequence
<220> FEATURE:
<223> OTHER INFORMATION: Synthetic: OX40.12 light chain

<400> SEQUENCE: 108

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 109
<211> LENGTH: 444
<212> TYPE: PRT
<213> ORGANISM: Artificial Sequence
<220> FEATURE:
<223> OTHER INFORMATION: Synthetic: OX40.13 heavy chain

<400> SEQUENCE: 109

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Ser Ser Arg Lys His Tyr Ala Asp Ser Val
    50                  55                  60

Lys Gly Arg Phe Ser Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Ser Leu Thr Met Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

```
Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 110
<211> LENGTH: 215
<212> TYPE: PRT
<213> ORGANISM: Artificial Sequence
<220> FEATURE:
<223> OTHER INFORMATION: Synthetic: OX40.13 light chain

<400> SEQUENCE: 110

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
            115                 120                 125
```

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 111
<211> LENGTH: 444
<212> TYPE: PRT
<213> ORGANISM: Artificial Sequence
<220> FEATURE:
<223> OTHER INFORMATION: Synthetic: OX40.14 heavy chain

<400> SEQUENCE: 111

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Ala Leu His Trp Val Arg Gln Ala Pro Gly Lys Gly Leu Glu Trp Val
            35                  40                  45

Ala Leu Ile Ser Tyr Ser Gly Ser Arg Lys His Tyr Ala Asp Ser Val
50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Tyr Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

```
Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 112
<211> LENGTH: 215
<212> TYPE: PRT
<213> ORGANISM: Artificial Sequence
<220> FEATURE:
<223> OTHER INFORMATION: Synthetic: OX40.14 light chain

<400> SEQUENCE: 112

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 113
<211> LENGTH: 444
<212> TYPE: PRT
<213> ORGANISM: Artificial Sequence
<220> FEATURE:
<223> OTHER INFORMATION: Synthetic: OX40.15 heavy chain

<400> SEQUENCE: 113

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Tyr Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

```
Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 114
<211> LENGTH: 215
<212> TYPE: PRT
<213> ORGANISM: Artificial Sequence
<220> FEATURE:
<223> OTHER INFORMATION: Synthetic: OX40.15 light chain

<400> SEQUENCE: 114

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 115
<211> LENGTH: 446
<212> TYPE: PRT
<213> ORGANISM: Artificial Sequence
<220> FEATURE:
```

<223> OTHER INFORMATION: Synthetic: OX40.16 heavy chain

<400> SEQUENCE: 115

```
Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Gly Thr Phe Tyr Ala Asp Ser Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 116
<211> LENGTH: 214
<212> TYPE: PRT
<213> ORGANISM: Artificial Sequence
<220> FEATURE:
<223> OTHER INFORMATION: Synthetic: OX40.16 light chain (shared by
      OX40.20, OX40.21, OX40.22)

<400> SEQUENCE: 116

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 117
<211> LENGTH: 446
<212> TYPE: PRT
<213> ORGANISM: Artificial Sequence
<220> FEATURE:
<223> OTHER INFORMATION: Synthetic: OX40.17 heavy chain

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Thr Thr Gly Lys Gly Leu Glu Trp Val
```

```
            35                  40                  45
Ser Val Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Gly Gly Met Gly Asn Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 118
```

```
<211> LENGTH: 214
<212> TYPE: PRT
<213> ORGANISM: Artificial Sequence
<220> FEATURE:
<223> OTHER INFORMATION: Synthetic: OX40.17 light chain

<400> SEQUENCE: 118

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 119
<211> LENGTH: 449
<212> TYPE: PRT
<213> ORGANISM: Artificial Sequence
<220> FEATURE:
<223> OTHER INFORMATION: Synthetic: OX40.18 heavy chain

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Ser Ser Ser Tyr Asn Trp Phe Asp Tyr Trp Gly Gln
```

```
            100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 120
<211> LENGTH: 214
<212> TYPE: PRT
<213> ORGANISM: Artificial Sequence
<220> FEATURE:
<223> OTHER INFORMATION: Synthetic: OX40.18 light chain

<400> SEQUENCE: 120

Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 444
<212> TYPE: PRT
<213> ORGANISM: Artificial Sequence
<220> FEATURE:
<223> OTHER INFORMATION: Synthetic: OX40.19 heavy chain

<400> SEQUENCE: 121

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Ala Leu His Trp Val Arg Gln Ala Pro Gly Lys Gly Leu Glu Trp Val
            35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Leu Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 122
<211> LENGTH: 215
<212> TYPE: PRT
<213> ORGANISM: Artificial Sequence
<220> FEATURE:
<223> OTHER INFORMATION: Synthetic: OX40.19 light chain

<400> SEQUENCE: 122

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 123
<211> LENGTH: 446
<212> TYPE: PRT
<213> ORGANISM: Artificial Sequence
<220> FEATURE:
<223> OTHER INFORMATION: Synthetic: OX40.20 heavy chain

<400> SEQUENCE: 123

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
                20                  25                  30

Ala Met Tyr Trp Val Arg Gln Ala Pro Gly Lys Gly Leu Glu Trp Val
            35                  40                  45

Ser Ala Ile Asp Thr Ser Gly Gly Thr Phe Tyr Ala Asp Ser Val Arg
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220
```

```
Thr Cys Pro Pro Cys Pro Ala Pro Glu Leu Leu Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 124
<211> LENGTH: 446
<212> TYPE: PRT
<213> ORGANISM: Artificial Sequence
<220> FEATURE:
<223> OTHER INFORMATION: Synthetic: OX40.21 heavy chain

<400> SEQUENCE: 124

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Ala Gly Thr Phe Tyr Ala Asp Ser Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 125
<211> LENGTH: 446
<212> TYPE: PRT
<213> ORGANISM: Artificial Sequence
<220> FEATURE:
<223> OTHER INFORMATION: Synthetic: OX40.22 heavy chain

<400> SEQUENCE: 125

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Ser Thr Gly Thr Phe Tyr Ala Asp Ser Val Arg
    50                  55                  60

```
Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Phe Cys Ala
                 85                  90                  95

Arg Leu Gly Glu Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 126
<211> LENGTH: 360
<212> TYPE: DNA
<213> ORGANISM: Artificial Sequence
<220> FEATURE:
```

<223> OTHER INFORMATION: Synthetic: 3F4 VH (nucleotide sequence)

<400> SEQUENCE: 126

```
caggtgcagc tggtgcagtc tggggctgag gtgaagaagc ctggggcctc agtgaaggtc      60
tcctgcaagg cttctggaaa caccttcacc agttatgatg tcaactgggt gcgacaggcc     120
actggacaag gcttgagtg gatgggatgg atgaacccta acagtggtaa cacaggctat      180
gcaccgaagt tccagggcag agtcaccatg accaggaaca cctccataag cacagcctac     240
atggagctga gcagcctgag atctgaggac acggccgttt attactgtgc gagaatatat     300
agcagctcgt acaactggtt cgaccctgg ggccagggaa ccctggtcac cgtctcctca      360
```

<210> SEQ ID NO 127
<211> LENGTH: 321
<212> TYPE: DNA
<213> ORGANISM: Artificial Sequence
<220> FEATURE:
<223> OTHER INFORMATION: Synthetic: 3F4 VL

<400> SEQUENCE: 127

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggcgga     300
gggaccaagg tggagatcaa a                                                321
```

<210> SEQ ID NO 128
<211> LENGTH: 354
<212> TYPE: DNA
<213> ORGANISM: Artificial Sequence
<220> FEATURE:
<223> OTHER INFORMATION: Synthetic: 14B6 VH

<400> SEQUENCE: 128

```
gaggtgcagc tggagcagtc tggagcagag gtgaaaaagc ccggggagtc tctgaagatc      60
tcctgtaagg gttctggata cagctttacc agcaactgga tcggctgggt gcgccagatg     120
cccgggaaag gcctggagtg gatggggttc atctatcctg gtgactctga taccaggtac     180
agcccgtcct ccaaggcca ggtcaccatc tcagccgaca gtccatcag caccgcctac      240
ctgcagtgga gcagcctcaa ggcctcggac atcgccatgt attactgtgc gagatatggg     300
gatgactggt acttcgatct ctggggccgt ggcaccctgg tcactgtctc ctca           354
```

<210> SEQ ID NO 129
<211> LENGTH: 321
<212> TYPE: DNA
<213> ORGANISM: Artificial Sequence
<220> FEATURE:
<223> OTHER INFORMATION: Synthetic: 14B6 VL1

<400> SEQUENCE: 129

```
gaaattgtgt tgacacagtc tccagccacc ctgtctttgt ctccagggga aagagccacc      60
ctctcctgca gggccagtca gagtgttagc agctacttag cctggttcca acagagacct     120
ggccaggctc ccaggctcct catctatgat gcatccaaca gggccactgg catcccagcc     180
aggttcagtg gcagtgggtc tgggacagac ttctctctca ccatcagcag cctagagcct     240
gaagattttg cagtttatta ctgtcagcag cgtggcgact ggcccatcac cttcggccaa     300
```

```
gggacacgac tggagattaa a                                             321
```

<210> SEQ ID NO 130
<211> LENGTH: 324
<212> TYPE: DNA
<213> ORGANISM: Artificial Sequence
<220> FEATURE:
<223> OTHER INFORMATION: Synthetic: 14B6 VL2

<400> SEQUENCE: 130

```
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt accctcggat caccttcggc   300
caagggacac gactggagat taaa                                          324
```

<210> SEQ ID NO 131
<211> LENGTH: 351
<212> TYPE: DNA
<213> ORGANISM: Artificial Sequence
<220> FEATURE:
<223> OTHER INFORMATION: Synthetic: 23H3 VH

<400> SEQUENCE: 131

```
gaggttcagc tggtgcagtc tggggggaggc ttggtacatc ctgggggggtc cctgagactc   60
tcctgtgcag gctctggatt caccttcagt aactatgcta tgtactgggt tcgccaggct  120
ccaggaaaag gtctggagtg ggtatcagcc attggtattg gtggtgacac attctataca  180
gactccgtga agggccgatt caccatctcc agagacaatg ccaagaactc cttgtctctt  240
caaatgaaca gcctgagagc cgaggacatg gctgtgtatt actgtgcaag aatgggaact  300
gggtacttct ttgactactg gggccaggga accctggtca ccgtctcctc a            351
```

<210> SEQ ID NO 132
<211> LENGTH: 321
<212> TYPE: DNA
<213> ORGANISM: Artificial Sequence
<220> FEATURE:
<223> OTHER INFORMATION: Synthetic: 23H3 VL

<400> SEQUENCE: 132

```
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggccct   300
gggaccaaag tggatatcaa a                                             321
```

<210> SEQ ID NO 133
<211> LENGTH: 363
<212> TYPE: DNA
<213> ORGANISM: Artificial Sequence
<220> FEATURE:
<223> OTHER INFORMATION: Synthetic: 6E1 VH

<400> SEQUENCE: 133

```
caggtgcagc tggtggagtc tggggggaggc gtggtccagc ctgggaggtc cctgagactc      60
tcctgtgcag cctctggatt caccttcagt agctttgcta tgcactgggt ccgccaggct     120
ccaggcaagg ggctggagtg ggtgacagtt atttcatatg atggaagcat aaatactac      180 acagactccg tgaagggccg attcaccttc tccagagaca attccaagaa cactctgtat     240
ctgcaaatga acagcctgag agctgaggac acggctgtgt attactgtac gagagatgga     300
aactatggtt cggcgagata cttccagcac tggggccagg gcaccctggt caccgtctcc     360
tca                                                                    363

<210> SEQ ID NO 134
<211> LENGTH: 321
<212> TYPE: DNA
<213> ORGANISM: Artificial Sequence
<220> FEATURE:
<223> OTHER INFORMATION: Synthetic: 6E1 VL1

<400> SEQUENCE: 134
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt accctcggac gttcggccaa     300
gggaccaagg tggaaatcaa a                                                321

<210> SEQ ID NO 135
<211> LENGTH: 321
<212> TYPE: DNA
<213> ORGANISM: Artificial Sequence
<220> FEATURE:
<223> OTHER INFORMATION: Synthetic: 6E1 VL2

<400> SEQUENCE: 135
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgtacac ttttggccag     300
gggaccaagc tggagatcaa a                                                321

<210> SEQ ID NO 136
<211> LENGTH: 360
<212> TYPE: DNA
<213> ORGANISM: Artificial Sequence
<220> FEATURE:
<223> OTHER INFORMATION: Synthetic: 18E9 VH

<400> SEQUENCE: 136
gaggttcagc tggtgcagtc tggggggaggc ttggttcatc ctgggggggtc cctgagactc     60 tcctgtgcac actctggatt caccttcact agctctgcta tgcactgggt tcgccaggct    120
ccaggaaaag gtctggaatg gatatcagct attggtactg gtggtgacac atactatgca    180
gactccgtga agggccgatt caccatctcc agagacaatg ccaagaactc cttgtatctt    240
caaataaaca gcctgagagc cgaggacatg gctgtatatt actgtgcaag agacttttac    300
gatattttga ctggtatctt tgactactgg ggccagggaa ccctggtcac cgtctcctca    360
```

<210> SEQ ID NO 137
<211> LENGTH: 321
<212> TYPE: DNA
<213> ORGANISM: Artificial Sequence
<220> FEATURE:
<223> OTHER INFORMATION: Synthetic: 18E9 VL

<400> SEQUENCE: 137

```
gacatccaga tgacccagtc tccatcttcc gtgtctgcat ctgtaggaga cagagtcacc      60
atcacttgtc gggcgagtca gggtattagc agctggttag cctggtatca gcataaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaatagtt tcccttcgac gttcggccaa    300
gggaccaagg tggaaatcaa a                                              321
```

<210> SEQ ID NO 138
<211> LENGTH: 408
<212> TYPE: DNA
<213> ORGANISM: Artificial Sequence
<220> FEATURE:
<223> OTHER INFORMATION: Synthetic: 8B11 VH

<400> SEQUENCE: 138

```
atggagtttg tgctgagctg ggttttcctt gttgctatat taaaaggtgt ccagtgtgaa      60
attcagctgg tgcagtctgg gggaggcttg gtacatcctg gggggtccct gagactctcc    120
tgtgcaggct ctggattcac cttcagtagc gatgctatgt actgggttcg ccaggctcca    180
ggaaaaggtc tggagtgggt atcagctatt ggtattggtg gtgacacata ctatacagac    240
tccgtgatgg gccgattcac catctccaga gacaatgcca agaactcctt gtatcttcaa    300
atgaacagcc tgagagccga ggacatggct gtgtattact gtgcaaggct ggggatgggg    360
tactactttg actactgggg ccagggaacc ctggtcaccg tctcctca                 408
```

<210> SEQ ID NO 139
<211> LENGTH: 321
<212> TYPE: DNA
<213> ORGANISM: Artificial Sequence
<220> FEATURE:
<223> OTHER INFORMATION: Synthetic: 8B11 VL

<400> SEQUENCE: 139

```
gaaattgtgt tgacacagtc tccagccacc ctgtctttgt ctccagggga aagagccacc      60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgac gttcggccaa    300
gggaccaagg tggaaatcaa a                                              321
```

<210> SEQ ID NO 140
<211> LENGTH: 351
<212> TYPE: DNA
<213> ORGANISM: Artificial Sequence
<220> FEATURE:
<223> OTHER INFORMATION: Synthetic: 20B3 VH

<400> SEQUENCE: 140

```
gaggtgcagc tggtggagtc tggggaggc ttggtacagc ctggggggtc cctgagactc      60
tcctgtgcag cctctggatt caccttcagt agctacgaca tgcactgggt ccgccaaact     120
acaggaaaag gtctggagtg gtctcagtt attggtactg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag agggggatg     300 gggaactact ttgactactg gggccaggga accctggtca ccgtctcctc a             351
```

<210> SEQ ID NO 141
<211> LENGTH: 321
<212> TYPE: DNA
<213> ORGANISM: Artificial Sequence
<220> FEATURE:
<223> OTHER INFORMATION: Synthetic: 20B3 VL

<400> SEQUENCE: 141

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggccgctcac tttcggcgga     300
gggaccaagg tggagatcaa a                                                321
```

<210> SEQ ID NO 142
<211> LENGTH: 345
<212> TYPE: DNA
<213> ORGANISM: Artificial Sequence
<220> FEATURE:
<223> OTHER INFORMATION: Synthetic: 14A2 VH

<400> SEQUENCE: 142

```
caggtgcagc tggtggagtc tggggaggc gtggtccagc ctggggaggtc cctgagactc      60 tcctgtgcag cctctggatt caccttcagt aactatgctc tgcactgggt ccgccaggct     120
ccaggcaagg ggctggagtg gtggcactt atatcatatg atggaagcag gaaacactac     180
gcagactccg tgaagggccg attcagtatc tccagagaca attccaagaa cacactgtat     240
ctgcaaatga acagcctgag agctgaggac acggctgtgt attactgtgc gagtcttact     300
atggttcggg aggggggcca gggaaccctg gtcaccgtct cctca                     345
```

<210> SEQ ID NO 143
<211> LENGTH: 324
<212> TYPE: DNA
<213> ORGANISM: Artificial Sequence
<220> FEATURE:
<223> OTHER INFORMATION: Synthetic: 14A2 VL1

<400> SEQUENCE: 143

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccatt cactttcggc     300
cctgggacca aagtggatat caaa                                             324
```

```
<210> SEQ ID NO 144
<211> LENGTH: 321
<212> TYPE: DNA
<213> ORGANISM: Artificial Sequence
<220> FEATURE:
<223> OTHER INFORMATION: Synthetic: 14A2 VL2

<400> SEQUENCE: 144
gacatccagt tgacccagtc tccatcctcc ctgtctgcat ctgtaggaga cagagtcacc      60
atcacttgcc gggtgagtca gggcattagc agttatttaa attggtatcg gcagaaacca     120
gggaaagttc ctaagctcct gatctatagt gcatccaatt tgcaatctgg agtcccatct     180
cggttcagtg gcagtggatc tgggacagat ttcactctca ctatcagcag cctgcagcct     240
gaagatgttg caacttatta cggtcaacgg acttacaatg ccccttacac tttcggcgga     300
gggaccaagg tggagatcaa a                                               321

<210> SEQ ID NO 145
<211> LENGTH: 351
<212> TYPE: DNA
<213> ORGANISM: Artificial Sequence
<220> FEATURE:
<223> OTHER INFORMATION: Synthetic: 20C1 VH

<400> SEQUENCE: 145
gaggctcagc tggtgcagtc tggggggaggc ttggttcatc ctgggggtc cctgagactc      60 tcctgtgcag actctggatt caccttcagt agctatgcta tgtactgggt tcgccaggct     120
ccaggaaaag gtctggagtg gtatcagct attgatactg atggtggcac attctatgca     180
gactccgtgc ggggccgatt caccatctcc agagacaatg ccaagaactc cttgtatctt     240
caaatgaacg gcctgagagc cgaggacatg gctgtgtatt tctgtgcaag acttggggaa     300
gggtacttct ttgactactg ggccaggga accctggtca ccgtctcctc a               351

<210> SEQ ID NO 146
<211> LENGTH: 321
<212> TYPE: DNA
<213> ORGANISM: Artificial Sequence
<220> FEATURE:
<223> OTHER INFORMATION: Synthetic: 20C1 VL

<400> SEQUENCE: 146
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccac tttcggcgga     300 gggaccaagg tggagatcaa a                                               321

<210> SEQ ID NO 147
<211> LENGTH: 1338
<212> TYPE: DNA
<213> ORGANISM: Artificial Sequence
<220> FEATURE:
<223> OTHER INFORMATION: Synthetic: OX40.6 heavy chain

<400> SEQUENCE: 147
gaggttcagc tggtgcagtc tggggggaggc ttggtacagc ctgggggtc cctgagactc      60 tcctgtgcag gctctggatt caccttcagt aactatgcta tgtactgggt tcgccaggct    120
```

| | |
|---|---|
| ccaggaaaag gtctggagtg ggtatcagcc attggtattg gtggtgacac attctataca | 180 |
| gactccgtga agggccgatt caccatctcc agagacaatg ccaagaactc cttgtctctt | 240 |
| caaatgaaca gcctgagagc cgaggacacg gctgtgtatt actgtgcaag aatgggaact | 300 |
| gggtacttct ttgactactg gggccaggga accctggtca ccgtctcctc agctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga gagttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| ggcagccccg agaaccacag gtgtacaccc tgcccccat ccgggagga tgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta tagcaagctc accgtggaca agagcaggtg gcagcagggg | 1260 |
| aacgtcttct catgctccgt gatgcatgag gctctgcaca accactacac gcagaagagc | 1320 |
| ctctccctgt ccccgggt | 1338 |

<210> SEQ ID NO 148
<211> LENGTH: 642
<212> TYPE: DNA
<213> ORGANISM: Artificial Sequence
<220> FEATURE:
<223> OTHER INFORMATION: Synthetic: OX40.6 light chain

<400> SEQUENCE: 148

| | |
|---|---|
| gaaattgtgt tgacacagtc tccagccacc ctgtctttgt ctccagggga aagagccacc | 60 |
| ctctcctgca gggccagtca gagtgttagc agctacttag cctggtacca acagaaacct | 120 |
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg cagtttatta ctgtcagcag cgtagcaact ggcctctcac tttcggccct | 300 |
| gggaccaaag tggatatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 149
<211> LENGTH: 1338
<212> TYPE: DNA
<213> ORGANISM: Artificial Sequence

```
<220> FEATURE:
<223> OTHER INFORMATION: Synthetic: OX40.7 heavy chain

<400> SEQUENCE: 149
gaggttcagc tggtgcagtc tggggggaggc ttggtacatc ctgggggggtc cctgagactc      60
tcctgtgcag gctctggatt caccttcagt aactatgcta tgtactgggt tcgccaggct     120
ccaggaaaag gtctggagtg ggtatcagcc attggtattg gtggtgacac attctataca     180
gactccgtga agggccgatt caccatctcc agagacaatg ccaagaactc cttgtctctt     240
caaatgaaca gcctgagagc cgaggacacg gctgtgtatt actgtgcaag atatggaact     300
gggtacttct ttgactactg gggccaggga accctggtca ccgtctcctc agctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga gagttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ccccgggt                                                   1338

<210> SEQ ID NO 150
<211> LENGTH: 642
<212> TYPE: DNA
<213> ORGANISM: Artificial Sequence
<220> FEATURE:
<223> OTHER INFORMATION: Synthetic: OX40.7 light chain

<400> SEQUENCE: 150
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggccct     300
gggaccaaag tggatatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg     540
```

```
ctgagcaaag cagactacga aaacacaaa gtctacgcct gcgaagtcac ccatcagggc      600
ctgagctcgc ccgtcacaaa gagcttcaac aggggagagt gt                        642

<210> SEQ ID NO 151
<211> LENGTH: 1332
<212> TYPE: DNA
<213> ORGANISM: Artificial Sequence
<220> FEATURE:
<223> OTHER INFORMATION: Synthetic: OX40.8 heavy chain

<400> SEQUENCE: 151
caggtgcagc tggtggagtc tgggggaggc gtggtccagc ctgggaggtc cctgagactc       60
tcctgtgcag cctctggatt caccttcagt aactatgctc tgcactgggt ccgccaggct      120
ccaggcaagg gctggagtg gtggcactt atatcatatg atggaagcag aaacactac         180 gcagactccg tgaagggccg attcagtatc tccagagaca attccaagaa cacactgtat      240
ctgcaaatga acagcctgag agctgaggac acggctgtgt attactgtgc gagtcttact      300
atggttcggg agtggggcca gggaaccctg gtcaccgtct cctcagctag caccaagggc      360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagagagttg agcccaaatc ttgtgacaaa      660
actcacacat gcccaccgtg cccagcacct gaactcctgg ggggaccgtc agtcttcctc      720
ttccccccaa aacccaagga caccctcatg atctcccgga cccctgaggt cacatgcgtg      780
gtggtggacg tgagccacga agaccctgag gtcaagttca actggtacgt ggacggcgtg      840
gaggtgcata atgccaagac aaagccgcgg gaggagcagt acaacagcac gtaccgtgtg      900
gtcagcgtcc tcaccgtcct gcaccaggac tggctgaatg gcaaggagta caagtgcaag      960
gtctccaaca agccctccc agccccatc gagaaaacca tctccaaagc caaagggcag      1020 cccgagaac acaggtgta caccctgccc ccatcccggg aggagatgac caagaaccag      1080
gtcagcctga cctgcctggt caaaggcttc tatcccagcg acatcgccgt ggagtgggag      1140
agcaatgggc agccggagaa caactacaag accacgcctc ccgtgctgga ctccgacggc      1200
tccttcttcc tctatagcaa gctcaccgtg gacaagagca ggtggcagca ggggaacgtc      1260
ttctcatgct ccgtgatgca tgaggctctg cacaaccact acacgcagaa gagcctctcc      1320
ctgtccccgg gt                                                         1332

<210> SEQ ID NO 152
<211> LENGTH: 645
<212> TYPE: DNA
<213> ORGANISM: Artificial Sequence
<220> FEATURE:
<223> OTHER INFORMATION: Synthetic: OX40.8 light chain

<400> SEQUENCE: 152
gaaattgtgt tgacgcagtc tccaggcacc ctgtctttgt ctccagggga aagagccacc       60
ctctcctgca gggccagtca gagtgttagc agcagctact tagcctggta ccagcagaaa      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcaccatt cactttcggc      300
```

```
cctgggacca aagtggatat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac  aaagtctacg cctgcgaagt cacccatcag    600
ggcctgagct cgcccgtcac aaagagcttc aacaggggag agtgt                    645

<210> SEQ ID NO 153
<211> LENGTH: 1332
<212> TYPE: DNA
<213> ORGANISM: Artificial Sequence
<220> FEATURE:
<223> OTHER INFORMATION: Synthetic: OX40.9 heavy chain

<400> SEQUENCE: 153
caggtgcagc tggtggagtc tgggggaggc gtggtccagc ctgggaggtc cctgagactc     60
tcctgtgcag cctctggatt caccttcagt aactatgctc tgcactgggt ccgccaggct    120
ccaggcaagg ggctggagtg ggtggcactt atatcatatg atggaagcag gaaacactac    180
gcagactccg tgaagggccg attcagtatc tccagagaca attccaagaa cacactgtat    240
ctgcaaatga acagcctgag agctgaggac acggctgtgt attactgtgc gagtcttact    300
tacgttcggg agtggggcca gggaaccctg gtcaccgtct cctcagctag caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
ccccgagaac cacaggtgta caccctgccc ccatcccggg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtccccgg gt                                                       1332

<210> SEQ ID NO 154
<211> LENGTH: 645
<212> TYPE: DNA
<213> ORGANISM: Artificial Sequence
<220> FEATURE:
<223> OTHER INFORMATION: Synthetic: OX40.9 light chain

<400> SEQUENCE: 154
```

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccatt cactttcggc     300
cctgggacca agtggatat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgt                     645
```

<210> SEQ ID NO 155
<211> LENGTH: 1332
<212> TYPE: DNA
<213> ORGANISM: Artificial Sequence
<220> FEATURE:
<223> OTHER INFORMATION: Synthetic: OX40.10 heavy chain

<400> SEQUENCE: 155

```
caggtgcagc tggtggagtc tgggggaggc gtggtccagc ctgggaggtc cctgagactc      60
tcctgtgcag cctctggatt caccttcagt aactatgctc tgcactgggt ccgccaggct     120
ccaggcaagg ggctggagtg ggtggcactt atatcatata gtggaagcag aaaacactac     180
gcagactccg tgaagggccg attcagtatc tccagagaca attccaagaa cacactgtat     240
ctgcaaatga acagcctgag agctgaggac acggctgtgt attactgtgc gagtcttact     300
atggttcggg agggggggcca gggaaccctg gtcaccgtct cctcagctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaactcctgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccggg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtccccgg gt                                                       1332
```

<210> SEQ ID NO 156
<211> LENGTH: 645
<212> TYPE: DNA
<213> ORGANISM: Artificial Sequence
<220> FEATURE:
<223> OTHER INFORMATION: Synthetic: OX40.10 light chain

<400> SEQUENCE: 156

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccatt cactttcggc     300
cctgggacca agtggatat caaacgtacg gtggctgcac catctgtctt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag      600
ggcctgagct cgcccgtcac aaagagcttc aacaggggag agtgt                    645
```

<210> SEQ ID NO 157
<211> LENGTH: 1332
<212> TYPE: DNA
<213> ORGANISM: Artificial Sequence
<220> FEATURE:
<223> OTHER INFORMATION: Synthetic: OX40.11 heavy chain

<400> SEQUENCE: 157

```
caggtgcagc tggtggagtc tgggggaggc gtggtccagc ctggagggtc cctgagactc      60
tcctgtgcag cctctggatt caccttcagt aactatgctc tgcactgggt ccgccaggct     120
ccaggcaagg ggctggagtg ggtggcactt atatcatatg atagtagcag gaaacactac     180
gcagactccg tgaagggccg attcagtatc tccagagaca attccaagaa cacactgtat     240
ctgcaaatga acagcctgag agctgaggac acggctgtgt attactgtgc gagtcttact     300
atggttcggg agggggggcca gggaaccctg gtcaccgtct cctcagctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaactcctgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccggg aggagatgac caagaaccag    1080
gtcagcctga cctgcctggt caaaggcttc tatcccagcg acatcgccgt ggagtgggag    1140
```

```
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtccccgg gt                                                        1332

<210> SEQ ID NO 158
<211> LENGTH: 645
<212> TYPE: DNA
<213> ORGANISM: Artificial Sequence
<220> FEATURE:
<223> OTHER INFORMATION: Synthetic: OX40.11 light chain

<400> SEQUENCE: 158
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccatt cactttcggc     300
cctgggacca aagtggatat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt                    645

<210> SEQ ID NO 159
<211> LENGTH: 1332
<212> TYPE: DNA
<213> ORGANISM: Artificial Sequence
<220> FEATURE:
<223> OTHER INFORMATION: Synthetic: OX40.12 heavy chain

<400> SEQUENCE: 159
caggtgcagc tggtggagtc tgggggaggc gtggtccagc ctgggaggtc cctgagactc      60
tcctgtgcag cctctggatt caccttcagt aactatgctc tgcactgggt ccgccaggct    120
ccaggcaagg ggctggagtg ggtggcactt atatcatata gtggaagcag gaaacactac    180
gcagactccg tgaagggccg attcagtatc tccagagaca attccaagaa cacactgtat    240
ctgcaaatga acagcctgag agctgaggac acggctgtgt attactgtgc gagtcttact    300
atggttcggg agtggggcca gggaaccctg gtcaccgtct cctcagctag caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
```

```
gtcagcgtcc tcaccgtcct gcaccaggac tggctgaatg gcaaggagta caagtgcaag    960
gtctccaaca aagccctccc agcccccatc gagaaaacca tctccaaagc caagggcag    1020 ccccgagaac acaggtgta caccctgccc ccatcccggg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
ctgtccccgg gt                                                        1332
```

<210> SEQ ID NO 160
<211> LENGTH: 645
<212> TYPE: DNA
<213> ORGANISM: Artificial Sequence
<220> FEATURE:
<223> OTHER INFORMATION: Synthetic: OX40.12 light chain

<400> SEQUENCE: 160

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccatt cactttcggc    300
cctgggacca aagtggatat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 161
<211> LENGTH: 1332
<212> TYPE: DNA
<213> ORGANISM: Artificial Sequence
<220> FEATURE:
<223> OTHER INFORMATION: Synthetic: OX40.13 heavy chain

<400> SEQUENCE: 161

```
caggtgcagc tggtggagtc tgggggaggc gtggtccagc ctgggaggtc cctgagactc     60
tcctgtgcag cctctggatt caccttcagt aactatgctc tgcactgggt ccgccaggct    120
ccaggcaagg gctggagtg gtggcactt atatcatatg atagtagcag aaacactac    180 gcagactccg tgaagggccg attcagtatc tccagagaca attccaagaa cacactgtat    240
ctgcaaatga acagcctgag agctgaggac acggctgtgt attactgtgc gagtcttact    300
atggttcggg agtggggcca gggaaccctg gtcaccgtct cctcagctag caccaagggc    360
ccatcggtct tcccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
```

```
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa acccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020 cccccgagaac cacaggtgta caccctgccc ccatcccggg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtccccgg gt                                                        1332
```

<210> SEQ ID NO 162
<211> LENGTH: 645
<212> TYPE: DNA
<213> ORGANISM: Artificial Sequence
<220> FEATURE:
<223> OTHER INFORMATION: Synthetic: OX40.13 light chain

<400> SEQUENCE: 162

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccatt cactttcggc    300
cctgggacca agtggatat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 163
<211> LENGTH: 1332
<212> TYPE: DNA
<213> ORGANISM: Artificial Sequence
<220> FEATURE:
<223> OTHER INFORMATION: Synthetic: OX40.14 heavy chain

<400> SEQUENCE: 163

```
caggtgcagc tggtggagtc tgggggaggc gtggtccagc ctgggaggtc cctgagactc     60
tcctgtgcag cctctggatt caccttcagt aactatgctc tgcactgggt ccgccaggct    120
ccaggcaagg ggctggagtg ggtggcactt atatcatata gtggaagcag aaacactac    180 gcagactccg tgaagggccg attcagtatc tccagagaca attccaagaa cacactgtat    240
ctgcaaatga acagcctgag agctgaggac acggctgtgt attactgtgc gagtcttact    300
tacgttcggg agtgggggcca gggaaccctg gtcaccgtct cctcagctag caccaagggc    360
```

```
ccatcggtct tcccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
ccccgagaac cacaggtgta caccctgccc ccatcccggg aggagatgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctatagcaa gctcaccgtg gacaagagca ggtggcagca ggggaacgtc   1260
ttctcatgct ccgtgatgca tgaggctctg cacaaccact acacgcagaa gagcctctcc   1320
ctgtccccgg gt                                                        1332

<210> SEQ ID NO 164
<211> LENGTH: 645
<212> TYPE: DNA
<213> ORGANISM: Artificial Sequence
<220> FEATURE:
<223> OTHER INFORMATION: Synthetic: OX40.14 light chain

<400> SEQUENCE: 164
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccatt cactttcggc    300
cctgggacca agtggatat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg cctccaatc gggtaactcc    480 caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                    645

<210> SEQ ID NO 165
<211> LENGTH: 1332
<212> TYPE: DNA
<213> ORGANISM: Artificial Sequence
<220> FEATURE:
<223> OTHER INFORMATION: Synthetic: OX40.15 heavy chain

<400> SEQUENCE: 165
caggtgcagc tggtggagtc tgggggaggc gtggtccagc ctgggaggtc cctgagactc     60
```

| | |
|---|---|
| tcctgtgcag cctctggatt caccttcagt aactatgctc tgcactgggt ccgccaggct | 120 |
| ccaggcaagg ggctggagtg ggtggcactt atatcatatg atagtagcag gaaacactac | 180 |
| gcagactccg tgaagggccg attcagtatc tccagagaca attccaagaa cacactgtat | 240 |
| ctgcaaatga acagcctgag agctgaggac acggctgtgt attactgtgc gagtcttact | 300 |
| tacgttcggg agtgggggcca gggaaccctg gtcaccgtct cctcagctag caccaagggc | 360 |
| ccatcggtct tccccctggc accctcctcc aagagcacct ctgggggcac agcggccctg | 420 |
| ggctgcctgg tcaaggacta cttccccgaa ccggtgacgg tgtcgtggaa ctcaggcgcc | 480 |
| ctgaccagcg gcgtgcacac cttcccggct gtcctacagt cctcaggact ctactccctc | 540 |
| agcagcgtgg tgaccgtgcc ctccagcagc ttgggcaccc agacctacat ctgcaacgtg | 600 |
| aatcacaagc ccagcaacac caaggtggac aagagagttg agcccaaatc ttgtgacaaa | 660 |
| actcacacat gcccaccgtg cccagcacct gaactcctgg ggggaccgtc agtcttcctc | 720 |
| ttccccccaa aacccaagga caccctcatg atctcccgga cccctgaggt cacatgcgtg | 780 |
| gtggtggacg tgagccacga agaccctgag gtcaagttca actggtacgt ggacggcgtg | 840 |
| gaggtgcata atgccaagac aaagccgcgg gaggagcagt acaacagcac gtaccgtgtg | 900 |
| gtcagcgtcc tcaccgtcct gcaccaggac tggctgaatg gcaaggagta caagtgcaag | 960 |
| gtctccaaca aagccctccc agcccccatc gagaaaacca tctccaaagc caaagggcag | 1020 |
| ccccgagaac cacaggtgta caccctgccc ccatcccggg aggagatgac caagaaccag | 1080 |
| gtcagcctga cctgcctggt caaaggcttc tatcccagcg acatcgccgt ggagtgggag | 1140 |
| agcaatgggc agccggagaa caactacaag accacgcctc ccgtgctgga ctccgacggc | 1200 |
| tccttcttcc tctatagcaa gctcaccgtg gacaagagca ggtggcagca ggggaacgtc | 1260 |
| ttctcatgct ccgtgatgca tgaggctctg cacaaccact acacgcagaa gagcctctcc | 1320 |
| ctgtccccgg gt | 1332 |

<210> SEQ ID NO 166
<211> LENGTH: 645
<212> TYPE: DNA
<213> ORGANISM: Artificial Sequence
<220> FEATURE:
<223> OTHER INFORMATION: Synthetic: OX40.15 light chain

<400> SEQUENCE: 166

| | |
|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcaccatt cactttcggc | 300 |
| cctgggacca aagtggatat caaacgtacg gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaagtctacg cctgcgaagt cacccatcag | 600 |
| ggcctgagct cgcccgtcac aaagagcttc aacaggggag agtgt | 645 |

<210> SEQ ID NO 167
<211> LENGTH: 1341

```
<212> TYPE: DNA
<213> ORGANISM: Artificial Sequence
<220> FEATURE:
<223> OTHER INFORMATION: Synthetic: OX40.16 heavy chain

<400> SEQUENCE: 167
gaggttcagc tggtgcagtc tgggggaggc ttggttcagc ctggggggtc cctgagactc      60
tcctgtgcag gctctggatt caccttcagt agctatgcta tgtactgggt tcgccaggct     120
ccaggaaaag gtctggagtg gtatcagct attgatactg atggtggcac attctatgca     180
gactccgtgc ggggccgatt caccatctcc agagacaatg ccaagaactc cttgtatctt     240
caaatgaaca gcctgagagc cgaggacacg gctgtgtatt tctgtgcaag acttggggaa     300
gggtacttct ttgactactg gggccaggga accctggtca ccgtctcctc agctagcacc     360
aagggcccat cggtcttccc cctggcaccc tcctccaaga gcacctctgg ggcacagcg      420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga gagttgagcc caaatcttgt     660
gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ccccgggttg a                                              1341

<210> SEQ ID NO 168
<211> LENGTH: 645
<212> TYPE: DNA
<213> ORGANISM: Artificial Sequence
<220> FEATURE:
<223> OTHER INFORMATION: Synthetic: OX40.16 light chain (shared by
      OX40.20, OX40.21, OX40.22)

<400> SEQUENCE: 168
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccac tttcggcgga     300
gggaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
```

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 169
<211> LENGTH: 1341
<212> TYPE: DNA
<213> ORGANISM: Artificial Sequence
<220> FEATURE:
<223> OTHER INFORMATION: Synthetic: OX40.17 heavy chain

<400> SEQUENCE: 169

```
gaggtgcagc tggtggagtc tgggggaggc ttggtacagc ctggggggtc cctgagactc     60
tcctgtgcag cctctggatt caccttcagt agctacgaca tgcactgggt ccgccaaact    120
acaggaaaag gtctggagtg ggtctcagtt attggtactg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag agggggggatg    300 gggaactact ttgactactg gggccaggga accctggtca ccgtctcctc agctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctggggggg accgtcagtc    720 ttcctcttcc cccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca gagcaggtg gcagcagggg    1260 aacgtcttct catgctccgt gatgcatgag gctctgcaca accactacac gcagaagagc    1320
ctctccctgt ccccgggttg a                                              1341
```

<210> SEQ ID NO 170
<211> LENGTH: 645
<212> TYPE: DNA
<213> ORGANISM: Artificial Sequence
<220> FEATURE:
<223> OTHER INFORMATION: Synthetic: OX40.17 light chain

<400> SEQUENCE: 170

```
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
```

```
aggttcagtg gcagtgggtc tgggacagac ttcactctca ccatcagcag cctagagcct      240
gaagattttg cagtttatta ctgtcagcag cgtagcaact ggccgctcac tttcggcgga      300
gggaccaagg tggagatcaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttag                      645

<210> SEQ ID NO 171
<211> LENGTH: 1350
<212> TYPE: DNA
<213> ORGANISM: Artificial Sequence
<220> FEATURE:
<223> OTHER INFORMATION: Synthetic: OX40.18 heavy chain

<400> SEQUENCE: 171
caggtgcagc tggtgcagtc tggggctgag gtgaagaagc ctggggcctc agtgaaggtc       60
tcctgcaagg cttctggata caccttcacc agttatgatg tcaactgggt gcgacaggcc      120
actggacaag gcttgagtg gatgggatgg atgaacccta acagtggtaa cacaggctat      180
gcaccgaagt tccagggcag agtcaccatg accaggaca cctccataag cacagcctac      240
atggagctga gcagcctgag atctgaggac acggccgttt attactgtgc gagaatatat      300
agcagctcgt acaactggtt cgactactgg ggccagggaa ccctggtcac cgtctcctca      360
gctagcacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagag agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag gcagccccg agaaccacag gtgtacaccc tgcccccatc ccgggaggag     1080
atgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctat agcaagctca ccgtggacaa gagcaggtgg     1260
cagcagggga acgtcttctc atgctccgtg atgcatgagg ctctgcacaa ccactacacg     1320
cagaagagcc tctccctgtc cccgggttga                                      1350

<210> SEQ ID NO 172
<211> LENGTH: 645
<212> TYPE: DNA
<213> ORGANISM: Artificial Sequence
<220> FEATURE:
<223> OTHER INFORMATION: Synthetic: OX40.18 light chain
```

<400> SEQUENCE: 172

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggcgga     300
gggaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645
```

<210> SEQ ID NO 173
<211> LENGTH: 1332
<212> TYPE: DNA
<213> ORGANISM: Artificial Sequence
<220> FEATURE:
<223> OTHER INFORMATION: Synthetic: OX40.19 heavy chain

<400> SEQUENCE: 173

```
caggtgcagc tggtggagtc tgggggaggc gtggtccagc ctgggaggtc cctgagactc      60
tcctgtgcag cctctggatt caccttcagt aactatgctc tgcactgggt ccgccaggct     120
ccaggcaagg ggctggagtg ggtggcactt atatcatatg atggaagcag gaaacactac     180
gcagactccg tgaagggccg attcagtatc tccagagaca attccaagaa cacactgtat     240
ctgcaaatga acagcctgag agctgaggac acggctgtgt attactgtgc gagtcttact     300
ctggttcggg agtggggcca gggaaccctg gtcaccgtct cctcagctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
actcacacat gcccaccgtg cccagcacct gaactcctgg ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc agcccccatc gagaaaacca tctccaaagc caaagggcag    1020
ccccgagaac cacaggtgta caccctgccc ccatcccggg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctatagcaa gctcaccgtg gacaagagca ggtggcagca ggggaacgtc    1260
ttctcatgct ccgtgatgca tgaggctctg cacaaccact acacgcagaa gagcctctcc    1320
```

| | |
|---|---|
| ctgtccccgg gt | 1332 |

<210> SEQ ID NO 174
<211> LENGTH: 645
<212> TYPE: DNA
<213> ORGANISM: Artificial Sequence
<220> FEATURE:
<223> OTHER INFORMATION: Synthetic: OX40.19 light chain

<400> SEQUENCE: 174

| | |
|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcaccatt cactttcggc | 300 |
| cctgggacca aagtggatat caaacgtacg gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaagtctacg cctgcgaagt cacccatcag | 600 |
| ggcctgagct cgcccgtcac aaagagcttc aacaggggag agtgt | 645 |

<210> SEQ ID NO 175
<211> LENGTH: 1341
<212> TYPE: DNA
<213> ORGANISM: Artificial Sequence
<220> FEATURE:
<223> OTHER INFORMATION: Synthetic: OX40.20 heavy chain

<400> SEQUENCE: 175

| | |
|---|---|
| gaggttcagc tggtgcagtc tggggggaggc ttggttcagc ctggggggtc cctgagactc | 60 |
| tcctgtgcag gctctggatt caccttcagt agctatgcta tgtactgggt tcgccaggct | 120 |
| ccaggaaaag gtctggagtg ggtatcagct attgatacta gtggtggcac attctatgca | 180 |
| gactccgtgc ggggccgatt caccatctcc agagacaatg ccaagaactc cttgtatctt | 240 |
| caaatgaaca gcctgagagc cgaggacacg gctgtgtatt tctgtgcaag acttggggaa | 300 |
| gggtacttct ttgactactg gggccaggga accctggtca ccgtctcctc agctagcacc | 360 |
| aagggcccat cggtcttccc cctggcaccc tcctccaaga gcacctctgg ggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga gagttgagcc caaatcttgt | 660 |
| gacaaaactc acacatgccc accgtgccca gcacctgaac tcctgggggg accgtcagtc | 720 |
| ttcctcttcc cccaaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |

```
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ccccgggttg a                                              1341
```

<210> SEQ ID NO 176  
<211> LENGTH: 1341  
<212> TYPE: DNA  
<213> ORGANISM: Artificial Sequence  
<220> FEATURE:  
<223> OTHER INFORMATION: Synthetic: OX40.21 heavy chain

<400> SEQUENCE: 176

```
gaggttcagc tggtgcagtc tgggggaggc ttggttcagc ctgggggtc cctgagactc      60 tcctgtgcag gctctggatt caccttcagt agctatgcta tgtactgggt tcgccaggct    120
ccaggaaaag gtctggagtg ggtatcagct attgatactg atgctggcac attctatgca    180
gactccgtgc ggggccgatt caccatctcc agagacaatg ccaagaactc cttgtatctt    240
caaatgaaca gcctgagagc cgaggacacg gctgtgtatt tctgtgcaag acttggggaa    300
gggtacttct ttgactactg gggccaggga accctggtca ccgtctcctc agctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc cccaaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaccatctc aaagccaaa    1020 ggcagcccc gagaaccaca ggtgtacacc ctgcccccat cccgggagga tgaccaag    1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ccccgggttg a                                              1341
```

<210> SEQ ID NO 177  
<211> LENGTH: 1341  
<212> TYPE: DNA  
<213> ORGANISM: Artificial Sequence  
<220> FEATURE:  
<223> OTHER INFORMATION: Synthetic: OX40.22 heavy chain

<400> SEQUENCE: 177

```
gaggttcagc tggtgcagtc tgggggaggc ttggttcagc ctgggggtc cctgagactc      60
```

```
tcctgtgcag gctctggatt caccttcagt agctatgcta tgtactgggt tcgccaggct    120
ccaggaaaag gtctggagtg ggtatcagct attgatacta gtactggcac attctatgca    180
gactccgtgc ggggccgatt caccatctcc agagacaatg ccaagaactc cttgtatctt    240
caaatgaaca gcctgagagc cgaggacacg gctgtgtatt tctgtgcaag acttggggaa    300
gggtacttct ttgactactg gggccaggga accctggtca ccgtctcctc agctagcacc    360
aagggcccat cggtcttccc cctggcaccc tcctccaaga gcacctctgg ggcacagcg    420 gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag     1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta tagcaagctc accgtggaca agagcaggtg gcagcagggg    1260
aacgtcttct catgctccgt gatgcatgag gctctgcaca accactacac gcagaagagc    1320
ctctccctgt ccccgggttg a                                              1341
```

<210> SEQ ID NO 178
<211> LENGTH: 17
<212> TYPE: PRT
<213> ORGANISM: Artificial Sequence
<220> FEATURE:
<223> OTHER INFORMATION: Synthetic: hOX40 epitope

<400> SEQUENCE: 178

Asp Val Val Ser Ser Lys Pro Cys Lys Pro Cys Thr Trp Cys Asn Leu
1               5                   10                  15

Arg

<210> SEQ ID NO 179
<211> LENGTH: 36
<212> TYPE: PRT
<213> ORGANISM: Artificial Sequence
<220> FEATURE:
<223> OTHER INFORMATION: Synthetic: hOX40 epitope

<400> SEQUENCE: 179

Asp Ser Tyr Lys Pro Gly Val Asp Cys Ala Pro Cys Pro Pro Gly His
1               5                   10                  15

Phe Ser Pro Gly Asp Asn Gln Ala Cys Lys Pro Trp Thr Asn Cys Thr
            20                  25                  30

Leu Ala Gly Lys
        35

```
<210> SEQ ID NO 180
<211> LENGTH: 5
<212> TYPE: PRT
<213> ORGANISM: Artificial Sequence
<220> FEATURE:
<223> OTHER INFORMATION: Synthetic: peptide linker

<400> SEQUENCE: 180

Pro Val Gly Val Val
1               5

<210> SEQ ID NO 181
<211> LENGTH: 5
<212> TYPE: PRT
<213> ORGANISM: Artificial Sequence
<220> FEATURE:
<223> OTHER INFORMATION: Synthetic: sortase A recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 181

Leu Pro Xaa Thr Gly
1               5

<210> SEQ ID NO 182
<211> LENGTH: 31
<212> TYPE: PRT
<213> ORGANISM: Artificial Sequence
<220> FEATURE:
<223> OTHER INFORMATION: Synthetic: hOX40 epitope

<400> SEQUENCE: 182

Gln Asn Thr Val Cys Arg Pro Cys Gly Pro Gly Phe Tyr Asn Asp Val
1               5                   10                  15

Val Ser Ser Lys Pro Cys Lys Pro Cys Thr Trp Cys Asn Leu Arg
                20                  25                  30

<210> SEQ ID NO 183
<211> LENGTH: 11
<212> TYPE: PRT
<213> ORGANISM: Artificial Sequence
<220> FEATURE:
<223> OTHER INFORMATION: Synthetic: hOX40 epitope

<400> SEQUENCE: 183

Pro Cys Lys Pro Cys Thr Trp Cys Asn Leu Arg
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Synthetic: hOX40 epitope

<400> SEQUENCE: 184

Gln Leu Cys Thr Ala Thr Gln Asp Thr Val Cys Arg
1               5                   10

<210> SEQ ID NO 185
<211> LENGTH: 15
<212> TYPE: PRT
<213> ORGANISM: Artificial Sequence
<220> FEATURE:
<223> OTHER INFORMATION: Synthetic: hOX40 epitope
```

```
<400> SEQUENCE: 185

Ser Gln Asn Thr Val Cys Arg Pro Cys Gly Pro Gly Phe Tyr Asn
1               5                   10                  15

<210> SEQ ID NO 186
<211> LENGTH: 5
<212> TYPE: PRT
<213> ORGANISM: Artificial Sequence
<220> FEATURE:
<223> OTHER INFORMATION: Synthetic: IgG1 C-termianl CH1 (same for IgG3
      (17-15-15-15), igG3 (17-15-15), IgG3 (17-15), IgG3 (15-15-15),
      IgG3 (15), and IgG4

<400> SEQUENCE: 186

Val Asp Lys Arg Val
1               5

<210> SEQ ID NO 187
<211> LENGTH: 5
<212> TYPE: PRT
<213> ORGANISM: Artificial Sequence
<220> FEATURE:
<223> OTHER INFORMATION: Synthetic: IgG2 C-terminal CH1

<400> SEQUENCE: 187

Val Asp Lys Thr Val
1               5

<210> SEQ ID NO 188
<211> LENGTH: 10
<212> TYPE: PRT
<213> ORGANISM: Artificial Sequence
<220> FEATURE:
<223> OTHER INFORMATION: Synthetic: IgG1 upper hinge

<400> SEQUENCE: 188

Glu Pro Lys Ser Cys Asp Lys Thr His Thr
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Synthetic: IgG3 (17-15-15-15) upper hinge
      (same for IgG3 (17-15-15) and IgG3 (17-15))

<400> SEQUENCE: 189

Glu Leu Lys Thr Pro Leu Gly Asp Thr Thr His Thr
1               5                   10

<210> SEQ ID NO 190
<211> LENGTH: 4
<212> TYPE: PRT
<213> ORGANISM: Artificial Sequence
<220> FEATURE:
<223> OTHER INFORMATION: Synthetic: IgG3 (15-15-15) upper hinge
      (same for IgG3(15))

<400> SEQUENCE: 190

Glu Pro Lys Ser
1

<210> SEQ ID NO 191
<211> LENGTH: 7
<212> TYPE: PRT
<213> ORGANISM: Artificial Sequence
```

```
<220> FEATURE:
<223> OTHER INFORMATION: Synthetic: IgG4 upper hinge

<400> SEQUENCE: 191

Glu Ser Lys Tyr Gly Pro Pro
1               5

<210> SEQ ID NO 192
<211> LENGTH: 5
<212> TYPE: PRT
<213> ORGANISM: Artificial Sequence
<220> FEATURE:
<223> OTHER INFORMATION: Synthetic: IgG1 middle hinge

<400> SEQUENCE: 192

Cys Pro Pro Cys Pro
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic: IgG2 middle hinge

<400> SEQUENCE: 193

Cys Cys Val Glu Cys Pro Pro Cys Pro
1               5

<210> SEQ ID NO 194
<211> LENGTH: 50
<212> TYPE: PRT
<213> ORGANISM: Artificial Sequence
<220> FEATURE:
<223> OTHER INFORMATION: Synthetic: IgG3 (17-15-15-15) middle hinge

<400> SEQUENCE: 194

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
                20                  25                  30

Arg Cys Pro Glu Pro Lys Ser Cys Asp Thr Pro Pro Pro Cys Pro Arg
            35                  40                  45

Cys Pro
    50

<210> SEQ ID NO 195
<211> LENGTH: 35
<212> TYPE: PRT
<213> ORGANISM: Artificial Sequence
<220> FEATURE:
<223> OTHER INFORMATION: Synthetic: IgG3 (17-15-15) middle hinge

<400> SEQUENCE: 195

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
                20                  25                  30

Arg Cys Pro
        35

<210> SEQ ID NO 196
<211> LENGTH: 20
<212> TYPE: PRT
```

```
<213> ORGANISM: Artificial Sequence
<220> FEATURE:
<223> OTHER INFORMATION: Synthetic: IgG3 (17-15) middle hinge

<400> SEQUENCE: 196

Cys Pro Arg Cys Pro Glu Pro Lys Ser Cys Asp Thr Pro Pro Pro Cys
1               5                   10                  15

Pro Arg Cys Pro
            20

<210> SEQ ID NO 197
<211> LENGTH: 41
<212> TYPE: PRT
<213> ORGANISM: Artificial Sequence
<220> FEATURE:
<223> OTHER INFORMATION: Synthetic: IgG3 (15-15-15) middle hinge

<400> SEQUENCE: 197

Cys Asp Thr Pro Pro Pro Cys Pro Arg Cys Pro Glu Pro Lys Ser Cys
1               5                   10                  15

Asp Thr Pro Pro Pro Cys Pro Arg Cys Pro Glu Pro Lys Ser Cys Asp
            20                  25                  30

Thr Pro Pro Cys Pro Arg Cys Pro
        35                  40

<210> SEQ ID NO 198
<211> LENGTH: 11
<212> TYPE: PRT
<213> ORGANISM: Artificial Sequence
<220> FEATURE:
<223> OTHER INFORMATION: Synthetic: IgG3 (15) middle hinge

<400> SEQUENCE: 198

Cys Asp Thr Pro Pro Pro Cys Pro Arg Cys Pro
1               5                   10

<210> SEQ ID NO 199
<211> LENGTH: 5
<212> TYPE: PRT
<213> ORGANISM: Artificial Sequence
<220> FEATURE:
<223> OTHER INFORMATION: Synthetic: IgG4 middle hinge

<400> SEQUENCE: 199

Cys Pro Ser Cys Pro
1               5

<210> SEQ ID NO 200
<211> LENGTH: 7
<212> TYPE: PRT
<213> ORGANISM: Artificial Sequence
<220> FEATURE:
<223> OTHER INFORMATION: Synthetic: IgG1 lower hinge (same for IgG3
      (17-15-15-15), IgG3 (17-15-15), IgG3 (17-15), IgG3 (15-15-15),
      IgG3 (15), and IgG4)

<400> SEQUENCE: 200

Ala Pro Glu Leu Leu Gly Gly
1               5

<210> SEQ ID NO 201
<211> LENGTH: 6
<212> TYPE: PRT
<213> ORGANISM: Artificial Sequence
<220> FEATURE:
<223> OTHER INFORMATION: Synthetic: IgG2 lower hinge
```

<400> SEQUENCE: 201

Ala Pro Pro Val Ala Gly
1               5

<210> SEQ ID NO 202
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: Wildtype human IgG1 CH1

<400> SEQUENCE: 202

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 203
<211> LENGTH: 98
<212> TYPE: PRT
<213> ORGANISM: Homo sapiens
<220> FEATURE:
<221> NAME/KEY: misc_feature
<222> LOCATION: (1)..(98)
<223> OTHER INFORMATION: Wildtype human IgG2 CH1

<400> SEQUENCE: 203

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 204
<211> LENGTH: 103
<212> TYPE: PRT
<213> ORGANISM: Homo sapiens
<220> FEATURE:
<221> NAME/KEY: misc_feature
<222> LOCATION: (1)..(103)
<223> OTHER INFORMATION: Wildtype human IgG1 CH2

<400> SEQUENCE: 204

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys
            100

<210> SEQ ID NO 205
<211> LENGTH: 103
<212> TYPE: PRT
<213> ORGANISM: Homo sapiens
<220> FEATURE:
<221> NAME/KEY: misc_feature
<222> LOCATION: (1)..(103)
<223> OTHER INFORMATION: Wildtype human IgG2 CH2

<400> SEQUENCE: 205

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Phe Arg
    50                  55                  60

Val Val Ser Val Leu Thr Val Val His Gln Asp Trp Leu Asn Gly Lys
65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys
            100

<210> SEQ ID NO 206
<211> LENGTH: 106
<212> TYPE: PRT
<213> ORGANISM: Homo sapiens
<220> FEATURE:
<221> NAME/KEY: misc_feature
<222> LOCATION: (1)..(106)
<223> OTHER INFORMATION: Wildtype human IgG1 CH3

<400> SEQUENCE: 206

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe

```
                    50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                     85                  90                  95

Thr Gln Lys Ser Leu Ser Leu Ser Pro Gly
                100                 105

<210> SEQ ID NO 207
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Wildtype human IgG2 CH3

<400> SEQUENCE: 207

Gly Gln Pro Arg Glu Pro Gln Val Tyr Thr Leu Pro Pro Ser Arg Glu
 1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Met Leu Asp Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                     85                  90                  95

Thr Gln Lys Ser Leu Ser Leu Ser Pro Gly Lys
                100                 105

<210> SEQ ID NO 208
<211> LENGTH: 18
<212> TYPE: PRT
<213> ORGANISM: Artificial Sequence
<220> FEATURE:
<223> OTHER INFORMATION: Synthetic: Alternative hinge

<400> SEQUENCE: 208

Glu Arg Lys Cys Cys Val Glu Cys Pro Pro Cys Pro Ala Pro Pro Val
 1               5                   10                  15

Ala Gly

<210> SEQ ID NO 209
<211> LENGTH: 18
<212> TYPE: PRT
<213> ORGANISM: Artificial Sequence
<220> FEATURE:
<223> OTHER INFORMATION: Synthetic: Alternative hinge

<400> SEQUENCE: 209

Glu Arg Lys Ser Cys Val Glu Cys Pro Pro Cys Pro Ala Pro Pro Val
 1               5                   10                  15

Ala Gly

<210> SEQ ID NO 210
<211> LENGTH: 18
<212> TYPE: PRT
<213> ORGANISM: Artificial Sequence
```

```
<220> FEATURE:
<223> OTHER INFORMATION: Synthetic: Alternative hinge

<400> SEQUENCE: 210

Glu Arg Lys Cys Ser Val Glu Cys Pro Pro Cys Pro Ala Pro Pro Val
1               5                   10                  15

Ala Gly

<210> SEQ ID NO 211
<211> LENGTH: 18
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (4)..(4)
<223> OTHER INFORMATION: Xaa can be any naturally occurring amino acid

<400> SEQUENCE: 211

Glu Arg Lys Xaa Cys Val Glu Cys Pro Pro Cys Pro Ala Pro Pro Val
1               5                   10                  15

Ala Gly

<210> SEQ ID NO 212
<211> LENGTH: 18
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (5)..(5)
<223> OTHER INFORMATION: Xaa can be any naturally occurring amino acid

<400> SEQUENCE: 212

Glu Arg Lys Cys Xaa Val Glu Cys Pro Pro Cys Pro Ala Pro Pro Val
1               5                   10                  15

Ala Gly

<210> SEQ ID NO 213
<211> LENGTH: 19
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (19)..(19)
<223> OTHER INFORMATION: Xaa can be any naturally occurring amino acid

<400> SEQUENCE: 213

Glu Arg Lys Cys Cys Val Glu Cys Pro Pro Cys Pro Ala Pro Pro Val
1               5                   10                  15

Ala Gly Xaa

<210> SEQ ID NO 214
<211> LENGTH: 19
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (19)..(19)
<223> OTHER INFORMATION: Xaa can be any naturally occurring amino acid
```

<400> SEQUENCE: 214

Glu Arg Lys Ser Cys Val Glu Cys Pro Pro Cys Pro Ala Pro Pro Val
1               5                   10                  15

Ala Gly Xaa

<210> SEQ ID NO 215
<211> LENGTH: 19
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (19)..(19)
<223> OTHER INFORMATION: Xaa can be any naturally occurring amino acid

<400> SEQUENCE: 215

Glu Arg Lys Cys Ser Val Glu Cys Pro Pro Cys Pro Ala Pro Pro Val
1               5                   10                  15

Ala Gly Xaa

<210> SEQ ID NO 216
<211> LENGTH: 19
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 216

Glu Arg Lys Xaa Cys Val Glu Cys Pro Pro Cys Pro Ala Pro Pro Val
1               5                   10                  15

Ala Gly Xaa

<210> SEQ ID NO 217
<211> LENGTH: 19
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 217

Glu Arg Lys Cys Xaa Val Glu Cys Pro Pro Cys Pro Ala Pro Pro Val
1               5                   10                  15

Ala Gly Xaa

<210> SEQ ID NO 218
<211> LENGTH: 19
<212> TYPE: PRT
<213> ORGANISM: Artificial Sequence
<220> FEATURE:
<223> OTHER INFORMATION: Synthetic: Alternative hinge

<400> SEQUENCE: 218

Glu Arg Lys Cys Cys Val Glu Cys Pro Pro Cys Pro Ala Pro Glu Leu
1               5                   10                  15

Leu Gly Gly

<210> SEQ ID NO 219
<211> LENGTH: 19
<212> TYPE: PRT
<213> ORGANISM: Artificial Sequence
<220> FEATURE:
<223> OTHER INFORMATION: Synthetic: Alternative hinge

<400> SEQUENCE: 219

Glu Arg Lys Ser Cys Val Glu Cys Pro Pro Cys Pro Ala Pro Glu Leu
1               5                   10                  15

Leu Gly Gly

<210> SEQ ID NO 220
<211> LENGTH: 20
<212> TYPE: PRT
<213> ORGANISM: Artificial Sequence
<220> FEATURE:
<223> OTHER INFORMATION: Synthetic: Alternative hinge

<400> SEQUENCE: 220

Glu Arg Lys Cys Cys Ser Val Glu Cys Pro Pro Cys Pro Ala Pro Glu
1               5                   10                  15

Leu Leu Gly Gly
            20

<210> SEQ ID NO 221
<211> LENGTH: 19
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (4)..(4)
<223> OTHER INFORMATION: Xaa can be any naturally occurring amino acid

<400> SEQUENCE: 221

Glu Arg Lys Xaa Cys Val Glu Cys Pro Pro Cys Pro Ala Pro Glu Leu
1               5                   10                  15

Leu Gly Gly

<210> SEQ ID NO 222
<211> LENGTH: 19
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (5)..(5)
<223> OTHER INFORMATION: Xaa can be any naturally occurring amino acid

<400> SEQUENCE: 222

Glu Arg Lys Cys Xaa Val Glu Cys Pro Pro Cys Pro Ala Pro Glu Leu
1               5                   10                  15

Leu Gly Gly

<210> SEQ ID NO 223

```
<211> LENGTH: 18
<212> TYPE: PRT
<213> ORGANISM: Artificial Sequence
<220> FEATURE:
<223> OTHER INFORMATION: Synthetic: Alternative hinge

<400> SEQUENCE: 223

Glu Arg Lys Cys Cys Val Glu Cys Pro Pro Cys Pro Ala Pro Glu Leu
1               5                   10                  15

Leu Gly

<210> SEQ ID NO 224
<211> LENGTH: 18
<212> TYPE: PRT
<213> ORGANISM: Artificial Sequence
<220> FEATURE:
<223> OTHER INFORMATION: Synthetic: Alternative hinge

<400> SEQUENCE: 224

Glu Arg Lys Ser Cys Val Glu Cys Pro Pro Cys Pro Ala Pro Glu Leu
1               5                   10                  15

Leu Gly

<210> SEQ ID NO 225
<211> LENGTH: 19
<212> TYPE: PRT
<213> ORGANISM: Artificial Sequence
<220> FEATURE:
<223> OTHER INFORMATION: Synthetic: Alternative hinge

<400> SEQUENCE: 225

Glu Arg Lys Cys Cys Ser Val Glu Cys Pro Pro Cys Pro Ala Pro Glu
1               5                   10                  15

Leu Leu Gly

<210> SEQ ID NO 226
<211> LENGTH: 18
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (4)..(4)
<223> OTHER INFORMATION: Xaa can be any naturally occurring amino acid

<400> SEQUENCE: 226

Glu Arg Lys Xaa Cys Val Glu Cys Pro Pro Cys Pro Ala Pro Glu Leu
1               5                   10                  15

Leu Gly

<210> SEQ ID NO 227
<211> LENGTH: 18
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (5)..(5)
<223> OTHER INFORMATION: Xaa can be any naturally occurring amino acid

<400> SEQUENCE: 227

Glu Arg Lys Cys Xaa Val Glu Cys Pro Pro Cys Pro Ala Pro Glu Leu
1               5                   10                  15
```

Leu Gly

```
<210> SEQ ID NO 228
<211> LENGTH: 14
<212> TYPE: PRT
<213> ORGANISM: Artificial Sequence
<220> FEATURE:
<223> OTHER INFORMATION: Synthetic: Alternative hinge

<400> SEQUENCE: 228

Glu Arg Lys Cys Cys Val Glu Cys Pro Pro Cys Pro Ala Pro
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Synthetic: Alternative hinge

<400> SEQUENCE: 229

Glu Arg Lys Ser Cys Val Glu Cys Pro Pro Cys Pro Ala Pro
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Synthetic: Alternative hinge

<400> SEQUENCE: 230

Glu Arg Lys Cys Ser Val Glu Cys Pro Pro Cys Pro Ala Pro
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (4)..(4)
<223> OTHER INFORMATION: Xaa can be any naturally occurring amino acid

<400> SEQUENCE: 231

Glu Arg Lys Xaa Cys Val Glu Cys Pro Pro Cys Pro Ala Pro
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Synthetic: Alternative hinge
<220> FEATURE:
<221> NAME/KEY: misc_feature
<222> LOCATION: (5)..(5)
<223> OTHER INFORMATION: Xaa can be any naturally occurring amino acid

<400> SEQUENCE: 232

Glu Arg Lys Cys Xaa Val Glu Cys Pro Pro Cys Pro Ala Pro
1               5                   10

<210> SEQ ID NO 233
<211> LENGTH: 4
<212> TYPE: PRT
```

```
<213> ORGANISM: Artificial Sequence
<220> FEATURE:
<223> OTHER INFORMATION: Synthetic: Portion of hinge

<400> SEQUENCE: 233

Pro Val Ala Gly
1

<210> SEQ ID NO 234
<211> LENGTH: 4
<212> TYPE: PRT
<213> ORGANISM: Artificial Sequence
<220> FEATURE:
<223> OTHER INFORMATION: Synthetic: Portion of hinge

<400> SEQUENCE: 234

Glu Leu Leu Gly
1

<210> SEQ ID NO 235
<211> LENGTH: 5
<212> TYPE: PRT
<213> ORGANISM: Artificial Sequence
<220> FEATURE:
<223> OTHER INFORMATION: Synthetic: Portion of hinge

<400> SEQUENCE: 235

Glu Leu Leu Gly Gly
1               5

<210> SEQ ID NO 236
<211> LENGTH: 7
<212> TYPE: PRT
<213> ORGANISM: Artificial Sequence
<220> FEATURE:
<223> OTHER INFORMATION: Synthetic: Portion of hinge

<400> SEQUENCE: 236

Ser Cys Asp Lys Thr His Thr
1               5

<210> SEQ ID NO 237
<211> LENGTH: 4
<212> TYPE: PRT
<213> ORGANISM: Artificial Sequence
<220> FEATURE:
<223> OTHER INFORMATION: Synthetic: Portion of hinge

<400> SEQUENCE: 237

Cys Cys Val Glu
1

<210> SEQ ID NO 238
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: WT human IgG2 hinge

<400> SEQUENCE: 238

Glu Arg Lys Cys Cys Val Glu Cys Pro Pro Cys Pro Ala Pro Pro Val
1               5                   10                  15

Ala Gly
```

```
<210> SEQ ID NO 239
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Human IgG2 hinge with C219S

<400> SEQUENCE: 239

Glu Arg Lys Ser Cys Val Glu Cys Pro Pro Cys Pro Ala Pro Pro Val
1               5                   10                  15

Ala Gly

<210> SEQ ID NO 240
<211> LENGTH: 19
<212> TYPE: PRT
<213> ORGANISM: Artificial Sequence
<220> FEATURE:
<223> OTHER INFORMATION: Synthetic: IgG2/IgG1 hinge

<400> SEQUENCE: 240

Glu Arg Lys Cys Cys Val Glu Cys Pro Pro Cys Pro Ala Pro Glu Leu
1               5                   10                  15

Leu Gly Gly

<210> SEQ ID NO 241
<211> LENGTH: 19
<212> TYPE: PRT
<213> ORGANISM: Artificial Sequence
<220> FEATURE:
<223> OTHER INFORMATION: Synthetic: IgG2 (C219S)/IgG1 hinge

<400> SEQUENCE: 241

Glu Arg Lys Ser Cys Val Glu Cys Pro Pro Cys Pro Ala Pro Glu Leu
1               5                   10                  15

Leu Gly Gly

<210> SEQ ID NO 242
<211> LENGTH: 22
<212> TYPE: PRT
<213> ORGANISM: Homo sapiens
<220> FEATURE:
<221> NAME/KEY: misc_feature
<222> LOCATION: (1)..(22)
<223> OTHER INFORMATION: Wild type human IgG1 hinge

<400> SEQUENCE: 242

Glu Pro Lys Ser Cys Asp Lys Thr His Thr Cys Pro Pro Cys Pro Ala
1               5                   10                  15

Pro Glu Leu Leu Gly Gly
                20

<210> SEQ ID NO 243
<211> LENGTH: 103
<212> TYPE: PRT
<213> ORGANISM: Homo sapiens
<220> FEATURE:
<221> NAME/KEY: misc_feature
<222> LOCATION: (1)..(103)
<223> OTHER INFORMATION: Human IgG1 CH2 with A330S/P331S

<400> SEQUENCE: 243

Pro Ser Val Phe Leu Phe Pro Pro Lys Pro Lys Asp Thr Leu Met Ile
1               5                   10                  15
```

```
Ser Arg Thr Pro Glu Val Thr Cys Val Val Asp Val Ser His Glu
         20                  25                  30

Asp Pro Glu Val Lys Phe Asn Trp Tyr Val Asp Gly Val Glu Val His
             35                  40                  45

Asn Ala Lys Thr Lys Pro Arg Glu Glu Gln Tyr Asn Ser Thr Tyr Arg
 50                      55                      60

Val Val Ser Val Leu Thr Val Leu His Gln Asp Trp Leu Asn Gly Lys
 65                  70                  75                  80

Glu Tyr Lys Cys Lys Val Ser Asn Lys Ala Leu Pro Ser Ser Ile Glu
                 85                  90                  95

Lys Thr Ile Ser Lys Ala Lys
                100
```

<210> SEQ ID NO 244
<211> LENGTH: 326
<212> TYPE: PRT
<213> ORGANISM: Artificial Sequence
<220> FEATURE:
<223> OTHER INFORMATION: Synthetic: IgG1-IgG2-IgG1f

<400> SEQUENCE: 244

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Arg Lys Cys Cys Val Glu Cys Pro Pro Cys Pro Ala Pro
                100                 105                 110

Glu Leu Leu Gly Gly Pro Ser Val Phe Leu Phe Pro Pro Lys Pro Lys
             115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 245
<211> LENGTH: 325
<212> TYPE: PRT
<213> ORGANISM: Artificial Sequence
<220> FEATURE:
<223> OTHER INFORMATION: Synthetic: IgG1-IgG2-1gG1f2

<400> SEQUENCE: 245

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
    195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300
```

Ser Val Met His Glu Ala Leu His Asn His Tyr Thr Gln Lys Ser Leu
305                 310                 315                 320

Ser Leu Ser Pro Gly
                325

<210> SEQ ID NO 246
<211> LENGTH: 325
<212> TYPE: PRT
<213> ORGANISM: Artificial Sequence
<220> FEATURE:
<223> OTHER INFORMATION: Synthetic: IgG1-IgG2CS-IgG1f

<400> SEQUENCE: 246

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

```
<210> SEQ ID NO 247
<211> LENGTH: 325
<212> TYPE: PRT
<213> ORGANISM: Artificial Sequence
<220> FEATURE:
<223> OTHER INFORMATION: Synthetic: IgG1-IgG2CS-IgG1f2

<400> SEQUENCE: 247

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 248
<211> LENGTH: 326
<212> TYPE: PRT
<213> ORGANISM: Artificial Sequence
<220> FEATURE:
```

<223> OTHER INFORMATION: Synthetic: IgG2-IgG1f

<400> SEQUENCE: 248

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
                100                 105                 110
Glu Leu Leu Gly Gly Pro Ser Val Phe Leu Phe Pro Pro Lys Pro Lys
            115                 120                 125
Asp Thr Leu Met Ile Ser Arg Thr Pro Glu Val Thr Cys Val Val Val
        130                 135                 140
Asp Val Ser His Glu Asp Pro Glu Val Lys Phe Asn Trp Tyr Val Asp
145                 150                 155                 160
Gly Val Glu Val His Asn Ala Lys Thr Lys Pro Arg Glu Glu Gln Tyr
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Ala Leu
            195                 200                 205
Pro Ala Pro Ile Glu Lys Thr Ile Ser Lys Ala Lys Gly Gln Pro Arg
        210                 215                 220
Glu Pro Gln Val Tyr Thr Leu Pro Pro Ser Arg Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
            275                 280                 285
Lys Leu Thr Val Asp Lys Ser Arg Trp Gln Gln Gly Asn Val Phe Ser
        290                 295                 300
Cys Ser Val Met His Glu Ala Leu His Asn His Tyr Thr Gln Lys Ser
305                 310                 315                 320
Leu Ser Leu Ser Pro Gly
                325
```

<210> SEQ ID NO 249
<211> LENGTH: 325
<212> TYPE: PRT
<213> ORGANISM: Artificial Sequence
<220> FEATURE:
<223> OTHER INFORMATION: Synthetic: IgG2-IgG1f2

<400> SEQUENCE: 249

```
Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 250
<211> LENGTH: 326
<212> TYPE: PRT
<213> ORGANISM: Artificial Sequence
<220> FEATURE:
<223> OTHER INFORMATION: Synthetic: IgG2CS-IgG1f

<400> SEQUENCE: 250

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
            210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 251
<211> LENGTH: 325
<212> TYPE: PRT
<213> ORGANISM: Artificial Sequence
<220> FEATURE:
<223> OTHER INFORMATION: Synthetic: IgG2CS-IgG1f2

<400> SEQUENCE: 251

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

```
Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 252
<211> LENGTH: 325
<212> TYPE: PRT
<213> ORGANISM: Artificial Sequence
<220> FEATURE:
<223> OTHER INFORMATION: Synthetic: IgG1-IgG2-IgG1.1f

<400> SEQUENCE: 252

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 253
<211> LENGTH: 325
<212> TYPE: PRT
<213> ORGANISM: Artificial Sequence
<220> FEATURE:
<223> OTHER INFORMATION: Synthetic: IgG1-IgG2CS-IgG1.1f

<400> SEQUENCE: 253

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
            165                 170                 175

Ser Thr Tyr Arg Val Val Ser Val Leu Thr Val Leu His Gln Asp Trp
        180                 185                 190

Leu Asn Gly Lys Glu Tyr Lys Cys Lys Val Ser Asn Lys Ala Leu Pro
            195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 254
<211> LENGTH: 325
<212> TYPE: PRT
<213> ORGANISM: Artificial Sequence
<220> FEATURE:
<223> OTHER INFORMATION: Synthetic: IgG2-IgG1.1f

<400> SEQUENCE: 254

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
            165                 170                 175
```

```
Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 255
<211> LENGTH: 326
<212> TYPE: PRT
<213> ORGANISM: Artificial Sequence
<220> FEATURE:
<223> OTHER INFORMATION: Synthetic: IgG2CS-IgG1.1f

<400> SEQUENCE: 255

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205
```

```
Pro Ala Pro Ile Glu Lys Thr Ile Ser Lys Ala Lys Gly Gln Pro Arg
        210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 256
<211> LENGTH: 330
<212> TYPE: PRT
<213> ORGANISM: Artificial Sequence
<220> FEATURE:
<223> OTHER INFORMATION: Synthetic: IgG1f

<400> SEQUENCE: 256

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 257
<211> LENGTH: 330
<212> TYPE: PRT
<213> ORGANISM: Artificial Sequence
<220> FEATURE:
<223> OTHER INFORMATION: Synthetic: IgG1.1f

<400> SEQUENCE: 257

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 258
<211> LENGTH: 326
<212> TYPE: PRT
<213> ORGANISM: Artificial Sequence
<220> FEATURE:
<223> OTHER INFORMATION: Synthetic: IgG2.3

<400> SEQUENCE: 258

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Gly Lys
                325

<210> SEQ ID NO 259
<211> LENGTH: 326
<212> TYPE: PRT
<213> ORGANISM: Artificial Sequence
<220> FEATURE:
<223> OTHER INFORMATION: Synthetic: IgG2.5

<400> SEQUENCE: 259

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 260
<211> LENGTH: 326
<212> TYPE: PRT
<213> ORGANISM: Artificial Sequence
<220> FEATURE:
<223> OTHER INFORMATION: Synthetic: IgG2.3G1-KH

<400> SEQUENCE: 260

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 261
<211> LENGTH: 326
<212> TYPE: PRT
<213> ORGANISM: Artificial Sequence
<220> FEATURE:
<223> OTHER INFORMATION: Synthetic: IgG2.5G1-KH

<400> SEQUENCE: 261

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 262
<211> LENGTH: 327
<212> TYPE: PRT
<213> ORGANISM: Artificial Sequence
<220> FEATURE:
<223> OTHER INFORMATION: Synthetic: IgG2.3G1-AY

<400> SEQUENCE: 262

Ala Ser Thr Lys Gly Pro Ser Val Phe Pro Leu Ala Pro Cys Ser Arg

```
              1               5                  10                  15
            Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Asn Phe Gly Thr Gln Thr
             65                  70                  75                  80

Tyr Thr Cys Asn Val Asp His Lys Pro Ser Asn Thr Lys Val Asp Lys
                            85                  90                  95

Thr Val Glu Arg Lys Ser Cys Val Glu Cys Pro Pro Cys Pro Ala Pro
                        100                 105                 110

Glu Leu Leu Gly Gly Pro Ser Val Phe Leu Phe Pro Pro Lys Pro Lys
                        115                 120                 125

Asp Thr Leu Met Ile Ser Arg Thr Pro Glu Val Thr Cys Val Val Val
             130                 135                 140

Asp Val Ser His Glu Asp Pro Glu Val Lys Phe Asn Trp Tyr Val Asp
            145                 150                 155                 160

Gly Val Glu Val His Asn Ala Lys Thr Lys Pro Arg Glu Glu Gln Tyr
                            165                 170                 175

Asn Ser Thr Tyr Arg Val Val Ser Val Leu Thr Val Leu His Gln Asp
                        180                 185                 190

Trp Leu Asn Gly Lys Glu Tyr Lys Cys Lys Val Ser Asn Lys Ala Leu
                        195                 200                 205

Pro Ala Pro Ile Glu Lys Thr Ile Ser Lys Ala Lys Gly Gln Pro Arg
             210                 215                 220

Glu Pro Gln Val Tyr Thr Leu Pro Pro Ser Arg Glu Glu Met Thr Lys
            225                 230                 235                 240

Asn Gln Val Ser Leu Thr Cys Leu Val Lys Gly Phe Tyr Pro Ser Asp
                            245                 250                 255

Ile Ala Val Glu Trp Glu Ser Asn Gly Gln Pro Glu Asn Asn Tyr Lys
                        260                 265                 270

Thr Thr Pro Pro Val Leu Asp Ser Asp Gly Ser Phe Phe Leu Tyr Ser
                        275                 280                 285

Lys Leu Thr Val Asp Lys Ser Arg Trp Gln Gln Gly Asn Val Phe Ser
             290                 295                 300

Cys Ser Val Met His Glu Ala Leu His Asn His Tyr Thr Gln Lys Ser
            305                 310                 315                 320

Leu Ser Leu Ser Pro Gly Lys
                        325

<210> SEQ ID NO 263
<211> LENGTH: 327
<212> TYPE: PRT
<213> ORGANISM: Artificial Sequence
<220> FEATURE:
<223> OTHER INFORMATION: Synthetic: IgG2.5G1-AY

<400> SEQUENCE: 263

Ala Ser Thr Lys Gly Pro Ser Val Phe Pro Leu Ala Pro Ser Ser Arg
             1               5                  10                  15

Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
```

```
                    35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 264
<211> LENGTH: 326
<212> TYPE: PRT
<213> ORGANISM: Artificial Sequence
<220> FEATURE:
<223> OTHER INFORMATION: Synthetic: IgG2.3G1.1f-KH

<400> SEQUENCE: 264

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
```

```
                65                  70                  75                  80
Tyr Thr Cys Asn Val Asp His Lys Pro Ser Asn Thr Lys Val Asp Lys
                    85                  90                  95

Thr Val Glu Arg Lys Ser Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 265
<211> LENGTH: 326
<212> TYPE: PRT
<213> ORGANISM: Artificial Sequence
<220> FEATURE:
<223> OTHER INFORMATION: Synthetic: IgG2.5G1.1f-KH

<400> SEQUENCE: 265

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
```

```
                100             105             110
Pro Val Ala Gly Pro Ser Val Phe Leu Phe Pro Lys Pro Lys Asp
            115                 120                 125
Thr Leu Met Ile Ser Arg Thr Pro Glu Val Thr Cys Val Val Asp
        130                 135                 140
Val Ser His Glu Asp Pro Glu Val Lys Phe Asn Trp Tyr Val Asp Gly
145                 150                 155                 160
Val Glu Val His Asn Ala Lys Thr Lys Pro Arg Glu Glu Gln Tyr Asn
                165                 170                 175
Ser Thr Tyr Arg Val Val Ser Val Leu Thr Val Leu His Gln Asp Trp
            180                 185                 190
Leu Asn Gly Lys Glu Tyr Lys Cys Lys Val Ser Asn Lys Ala Leu Pro
        195                 200                 205
Ser Ser Ile Glu Lys Thr Ile Ser Lys Ala Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Val Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 266
<211> LENGTH: 327
<212> TYPE: PRT
<213> ORGANISM: Artificial Sequence
<220> FEATURE:
<223> OTHER INFORMATION: Synthetic: IgG2.5G1-V27

<400> SEQUENCE: 266

Ala Ser Thr Lys Gly Pro Ser Val Phe Pro Leu Ala Pro Ser Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Glu Leu Leu Gly Gly Pro Ser Val Phe Leu Phe Pro Lys Pro Lys
        115                 120                 125
Asp Thr Leu Met Ile Ser Arg Thr Pro Glu Val Thr Cys Val Val Val
```

```
                130                 135                 140
Asp Val Glu His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Ala Leu
                195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Lys Leu Thr Val Asp Lys Ser Arg Trp Gln Gln Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 267
<211> LENGTH: 326
<212> TYPE: PRT
<213> ORGANISM: Artificial Sequence
<220> FEATURE:
<223> OTHER INFORMATION: Synthetic: IgG2.3-V13

<400> SEQUENCE: 267

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Asp Ser Val Phe Leu Phe Pro Pro Lys Pro Lys Asp
                115                 120                 125

Thr Leu Met Ile Ser Arg Thr Pro Glu Val Thr Cys Val Val Val Asp
                130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                165                 170                 175
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 268
<211> LENGTH: 326
<212> TYPE: PRT
<213> ORGANISM: Artificial Sequence
<220> FEATURE:
<223> OTHER INFORMATION: Synthetic: IgG2.3-V14

<400> SEQUENCE: 268

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Asp Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
```

```
                195                 200                 205
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 269
<211> LENGTH: 326
<212> TYPE: PRT
<213> ORGANISM: Artificial Sequence
<220> FEATURE:
<223> OTHER INFORMATION: Synthetic: IgG2.3-V15

<400> SEQUENCE: 269

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Asp Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Asp Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
```

```
                225                 230                 235                 240
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 270
<211> LENGTH: 326
<212> TYPE: PRT
<213> ORGANISM: Artificial Sequence
<220> FEATURE:
<223> OTHER INFORMATION: Synthetic: IgG2.3-V16

<400> SEQUENCE: 270

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Asp Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Arg Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
```

```
                260             265             270
Thr Pro Pro Met Leu Asp Ser Asp Gly Ser Phe Phe Leu Tyr Ser Lys
            275             280             285

Leu Thr Val Asp Lys Ser Arg Trp Gln Gln Gly Asn Val Phe Ser Cys
            290             295             300

Ser Val Met His Glu Ala Leu His Asn His Tyr Thr Gln Lys Ser Leu
305             310             315             320

Ser Leu Ser Pro Gly Lys
                325

<210> SEQ ID NO 271
<211> LENGTH: 326
<212> TYPE: PRT
<213> ORGANISM: Artificial Sequence
<220> FEATURE:
<223> OTHER INFORMATION: Synthetic: IgG2.3-V17

<400> SEQUENCE: 271

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Asp Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Asp Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Arg Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
```

```
                 290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 272
<211> LENGTH: 326
<212> TYPE: PRT
<213> ORGANISM: Artificial Sequence
<220> FEATURE:
<223> OTHER INFORMATION: Synthetic: IgG2.3-V18

<400> SEQUENCE: 272

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Glu His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
```

<210> SEQ ID NO 273
<211> LENGTH: 326
<212> TYPE: PRT
<213> ORGANISM: Artificial Sequence
<220> FEATURE:
<223> OTHER INFORMATION: Synthetic: IgG2.3-V19

<400> SEQUENCE: 273

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Glu His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Phe Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 274
<211> LENGTH: 327
<212> TYPE: PRT

<213> ORGANISM: Artificial Sequence
<220> FEATURE:
<223> OTHER INFORMATION: Synthetic: IgG2.3G1-AY-V20

<400> SEQUENCE: 274

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 275
<211> LENGTH: 327
<212> TYPE: PRT
<213> ORGANISM: Artificial Sequence
<220> FEATURE:
<223> OTHER INFORMATION: Synthetic: IgG2.3G1-AY-V21

<400> SEQUENCE: 275

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 276
<211> LENGTH: 327
<212> TYPE: PRT
<213> ORGANISM: Artificial Sequence
<220> FEATURE:
<223> OTHER INFORMATION: Synthetic: IgG2.3G1-AY-V22

<400> SEQUENCE: 276

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 277
<211> LENGTH: 327
<212> TYPE: PRT
<213> ORGANISM: Artificial Sequence
<220> FEATURE:
<223> OTHER INFORMATION: Synthetic: IgG2.3G1-AY-V23

<400> SEQUENCE: 277

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

```
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Glu Cys Pro Pro Cys Pro Ala Pro
            100                 105                 110

Glu Leu Leu Gly Gly Asp Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 278
<211> LENGTH: 327
<212> TYPE: PRT
<213> ORGANISM: Artificial Sequence
<220> FEATURE:
<223> OTHER INFORMATION: Synthetic: IgG2.3G1-AY-V24

<400> SEQUENCE: 278

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95
```

Thr Val Glu Arg Lys Ser Cys Val Glu Cys Pro Pro Cys Pro Ala Pro
                100                 105                 110

Glu Leu Leu Gly Gly Asp Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 279
<211> LENGTH: 327
<212> TYPE: PRT
<213> ORGANISM: Artificial Sequence
<220> FEATURE:
<223> OTHER INFORMATION: Synthetic: IgG2.3G1-AY-V25

<400> SEQUENCE: 279

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Glu Leu Leu Gly Asp Asp Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 280
<211> LENGTH: 327
<212> TYPE: PRT
<213> ORGANISM: Artificial Sequence
<220> FEATURE:
<223> OTHER INFORMATION: Synthetic: IgG2.3G1-AY-V26

<400> SEQUENCE: 280

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Asp Leu Leu Gly Asp Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Asp Glu Asp Gly Val Lys Phe Asn Trp Tyr Val Asp
145                 150                 155                 160

```
Gly Val Glu Val His Asn Ala Lys Thr Lys Pro Arg Glu Glu Gln Tyr
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Ala Leu
        195                 200                 205
Pro Arg Pro Ile Glu Lys Thr Ile Ser Lys Ala Lys Gly Gln Pro Arg
    210                 215                 220
Glu Pro Gln Val Tyr Thr Leu Pro Pro Ser Arg Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Lys Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Pro Gly Lys
                325

<210> SEQ ID NO 281
<211> LENGTH: 327
<212> TYPE: PRT
<213> ORGANISM: Artificial Sequence
<220> FEATURE:
<223> OTHER INFORMATION: Synthetic: IgG2.3G1-AY-V28

<400> SEQUENCE: 281

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Ser Cys Val Glu Cys Pro Pro Cys Pro Ala Pro
            100                 105                 110
Glu Leu Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Glu His Glu Asp Pro Glu Val Lys Phe Asn Trp Tyr Val Asp
145                 150                 155                 160
Gly Val Glu Val His Asn Ala Lys Thr Lys Pro Arg Glu Glu Gln Tyr
                165                 170                 175
Asn Ser Thr Tyr Arg Val Val Ser Val Leu Thr Val Leu His Gln Asp
            180                 185                 190
```

Trp Leu Asn Gly Lys Glu Tyr Lys Cys Lys Val Ser Asn Lys Ala Phe
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
            325

<210> SEQ ID NO 282
<211> LENGTH: 443
<212> TYPE: PRT
<213> ORGANISM: Artificial Sequence
<220> FEATURE:
<223> OTHER INFORMATION: Synthetic: OX40.6-Vh-hHC-IgG2.3

<400> SEQUENCE: 282

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Ala Met Tyr Trp Val Arg Gln Ala Pro Gly Lys Gly Leu Glu Trp Val
            35                  40                  45

Ser Ala Ile Gly Ile Gly Gly Asp Thr Phe Tyr Thr Asp Ser Val Lys
50                  55                  60

Gly Arg Phe Thr Ile Ser Arg Asp Asn Ala Lys Asn Ser Leu Ser Leu
65                  70                  75                  80

Gln Met Asn Ser Leu Arg Ala Glu Asp Thr Ala Val Tyr Tyr Cys Ala
            85                  90                  95

Arg Met Gly Thr Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Ser Cys Val Glu Cys Pro
210                 215                 220

```
Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 283
<211> LENGTH: 441
<212> TYPE: PRT
<213> ORGANISM: Artificial Sequence
<220> FEATURE:
<223> OTHER INFORMATION: Synthetic: OX40.8-Vh-hHC-IgG2.3

<400> SEQUENCE: 283

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Met Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
            195                 200                 205

Val Asp Lys Thr Val Glu Arg Lys Ser Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
            275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
            325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 284
<211> LENGTH: 443
<212> TYPE: PRT
<213> ORGANISM: Artificial Sequence
<220> FEATURE:
<223> OTHER INFORMATION: Synthetic: OX40.16-Vh-hHC-IgG2.3

<400> SEQUENCE: 284

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
            35                  40                  45

Ser Ala Ile Asp Thr Asp Gly Gly Thr Phe Tyr Ala Asp Ser Val Arg
50                  55                  60
```

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
            85                  90                  95

Arg Leu Gly Glu Gly Tyr Phe Phe Asp Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 285
<211> LENGTH: 444
<212> TYPE: PRT
<213> ORGANISM: Artificial Sequence
<220> FEATURE:
<223> OTHER INFORMATION: Synthetic: OX40.6-Vh-hHC-IgG2.3G1

<400> SEQUENCE: 285

```
Glu Val Gln Leu Val Gln Ser Gly Gly Gly Leu Val Gln Pro Gly Gly
1               5                   10                  15
Ser Leu Arg Leu Ser Cys Ala Gly Ser Gly Phe Thr Phe Ser Asn Tyr
            20                  25                  30
Ala Met Tyr Trp Val Arg Gln Ala Pro Gly Lys Gly Leu Glu Trp Val
        35                  40                  45
Ser Ala Ile Gly Ile Gly Gly Asp Thr Phe Tyr Thr Asp Ser Val Lys
    50                  55                  60
Gly Arg Phe Thr Ile Ser Arg Asp Asn Ala Lys Asn Ser Leu Ser Leu
65                  70                  75                  80
Gln Met Asn Ser Leu Arg Ala Glu Asp Thr Ala Val Tyr Tyr Cys Ala
                85                  90                  95
Arg Met Gly Thr Gly Tyr Phe Phe Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
        195                 200                 205
Thr Lys Val Asp Lys Thr Val Glu Arg Lys Ser Cys Val Glu Cys Pro
    210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
```

```
                    405                 410                 415
Gly Asn Val Phe Ser Cys Ser Val Met His Glu Ala Leu His Asn His
                420                 425                 430

Tyr Thr Gln Lys Ser Leu Ser Leu Ser Pro Gly Lys
        435                 440

<210> SEQ ID NO 286
<211> LENGTH: 442
<212> TYPE: PRT
<213> ORGANISM: Artificial Sequence
<220> FEATURE:
<223> OTHER INFORMATION: Synthetic: OX40.8-Vh-hHC-IgG2.3G1

<400> SEQUENCE: 286

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Met Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Ser Cys Val Glu Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
```

```
                    325                 330                 335
Gln Pro Arg Glu Pro Gln Val Tyr Thr Leu Pro Pro Ser Arg Glu Glu
                340                 345                 350
Met Thr Lys Asn Gln Val Ser Leu Thr Cys Leu Val Lys Gly Phe Tyr
                355                 360                 365
Pro Ser Asp Ile Ala Val Glu Trp Glu Ser Asn Gly Gln Pro Glu Asn
                370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
                420                 425                 430
Gln Lys Ser Leu Ser Leu Ser Pro Gly Lys
                435                 440

<210> SEQ ID NO 287
<211> LENGTH: 444
<212> TYPE: PRT
<213> ORGANISM: Artificial Sequence
<220> FEATURE:
<223> OTHER INFORMATION: Synthetic: OX40.16-Vh-hHC-IgG2.3G1

<400> SEQUENCE: 287

Glu Val Gln Leu Val Gln Ser Gly Gly Gly Leu Val Gln Pro Gly Gly
1               5                   10                  15
Ser Leu Arg Leu Ser Cys Ala Gly Ser Gly Phe Thr Phe Ser Ser Tyr
                20                  25                  30
Ala Met Tyr Trp Val Arg Gln Ala Pro Gly Lys Gly Leu Glu Trp Val
                35                  40                  45
Ser Ala Ile Asp Thr Asp Gly Gly Thr Phe Tyr Ala Asp Ser Val Arg
                50                  55                  60
Gly Arg Phe Thr Ile Ser Arg Asp Asn Ala Lys Asn Ser Leu Tyr Leu
65                  70                  75                  80
Gln Met Asn Ser Leu Arg Ala Glu Asp Thr Ala Val Tyr Phe Cys Ala
                85                  90                  95
Arg Leu Gly Glu Gly Tyr Phe Phe Asp Tyr Trp Gly Gln Gly Thr Leu
                100                 105                 110
Val Thr Val Ser Ser Ala Ser Thr Lys Gly Pro Ser Val Phe Pro Leu
                115                 120                 125
Ala Pro Cys Ser Arg Ser Thr Ser Glu Ser Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
                180                 185                 190
Phe Gly Thr Gln Thr Tyr Thr Cys Asn Val Asp His Lys Pro Ser Asn
                195                 200                 205
Thr Lys Val Asp Lys Thr Val Glu Arg Lys Ser Cys Val Glu Cys Pro
                210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
```

```
                    245                 250                 255
Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 288
<211> LENGTH: 444
<212> TYPE: PRT
<213> ORGANISM: Artificial Sequence
<220> FEATURE:
<223> OTHER INFORMATION: Synthetic: OX40.6-Vh-hHC-IgG2.3G1-V27

<400> SEQUENCE: 288

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ser Ala Ile Gly Ile Gly Gly Asp Thr Phe Tyr Thr Asp Ser Val Lys
    50                  55                  60

Gly Arg Phe Thr Ile Ser Arg Asp Asn Ala Lys Asn Ser Leu Ser Leu
65                  70                  75                  80

Gln Met Asn Ser Leu Arg Ala Glu Asp Thr Ala Val Tyr Tyr Cys Ala
                85                  90                  95

Arg Met Gly Thr Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
                165                 170                 175
Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Ser Cys Val Glu Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Glu His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 289
<211> LENGTH: 442
<212> TYPE: PRT
<213> ORGANISM: Artificial Sequence
<220> FEATURE:
<223> OTHER INFORMATION: Synthetic: OX40.8-Vh-hHC-IgG2.3G1-V27

<400> SEQUENCE: 289

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
              85                  90                  95
Ala Ser Leu Thr Met Val Arg Glu Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
            195                 200                 205

Val Asp Lys Thr Val Glu Arg Lys Ser Cys Val Glu Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Glu His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 290
<211> LENGTH: 444
<212> TYPE: PRT
<213> ORGANISM: Artificial Sequence
<220> FEATURE:
<223> OTHER INFORMATION: Synthetic: OX40.16-Vh-hHC-IgG2.3G1-V27

<400> SEQUENCE: 290

Glu Val Gln Leu Val Gln Ser Gly Gly Gly Leu Val Gln Pro Gly Gly
```

-continued

```
1               5                   10                  15
Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
            35                  40                  45

Ser Ala Ile Asp Thr Asp Gly Thr Phe Tyr Ala Asp Ser Val Arg
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Phe Cys Ala
            85                  90                  95

Arg Leu Gly Glu Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Ser Cys Val Glu Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Glu His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430
```

Tyr Thr Gln Lys Ser Leu Ser Leu Ser Pro Gly Lys
        435                 440

<210> SEQ ID NO 291
<211> LENGTH: 443
<212> TYPE: PRT
<213> ORGANISM: Artificial Sequence
<220> FEATURE:
<223> OTHER INFORMATION: Synthetic: OX40.6-Vh-hHC-IgG2.5

<400> SEQUENCE: 291

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Ala Met Tyr Trp Val Arg Gln Ala Pro Gly Lys Gly Leu Glu Trp Val
        35                  40                  45

Ser Ala Ile Gly Ile Gly Gly Asp Thr Phe Tyr Thr Asp Ser Val Lys
    50                  55                  60

Gly Arg Phe Thr Ile Ser Arg Asp Asn Ala Lys Asn Ser Leu Ser Leu
65                  70                  75                  80

Gln Met Asn Ser Leu Arg Ala Glu Asp Thr Ala Val Tyr Tyr Cys Ala
                85                  90                  95

Arg Met Gly Thr Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

-continued

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 292
<211> LENGTH: 441
<212> TYPE: PRT
<213> ORGANISM: Artificial Sequence
<220> FEATURE:
<223> OTHER INFORMATION: Synthetic: OX40.8-Vh-hHC-IgG2.5

<400> SEQUENCE: 292

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Leu His Trp Val Arg Gln Ala Pro Gly Lys Gly Leu Glu Trp Val
        35                  40                  45

Ala Leu Ile Ser Tyr Asp Gly Ser Arg Lys His Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Thr Met Val Arg Glu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
            435                 440

<210> SEQ ID NO 293
<211> LENGTH: 443
<212> TYPE: PRT
<213> ORGANISM: Artificial Sequence
<220> FEATURE:
<223> OTHER INFORMATION: Synthetic: OX40.16-Vh-hHC-IgG2.5

<400> SEQUENCE: 293

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Gly Gly Thr Phe Tyr Ala Asp Ser Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

```
Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
        290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 294
<211> LENGTH: 443
<212> TYPE: PRT
<213> ORGANISM: Artificial Sequence
<220> FEATURE:
<223> OTHER INFORMATION: Synthetic: OX40.21-Vh-hHC-IgG2.5

<400> SEQUENCE: 294

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Ala Gly Thr Phe Tyr Ala Asp Ser Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Phe Asp Tyr Trp Gly Gln Gly Thr Leu
            100                 105                 110
```

-continued

Val Thr Val Ser Ser Ala Ser Thr Lys Gly Pro Ser Val Phe Pro Leu
            115                 120                 125

Ala Pro Ser Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 295
<211> LENGTH: 444
<212> TYPE: PRT
<213> ORGANISM: Artificial Sequence
<220> FEATURE:
<223> OTHER INFORMATION: Synthetic: OX40.21-Vh-hHC-IgG2.5G1

<400> SEQUENCE: 295

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

```
Ala Met Tyr Trp Val Arg Gln Ala Pro Gly Lys Gly Leu Glu Trp Val
        35                  40                  45

Ser Ala Ile Asp Thr Asp Ala Gly Thr Phe Tyr Ala Asp Ser Val Arg
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
                180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
        210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440
```

```
<210> SEQ ID NO 296
<211> LENGTH: 444
<212> TYPE: PRT
<213> ORGANISM: Artificial Sequence
<220> FEATURE:
<223> OTHER INFORMATION: Synthetic: OX40.21-Vh-hHC-IgG2.5G1-V27

<400> SEQUENCE: 296

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Ala Gly Thr Phe Tyr Ala Asp Ser Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Glu His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365
```

```
Phe Tyr Pro Ser Asp Ile Ala Val Glu Trp Glu Ser Asn Gly Gln Pro
    370             375                 380

Glu Asn Asn Tyr Lys Thr Thr Pro Pro Val Leu Asp Ser Asp Gly Ser
385             390             395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 297
<211> LENGTH: 327
<212> TYPE: PRT
<213> ORGANISM: Artificial Sequence
<220> FEATURE:
<223> OTHER INFORMATION: Synthetic: IgG2.3G1-V27

<400> SEQUENCE: 297

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Glu His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Lys Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Pro Gly Lys
                325

<210> SEQ ID NO 298
<211> LENGTH: 103
<212> TYPE: PRT
<213> ORGANISM: Artificial Sequence
<220> FEATURE:
<223> OTHER INFORMATION: Synthetic: Human IgG1 CH2 with A330S/P331S

<400> SEQUENCE: 298

Pro Ser Val Phe Leu Phe Pro Pro Lys Pro Lys Asp Thr Leu Met Ile
1               5                   10                  15
Ser Arg Thr Pro Glu Val Thr Cys Val Val Val Asp Val Ser His Glu
                20                  25                  30
Asp Pro Glu Val Lys Phe Asn Trp Tyr Val Asp Gly Val Glu Val His
            35                  40                  45
Asn Ala Lys Thr Lys Pro Arg Glu Glu Gln Tyr Asn Ser Thr Tyr Arg
    50                  55                  60
Val Val Ser Val Leu Thr Val Leu His Gln Asp Trp Leu Asn Gly Lys
65                  70                  75                  80
Glu Tyr Lys Cys Lys Val Ser Asn Lys Ala Leu Pro Ser Ser Ile Glu
                85                  90                  95
Lys Thr Ile Ser Lys Ala Lys
            100

<210> SEQ ID NO 299
<211> LENGTH: 440
<212> TYPE: PRT
<213> ORGANISM: Artificial Sequence
<220> FEATURE:
<223> OTHER INFORMATION: Synthetic: Heavy chain  nivolumab

<400> SEQUENCE: 299

Gln Val Gln Leu Val Glu Ser Gly Gly Gly Val Val Gln Pro Gly Arg
1               5                   10                  15
Ser Leu Arg Leu Asp Cys Lys Ala Ser Gly Ile Thr Phe Ser Asn Ser
                20                  25                  30
Gly Met His Trp Val Arg Gln Ala Pro Gly Lys Gly Leu Glu Trp Val
            35                  40                  45
Ala Val Ile Trp Tyr Asp Gly Ser Lys Arg Tyr Tyr Ala Asp Ser Val
    50                  55                  60
Lys Gly Arg Phe Thr Ile Ser Arg Asp Asn Ser Lys Asn Thr Leu Phe
65                  70                  75                  80
Leu Gln Met Asn Ser Leu Arg Ala Glu Asp Thr Ala Val Tyr Tyr Cys
                85                  90                  95
Ala Thr Asn Asp Asp Tyr Trp Gly Gln Gly Thr Leu Val Thr Val Ser
            100                 105                 110
Ser Ala Ser Thr Lys Gly Pro Ser Val Phe Pro Leu Ala Pro Cys Ser
        115                 120                 125
Arg Ser Thr Ser Glu Ser Thr Ala Ala Leu Gly Cys Leu Val Lys Asp
    130                 135                 140
Tyr Phe Pro Glu Pro Val Thr Val Ser Trp Asn Ser Gly Ala Leu Thr
145                 150                 155                 160
```

```
Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 300
<211> LENGTH: 214
<212> TYPE: PRT
<213> ORGANISM: Artificial Sequence
<220> FEATURE:
<223> OTHER INFORMATION: Synthetic: Light chain  nivolumab

<400> SEQUENCE: 300

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 301
<211> LENGTH: 113
<212> TYPE: PRT
<213> ORGANISM: Artificial Sequence
<220> FEATURE:
<223> OTHER INFORMATION: Synthetic: Heavy chain variable region
      nivolumab

<400> SEQUENCE: 301

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 302
<211> LENGTH: 107
<212> TYPE: PRT
<213> ORGANISM: Artificial Sequence
<220> FEATURE:
<223> OTHER INFORMATION: Synthetic: Light chain variable region
      nivolumab

<400> SEQUENCE: 302

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105

<210> SEQ ID NO 303
<211> LENGTH: 5
<212> TYPE: PRT
<213> ORGANISM: Artificial Sequence
<220> FEATURE:
<223> OTHER INFORMATION: Synthetic: HCDR1  nivolumab

<400> SEQUENCE: 303

Asn Ser Gly Met His
1               5

<210> SEQ ID NO 304
<211> LENGTH: 17
<212> TYPE: PRT
<213> ORGANISM: Artificial Sequence
<220> FEATURE:
<223> OTHER INFORMATION: Synthetic: HCDR2  nivolumab

<400> SEQUENCE: 304

Val Ile Trp Tyr Asp Gly Ser Lys Arg Tyr Tyr Ala Asp Ser Val Lys
1               5                   10                  15

Gly

<210> SEQ ID NO 305
<211> LENGTH: 4
<212> TYPE: PRT
<213> ORGANISM: Artificial Sequence
<220> FEATURE:
<223> OTHER INFORMATION: Synthetic: HCDR3  nivolumab

<400> SEQUENCE: 305

Asn Asp Asp Tyr
1

<210> SEQ ID NO 306
<211> LENGTH: 11
<212> TYPE: PRT
<213> ORGANISM: Artificial Sequence
<220> FEATURE:
<223> OTHER INFORMATION: Synthetic: LCDR1  nivolumab

<400> SEQUENCE: 306

Arg Ala Ser Gln Ser Val Ser Ser Tyr Leu Ala
1               5                   10

<210> SEQ ID NO 307
<211> LENGTH: 7
<212> TYPE: PRT
<213> ORGANISM: Artificial Sequence
<220> FEATURE:
<223> OTHER INFORMATION: Synthetic: LCDR2  nivolumab

<400> SEQUENCE: 307
```

-continued

Asp Ala Ser Asn Arg Ala Thr
1               5

<210> SEQ ID NO 308
<211> LENGTH: 9
<212> TYPE: PRT
<213> ORGANISM: Artificial Sequence
<220> FEATURE:
<223> OTHER INFORMATION: Synthetic: LCDR3  nivolumab

<400> SEQUENCE: 308

Gln Gln Ser Ser Asn Trp Pro Arg Thr
1               5

<210> SEQ ID NO 309
<211> LENGTH: 118
<212> TYPE: PRT
<213> ORGANISM: Artificial Sequence
<220> FEATURE:
<223> OTHER INFORMATION: Synthetic: Heavy chain variable region
      ipilimumab (from WO01/014424)

<400> SEQUENCE: 309

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 310
<211> LENGTH: 108
<212> TYPE: PRT
<213> ORGANISM: Artificial Sequence
<220> FEATURE:
<223> OTHER INFORMATION: Synthetic: Light chain variable region
      ipilimumab (from WO01/014424)

<400> SEQUENCE: 310

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 311
<211> LENGTH: 5
<212> TYPE: PRT
<213> ORGANISM: Artificial Sequence
<220> FEATURE:
<223> OTHER INFORMATION: Synthetic: HCDR1  ipilimumab (from WO01/014424)

<400> SEQUENCE: 311

Ser Tyr Thr Met His
1               5

<210> SEQ ID NO 312
<211> LENGTH: 17
<212> TYPE: PRT
<213> ORGANISM: Artificial Sequence
<220> FEATURE:
<223> OTHER INFORMATION: Synthetic: HCDR2  ipilimumab (from WO01/014424)

<400> SEQUENCE: 312

Phe Ile Ser Tyr Asp Gly Asn Asn Lys Tyr Tyr Ala Asp Ser Val Lys
1               5                   10                  15

Gly

<210> SEQ ID NO 313
<211> LENGTH: 9
<212> TYPE: PRT
<213> ORGANISM: Artificial Sequence
<220> FEATURE:
<223> OTHER INFORMATION: Synthetic: HCDR3  ipilimumab (from WO01/014424)

<400> SEQUENCE: 313

Thr Gly Trp Leu Gly Pro Phe Asp Tyr
1               5

<210> SEQ ID NO 314
<211> LENGTH: 12
<212> TYPE: PRT
<213> ORGANISM: Artificial Sequence
<220> FEATURE:
<223> OTHER INFORMATION: Synthetic: LCDR1  ipilimumab (from WO01/014424)

<400> SEQUENCE: 314

Arg Ala Ser Gln Ser Val Gly Ser Ser Tyr Leu Ala
1               5                   10

<210> SEQ ID NO 315
<211> LENGTH: 7
<212> TYPE: PRT
<213> ORGANISM: Artificial Sequence
<220> FEATURE:
<223> OTHER INFORMATION: Synthetic: LCDR2  ipilimumab (from WO01/014424)

<400> SEQUENCE: 315

Gly Ala Phe Ser Arg Ala Thr
1               5

<210> SEQ ID NO 316
<211> LENGTH: 9
<212> TYPE: PRT
<213> ORGANISM: Artificial Sequence
<220> FEATURE:
<223> OTHER INFORMATION: Synthetic: LCDR3  ipilimumab (from WO01/014424)

```
<400> SEQUENCE: 316

Gln Gln Tyr Gly Ser Ser Pro Trp Thr
1               5

<210> SEQ ID NO 317
<211> LENGTH: 16
<212> TYPE: PRT
<213> ORGANISM: Artificial Sequence
<220> FEATURE:
<223> OTHER INFORMATION: Synthetic: HCDR2 of OX40.21

<400> SEQUENCE: 317

Ala Ile Asp Thr Asp Ala Gly Thr Phe Tyr Ala Asp Ser Val Arg Gly
1               5                   10                  15

<210> SEQ ID NO 318
<211> LENGTH: 117
<212> TYPE: PRT
<213> ORGANISM: Artificial Sequence
<220> FEATURE:
<223> OTHER INFORMATION: Synthetic: VH of OX40.21

<400> SEQUENCE: 318

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Ala Ile Asp Thr Asp Ala Gly Thr Phe Tyr Ala Asp Ser Val Arg
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Phe Cys Ala
                85                  90                  95

Arg Leu Gly Glu Gly Tyr Phe Phe Asp Tyr Trp Gly Gln Gly Thr Leu
            100                 105                 110

Val Thr Val Ser Ser
        115
```

US 10,683,357 B2

ANTIBODIES AGAINST OX40 AND USES THEREOF

REFERENCE TO RELATED APPLICATIONS

This application is a divisional of U.S. patent application Ser. No. 15/166,114, filed May 26, 2016, which claims priority to U.S. Provisional Application Nos. 62/333,556, 62/327,140, 62/264,691, 62/239,574 and 62/168,377, filed May 9, 2016, Apr. 25, 2016, Dec. 8, 2015, Oct. 9, 2015 and May 29, 2015, respectively. The contents of the aforementioned application are hereby incorporated by reference.

SEQUENCE LISTING

The instant application contains a Sequence Listing which has been submitted electronically in ASCII format and is hereby incorporated by reference in its entirety. Said ASCII copy, created on Mar. 30, 2017, is named MXI_543DV_Sequence_Listing.txt and is 417,552 bytes in size.

BACKGROUND

OX40 (TNFRSF4), also known as ACT35, IMD16, TXGP1L, and CD134, is a 50-kD type I transmembrane glycoprotein in the TNFSFR family of costimulatory receptors expressed on activated CD4+ T cells. In the context of cancer, OX40-expressing activated T cells are found in tumor infiltrating lymphocytes. OX40 and its ligand, OX40-L, play a crucial role in inducing and maintaining T-cell responses. Recent studies have demonstrated the utility of enhancing anti-tumor T cell function to fight cancer, with key components of an effective response including the activation of CD4+ T cells and promoting survival signals through memory and effector T cells. Given the ongoing need for improved strategies for treating diseases such as cancer through, e.g., enhancing immune responses such as T cell responses, novel agents that modulate T cell responses, such as those that target OX40, as well as therapies (e.g., combination therapies) that use such agents, would be therapeutically beneficial.

SUMMARY

Provided herein are antibodies, such as human monoclonal antibodies, that specifically bind OX40 and have desirable functional properties. These properties include high affinity binding to human OX40 and cynomolgus OX40 and the ability to stimulate antigen-specific T cell responses, e.g., in tumor-bearing subjects. Also provided herein are methods of detecting OX40 in a sample.

In one aspect, provided herein are antibodies, or antigen-binding portions thereof, which specifically bind to OX40 and exhibit at least one of the following properties:
(1) binding to soluble human OX40, e.g., with a $K_D$ of 10 nM or less (e.g., 0.01 nM to 10 nM), e.g., as measured by Biacore;
(2) binding to membrane bound human OX40, e.g., with an $EC_{50}$ of 1 nM or less (e.g., 0.01 nM to 1 nM), e.g., as measured by FACS;
(3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;
(4) inducing or enhancing T cell activation, as evidenced by (i) increased IL-2 and/or IFN-γ production in OX40-expressing T cells and/or (ii) enhanced T cell proliferation;
(5) inhibiting the binding of OX40 ligand to OX40, e.g., with an $EC_{50}$ of 1 nM or less as measured by FACS, e.g., in an assay with hOX40-293 cells;
(6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDN-QACKPWTNCTLAGK (SEQ ID NO: 179);
(7) competing for binding to human OX40 with 3F4, 14B6-1, 14B6-2, 23H3, 18E9, 8B11, 20B3, and 20C1;
(8) competing for binding to human OX40 with 6E1-1, 6E1-2, 14A2-1, and 14A2-2.

In certain embodiments, the anti-OX40 antibodies, or antigen binding portions thereof, described herein stimulate an anti-tumor immune response, for example, an antigen-specific T cell response. In certain embodiments, the antibodies, or antigen binding portions thereof, increase cytokine production (e.g., IL-2 and/or IFN-γ) in OX40-expressing T cells and/or increase T cell proliferation. In certain embodiments, the antibodies bind to the C1q component of human complement. In certain embodiments, the antibodies induce NK cell-mediated lysis of activated CD4+ T cells. In certain embodiments, the antibody promotes macrophage-mediated phagocytosis of OX40 expressing cells. In certain embodiments, the antibody inhibits regulatory T cell-mediated suppression of CD4+ T cell proliferation.

In certain embodiments, the anti-OX40 antibodies, or antigen binding portions thereof, bind to Fc receptors, such as one or more activating FcγRs. In certain embodiments, the antibodies, or antigen binding portions thereof, induce or enhance T cell activation through multivalent crosslinking.

Provided herein are isolated monoclonal antibodies, or antigen binding portions thereof, which specifically bind to OX40 and comprise the three variable heavy chain CDRs and the three variable light chain CDRs that are in the variable heavy chain and variable light chain pairs selected from: SEQ ID NOs: 318 and 94; SEQ ID NOs: 17 and 18; 28 and 29; 28 and 30; 37 and 38; 48 and 49; 48 and 50; 57 and 58; 65 and 66; 73 and 74; 84 and 85; 84 and 86; 93 and 94.

Also provided herein are monoclonal antibodies, or antigen binding portions thereof, which bind to OX40 and comprise:
(a) heavy chain CDR1, CDR2, and CDR3 sequences comprising SEQ ID NOs: 87, 317, and 89, respectively, and light chain CDR1, CDR2, and CDR3 sequences comprising SEQ ID NOs: 90-92, respectively;
(b) heavy chain CDR1, CDR2, and CDR3 sequences comprising SEQ ID NOs: 11-13, respectively, and light chain CDR1, CDR2, and CDR3 sequences comprising SEQ ID NOs: 14-16, respectively;
(c) heavy chain CDR1, CDR2, and CDR3 sequences comprising SEQ ID NOs: 19-21, respectively, and light chain CDR1, CDR2, and CDR3 sequences comprising SEQ ID NOs: 22-24, respectively;
(d) heavy chain CDR1, CDR2, and CDR3 sequences comprising SEQ ID NOs: 19-21, respectively, and light chain CDR1, CDR2, and CDR3 sequences comprising SEQ ID NOs: 25-27, respectively;

(e) heavy chain CDR1, CDR2, and CDR3 sequences comprising SEQ ID NOs: 31-33, respectively, and light chain CDR1, CDR2, and CDR3 sequences comprising SEQ ID NOs: 34-36, respectively;

(f) heavy chain CDR1, CDR2, and CDR3 sequences comprising SEQ ID NOs: 39-41, respectively, and light chain CDR1, CDR2, and CDR3 sequences comprising SEQ ID NOs: 42-44, respectively;

(g) heavy chain CDR1, CDR2, and CDR3 sequences comprising SEQ ID NOs: 39-41, respectively, and light chain CDR1, CDR2, and CDR3 sequences comprising SEQ ID NOs: 45-47, respectively;

(h) heavy chain CDR1, CDR2, and CDR3 sequences comprising SEQ ID NOs: 51-53, respectively, and light chain CDR1, CDR2, and CDR3 sequences comprising SEQ ID NOs: 54-56, respectively;

(i) heavy chain CDR1, CDR2, and CDR3 sequences comprising SEQ ID NOs: 59-61, respectively, and light chain CDR1, CDR2, and CDR3 sequences comprising SEQ ID NOs: 62-64, respectively;

(j) heavy chain CDR1, CDR2, and CDR3 sequences comprising SEQ ID NOs: 67-69, respectively, and light chain CDR1, CDR2, and CDR3 sequences comprising SEQ ID NOs: 70-72, respectively;

(k) heavy chain CDR1, CDR2, and CDR3 sequences comprising SEQ ID NOs: 75-77, respectively, and light chain CDR1, CDR2, and CDR3 sequences comprising SEQ ID NOs: 78-80, respectively;

(l) heavy chain CDR1, CDR2, and CDR3 sequences comprising SEQ ID NOs: 75-77, respectively, and light chain CDR1, CDR2, and CDR3 sequences comprising SEQ ID NOs: 81-83, respectively; or (m) heavy chain CDR1, CDR2, and CDR3 sequences comprising SEQ ID NOs: 87-89, respectively, and light chain CDR1, CDR2, and CDR3 sequences comprising SEQ ID NOs: 90-92, respectively.

Provided herein are monoclonal antibodies, or antigen binding portions thereof, which bind to OX40 and comprise heavy and light chain variable regions, wherein the heavy chain variable region comprises an amino acid sequence which is at least 90%, 95%, 96%, 97%, 98%, 99%, or 100% identical to the amino acid sequence selected from the group consisting of SEQ ID NOs: 318, 17, 28, 37, 48, 57, 65, 73, 84, and 93.

Provided herein are isolated monoclonal antibodies, or antigen binding portions thereof, which bind to OX40 and comprise heavy and light chain variable regions, wherein the light chain variable region comprises an amino acid sequence which is at least 90%, 95%, 96%, 97%, 98%, 99%, or 100% identical to the amino acid sequence selected from the group consisting of SEQ ID NOs: 94, 18, 29, 30, 38, 49, 50, 58, 66, 74, 85, 86, and 94.

Provided herein are isolated monoclonal antibodies, or antigen binding portions thereof, which bind to OX40 and comprise heavy and light chain variable region sequences at least 85% identical, for example, 90%, 95%, 96%, 97%, 98%, 99%, or 100% identical, to the amino acid sequences selected from the group consisting of: SEQ ID NOs: 318 and 94; 17 and 18; 28 and 29; 28 and 30; 37 and 38; 48 and 49; 48 and 50; 57 and 58; 65 and 66; 73 and 74; 84 and 85; 84 and 86; 93 and 94.

Provided herein are isolated monoclonal antibodies, or antigen binding portions thereof, which bind to OX40 and comprise heavy chain and light chain sequences at least 80%, 85%, 90%, 95%, 96%, 97%, 98% 99%, or 100% identical to the amino acid sequences selected from the group consisting of: SEQ ID NOs: 124 and 116; 95 and 96; 97 and 98; 99 and 100; 101 and 102; 103 and 104; 105 and 106; 107 and 108; 109 and 110; 111 and 112; 113 and 114; 115 and 116; 117 and 118; 119 and 120; 121 and 122; 123 and 116; 124 and 116; and 125 and 116.

In certain embodiments, the isolated monoclonal antibodies, or antigen binding portions thereof, (a) bind to the same epitope on OX40 as 3F4, 14B6-1, 14B6-2, 23H3, 18E9, 8B11, 20B3, or 20C1, or binds to the same epitope on OX40 as 6E1-1, 6E1-2, 14A2-1 or 14A2-2, and (b) inhibit binding of 3F4, 14B6-1, 14B6-2, 23H3, 6E1-1, 6E1-2, 18E9, 8B11, 20B3, 14A2-1, 14A2-2, and/or 20C1 to OX40 on activated T cells by at least 50%, 60%, 70%, 80% or 90% as measured by, e.g., FACS.

In certain embodiments, the anti-OX40 antibodies, or antigen binding portions thereof, bind within the regions DVVSSKPCKPCTWCNLR (SEQ ID NO: 178) or DSYK-PGVDCAPCPPGHFSPGDNQACKPWTNCTLAGK (SEQ ID NO: 179) of mature extracellular portion of human OX40 (SEQ ID NO: 2). In some embodiments, the anti-OX40 antibodies, or antigen binding portions thereof, described herein, bind to both human and cynomolgus OX40. In some embodiments, the anti-OX40 antibodies, or antigen binding portions thereof, described herein, do not bind to mouse and/or rat OX40.

In certain embodiments, the anti-OX40 antibodies, or antigen-binding portions thereof, are IgG1, IgG2, IgG3, or IgG4 antibodies, or variants thereof. In certain embodiments, methionine residues in the CDR regions of the anti-OX40 antibodies, or antigen-binding portions thereof, are substituted for amino acid residues that do not undergo oxidation. In certain embodiments, the anti-OX40 antibodies, or antigen-binding portions thereof, are human or humanized antibodies. In certain embodiments, the anti-OX40 antibodies comprise an Fc having enhanced binding to an activating FcγR.

Provided herein are isolated monoclonal antibodies, or antigen binding portions thereof, which bind to OX40 comprising a modified heavy chain constant region that comprises an IgG2 hinge and at least one of CH1, CH2 and CH3 that is not of an IgG2 isotype.

In certain embodiments, the heavy chain comprises an amino acid sequence selected from the group consisting of SEQ ID NOs: 95, 97, 99, 101, 103, 105, 107, 109, 111, 113, 115, 117, 119, 121, 123, 124 and 125, or a heavy chain that differs therefrom in at most 10 amino acids or is at least 95%, 96%, 97%, 98% or 99% identical to an amino acid sequence of SEQ ID NOs: 95, 97, 99, 101, 103, 105, 107, 109, 111, 113, 115, 117, 119, 121, 123, 124 and 125.

In certain embodiments, the light chain comprises an amino acid sequence selected from the group consisting of SEQ ID NOs: 96, 98, 100, 102, 104, 106, 108, 110, 112, 114, 116, 118, 120, and 122, or a light chain that differs therefrom in at most 10 amino acids or is at least 95%, 96%, 97%, 98% or 99% identical to an amino acid sequence of SEQ ID NOs: 96, 98, 100, 102, 104, 106, 108, 110, 112, 114, 116, 118, 120, and 122.

In certain embodiments, the anti-OX40 antibodies, or antigen-binding portions thereof, are not immunogenic.

In certain embodiments, the anti-OX40 antibodies, or antigen-binding portions thereof, lack an amino acid sequence that undergoes isomerization. For instance, if the amino acid sequence Asp-Gly is present in the heavy and/or light chain CDR sequences of the antibody, the sequence is substituted with an amino acid sequence that does not undergo isomerization. In one embodiment, the antibody comprises the heavy chain variable region CDR2 sequence set forth in SEQ ID NO: 76, but wherein the Asp or Gly in the Asp-Gly sequence (LISY<u>DG</u>SRKHYADSVKG; SEQ ID NO: 76) is replaced with an amino acid sequence that does not undergo isomerization, for example, an Asp-Ser or a Ser-Gly sequence. In another embodiment, the antibody comprises the heavy chain variable region CDR2 sequence set forth in SEQ ID NO: 88, but wherein the Asp or Gly in the Asp-Gly sequence (AIDT<u>DG</u>GTFYADSVRG; SEQ ID NO: 88) is replaced with an amino acid sequence that does not undergo isomerization, for example, a Ser-Gly, an Asp-Ala, or a Ser-Thr sequence.

Provided herein are antibodies which bind to OX40 comprising an amino acid selected from the group consisting of SEQ ID NOs: 282-296. In one embodiment, the antibodies comprise a heavy chain consisting of an amino acid sequence selected from the group consisting of SEQ ID NOs: 282-296.

Provided herein are bispecific molecules comprising an anti-OX40 antibody linked to a molecule having a second binding specificity.

Provided herein are nucleic acids encoding the heavy and/or light chain variable regions of the anti-OX40 antibodies, or antigen binding portions thereof, expression vectors comprising the nucleic acid molecules, and cells transformed with the expression vectors.

Provided herein are immunoconjugates comprising the anti-OX40 antibodies described herein, linked to an agent.

Provided herein are compositions comprising anti-OX40 antibodies, or antigen binding portions thereof, and a carrier.

Provided herein are kits comprising the anti-OX40 antibodies, or antigen binding portions thereof, and instructions for use. In certain embodiments, the kits further comprise an anti-CTLA4 antibody, anti-PD-1, or anti-PD-L1 antibody.

Provided herein is a method of preparing the anti-OX40 antibodies, comprising expressing an anti-OX40 antibody in a cell and isolating the antibody from the cell.

Provided herein is a method of stimulating an antigen-specific T cell response comprising contacting the T cell with an anti-OX40 antibody, or antigen binding portion thereof, such that an antigen-specific T cell response is stimulated.

Provided herein is a method of activating or co-stimulating a T cell, e.g., an effector T cell, comprising contacting a cell, e.g., an effector T cell, with an anti-OX40 antibody, or antigen binding portion thereof, and CD3, wherein the effector T cell is activated or co-stimulated.

Provided herein is a method of increasing IL-2 and/or IFN-γ production in and/or proliferation of a T cell comprising contacting the T cell with an effective amount of an anti-OX40 antibody, or antigen binding portion thereof.

Provided herein is a method of increasing IL-2 and/or IFN-γ production in T cells in a subject comprising administering an effective amount of an anti-OX40 antibody, or antigen binding portion thereof, bispecific molecule or conjugate comprising the anti-OX40 antibody, or composition comprising the anti-OX40 antibody, to increase IL-2 and/or IFN-γ production from the T cells.

Provided herein is a method of reducing or depleting the number of T regulatory cells in a tumor of a subject in need thereof comprising administering an effective amount of an anti-OX40 antibody, or antigen binding portion thereof, bispecific molecule or conjugate wherein the antibody, or antigen binding portion thereof, has effector or enhanced effector function, to reduce the number of T regulatory cells in the tumor.

Provided herein is a method of stimulating an immune response in a subject comprising administering an effective amount of an anti-OX40 antibody, or antigen binding portion thereof, bispecific molecule or conjugate to the subject such that an immune response in the subject is stimulated. In certain embodiments, the subject has a tumor and an immune response against the tumor is stimulated.

Provided herein is a method of inhibiting the growth of tumor cells in a subject comprising administering to the subject an anti-OX40 antibody, or antigen binding portion thereof, bispecific molecule or conjugate such that growth of the tumor is inhibited in the subject.

Provided herein is a method of treating cancer, e.g., by immunotherapy, comprising administering to a subject in need thereof a therapeutically effective amount an anti-OX40 antibody, or antigen binding portion thereof, bispecific molecule or conjugate comprising the anti-OX40 antibody, or composition comprising the anti-OX40 antibody, to treat the cancer. In certain embodiments, the cancer is selected from the group consisting of: bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer.

In certain embodiments, the methods described herein further comprise administering one or more additional therapeutics with an anti-OX40 antibody, for example, an anti-PD1 antibody, a LAG-3 antibody, a CTLA-4 antibody, and/or a PD-L1 antibody.

Provided herein is a method of detecting the presence of OX40 in a sample comprising contacting the sample with an anti-OX40 antibody, or an antigen binding portion thereof, under conditions that allow for formation of a complex between the antibody, or antigen binding portion thereof, and OX40, and detecting the formation of a complex.

Provided herein are uses of the anti-OX40 antibodies described herein for treating cancer, stimulating an immune response in a subject, stimulating an antigen-specific T cell response, activating or co-stimulating a T cell, increasing the production of cytokines, such as IL-2 and/or IFN-γ, in and/or proliferation of a T cell, reducing or depleting the number of T regulatory cells in a tumor, and/or inhibiting the growth of tumor cells. Also provided herein are uses of the anti-OX40 antibodies described herein for preparing a medicament for stimulating an immune response in a subject, stimulating an antigen-specific T cell response, activating or co-stimulating a T cell, increasing IL-2 and/or IFN-γ production in and/or proliferation of a T cell, reducing or depleting the number of T regulatory cells in a tumor, and/or inhibiting the growth of tumor cells.

Provided herein is a method of treating a solid tumor in a human subject, the method comprising administering to the subject an effective amount of an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94, wherein the method comprises at least one administration cycle, wherein the cycle is a period of two weeks, wherein for each of the at least one cycles, one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg.

In one embodiment, the method comprises further administering an anti-PD-1 antibody comprising CDR1, CDR2 and CDR3 domains of the heavy chain variable region having the sequence set forth in SEQ ID NO: 301, and CDR1, CDR2 and CDR3 domains of the light chain variable region having the sequence set forth in SEQ ID NO: 302, wherein the method comprises at least one administration cycle, wherein the cycle is a period of two, three, or four weeks, wherein for each of the at least one cycles, one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg, and one dose of the anti-PD-1 antibody is administered at a dose of 240, 360, or 480 mg or a dose of about 240, 360, or 480 mg.

In another embodiment, the method comprises further administering an anti-CTLA-4 antibody comprising CDR1, CDR2 and CDR3 domains of the heavy chain variable region having the sequence set forth in SEQ ID NO: 309, and CDR1, CDR2 and CDR3 domains of the light chain variable region having the sequence set forth in SEQ ID NO: 310, wherein the method comprises at least one administration cycle, wherein the cycle is a period of three weeks, wherein for each of the at least one cycles, one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg, and one dose of the anti-CTLA-4 antibody is administered at a dose of 1 mg/kg or a dose of about 1 mg/kg, wherein the anti-OX40 antibody is administered together with the anti-CTLA-4 antibody for at least one cycle, followed by anti-OX40 antibody monotherapy for at least one cycle. In some embodiments, the treatment consists of 8 cycles. In one embodiment, the anti-OX40 antibody is administered together with the anti-CTLA-4 antibody for the first 4 cycles, followed by anti-OX40 antibody monotherapy for the last 4 cycles.

In some embodiments, the anti-OX40 antibody comprises heavy and light chain sequences set forth in SEQ ID NOs: 124 and 116, respectively.

In certain embodiments, the anti-OX40 antibody, or anti-OX40 antibody and anti-PD-1 or anti-CTLA-4 antibody, are formulated for intravenous administration. In some embodiments, the anti-OX40 and anti-PD-1 or anti-CTLA-4 antibody are formulated together. In other embodiments, the anti-OX40 and anti-PD-1 or anti-CTLA-4 antibody are formulated separately.

In some embodiments, the treatment consists of 8 cycles. In one embodiment, the anti-OX40 antibody, or anti-OX40 antibody and anti-PD-1 or anti-CTLA-4 antibody, are administered on Day 1 of each cycle.

In certain embodiments, the anti-OX40 antibody is administered prior to administration of the anti-PD-1 or anti-CTLA-4 antibody. In one embodiment, the anti-OX40 antibody is administered within about 30 minutes prior to administration of the anti-PD-1 or anti-CTLA-4 antibody. In other embodiments, the anti-OX40 antibody is administered after administration of the anti-PD-1 or anti-CTLA-4 antibody. In yet other embodiments, the anti-OX40 antibody is administered concurrently with the anti-PD-1 or anti-CTLA-4 antibody.

In certain embodiments, the treatment produces at least one therapeutic effect chosen from a reduction in size of a tumor, reduction in number of metastatic lesions over time, complete response, partial response, and stable disease. In some embodiments, the tumor is associated with a cancer selected from the group consisting of: cervical cancer, bladder cancer, colorectal cancer, and ovarian cancer.

Other features and advantages of the instant disclosure will be apparent from the following detailed description and examples, which should not be construed as limiting.

BRIEF DESCRIPTION OF THE FIGURES

FIG. 1A shows the nucleotide sequence (SEQ ID NO: 126) and amino acid sequence (SEQ ID NO: 17) of the heavy chain variable region of the 3F4 human monoclonal antibody. The CDR1 (SEQ ID NO: 11), CDR2 (SEQ ID NO: 12) and CDR3 (SEQ ID NO: 13) regions are delineated and the V, D and J germline derivations are indicated.

FIG. 1B shows the nucleotide sequence (SEQ ID NO: 127) and amino acid sequence (SEQ ID NO: 18) of the kappa light chain variable region of the 3F4 human monoclonal antibody. The CDR1 (SEQ ID NO: 14), CDR2 (SEQ ID NO: 15) and CDR3 (SEQ ID NO: 16) regions are delineated and the V and J germline derivations are indicated.

FIG. 2A shows the nucleotide sequence (SEQ ID NO: 128) and amino acid sequence (SEQ ID NO: 28) of the heavy chain variable region of the 14B6 (14B6-1 and 14B6-2) human monoclonal antibody. The CDR1 (SEQ ID NO: 19), CDR2 (SEQ ID NO: 20) and CDR3 (SEQ ID NO: 21) regions are delineated and the V, D and J germline derivations are indicated.

FIG. 2B shows the nucleotide sequence (SEQ ID NO: 129) and amino acid sequence (SEQ ID NO: 29) of the kappa light chain variable region of the 14B6-1 human monoclonal antibody. The CDR1 (SEQ ID NO: 22), CDR2 (SEQ ID NO: 23) and CDR3 (SEQ ID NO: 24) regions are delineated and the V and J germline derivations are indicated.

FIG. 2C shows the nucleotide sequence (SEQ ID NO: 130) and amino acid sequence (SEQ ID NO: 30) of the kappa light chain variable region of the 14B6-2 human monoclonal antibody. The CDR1 (SEQ ID NO: 26), CDR2 (SEQ ID NO: 27) and CDR3 (SEQ ID NO: 28) regions are delineated and the V and J germline derivations are indicated.

FIG. 3A shows the nucleotide sequence (SEQ ID NO: 131) and amino acid sequence (SEQ ID NO: 37) of the heavy chain variable region of the 23H3 human monoclonal antibody. The CDR1 (SEQ ID NO: 31), CDR2 (SEQ ID NO: 32) and CDR3 (SEQ ID NO: 33) regions are delineated and the V, D and J germline derivations are indicated.

FIG. 3B shows the nucleotide sequence (SEQ ID NO: 132) and amino acid sequence (SEQ ID NO: 38) of the kappa light chain variable region of the 23H3 human monoclonal antibody. The CDR1 (SEQ ID NO: 34), CDR2 (SEQ ID NO: 35) and CDR3 (SEQ ID NO: 36) regions are delineated and the V and J germline derivations are indicated.

FIG. 4A shows the nucleotide sequence (SEQ ID NO: 133) and amino acid sequence (SEQ ID NO: 48) of the heavy chain variable region of the 6E1 (6E1-1 and 6E1-2) human monoclonal antibody. The CDR1 (SEQ ID NO: 39), CDR2 (SEQ ID NO: 40) and CDR3 (SEQ ID NO: 41) regions are delineated and the V, D and J germline derivations are indicated.

FIG. 4B shows the nucleotide sequence (SEQ ID NO: 134) and amino acid sequence (SEQ ID NO: 49) of the kappa light chain variable region of the 6E1-1 human monoclonal antibody. The CDR1 (SEQ ID NO: 42), CDR2

Figure 11A:
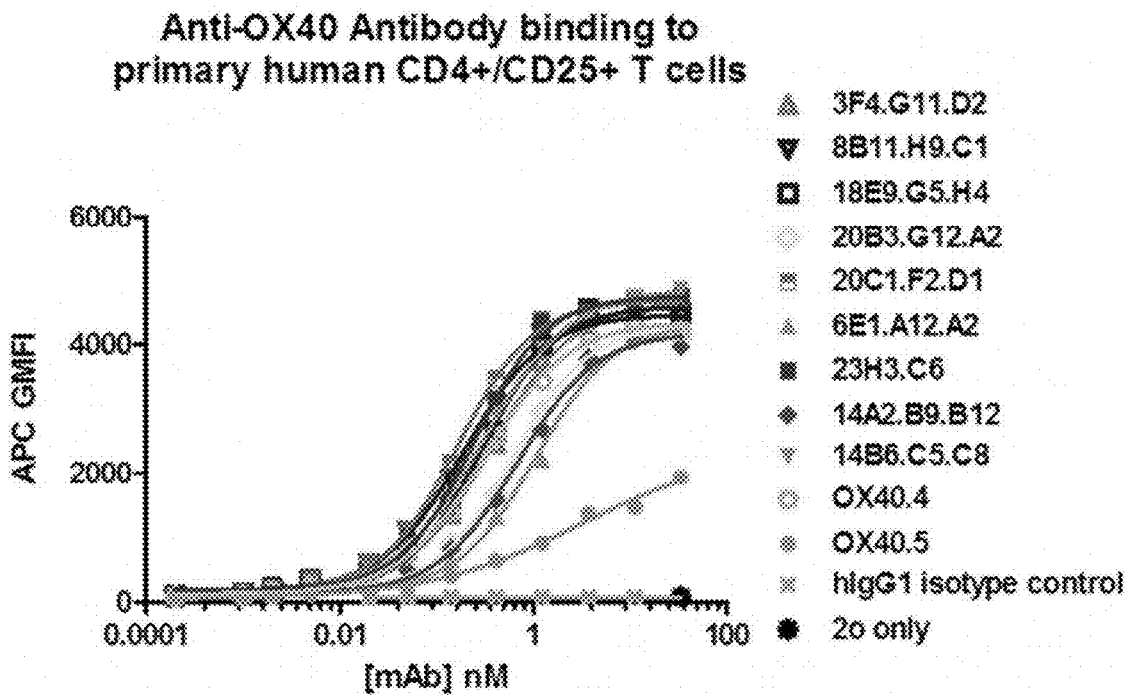

(SEQ ID NO: 43) and CDR3 (SEQ ID NO: 44) regions are delineated and the V and J germline derivations are indicated.

FIG. 4C shows the nucleotide sequence (SEQ ID NO: 135) and amino acid sequence (SEQ ID NO: 50) of the kappa light chain variable region of the 6E1-2 human monoclonal antibody. The CDR1 (SEQ ID NO: 45), CDR2 (SEQ ID NO: 46) and CDR3 (SEQ ID NO: 47) regions are delineated and the V and J germline derivations are indicated.

FIG. 5A shows the nucleotide sequence (SEQ ID NO: 136) and amino acid sequence (SEQ ID NO: 57) of the heavy chain variable region of the 18E9 human monoclonal antibody. The CDR1 (SEQ ID NO: 51), CDR2 (SEQ ID NO: 52) and CDR3 (SEQ ID NO: 53) regions are delineated and the V, D and J germline derivations are indicated.

FIG. 5B shows the nucleotide sequence (SEQ ID NO: 137) and amino acid sequence (SEQ ID NO: 58) of the kappa light chain variable region of the 18E9 human monoclonal antibody. The CDR1 (SEQ ID NO: 54), CDR2 (SEQ ID NO: 55) and CDR3 (SEQ ID NO: 56) regions are delineated and the V and J germline derivations are indicated.

FIG. 6A shows the nucleotide sequence (SEQ ID NO: 138) and amino acid sequence (SEQ ID NO: 65) of the heavy chain variable region of the 8B11 human monoclonal antibody. The CDR1 (SEQ ID NO: 59), CDR2 (SEQ ID NO: 60) and CDR3 (SEQ ID NO: 61) regions are delineated and the V, D and J germline derivations are indicated.

FIG. 6B shows the nucleotide sequence (SEQ ID NO: 139) and amino acid sequence (SEQ ID NO: 66) of the kappa light chain variable region of the 8B11 human monoclonal antibody. The CDR1 (SEQ ID NO: 62), CDR2 (SEQ ID NO: 63) and CDR3 (SEQ ID NO: 64) regions are delineated and the V and J germline derivations are indicated.

FIG. 7A shows the nucleotide sequence (SEQ ID NO: 140) and amino acid sequence (SEQ ID NO: 73) of the heavy chain variable region of the 20B3 human monoclonal antibody. The CDR1 (SEQ ID NO: 67), CDR2 (SEQ ID NO: 68) and CDR3 (SEQ ID NO: 69) regions are delineated and the V, D and J germline derivations are indicated.

FIG. 7B shows the nucleotide sequence (SEQ ID NO: 141) and amino acid sequence (SEQ ID NO: 74) of the kappa light chain variable region of the 20B3 human monoclonal antibody. The CDR1 (SEQ ID NO: 70), CDR2 (SEQ ID NO: 71) and CDR3 (SEQ ID NO: 72) regions are delineated and the V and J germline derivations are indicated.

FIG. 8A shows the nucleotide sequence (SEQ ID NO: 142) and amino acid sequence (SEQ ID NO: 84) of the heavy chain variable region of the 14A2 (14A2-1 and 14A2-2) human monoclonal antibody. The CDR1 (SEQ ID NO: 75), CDR2 (SEQ ID NO: 76) and CDR3 (SEQ ID NO: 77) regions are delineated and the V, D and J germline derivations are indicated.

FIG. 8B shows the nucleotide sequence (SEQ ID NO: 143) and amino acid sequence (SEQ ID NO: 85) of the kappa light chain variable region of the 14A2-1 human monoclonal antibody. The CDR1 (SEQ ID NO: 78), CDR2 (SEQ ID NO: 79) and CDR3 (SEQ ID NO: 80) regions are delineated and the V and J germline derivations are indicated.

FIG. 8C shows the nucleotide sequence (SEQ ID NO: 144) and amino acid sequence (SEQ ID NO: 86) of the kappa light chain variable region of the 14A2-2 human monoclonal antibody. The CDR1 (SEQ ID NO: 81), CDR2 (SEQ ID NO: 82) and CDR3 (SEQ ID NO: 83) regions are delineated and the V and J germline derivations are indicated.

FIG. 9A shows the nucleotide sequence (SEQ ID NO: 145) and amino acid sequence (SEQ ID NO: 93) of the heavy chain variable region of the 20C1 human monoclonal antibody. The CDR1 (SEQ ID NO: 87), CDR2 (SEQ ID NO: 88) and CDR3 (SEQ ID NO: 89) regions are delineated and the V, D and J germline derivations are indicated.

FIG. 9B shows the nucleotide sequence (SEQ ID NO: 146) and amino acid sequence (SEQ ID NO: 94) of the kappa light chain variable region of the 20C1 human monoclonal antibody. The CDR1 (SEQ ID NO: 90), CDR2 (SEQ ID NO: 91) and CDR3 (SEQ ID NO: 92) regions are delineated and the V and J germline derivations are indicated.

Figure 10B:
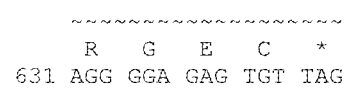

FIG. 10A shows the nucleotide sequence (SEQ ID NO: 176) and amino acid sequence (SEQ ID NO: 124) of the heavy chain of the OX40.21 human monoclonal antibody. The nucleotide sequence (SEQ ID NO: 168) and amino acid sequence (SEQ ID NO: 116) of the light chain is shown in FIG. 10B.

FIGS. 11A-11D show binding curves and $EC_{50}$s (in nM) of various anti-OX40 antibodies for activated human T cells, with hIgG1 and secondary antibodies serving as controls, as assessed by FACS.

Figure 12A:
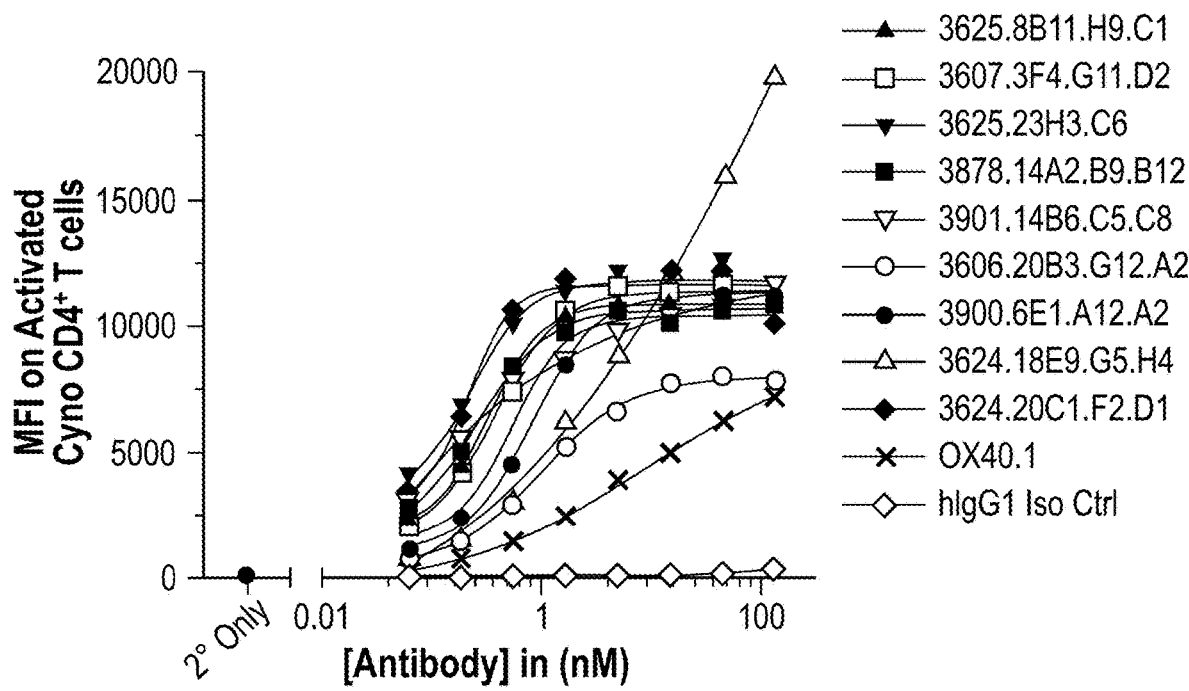
Figure 12B:
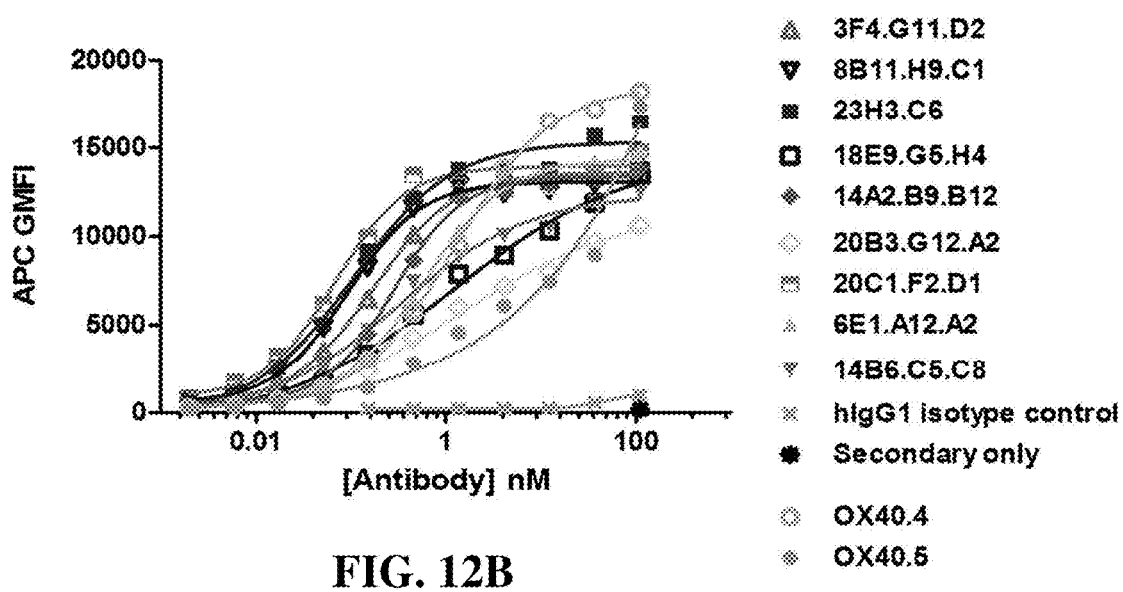
Figure 12C:
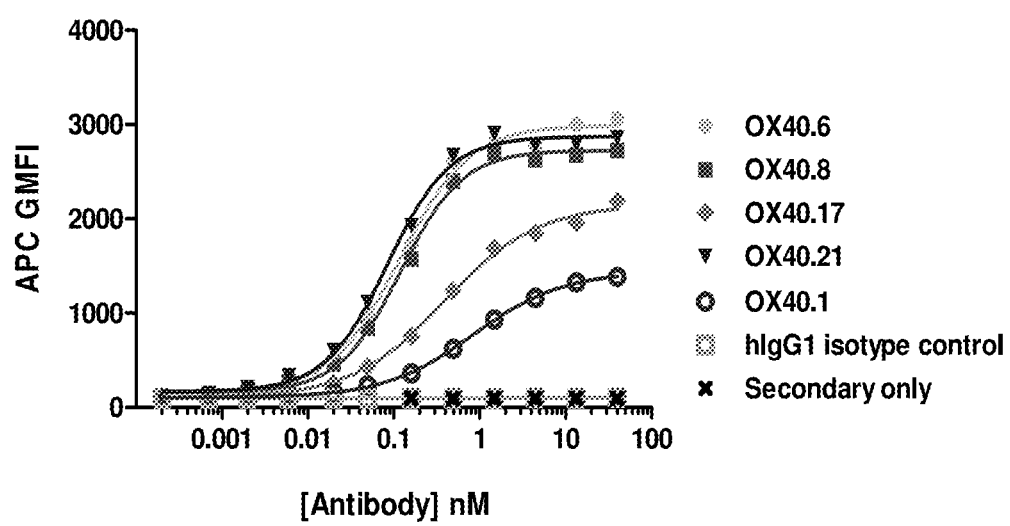

FIGS. 12A-12C show binding curves and $EC_{50}$s (in nM) of various anti-OX40 antibodies for activated cynomolgus T cells, with hIgG1 and secondary antibodies serving as controls, as assessed by FACS.

Figure 13A:
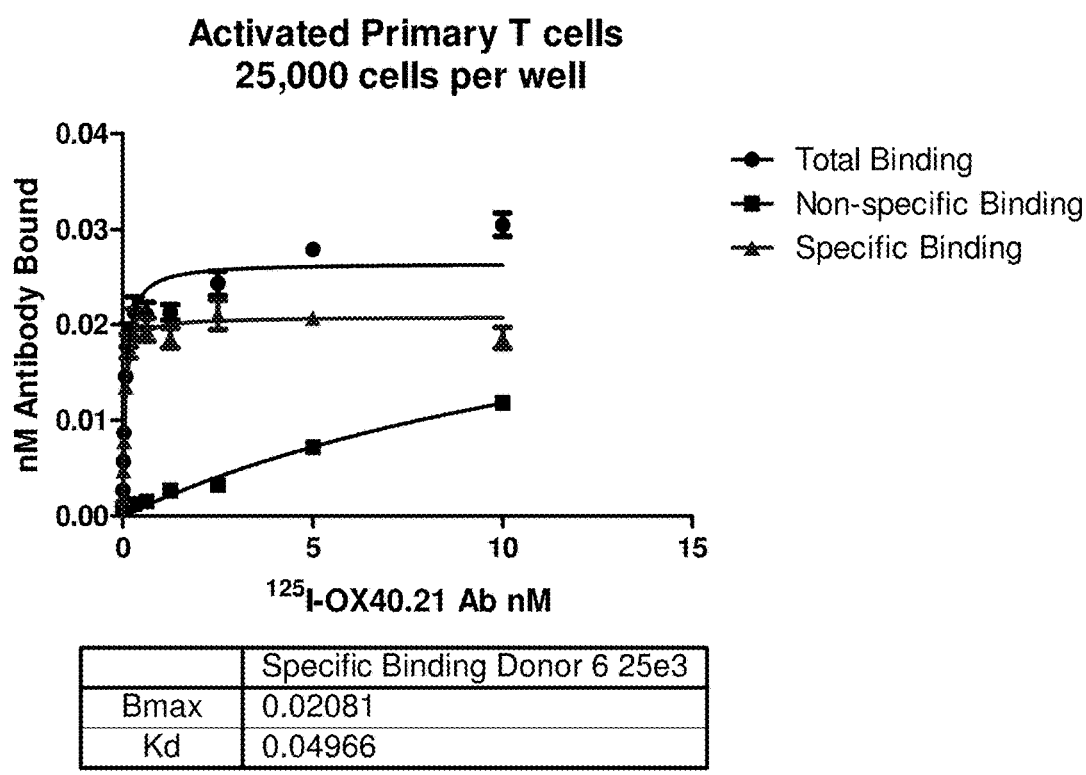
Figure 13B:
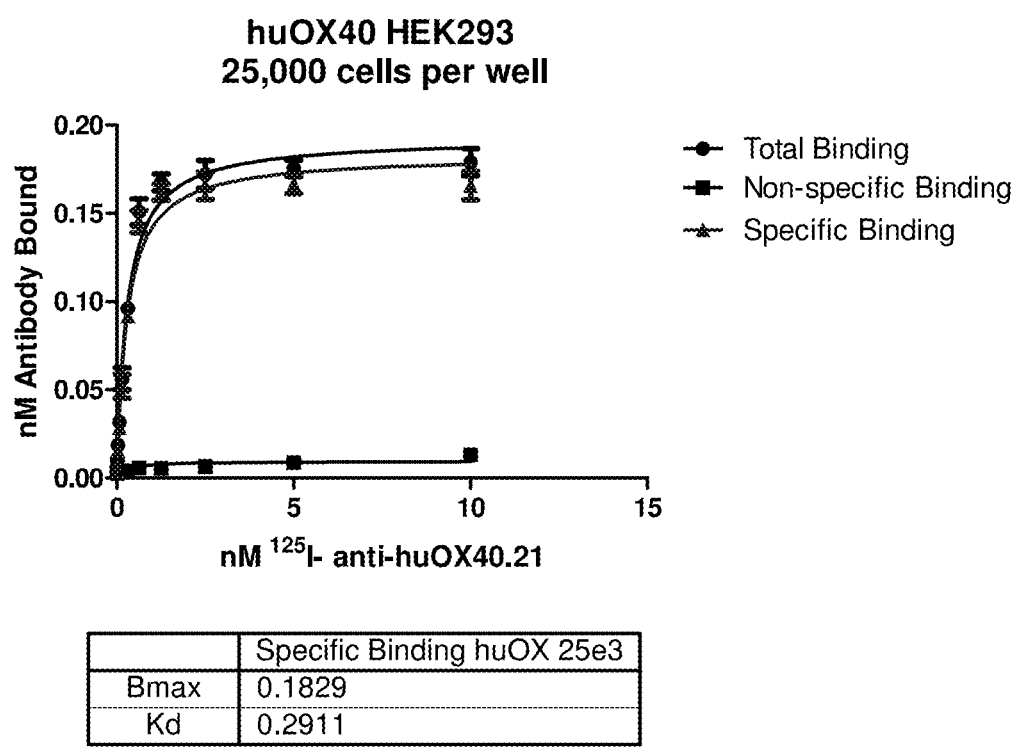
Figure 13C:
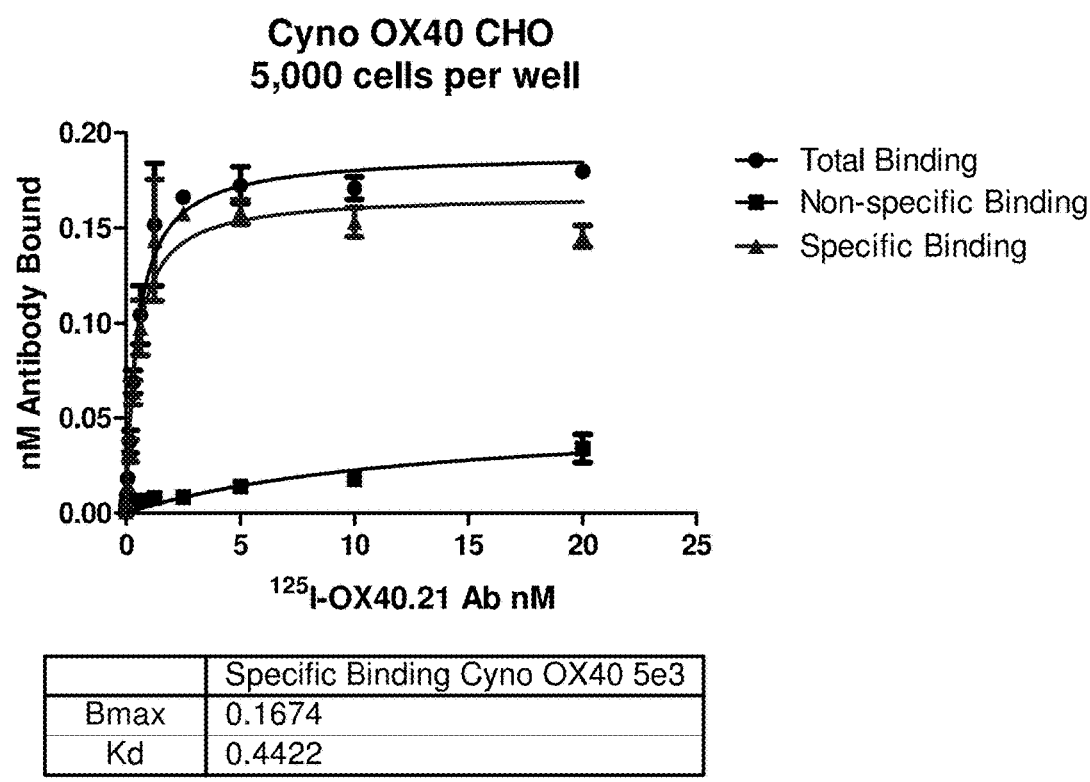

FIGS. 13A-13C show binding curves and $K_D$s of the anti-OX40 antibody, OX40.21, for activated human T cells, HEK293 cells overexpressing human OX40, and CHO cells overexpressing cynomolgus monkey OX40, as assessed by Scatchard analysis.

Figure 14A:
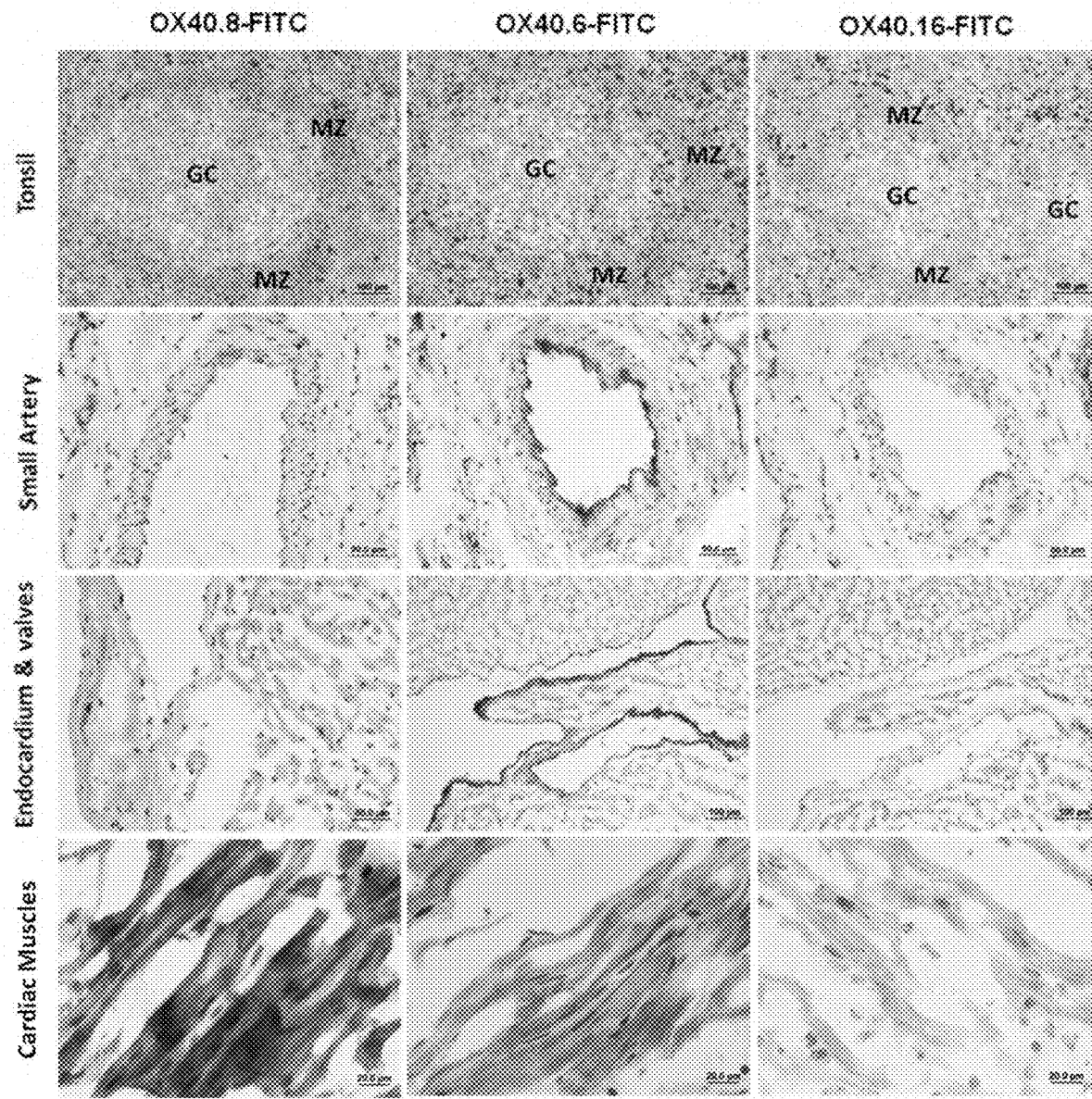

FIG. 14A shows immunohistological staining of various acetone-fixed frozen human tissue sections with the anti-OX40 antibodies OX40.8, OX40.6, and OX40.16. Images show representative staining at an antibody concentration of 1 µg/ml for hyperplasic tonsil and 5 µg/ml for other tissues, with the exception of OX40.16 at 10 µg/ml in the endocardium and valves. While all three antibodies positively stained a small subset of lymphocytes in the tonsil, OX40.8 also stained myofilament-like structures in the heart and OX40.6 stained the cardiac muscles, endothelium/subendothelium matrix in small arteries in the tonsil, and endocardium and valves in the heart. GC, germinal center; MZ, mantle zone.

Figure 14B:
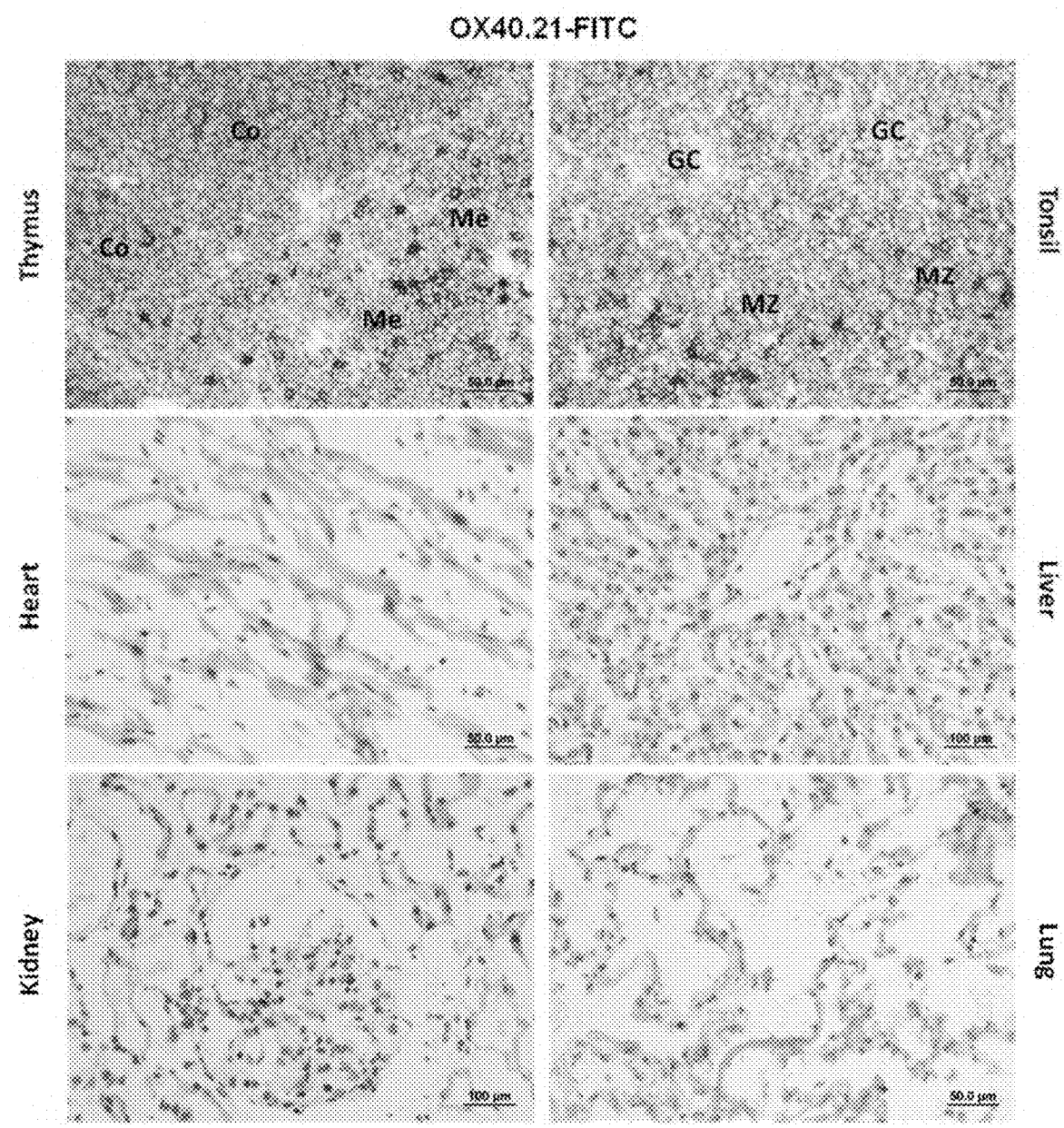

FIG. 14B shows immunostaining of various acetone-fixed frozen human tissue sections with the anti-OX40 antibody OX40.21 (a variant of OX40.16). Images show representative staining at an antibody concentration of 5 µg/ml. The antibody positively stained a small subset of lymphocytes in the tonsil and thymus. The positive cells in the tonsil were distributed in the germinal center, mantle zone, and interfollicular region, while the positive cells in the thymus were primarily localized in the medulla. No specific staining was observed in the heart, liver, kidney, and lung. GC, germinal center; Me, medulla; MZ, mantle zone.

Figure 15A:
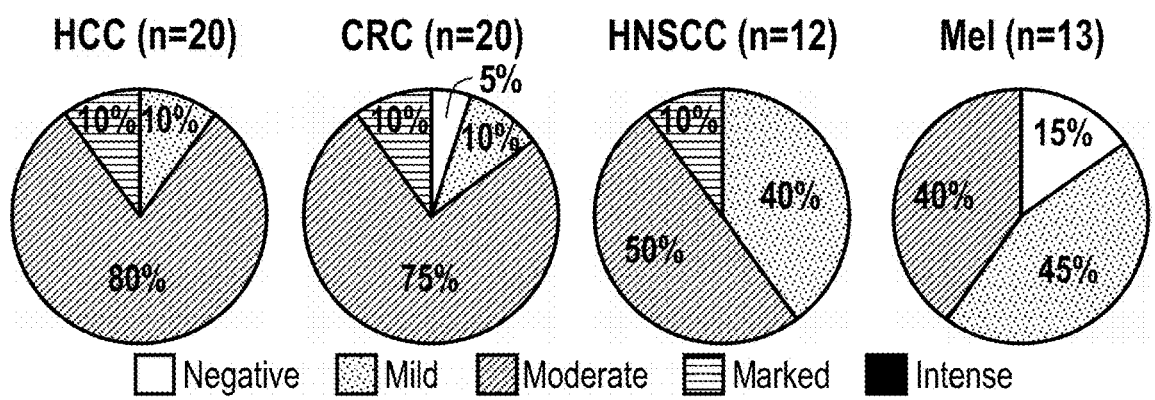

FIG. 15A shows the distribution of OX40+ tumor infiltrating lymphocytes in hepatocellular carcinoma (HCC), colorectal carcinoma (CRC), head and neck squamous cell carcinoma (HNSCC), and melanoma (Mel). A manual score of 12 to 20 cases for each tumor type was performed by estimation of number of positive cells under the 20× objective of a microscope. Minimum, <1 cells per 20× objective field; Mild, 1~<10 cells per 20× objective field; Moderate, 10-<50 cells per 20× objective field; Marked, 50-<200 cells per 20× objective; Intense, >200 cells per 20× objective field.

Figure 15B:
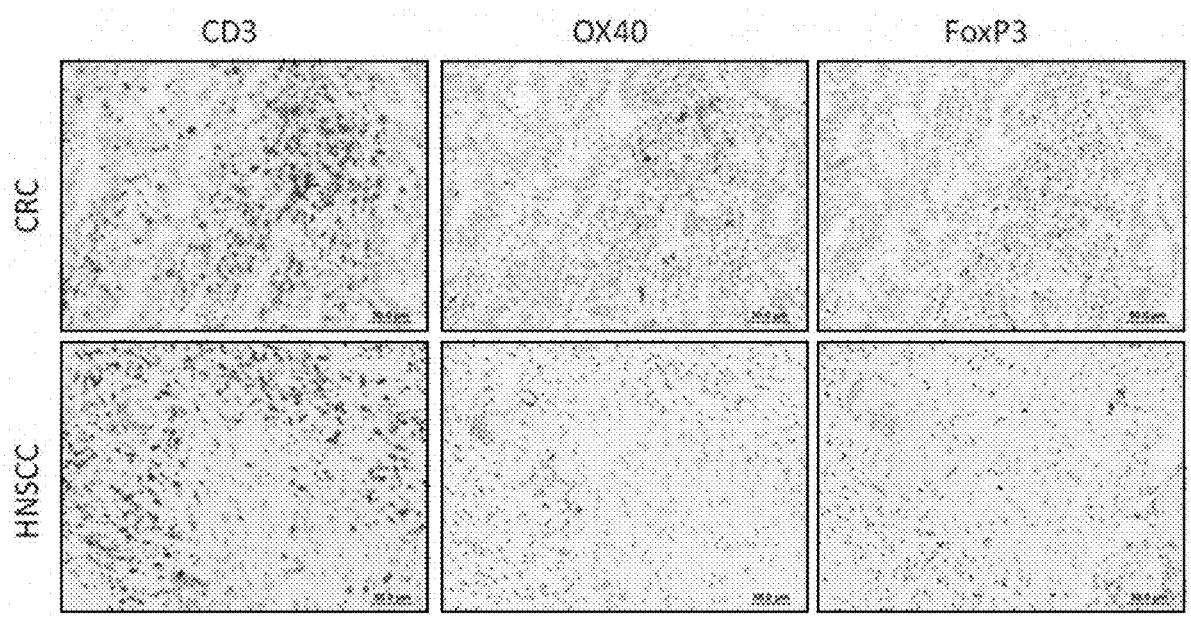
Figure 15C:
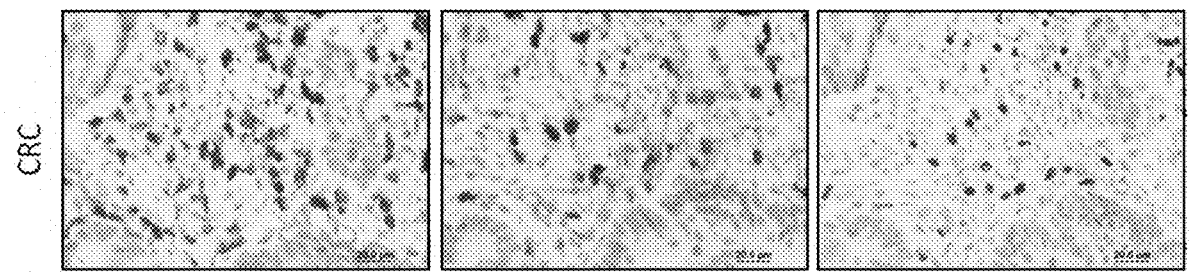

FIGS. 15B and 15C shows immunohistological staining for CD3, FoxP3, and OX40 on adjacent FFPE sections from colorectal carcinoma (CRC) and head and neck squamous cell carcinoma (HNSCC) samples. FIG. 15B is a low power view, showing that both OX40+ and FoxP3+ TILs are a small fraction of CD3+ TILs and primarily distributed in tumor stroma. FIG. 15C is a higher power view showing potential partial co-localization of OX40+ and FoxP3+ (Treg) TILs in CRC.

Figure 16:
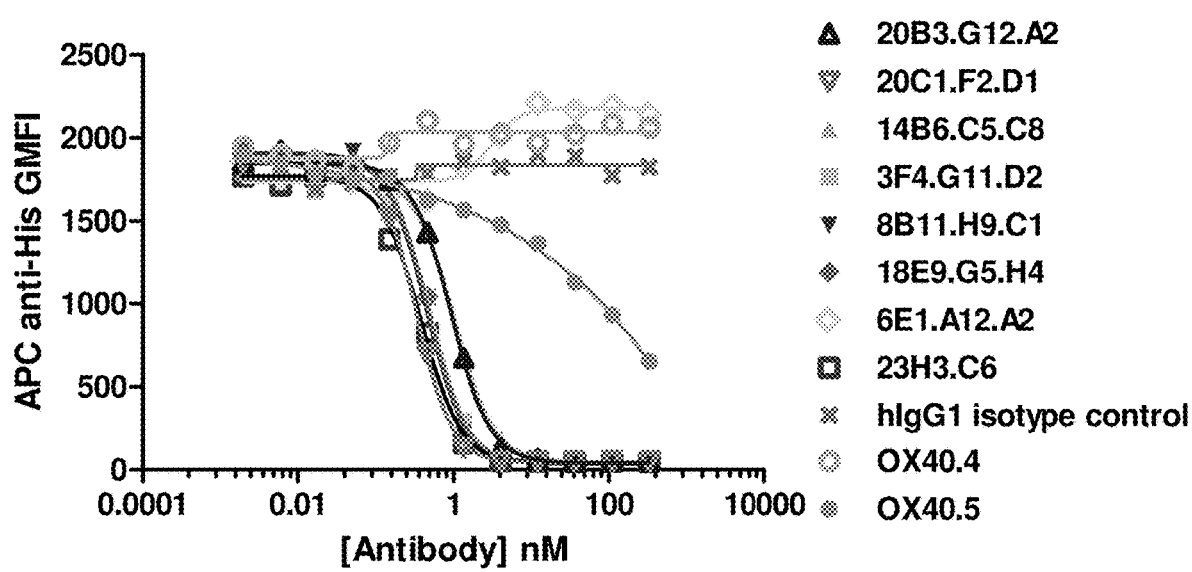

FIG. 16 shows the ability of various anti-OX40 antibodies to inhibit the binding of OX40 ligand (OX40-L) to human OX40-transfected 293 cells ("hOX40-293 cells"), with hIgG1 as the control.

Figure 17:
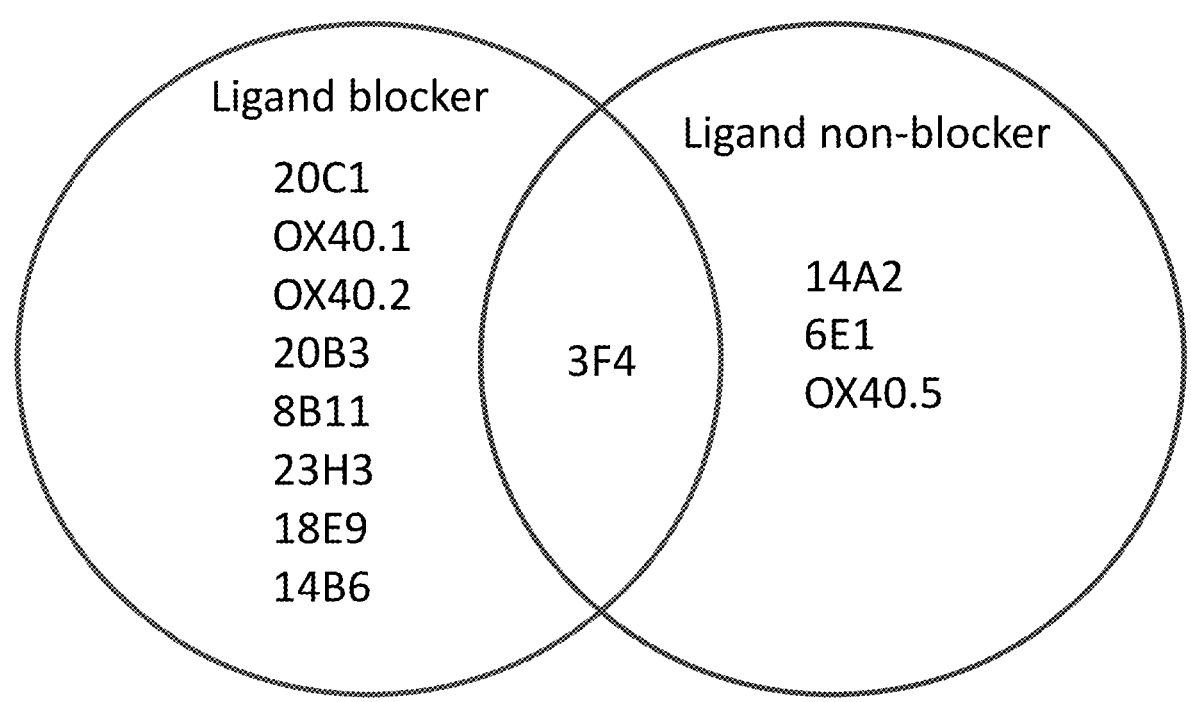

FIG. 17 summarizes the OX40-L blocking relationships between various anti-OX40 antibodies.

Figure 18:
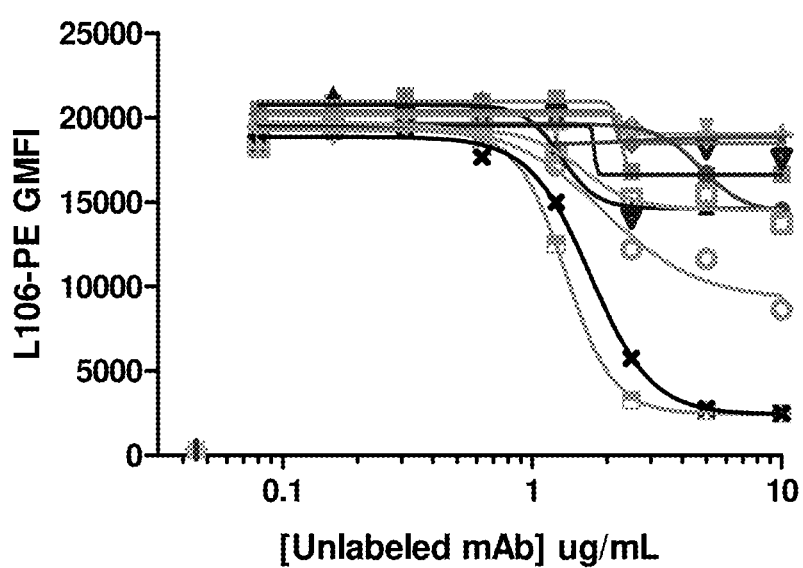

FIG. 18 shows the ability of various anti-OX40 antibodies to inhibit the binding of the anti-OX40 antibody clone L106 to hOX40-293 cells, as assessed by FACS, with PE-labeled L106 only, PE-labeled mIgG1, and unstained cells as controls.

Figure 19A:
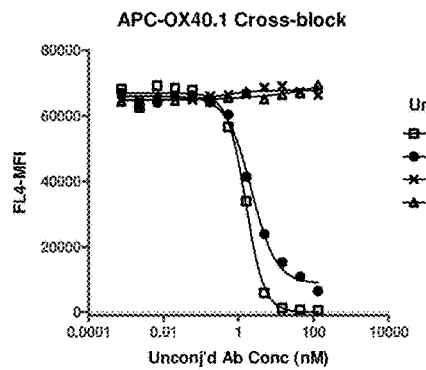
Figure 19B:
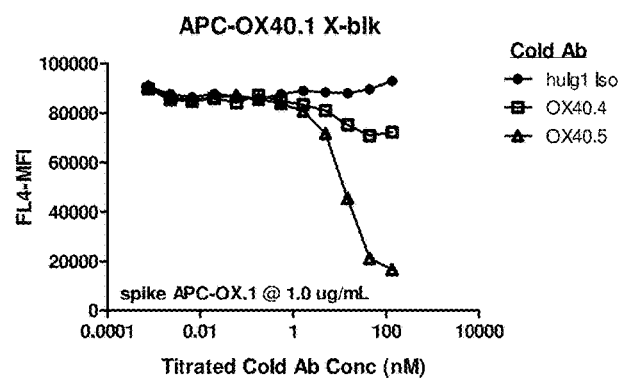
Figure 19C:
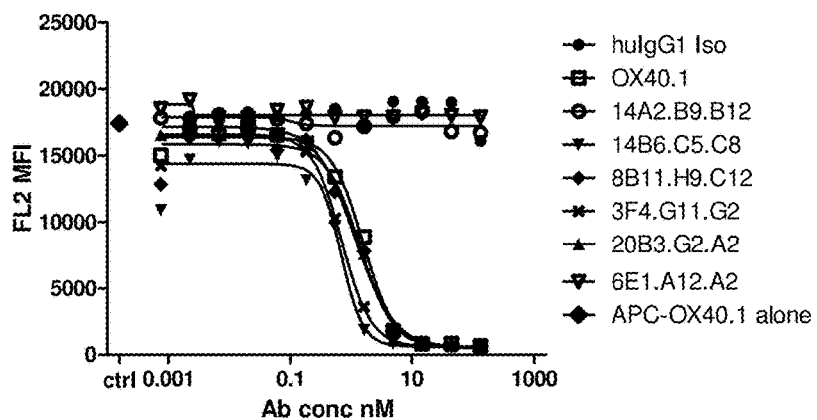

FIGS. 19A-19C show the ability of various anti-OX40 antibodies to inhibit the binding of allophycocyanin (APC)-conjugated OX40.1 antibody to hOX40-293 (FIGS. 19A and 19B) or hOX40-HT1080 cells (FIG. 19C), as assessed by FACS. hIgG1 and/or hIgG4 were used as controls.

FIGS. 19D-19G show the ability of various anti-OX40 antibodies to inhibit the binding of biotin-conjugated OX40.4 or OX40.5 antibody to hOX40-293 cells. hIgG1 and streptavidin-APC were used as controls.

Figure 19D:
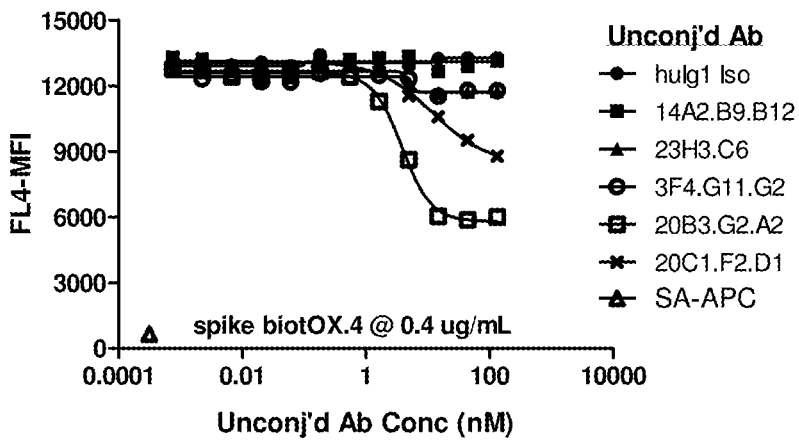
Figure 19E:
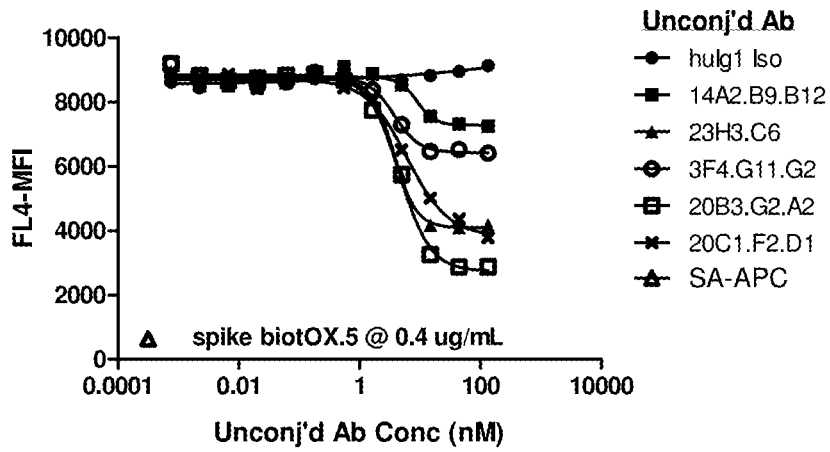
Figure 19F:
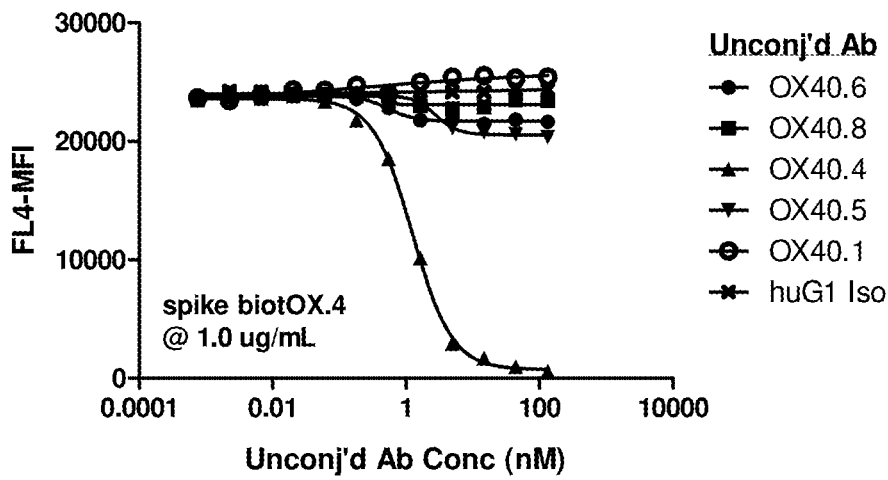
Figure 19G:
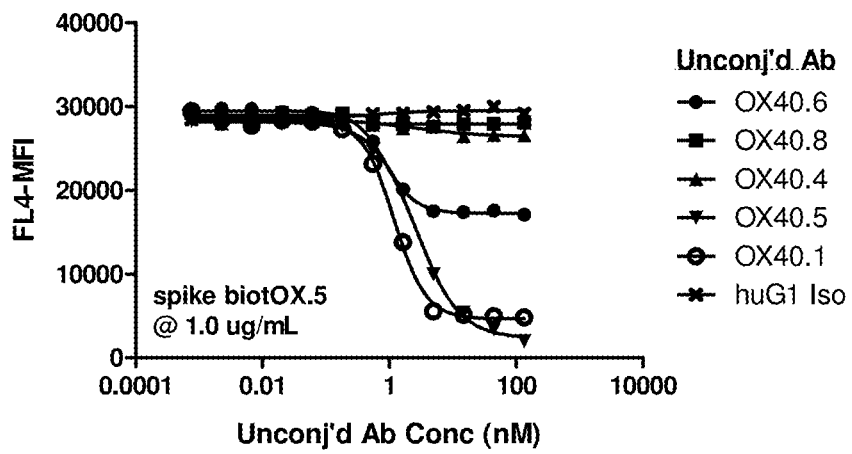
Figure 19H:
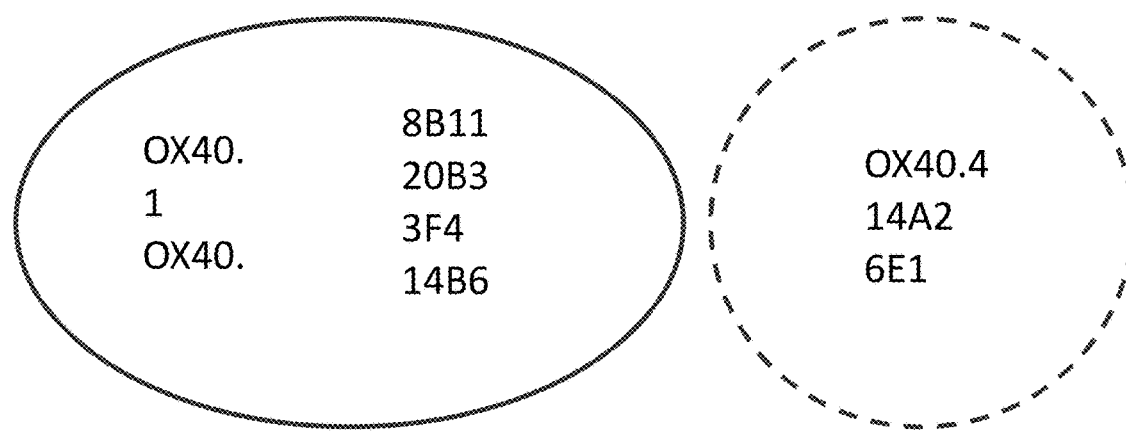

FIG. 19H summarize the epitope bins in relation to OX40.1 based on results shown in FIGS. 19A-19C.

Figure 19I:
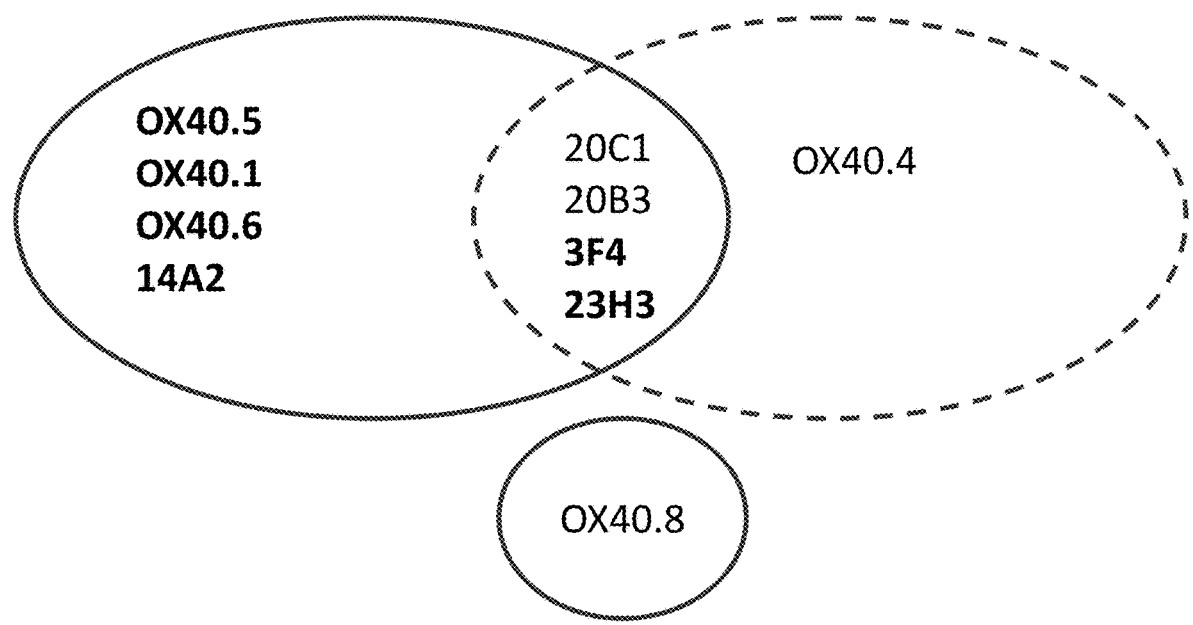

FIG. 19I summarizes the epitope bins in relation to OX40.5 or OX40.4 based on results shown in FIGS. 19D-19G.

Figure 20A:
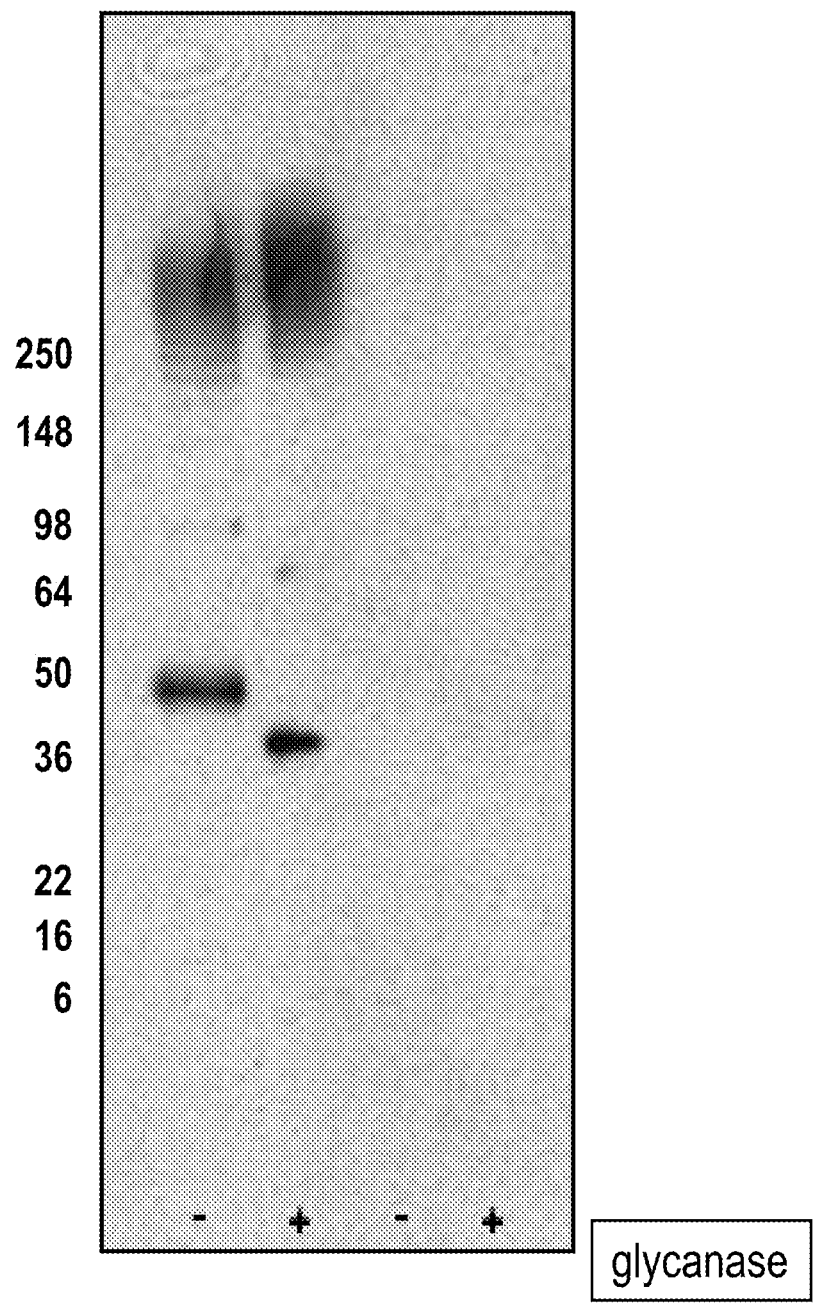

FIG. 20A shows that OX40.21 binds only to non-reduced human OX40, regardless of the presence of N-linked sugars.

FIGS. 20B and 20C show two N-glycopeptides that were identified by peptide mapping after deglycosylation: 60% occupancy for both AspN118 (FIG. 20B) and AspN12 (FIG. 20C).

Figure 20D:
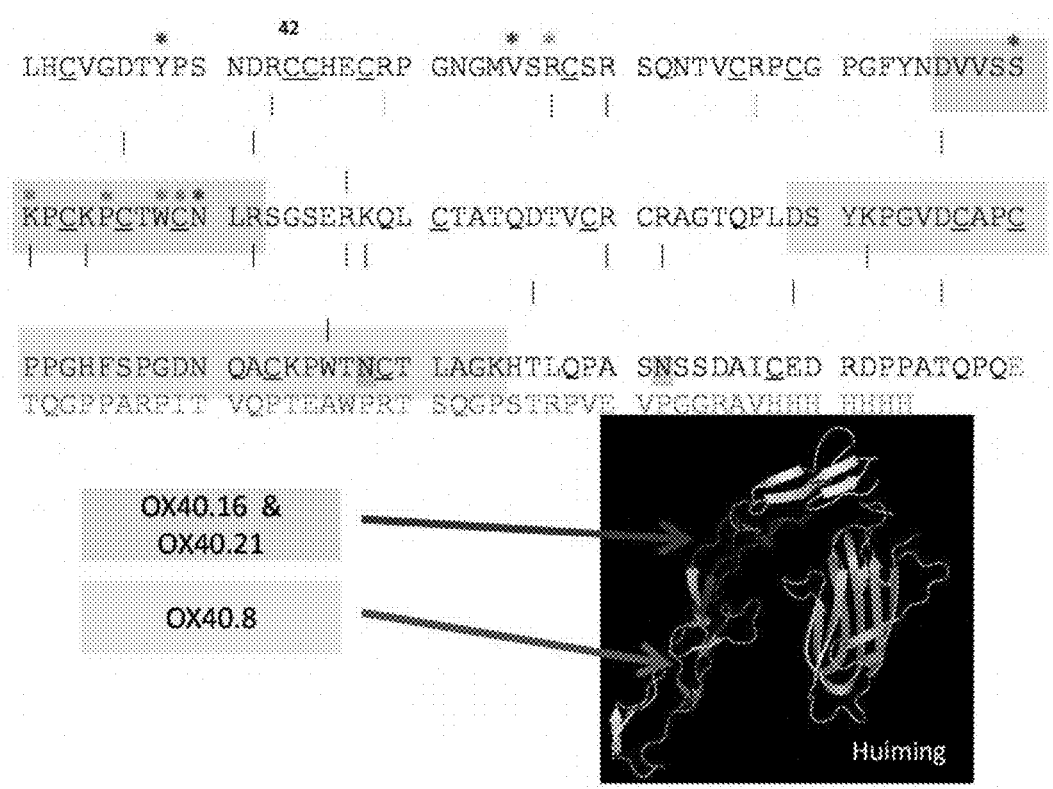

FIG. 20D depicts the regions in OX40 bound by OX40.16, OX40.21, and OX40.8.

Figure 20E:
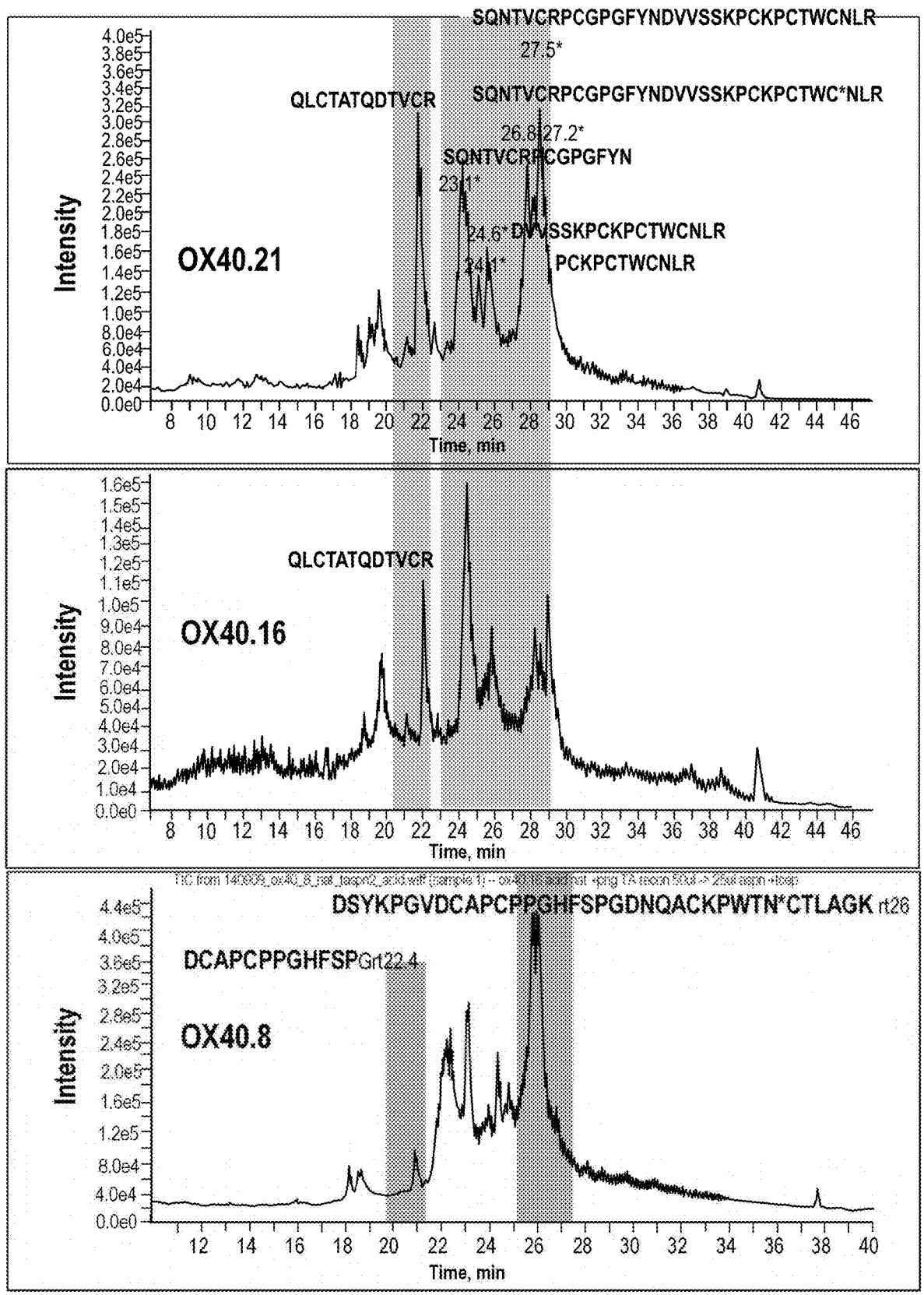
Figure 21A:
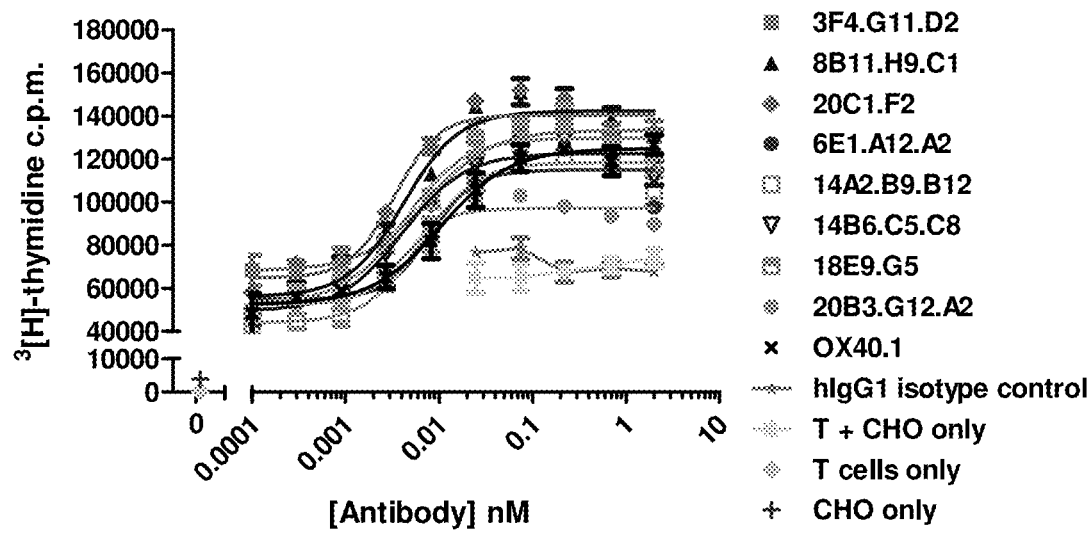
Figure 21B:
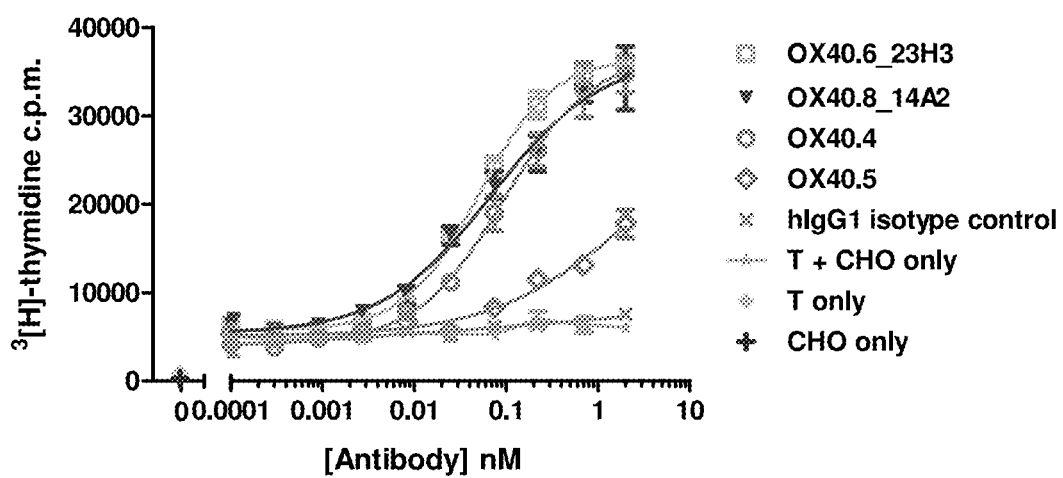
Figure 21C:
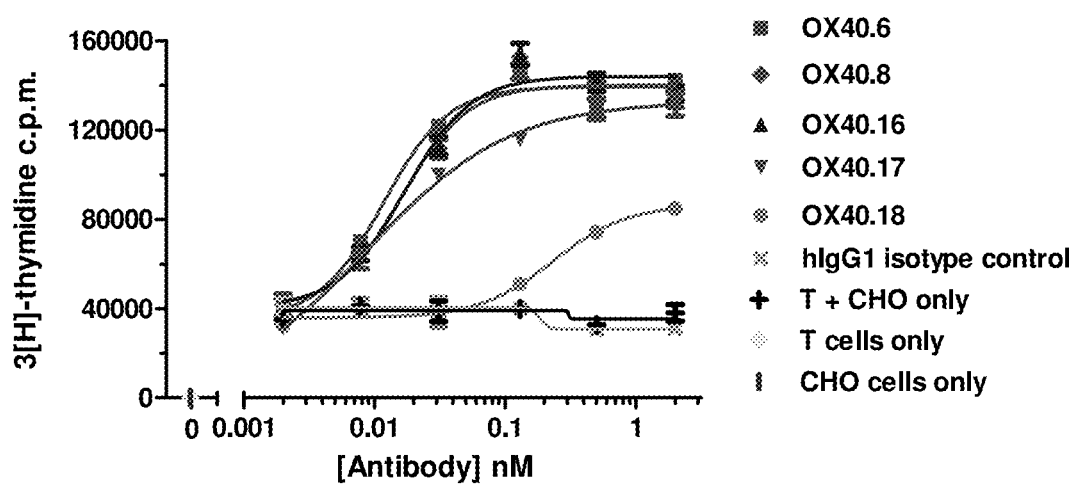
Figure 21D:
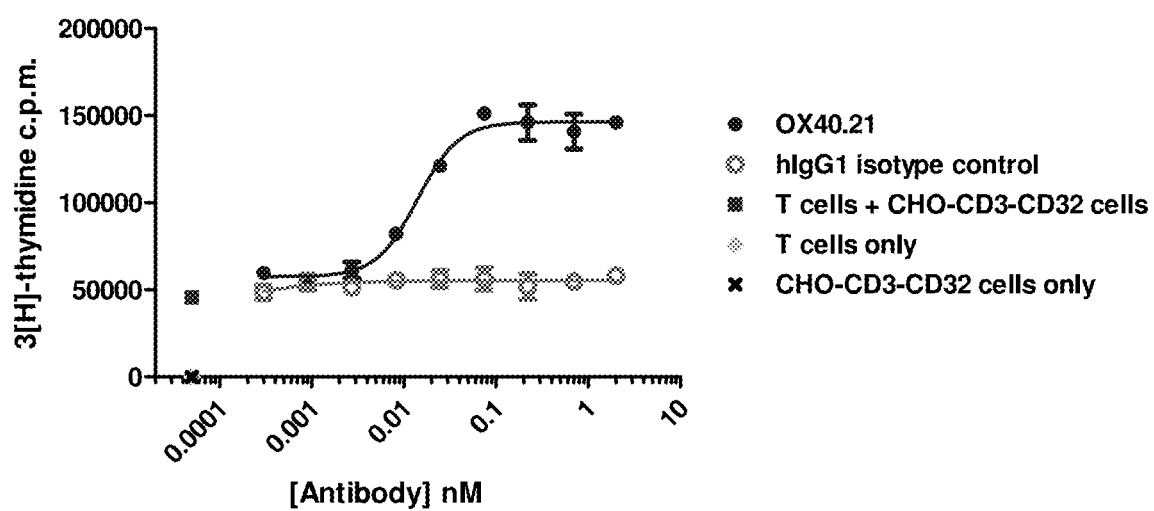
Figure 22A:
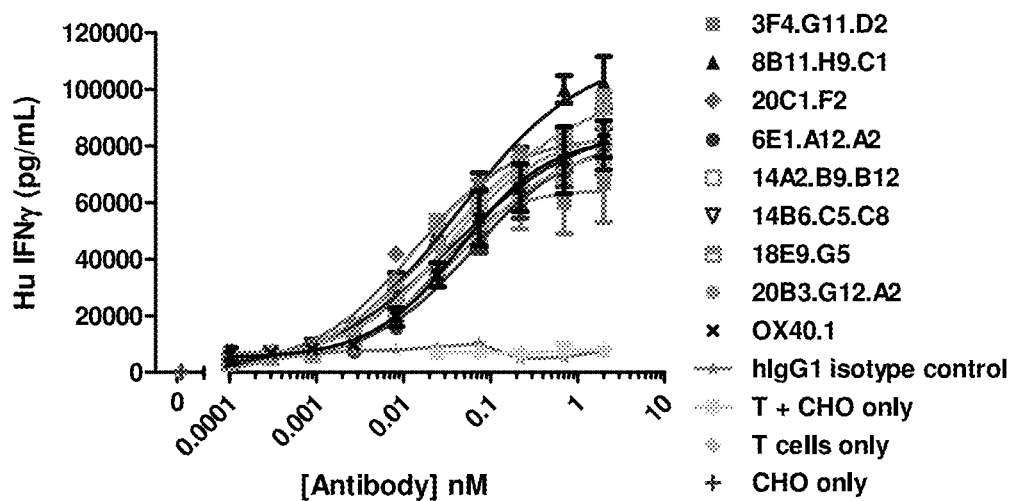
Figure 22B:
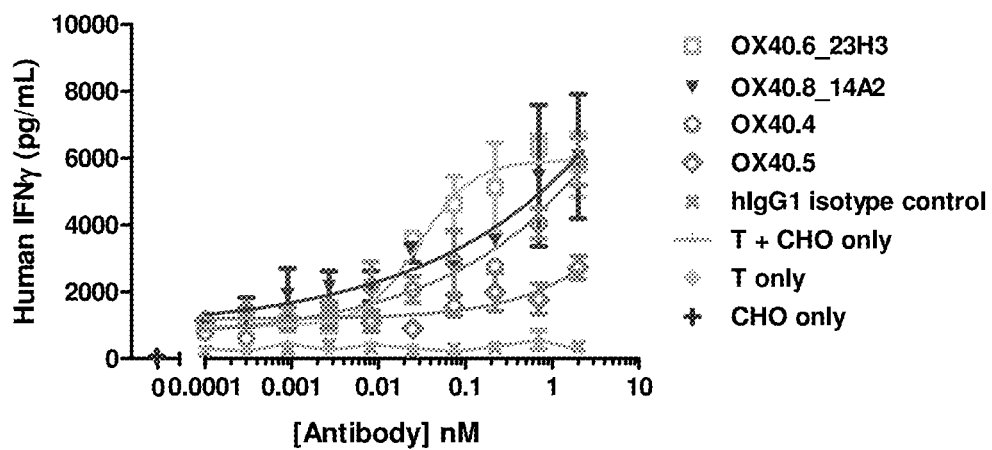
Figure 22C:
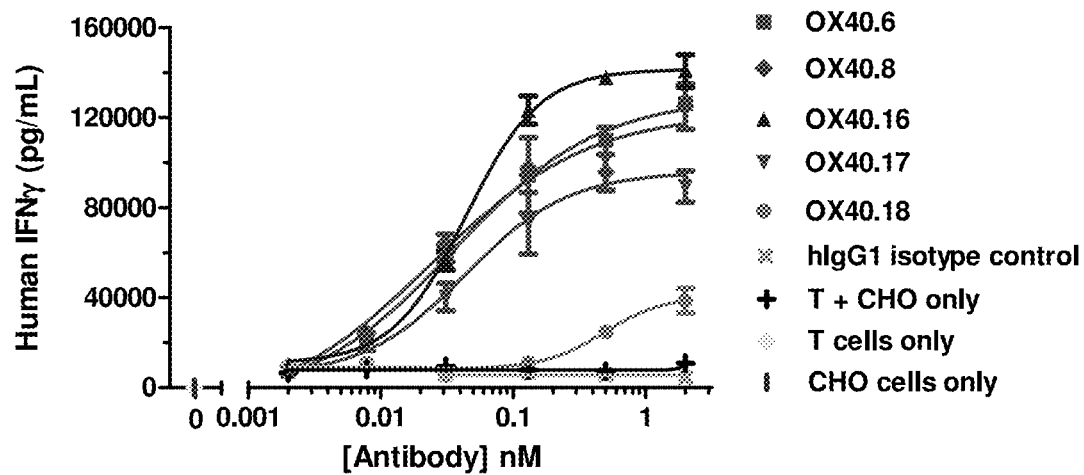
Figure 22D:
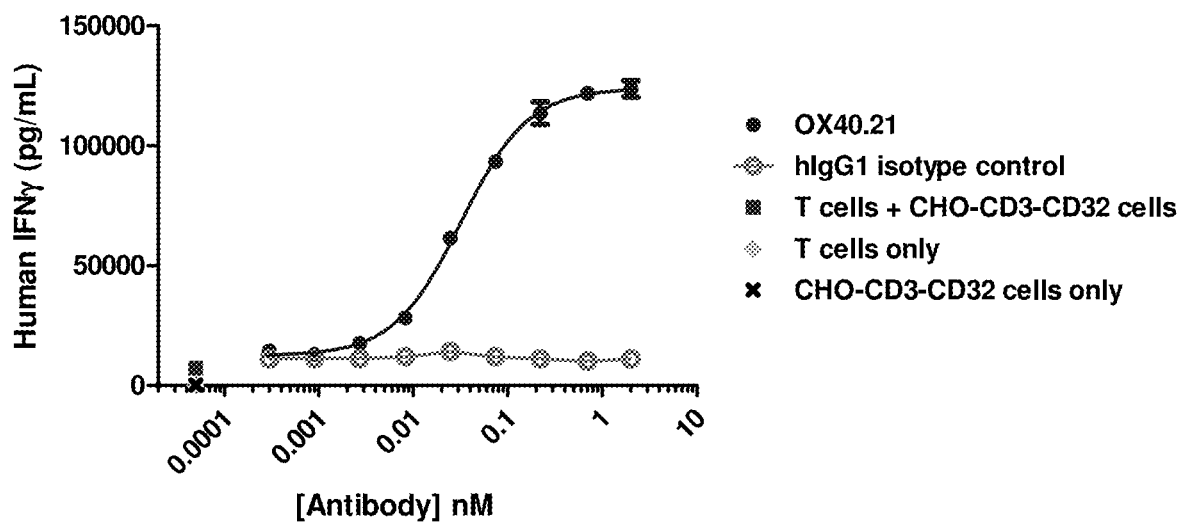

FIG. 20E shows the identification of the peptides recognized by OX40.16, OX40.21, and OX40.8 by LC-MS.

FIGS. 21A-21D show the effects of various anti-OX40 antibodies on human primary CD4+ T cell proliferation when co-cultured with CHO-CD3-CD32A cells. CHO cells only, T cells only, CHO cells co-cultured with T cells only, and hIgG1 were used as controls.

FIGS. 22A-22D show the effects of various anti-OX40 antibodies on interferon gamma (IFN-γ) secretion from human primary CD4+ T cells co-cultured with CHO-CD3-CD32A cells. CHO cells only, T cells only, CHO cells co-cultured with T cells only, and hIgG1 were used as controls.

FIGS. 23A-23F show the effects of various anti-OX40 antibodies on the stimulation of IL-2 secretion from primary T cells in cultures of staphylococcus enterotoxin B (SEB)-activated human peripheral blood mononuclear cells (PB-MCs), which were isolated from different donors.

Figure 24:
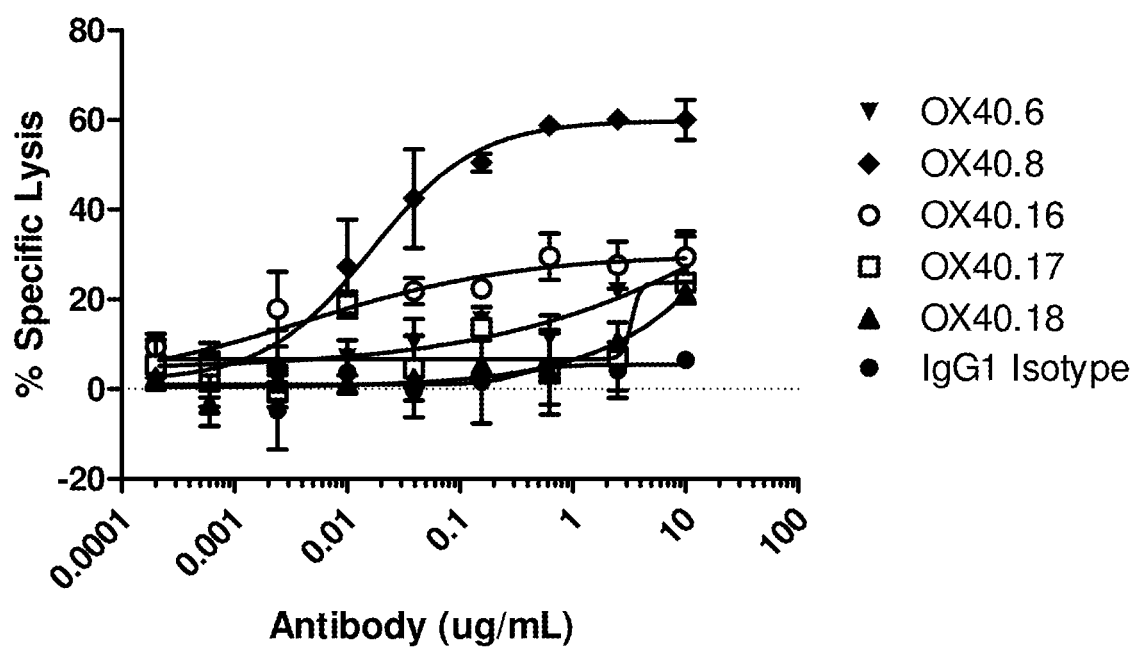

FIG. 24 shows the effects of various anti-OX40 antibodies on NK92 cell induced lysis of activated CD4+ cells.

Figure 25A:
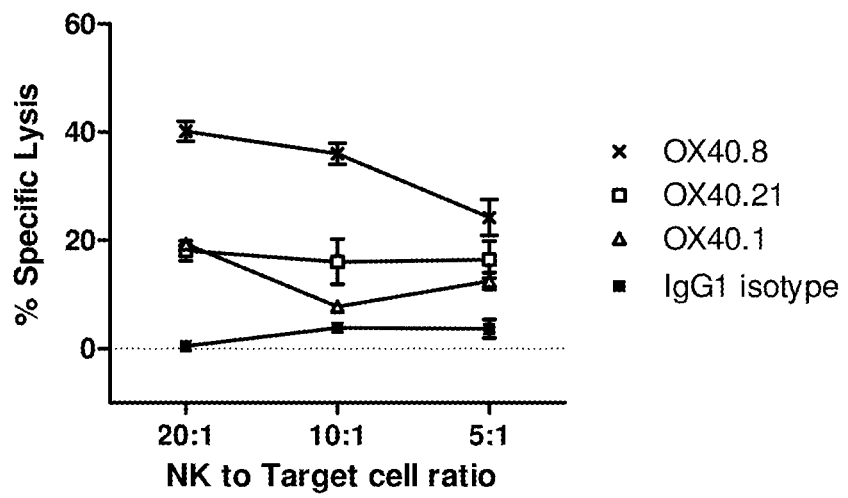
Figure 25B:
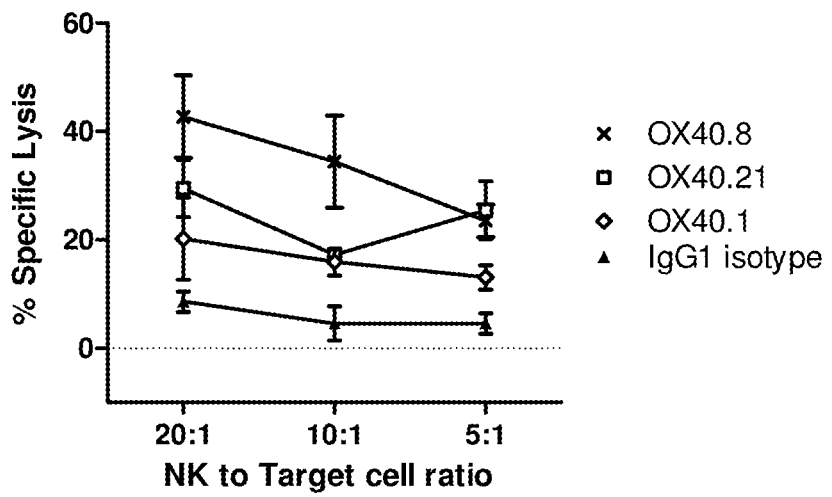

FIGS. 25A and 25B show the effects of various anti-OX40 antibodies on primary NK cell-mediated lysis of activated CD4+ T cells isolated from two donors by NK:target cell ratios.

Figure 26:
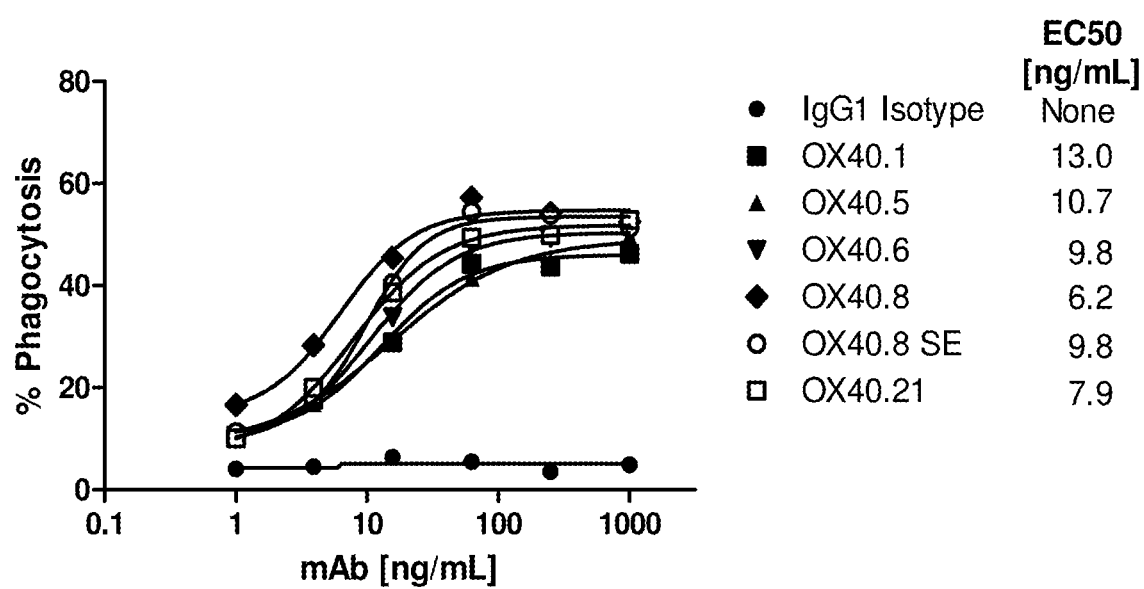

FIG. 26 shows the effects of various anti-OX40 antibodies on the phagocytosis of hOX40-293 cells by primary human macrophages.

Figure 27:
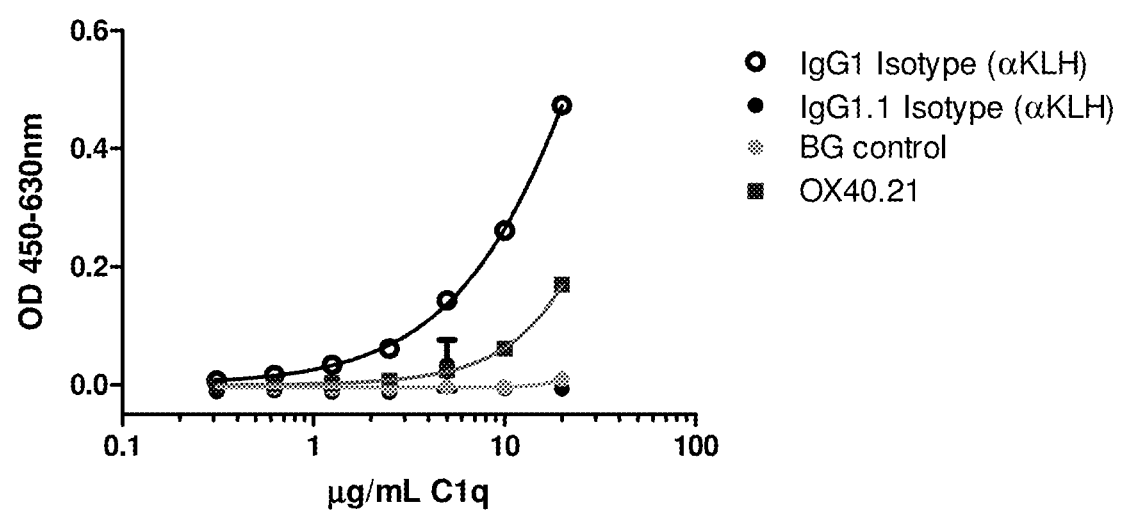

FIG. 27 shows the level of binding of the human complement C1q component to OX40.21. IgG1 and IgG1.1 (effectorless) were used as controls.

Figure 28A:
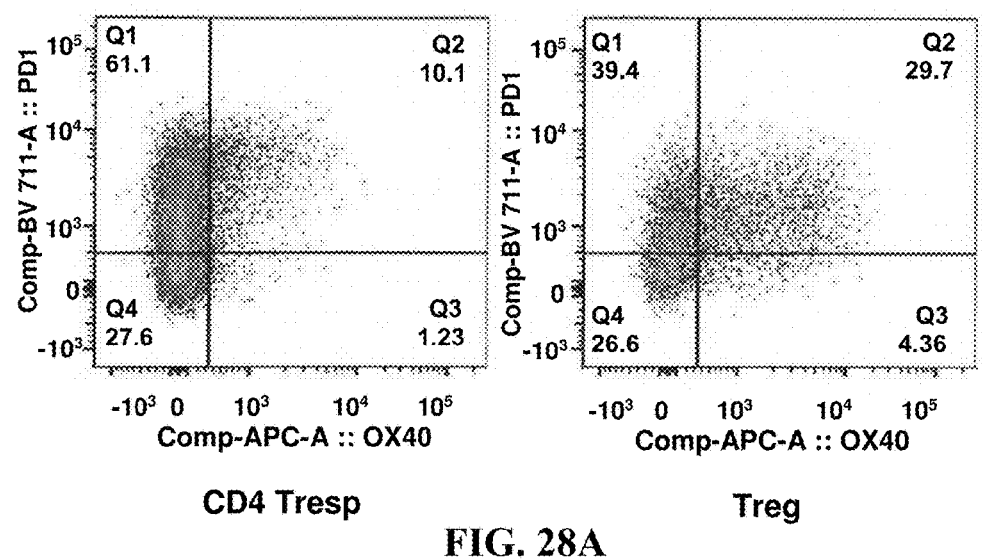
Figure 28B:
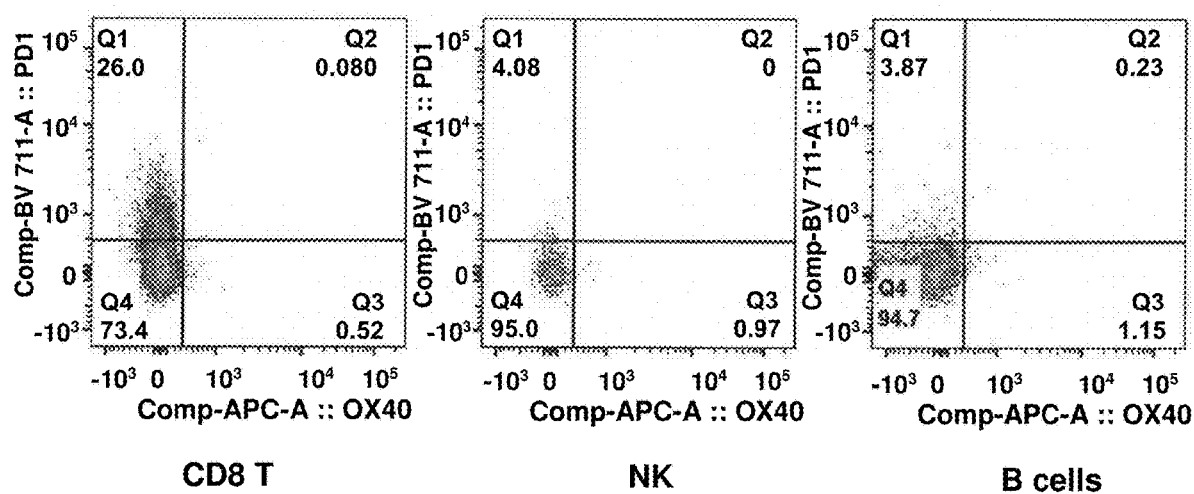
Figure 28C:
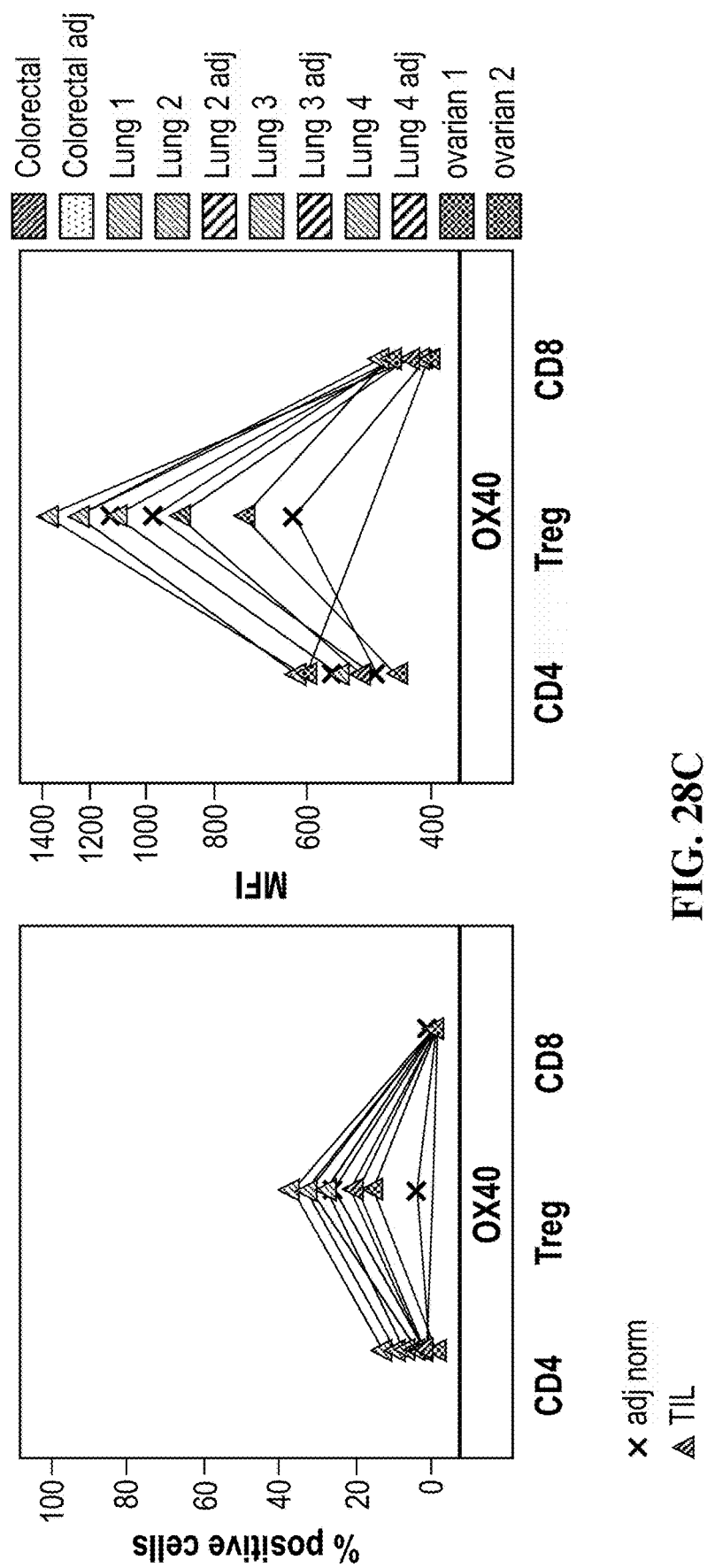

FIGS. 28A-28C show that OX40 is expressed in tumor infiltrating lymphocytes, with a pattern generally limited to CD4+ cells with minimal expression on CD8+ cells.

Figure 28D:
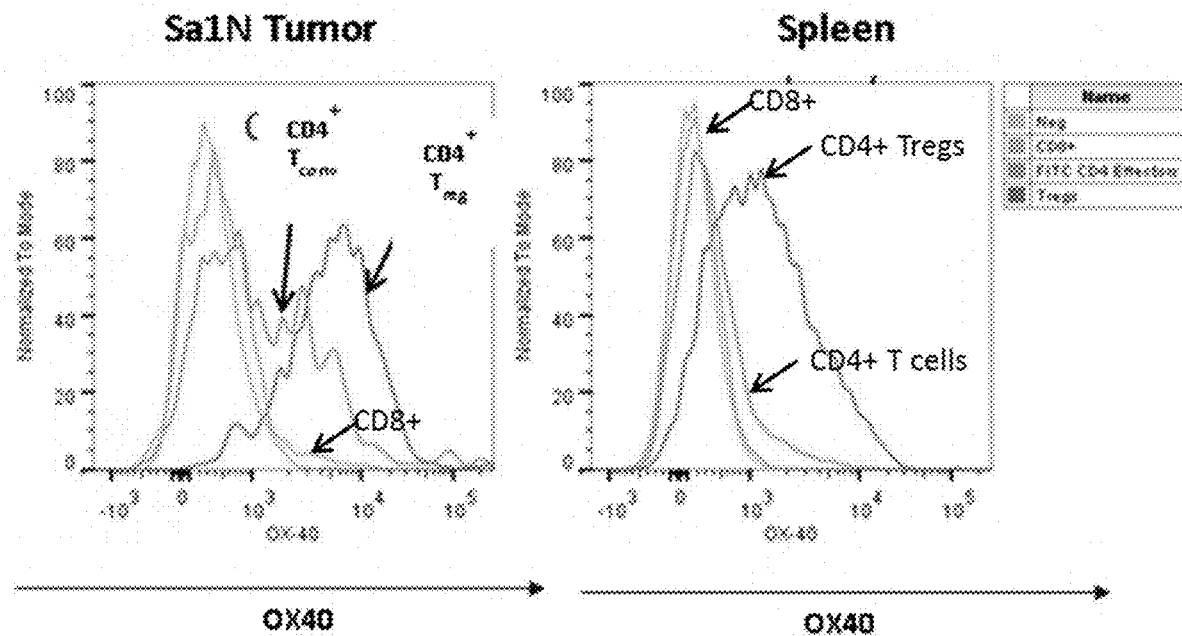

FIG. 28D shows that OX40 is expressed by CD4+ T cells and regulatory T cells in mouse Sa1N tumors.

Figure 28E:
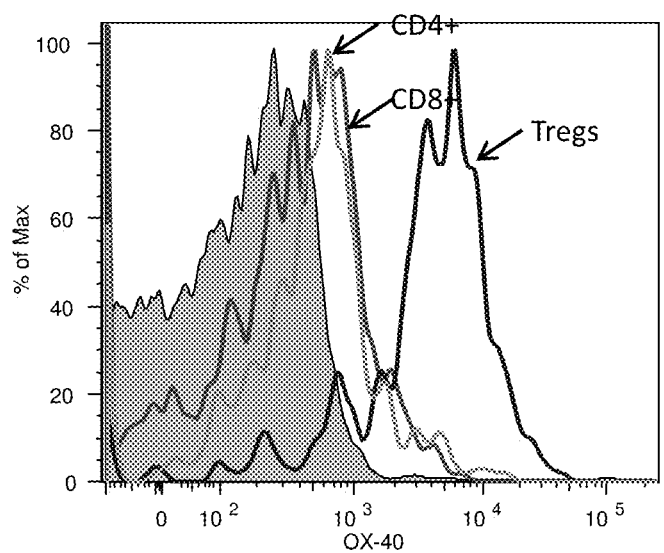

FIG. 28E shows that OX40 is expressed by CD4+ T cells, CD8+ T cells, and regulatory T cells in mouse MC38 tumors.

Figure 29:
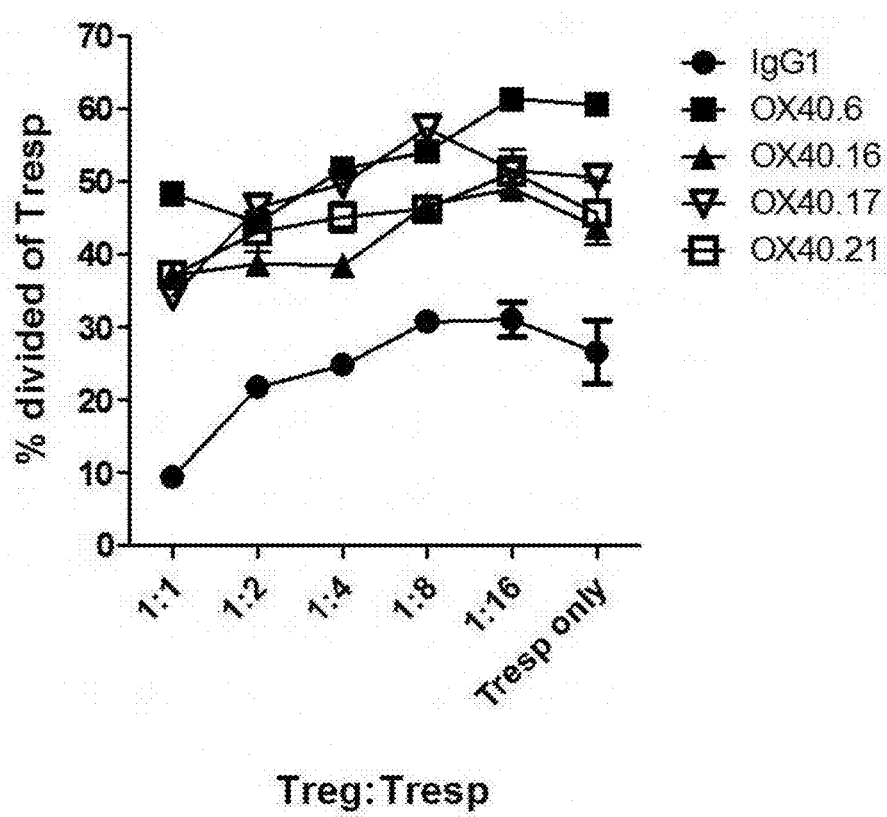

FIG. 29 shows the ability of various anti-OX40 antibodies to reverse regulatory T (Treg) cell-mediated suppression of human CD4+ T cells. In both the presence and absence of Treg cells, anti-OX40 antibodies increased the proliferation of T responder (Tresp) cells compared to the IgG1 isotype control.

Figure 30A:
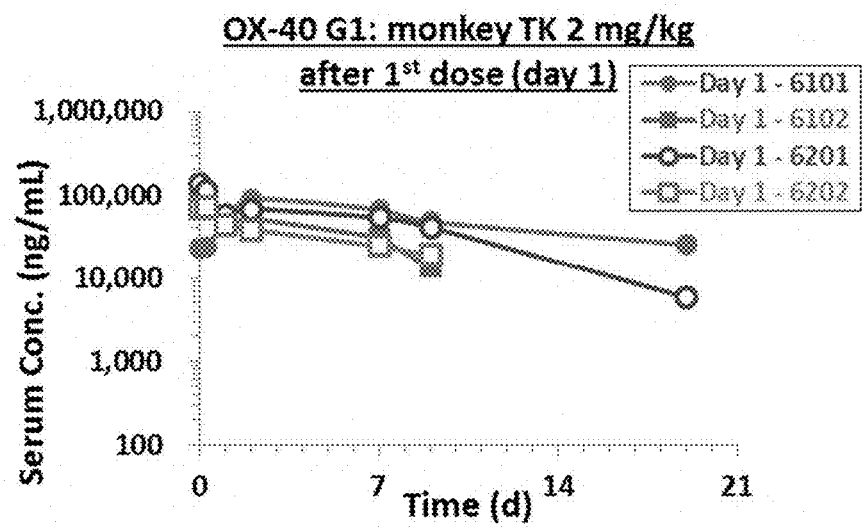
Figure 30B:
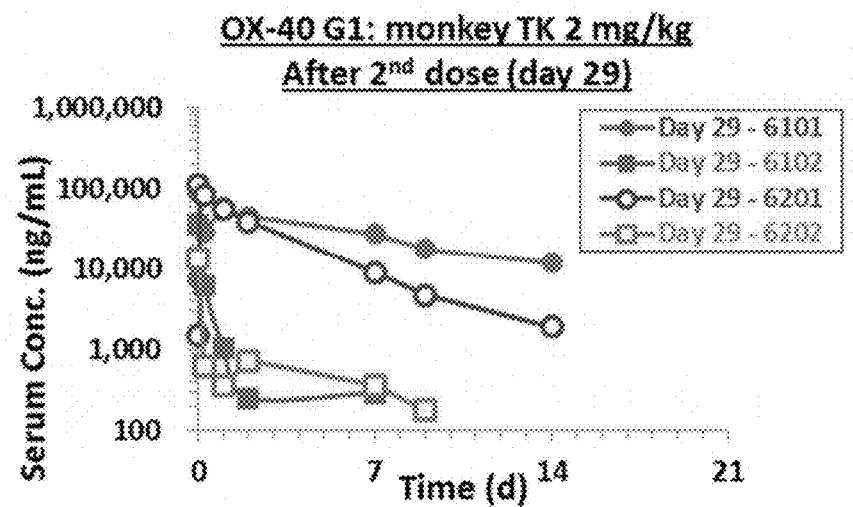

FIGS. 30A and 30B show the clearance of intravenously administered OX40.6 antibody from monkeys. Two of the monkeys showed accelerated clearance, which correlated with the formation of anti-drug antibodies.

Figure 31:
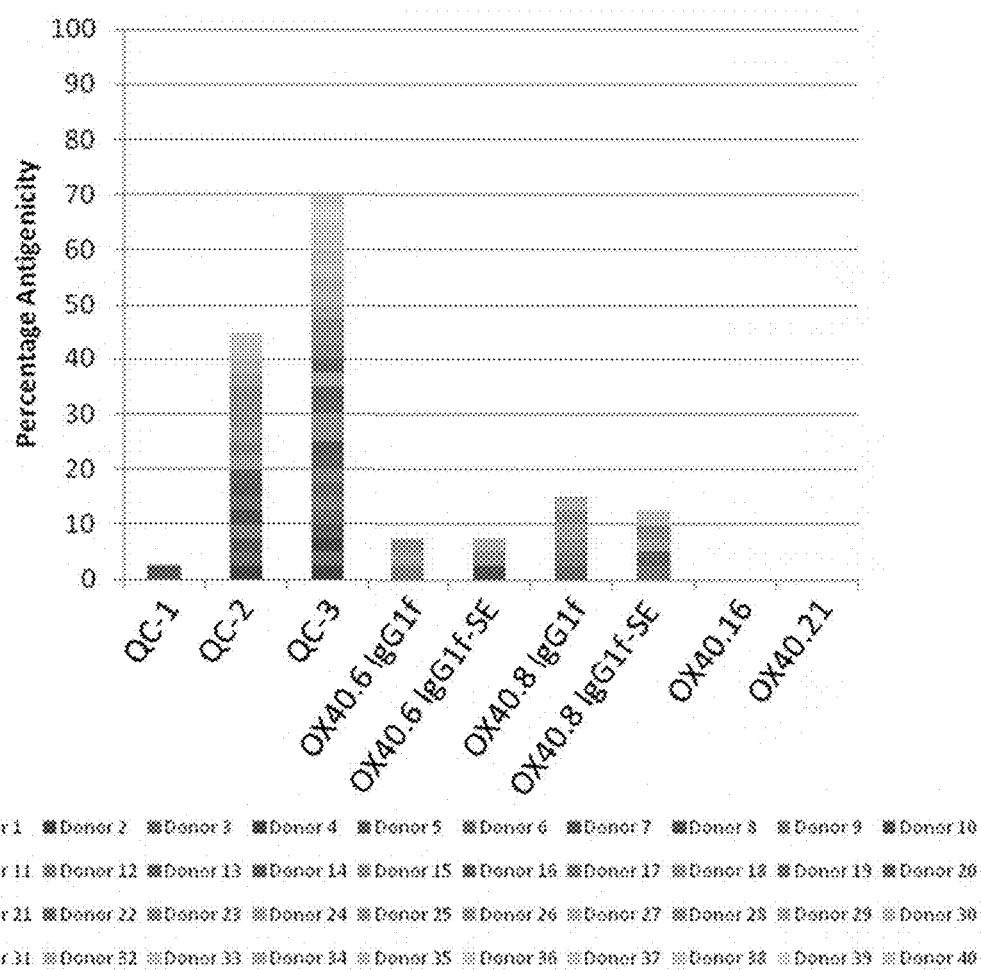

FIG. 31 is a graph depicting T-cell proliferation results for percentage antigenicity for various anti-OX40 antibodies, as well as quality control samples QC-1, QC-2, and QC-3.

Figure 32A:
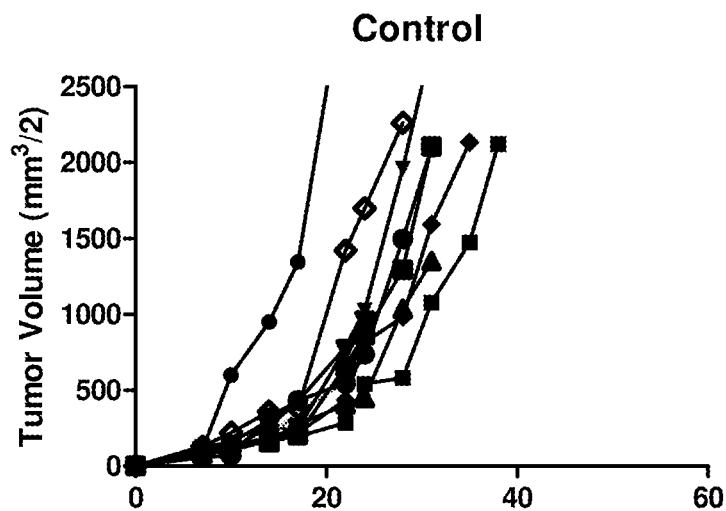
Figure 32B:
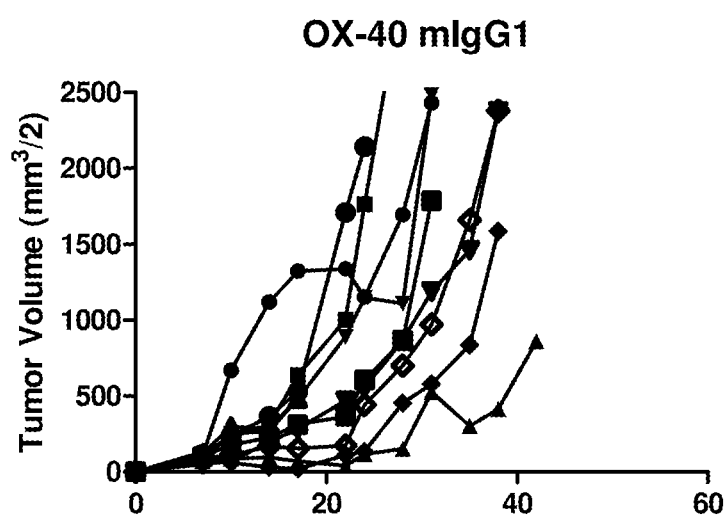
Figure 32C:
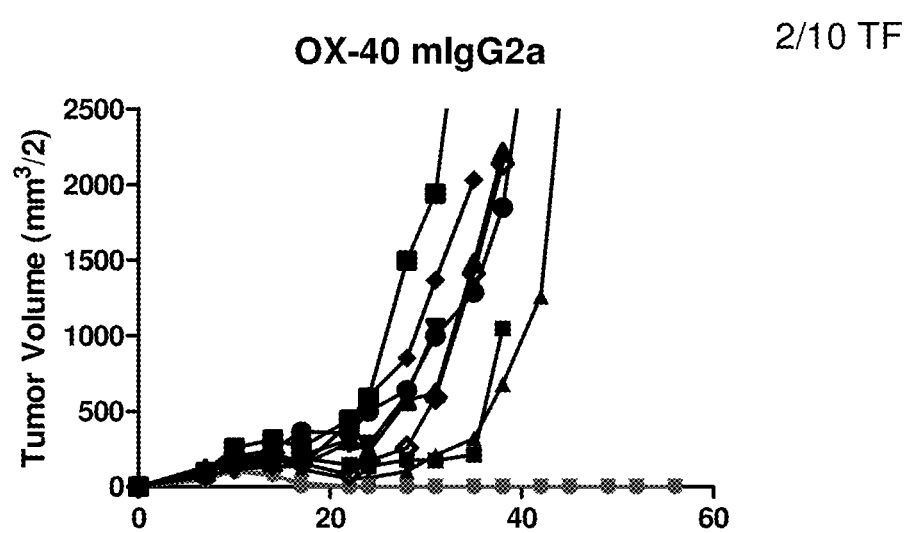

FIGS. 32A-32C show the effects of different isotypes of the chimeric OX86 antibody (an antibody having the rat variable regions of OX86 and mouse constant region that does not block the interaction between OX40 and OX40-L, i.e., a non-blocking antibody) on anti-tumor activity measured by changes in tumor volumes in individual mice treated with these isotypes (mIgG1 and mIgG2 isotypes) in a MC38 colon adenocarcinoma model: (FIG. 32A) control mouse IgG1 antibody ("control"), (FIG. 32B) OX86 mIgG1 antibody ("OX-40 mIgG1"), (FIG. 32C) OX86 mIgG2 antibody ("OX-40 mIgG2a").

Figure 33A:
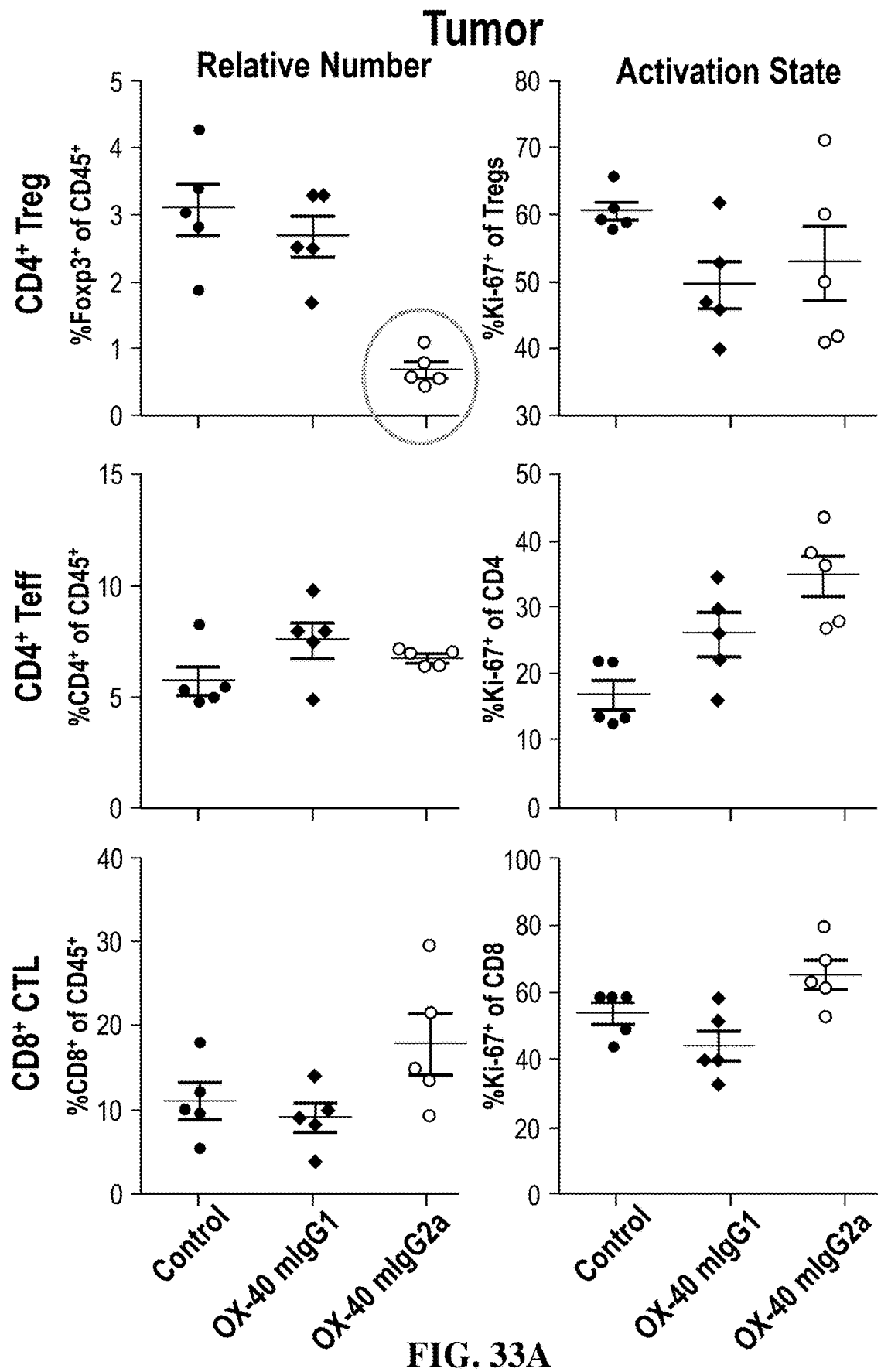
Figure 33B:
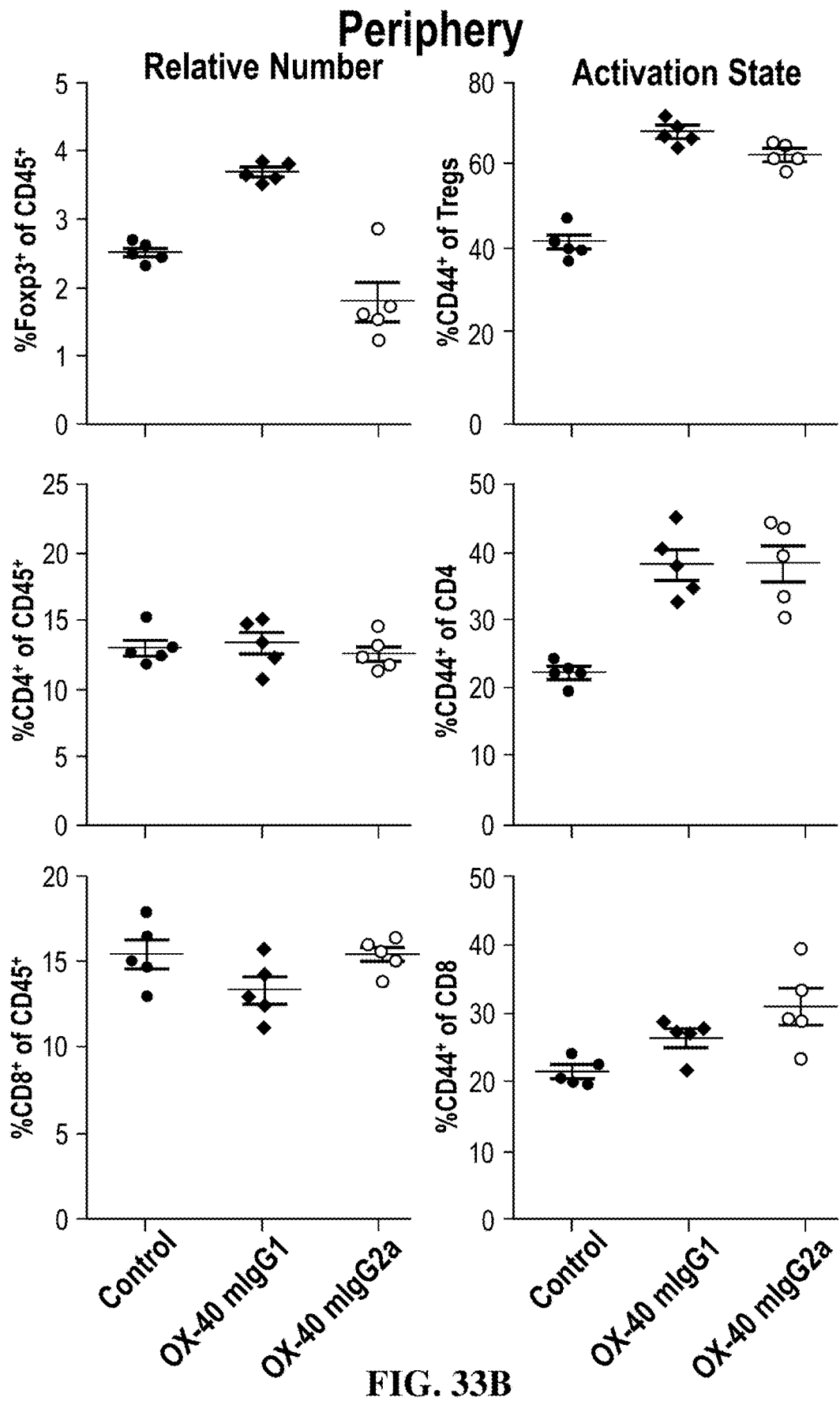
Figure 33C:
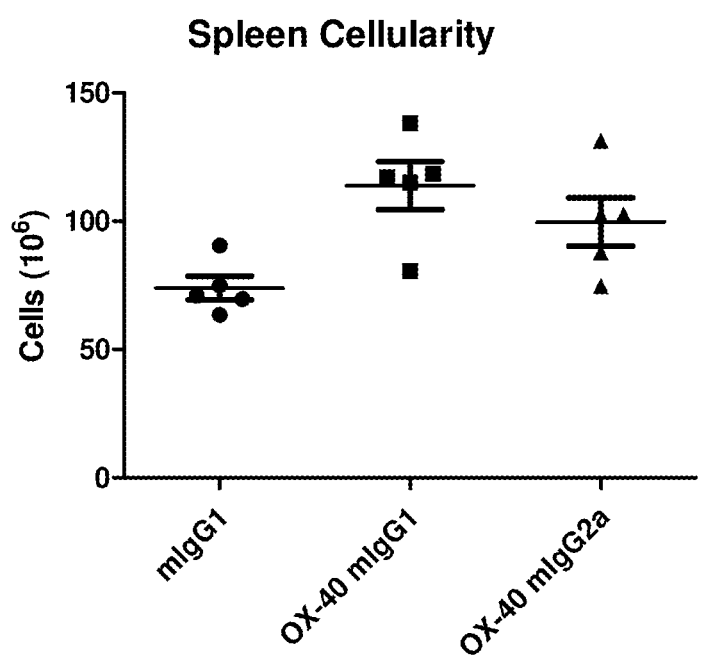

FIGS. 33A-33C show the effects of different isotypes (mIgG1 and mIgG2a) of the OX86 antibody on the number of CD4+ regulatory T cells in tumors and the periphery, and on cell numbers in the spleen.

Figure 34A:
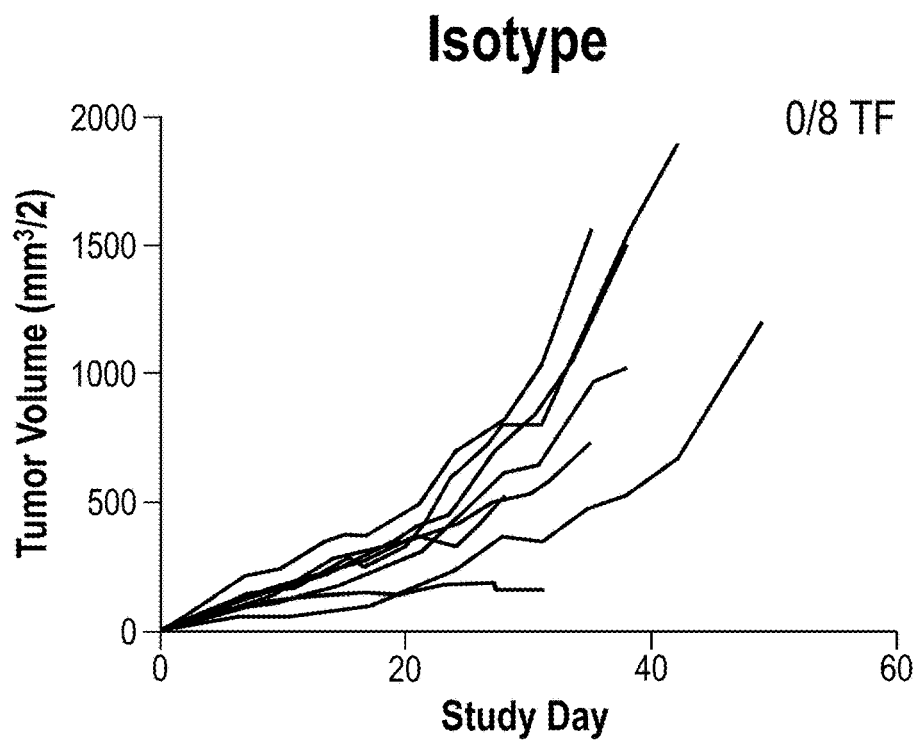
Figure 34B:
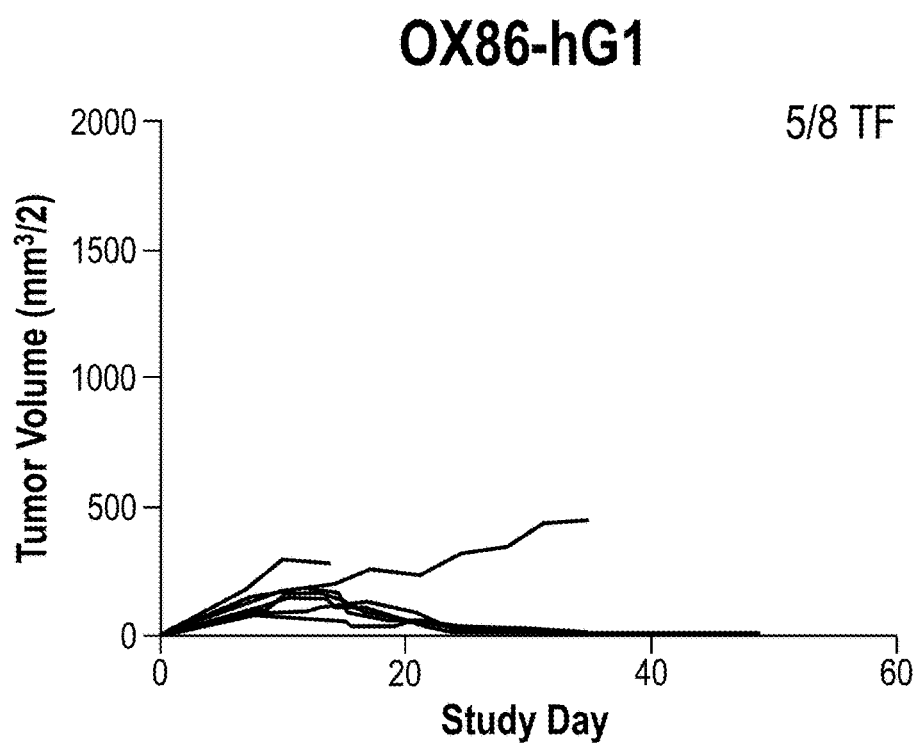
Figure 34C:
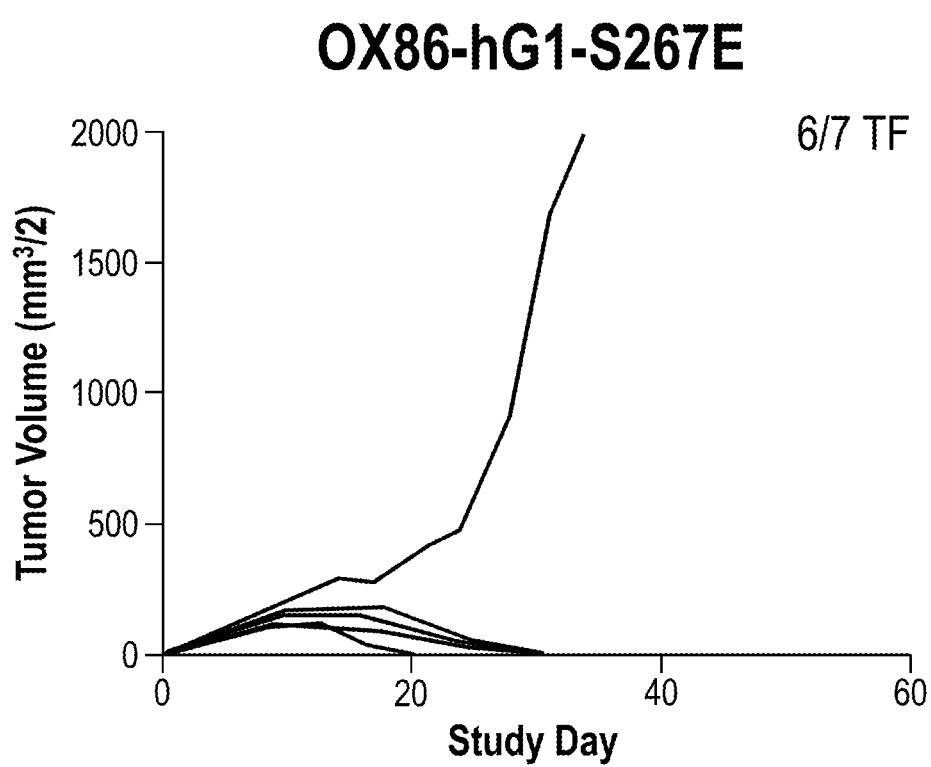

FIGS. 34A-34C show the effects of chimeric OX86 antibodies with a human IgG1 on anti-tumor activity measured by changes in tumor volumes in individual mice treated with the indicated antibodies in the MC38 colon adenocarcinoma model: (FIG. 34A) human IgG1 isotype control ("Isotype"), (FIG. 34B) OX86-hIgG1 chimeric antibody ("OX86-hG1"), (FIG. 34C) OX86-hIgG1-S267E antibody ("OX86-hG1-S267E"). The S267E substitution in hIgG1 increases its effector function by increasing binding to FcRs (CD32A and CD32B). OX86-hIgG1 exhibited potent anti-tumor activity.

FIGS. 35A-35D show the effects of chimeric OX86 hIgG1 antibody on regulatory T cell depletion.

FIGS. 36A-36E show the effects of a blocking (i.e., blocks the interaction between OX40 and OX40 ligand) hamster anti-mouse OX40 antibody (8E5) at different dosages on anti-tumor activity by changes in tumor volumes in individual mice treated with the indicated antibodies in the subcutaneous mouse CT-26 tumor model. (FIG. 36A) hamster Ig control, (FIG. 36B) 8E5 at 10 mg/kg, (FIG. 36C) 8E5 at 3 mg/kg, (FIG. 36D) 8E5 at 1 mg/kg, (FIG. 36E) 8E5 at 0.3 mg/kg.

FIGS. 37A-37D show the effects of combination therapy with the OX86-rG1 antibody and an anti-PD1 antibody on anti-tumor activity measured by changes in tumor volumes in individual mice treated with the indicated antibodies and combination in the MC38 colon adenocarcinoma model: (FIG. 37A) isotype control, (FIG. 37B) anti-PD1 antibody, (FIG. 37C) OX86-rG1 ("anti-OX40"), (FIG. 36D) OX86-rG1+ anti-PD1 antibody ("anti-OX40+ anti-PD1").

Figure 38A:
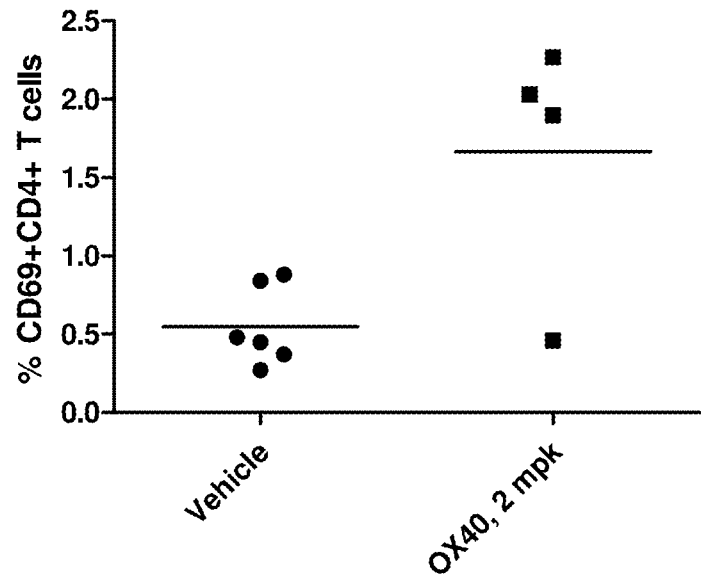
Figure 38B:
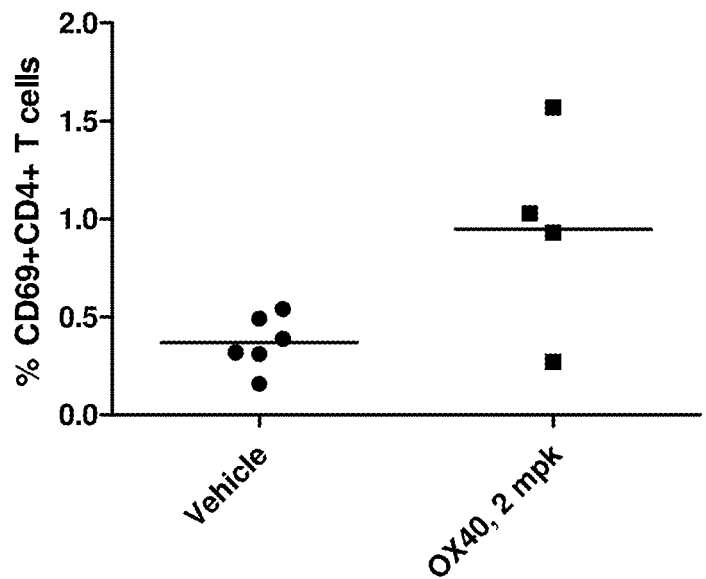

FIGS. 38A and 38B show the ex vivo recall response to KLH, CD69+ expressing CD4+CD8− T cells at Days 22 and 41, respectively. Animals were immunized with KLH on Study Day 1. Data points represent individual animal (males and females) results as a percentage of CD4+CD8− T cells. Horizontal bars represent group means.

Figure 39:
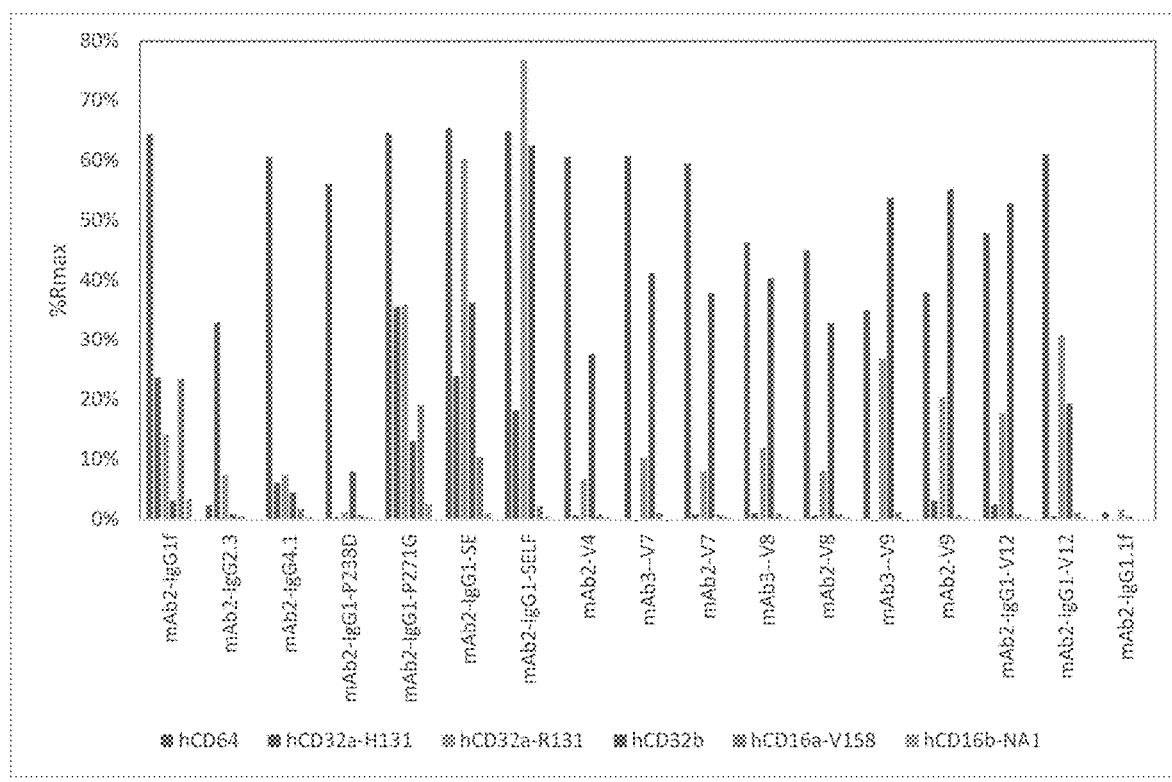

FIG. 39 shows antibody binding to anti-his Fab captured FcγR-his proteins. Binding responses are plotted as a percentage of the theoretical Rmax assuming a 1:1 mAb:FcγR binding stoichiometry. The bars for each antibody are shown in the order provided by the color legends at the bottom of the slide.

Figure 40:
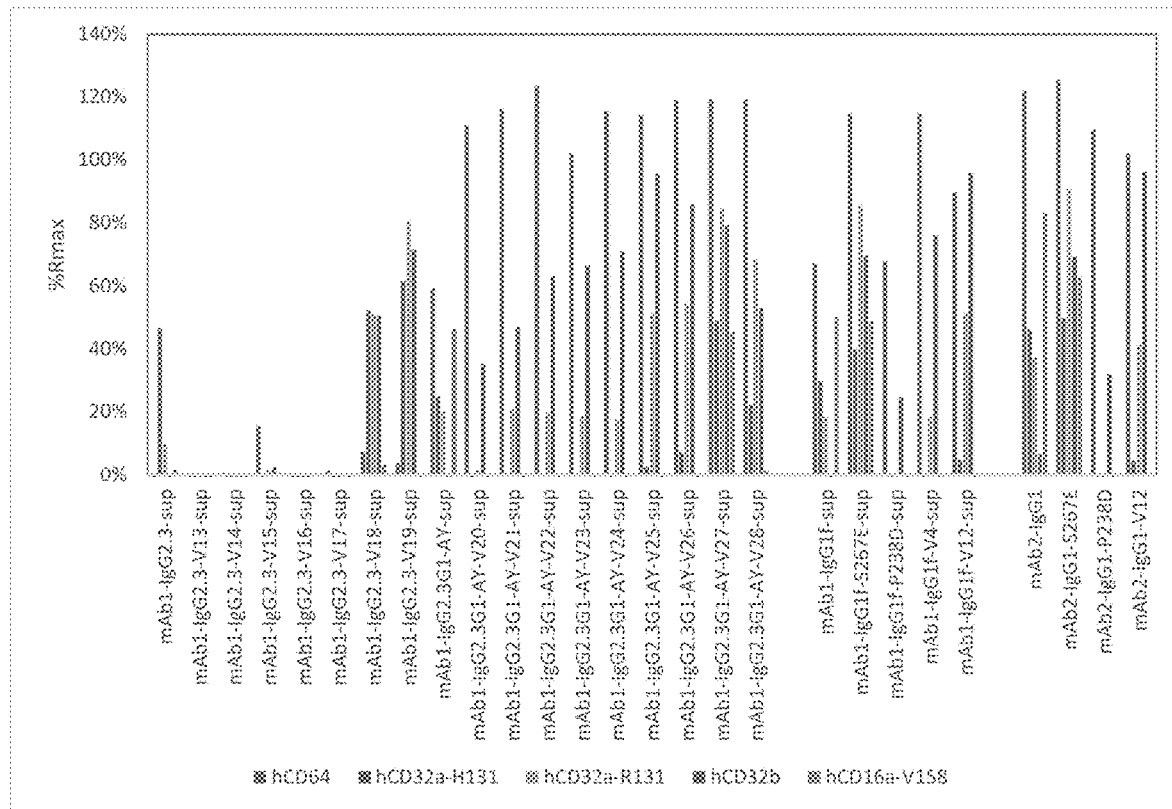
Figure 41A:
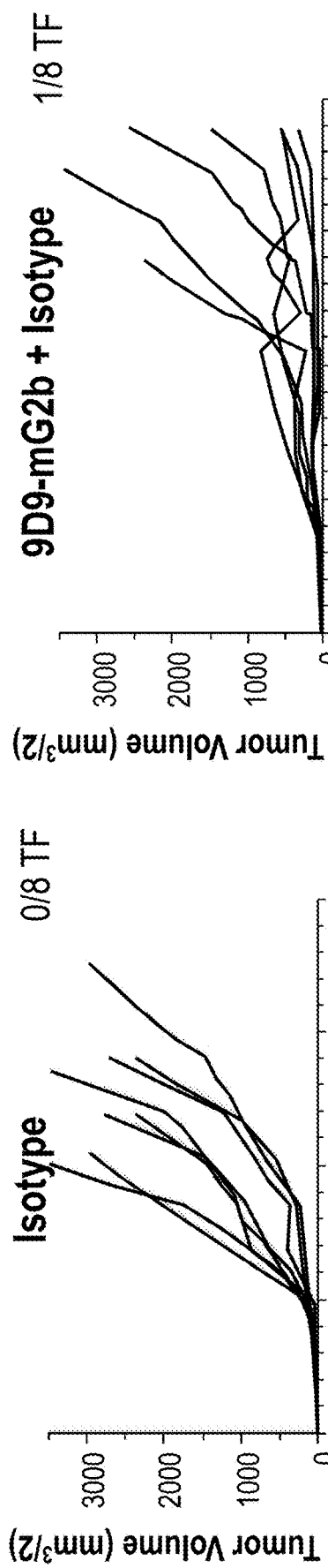
Figure 41B:
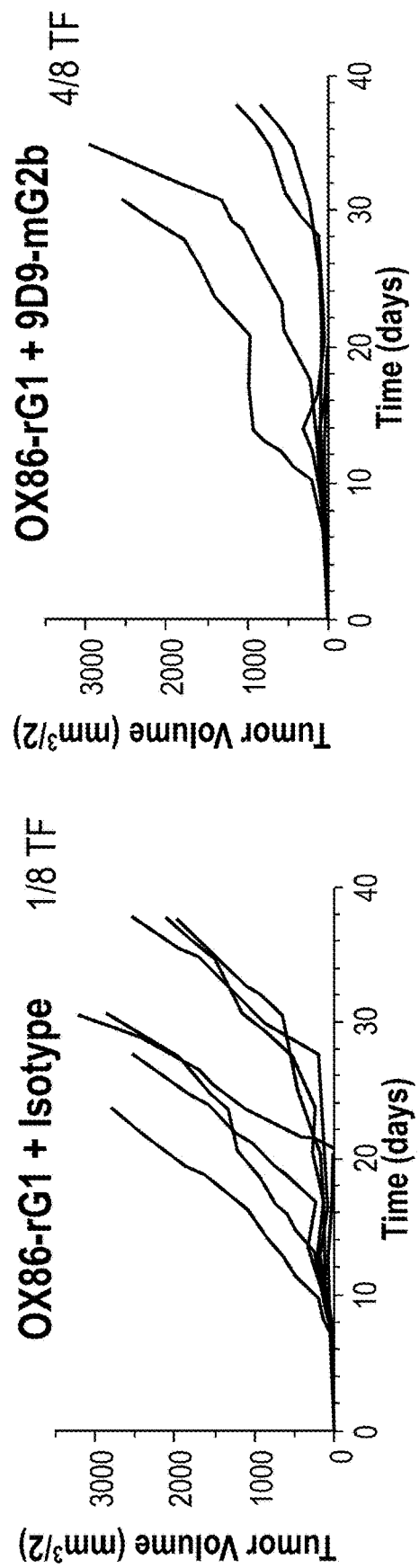
Figure 41C:
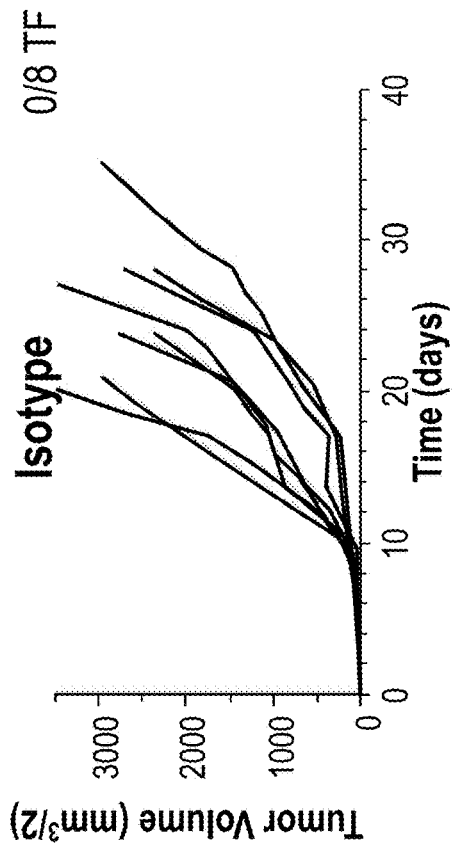
Figure 41D:
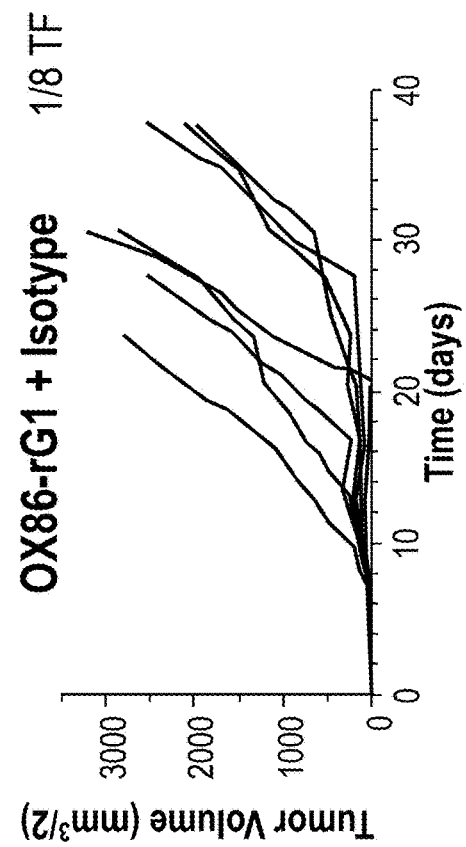

FIG. 40 shows antibody binding to anti-his Fab captured FcgR-his proteins. Binding responses are plotted as a percentage of the theoretical Rmax assuming a 1:1 mAb:FcγR binding stoichiometry. The bars for each antibody are shown in the order provided by the color legends at the bottom of the slide.

FIGS. 41A-41D show the effects of combination therapy with an agonistic anti-OX40 antibody (OX86-rG1) and an anti-CTLA-4 antibody (9D9-mG2b) on anti-tumor activity measured by changes in tumor volumes in individual mice treated with the indicated antibodies and combination in the CT26 colon adenocarcinoma model: (FIG. 41A) isotype control, (FIG. 41B) anti-CTLA-4 antibody, (FIG. 41C) OX86-rG1, (FIG. 41D) OX86-rG1+anti-CTLA-4 antibody.

Figure 42:
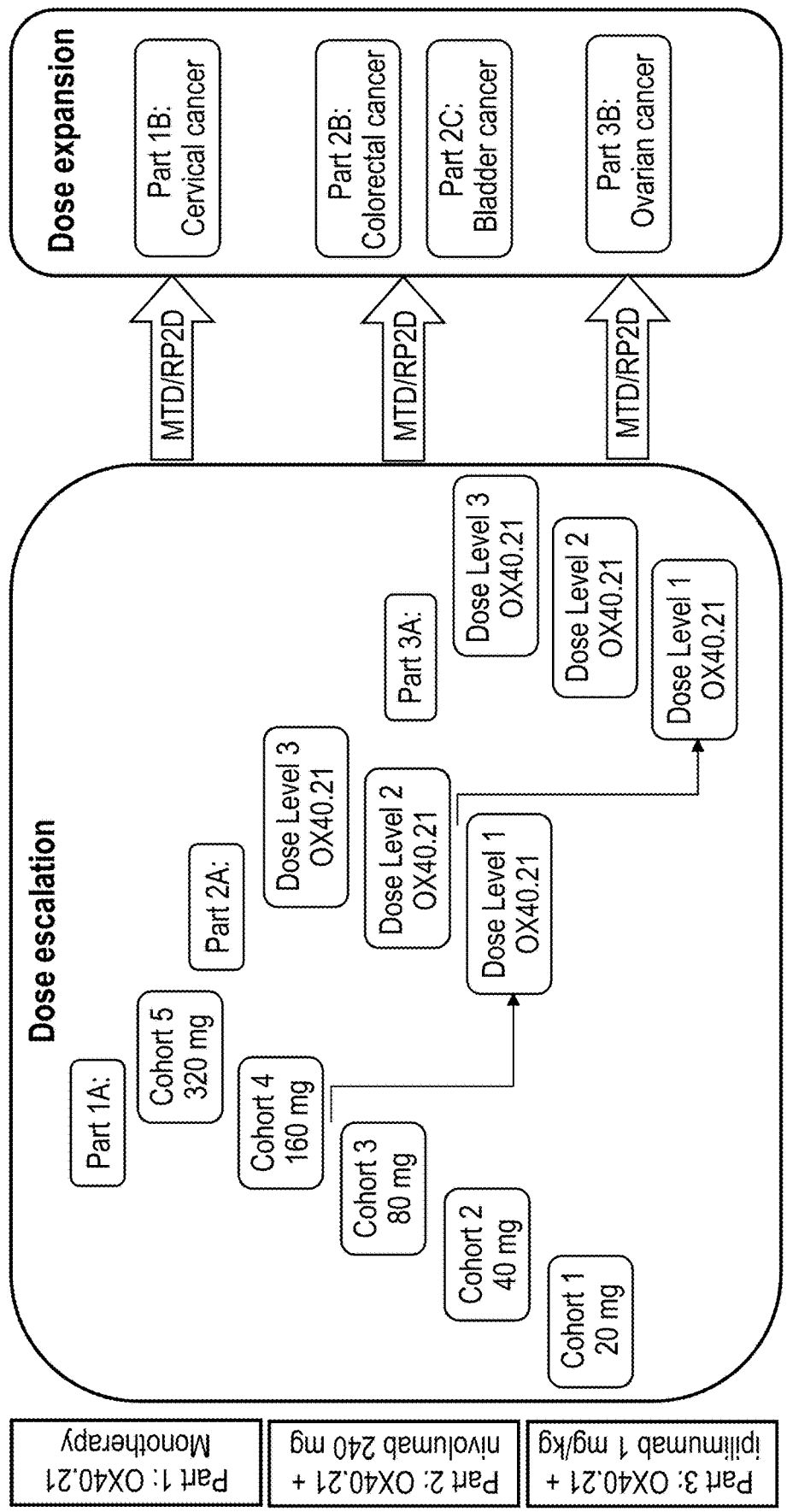

FIG. 42 is a schematic of the Phase 1/2a clinical trial protocol.

Figure 43:
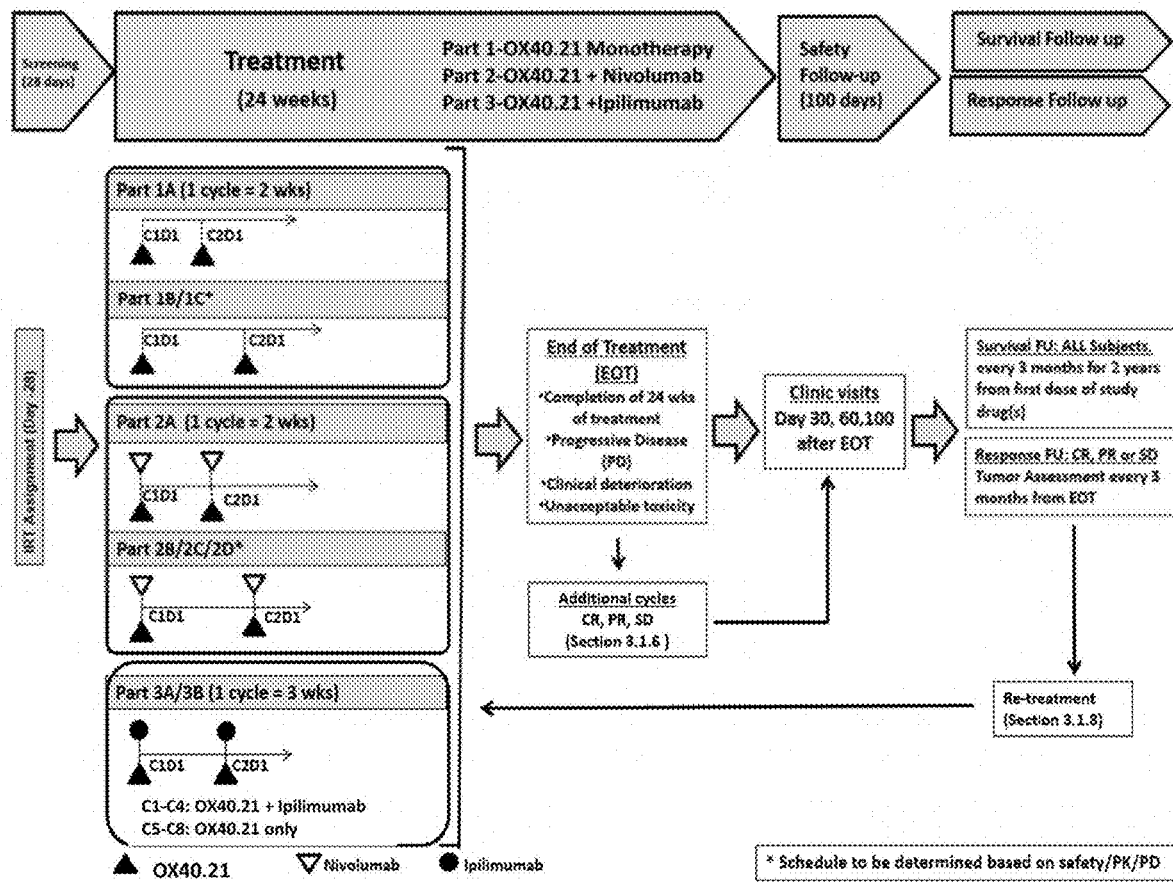

FIG. 43 is a schematic of the study visit schedule for the Phase 1/2a clinical trial.

DETAILED DESCRIPTION

Described herein are isolated antibodies, particularly monoclonal antibodies, e.g., human monoclonal antibodies, which specifically bind to OX40 and thereby activate downstream OX40 signaling ("agonist anti-OX40 antibodies"). In certain embodiments, the antibodies described herein are characterized by particular functional features and/or comprise particular structural features, such as CDR regions comprising specific amino acid sequences. Provided herein are isolated antibodies, methods of making such anti-OX40 antibodies, immunoconjugates, and bispecific molecules comprising such antibodies, and pharmaceutical compositions formulated to contain the antibodies. Also provided herein are methods of using the antibodies for immune response enhancement, alone or in combination with other immunostimulatory agents (e.g., antibodies) and/or cancer therapies. Accordingly, the anti-OX40 antibodies described herein may be used in a treatment in a wide variety of therapeutic applications, including, for example, inhibiting tumor growth and treating viral infections.

Definitions

In order that the present description may be more readily understood, certain terms are first defined. Additional definitions are set forth throughout the detailed description.

The term "OX40" as used herein refers to a receptor that is a member of the TNF-receptor superfamily, which binds to OX40 ligand (OX40-L). OX40 is also referred to as tumor necrosis factor receptor superfamily, member 4 (TNFRSF4), ACT35, IMD16, TXGP1L, and CD134. The term "OX40" includes any variants or isoforms of OX40 which are naturally expressed by cells. Accordingly, antibodies described herein may cross-react with OX40 from species other than human (e.g., cynomolgus OX40). Alternatively, the antibodies may be specific for human OX40 and may not exhibit any cross-reactivity with other species. OX40 or any variants and isoforms thereof, may either be isolated from cells or tissues which naturally express them or be recombinantly produced using well-known techniques in the art and/or those described herein.

The amino acid sequence of human OX40 precursor (Accession No. NP_003318.1) is set forth in SEQ ID NO: 1. The amino acid sequence of the extracellular domain of mature human OX40 is set forth in SEQ ID NO: 2. The amino acid sequence of cynomolgus OX40 is set forth in SEQ ID NO: 3. The amino acid sequence of human OX40-L is set forth in SEQ ID NO: 4.

The terms "Programmed Death 1," "Programmed Cell Death 1," "Protein PD-1," "PD-1," PD1," "PDCD1," "hPD-1" and "hPD-I," as used herein, are used interchangeably, and include variants, isoforms, species homologs of human PD-1, and analogs having at least one common epitope with PD-1. The complete PD-1 sequence can be found under GenBank Accession No. U64863.

The term "cytotoxic T lymphocyte-associated antigen-4," "CTLA-4," "CTLA4," "CTLA-4 antigen" and "CD152" (see, e.g., Murata (1999) Am. J. Pathol. 155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32). A complete sequence of human CTLA-4 is set forth in GenBank Accession No. L1 5006.

The term "antibody" as used to herein may include whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring IgG, IgD, and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an antibody that binds specifically to human OX40 may cross-react with OX40 from certain non-human primate species (e.g., cynomolgus monkey), but may not cross-react with OX40 from other species (e.g., murine OX40), or with an antigen other than OX40.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In certain embodiments, the anti-OX40 antibodies described herein are of the IgG1 or IgG2 subtype. Immunoglobulins, e.g., IgG1, exist in several allotypes, which differ from each other in at most a few amino acids. "Antibody" may include, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen (e.g., human OX40). It has been shown that the antigen-binding function of an antibody can be performed by fragments of a full-length antibody. Examples of binding fragments encompassed within the term "antigen-binding portion" of an antibody, e.g., an anti-OX40 antibody described herein, include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animals (e.g., a transgenic mouse having a genome comprising a human heavy chain transgene and a light chain), to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations that occur, for example, during antibody maturation. As known in the art (see, e.g., Lonberg (2005) *Nature Biotech.* 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most, or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al. (2009) mAbs 1:1). Antibodies described herein may be of any allotype. As used herein, antibodies referred to as "IgG1f" or "IgG1.1f" isotype are IgG1 and effectorless IgG1.1 antibodies, respectively, of the allotype "f," i.e., having 214R, 356E and 358M according to the EU index as in Kabat, as shown, e.g., in SEQ ID NO: 5 (see underlined residues in SEQ ID NO: 5 of Table 23).

The phrases "an antibody recognizing an antigen" and "an antibody specific for an antigen" are used interchangeably herein with the term "an antibody which binds specifically to an antigen."

An "isolated antibody," as used herein, is intended to refer to an antibody that is substantially free of other antibodies having different antigenic specificities (e.g., an isolated antibody that specifically binds to OX40 is substantially free of antibodies that specifically bind antigens other than OX40). An isolated antibody that specifically binds to an epitope of OX40 may, however, have cross-reactivity to other OX40 proteins from different species.

As used herein, an antibody that "inhibits binding of OX40-L to OX40" is intended to refer to an antibody that inhibits the binding of OX40-L to OX40, e.g., in binding assays using hOX40-293 cells, with an $EC_{50}$ of about 1 µg/mL or less, such as about 0.9 µg/mL or less, about 0.85 µg/mL or less, about 0.8 µg/mL or less, about 0.75 µg/mL or less, about 0.7 µg/mL or less, about 0.65 µg/mL or less, about 0.6 µg/mL or less, about 0.55 µg/mL or less, about 0.5 µg/mL or less, about 0.45 µg/mL or less, about 0.4 µg/mL or less, about 0.35 µg/mL or less, about 0.3 µg/mL or less, about 0.25 µg/mL or less, about 0.2 µg/mL or less, about 0.15 µg/mL or less, or about 0.1 µg/mL or less, in art-recognized methods, e.g., the FACS-based binding assays described herein.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are summarized in Table 1. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

TABLE 1

Properties of human FcγRs

| Fcγ | Allelic variants | Affinity for human IgG | Isotype preference | Cellular distribution |
|---|---|---|---|---|
| FcγRI | None described | High ($K_D$ ~10 nM) | IgG1 = 3 > 4 >> 2 | Monocytes, macrophages, activated neutrophils, dentritic cells? |
| FcγRIIA | H131 | Low to medium | IgG1 > 3 > 2 > 4 | Neutrophils, monocytes, |
| | R131 | Low | IgG1 > 3 > 4 > 2 | macrophages, eosinophils, dentritic cells, platelets |
| FcγRIIIA | V158 | Medium | IgG1 = 3 >> 4 > 2 | NK cells, |
| | F158 | Low | IgG1 = 3 >> 4 > 2 | monocytes, macrophages, mast cells, eosinophils, dentritic cells? |
| FcγRIIB | I232 | Low | IgG1 = 3 = 4 > 2 | B cells, |
| | T232 | Low | IgG1 = 3 = 4 > 2 | monocytes, macrophages, dentritic cells, mast cells |

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises $C_{H2}$ and $C_{H3}$ constant domains in each of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. Kabat et al. (1991) *Sequences of Proteins of Immunological Interest*, National Institutes of Health, Bethesda, Md.; see also FIGS. 3C-3F of U.S. Pat. App. Pub. No. 2008/0248028. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular, disulfide bonding between the two heavy chain constant regions. As used herein, a hinge starts at Glu216 and ends at Gly237 for all IgG isotypes (Roux et al., 1998 J Immunol 161:4083). The sequences of wildtype IgG1, IgG2, IgG3 and IgG4 hinges are shown in Tables 2 and 23.

TABLE 2

Hinge region amino acids

| Ig Type | C-terminal $C_H1$* | Upper Hinge | Middle Hinge | Lower Hinge |
|---|---|---|---|---|
| IgG1 | VDKRV (SEQ ID NO: 186) | EPKSCDKTHT (SEQ ID NO: 188) | CPPCP (SEQ ID NO: 192) | APELLGG (SEQ ID NO: 200) |
| IgG2 | VDKTV (SEQ ID NO: 187) | ERK | CCVECPPCP (SEQ ID NO: 193) | APPVAG (SEQ ID NO: 201) |
| IgG3 (17-15-15-15) | VDKRV (SEQ ID NO: 186) | ELKTPLGDTTHT (SEQ ID NO: 189) | CPRCP (EPKSCDTPPPCPRCP)₃ (SEQ ID NO: 194) | APELLGG (SEQ ID NO: 200) |
| IgG3 (17-15-15) | VDKRV (SEQ ID NO: 186) | ELKTPLGDTTHT (SEQ ID NO: 189) | CPRCP (EPKSCDTPPPCPRCP)₂ (SEQ ID NO: 195) | APELLGG (SEQ ID NO: 200) |
| IgG3 (17-15) | VDKRV (SEQ ID NO: 186) | ELKTPLGDTTHT (SEQ ID NO: 189) | CPRCP (EPKSCDTPPPCPRCP)₁ (SEQ ID NO: 196) | APELLGG (SEQ ID NO: 200) |
| IgG3 (15-15-15) | VDKRV (SEQ ID NO: 186) | EPKS (SEQ ID NO: 190) | CDTPPPCPRCP (EPKSCDTPPPCPRCP)₂ (SEQ ID NO: 197) | APELLGG (SEQ ID NO: 200) |
| IgG3 (15) | VDKRV (SEQ ID NO: 186) | EPKS (SEQ ID NO: 190) | CDTPPPCPRCP (SEQ ID NO: 198) | APELLGG (SEQ ID NO: 200) |
| IgG4 | VDKRV (SEQ ID NO: 186) | ESKYGPP (SEQ ID NO: 191) | CPSCP (SEQ ID NO: 199) | APEFLGG (SEQ ID NO: 200) |

*C-terminal amino acid sequences of the CH1 domains.

The term "hinge" includes wild-type hinges (such as those set forth in Table 23), as well as variants thereof (e.g., non-naturally-occurring hinges or modified hinges). For example, the term "IgG2 hinge" includes wildtype IgG2 hinge, as shown in Table 23, and variants having 1, 2, 3, 4, 5, 1-3, 1-5, 3-5 and/or at most 5, 4, 3, 2, or 1 mutations, e.g., substitutions, deletions or additions. Exemplary IgG2 hinge variants include IgG2 hinges in which 1, 2, 3 or all 4 cysteines (C219, C220, C226 and C229) are changed to another amino acid. In a specific embodiment, an IgG2 comprises a C219S substitution. In certain embodiments, a hinge is a hybrid hinge that comprises sequences from at least two isotypes. For example, a hinge may comprise the upper, middle or lower hinge from one isotype and the remainder of the hinge from one or more other isotypes. For example, a hinge can be an IgG2/IgG1 hinge, and may comprise, e.g., the upper and middle hinges of IgG2 and the lower hinge of IgG1. A hinge may have effector function or be deprived of effector function. For example, the lower hinge of wildtype IgG1 provides effector function.

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains (such as having SEQ ID NO: 202 for IgG1 and SEQ ID NO: 203 for IgG2; Table 23), as well as variants thereof (e.g., non-naturally occurring CH1 domains or modified CH1 domains). For example, the term "CH1 domain" includes wildtype CH1 domains and variants having 1, 2, 3, 4, 5, 1-3, 1-5, 3-5 and/or at most 5, 4, 3, 2, or 1 mutations, e.g., substitutions, deletions or additions. Exemplary CH1 domains include CH1 domains with mutations that modify a biological activity of an antibody, such as ADCC, CDC or half-life. Modifications to the CH1 domain that affect a biological activity of an antibody are provided herein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains (such as having SEQ ID NO: 204 for IgG1 and SEQ ID NO: 205 for IgG2; Table 23), as well as variants thereof (e.g., non-naturally occurring CH2 domains or modified CH2 domains). For example, the term "CH2 domain" includes wildtype CH2 domains and variants having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that modify a biological activity of an antibody, such as ADCC, CDC or half-life. In certain embodiments, a CH2 domain comprises the substitutions A330S/P331S that reduce effector function. Other modifications to the CH2 domain that affect a biological activity of an antibody are provided herein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains (such as having SEQ ID NO: 206 for IgG1 and SEQ ID NO: 207 for IgG2; Table 23), as well as variants thereof (e.g., non-naturally occurring CH3 domains or modified CH3 domains). For example, the term "CH3 domain" includes wildtype CH3 domains and variants having 1, 2, 3, 4, 5, 1-3, 1-5, 3-5 and/or at most 5, 4, 3, 2, or 1 mutations, e.g., substitutions, deletions or additions. Exemplary CH3 domains include CH3 domains with mutations that modify a biological activity of an antibody, such as ADCC, CDC or half-life. Modifications to the CH3 domain that affect a biological activity of an antibody are provided herein.

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fcs include the various allotypes of Fcs (see, e.g., Jefferis et al. (2009) mAbs 1:1).

The term "epitope" or "antigenic determinant" refers to a site on an antigen (e.g., OX40) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides (e.g., from OX40) are tested for reactivity with a given antibody (e.g., an anti-OX40 antibody). Methods of determining spatial conformation of epitopes include techniques in the art and those described herein, for example, x-ray crystallography, 2-dimensional nuclear magnetic resonance and HDX-MS (see, e.g., *Epitope Mapping Protocols in Methods in Molecular Biology*, Vol. 66, G. E. Morris, Ed. (1996)).

The term "epitope mapping" refers to the process of identification of the molecular determinants on the antigen involved in antibody-antigen recognition.

The term "binds to the same epitope" with reference to two or more antibodies means that the antibodies bind to the same group of amino acid residues, as determined by a given method. Techniques for determining whether antibodies bind to the "same epitope on OX40" with the antibodies described herein include art-recognized epitope mapping methods, such as x-ray analyses of crystals of antigen:antibody complexes which provides atomic resolution of the epitope and hydrogen/deuterium exchange mass spectrometry (HDX-MS). Other methods monitor the binding of the antibody to antigen fragments (e.g., proteolytic fragments) or to mutated variations of the antigen where loss of binding due to a modification of an amino acid residue within the antigen sequence is often considered an indication of an epitope component (e.g., alanine scanning mutagenesis—Cunningham & Wells (1985) *Science* 244:1081). In addition, computational combinatorial methods for epitope mapping can also be used. These methods rely on the ability of the antibody of interest to affinity isolate specific short peptides from combinatorial phage display peptide libraries. Antibodies having the same or closely related VH and VL or the same CDR1, 2 and 3 sequences are expected to bind to the same epitope.

Antibodies that "compete with another antibody for binding to a target" refer to antibodies that (partially or completely) inhibit the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope, or to adjacent epitopes (e.g., as evidenced by steric hindrance).

Other art-recognized competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 surface plasmon resonance (SPR) instrument using the predetermined antigen, e.g., recombinant human OX40, as the analyte and the antibody as the ligand, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human OX40" refers to an antibody that binds to soluble or cell bound human OX40 with a $K_D$ of $10^{-7}$ M or less, such as approximately less than $10^{-8}$ M, $10^{-9}$ M or $10^{-10}$ M or even lower. An antibody that "cross-reacts with cynomolgus OX40" refers to an antibody that binds to cynomolgus OX40 with a $K_D$ of $10^{-7}$ M or less, such as approximately less than $10^{-8}$ M, $10^{-9}$ M or $10^{-10}$ M or even lower. In certain embodiments, antibodies that do not cross-react with OX40 from a non-human species (e.g., murine OX40) exhibit essentially undetectable binding against these proteins in standard binding assays.

The term "$k_{assoc}$" or "$k_a$", as used herein, is intended to refer to the association rate constant of a particular antibody-antigen interaction, whereas the term "$k_{dis}$" or "$k_d$," as used herein, is intended to refer to the dissociation rate constant of a particular antibody-antigen interaction. The term "$K_D$", as used herein, is intended to refer to the equilibrium dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® SPR system or flow cytometry and Scatchard analysis.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "EC50" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "binds to immobilized OX40," refers to the ability of an antibody described herein to bind to OX40, for example, expressed on the surface of a cell or attached to a solid support.

The term "cross-reacts," as used herein, refers to the ability of an antibody described herein to bind to OX40 from a different species. For example, an antibody described herein that binds human OX40 may also bind OX40 from another species (e.g., cynomolgus OX40). As used herein, cross-reactivity may be measured by detecting a specific reactivity with purified antigen in binding assays (e.g., SPR, ELISA) or binding to, or otherwise functionally interacting with, cells physiologically expressing OX40. Methods for determining cross-reactivity include standard binding assays as described herein, for example, by BIACORE® surface plasmon resonance (SPR) analysis using a BIACORE® 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" of the sequences set forth herein, e.g., in Table 23, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into a sequence in Table 23 by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-OX40 antibody is preferably replaced with another amino acid residue from the same side chain family. Methods of identifying nucleotide and amino acid conservative substitutions that do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)). Alternatively, in another embodiment, mutations can be introduced randomly along all or part of an anti-OX40 antibody coding sequence, such as by saturation mutagenesis, and the resulting modified anti-OX40 antibodies can be screened for improved binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences when the sequences are optimally aligned (i.e., % homology=# of identical positions/total # of positions ×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated.

The term "vector" as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be OX40 or a fragment thereof. An antigen may also be a tumor antigen, against which protective or therapeutic immune responses are desired, e.g., antigens expressed by a tumor cell (e.g., for use as a tumor vaccine to be administered in combination with an anti-OX40 antibody). Antigens include tumor-associated antigens for the prevention or treatment of cancers. Examples of tumor-associated antigens include, but are not limited to, sequences comprising all or part of the sequences of βhCG, gp100 or Pmel17, HER2/neu, WT1, mesothelin, CEA, gp100, MART1, TRP-2, melan-A, NY-ESO-1, NY-BR-1, NY-CO-58, MN (gp250), idiotype, MAGE-1, MAGE-3, MAGE-A3, Tyrosinase, Telomerase, SSX2 and MUC-1 antigens, and germ cell derived tumor antigens. Tumor associated antigens also include the blood group antigens, for example, Le$^a$, Le$^b$, LeX, LeY, H-2, B-1, B-2 antigens. Alternatively, more than one antigen can be included in a construct. For example, a MAGE antigen can be combined with other antigens such as melanin A, tyrosinase, and gp100 along with adjuvants such as GM-CSF or IL-12, and linked to an anti-APC antibody.

Sequences of the foregoing antigens are well known in the art. For example, an example of a MAGE-3 cDNA sequence is provided in U.S. Pat. No. 6,235,525 (Ludwig Institute for Cancer Research); examples of NY-ESO-1 nucleic acid and protein sequences are provided in U.S. Pat. No. 5,804,381 and U.S. Pat. No. 6,069,233 (Ludwig Institute for Cancer Research); examples of Melan-A nucleic acid and protein sequences are provided in U.S. Pat. Nos. 5,620,886 and 5,854,203 (Ludwig Institute for Cancer Research); examples of NY-BR-1 nucleic acid and protein sequences are provided in U.S. Pat. Nos. 6,774,226 and 6,911,529 (Ludwig Institute for Cancer Research) and examples of NY-CO-58 nucleic acid and protein sequences are provided in WO 02/90986 (Ludwig Institute for Cancer Research); an example of an amino acid sequence for the HER-2/neu protein is available at GENBANK® Accession No. AAA58637; and a nucleotide sequence (mRNA) for human carcinoembryonic antigen-like 1 (CEA-1) is available at GENBANK® Accession No. NM020219.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

An "immunomodulator" or "immunoregulator" refers to an agent, e.g., a component of a signaling pathway, that may be involved in modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. In preferred embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

"T effector" ("T$_{eff}$") cells refers to T cells (e.g., CD4+ and CD8+ T cells) with cytolytic activities as well as T helper (Th) cells, which secrete cytokines and activate and direct other immune cells, but does not include regulatory T cells (Treg cells). Anti-OX40 antibodies described herein activate T$_{eff}$ cells, e.g., CD4+ and CD8+T$_{eff}$ cells.

An increased ability to stimulate an immune response or the immune system, can result from an enhanced agonist activity of T cell costimulatory receptors and/or an enhanced antagonist activity of inhibitory receptors. An increased ability to stimulate an immune response or the immune system may be reflected by a fold increase of the EC$_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity may be enhanced by at least 10%, 30%, 50%, 75%, 2 fold, 3 fold, 5 fold or more.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the term "T cell-mediated response" refers to a response mediated by T cells, including effector T cells (e.g., CD8$^+$ cells) and helper T cells (e.g., CD4$^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by $CD8^+$ T cells.

As used herein, the terms "inhibits" or "blocks" (e.g., referring to inhibition/blocking of binding of OX40-L to OX40 on cells) are used interchangeably and encompass both partial and complete inhibition/blocking. In certain embodiments, the anti-OX40 antibody inhibits binding of OX40-L to OX40 by at least about 50%, for example, about 60%, 70%, 80%, 90%, 95%, 99%, or 100%, determined, e.g., as further described herein. In certain embodiments, the anti-OX40 antibody inhibits binding of OX40-L to OX40 by no more than 50%, for example, by about 40%, 30%, 20%, 10%, 5% or 1%, determined, e.g., as further described herein.

As used herein, the term "inhibits growth" of a tumor includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

A "hematological malignancy" includes a lymphoma, leukemia, myeloma or a lymphoid malignancy, as well as a cancer of the spleen and the lymph nodes. Exemplary lymphomas include both B cell lymphomas (a B-cell hematological cancer) and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-associated cancers are encompassed by the term hematological malignancy.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction.

In reference to solid tumors, an effective amount comprises an amount sufficient to cause a tumor to shrink and/or to decrease the growth rate of the tumor (such as to suppress tumor growth) or to prevent or delay other unwanted cell proliferation. In certain embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit, i.e., slow to some extent and may stop, tumor metastasis; (v) inhibit tumor growth; (vi) prevent or delay occurrence and/or recurrence of tumor; and/or (vii) relieve to some extent one or more of the symptoms associated with the cancer. In one example, an "effective amount" is the amount of anti-OX40 antibody and the amount of anti-PD-1 antibody (e.g., nivolumab) or anti-CTLA-4 antibody (e.g., ipilimumab), in combination, clinically proven to affect a significant decrease in cancer or slowing of progression of cancer, such as an advanced solid tumor. As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent.

As used herein, a "body surface area (BSA)-based dose" refers to a dose that is adjusted to the body-surface area (BSA) of the individual patient. A BSA-based dose may be provided as mg/kg body weight. Various calculations have been published to arrive at the BSA without direct measurement, the most widely used of which is the Du Bois formula (see Du Bois D, Du Bois E F (June 1916) *Archives of Internal Medicine* 17 (6): 863-71; and Verbraecken, J. et al. (April 2006). *Metabolism—Clinical and Experimental* 55 (4): 515-24). Other exemplary BSA formulas include the Mosteller formula (Mosteller R D. *N Engl J Med.,* 1987; 317:1098), the Haycock formula (Haycock G B, et al., *J Pediatr* 1978, 93:62-66), the Gehan and George formula (Gehan E A, George S L, *Cancer Chemother Rep* 1970, 54:225-235), the Boyd formula (Current, J D (1998), *The Internet Journal of Anesthesiology* 2 (2); and Boyd, Edith (1935), University of Minnesota. The Institute of Child Welfare, Monograph Series, No. x. London: Oxford University Press), the Fujimoto formula (Fujimoto S, et al., Nippon Eiseigaku Zasshi 1968; 5:443-50), the Takahira formula (Fujimoto S, et al., Nippon Eiseigaku Zasshi 1968; 5:443-50), and the Schlich formula (Schlich E, et al., *Ernährungs Umschau* 2010; 57:178-183).

A "prophylactically effective amount" or a "prophylactically effective dosage" of a drug, is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that slows cancer progression or promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

The terms "patient" and "subject" refer to any human or non-human animal that receives either prophylactic or therapeutic treatment. For example, the methods and compositions described herein can be used to treat a subject or patient having cancer, such as an advanced solid tumor. The term "non-human animal" includes all vertebrates, e.g., mammals and non-mammals, such as non-human primates, sheep, dog, cow, chickens, amphibians, reptiles, etc.

Various aspects described herein are described in further detail in the following subsections.

I. Anti-OX40 Antibodies

Described herein are antibodies, e.g., fully human antibodies, which are characterized by particular functional features or properties. For example, the antibodies specifically bind human OX40. Additionally, antibodies may cross react with OX40 from one or more non-human primates, such as cynomolgus OX40. Such antibodies are useful in the treatment of cancer when used as monotherapy, or when used in combination with an immuno-oncology agent, such as an anti-PD-1 antibody (e.g., nivolumab) or anti-CTLA-4 antibody (e.g., ipilimumab).

Anti-OX40 antibodies described herein exhibit one or more or all of the following functional properties:

(1) binding to soluble human OX40, e.g., with a $K_D$ of 10 nM or less (e.g., 0.01 nM to 10 nM), e.g., as measured by BIACORE® SPR analysis;

(2) binding to membrane bound human OX40, e.g., with an $EC_{50}$ of 1 nM or less (e.g., 0.01 nM to 1 nM), e.g., as measured by FACS;

(3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;

(4) inducing or enhancing T cell activation, as evidenced by (i) increased IL-2 and/or IFN-γ production in OX40-expressing T cells and/or (ii) enhanced T cell proliferation;

(5) inhibiting the binding of OX40 ligand to OX40, e.g., with an $EC_{50}$ of 1 nM or less as measured by FACS, e.g., in an assay with hOX40-293 cells;

(6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDNQACKPWTNCTLAGK (SEQ ID NO: 179);

(7) competing for binding to human OX40 with 3F4, 14B6-1, 14B6-2, 23H3, 18E9, 8B11, 20B3, and 20C1;

(8) competing for binding to human OX40 with 6E1-1, 6E1-2, 14A2-1, and 14A2-2.

Preferably, the antibodies bind to OX40 with high affinity, for example, with a $K_D$ of $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. In certain embodiments, an anti-OX40 antibody binds to soluble human OX40, e.g., as determined by BIACORE® SPR analysis, with a $K_D$ of $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In certain embodiments, the anti-OX40 antibody binds to bound (e.g., cell membrane bound) human OX40, such as on activated human T cells, e.g., as determined by flow cytometry, with a $K_D$ of $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-8}$ M, $10^{-10}$ M to $10^{-8}$ M, $10^{-9}$ M to $10^{-8}$ M, $10^{-11}$ M to $10^{-9}$ M, or $10^{-10}$ M to $10^{-9}$ M. In certain embodiments, an anti-OX40 antibody binds to bound (e.g., cell membrane bound) human OX40, such as on activated human T cells, e.g., as determined by FACS, with an $EC_{50}$ of $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-8}$ M, $10^{-10}$ M to $10^{-8}$ M, $10^{-9}$ M to $10^{-8}$ M, $10^{-11}$ M to $10^{-9}$ M, or $10^{-10}$ M to $10^{-9}$ M. In certain embodiments, the anti-OX40 antibody binds to soluble human OX40 with a $K_D$ of $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M, and to cell membrane bound human OX40 with a $K_D$ or $EC_{50}$ of $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-8}$ M, $10^{-10}$ M to $10^{-8}$ M, $10^{-9}$ M to $10^{-8}$ M, $10^{-11}$ M to $10^{-9}$ M, or $10^{-10}$ M to $10^{-9}$ M.

Anti-OX40 antibodies described herein may bind to cynomolgus OX40, e.g., bind to membrane bound cynomolgus OX40, e.g., with an $EC_{50}$ of 100 nM or less, 10 nM or less, 100 nM to 0.01 nM, 100 nM to 0.1 nM, 100 nM to 1 nM, or 10 nM to 1 nM, e.g., as measured by FACS (e.g., as described in the Examples).

Anti-OX40 antibodies described herein may stimulate or enhance an immune response, e.g., by activating $T_{eff}$ cells, limiting the suppression of Teffector cells by Treg cells, depleting and/or inhibiting tumor Treg cells and/or activating NK cells, e.g., in the tumor. For example, the anti-OX40 antibodies may activate or costimulate $T_{eff}$ cells as evidenced, e.g., by enhanced cytokine (e.g., IL-2 and IFN-γ) secretion and/or enhanced proliferation. In certain embodiments, CD3 stimulation is also provided. In certain embodiments, the OX40 antibody increases IL-2 secretion by a factor of 50%, 100% (i.e., 2 fold), 3 fold, 4 fold, 5 fold or more, optionally with a maximum of up to 10 fold, 30 fold, 100 fold, as measured, e.g., on primary human T cells or T cells expressing human OX40 (e.g., as further described in the Examples). In certain embodiments, the OX40 antibody increases IFN-γ secretion by a factor of 50%, 100% (i.e., 2 fold), 3 fold, 4 fold, 5 fold or more, optionally with a maximum of up to 10 fold, 30 fold, 100 fold, as measured, e.g., on primary human T cells or T cells expressing human OX40 (e.g., as further described in the Examples).

Anti-OX40 antibodies described herein may inhibit binding of human OX40L to human OX40 on cells, e.g., 293 cells expressing human OX40 (i.e., hOX40-293 cells), e.g., with an $EC_{50}$ of 10 nM or less, 1 nM or less, 0.01 nM to 10 nM, 0.1 nM to 10 nM, or 0.1 nM to 1 nM (see Example 6).

Anti-OX40 antibodies described herein bind to an epitope on OX40, as determined, for example, by binding to fragments of human OX40. For example, in certain embodiments, the antibody binds to all or a portion of the sequence DVVSSKPCKPCTWCNLR (SEQ ID NO: 178) of human OX40 (SEQ ID NO: 2) as determined, for example, by HDX or by binding of the antibodies to fragments of human OX40, followed by enzymatic cleavage (see Example 11). In other embodiments, the antibody binds to all or a portion of the sequence DSYKPGVDCAPCPPGHFSPGDNQACKPWTNCTLAGK (SEQ ID NO: 179) of human OX40 (SEQ ID NO: 2).

In certain embodiments, the anti-OX40 antibodies described herein bind to all or a portion of the sequence SQNTVCRPCGPGFYNDVVSSKPCKPCTWCNLR (SEQ ID NO: 182).

In other embodiments, the anti-OX40 antibodies described herein bind to all or a portion of the sequence PCKPCTWCNLR (SEQ ID NO: 183).

In yet other embodiments, the anti-OX40 antibodies that bind to all or a portion of the sequence DVVSSKPCKPCTWCNLR (SEQ ID NO: 178) further bind to all or a portion of the sequence QLCTATQDTVCR (SEQ ID NO: 184).

In additional embodiments, the anti-OX40 antibodies described herein bind to all or a portion of the sequence SQNTVCRPCGPGFYN (SEQ ID NO: 185).

Anti-OX40 antibodies described herein may compete for binding to OX40 with (or inhibit binding of) anti-OX40 antibodies comprising CDRs or variable regions described herein, e.g., 3F4, 14B6-1, 14B6-2, 23H3, 6E1-1, 6E1-2, 18E9, 8B11, 20B3, 14A2-1, 14A2-2, and/or 20C1. In certain embodiments, anti-OX40 antibodies inhibit binding of 3F4, 14B6-1, 14B6-2, 23H3, 6E1-1, 6E1-2, 18E9, 8B11, 20B3, 14A2-1, 14A2-2, and/or 20C1 to human OX40 by at least 10%, 20%, 30%, 40%, 50%, 60%, 70%, 80%, 90% or by 100%. In certain embodiments, 3F4, 14B6-1, 14B6-2, 23H3, 6E1-1, 6E1-2, 18E9, 8B11, 20B3, 14A2-1, 14A2-2, and 20C1 inhibit binding of anti-OX40 antibodies to human OX40 by at least 10%, 20%, 30%, 40%, 50%, 60%, 70%, 80%, 90% or by 100%.

In certain embodiments, the antibodies induce or enhance T cell activation with multivalent crosslinking through, e.g., FcR binding. In certain embodiments, the antibodies are multivalent, e.g., bivalent. In certain embodiments, the antibodies are not monovalent.

In certain embodiments, the antibodies have 1, 2, 3, 4, 5, or 6 of the following features:
  (1) binding to soluble human OX40, e.g., with a $K_D$ of 10 nM or less (e.g., 0.01 nM to 10 nM), e.g., as measured by BIACORE® SPR analysis;
  (2) binding to membrane bound human OX40, e.g., with an $EC_{50}$ of 1 nM or less (e.g., 0.01 nM to 1 nM), e.g., as measured by FACS;
  (3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;
  (4) inducing or enhancing T cell activation, as evidenced by (i) increased IL-2 and/or IFN-γ production in OX40-expressing T cells and/or (ii) enhanced T cell proliferation;
  (5) inhibiting the binding of OX40 ligand to OX40, e.g., with an $EC_{50}$ of 1 nM or less as measured by FACS, e.g., in an assay with hOX40-293 cells;
  (6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDNQACKPWTNCTLAGK (SEQ ID NO: 179);
  (7) competing for binding to human OX40 with 3F4, 14B6-1, 14B6-2, 23H3, 18E9, 8B11, 20B3, and 20C1;
  (8) competing for binding to human OX40 with 6E1-1, 6E1-2, 14A2-1, and 14A2-2.

Accordingly, an antibody that exhibits one or more of these functional properties (e.g., biochemical, immunochemical, cellular, physiological or other biological activities, or the like) as determined according to methodologies known to the art and described herein, will be understood to relate to a statistically significant difference in the particular activity relative to that seen in the absence of the antibody (e.g., or when a control antibody of irrelevant specificity is present). Preferably, the anti-OX40 antibody increases a measured parameter (e.g., T cell proliferation, cytokine production) by at least 10% of the measured parameter, more preferably by at least 20%, 30%, 40%, 50%, 60%, 70%, 80%, 90%, 95%, 100% (i.e., 2 fold), 3 fold, 5 fold, or 10 fold. Conversely, the antibody may decrease a measured parameter (e.g., tumor volume, OX40-L binding to OX40, quantity of regulatory T cells in tumors) by at least 10% of the measured parameter, more preferably by at least 20%, 30%, 40%, 50%, 60%, 70%, 80% or 90%, 95%, or 99%.

Standard assays to evaluate the binding ability of the antibodies toward OX40 of various species are known in the art, including for example, ELISAs, Western blots, and RIAs. Suitable assays are described in detail in the Examples. The binding kinetics (e.g., binding affinity) of the antibodies also can be assessed by standard assays known in the art, such as by BIACORE® SPR analysis. Assays to evaluate the effects of the antibodies on functional properties of OX40 (e.g., ligand binding, T cell proliferation, cytokine production) are described in further detail infra and in the Examples.

In certain embodiments, the anti-OX40 antibodies are not native antibodies or are not naturally-occurring antibodies, e.g., anti-OX40 antibodies with post-translational modifications that are different from those of antibodies that are naturally occurring, such as by having more, less, or a different type of post-translational modification.

II. Exemplary Anti-OX40 Antibodies

Particular antibodies described herein are antibodies, e.g., monoclonal antibodies, having the CDR and/or variable region sequences of antibodies 3F4, 14B6-1, 14B6-2, 23H3, 6E1-1, 6E1-2, 18E9, 8B11, 20B3, 14A2-1, 14A2-2, and 20C1, isolated and structurally characterized as described in Example 1, as well as antibodies having at least 80% identity (e.g., at least 85%, at least 90%, at least 95%, or at least 99% identity) to the variable region or CDR sequences of antibodies 3F4, 14B6-1, 14B6-2, 23H3, 6E1-1, 6E1-2, 18E9, 8B11, 20B3, 14A2-1, 14A2-2, and 20C1. The $V_H$ amino acid sequences of 3F4, 14B6 (14B6-1 and 14B6-2), 23H3, 6E1 (6E1-1 and 6E1-2), 18E9, 8B11, 20B3, 14A2 (14A2-1 and 14A2-2), and 20C1 are set forth in SEQ ID NOs: 17, 28, 37, 48, 57, 65, 73, 84, and 93, respectively. The $V_L$ amino acid sequences of 3F4, 14B6-1, 14B6-2, 23H3, 6E1-1, 6E1-2, 18E9, 8B11, 20B3, 14A2-1, 14A2-2, and 20C1 are set forth in SEQ ID NOs: 18, 29, 30, 38, 49, 50, 58, 66, 74, 85, 86, and 94, respectively.

Accordingly, provided herein are antibodies, or antigen binding portion thereof, comprising heavy and light chain variable regions, wherein the heavy chain variable region comprises an amino acid sequence selected from the group consisting of SEQ ID NOs: 17, 28, 37, 48, 57, 65, 73, 84, and 93.

Also provided are antibodies, or antigen binding portions thereof, comprising heavy and light chain variable regions, wherein the light chain variable region comprises an amino acid sequence selected from the group consisting of SEQ ID NOs: 18, 29, 30, 38, 49, 50, 58, 66, 74, 85, 86, and 94.

Provided herein are antibodies, or antigen-binding portion thereof, comprising: heavy and light chain variable region sequences comprising SEQ ID NOs: 17 and 18; 28 and 29; 28 and 30; 37 and 38; 48 and 49; 48 and 50; 57 and 58; 65 and 66; 73 and 74; 84 and 85; 84 and 86; 93 and 94.

Anti-OX40 antibodies described herein may comprise the heavy and light chain CDR1s, CDR2s and CDR3s of 3F4, 14B6-1, 14B6-2, 23H3, 6E1-1, 6E1-2, 18E9, 8B11, 20B3, 14A2-1, 14A2-2, and 20C1, or combinations thereof. The amino acid sequences of the $V_H$ CDR1s of 3F4, 14B6 (14B6-1 and 14B6-2), 23H3, 6E1 (6E1-1 and 6E1-2), 18E9, 8B11, 20B3, 14A2 (14A2-1 and 14A2-2), and 20C1 are set forth in SEQ ID NOs: 11, 19, 31, 39, 51, 59, 67, 75, and 87, respectively. The amino acid sequences of the $V_H$ CDR2s of 3F4, 14B6 (14B6-1 and 14B6-2), 23H3, 6E1 (6E1-1 and 6E1-2), 18E9, 8B11, 20B3, 14A2 (14A2-1 and 14A2-2), and 20C1 are set forth in SEQ ID NOs: 12, 20, 32, 40, 52, 60, 68, 76, and 88, respectively. The amino acid sequences of the $V_H$ CDR3s of 3F4, 14B6 (14B6-1 and 14B6-2), 23H3, 6E1 (6E1-1 and 6E1-2), 18E9, 8B11, 20B3, 14A2 (14A2-1 and 14A2-2), and 20C1 are set forth in SEQ ID NOs: 13, 21, 33, 41, 53, 61, 69, 77, and 89. The amino acid sequences of the $V_L$ CDR1s of 3F4, 14B6-1, 14B6-2, 23H3, 6E1-1, 6E1-2, 18E9, 8B11, 20B3, 14A2-1, 14A2-2, and 20C1 are set forth in SEQ ID NOs: 14, 22, 25, 34, 42, 45, 54, 62, 70, 78, 81, and 90, respectively. The amino acid sequences of the $V_L$ CDR2s of 3F4, 14B6-1, 14B6-2, 23H3, 6E1-1, 6E1-2, 18E9, 8B11, 20B3, 14A2-1, 14A2-2, and 20C1 are set forth in SEQ ID NOs: 15, 23, 26, 35, 43, 46, 55, 63, 71, 79, 82, and 91, respectively. The amino acid sequences of the $V_L$ CDR3s of 3F4, 14B6-1, 14B6-2, 23H3, 6E1-1, 6E1-2, 18E9, 8B11, 20B3, 14A2-1, 14A2-2, and 20C1 are set forth in SEQ ID NOs: 16, 24, 27, 36, 44, 47, 56, 64, 72, 80, 83, and 92, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies bind to OX40 and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, although each antibody must contain a $V_H$ CDR1, 2 and 3 and a $V_L$ CDR1, 2 and 3) to create other anti-OX40 binding antibodies. OX40 binding of such "mixed and matched" antibodies can be tested using the binding assays described above and in the Examples (e.g., ELISAs). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 3F4, 14B6-1, 14B6-2, 23H3, 6E1-1, 6E1-2, 18E9, 8B11, 20B3, 14A2-1, 14A2-2, and 20C1. "Mixed and matched" antibodies having binding affinity, bioactivity and/or other properties equivalent or superior to the specific antibodies disclosed herein may be selected for use in the methods of the present invention.

Provided herein are isolated antibodies, or antigen binding portion thereof comprising:

(a) a heavy chain variable region CDR1 comprising an amino acid sequence selected from the group consisting of SEQ ID NOs: 11, 19, 31, 39, 51, 59, 67, 75, and 87;

(b) a heavy chain variable region CDR2 comprising an amino acid sequence selected from the group consisting of SEQ ID NOs: 12, 20, 32, 40, 52, 60, 68, 76, and 88;

(c) a heavy chain variable region CDR3 comprising an amino acid sequence selected from the group consisting of SEQ ID NOs: 13, 21, 33, 41, 53, 61, 69, 77, and 89;

(d) a light chain variable region CDR1 comprising an amino acid sequence selected from the group consisting of SEQ ID NOs: 14, 22, 25, 34, 42, 45, 54, 62, 70, 78, 81, and 90;

(e) a light chain variable region CDR2 comprising an amino acid sequence selected from the group consisting of SEQ ID NOs: 15, 23, 26, 35, 43, 46, 55, 63, 71, 79, 82, and 91; and (f) a light chain variable region CDR3 comprising an amino acid sequence selected from the group consisting of SEQ ID NOs: 16, 24, 27, 36, 44, 47, 56, 64, 72, 80, 83, and 92;

wherein the antibody specifically binds to human OX40.

In one embodiment, the antibody comprises heavy and light chain variable regions, wherein the heavy chain variable region CDR1, CDR2, and CDR3 regions comprise: SEQ ID NOs: 11-13; 19-21; 31-33; 39-41; 51-53; 59-61; 67-69; 74-77; 87-89; and 87, 317, and 89, respectively;

wherein the antibody specifically binds to human OX40.

In another embodiment, the antibody comprises heavy and light chain variable regions, wherein the light chain variable region CDR1, CDR2, and CDR3 regions comprise: SEQ ID NOs: 14-16; 22-24; 25-27; 34-36; 42-44; 45-47; 54-56; 62-64; 70-72; 78-80; 81-83; and 90-92, respectively;

wherein the antibody specifically binds to human OX40.

In a particular embodiment, the antibody comprises heavy and light chain variable regions, wherein the antibody comprises:

(a) heavy chain CDR1, CDR2, and CDR3 sequences comprising SEQ ID NOs: 87, 317, and 89, respectively, and/or light chain CDR1, CDR2, and CDR3 sequences comprising SEQ ID NOs: 90-92, respectively;

(b) heavy chain CDR1, CDR2, and CDR3 sequences comprising SEQ ID NOs: 11-13, respectively, and/or light chain CDR1, CDR2, and CDR3 sequences comprising SEQ ID NOs: 14-16, respectively;

(c) heavy chain CDR1, CDR2, and CDR3 sequences comprising SEQ ID NOs: 19-21, respectively, and/or light chain CDR1, CDR2, and CDR3 sequences comprising SEQ ID NOs: 22-24, respectively;

(d) heavy chain CDR1, CDR2, and CDR3 sequences comprising SEQ ID NOs: 19-21, respectively, and/or light chain CDR1, CDR2, and CDR3 sequences comprising SEQ ID NOs: 25-27, respectively;

(e) heavy chain CDR1, CDR2, and CDR3 sequences comprising SEQ ID NOs: 31-33, respectively, and/or light chain CDR1, CDR2, and CDR3 sequences comprising SEQ ID NOs: 34-36, respectively;

(f) heavy chain CDR1, CDR2, and CDR3 sequences comprising SEQ ID NOs: 39-41, respectively, and/or light chain CDR1, CDR2, and CDR3 sequences comprising SEQ ID NOs: 42-44, respectively;

(g) heavy chain CDR1, CDR2, and CDR3 sequences comprising SEQ ID NOs: 39-41, respectively, and/or light chain CDR1, CDR2, and CDR3 sequences comprising SEQ ID NOs: 45-47, respectively;

(h) heavy chain CDR1, CDR2, and CDR3 sequences comprising SEQ ID NOs: 51-53, respectively, and/or light chain CDR1, CDR2, and CDR3 sequences comprising SEQ ID NOs: 54-56, respectively;

(i) heavy chain CDR1, CDR2, and CDR3 sequences comprising SEQ ID NOs: 59-61, respectively, and/or light chain CDR1, CDR2, and CDR3 sequences comprising SEQ ID NOs: 62-64, respectively;

(j) heavy chain CDR1, CDR2, and CDR3 sequences comprising SEQ ID NOs: 67-69, respectively, and/or light chain CDR1, CDR2, and CDR3 sequences comprising SEQ ID NOs: 70-72, respectively;

(k) heavy chain CDR1, CDR2, and CDR3 sequences comprising SEQ ID NOs: 75-77, respectively, and/or light chain CDR1, CDR2, and CDR3 sequences comprising SEQ ID NOs: 78-80, respectively;

(l) heavy chain CDR1, CDR2, and CDR3 sequences comprising SEQ ID NOs: 75-77, respectively, and/or light chain CDR1, CDR2, and CDR3 sequences comprising SEQ ID NOs: 81-83, respectively; or (m) heavy chain CDR1, CDR2, and CDR3 sequences comprising SEQ ID NOs: 87-89, respectively, and/or light chain CDR1, CDR2, and CDR3 sequences comprising SEQ ID NOs: 90-92, respectively;

wherein the antibody specifically binds to human OX40.

In another embodiment, the antibody comprises heavy and light chain variable regions, wherein the antibody comprises:

(a) heavy chain CDR1, CDR2, and CDR3 sequences consisting of SEQ ID NOs: 87, 317, and 89, respectively, and/or light chain CDR1, CDR2, and CDR3 sequences consisting of SEQ ID NOs: 90-92, respectively;

(b) heavy chain CDR1, CDR2, and CDR3 sequences consisting of SEQ ID NOs: 11-13, respectively, and/or light chain CDR1, CDR2, and CDR3 sequences consisting of SEQ ID NOs: 14-16, respectively;

(c) heavy chain CDR1, CDR2, and CDR3 sequences consisting of SEQ ID NOs: 19-21, respectively, and/or light chain CDR1, CDR2, and CDR3 sequences consisting of SEQ ID NOs: 22-24, respectively;

(d) heavy chain CDR1, CDR2, and CDR3 sequences consisting of SEQ ID NOs: 19-21, respectively, and/or light chain CDR1, CDR2, and CDR3 sequences consisting of SEQ ID NOs: 25-27, respectively;

(e) heavy chain CDR1, CDR2, and CDR3 sequences consisting of SEQ ID NOs: 31-33, respectively, and/or light chain CDR1, CDR2, and CDR3 sequences consisting of SEQ ID NOs: 34-36, respectively;

(f) heavy chain CDR1, CDR2, and CDR3 sequences consisting of SEQ ID NOs: 39-41, respectively, and/or light chain CDR1, CDR2, and CDR3 sequences consisting of SEQ ID NOs: 42-44, respectively;

(g) heavy chain CDR1, CDR2, and CDR3 sequences consisting of SEQ ID NOs: 39-41, respectively, and/or light chain CDR1, CDR2, and CDR3 sequences consisting of SEQ ID NOs: 45-47, respectively;

(h) heavy chain CDR1, CDR2, and CDR3 sequences consisting of SEQ ID NOs: 51-53, respectively, and/or light chain CDR1, CDR2, and CDR3 sequences consisting of SEQ ID NOs: 54-56, respectively;

(i) heavy chain CDR1, CDR2, and CDR3 sequences consisting of SEQ ID NOs: 59-61, respectively, and/or light chain CDR1, CDR2, and CDR3 sequences consisting of SEQ ID NOs: 62-64, respectively;

(j) heavy chain CDR1, CDR2, and CDR3 sequences consisting of SEQ ID NOs: 67-69, respectively, and/or light chain CDR1, CDR2, and CDR3 sequences consisting of SEQ ID NOs: 70-72, respectively;

(k) heavy chain CDR1, CDR2, and CDR3 sequences consisting of SEQ ID NOs: 75-77, respectively, and/or light chain CDR1, CDR2, and CDR3 sequences consisting of SEQ ID NOs: 78-80, respectively;

(l) heavy chain CDR1, CDR2, and CDR3 sequences consisting of SEQ ID NOs: 75-77, respectively, and/or light chain CDR1, CDR2, and CDR3 sequences consisting of SEQ ID NOs: 81-83, respectively; or (m) heavy chain CDR1, CDR2, and CDR3 sequences consisting of SEQ ID NOs: 87-89, respectively, and/or light chain CDR1, CDR2, and CDR3 sequences consisting of SEQ ID NOs: 90-92, respectively.

A VH domain, or one or more CDRs thereof, described herein may be linked to a constant domain for forming a heavy chain, e.g., a full length heavy chain. Similarly, a VL domain, or one or more CDRs thereof, described herein may be linked to a constant domain for forming a light chain, e.g., a full length light chain. A full length heavy chain (with the exception of the C-terminal lysine (K) or with the exception of the C-terminal glycine and lysine (GK), which may be absent) and full length light chain combine to form a full length antibody. N-terminal glutamine and glutamate residues may also be converted to pyroglutamate residues on both light and heavy chains.

A VH domain described herein may be fused to the constant domain of a human IgG, e.g., IgG1, IgG2, IgG3 or IgG4, which are either naturally-occurring or modified, e.g., as further described herein. For example, a heavy chain may comprise the amino acid sequence of any VH domain described herein fused to the human IgG1 amino acid sequence set forth in SEQ ID NO: 5.

The human IgG1 constant domain may also be that of an allotypic variant. For example, an allotypic variant of IgG1 comprises an R107K, E189D and M191L (underlined above, with numbering according to that in SEQ ID NO: 6). Within the full length heavy region, these amino acid substitutions are numbered R214K, E356D and M358L.

A VL domain described herein may be fused to the constant domain of a human kappa or lambda light chain. For example, a light chain may comprise the amino acid sequence of any VL domain described herein fused to the human IgG1 kappa light chain amino acid sequence set forth in SEQ ID NO: 7.

In certain embodiments, the heavy chain constant region comprises a lysine or another amino acid at the C-terminus, e.g., it comprises the following last amino acids: LSPGK (SEQ ID NO: 8) for the heavy chain. In certain embodiments, the heavy chain constant region is lacking one or more amino acids at the C-terminus, and has, e.g., the C-terminal sequence LSPG (SEQ ID NO: 9) or LSP.

The amino acid sequences of exemplary heavy and light chains are set forth in Table 23 and correspond to SEQ ID NOs: 95, 97, 99, 101, 103, 105, 107, 109, 111, 113, 115, 117, 119, 121, 123, 124 and 125 for the heavy chains and SEQ ID NOs: 96, 98, 100, 102, 104, 106, 108, 110, 112, 114, 116, 118, 120, and 122 for the light chains.

Heavy and light chains comprising an amino acid sequence that is at least 99%, 98%, 97%, 96%, 95%, 90%, 85%, 80%, 75% or 70% identical to any of the heavy or light chains set forth in Table 23 (or their variable regions), e.g., SEQ ID NOs: 95 and 96; 97 and 98; 99 and 100; 101 and 102; 103 and 104; 105 and 106; 107 and 108; 109 and 110; 111 and 112; 113 and 114; 115 and 116; 117 and 118; 119 and 120; 121 and 122; 123 and 116; 124 and 116; and 125 and 116 may be used for forming anti-human OX40 antibodies having the desired characteristics, e.g., those further described herein. Exemplary variants are those comprising an allotypic variation, e.g., in the constant domain, and/or a mutation in the variable or constant regions, such as the mutations disclosed herein. Heavy and light chains comprising an amino acid sequence that differs in at most 1-30, 1-25, 1-20, 1-15, 1-10, 1-5, 1-4, 1-3, 1-2 or 1 amino acid (by substitution, addition or deletion) from any of the heavy or light chains set forth in Table 23 (or their variable regions) may be used for forming anti-human OX40 antibodies having the desired characteristics, e.g., those further described herein.

In various embodiments, the antibodies described above exhibit one or more, two or more, three or more, four or more, five or more, six, or all of the following functional properties:
(1) binding to soluble human OX40, e.g., with a $K_D$ of 10 nM or less (e.g., 0.01 nM to 10 nM), e.g., as measured by Biacore;
(2) binding to membrane bound human OX40, e.g., with an $EC_{50}$ of 1 nM or less (e.g., 0.01 nM to 1 nM), e.g., as measured by FACS;
(3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;
(4) inducing or enhancing T cell activation, as evidenced by (i) increased IL-2 and/or IFN-γ production in OX40-expressing T cells and/or (ii) enhanced T cell proliferation;
(5) inhibiting the binding of OX40 ligand to OX40, e.g., with an $EC_{50}$ of 1 nM or less as measured by FACS, e.g., in an assay with hOX40-293 cells;
(6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDN-QACKPWTNCTLAGK (SEQ ID NO: 179);
(7) competing for binding to human OX40 with 3F4, 14B6-1, 14B6-2, 23H3, 18E9, 8B11, 20B3, and 20C1;
(8) competing for binding to human OX40 with 6E1-1, 6E1-2, 14A2-1, and 14A2-2.

Such antibodies include, for example, human antibodies, humanized antibodies, or chimeric antibodies.

In certain embodiments, the anti-OX40 antibodies described herein bind to amino acid residues within the following region of mature human OX40 (SEQ ID NO: 2):

```
                                        (SEQ ID NO: 178)
            DVVSSKPCKPCTWCNLR,
``` corresponding to amino acid residues 46-62 of mature human OX40 (SEQ ID NO: 2).

In certain embodiments, the anti-OX40 antibodies described herein bind to amino acid residues within the following region of mature human OX40 (SEQ ID NO: 2):

```
                                        (SEQ ID NO: 179)
       DSYKPGVDCAPCPPGHFSPGDNQACKPWTNCTLAGK,
``` corresponding to amino acid residues 89-124 of mature human OX40 (SEQ ID NO: 2).

In certain embodiments, the anti-OX40 antibodies described herein that bind to all or a portion of the sequence DVVSSKPCKPCTWCNLR (SEQ ID NO: 178) bind to all or a portion of the sequence SQNTVCRPCGPGFYNDV-VSSKPCKPCTWCNLR (SEQ ID NO: 182).

In other embodiments, the anti-OX40 antibodies described herein that bind to all or a portion of the sequence DVVSSKPCKPCTWCNLR (SEQ ID NO: 178) bind to all or a portion of the sequence PCKPCTWCNLR (SEQ ID NO: 183).

In yet other embodiments, the anti-OX40 antibodies that bind to all or a portion of the sequence DVVSSKPCK-PCTWCNLR (SEQ ID NO: 178) further bind to all or a portion of the sequence QLCTATQDTVCR (SEQ ID NO: 184).

In additional embodiments, the anti-OX40 antibodies described herein that bind to all or a portion of the sequence DVVSSKPCKPCTWCNLR (SEQ ID NO: 178) further bind to all or a portion of the sequence SQNTVCRPCGPGFYN (SEQ ID NO: 185).

Modified Heavy Chain Constant Domains

The heavy chain constant region of anti-OX40 antibodies described herein may be of any isotype, e.g., IgG1, IgG2, IgG3 and IgG4, or combinations thereof and/or modifications thereof. In certain embodiments, anti-OX40 antibodies comprise a modified heavy chain constant region that alters the properties of the antibody.

As discussed further herein and in the Examples, cross-linking of anti-OX40 antibodies with unmodified hIgG1 constant regions (hIgG1 isotype antibodies) induce OX40 signaling and promote T cell activation, and specifically to promote T cell proliferation, IFN-γ secretion, and IL-2 secretion. Cross-linking can occur by, e.g., binding to human CD32A Fcγ receptors (FcγRs) expressed on the surface of transfected CHO cells in an assay utilizing co-cultures of CHO-CD3-CD32A cells and human primary CD4 T cells. Cross-linking can also occur, e.g., by adding a soluble polyclonal anti-human Fcγ antibody in cultures of staphylococcus enterotoxin B (SEB)-activated human peripheral blood mononuclear cells (PBMCs).

Anti-OX40 antibodies with modified heavy chain constant regions (e.g., IgG1 constant region wherein the CH1/hinge region is replaced with an hIgG2 CH1/hinge region) may have the ability to alter the activities of the antibodies relative to antibodies with a fully IgG1 heavy chain constant region. Exemplary activities that may be altered include, but are not limited to, (1) T cell activation in the presence or absence of cross-linking, (2) T cell proliferation in the presence or absence of cross-linking, and/or (3) cytokine secretion (e.g., IFN-γ, IL-2) in the presence or absence of cross-linking. The methods described in the Examples can be used to determine whether the anti-OX40 antibodies with modified heavy chain constant regions exhibit these altered activities (see, e.g., Example 27). In preferred embodiments, these altered activities do not markedly affect the antigen-binding properties of the antibodies, which can be assessed using, e.g., FACS, SPR).

Accordingly, provided herein are methods of altering the activity of anti-OX40 antibodies comprising providing an anti-OX40 antibody that has a non-IgG2 hinge, and replacing the non-IgG2 hinge with an IgG2 hinge. In certain embodiments, a modified heavy chain constant region comprises a hinge of the IgG2 isotype (an "IgG2 hinge") and a CH1, CH2 and CH3 domain. In certain embodiments, a modified heavy chain constant region comprises an IgG2 hinge and a CH1, CH2 and CH3 domain, wherein at least one of the CH1, CH2 and CH3 domains is not of the IgG2 isotype. The IgG2 hinge may be a wildtype IgG2 hinge, e.g., a wildtype human IgG2 hinge (e.g., ERKCCVECPPCPAPPVAG; SEQ ID NO: 208) or a variant thereof, provided that the IgG2 hinge retains the ability to confer to the antibody an altered activity relative to the same antibody that comprises a non-IgG2 hinge. In certain embodiments, an IgG2 hinge variant retains similar rigidity or stiffness to that of a wildtype IgG2 hinge. The rigidity of a hinge can be determined, e.g., by computer modeling, electron microscopy, spectroscopy such as Nuclear Magnetic Resonance (NMR), X-ray crystallography (B-factors), or Sedimentation Velocity Analytical ultracentrifugation (AUC) to measure or compare the radius of gyration of antibodies comprising the hinge. A hinge may have similar or higher rigidity relative to another hinge if an antibody comprising the hinge has a value obtained from one of the tests described in the previous sentence that differs from the value of the same antibody with a different hinge, e.g., an IgG1 hinge, in less than 5%, 10%, 25%, 50%, 75%, or 100%. A person of skill in the art would be able to determine from the tests whether a hinge has at least similar rigidity to that of another hinge by interpreting the results of these tests. An exemplary human IgG2 hinge variant is an IgG2 hinge that comprises a substitution of one or more of the four cysteine residues (i.e., C219, C220, C226 and C229). A cysteine may be replaced by a serine. An exemplary IgG2 hinge is a human IgG2 hinge comprising a C219S mutation (e.g., ERKSCVECPPCPAPPVAG; SEQ ID NO: 209). Other IgG2 hinge variants that may be used include human IgG2 hinges comprising a C220, C226 and/or C229 substitution, e.g., a C220S, C226S or C229S mutation (which may be combined with a C219S mutation). An IgG2 hinge may also be an IgG2 hinge in which a portion of the hinge is that of another isotype (i.e., it is a chimeric hinge), provided that the rigidity of the chimeric hinge is at least similar to that of a wildtype IgG2 hinge. For example, an IgG2 hinge may be an IgG2 hinge in which the lower hinge (as defined in Table 2) is of an IgG1 isotype, and is, e.g., a wildtype IgG1 lower hinge.

Additional IgG2 hinge mutations that may be used in an IgG2 hinge include the SE (S267E), SELF (S267E/L328F), SDIE (S239D/I332E), SEFF and GASDALIE (G236A/S239D/A330L/I332E) mutations.

A "hybrid" or "chimeric" hinge is referred to as being of a specific isotype if more than half of the consecutive amino acids of the hinge are from that isotype. For example, a hinge having an upper and middle hinge of IgG2 and the lower hinge of IgG1 is considered to be an IgG2 hinge.

In certain embodiments, an anti-OX40 antibody comprises a modified heavy chain constant region that comprises an IgG2 hinge comprising one of the following sequences:

```
                           (SEQ ID NO: 208)
ERKCCVECPPCPAPPVAG;

(SEQ ID NO: 209)
ERKSCVECPPCPAPPVAG;

(SEQ ID NO: 210)
ERKCSVECPPCPAPPVAG;

(SEQ ID NO: 211)
ERKXCVECPPCPAPPVAG;

(SEQ ID NO: 212)
ERKCXVECPPCPAPPVAG;

(SEQ ID NO: 213)
ERKCCVECPPCPAPPVAGX;

(SEQ ID NO: 214)
ERKSCVECPPCPAPPVAGX;

(SEQ ID NO: 215)
ERKCSVECPPCPAPPVAGX;

(SEQ ID NO: 216)
ERKXCVECPPCPAPPVAGX;

(SEQ ID NO: 217)
ERKCXVECPPCPAPPVAGX;

(SEQ ID NO: 218)
ERKCCVECPPCPAPELLGG;

(SEQ ID NO: 219)
ERKSCVECPPCPAPELLGG;

(SEQ ID NO: 220)
ERKCCSVECPPCPAPELLGG;

(SEQ ID NO: 221)
ERKXCVECPPCPAPELLGG;

(SEQ ID NO: 222)
ERKCXVECPPCPAPELLGG;

(SEQ ID NO: 223)
ERKCCVECPPCPAPELLG;

(SEQ ID NO: 224)
ERKSCVECPPCPAPELLG;

(SEQ ID NO: 225)
ERKCCSVECPPCPAPELLG;

(SEQ ID NO: 226)
ERKXCVECPPCPAPELLG;

(SEQ ID NO: 227)
ERKCXVECPPCPAPELLG;

(SEQ ID NO: 228)
ERKCCVECPPCPAP;

(SEQ ID NO: 229)
ERKSCVECPPCPAP;
```

-continued

ERKCSVECPPCPAP; (SEQ ID NO: 230)

ERKXCVECPPCPAP; (SEQ ID NO: 231)
or

ERKCXVECPPCPAP, (SEQ ID NO: 232)

wherein X is any amino acid, except a cysteine, or any of the above sequences, in which 1-5, 1-3, 1-2 or 1 amino acid is inserted between amino acid residues CVE and CPP. In certain embodiments, THT or GGG is inserted. In certain embodiments, 1, 1-2, or 1-3 amino acids are inserted between the hinge and CH2 domain. For example, a glycine may be inserted between the hinge and CH2 domain.

In certain embodiments, the hinge comprises SEQ ID NO: 208, 209, 210, 211, or 212, wherein 1, 2, 3 or all 4 amino acids P233, V234, A235 and G237 (corresponding to the C-terminal 4 amino acids "PVAG" (SEQ ID NO: 233) are deleted or substituted with another amino acid, e.g., the amino acids of the C-terminus of the IgG1 hinge (ELLG (SEQ ID NO: 234) or ELLGG (SEQ ID NO: 235). In certain embodiments, the hinge comprises SEQ ID NO: 208, 209, 210, 211, or 212, wherein V234, A235 and G237 are deleted or substituted with another amino acid. In certain embodiments, the hinge comprises SEQ ID NO: 208, 209, 210, 211, or 212, wherein A235 and G237 are deleted or substituted with another amino acid. In certain embodiments, the hinge comprises SEQ ID NO: 208, 209, 210, 211, or 212, wherein G237 is deleted or substituted with another amino acid. In certain embodiments, the hinge comprises SEQ ID NO: 447, 448, 449, 450, or 451, wherein V234 and A235 are deleted or substituted with another amino acid. Substitution of PVAG (SEQ ID NO: 233) in an IgG2 with the corresponding amino acids of an IgG1 hinge, i.e., (ELLG (SEQ ID NO: 234) or ELLGG (SEQ ID NO: 235)) to obtain a hybrid hinge, e.g., shown above, that provides a hinge having the advantages of an IgG2 hinge and the effector function of IgG1 hinges.

In certain embodiments, a modified heavy chain constant region comprises a hinge that consists of or consists essentially of one of the sequences shown above, e.g., any one of SEQ ID NOs: 208-232, and in certain embodiments, does not comprise additional hinge amino acid residues.

In certain embodiments, a modified heavy chain constant region comprises a CH1 domain that is a wildtype CH1 domain of the IgG1 or IgG2 isotype ("IgG1 CH1 domain" or "IgG2 CH1 domain," respectively). CH1 domains of the isotypes IgG3 and IgG4 ("IgG3 CH1 domain and "IgG2 CH1 domain," respectively) may also be used. A CH1 domain may also be a variant of a wildtype CH1 domain, e.g., a variant of a wildtype IgG1, IgG2, IgG3 or IgG4 CH1 domain. Exemplary variants of CH1 domains include A114C and T173C and/or C131, e.g., C131S.

In certain embodiments, a modified heavy chain constant region comprises a CH2 domain that is a wildtype CH2 domain of the IgG1, IgG2, IgG3 or IgG4 isotype ("IgG1 CH2 domain," "IgG2 CH2 domain," "IgG3 CH2 domain," or "IgG4 CH2 domain," respectively). A CH2 domain may also be a variant of a wildtype CH2 domain, e.g., a variant of a wildtype IgG1, IgG2, IgG3 or IgG4 CH2 domain. Exemplary variants of CH2 domains include variants that modulate a biological activity of the Fc region of an antibody, such as ADCC or CDC or modulate the half-life of the antibody or its stability. In one embodiment, the CH2 domain is a human IgG1 CH2 domain with an A330S and P331S mutation, wherein the CH2 domain has reduced effector function relative to the same CH2 mutation without the mutations. Other mutations are further set forth herein elsewhere.

In certain embodiments, a modified heavy chain constant region comprises a CH3 domain that is a wildtype CH3 domain of the IgG1, IgG2, IgG3 or IgG4 isotype ("IgG1 CH3 domain," "IgG2 CH3 domain," "IgG3 CH3 domain," or "IgG4 CH3 domain," respectively). A CH3 domain may also be a variant of a wildtype CH3 domain, e.g., a variant of a wildtype IgG1, IgG2, IgG3 or IgG4 CH3 domain. Exemplary variants of CH3 domains include variants that modulate a biological activity of the Fc region of an antibody, such as ADCC or CDC or modulate the half-life of the antibody or its stability.

Generally, variants of the CH1, hinge, CH2 or CH3 domains may comprise 1, 2, 3, 4, 5, 6, 7, 8, 9, 10 or more mutations, and/or at most 10, 9, 8, 7, 6, 5, 4, 3, 2 or 1 mutation, or 1-10 or 1-5 mutations, or comprise an amino acid sequence that is at least about 75%, 80%, 85%, 90%, 95%, 96%, 97%, 98%, or 99% identical to that of the corresponding wildtype domain (CH1, hinge, CH2, or CH3 domain, respectively), provided that the heavy chain constant region comprising the specific variant retains the necessary biological activity.

Table 3 sets forth exemplary human heavy chain constant regions comprising a human CH1, hinge, CH2 and/or CH3 domains, wherein each domain is either a wildtype domain or a variant thereof that provides the desired biological activity to the heavy chain constant region. An unfilled cell in Table 3 indicates that the domain is present or not, and if present can be of any isotype, e.g., IgG1, IgG2, IgG3 or IgG4. For example, an antibody comprising the heavy chain constant region 1 in Table 3 is an antibody that comprises a heavy chain constant region comprising at least an IgG2 hinge, and which may also comprise a CH1, CH2 and/or CH3 domain, and if present, which CH1, CH2 and/or CH3 domain is of an IgG1, IgG2, IgG3 or IgG4 isotype. As another example for understanding Table 3, an antibody comprising a heavy chain constant region 8 is an antibody comprising a heavy chain constant region comprising an IgG1 CH1 domain, and IgG2 hinge, an IgG1 CH2 domain, and which may or may not also comprise a CH3 domain, which if present, may be of an IgG1, IgG2, IgG3 or IgG4 isotype.

TABLE 3

Exemplary configurations of human heavy chain constant regions

| MHCCR* | CH1 | Hinge | CH2 | CH3 |
|---|---|---|---|---|
| 1 | | IgG2 | | |
| 2 | IgG1 | IgG2 | | |
| 3 | IgG2 | IgG2 | | |
| 4 | | IgG2 | IgG1 | |
| 5 | | IgG2 | IgG2 | |
| 6 | | IgG2 | | IgG1 |
| 7 | | IgG2 | | IgG2 |
| 8 | IgG1 | IgG2 | IgG1 | |
| 9 | IgG1 | IgG2 | IgG2 | |
| 10 | IgG2 | IgG2 | IgG1 | |
| 11 | IgG2 | IgG2 | IgG2 | |
| 12 | IgG1 | IgG2 | | IgG1 |
| 13 | IgG1 | IgG2 | | IgG2 |
| 14 | IgG2 | IgG2 | | IgG1 |
| 15 | IgG2 | IgG2 | | IgG2 |
| 16 | | IgG2 | IgG1 | IgG1 |

TABLE 3-continued

Exemplary configurations of human heavy chain constant regions

| MHCCR* | CH1 | Hinge | CH2 | CH3 |
|---|---|---|---|---|
| 17 |  | IgG2 | IgG1 | IgG2 |
| 18 |  | IgG2 | IgG2 | IgG1 |
| 19 |  | IgG2 | IgG2 | IgG2 |
| 20 | IgG1 | IgG2 | IgG1 | IgG1 |
| 21 | IgG1 | IgG2 | IgG1 | IgG2 |
| 22 | IgG1 | IgG2 | IgG2 | IgG1 |
| 23 | IgG1 | IgG2 | IgG2 | IgG2 |
| 24 | IgG2 | IgG2 | IgG1 | IgG1 |
| 25 | IgG2 | IgG2 | IgG1 | IgG2 |
| 26 | IgG2 | IgG2 | IgG2 | IgG1 |
| 27 | IgG2 | IgG2 | IgG2 | IgG2 |

*Modified heavy chain constant region

In certain embodiments, an anti-OX40 antibody comprises a heavy chain constant region shown in Table 3 and may have altered activity relative to the same antibody comprising a heavy chain constant region that does not comprise that specific heavy chain constant region. In certain embodiments, an antibody comprising a heavy chain constant region shown in Table 3 or 4 may have an altered activity relative to the same antibody comprising a heavy chain constant region that does not comprise an IgG2 hinge or the same IgG2 hinge. In certain embodiments, an antibody comprising a heavy chain constant region shown in Table 3 or 4 may have an altered activity relative to the same antibody comprising a heavy chain constant region that comprises a non-IgG2 hinge, and comprises, e.g., an IgG1, IgG3 or IgG4 hinge. In certain embodiments, an antibody comprising a heavy chain constant region shown in Table 3 or 4 may have an altered activity relative to the same antibody comprising a heavy chain constant region that does not comprise one or more of the same CH1, hinge, CH2 or CH3 domain. For example, in certain embodiments, an antibody comprising a heavy chain constant region shown in Table 3 or 4 may have an altered activity relative to the same antibody comprising a heavy chain constant region that does not comprise an IgG2 hinge and a CH1, CH2 and/or CH3 domain of the specific isotype. For example, an antibody comprising a heavy chain constant region 22 shown in Table 3, may have an altered activity relative to (i) the same antibody comprising a heavy chain constant region that does not comprise an IgG2 hinge, and comprises, e.g., a non-IgG2 hinge (e.g., an IgG1, IgG3 or IgG4 hinge); (ii) the same antibody comprising a heavy chain constant region that does not comprise an IgG2 hinge and an IgG1 CH1, and comprises, e.g., a non-IgG2 hinge and/or a non-IgG1 CH1; (iii) the same antibody comprising a heavy chain constant region that does not comprise an IgG2 hinge and an IgG2 CH2, and comprises, e.g., a non-IgG2 hinge and/or a non-IgG2 CH2; (iv) the same antibody comprising a heavy chain constant region that does not comprise an IgG2 hinge and an IgG1 CH3, and comprises, e.g., a non-IgG2 hinge and/or a non-IgG1 CH3; (v) the same antibody comprising a heavy chain constant region that does not comprise an IgG2 hinge, an IgG1 CH1 and an IgG2 CH2, and comprises, e.g., a non-IgG2 hinge and/or a non-IgG1 CH1 and/or a non-IgG2 CH2; (vi) the same antibody comprising a heavy chain constant region that does not comprise an IgG2 hinge, an IgG1 CH1 and an IgG1 CH3, and comprises, e.g., a non-IgG2 hinge and/or a non-IgG1 CH1 and/or a non-IgG1 CH3; (vii) the same antibody comprising a heavy chain constant region that does not comprise an IgG2 hinge, an IgG2 CH2 and an IgG1 CH3, and comprises, e.g., a non-IgG2 hinge and/or a non-IgG2 CH and/or a non-IgG1 CH3; (viii) or the same antibody comprising a heavy chain constant region that does not comprise an IgG2 hinge, an IgG1 CH1, IgG2 CH2 and an IgG1 CH3, and comprises, e.g., a non-IgG2 hinge and/or a non-IgG1 CH1 and/or a non-IgG2 CH2 and/or a non-IgG1 CH3.

Exemplary modified heavy chain constant regions that may be linked to anti-OX40 variable regions, e.g., the variable regions described herein, are provided in Table 4, which sets forth the identity of each of the domains.

TABLE 4

Exemplary modified heavy chain constant regions

| Modified heavy chain constant region | CH1 | Hinge | CH2 | CH3 | SEQ ID NO of whole MHCCR |
|---|---|---|---|---|---|
| IgG1-IgG2-IgG1f | IgG1 wildtype SEQ ID NO: 202 | IgG2/IgG1 SEQ ID NO: 240 | IgG1 wildtype SEQ ID NO: 204 | IgG1 wildtype SEQ ID NO: 204 | SEQ ID NO: 244 |
| IgG1-IgG2-IgG1f2 | IgG1 wildtype SEQ ID NO: 202 | IgG2 wildtype SEQ ID NO: 238 | IgG1 wildtype SEQ ID NO: 204 | IgG1 wildtype SEQ ID NO:206 | SEQ ID NO: 245 |
| IgG1-IgG2CS-IgG1f | IgG1 wildtype SEQ ID NO: 202 | IgG2C219S/ IgG1 SEQ ID NO: 241 | IgG1 wildtype SEQ ID NO: 204 | IgG1 wildtype SEQ ID NO: 206 | SEQ ID NO: 246 |
| IgG1-IgG2CS-IgG1f2 | IgG1 wildtype SEQ ID NO: 202 | IgG2 C219S SEQ ID NO: 239 | IgG1 wildtype SEQ ID NO: 204 | IgG1 wildtype SEQ ID NO: 206 | SEQ ID NO: 247 |
| IgG2-IgG1f | IgG2 wildtype | IgG2/IgG1 SEQ ID | IgG1 wildtype | IgG1 wildtype | SEQ ID NO: 248 |

TABLE 4-continued

Exemplary modified heavy chain constant regions

| Modified heavy chain constant region | CH1 | Hinge | CH2 | CH3 | SEQ ID NO of whole MHCCR |
|---|---|---|---|---|---|
| | | SEQ ID NO: 240 | SEQ ID NO: 204 | SEQ ID NO: 206 | |
| IgG2-IgG1f2 | IgG2 wildtype SEQ ID NO:203 | IgG2 wildtype SEQ ID NO: 238 | IgG1 wildtype SEQ ID NO: 204 | IgG1 wildtype SEQ ID NO: 206 | SEQ ID NO: 249 |
| IgG2CS-IgG1f | IgG2 wildtype SEQ ID NO: 203 | IgG2C219S/ IgG1 SEQ ID NO: 241 | IgG1 wildtype SEQ ID NO: 204 | IgG1 wildtype SEQ ID NO: 206 | SEQ ID NO: 250 |
| IgG2CS-IgG1f2 | IgG2 wildtype SEQ ID NO: 203 | IgG2 C219S SEQ ID NO: 239 | IgG1 wildtype SEQ ID NO: 204 | IgG1 wildtype SEQ ID NO: 206 | SEQ ID NO: 251 |
| IgG1-IgG2-IgG1.1f | IgG1 wildtype SEQ ID NO: 202 | IgG2 wildtype SEQ ID NO: 238 | IgG1 A330S/ P331S SEQ ID NO: 243 | IgG1 wildtype SEQ ID NO:206 | SEQ ID NO: 252 |
| IgG1-IgG2CS-IgG1.1f | IgG1 wildtype SEQ ID NO: 202 | IgG2 C219S SEQ ID NO: 239 | IgG1 A330S/ P331S SEQ ID NO: 243 | IgG1 wildtype SEQ ID NO: 206 | SEQ ID NO: 253 |
| IgG2-IgG1.1f | IgG2 wildtype SEQ ID NO: 203 | IgG2 wildtype SEQ ID NO: 238 | IgG1 A330S/ P331S SEQ ID NO: 243 | IgG1 wildtype SEQ ID NO: 206 | SEQ ID NO: 254 |
| IgG2CS-IgG1.1f | IgG2 wildtype SEQ ID NO: 203 | IgG2 C219S SEQ ID NO: 239 | IgG1 A330S/ P331S SEQ ID NO: 243 | IgG1 wildtype SEQ ID NO: 206 | SEQ ID NO: 255 |

Additional exemplary modified heavy chain constant regions are provided in Table 5.

TABLE 5

| Constructs | SEQ ID NO of constant region | Description |
|---|---|---|
| IgG1f | 256 | wild type IgG1f |
| IgG1.1f | 257 | standard inert IgG1.1f |
| IgG2.3 | 258 | IgG2 A-form (C219S) |
| IgG2.5 | 259 | IgG2 B-form (C131S) |
| IgG2.3G1-KH | 260 | CH1, upper hinge and lower hinge/upper CH2 of IgG2.3, all else IgG1f |
| IgG2.5G1-KH | 261 | CH1, upper hinge and lower hinge/upper CH2 of IgG2.5, all else IgG1f |
| IgG2.3G1-AY | 262 | CH1 and upper hinge of IgG2.3, all else IgG1f |
| IgG2.5G1-AY | 263 | CH1 and upper hinge of IgG2.5, all else IgG1f |
| IgG2.3G1.1f-KH | 264 | CH1, upper hinge and lower hinge/upper CH2 of IgG2.3, all else IgG1.1f |
| IgG2.5G1.1f-KH | 265 | CH1, upper hinge and lower hinge/upper CH2 of IgG2.5, all else IgG1.1f |
| IgG2.5G1-V27 | 266 | IgG2-B-form variant |
| IgG2.3G1-V27 | 297 | hHC-IgG2-C219S/hHC-IgG1f-S267E |

In certain embodiments, an anti-OX40 antibody comprises a modified heavy chain constant region comprising an IgG2 hinge comprising any one of SEQ ID NOs: 238, 239, 240, 241, and 208-232 or a variant thereof, such as an IgG2 hinge comprising an amino acid sequence that (i) differs from any one of SEQ ID NOs: 238, 239, 240, 241, and 208-232 in 1, 2, 3, 4 or 5 amino acids substitutions, additions or deletions; (ii) differs from any one of SEQ ID NOs: 238, 239, 240, 241, and 208-232 in at most 5, 4, 3, 2, or 1 amino acids substitutions, additions or deletions; (iii) differs from any one of SEQ ID NOs: 238, 239, 240, 241, and 208-232 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to any one of SEQ ID NOs: 238, 239, 240, 241, and 208-232, wherein in any of (i)-(iv), an amino acid substitution may be a conservative amino acid substitution or a non-conservative amino acid substitution; and wherein the modified heavy chain constant region provides an altered activity to an anti-OX40 antibody relative to another heavy chain constant region, e.g., a heavy chain constant region that comprises a non-IgG2 hinge or relative to the same modified heavy chain constant region that comprises a non-IgG2 hinge.

In certain embodiments, an anti-OX40 antibody comprises a modified heavy chain constant region comprising an IgG1 CH1 domain comprising SEQ ID NO: 202 or an IgG2 CH1 domain comprising SEQ ID NO: 203, or a variant of SEQ ID NO: 202 or 203, which variant (i) differs from SEQ ID NO: 202 or 203 in 1, 2, 3, 4 or 5 amino acids substitutions, additions or deletions; (ii) differs from SEQ ID NO: 202 or 203 in at most 5, 4, 3, 2, or 1 amino acids substitutions, additions or deletions; (iii) differs from SEQ ID NO: 202 or 203 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 202 or 203, wherein in any of (i)-(iv), an amino acid substitution may be a conservative amino acid substitution or a non-conservative amino acid substitution; and wherein the anti-OX40 antibody comprising a modified heavy chain constant region may have an altered activity relative to that of the anti-OX40 antibody but with another heavy chain constant region, e.g., a heavy chain constant region that comprises a non-IgG2 hinge or relative to the same modified heavy chain constant region that comprises a non-IgG2 hinge.

In certain embodiments, an anti-OX40 antibody comprises a modified heavy chain constant region comprising an IgG1 CH2 domain comprising SEQ ID NO: 204 or 298, or a variant of SEQ ID NO: 204 or 298, which variant (i) differs from SEQ ID NO: 204 or 298 in 1, 2, 3, 4 or 5 amino acids substitutions, additions or deletions; (ii) differs from SEQ ID NO: 204 or 298 in at most 5, 4, 3, 2, or 1 amino acids substitutions, additions or deletions; (iii) differs from SEQ ID NO: 204 or 298 in 1-5, 1-3, 1-2, 2-5 or 3-5 amino acids substitutions, additions or deletions or (iv) comprises an amino acid sequence that is at least about 75%, 80%, 85%, 90%, 95%, 96%, 97%, 98% or 99% identical to SEQ ID NO: 204 or 298, wherein in any of (i)-(iv), an amino acid substitution may be a conservative amino acid substitution or a non-conservative amino acid substitution; and wherein the modified heavy chain constant region may provide an altered activity to an anti-OX40 antibody relative to that of another heavy chain constant region, e.g., a heavy chain constant region that comprises a non-IgG2 hinge or relative to the same modified heavy chain constant region that comprises a non-IgG2 hinge.

In certain embodiments, an anti-OX40 antibody comprises a modified heavy chain constant region comprising an IgG1 CH3 domain comprising SEQ ID NO: 206, or a variant of SEQ ID NO: 206, which variant (i) differs from SEQ ID NO: 206 in 1, 2, 3, 4 or 5 amino acids substitutions, additions or deletions; (ii) differs from SEQ ID NO: 206 in at most 5, 4, 3, 2, or 1 amino acids substitutions, additions or deletions; (iii) differs from SEQ ID NO: 206 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 206, wherein in any of (i)-(iv), an amino acid substitution may be a conservative amino acid substitution or a non-conservative amino acid substitution; and wherein the modified heavy chain constant region may provide an altered activity relative to that of another heavy chain constant region, e.g., a heavy chain constant region that comprises a non-IgG2 hinge or relative to the same modified heavy chain constant region that comprises a non-IgG2 hinge.

Modified heavy chain constant regions may also comprise a combination of the CH1, hinge, CH2 and CH3 domains described above.

In certain embodiments, an anti-OX40 antibody comprises a modified heavy chain constant region comprising any one of SEQ ID NOs: 244-281, or a variant of any one of SEQ ID NOs: 244-281, which variant (i) differs from any one of SEQ ID NOs: 244-281 in 1, 2, 3, 4, 5, 6, 7, 8, 9, 10 or more amino acids substitutions, additions or deletions; (ii) differs from any one of SEQ ID NOs: 244-281 in at most 10, 9, 8, 7, 6, 5, 4, 3, 2, or 1 amino acids substitutions, additions or deletions; (iii) differs from any one of SEQ ID NOs: 244-281 in 1-5, 1-3, 1-2, 2-5, 3-5, 1-10, or 5-10 amino acids substitutions, additions or deletions and/or (iv) comprises an amino acid sequence that is at least about 75%, 80%, 85%, 90%, 95%, 96%, 97%, 98% or 99% identical to any one of SEQ ID NOs: 244-281, wherein in any of (i)-(iv), an amino acid substitution may be a conservative amino acid substitution or a non-conservative amino acid substitution; and wherein the modified heavy chain constant region may provide an altered activity relative to that of another heavy chain constant region, e.g., a heavy chain constant region that comprises a non-IgG2 hinge or relative to the same modified heavy chain constant region that comprises a non-IgG2 hinge.

Modified heavy chain constant regions may have (i) similar, reduced or increased effector function (e.g., binding to an FcγR) relative to a wildtype heavy chain constant region and or (ii) similar, reduced or increased half-life (or binding to the FcRn receptor) relative to a wildtype heavy chain constant region.

III. Antibodies Having Particular Germline Sequences

In certain embodiments, anti-OX40 antibodies described herein comprise a heavy chain variable region from a particular germline heavy chain immunoglobulin gene and/or a light chain variable region from a particular germline light chain immunoglobulin gene.

As discussed in the Examples of the present disclosure, human antibodies specific for OX40 have been prepared that comprise a heavy chain variable region that is the product of or derived from human germline VH 1-08 gene, VH 6-6 gene, VH 5-51 gene, VH 3-9 gene, VH DP44 gene, VH 3-30.3 gene, VH 3-10 gene, and/or VH 3-13 gene. Accordingly, provided herein are isolated monoclonal antibodies specific for human OX40, or antigen-binding portions thereof, comprising a heavy chain variable region that is the product of or derived from a human VH germline gene selected from the group consisting of: VH 1-08 gene, VH 6-6 gene, VH 5-51 gene, VH 3-9 gene, VH DP44 gene, VH 3-30.3 gene, VH 3-10 gene, and VH 3-13 gene.

Human antibodies specific for OX40 have been prepared that comprise a light chain variable region that is the product of or derived from human germline VK L5 gene, VK L6 gene, VK L15 gene, VK A27 gene, and/or VK O14/O4 gene. Accordingly, provide herein are isolated monoclonal antibodies, or antigen-binding portions thereof, comprising a light chain variable region that is the product of or derived from a human VK germline gene selected from the group consisting of: VK L5 gene, VK L6 gene, VK L15 gene, VK A27 gene, and VK O14/O4 gene.

Preferred antibodies described herein are those comprising a heavy chain variable region that is the product of or derived from one of the above-listed human germline VH genes and also comprising a light chain variable region that is the product of or derived from one of the above-listed human germline VK genes.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

IV. Homologous Antibodies

Provided herein are antibodies having heavy and light chain variable regions comprising amino acid sequences that are homologous to the amino acid sequences of the preferred antibodies described herein, and wherein the antibodies retain the desired functional properties of the anti-OX40 antibodies described herein.

For example, an isolated anti-OX40 antibody, or antigen binding portion thereof, may comprise a heavy chain variable region and a light chain variable region, wherein:

(a) the heavy chain variable region comprises an amino acid sequence that is at least 80%, 85%, 90%, 95%, 96%, 97%, 98% or 99% identical to an amino acid sequence selected from the group consisting of SEQ ID NOs: 318, 17, 28, 37, 48, 57, 65, 73, 84, and 93, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 318, 17, 28, 37, 48, 57, 65, 73, 84, and 93;

(b) the light chain variable region comprises an amino acid sequence that is at least 80%, 85%, 90%, 95%, 96%, 97%, 98% or 99% identical to an amino acid sequence selected from the group consisting of SEQ ID NOs: 18, 29, 30, 38, 49, 50, 58, 66, 74, 85, 86, and 94, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 18, 29, 30, 38, 49, 50, 58, 66, 74, 85, 86, and 94;

(c) the antibody specifically binds to OX40, and (d) the antibody exhibits 1, 2, 3, 4, 5, 6, or all of the following functional properties:

(1) binding to soluble human OX40, e.g., with a $K_D$ of 10 nM or less (e.g., 0.01 nM to 10 nM), e.g., as measured by Biacore;

(2) binding to membrane bound human OX40, e.g., with an $EC_{50}$ of 1 nM or less (e.g., 0.01 nM to 1 nM), e.g., as measured by FACS;

(3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;

(4) inducing or enhancing T cell activation, as evidenced by (i) increased IL-2 and/or IFN-γ production in OX40-expressing T cells and/or (ii) enhanced T cell proliferation;

(5) inhibiting the binding of OX40 ligand to OX40, e.g., with an $EC_{50}$ of 1 nM or less as measured by FACS, e.g., in an assay with hOX40-293 cells;

(6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDN-QACKPWTNCTLAGK (SEQ ID NO: 179);

(7) competing for binding to human OX40 with 3F4, 14B6-1, 14B6-2, 23H3, 18E9, 8B11, 20B3, and 20C1;

(8) competing for binding to human OX40 with 6E1-1, 6E1-2, 14A2-1, and 14A2-2.

The antibody can be, for example, a human antibody, a humanized antibody or a chimeric antibody.

In certain embodiments, the anti-OX40 antibody, or antigen binding portion thereof, may comprise a heavy chain and a light chain, wherein:

(a) the heavy chain comprises an amino acid sequence that is at least 80%, 85%, 90%, 95%, 96%, 97%, 98% or 99% identical to an amino acid sequence selected from the group consisting of SEQ ID NOs: 95, 97, 99, 101, 103, 105, 107, 109, 111, 113, 115, 117, 119, 121, 123, 124 and 125, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 95, 97, 99, 101, 103, 105, 107, 109, 111, 113, 115, 117, 119, 121, 123, 124 and 125;

(b) the light chain comprises an amino acid sequence that is at least 80%, 85%, 90%, 95%, 96%, 97%, 98% or 99% identical to an amino acid sequence selected from the group consisting of SEQ ID NOs: 96, 98, 100, 102, 104, 106, 108, 110, 112, 114, 116, 118, 120, and 122, or comprises 1, 2, 3, 4, 5, 1-2, 1-3, 1-4, 1-5, 1-10, 1-15, 1-20, 1-25, or 1-50 amino acid changes (i.e., amino acid substitutions, additions or deletions) relative to an amino acid sequence selected from the group consisting of SEQ ID NOs: 96, 98, 100, 102, 104, 106, 108, 110, 112, 114, 116, 118, 120, and 122;

(c) the antibody specifically binds to OX40, and (d) the antibody exhibits 1, 2, 3, 4, 5, 6, or all of the following functional properties:
(1) binding to soluble human OX40, e.g., with a $K_D$ of 10 nM or less (e.g., 0.01 nM to 10 nM), e.g., as measured by Biacore;
(2) binding to membrane bound human OX40, e.g., with an $EC_{50}$ of 1 nM or less (e.g., 0.01 nM to 1 nM), e.g., as measured by FACS;
(3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;
(4) inducing or enhancing T cell activation, as evidenced by (i) increased IL-2 and/or IFN-γ production in OX40-expressing T cells and/or (ii) enhanced T cell proliferation;
(5) inhibiting the binding of OX40 ligand to OX40, e.g., with an $EC_{50}$ of 1 nM or less as measured by FACS, e.g., in an assay with hOX40-293 cells;
(6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDNQACKPWTNCTLAGK (SEQ ID NO: 179);
(7) competing for binding to human OX40 with 3F4, 14B6-1, 14B6-2, 23H3, 18E9, 8B11, 20B3, and 20C1;
(8) competing for binding to human OX40 with 6E1-1, 6E1-2, 14A2-1, and 14A2-2.

Also provided are anti-OX40 antibodies comprising a VHCDR1, VHCDR2, VHCDR3, VLCDR1, VLCDR2, and/or VLCDR3 that differs from the corresponding CDR of 3F4, 14B6-1, 14B6-2, 23H3, 6E1-1, 6E1-2, 18E9, 8B11, 20B3, 14A2-1, 14A2-2, and/or 20C1, in 1, 2, 3, 4, 5, 1-2, 1-3, 1-4, or 1-5 amino acid changes (i.e., amino acid substitutions, additions or deletions). In certain embodiments, the antibody comprises 1-5 amino acid changes in each of 1, 2, 3, 4, 5 or 6 of the CDRs relative to the corresponding sequence in 3F4, 14B6-1, 14B6-2, 23H3, 6E1-1, 6E1-2, 18E9, 8B11, 20B3, 14A2-1, 14A2-2, and/or 20C1. In certain embodiments, the antibody comprises at total of 1-5 amino acid changes across all CDRs relative to the CDRs in 3F4, 14B6-1, 14B6-2, 23H3, 6E1-1, 6E1-2, 18E9, 8B11, 20B3, 14A2-1, 14A2-2, and/or 20C1.

Antibodies having sequences with homology to those of 3F4, 14B6 (14B6-1 and 14B6-2), 23H3, 6E1 (6E1-1 and 6E1-2), 18E9, 8B11, 20B3, 14A2 (14A2-1 and 14A2-2), and 20C1, e.g., the $V_H$ and $V_L$ regions of SEQ ID NOs: 17 and 18; 28 and 29; 28 and 30; 37 and 38; 48 and 49; 48 and 50; 57 and 58; 65 and 66; 73 and 74; 84 and 85; 84 and 86; 93 and 94, respectively, or heavy and light chains of SEQ ID NOs: 95 and 96; 97 and 98; 99 and 100; 101 and 102; 103 and 104; 105 and 106; 107 and 108; 109 and 110; 111 and 112; 113 and 114; 115 and 116; 117 and 118; 119 and 120; 121 and 122; 123 and 116; 124 and 116; and 125 and 116, respectively, or CDRs can be obtained by mutagenesis (e.g., site-directed or PCR-mediated mutagenesis) of nucleic acid molecules encoding SEQ ID NOs: 17, 28, 37, 48, 57, 65, 73, 84, and 93 and/or SEQ ID NOs: 18, 29, 30, 38, 49, 50, 58, 66, 74, 85, 86, and 94 or SEQ ID NOs: 95, 97, 99, 101, 103, 105, 107, 109, 111, 113, 115, 117, 119, 121, 123, 124 and 125 and/or SEQ ID NOs: 96, 98, 100, 102, 104, 106, 108, 110, 112, 114, 116, 118, 120, and 122, followed by testing of the encoded altered antibody for retained function (i.e., the functions set forth in (1) through (7) above) using the functional assays described herein.

V. Antibodies with Conservative Modifications

Anti-OX40 antibodies provided herein may comprise a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the antibodies described herein (e.g., 3F4, 14B6-1, 14B6-2, 23H3, 6E1-1, 6E1-2, 18E9, 8B11, 20B3, 14A2-1, 14A2-2, and 20C1), or conservative modifications thereof, and wherein the antibodies retain the desired functional properties of the anti-OX40 antibodies described herein. Accordingly, the anti-OX40 antibody, or antigen binding portion thereof, may comprise a heavy chain variable region comprising CDR1, CDR2, and CDR3 sequences and a light chain variable region comprising CDR1, CDR2, and CDR3 sequences, wherein:
(a) the heavy chain variable region CDR3 sequence comprises an amino acid sequence selected from the group consisting of amino acid sequences of SEQ ID NOs: 13, 21, 33, 41, 53, 61, 69, 77, and 89, and conservative modifications thereof, e.g., 1, 2, 3, 4, 5, 1-2, 1-3, 1-4 or 1-5 conservative amino acid substitutions;
(b) the light chain variable region CDR3 sequence comprises an amino acid sequence selected from the group consisting of amino acid sequence of SEQ ID NOs: 16, 24, 27, 36, 44, 47, 56, 64, 72, 80, 83, and 92, and conservative modifications thereof, e.g., 1, 2, 3, 4, 5, 1-2, 1-3, 1-4 or 1-5 conservative amino acid substitutions;
(c) the antibody specifically binds to OX40, and
(d) the antibody exhibits 1, 2, 3, 4, 5, 6, or all of the following functional properties:
(1) binding to soluble human OX40, e.g., with a $K_D$ of 10 nM or less (e.g., 0.01 nM to 10 nM), e.g., as measured by Biacore;
(2) binding to membrane bound human OX40, e.g., with an $EC_{50}$ of 1 nM or less (e.g., 0.01 nM to 1 nM), e.g., as measured by FACS;
(3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;
(4) inducing or enhancing T cell activation, as evidenced by (i) increased IL-2 and/or IFN-γ production in OX40-expressing T cells and/or (ii) enhanced T cell proliferation;
(5) inhibiting the binding of OX40 ligand to OX40, e.g., with an $EC_{50}$ of 1 nM or less as measured by FACS, e.g., in an assay with hOX40-293 cells;
(6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDNQACKPWTNCTLAGK (SEQ ID NO: 179);
(7) competing for binding to human OX40 with 3F4, 14B6-1, 14B6-2, 23H3, 18E9, 8B11, 20B3, and 20C1;
(8) competing for binding to human OX40 with 6E1-1, 6E1-2, 14A2-1, and 14A2-2.

In a preferred embodiment, the heavy chain variable region CDR2 sequence comprises an amino acid sequence selected from the group consisting of amino acid sequences of SEQ ID NOs: 12, 20, 32, 40, 52, 60, 68, 76, 88, and 317, and conservative modifications thereof, e.g., 1, 2, 3, 4, 5, 1-2, 1-3, 1-4 or 1-5 conservative amino acid substitutions; and the light chain variable region CDR2 sequence comprises an amino acid sequence selected from the group consisting of amino acid sequences of SEQ ID NOs: 15, 23, 26, 35, 43, 46, 55, 63, 71, 79, 82, and 91, and conservative modifications thereof, e.g., 1, 2, 3, 4, 5, 1-2, 1-3, 1-4 or 1-5 conservative amino acid substitutions. In another preferred embodiment, the heavy chain variable region CDR1 sequence comprises an amino acid sequence selected from the group consisting of amino acid sequences of SEQ ID NOs: 11, 19, 31, 39, 51, 59, 67, 75, and 87, and conservative modifications thereof, e.g., 1, 2, 3, 4, 5, 1-2, 1-3, 1-4 or 1-5 conservative amino acid substitutions; and the light chain variable region CDR1 sequence comprises an amino acid sequence selected from the group consisting of amino acid sequences of SEQ ID NOs: 14, 22, 25, 34, 42, 45, 54, 62, 70, 78, 81, and 90, and conservative modifications thereof, e.g., 1, 2, 3, 4, 5, 1-2, 1-3, 1-4 or 1-5 conservative amino acid substitutions.

In various embodiments, the antibodies can be, for example, human antibodies, humanized antibodies or chimeric antibodies.

Conservative amino acid substitutions may also be made in portions of the antibodies other than, or in addition to, the CDRs. For example, conservative amino acid modifications may be made in a framework region or in the Fc region. A variable region or a heavy or light chain may comprise 1, 2, 3, 4, 5, 1-2, 1-3, 1-4, 1-5, 1-10, 1-15, 1-20, 1-25, or 1-50 conservative amino acid substitutions relative to the anti-OX40 antibody sequences provided herein. In certain embodiments, the anti-OX40 antibody comprises a combination of conservative and non-conservative amino acid modification.

VI. Competing Antibodies and Same Epitope Binding Antibodies

Also provided herein are antibodies that compete for binding to OX40 with the anti-OX40 antibodies described herein (e.g., antibodies 3F4, 14B6-1, 14B6-2, 23H3, 6E1-1, 6E1-2, 18E9, 8B11, 20B3, 14A2-1, 14A2-2, and 20C1). Such competing antibodies can be identified based on their ability to competitively inhibit binding to OX40 of one or more of monoclonal antibodies 3F4, 14B6-1, 14B6-2, 23H3, 6E1-1, 6E1-2, 18E9, 8B11, 20B3, 14A2-1, 14A2-2, and 20C1 in standard OX40 binding assays. For example, standard ELISA assays or competitive ELISA assays can be used in which a recombinant human OX40 protein is immobilized on a plate, various concentrations of unlabeled first antibody are added, the plate is washed, labeled second antibody is added, washed, and the amount of bound label is measured. If the increasing concentration of the unlabeled (first) antibody (also referred to as the "blocking antibody") inhibits the binding of the labeled (second) antibody, the first antibody is said to inhibit the binding of the second antibody to the target on the plate, or is said to compete with the binding of the second antibody. Additionally or alternatively, BIA-CORE® SPR analysis can be used to assess the ability of the antibodies to compete. The ability of a test antibody to inhibit the binding of an anti-OX40 antibody described herein to OX40 demonstrates that the test antibody can compete with the antibody for binding to OX40.

Accordingly, provided herein are anti-OX40 antibodies that inhibit the binding of the anti-OX40 antibodies described herein to OX40 on cells, e.g., activated T cells, by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100%, by using, e.g., FACS as described in the Examples.

In other embodiments, provided herein are anti-OX40 antibodies which bind to the same epitope as one or more of the anti-OX40 antibodies described herein (e.g., antibodies 3F4, 14B6-1, 14B6-2, 23H3, 6E1-1, 6E1-2, 18E9, 8B11, 20B3, 14A2-1, 14A2-2, and 20C1), as determined using art-recognized epitope mapping techniques, such as those described below.

Art-recognized epitope mapping techniques include, for example, structural methods, such as X-ray crystal structure determination (e.g., WO2005/044853), molecular modeling and nuclear magnetic resonance (NMR) spectroscopy, including NMR determination of the H-D exchange rates of labile amide hydrogens in OX40 when free and when bound in a complex with an antibody of interest (Zinn-Justin et al. *Biochemistry* 1992; 31:11335-47; Zinn-Justin et al. *Biochemistry* 1993; 32, 6884-91).

For X-ray crystallography, crystallization may be accomplished using any known method in the art (e.g. Giege et al. *Acta Crystallogr* 1994; D50:339-50; McPherson, *Eur J Biochem* 1990; 189:1-23), including microbatch (e.g. Chayen, *Structure* 19976; 5:1269-74), hanging-drop vapor diffusion (e.g. McPherson, *J Biol Chem* 1976; 251:6300-3), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g., glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of such buffers include, but are not limited to, HEPES, Tris, MES and acetate. Crystals may be grow at a wide range of temperatures, including 2° C., 4° C., 8° C. and 26° C. Antibody:antigen crystals may be studied using well-known X-ray diffraction techniques and may be refined using computer software such as X-PLOR (Yale University, 1992, distributed by Molecular Simulations, Inc.; see e.g. Blundell & Johnson, *Meth. Enzymol.* 1985; 114 & 115, H. W. Wyckoff et al., eds., Academic Press; U.S. Patent Application Publication No. 2004/0014194), and BUSTER (Bricogne, *Acta Cryst* 1993; D49:37-60; Bricogne, Meth Enzymol 1997; 276A:361-423; Carter & Sweet, eds.; Roversi et al., *Acta Cryst.* 2000; D56:1313-23).

Other epitope mapping methods monitor the binding of the antibody to antigen fragments or mutated variations of the antigen where loss of binding due to a modification of an amino acid residue within the antigen sequence is often considered an indication of an epitope component. One such method is alanine scanning mutagenesis, as described, e.g., by Cunningham and Wells, *Science* 1989; 244:1081-5. Another suitable method is deep mutational scanning (see, e.g., Araya et al., *Trends in Biotechnology* 2011; 29:435-42; Forsyth et al., *mAbs* 2013; 5:523-32).

Additionally or alternatively, computational combinatorial methods for epitope mapping, including the mapping of conformational discontinuous epitopes, can be used.

Additionally or alternatively, epitope mapping can be achieved by testing binding of an antibody to peptides comprising fragments of OX40, e.g., non-denatured or denatured fragments. A series of overlapping peptides encompassing the sequence of OX40 (e.g., human OX40) may be synthesized and screened for binding, e.g., in a direct ELISA, a competitive ELISA (where the peptide is assessed for its ability to prevent binding of an antibody to OX40 bound to a well of a microtiter plate) or on a chip. Other methods rely on the ability of an antibody of interest to affinity isolate specific short peptides (either in native three dimensional form or in denatured form) from combinatorial phage display peptide libraries. The peptides are then regarded as leads for the definition of the epitope recognized by the antibody used to screen the peptide library.

Epitopes also can be identified by MS-based protein footprinting, such as Hydrogen/deuterium exchange mass spectrometry (HDX-MS) and Fast Photochemical Oxidation of Proteins (FPOP). HDX-MS may be conducted, for example, as described in the Examples herein and by Wei et al., *Drug Discovery Today* 2014; 19:95. FPOP may be conducted, for example, as described by Hambley et al. (*J American Soc Mass. Spectrometry* 2005; 16:2057).

Antibodies that compete for binding with the anti-OX40 antibodies described herein may be produced and identified using art-known methods. For example, mice may be immunized with human OX40 as described herein, hybridomas produced, and the resulting monoclonal antibodies screened for the ability to compete with an antibody described herein for binding to OX40 using the methods described above.

Antibodies that bind to the same epitope as the anti-OX40 antibodies described herein may be produced by immunizing mice with a smaller fragment of OX40 containing the epitope to which the antibody binds. The epitope or region comprising the epitope can be identified using the methods described above. Alternatively, the method of Jespers et al. (*Biotechnology* 1994; 12:899) may be used to guide the selection of antibodies recognizing the same epitope and therefore exhibiting similar properties to the anti-OX40 antibodies described herein. For example, using phage display, first the heavy chain of the anti-OX40 antibody is paired with a repertoire of (preferably human) light chains to select a OX40-binding antibody, and then the new light chain is paired with a repertoire of (preferably human) heavy chains to select a (preferably human) OX40-binding antibody recognizing the same epitope or epitope region on OX40 as an anti-OX40 antibody described herein. Alternatively variants of an antibody described herein can be obtained by mutagenesis of cDNA encoding the heavy and light chains of the antibody.

In some embodiments, provided herein are antibodies which bind to all or a portion of the sequence DVVSSKPCKPCTWCNLR (SEQ ID NO: 178), corresponding to amino acid residues 46-62 of mature human OX40 (SEQ ID NO: 2), as determined by the methods in the Examples.

In certain embodiments, the anti-OX40 antibodies described herein that bind to all or a portion of the sequence SQNTVCRPCGPGFYNDVVSSKPCKPCTWCNLR (SEQ ID NO: 182), as determined by the methods in the Examples.

In other embodiments, the anti-OX40 antibodies described herein that bind to all or a portion of the sequence PCKPCTWCNLR (SEQ ID NO: 183), as determined by the methods in the Examples.

In yet other embodiments, the anti-OX40 antibodies that bind to all or a portion of the sequence DVVSSKPCKPCTWCNLR (SEQ ID NO: 178) further bind to all or a portion of the sequence QLCTATQDTVCR (SEQ ID NO: 184), as determined by the methods in the Examples.

In additional embodiments, the anti-OX40 antibodies described herein that bind to all or a portion of the sequence SQNTVCRPCGPGFYN (SEQ ID NO: 185), as determined by the methods in the Examples.

In additional embodiments, the anti-OX40 antibody binds within the region DSYKPGVDCAPCPPGHFSPGDNQACKPWTNCTLAGK (SEQ ID NO: 179), corresponding to amino acid residues 89-124 of mature human OX40 (SEQ ID NO: 2), as determined by the methods in the Examples.

VII. Engineered and Modified Antibodies

VH and VL Regions

Also provided herein are engineered and modified antibodies that can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific reference antibodies by constructing expression vectors that include CDR sequences from the specific reference antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment pertains to a monoclonal antibody, or antigen binding portion thereof, comprising a heavy chain variable region comprising CDR1, CDR2, and CDR3 sequences comprising an amino acid sequence selected from the group consisting of SEQ ID SEQ ID NOs: 11-13; 19-21; 31-33; 39-41; 51-53; 59-61; 67-69; 74-77; and 87-89, respectively, and a light chain variable region comprising CDR1, CDR2, and CDR3 sequences comprising an amino acid sequence selected from the group consisting of SEQ ID NOs: 14-16; 22-24; 25-27; 34-36; 42-44; 45-47; 54-56; 62-64; 70-72; 78-80; 81-83; and 90-92, respectively. Thus, such antibodies contain the $V_H$ and $V_L$ CDR sequences of monoclonal antibodies 3F4, 14B6-1, 14B6-2, 23H3, 6E1-1, 6E1-2, 18E9, 8B11, 20B3, 14A2-1, 14A2-2, and 20C1, yet may contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Engineered antibodies described herein include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the CDR regions to improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid additions, deletions, or preferably substitutions. Moreover, typically no more than one, two, three, four or five residues within a CDR region are altered.

Accordingly, also provided herein are anti-OX40 monoclonal antibodies, or antigen binding portions thereof, comprising a heavy chain variable region comprising: (a) a $V_H$ CDR1 region comprising an amino acid sequence selected from the group consisting of SEQ ID NOs: 11, 19, 31, 39, 51, 59, 67, 75, and 87, or an amino acid sequence having one, two, three, four or five amino acid substitutions, deletions or additions as compared to SEQ ID NOs: 11, 19, 31, 39, 51, 59, 67, 75, and 87; (b) a $V_H$ CDR2 region comprising an amino acid sequence selected from the group consisting of SEQ ID NOs: 12, 20, 32, 40, 52, 60, 68, 76, 88, and 317, or an amino acid sequence having one, two, three, four or five amino acid substitutions, deletions or additions as compared to SEQ ID NOs: 12, 20, 32, 40, 52, 60, 68, 76, and 88; (c) a $V_H$ CDR3 region comprising an amino acid sequence selected from the group consisting of SEQ ID NOs: 13, 21, 33, 41, 53, 61, 69, 77, and 89, or an amino acid sequence having one, two, three, four or five amino acid substitutions, deletions or additions as compared to SEQ ID NOs: 13, 21, 33, 41, 53, 61, 69, 77, and 89; (d) a $V_L$ CDR1 region comprising an amino acid sequence selected from the group consisting of SEQ ID NOs: 14, 22, 25, 34, 42, 45, 54, 62, 70, 78, 81, and 90, or an amino acid sequence having one, two, three, four or five amino acid substitutions, deletions or additions as compared to SEQ ID NOs: 14, 22, 25, 34, 42, 45, 54, 62, 70, 78, 81, and 90; (e) a $V_L$ CDR2 region comprising an amino acid sequence selected from the group consisting of SEQ ID NOs: 15, 23, 26, 35, 43, 46, 55, 63, 71, 79, 82, and 91, or an amino acid sequence having one, two, three, four or five amino acid substitutions, deletions or additions as compared to SEQ ID NOs: 15, 23, 26, 35, 43, 46, 55, 63, 71, 79, 82, and 91; and (f) a $V_L$ CDR3 region comprising an amino acid sequence selected from the group consisting of SEQ ID NOs: 16, 24, 27, 36, 44, 47, 56, 64, 72, 80, 83, and 92, or an amino acid sequence having one, two, three, four or five amino acid substitutions, deletions or additions as compared to SEQ ID NOs: 16, 24, 27, 36, 44, 47, 56, 64, 72, 80, 83, and 92.

Methionine residues in CDRs of antibodies can be oxidized, resulting in potential chemical degradation and consequent reduction in potency of the antibody. Accordingly, one or more methionine residues in the heavy and/or light chain CDRs of the anti-OX40 antibodies described herein may be replaced with amino acid residues that do not undergo oxidative degradation.

Similarly, deamidation sites may be removed from the antibodies, particularly in the CDRs.

Potential glycosylation sites within the antigen binding domain are preferably eliminated to prevent glycosylation that may interfere with antigen binding. See, e.g., U.S. Pat. No. 5,714,350.

Targeted Antigen Binding

In various embodiments, the antibodies described herein are modified to selectively block antigen binding in tissues and environments where antigen binding would be detrimental, but allow antigen binding where it would be beneficial. In one embodiment, a blocking peptide "mask" is generated that specifically binds to the antigen binding surface of the antibody and interferes with antigen binding, which mask is linked to each of the binding arms of the antibody by a peptidase cleavable linker. See, e.g., U.S. Pat. No. 8,518,404 to CytomX. Such constructs are useful for treatment of cancers in which protease levels are greatly increased in the tumor microenvironment compared with non-tumor tissues. Selective cleavage of the cleavable linker in the tumor microenvironment allows disassociation of the masking/blocking peptide, enabling antigen binding selectively in the tumor, rather than in peripheral tissues in which antigen binding might cause unwanted side effects.

Alternatively, in a related embodiment, a bivalent binding compound ("masking ligand") comprising two antigen binding domains is developed that binds to both antigen binding surfaces of the (bivalent) antibody and interfere with antigen binding, in which the two binding domains masks are linked to each other (but not the antibody) by a cleavable linker, for example cleavable by a peptidase. See, e.g., Int'l Pat. App. Pub. No. WO 2010/077643 to Tegopharm Corp. Masking ligands may comprise, or be derived from, the antigen to which the antibody is intended to bind, or may be independently generated. Such masking ligands are useful for treatment of cancers in which protease levels are greatly increased in the tumor microenvironment compared with non-tumor tissues. Selective cleavage of the cleavable linker in the tumor microenvironment allows disassociation of the two binding domains from each other, reducing the avidity for the antigen-binding surfaces of the antibody. The resulting dissociation of the masking ligand from the antibody enables antigen binding selectively in the tumor, rather than in peripheral tissues in which antigen binding might cause unwanted side effects.

Fcs and Modified Fcs

In addition to the activity of a therapeutic antibody arising from binding of the antigen binding domain to the antigen (e.g. blocking of a cognate ligand or receptor protein in the case of antagonist antibodies, or induced signaling in the case of agonist antibodies), the Fc portion of the antibody interact with the immune system generally in complex ways to elicit any number of biological effects. Effector functions, such as the Fc region of an immunoglobulin, are responsible for many important antibody functions, such as antigen-dependent cellular cytotoxicity (ADCC), complement dependent cytotoxicity (CDC), and antibody-dependent cell-mediated phagocytosis (ADCP), result in killing of target cells, albeit by different mechanisms. There are five major classes, or isotypes, of heavy chain constant region (IgA, IgG, IgD, IgE, IgM), each with characteristic effector functions. These isotypes can be further subdivided into subclasses, for example, IgG is separated into four subclasses known as IgG1, IgG2, IgG3, and IgG4. IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to the neonatal Fc receptor (FcRn).

Anti-OX40 antibodies described herein may comprise the variable domains of the invention combined with constant domains comprising different Fc regions, selected based on the biological activities (if any) of the antibody for the intended use. Salfeld (2007) *Nat. Biotechnol.* 25:1369. Human IgGs, for example, can be classified into four subclasses, IgG1, IgG2, IgG3, and IgG4, and each these of these comprises an Fc region having a unique profile for binding to one or more of Fcγ receptors (activating receptors FcγRI (CD64), FcγRIIA, FcγRIIC (CD32); FcγRIIIA and FcγRIIIB (CD16) and inhibiting receptor FcγRIIB), and for the first component of complement (C1q). Human IgG1 and IgG3 bind to all Fcγ receptors; IgG2 binds to FcγRIIA$_{H131}$, and with lower affinity to FcγRIIA$_{R131}$ FcγRIIIA$_{V158}$; IgG4 binds to FcγRI, FcγRIIA, FcγRIIB, FcγRIIC, and FcγRIIIA$_{V158}$; and the inhibitory receptor FcγRIIB has a lower affinity for IgG1, IgG2 and IgG3 than all other Fcγ receptors. Bruhns et al. (2009) *Blood* 113:3716. Studies have shown that FcγRI does not bind to IgG2, and FcγRIIIB does not bind to IgG2 or IgG4. Id. In general, with regard to ADCC activity, human IgG1≥IgG3>>IgG4≥IgG2. As a consequence, for example, an IgG1 constant domain, rather than an IgG2 or IgG4, might be chosen for use in a drug where ADCC is desired; IgG3 might be chosen if activation of FcγRIIIA-expressing NK cells, monocytes, or macrophages; and IgG4 might be chosen if the antibody is to be used to desensitize allergy patients. IgG4 may also be selected if it is desired that the antibody lack all effector function.

Accordingly, anti-OX40 variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16(t), G3m6(c3), G3m24(c5), G3m26(u), G3m27(v);. See, e.g., Jefferis et al. (2009) mAbs 1:1). Selection of allotype may be influenced by the potential immunogenicity concerns, e.g. to minimize the formation of anti-drug antibodies.

In certain embodiments, anti-OX40 variable regions described herein are linked to an Fc that binds to one or more activating Fc receptors (FcγI/CD64, FcγIIa/CD32 or FcγIIIa/CD16), and thereby stimulate ADCC and may cause T cell depletion. In particular embodiments, anti-OX40 variable regions described herein are linked to an Fc that causes depletion. In other embodiments, anti-OX40 variable regions described herein are linked to a human IgG1 or IgG3 Fc, i.e., the antibodies are of the IgG1 or IgG3 isotype. In other embodiments, anti-OX40 antibodies are depleting antibodies. For example, they may deplete $T_{reg}$ cells that are in the tumor microenvironment (and thereby enhance anti-tumor activity), but not significantly deplete $T_{eff}$ cells that are in the tumor microenvironment and mediate the anti-tumor effect, and/or not significantly deplete $T_{reg}$ and $T_{eff}$ cells that are outside of the tumor, e.g., in the periphery. In other embodiments, anti-OX40 antibodies are of an isotype, (either naturally occurring or non-naturally occurring (e.g., including mutation(s)) isotype that stimulate $T_{reg}$ cell depletion or elimination at the tumor site and concomitant activation of $T_{eff}$ cells. In other embodiments, anti-OX40 antibodies create an elevated $T_{eff}$ to $T_{reg}$ ratio at the tumor site, which is indicative of potent anti-tumor activity, and preferably without significantly depleting $T_{reg}$ and $T_{eff}$ cells that are outside of the tumor, e.g., in the periphery.

In certain embodiments, anti-OX40 antibodies block the immunosuppressive activity of $T_{regs}$. In other embodiments, anti-OX40 antibodies have an Fc receptor with reduced or eliminated FcR binding, e.g., reduced binding to activating FcRs. In certain embodiments, anti-OX40 antibodies have an Fc that binds to or has enhanced binding to FcRIIb, which can provide enhanced agonism. See, e.g., WO 2012/087928; Li & Ravetch (2011) *Science* 333:1030; Wilson et al. (2011) *Cancer Cell* 19:101; White et al. (2011) *J. Immunol.* 187: 1754.

Anti-OX40 variable regions described herein may be linked to a non-naturally occurring Fc region, e.g., an effectorless or mostly effectorless Fc (e.g., human IgG2 or IgG4) or, alternatively, an Fc with enhanced binding to one or more activating Fc receptors (FcγI, FcγIIa or FcγIIIa), such as to enhance $T_{reg}$ depletion in the tumor environment.

Variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or it may be modified to alter its glycosylation, to alter one or more functional properties of the antibody. Each of these embodiments is described in further detail below. The numbering of residues in the Fc region is that of the EU index of Kabat. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g. if sequences differ between naturally occurring isotypes, or if multiple mutations may be substituted at the position, they are separated by slashes (e.g. "X/Y/Z").

For example, one may make modifications in the Fc region in order to generate an Fc variant with (a) increased or decreased antibody-dependent cell-mediated cytotoxicity (ADCC), (b) increased or decreased complement mediated cytotoxicity (CDC). (c) increased or decreased affinity for C1q and/or (d) increased or decreased affinity for a Fc receptor relative to the parent Fc. Such Fc region variants will generally comprise at least one amino acid modification in the Fc region. Combining amino acid modifications is thought to be particularly desirable. For example, the variant Fe region may include two, three, four, five, etc substitutions therein, e.g. of the specific Fe region positions identified herein. Exemplary Fc sequence variants are disclosed herein, and are also provided at U.S. Pat. Nos. 5,624,821; 6,277,375; 6,737,056; 6,194,551; 7,317,091; 8,101,720; PCT Patent Publications WO 00/42072; WO 01/58957; WO 04/016750; WO 04/029207; WO 04/035752; WO 04/074455; WO 04/099249; WO 04/063351; WO 05/070963; WO 05/040217, WO 05/092925 and WO 06/020114.

Reducing Effector Function

ADCC activity may be reduced by modifying the Fe region. In certain embodiments, sites that affect binding to Fe receptors may be removed, preferably sites other than salvage receptor binding sites. In other embodiments, an Fe region may be modified to remove an ADCC site. ADCC sites are known in the art; see, for example, Sarmay et al. (1992) *Molec. Immunol.* 29 (5): 633-9 with regard to ADCC sites in IgG1. In one embodiment, the G236R and L328R variant of human IgG1 effectively eliminates FcγR binding. Horton et al. (2011) *J. Immunol.* 186:4223 and Chu et al. (2008) *Mol. Immunol.* 45:3926. In other embodiments, the Fc having reduced binding to FcγRs comprised the amino acid substitutions L234A, L235E and G237A. Gross et al. (2001) *Immunity* 15:289.

CDC activity may also be reduced by modifying the Fe region. Mutations at IgG1 positions D270, K322, P329 and P331, specifically alanine mutations D270A, K322A, P329A and P331A, significantly reduce the ability of the corresponding antibody to bind C1q and activate complement. Idusogie et al. (2000) *J. Immunol.* 164:4178; WO 99/51642. Modification of position 331 of IgG1 (e.g. P331S) has been shown to reduce complement binding. Tao et al. (1993) *J. Exp. Med.* 178:661 and Canfield & Morrison (1991) *J. Exp. Med.* 173:1483. In another example, one or more amino acid residues within amino acid positions 231 to 239 are altered to thereby reduce the ability of the antibody to fix complement. WO 94/29351.

In some embodiments, the Fc with reduced complement fixation has the amino acid substitutions A330S and P331S. Gross et al. (2001) *Immunity* 15:289.

For uses where effector function is to be avoided altogether, e.g. when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g. N297A). Alternatively, a hybrid construct of human IgG2 ($C_H1$ domain and hinge region) and human IgG4 ($C_H2$ and $C_H3$ domains) has been generated that is devoid of effector function, lacking the ability to bind the FcγRs (like IgG2) and unable to activate complement (like IgG4). Rother et al. (2007) *Nat. Biotechnol.* 25:1256. See also Mueller et al. (1997) *Mol. Immunol.* 34:441; Labrijn et al. (2008) *Curr. Op. Immunol.* 20:479 (discussing Fc modifications to reduce effector function generally).

In other embodiments, the Fc region is altered by replacing at least one amino acid residue with a different amino acid residue to reduce all effector function(s) of the antibody. For example, one or more amino acids selected from amino acid residues 234, 235, 236, 237, 297, 318, 320 and 322 can be replaced with a different amino acid residue such that the antibody has decreased affinity for an effector ligand but retains the antigen-binding ability of the parent antibody. The effector ligand to which affinity is altered can be, for example, an Fc receptor (residues 234, 235, 236, 237, 297) or the C1 component of complement (residues 297, 318, 320, 322). U.S. Pat. Nos. 5,624,821 and 5,648,260, both by Winter et al.

One early patent application proposed modifications in the IgG Fc region to decrease binding to FcγRI to decrease ADCC (234A; 235E; 236A; G237A) or block binding to complement component C1q to eliminate CDC (E318A or V/K320A and K322A/Q). WO 88/007089. See also Duncan & Winter (1988) *Nature* 332:563; Chappel et al. (1991) *Proc. Nat'l Acad. Sci.* (*USA*) 88:9036; and Sondermann et al. (2000) *Nature* 406:267 (discussing the effects of these mutations on FcγRIII binding).

Fc modifications reducing effector function also include substitutions, insertions, and deletions at positions 234, 235, 236, 237, 2.67, 269, 325, and 328, such as 234G, 235G, 236R, 237K, 267R, 269R. 325L, and 328R. An Fe variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V. These and other modifications are reviewed in Strohl (2009) *Current Opinion in Biotechnology* 20:685-691. Effector functions (both ADCC and complement activation) can be reduced, while maintaining neonatal FcR binding (maintaining half-life), by mutating IgG residues at one or more of positions 233-236 and 327-331, such as E233P, L234V, L235A, optionally G2364, A327G, A330S and P331S in IgG1; E233P, F234V, L235A, optionally G2364 in IgG4; and A330S and P331S in IgG2. See Armour et al. (1999) *Eur. J. Immunol.* 29:2613; WO 99/58572. Other mutations that reduce effector function include L234A and L235A in IgG1 (Alegre et al. (1994) *Transplantation* 57:1537); V234A and G237A in IgG2 (Cole et al. (1997) *J. Immunol.* 159:3613; see also U.S. Pat. No. 5,834,597); and S228P and L235E for IgG4 (Reddy et al. (2000) *J. Immunol.* 164:1925). Another combination of mutations for reducing effector function in a human IgG1 include L234F, L235E and P331S. Oganesyan et al. (2008) *Acta Crystallogr. D. Biol. Crystallogr.* 64:700. See generally Labrijn et gal. (2008) *Curr. Op. Immunol.* 20:479. Additional mutations found to decrease effector function in the context of an Fc (IgG1) fusion protein (abatacept) are C226S, C229S and P238S (EU residue numbering). Davis et al. (2007) *J. Immunol.* 34:2204.

Other Fc variants having reduced ADCC and/or CDC are disclosed at Glaesner et al. (2010) *Diabetes Metab. Res. Rev.* 26:287 (F234A and L235A to decrease ADCC and ADCP in an IgG4); Hutchins et al. (1995) *Proc. Nat'l Acad. Sci. (USA)* 92:11980 (F234A, G237A and E318A in an IgG4); An et al. (2009) *MAbs* 1:572 and U.S. Pat. App. Pub. 2007/0148167 (H268Q, V309L, A330S and P331S in an IgG2); McEarchern et al. (2007) *Blood* 109:1185 (C226S, C229S, E233P, L234V, L235A in an IgG1); Vafa et al. (2014) *Methods* 65:114 (V234V, G237A, P238S, H268A, V309L, A330S, P331S in an IgG2).

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S. Gross et al. (2001) *Immunity* 15:289. Exemplary heavy chains comprising these mutations are set forth in the Sequence Listing, as detailed at Table 23 (e.g. SEQ ID NO: 11). These five substitutions may be combined with N297A to eliminate glycosylation as well.

Enhancing Effector Function

Alternatively. ADCC activity may be increased by modifying the Fc region. With regard to ADCC activity, human IgG1≥IgG3>>IgG4≥IgG2, so an IgG1 constant domain, rather than an IgG2 or IgG4, might be chosen for use in a drug where ADCC is desired. Alternatively, the Fc region may be modified to increase antibody dependent cellular cytotoxicity (ADCC) and/or to increase the affinity for an Fcy receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. See WO 2012/142515; see also WO 00/42072. Exemplary substitutions include 236A, 239D, 239E, 268D, 267E, 268E, 268F, 324T, 332D, and 332E. Exemplary variants include 239D/332E, 2361/332E, 236A/239D/332E, 268F/324T, 267E/268F, 267E/324T, and 267E/268F/324T. For example, human IgG1 Fcs comprising the G236A variant, which can optionally be combined with 1332E, have been shown to increase the FcγIIA/FcγIIB binding affinity ratio approximately 15-fold. Richards et al. (2008) *Mol. Cancer Therap.* 7:2517; Moore et al. (2010) mAbs 2:181. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl (2009) *Current Opinion in Biotechnology* 20:685-691. Specifically, both ADCC and CDC may be enhanced by changes at position E333 of IgG1, e.g. E333A. Shields et al. (2001) *J. Biol. Chem.* 276:6591. The use of P247I and A339D/Q mutations to enhance effector function in an IgG1 is disclosed in WO2006/020114, and D280H, K290S±S298D/V is disclosed in WO2004/074455. The K326A/W and E333A/S variants have been shown to increase effector function in human IgG1, and E333S in IgG2. Idusogie et al. (2001) *J. Immunol.* 166:2571.

Specifically, the binding sites on human IgG1 for FcγR1, FcγRII, FcγRIII and FcRn have been mapped, and variants with improved binding have been described. Shields et al. (2001) *J. Biol. Chem.* 276:6591-6604. Specific mutations at positions 256, 290, 298, 333, 334 and 339 were shown to improve binding to FcγRIII, including the combination mutants T256A/S298A, S298A/E333A, S298A/K224A and S298A/E333A/K334A (having enhanced FcγRIIIa binding and ADCC activity). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys. Lazar et al. (2006) *Proc. Nat'l Acad Sci. (USA)* 103:4005; Awan et al. (2010) *Blood* 115:1204; Desjarlais & Lazar (2011) *Exp. Cell Res.* 317:1278. Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys. Lazar et al. (2006) *Proc. Nat'l Acad Sci. (USA)* 103:4005. In addition, IgG1 mutants containing L235V, F243L, R292P, Y300L, V3051 and P396L mutations which exhibited enhanced binding to FcγRIIIa and concomitantly enhanced ADCC activity in transgenic mice expressing human FcγRIIIa in models of B cell malignancies and breast cancer have been identified. Stavenhagen et al. (2007) *Cancer Res.* 67:8882; U.S. Pat. No. 8,652,466; Nordstrom et al. (2011) *Breast Cancer Res.* 13:R123.

Different IgG isotypes also exhibit differential CDC activity (IgG3>IgG1>>IgG2≈IgG4). Dangl et al. (1988) *EMBO J.* 7:1989. For uses in which enhanced CDC is desired, it is also possible to introduce mutations that increase binding to C1q. The ability to recruit complement (CDC) may be enhanced by mutations at K326 and/or E333 in an IgG2, such as K326W (which reduces ADCC activity) and E333S, to increase binding to C1q, the first component of the complement cascade. Idusogie et al. (2001) *J. Immunol.* 166:2571. Introduction of S267E/H268F/S324T (alone or in any combination) into human IgG1 enhances C1q binding. Moore et al. (2010) mAbs 2:181. The Fc region of the IgG1/IgG3 hybrid isotype antibody "113F" of Natsume et al. (2008) *Cancer Res.* 68:3863 (FIG. 1 therein) also confers enhanced CDC. See also Michaelsen et al. (2009) *Scand. J. Immunol.* 70:553 and Redpath et al. (1998) *Immunology* 93:595.

Additional mutations that can increase or decrease effector function are disclosed at Dall'Acqua et al. (2006) *J. Immunol.* 177:1129. See also Carter (2006) *Nat. Rev. Immunol.* 6:3439 Presta (2008) *Curr, Op. Immunol.* 20:460.

Fc variants that enhance affinity for the inhibitory receptor FcγRIIb may also be used, e.g. to enhance apoptosis-inducing or adjuvant activity. Li & Ravetch (2011) *Science* 333:1030; Li & Ravetch (2012) *Proc. Nat'l Acad. Sci (USA)* 109:10966; U.S. Pat. App. Pub. 2014/0010812. Such variants may provide an antibody with immunomodulatory activities related to FcγRIIb$^+$ cells, including for example B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 2681), 268E, 328F, 328W, and 328Y. Other Fc variants for enhancing binding to FcγRIIb include 235Y/267E, 236D/267E, 2:39D/268D, 239D/267E, 267E/268D, 267E/268E, and 267E/328F. Specifically, the S267E, G236D, S239D, L328F and I332E variants, including the S267E+L328F double variant, of human IgG1 are of particular value in specifically enhancing affinity for the inhibitory FcγRIIb receptor. Chu et al. (2008) *Mol. Immunol.* 45:3926; U.S. Pat. App. Pub. 2006/024298; WO 2012/087928. Enhanced specificity for FcγRIIb (as distinguished from FcγRIIa$^{R131}$) may be obtained by adding the P238D substitution. Mimoto et al. (2013) *Protein. Eng. Des. & Selection* 26:589; WO 2012/115241.

In certain embodiments, the antibody is modified to increase its biological half-life. Various approaches are possible. For example, this may be done by increasing the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/ 428L (Hinton et al., 2004, J. Biol. Chem. 279(8): 6213-6216, Hinton et al. 2006 Journal of Immunology 176:346-356), 256A, 272A, 305A, 307A, 311A, 312A, 378Q, 380A, 382A, 434A (Shields et al, Journal of Biological Chemistry, 2001, 276(9):6591-6604), 252F, 252Y, 252W, 254T, 256Q, 256E, 256D, 433R, 434F, 434Y, 252Y/254T/256E, 433K/434F/ 436H (Dall Acqua et al. Journal of Immunology, 2002, 169:5171-5180, Dall'Acqua et al., 2006, Journal of Biological Chemistry 281:23514-23524), See U.S. Pat. No. 8,367, 805.

Modification of certain conserved residues in IgG Fc (I253/H310/Q311/H433/N434), such as the N434A variant (Yeung et al. (2009) *J. Immunol.* 182:7663), has been proposed as a way to increase FcRn affinity, thus increasing the half-life of the antibody in circulation. WO 98/023289. The combination Fc variant comprising M428L and N434S has been shown to increase FcRn binding and increase serum half-life up to five-fold. Zalev sky et al. (2010) *Nat. Biotechnol.* 28:157. The combination Fc variant comprising T307A, E380A and N434A modifications also extends half-life of IgG1 antibodies. Petkova et al. (2006) *Int. Immunol.* 18:1759. In addition, combination Fc variants comprising M252Y/M428L, M428L/N434L1, M428L/N434F, M428L/ N434Y, M428L/N434A, M428L/N434M, and M428L/ N434S variants have also been shown to extend half-life. WO 2009/086320.

Further, a combination Fc variant comprising M252Y, S254T and T256E, increases half-life-nearly 4-fold. Dall'Acqua et al. (2006) *J. Biol. Chem.* 281:23514. A related IgG1 modification providing increased FcRn affinity but reduced pH dependence (M252Y/S254T/T256E/H433K/ N434F) has been used to create an IgG1 construct ("MST- HN Abdeg") for use as a competitor to prevent binding of other antibodies to FcRn, resulting in increased clearance of that other antibody, either endogenous IgG (e.g. in an autoimmune setting) or another exogenous (therapeutic) mAb. Vaccaro et al. (2005) *Nat. Biotechnol.* 23:1283; WO 2006/130834.

Other modifications for increasing FcRn binding are described in Yeung et al. (2010) *J. Immunol.* 182:7663-7671; 6,277,375; 6,821,505; WO 97/34631; WO 2002/060919.

In certain embodiments, hybrid IgG isotypes may be used to increase FcRn binding, and potentially increase half-life. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A. See U.S. Pat. No. 8,629,113. A hybrid of IgG1/IgG2/IgG4 sequences has been generated that purportedly increases serum half-life and improves expression. U.S. Pat. No. 7,867,491 (sequence number 18 therein).

The serum half-life of the antibodies of the present invention can also be increased by pegylation. An antibody can be pegylated to, for example, increase the biological (e.g., serum) half-life of the antibody. To pegylate an antibody, the antibody, or fragment thereof, typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0154316 by Nishimura et al. and EP 0401384 by Ishikawa et al.

Alternatively, under some circumstances it may be desirable to decrease the half-life of an antibody, rather than increase it. Modifications such as I253A (Hornick et al. (2000) *J. Nucl. Med.* 41:355) and H435A/R I253A or H310A (Kim et al. (2000) *Eur. J. Immunol.* 29:2819) in Fc of human IgG1 can decrease FcRn binding, thus decreasing half-life (increasing clearance) for use in situations where rapid clearance is preferred, such a medical imaging. See also Kenanova et al. (2005) *Cancer Res.* 65:622. Other means to enhance clearance include formatting the antigen binding domains of the present invention as antibody fragments lacking the ability to bind FcRn, such as Fab fragments. Such modification can reduce the circulating half-life of an antibody from a couple of weeks to a matter of hours. Selective PEGylation of antibody fragments can then be used to fine-tune (increase) the half-life of the antibody fragments if necessary. Chapman et al. (1999) *Nat. Biotechnol.* 17:780. Antibody fragments may also be fused to human serum albumin, e.g. in a fusion protein construct, to increase half-life. Yeh et al. (1992) *Proc. Nat'l Acad. Sci.* 89:1904. Alternatively, a bispecific antibody may be constructed with a first antigen binding domain of the present invention and a second antigen binding domain that binds to human serum albumin (HSA). See Int'l Pat. Appl. Pub. WO 2009/127691 and patent references cited therein. Alternatively, specialized polypeptide sequences can be added to antibody fragments to increase half-life, e.g. "XTEN" poly-

Additional Fc Variants

When using an IgG4 constant domain, it is preferable to include the substitution S228P, which mimics the hinge sequence in IgG1 and thereby stabilizes IgG4 molecules, e.g. reducing Fab-arm exchange between the therapeutic antibody and endogenous IgG4 in the patient being treated. Labrijn et al. (2009) *Nat. Biotechnol.* 27:767; Reddy et al. (2000) *J. Immunol.* 164:1925.

A potential protease cleavage site in the hinge of IgG1 constructs can be eliminated by D221G and K222S modifications, increasing the stability of the antibody. WO 2014/043344.

The affinities and binding properties of an Fc variant for its ligands (Fc receptors) may be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE® SPR analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999) which focuses on antibody-immunogen interactions.

In still other embodiments, the glycosylation of an antibody is modified to increase or decrease effector function. For example, an aglycoslated antibody can be made that lacks all effector function by mutating the conserved asparagine residue at position 297 (e.g. N297A), thus abolishing complement and FcγRI binding. Bolt et al. (1993) *Eur. J. Immunol.* 23:403. See also Tao & Morrison (1989) *J. Immunol.* 143:2595 (using N297Q in IgG1 to eliminate glycosylation at position 297).

Although aglycosylated antibodies generally lack effector function, mutations can be introduced to restore that function. Aglycosylated antibodies, e.g. those resulting from N297A/C/D/or H mutations or produced in systems (e.g. *E. coli*) that do not glycosylate proteins, can be further mutated to restore FcγR binding, e.g. S298G and/or T299A/G/or H (WO 2009/079242), or E382V and M428I (Jung et al. (2010) *Proc. Nat'l Acad. Sci (USA)* 107:604).

Additionally, an antibody with enhanced ADCC can be made by altering glycosylation. For example, removal of fucose from heavy chain Asn297-linked oligosaccharides has been shown to enhance ADCC, based on improved binding to FcγRIIIa. Shields et al. (2002) *JBC* 277:26733; Niwa et al. (2005) *J. Immunol. Methods* 306: 151; Cardarelli et al. (2009) *Clin. Cancer Res.* 15:3376 (MDX-1401); Cardarelli et al. (2010) *Cancer Immunol. Immunotherap.* 59:257 (MDX-1342). Such low fucose antibodies may be produced, e.g., in knockout Chinese hamster ovary (CHO) cells lacking fucosyltransferase (FUT8) (Yamane-Ohnuki et al. (2004) *Biotechnol. Bioeng.* 87:614), or in other cells that generate afucosylated antibodies. See, e.g., Zhang et al. (2011) *mAbs* 3:289 and Li et al. (2006) *Nat. Biotechnol.* 24:210 (both describing antibody production in glycoengineered *Pichia pastoris*); Mossner et al. (2010) *Blood* 115: 4393; Shields et al. (2002) *J. Biol. Chem.* 277:26733; Shinkawa et al. (2003) *J. Biol. Chem.* 278:3466; EP 1176195B1. ADCC can also be enhanced as described in PCT Publication WO 03/035835, which discloses use of a variant CHO cell line, Lec13, with reduced ability to attach fucose to Asn(297)-linked carbohydrates, also resulting in hypofucosylation of antibodies expressed in that host cell (see also Shields, R. L. et al. (2002) *J. Biol. Chem.* 277: 26733-26740). Alternatively, fucose analogs may be added to culture medium during antibody production to inhibit incorporation of fucose into the carbohydrate on the antibody (see, e.g., WO 2009/135181).

Increasing bisecting GlcNac structures in antibody-linked oligosaccharides also enhances ADCC. PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Additional glycosylation variants have been developed that are devoid of galactose, sialic acid, fucose and xylose residues (so-called GNGN glycoforms), which exhibit enhanced ADCC and ADCP but decreased CDC, as well as others that are devoid of sialic acid, fucose and xylose (so-called G1/G2 glycoforms), which exhibit enhanced ADCC, ADCP and CDC. U.S. Pat. App. Pub. No. 2013/0149300. Antibodies having these glycosylation patterns are optionally produced in genetically modified *N. benthamiana* plants in which the endogenous xylosyl and fucosyl transferase genes have been knocked-out.

Glycoengineering can also be used to modify the anti-inflammatory properties of an IgG construct by changing the α2,6 sialyl content of the carbohydrate chains attached at Asn297 of the Fc regions, wherein an increased proportion of α2,6 sialylated forms results in enhanced anti-inflammatory effects. See Nimmerjahn et al. (2008) *Ann. Rev. Immunol.* 26:513. Conversely, reduction in the proportion of antibodies having α2,6 sialylated carbohydrates may be useful in cases where anti-inflammatory properties are not wanted. Methods of modifying α2,6 sialylation content of antibodies, for example by selective purification of α2,6 sialylated forms or by enzymatic modification, are provided at U.S. Pat. Appl. Pub. No. 2008/0206246. In other embodiments, the amino acid sequence of the Fc region may be modified to mimic the effect of α2,6 sialylation, for example by inclusion of an F241A modification (see, e.g., WO 2013/095966).

VIII. Antibody Physical Properties

Antibodies described herein can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J. Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. In some some embodiments, the anti-OX40 antibody does not contain variable region glycosylation. This can be achieved either by selecting antibodies that do not contain the glycosylation motif in the variable region or by mutating residues within the glycosylation region.

In certain embodiments, the antibodies described herein do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect). For instance, if the amino acid sequence Asp-Gly is present in the heavy and/or light chain CDR sequences of the antibody, the sequence is substituted with an amino acid sequence that does not undergo isomerization. In one embodiment, the antibody comprises the heavy chain variable region CDR2 sequence set forth in SEQ ID NO: 76, but wherein the Asp or Gly in the Asp-Gly sequence (LISYDGSRKHYADSVKG; SEQ ID NO: 76) is replaced with an amino acid sequence that does not undergo isomerization, for example, an Asp-Ser or a Ser-Gly sequence. In another embodiment, the antibody comprises the heavy chain variable region CDR2 sequence set forth in SEQ ID NO: 88, but wherein the Asp or Gly in the Asp-Gly sequence (AIDTDGGTFYADSVRG; SEQ ID NO: 88) is replaced with an amino acid sequence that does not undergo isomerization, for example, a Ser-Gly, an Asp-Ala, or a Ser-Thr sequence.

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-OX40 antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, it is preferred that the $T_{M1}$ (the temperature of initial unfolding) be greater than 60° C., preferably greater than 65° C., even more preferably greater than 70° C. The melting point of an antibody can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9). In a preferred embodiment, antibodies are selected that do not degrade rapidly. Degradation of an antibody can be measured using capillary electrophoresis (CE) and MALDI-MS (Alexander A J and Hughes D E (1995) *Anal Chem* 67:3626-32). In certain embodiments, the anti-OX40 antibodies disclosed herein (e.g., the OX40.21 antibody) have increased stability.

Accordingly, in other embodiments, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

IX. Methods of Engineering Antibodies

As discussed herein, anti-OX40 antibodies having $V_H$ and $V_L$ sequences disclosed herein can be used to create new anti-OX40 antibodies by modifying the VH and/or VL sequences, or the constant region(s) of the antibodies. Thus, in another embodiment, the structural features of anti-OX40 antibodies described herein, e.g. 3F4, 14B6-1, 14B6-2, 23H3, 6E1-1, 6E1-2, 18E9, 8B11, 20B3, 14A2-1, 14A2-2, and 20C1, are used to create structurally related anti-OX40 antibodies that retain at least one functional property of the antibodies described herein, such as binding to human OX40 and cynomolgus OX40. For example, one or more CDR regions of 3F4, 14B6-1, 14B6-2, 23H3, 6E1-1, 6E1-2, 18E9, 8B11, 20B3, 14A2-1, 14A2-2, and 20C1, or mutations thereof, can be combined recombinantly with known framework regions and/or other CDRs to create additional, recombinantly-engineered, anti-OX40 antibodies, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, provided herein are methods for generating anti-OX40 antibodies comprising:

(a) providing: (i) a heavy chain variable region antibody sequence comprising a CDR1 sequence selected from the group consisting of SEQ ID NOs: 11, 19, 31, 39, 51, 59, 67, 75, and 87, a CDR2 sequence selected from the group consisting of SEQ ID NOs: 12, 20, 32, 40, 52, 60, 68, 76, 88, and 317 and/or a CDR3 sequence selected from the group consisting of SEQ ID NOs: 13, 21, 33, 41, 53, 61, 69, 77, and 89; and (ii) a light chain variable region antibody sequence comprising a CDR1 sequence selected from the group consisting of SEQ ID NOs: 14, 22, 25, 34, 42, 45, 54, 62, 70, 78, 81, and 90, a CDR2 sequence selected from the group consisting of SEQ ID NOs: 15, 23, 26, 35, 43, 46, 55, 63, 71, 79, 82, and 91, and/or a CDR3 sequence selected from the group consisting of SEQ ID NOs: 16, 24, 27, 36, 44, 47, 56, 64, 72, 80, 83, and 92;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-OX40 antibodies described herein, which include, (1) binding to soluble human OX40, e.g., with a $K_D$ of 10 nM or less (e.g., 0.01 nM to 10 nM), e.g., as measured by Biacore;

(2) binding to membrane bound human OX40, e.g., with an $EC_{50}$ of 1 nM or less (e.g., 0.01 nM to 1 nM), e.g., as measured by FACS;

(3) binding to cynomolgus OX40, e.g., binding to membrane bound cynomolgus OX40, e.g., with an $EC_{50}$ of 10 nM or less (e.g., 0.01 nM to 10 nM), e.g., as measured by FACS;

(4) inducing or enhancing T cell activation, as evidenced by (i) increased IL-2 and/or IFN-γ production in OX40-expressing T cells and/or (ii) enhanced T cell proliferation;

(5) inhibiting the binding of OX40 ligand to OX40, e.g., with an $EC_{50}$ of 1 nM or less as measured by FACS, e.g., in an assay with hOX40-293 cells;

(6) binding to an epitope on the extracellular portion of mature human OX40 (SEQ ID NO: 2), e.g., an epitope within the region DVVSSKPCKPCTWCNLR (SEQ ID NO: 178) or DSYKPGVDCAPCPPGHFSPGDN-QACKPWTNCTLAGK (SEQ ID NO: 179);

(7) competing for binding to human OX40 with 3F4, 14B6-1, 14B6-2, 23H3, 18E9, 8B11, 20B3, and 20C1;

(8) competing for binding to human OX40 with 6E1-1, 6E1-2, 14A2-1, and 14A2-2.

The altered antibody may exhibit one or more, two or more, three or more, four or more, five or more, six, or all of the functional properties set forth as (1) through (7) above. The functional properties of the altered antibodies can be assessed using standard assays available in the art and/or described herein, such as those set forth in the Examples (e.g., ELISAs, FACS).

In certain embodiments of the methods of engineering antibodies described herein, mutations can be introduced randomly or selectively along all or part of an anti-OX40 antibody coding sequence and the resulting modified anti-OX40 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

X. Nucleic Acid Molecules

Also provided herein are nucleic acid molecules that encode the antibodies described herein. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid can be, for example, DNA or RNA and may or may not contain intronic sequences. In a certain embodiments, the nucleic acid is a cDNA molecule.

Nucleic acids provided herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules are those encoding the VH and VL sequences of 3F4, 14B6-1, 14B6-2, 23H3, 6E1-1, 6E1-2, 18E9, 8B11, 20B3, 14A2-1, 14A2-2, and 20C1. Exemplary DNA sequences encoding the VH sequences of 3F4, 14B6, 23H3, 6E1, 18E9, 8B11, 20B3, 14A2, and 20C1 are set forth in SEQ ID NOs: 126, 128, 131, 133, 136, 138, 140, 142, and 145, respectively. Exemplary DNA sequences encoding the VL sequences of 3F4, 14B6-1, 14B6-2, 23H3, 6E1-1, 6E1-2, 18E9, 8B11, 20B3, 14A2-1, 14A2-2, and 20C1 are set forth in SEQ ID NOs: 127, 129, 130, 132, 134, 135, 137, 139, 141, 143, 144, and 146, respectively. Exemplary DNA sequences encoding heavy chain sequences are set forth in SEQ ID NOs: 147, 149, 151, 153, 155, 157, 159, 161, 163, 165, 167, 169, 171, 173, 175, 176, and 177. Exemplary DNA sequences encoding light chain sequences are set forth in SEQ ID NOs: 148, 150, 152, 154, 156, 158, 160, 162, 164, 166, 168, 170, 172, and 174.

Exemplary nucleotide sequences encoding the mature VH and VL domains of an anti-OX40 antibody are set forth in SEQ ID NOs: 145 and 146, respectively. An exemplary nucleotide sequence encoding the heavy chain of an anti-OX40 antibody is set forth in SEQ ID NO: 177. An exemplary nucleotide sequence encoding the light chain of an OX40 antibody is set forth in SEQ ID NO: 168.

Methods for making the anti-OX40 antibodies provided herein can include expressing the heavy chain and the light chains in a cell line comprising the nucleotide sequences encoding the heavy and light chains with a signal peptide. Host cells comprising these nucleotide sequences are also provided herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, refers to the joining of the two DNA fragments such that the amino acid sequences they encode remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)$_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Also provided herein are nucleic acid molecules encoding VH and VL sequences that are homologous to those of the 3F4, 14B6-1, 14B6-2, 23H3, 6E1-1, 6E1-2, 18E9, 8B11, 20B3, 14A2-1, 14A2-2, and 20C1 monoclonal antibodies. Exemplary nucleic acid molecules encode VH and VL sequences that are at least 70% identical, for example, at least 75%, at least 80%, at least 85%, at least 90%, at least 95%, or at least 99% identical, to nucleic acid molecules encoding the VH and VL sequences of the 3F4, 14B6-1, 14B6-2, 23H3, 6E1-1, 6E1-2, 18E9, 8B11, 20B3, 14A2-1, 14A2-2, and 20C1 monoclonal antibodies. Also provided herein are nucleic acid molecules with conservative substitutions (i.e., substitutions that do not alter the resulting amino acid sequence upon translation of nucleic acid molecule), e.g., for codon optimization.

XI. Antibody Generation

Anti-OX40 antibodies described herein can be produced using a variety of known techniques, such as the standard somatic cell hybridization technique described by Kohler and Milstein, *Nature* 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one embodiment, the antibodies described herein are human monoclonal antibodies. Such human monoclonal antibodies directed against OX40 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In certain embodiments, antibodies described herein are raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-OX40 antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-OX40 antibodies described herein. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-OX40 antibodies described herein.

Additional mouse systems described in the art for raising human antibodies, e.g., human anti-OX40 antibodies, include (i) the VelocImmune® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/

0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunizations

To generate fully human antibodies to OX40, transgenic or transchromosomal mice containing human immunoglobulin genes (e.g., HCo12, HCo7 or KM mice) can be immunized with a purified or enriched preparation of the OX40 antigen and/or cells expressing OX40 or fragment thereof, as described for other antigens, for example, by Lonberg et al. (1994) *Nature* 368(6474): 856-859; Fishwild et al. (1996) *Nature Biotechnology* 14: 845-851 and WO 98/24884. Alternatively, mice can be immunized with DNA encoding human OX40 or fragment thereof. Preferably, the mice will be 6-16 weeks of age upon the first infusion. For example, a purified or enriched preparation (5-50 μg) of the recombinant OX40 antigen can be used to immunize the HuMAb mice intraperitoneally. In the event that immunizations using a purified or enriched preparation of the OX40 antigen do not result in antibodies, mice can also be immunized with cells expressing OX40, e.g., a cell line, to promote immune responses. Exemplary cell lines include OX40-overexpressing stable CHO and Raji cell lines.

Cumulative experience with various antigens has shown that the HuMAb transgenic mice respond best when initially immunized intraperitoneally (IP) or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-OX40 human immunoglobulin can be used for fusions. Mice can be boosted intravenously with antigen 3 days before sacrifice and removal of the spleen and lymph nodes. It is expected that 2-3 fusions for each immunization may need to be performed. Between 6 and 24 mice are typically immunized for each antigen. Usually, HCo7, HCo12, and KM strains are used. In addition, both HCo7 and HCo12 transgene can be bred together into a single mouse having two different human heavy chain transgenes (HCo7/HCo12).

Generation of Hybridomas Producing Monoclonal Antibodies to OX40

To generate hybridomas producing the antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 nonsecreting mouse myeloma cells (ATCC, CRL 1581) with 50% PEG. Cells are plated at approximately $2 \times 10^5$ in flat bottom microtiter plate, followed by a two week incubation in selective medium containing 10% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify the antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The antibodies can then be aliquoted and stored at −80° C.

Generation of Transfectomas Producing Monoclonal Antibodies to OX40

Antibodies can be produced in a host cell transfectoma using, for example, a combination of recombinant DNA techniques and gene transfection methods as is well known in the art (Morrison, S. (1985) *Science* 229:1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector.

Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein). Exemplary signal sequences for use in antibody heavy and light chains include the signal sequences originally found in the anti-OX40 antibodies described herein.

In addition to the antibody chain genes, recombinant expression vectors may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13). The antibodies disclosed herein can also be produced in glycoengineered strains of the yeast *Pichia pastoris*. Li et al. (2006) *Nat. Biotechnol.* 24:210.

Preferred mammalian host cells for expressing the recombinant antibodies described herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications. For example, C-terminal lysine residues are often missing from antibody heavy chains. Dick et al. (2008) *Biotechnol. Bioeng.* 100:1132. N-terminal glutamine residues, and to a lesser extent glutamate residues, are frequently converted to pyroglutamate residues on both light and heavy chains of therapeutic antibodies. Dick et al. (2007) *Biotechnol. Bioeng.* 97:544; Liu et al. (2011) *JBC* 28611211; Liu et al. (2011) *J. Biol. Chem.* 286:11211.

XII. Assays

Anti-OX40 antibodies described herein can be tested for binding to OX40 by, for example, standard ELISA. Briefly, microtiter plates are coated with purified OX40 at 1-2 μg/ml in PBS, and then blocked with 5% bovine serum albumin in PBS. Dilutions of antibody (e.g., dilutions of plasma from OX40-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human OX40, but not to a control cell line that does not express OX40. Briefly, the binding of anti-OX40 antibodies is assessed by incubating OX40 expressing CHO cells with the anti-OX40 antibody at 1:20 dilution. The cells are washed and binding is detected with a PE-labeled anti-human IgG Ab. Flow cytometric analyses are performed using a FACScan flow cytometry (Becton Dickinson, San Jose, Calif.). Preferably, mice which develop the highest titers will be used for fusions.

An ELISA assay as described above can be used to screen for antibodies and, thus, hybridomas that produce antibodies that show positive reactivity with the OX40 immunogen. Hybridomas that produce antibodies that bind, preferably with high affinity, to OX40 can then be subcloned and further characterized. One clone from each hybridoma, which retains the reactivity of the parent cells (by ELISA), can then be chosen for making a cell bank, and for antibody purification.

To purify anti-OX40 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-OX40 antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using OX40 coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of antibodies to live cells expressing OX40, flow cytometry can be used, as described in the Examples. Briefly, cell lines expressing membrane-bound OX40 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-OX40 antibodies can be further tested for reactivity with the OX40 antigen by Western blotting. Briefly, cell extracts from cells expressing OX40 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics include standard assays known in the art, for example, BIACORE® SPR analysis using a BIACORE® 2000 SPR instrument (Biacore AB, Uppsala, Sweden).

In certain embodiments, the anti-OX40 antibody specifically binds to the extracellular region of human OX40. For example, the antibody may specifically bind to a particular domain (e.g., a functional domain) within the extracellular domain of OX40. In a particular embodiment, the antibody specifically binds to the site on OX40 to which OX40-L binds. In other embodiments, the antibody specifically binds to the extracellular region of human OX40 and the extracellular region of cynomolgus OX40.

XIII. Immunoconjugates, Antibody Derivatives and Diagnostics

Anti-OX40 antibodies described herein can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, biotin, luminescent markers, phosphorescent markers and the like, as well as enzyme labels that convert a given substrate to a detectable marker, and polynucleotide tags that are revealed following amplification such as by polymerase chain reaction. A biotinylated antibody would then be detectable by avidin or streptavidin binding. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Preferably, conjugation methods result in linkages which are substantially (or nearly) non-immunogenic, e.g., peptide- (i.e. amide-), sulfide-, (sterically hindered), disulfide-, hydrazone-, and ether linkages. These linkages are nearly non-immunogenic and show reasonable stability within serum (see e.g. Senter, P. D., Curr. Opin. Chem. Biol. 13 (2009) 235-244; WO 2009/059278; WO 95/17886).

Depending on the biochemical nature of the moiety and the antibody, different conjugation strategies can be employed. In case the moiety is naturally occurring or recombinant polypeptide of between 50 to 500 amino acids, there are standard procedures in text books describing the chemistry for synthesis of protein conjugates, which can be easily followed by the skilled artisan (see e.g. Hackenberger, C. P. R., and Schwarzer, D., Angew. Chem. Int. Ed. Engl. 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, J., *Org. Biomol. Chem.* 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., Chem Bio Chem. 10 (2009) 425-427). It is also possible to obtain a desired amino acid modification by utilizing the specific enzymatic reactivity of certain enzymes with a natural amino acid in a given sequence context (see, e.g., Taki, M. et al., *Prot. Eng. Des. Sel.* 17 (2004) 119-126; Gautier, A. et al. *Chem. Biol.* 15 (2008) 128-136; and Protease-catalyzed formation of C—N bonds is described in Bordusa, F., *Highlights in Bioorganic Chemistry* (2004) 389-403).

Site specific reaction and covalent coupling can also be achieved by the selective reaction of terminal amino acids with appropriate modifying reagents.

The reactivity of an N-terminal cysteine with benzonitrils (see Ren et al., *Angew. Chem. Int. Ed. Engl.* 48 (2009) 9658-9662) can be used to achieve a site-specific covalent coupling.

Native chemical ligation can also rely on C-terminal cysteine residues (Taylor, E. Vogel; Imperiali, B, *Nucleic Acids and Molecular Biology* (2009), 22 (Protein Engineering), 65-96).

EP 1 074 563 describes a conjugation method which is based on the faster reaction of a cysteine within a stretch of negatively charged amino acids than a cysteine located in a stretch of positively charged amino acids.

The moiety may also be a synthetic peptide or peptide mimic. In case a polypeptide is chemically synthesized, amino acids with orthogonal chemical reactivity can be incorporated during such synthesis (see e.g. de Graaf et al., *Bioconjug. Chem.* 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry may be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

In one embodiment, the moiety attached to the anti-OX40 antibody is selected from the group consisting of a binding moiety, a labeling moiety, and a biologically active moiety.

Anti-OX40 antibodies described herein also may be conjugated to a therapeutic agent to form an immunoconjugate such as an antibody-drug conjugate (ADC). Suitable therapeutic agents include antimetabolites, alkylating agents, DNA minor groove binders, DNA intercalators, DNA cross-linkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO: 180), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference.

More specifically, in an ADC, the antibody is conjugated to a drug, with the antibody functioning as a targeting agent for directing the ADC to a target cell expressing its antigen, such as a cancer cell. Preferably, the antigen is a tumor associated antigen, i.e., one that is uniquely expressed or overexpressed by the cancer cell. Once there, the drug is released, either inside the target cell or in its vicinity, to act as a therapeutic agent. For a review on the mechanism of action and use of ADCs in cancer therapy, see Schrama et al., *Nature Rev. Drug Disc.* 2006, 5, 147.

For cancer treatment, the drug preferably is a cytotoxic drug that causes death of the targeted cancer cell. Cytotoxic drugs that can be used in ADCs include the following types of compounds and their analogs and derivatives:

(a) enediynes such as calicheamicin (see, e.g., Lee et al., *J. Am. Chem. Soc.* 1987, 109, 3464 and 3466) and uncialamycin (see, e.g., Davies et al., WO 2007/038868 A2 (2007) and Chowdari et al., U.S. Pat. No. 8,709,431 B2 (2012));

(b) tubulysins (see, e.g., Domling et al., U.S. Pat. No. 7,778,814 B2 (2010); Cheng et al., U.S. Pat. No. 8,394,922 B2 (2013); and Cong et al., U.S. Ser. No. 14/177,376, filed Feb. 11, 2014));

(c) CC-1065 and duocarmycin (see, e.g., Boger, U.S. Pat. No. 6,5458,530 B1 (2003); Sufi et al., U.S. Pat. No. 8,461,117 B2 (2013); and Zhang et al., US 2012/0301490 A1 (2012));

(d) epothilones (see, e.g., Vite et al., US 2007/0275904 A1 (2007) and U.S. RE42930 E (2011));

(e) auristatins (see, e.g., Senter et al., U.S. Pat. No. 6,844,869 B2 (2005) and Doronina et al., U.S. Pat. No. 7,498,298 B2 (2009));

(f) pyrrolobezodiazepine (PBD) dimers (see, e.g., Howard et al., US 2013/0059800 A1(2013); US 2013/0028919 A1 (2013); and WO 2013/041606 A1 (2013)); and (g) maytansinoids such as DM1 and DM4 (see, e.g., Chari et al., U.S. Pat. No. 5,208,020 (1993) and Amphlett et al., U.S. Pat. No. 7,374,762 B2 (2008)).

In an ADC, a linker covalently connects the antibody and the drug. Typically, there is one drug molecule attached to each linker, but the linker can be branched, allowing the attachment of plural drug molecules to increase the drug payload delivered per ADC. Further, each antibody may have more than one linker attached. The number drug molecules carried on an ADC is referred to as the drug-antibody ratio (DAR). For instance, if each heavy chain of the antibody has attached to it one linker that in turn has one drug molecule attached, the DAR is 2. Preferably, the DAR is between 1 and 5, more preferably between 2 and 4. Those skilled in the art will also appreciate that, while in each individual ADC the antibody is conjugated to an integer number of drug molecules, as a whole, a preparation of the ADC may analyze for a non-integer DAR, reflecting a statistical average. In summary, the architecture of an ADC may be represented by the following formula:

$$[\text{Antibody}]-[\text{Linker}-(\text{Drug})_n]_m$$

where typically m is 1, 2, 3, 4, 5, or 6 (preferably 2, 3, or 4) and n is 1, 2, or 3.

In some embodiments, the linker contains a cleavable group that is cleaved inside or in the vicinity of the target cell, to release the drug. In other embodiments, the linker does not contain a cleavable group but, rather, the ADC relies on catabolism of the antibody to release the drug.

One type of cleavable group is a pH sensitive group. The pH in blood plasma is slightly above neutral, while the pH inside a lysosome—where most ADCs end up after internalization inside a target cell—is acidic, circa 5. Thus, a cleavable group whose cleavage is acid catalyzed will cleave at a rate several orders of magnitude faster inside a lysosome than in the blood plasma. Examples of acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 1981, 102, 1048; and Yang et al., *Proc. Nat'l Acad. Sci* (*USA*), 1988, 85, 1189; the disclosures of which are incorporated herein by reference.

In another embodiment, the cleavable group is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly, i.e., after internalization of the ADC. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 1988, 48, 6396; Santi et al., U.S. Pat. No. 7,541,530 B2 (2009); Ng et al., U.S. Pat. No. 6,989,452 B2 (2006); Ng et al., WO 2002/096910 A1 (2002); Boyd et al., U.S. Pat. No. 7,691,962 B2 (2010); and Sufi et al., US 2010/0145036 A1 (2010); the disclosures of which are incorporated herein by reference.

A preferred cleavable group is a peptide that is cleaved selectively by a protease inside the target cell, as opposed to by a protease in the serum. Typically, a cleavable peptide group comprises from 1 to 20 amino acids, preferably from 1 to 6 amino acids, more preferably from 1 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this context, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, a cleavable peptide group contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

More preferably, a cleavable peptide group comprises an amino acid sequence selected for cleavage by an endosomal or lysosomal protease, especially the latter. Examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys, written in the N-to-C direction. For additional information regarding cathepsin-cleavable groups, see Dubowchik et al., *Biorg. Med. Chem. Lett.* 1998, 8, 3341; Dubowchik et al., *Bioorg. Med. Chem. Lett.*, 1998, 8, 3347; and Dubowchik et al., *Bioconjugate Chem.* 2002, 13, 855; the disclosures of which are incorporated by reference. Another enzyme that can be utilized for cleaving peptidyl linkers is legumain, a lysosomal cysteine protease that preferentially cleaves at Ala-Ala-Asn.

In a preferred embodiment, the linker in ADCs comprises a di- or tripeptide that is preferentially cleaved by a protease located inside the target cell. Preferably, the di- or tripeptide is cleavable by cathepsin B, more preferably a Val-Cit or Val-Lys dipeptide.

Single amino acid cleavable peptide groups also can be used, as disclosed in Chen et al., US 2010/0113476 A1 (2010), the disclosure of which is incorporated herein by reference.

For conjugates that are not intended to be internalized by a cell, the cleavable group can be chosen such that it is cleaved by a protease present in the extracellular matrix in the vicinity of the target cell, e.g., a protease released by nearby dying cells or a tumor-associated protease. Exemplary extracellular tumor-associated proteases are matrix metalloproteases (MMP), plasmin, thimet oligopeptidase (TOP) and CD10. See, e.g., Trouet et al., *U.S. Pat. No.* 5,962,216 (1999) and U.S. Pat. No. 7,402,556 B2 (2008); Dubois et al., U.S. Pat. No. 7,425,541 B2 (2008); and Bebbington et al., U.S. Pat. No. 6,897,034 B2 (2005); the disclosures of which are incorporated herein by reference.

The linker can perform other functions in addition to covalently linking the antibody and the drug. For instance, the linker can contain poly(ethylene glycol) (PEG) groups, which enhance solubility either during the performance the conjugation chemistry or in the final ADC product.

The linker can further include a self-immolating moiety located adjacent to a cleavable peptide group. The self-immolating group serves as a spacer that prevents the antibody and/or the drug moiety from sterically interfering with the cleavage of the peptide group by a protease but thereafter spontaneously releases itself (i.e., self-immolates) so as to not interfere with the action of the drug. See Carl et al., *J. Med. Chem.* 1981, 24 (3), 479; Carl et al., WO 81/01145 (1981); Dubowchik et al., *Pharmacology & Therapeutics* 1999, 83, 67; Firestone et al., U.S. Pat. No. 6,214,345 B1 (2001); Toki et al., *J. Org. Chem.* 2002, 67, 1866; Doronina et al., *Nature Biotechnology* 2003, 21 (7), 778 (erratum, p. 941); de Groot et al., *Org. Chem.* 2001, 66, 8815; Boyd et al., U.S. Pat. No. 7,691,962 B2 (2010); Boyd et al., US 2008/0279868 A1 (2008); Sufi et al., WO 2008/083312 A2 (2008); Feng, U.S. Pat. No. 7,375,078 B2 (2008); Jeffrey, U.S. Pat. No. 8,039,273 B2 (2011); and Senter et al., US 2003/0096743 A1 (2003); the disclosures of which are incorporated by reference.

A preferred self-immolating group is a p-aminobenzyl oxycarbonyl (PABC) group, whose structure and mechanism of action is depicted below:

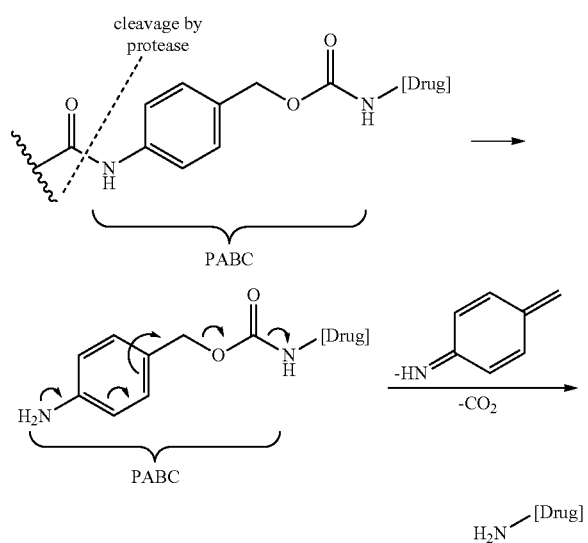

Thus, in a preferred embodiment, an ADC has a linker comprising a di- or tripeptide that is preferentially cleaved by a protease located inside the target cell and, adjacent to the di- or tripeptide, a self-immolating group. Preferably, the di- or tripeptide is cleavable by cathepsin B. Preferably, the self-immolating group is a PABC group.

Numerous techniques can be used for conjugating the antibody and the drug. In a preferred one, an ε-amino group in the side chain of a lysine residue in the antibody is reacted with 2-iminothiolane to introduce a free thiol (—SH) group. The thiol group can react with a maleimide or other nucleophile acceptor group to effect conjugation, as illustrated below:

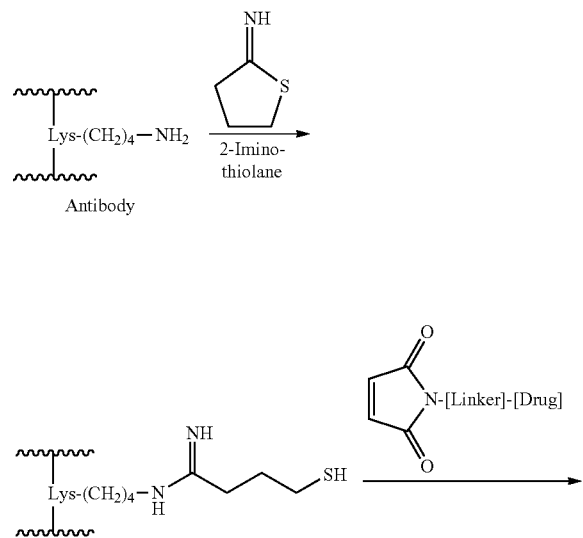

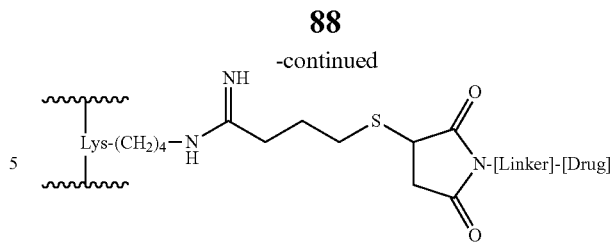

Typically, a thiolation level of two to three thiols per antibody is achieved. For a representative procedure, see Chowdari et al., U.S. Pat. No. 8,709,431 B2 (2014), the disclosure of which is incorporated herein by reference. Thus, in one embodiment, an antibody of this invention has one or more lysine residues (preferably two or three) modified by reaction with iminothiolane.

An alternative conjugation technique employs copper-free "click chemistry," in which an azide group adds across the strained alkyne bond of a cyclooctyne to form an 1,2,3-triazole ring. See, e.g., Agard et al., *J. Amer. Chem. Soc.* 2004, 126, 15046; Best, *Biochemistry* 2009, 48, 6571, the disclosures of which are incorporated herein by reference. The azide can be located on the antibody and the cyclooctyne on the drug moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody:

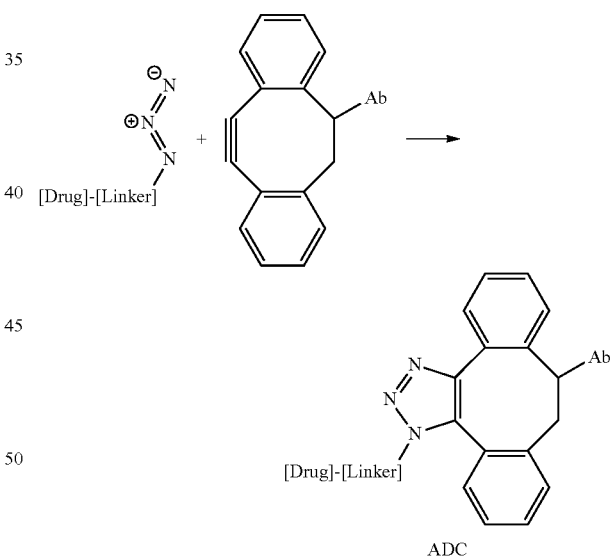

In an ADC made by this technique, the linker comprises a 1,2,3-triazole ring.

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenyalanine can be a conjugation site by the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., *Biotechnol. Bioeng.* 2009, 102 (2), 400-416. The foregoing disclosures are incorporated herein by reference. Thus, in one embodiment, the antibody has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase or BTG), as taught in Jeger et al., *Angew. Chem. Int. Ed.* 2010, 49, 9995. BTG forms an amide bond between the side chain carboxamide of a glutamine and an alkyleneamino group, which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

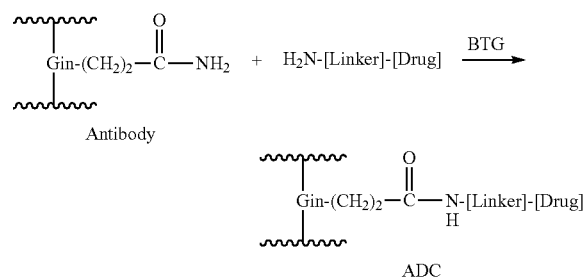

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297)—nearby glutamine 295 (Q295) is rendered BTG susceptible. Alternatively, an antibody can be synthesized glycoside free by introducing an N297A mutation in the constant region, to eliminate the N297 glycosylation site. Further, it has been shown that an N297Q substitution in an antibody not only eliminates glycosylation, but also introduces a second glutamine residue (at position 297) that too is susceptible BTG-mediated transamidation. Thus, in one embodiment, the anti-OX40 antibody is deglycosylated. In another embodiment, the anti-OX40 antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

Further, another conjugation technique uses the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005), the disclosures of which are incorporated herein by reference. The Sortase A recognition motif (typically LPXTG (SEQ ID NO: 181), where X is any natural amino acid) may be attached to the antibody and the nucleophilic acceptor motif (typically GGG) may be located on the drug moiety, or vice-versa.

Anti-OX40 antibodies described herein also can be used for detecting OX40, such as human OX40, e.g., human OX40 in tissues or tissue samples. The antibodies may be used, e.g., in an ELISA assay or in flow cytometry. In certain embodiments, the anti-OX40 antibody is contacted with cells, e.g., cells in a tissue, for a time appropriate for specific binding to occur, and then a reagent, e.g., an antibody that detects the anti-OX40 antibody, is added. Exemplary assays are provided in the Examples. The anti-OX40 antibody may be a fully human antibody, or it may be a chimeric antibody, such as an antibody having human variable regions and murine constant regions or a portion thereof. Exemplary methods for detecting OX40, e.g., human OX40, in a sample (cell or tissue sample) comprise (i) contacting a sample with an anti-OX40 antibody, for a time sufficient for allowing specific binding of the anti-OX40 antibody to OX40 in the sample, and (2) contacting the sample with a detection reagent, e.g., an antibody, that specifically binds to the anti-OX40 antibody, such as to the Fc region of the anti-OX40 antibody, to thereby detect OX40 bound by the anti-OX40 antibody. Wash steps may be included after the incubation with the antibody and/or detection reagent. Anti-OX40 antibodies for use in these methods do not have to be linked to a label or detection agents, as a separate detection agent can be used.

XIV. Bispecific Molecules

Anti-OX40 antibodies described herein may be used for forming bispecific molecules. For example, the antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. In one embodiment, the anti-OX40 antibody may be linked to an antibody or scFv that binds specifically to any protein that may be used as potential targets for combination treatments, such as the proteins described herein (e.g., antibodies to PD-1, PD-L1, or LAG-3). Alternatively, the antibody may be derivatized or linked to more than one other functional molecule to generate multispecific molecules that bind to more than two different binding sites and/or target molecules. Such multispecific molecules are also intended to be encompassed by the term "bispecific molecule" as used herein. To create a bispecific molecule described herein, the anti-OX40 antibody can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for OX40 and a second binding specificity for a second target epitope. In one embodiment, the bispecific molecule is multispecific, e.g., the molecule further includes a third binding specificity.

In certain embodiments, the bispecific molecules comprises as a binding specificity at least one antibody, or an antibody fragment thereof, including, e.g., an Fab, Fab', F(ab')$_2$, Fv, or a single chain Fv (scFv). The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies can be employed in the bispecific molecules described herein, including, e.g., murine, chimeric and humanized antibodies.

Bispecific molecules provided herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb× (scFv)$_2$, Fab×F(ab')$_2$ or ligand x Fab fusion protein. A bispecific antibody may comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

XV. Compositions

Further provided are compositions, e.g., a pharmaceutical compositions, containing one or more anti-OX40 antibodies, alone or in combination with antibodies to other targets, formulated together with a pharmaceutically acceptable carrier. Such compositions may include one or a combination of (e.g., two or more different) antibodies, or immunoconjugates or bispecific molecules described herein. For example, the composition can comprise a combination of antibodies (or immunoconjugates or bispecifics) described herein that bind to different epitopes on OX40 or that have complementary activities.

In certain embodiments, the composition comprises an anti-OX40 antibody at a concentration of at least 1 mg/ml, 5 mg/ml, 10 mg/ml, 50 mg/ml, 100 mg/ml, 150 mg/ml, 200 mg/ml, 1-300 mg/ml, or 100-300 mg/ml.

Pharmaceutical compositions described herein also can be administered in combination therapies, i.e., combined with other agents. For example, the combination therapy can include administration of an anti-OX40 antibody described herein combined with at least one other anti-cancer and/or T-cell stimulating (e.g., activating) agent. Examples of therapeutic agents that can be used in combination therapy are described in greater detail below in the section on uses of the antibodies described herein.

In certain embodiments, therapeutic compositions disclosed herein include other compounds, drugs, and/or agents used for the treatment of cancer. Such compounds, drugs, and/or agents can include, for example, chemotherapy drugs, small molecule drugs or antibodies that stimulate the immune response to a given cancer. In some instances, therapeutic compositions can include, for example, one or more of an anti-CTLA-4 antibody, an anti-PD-1 antibody, an anti-PDL-1 antibody, an anti-GITR antibody, an anti-CD137 antibody, or an anti-LAG-3 antibody.

As used herein, "pharmaceutically acceptable carriers" include any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compositions described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical compositions described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the anti-OX40 antibody, the dosage ranges from about 0.0001 to 100 mg/kg, about 0.01 to 5 mg/kg, about 0.01 to 10 mg/kg, about 0.1 to 1 mg/kg, about 0.1 to 0.5 mg/kg, or about 0.5 to 0.8 mg/kg of the host body weight. For example, dosages can be 0.2 mg/kg body weight, 0.3 mg/kg body weight, 0.5 mg/kg body weight, 1 mg/kg body weight, 3 mg/kg body weight, 5 mg/kg body weight or 10 mg/kg body weight or within the range of 1-10 mg/kg. In certain embodiments, the dosage is 0.2 mg/kg. In some embodiments, the dosage is 0.25 mg/kg. In other embodiments, the dosage is 0.5 mg/kg. An exemplary treatment regime entails administration once per week, once every two weeks, once every three weeks, once every four weeks, once a month, once every 3 months or once every three to 6 months. Exemplary dosage regimens for the antibodies described herein include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In certain embodiments, for combination treatment with an anti-OX40 antibody and anti-PD-1 or anti-CTLA-4 antibody, the antibodies are administered at a fixed dose. Accordingly, in some embodiments, the anti-OX40 antibody is administered at a fixed dose of about 25 to about 320 mg, for example, about 25 to about 160 mg, about 25 to about 80 mg, about 25 to about 40 mg, about 40 to about 320 mg, about 40 to about 160 mg, about 40 to about 80 mg, about 80 to about 320 mg, about 30 to about 160 mg, or about 160 to about 320 mg. In one embodiment, the anti-OX40 antibody is administered at a dose of 20 mg or about 20 mg. In another embodiment, the anti-OX40 antibody is administered at a dose of 40 mg or about 40 mg. In another embodiment, the anti-OX40 antibody is administered at a dose of 80 mg or about 80 mg. In another embodiment, the anti-OX40 antibody is administered at a dose of 160 mg or about 160 mg. In another embodiment, the anti-OX40 antibody is administered at a dose of 320 mg or about 320 mg.

In some embodiments, the anti-PD-1 antibody is administered at a fixed dose of about 100 to 300 mg, For example, the dosage of the immuno-oncology agent can be 240 mg or about 240 mg, 360 mg or about 360 mg, or 480 mg or about 480 mg. In certain embodiments, the dose of the anti-PD1 antibody ranges from about 0.0001 to 100 mg/kg, and more usually 0.01 to 5 mg/kg, of the host body weight. For example dosages can be 0.3 mg/kg body weight or about 0.3 mg/kg body weight, 1 mg/kg body weight or about 1 mg/kg body weight, 3 mg/kg body weight or about 3 mg/kg body weight, 5 mg/kg body weight or about 5 mg/kg body weight, or 10 mg/kg body weight or about 10 mg/kg body weight, or within the range of 1-10 mg/kg. In some embodiments, the dosage of the anti-PD-1 antibody is 240 mg or about 240 mg administered once every 2 weeks (Q2W). This dosage can be adjusted proportionately (at 120 mg per week) for longer or shorter periods, e.g., 360 mg administered once every 3 weeks (Q3W) or 480 mg administered once every 4 weeks (Q4W).

In some embodiments, the anti-CTLA-4 antibody is administered at a dose of about 0.1 mg/kg to about 10 mg/kg. For example, dosages can be 1 mg/kg or about 1 mg/kg or 3 mg/kg or about 3 mg/kg, of the host body weight.

Exemplary dosage regimens for combination treatment with an anti-OX40 and anti-PD-1 or anti-CTLA-4 antibody are provided infra under the section titled "Uses and Methods."

In certain embodiments, the anti-OX40 antibody is administered to a patient with an infusion duration of about 15 minutes to about 60 minutes, for example, about 30 minutes.

In certain embodiments, the anti-PD-1 antibody (e.g., nivolumab) is administered to a patient with an infusion duration of about 15 minutes to about 60 minutes, for example, about 30 minutes, when administered at a dose of 3 mg/kg (0.1 mg/kg/min). In certain embodiments, the anti-PD-1 antibody is administered to a patient with an infusion duration of about 45 minutes to 75 minutes, for example, about 60 minutes, when administered at a dose of 10 mg/kg.

In certain embodiments, the anti-CTLA-4 antibody (e.g., ipilimumab) is administered to a patient with an infusion duration of about 15 minutes to 120 minutes, for example, about 30 minutes when administered at a dose of 3 mg/kg. In certain embodiments, the anti-CTLA-4 antibody is administered to a patient with an infusion duration of about 15 minutes to 120 minutes, for example, 90 minutes, when administered at a dose of 10 mg/kg.

In certain embodiments, when administered on the same day, the anti-OX40 antibody is administered before the anti-PD-1 or anti-CTLA-4 antibody. In certain embodiments, when administered on the same day, the anti-OX40 antibody is administered after the anti-PD-1 or anti-CTLA-4 antibody. In certain embodiments, when administered on the same day, the anti-OX40 antibody is administered simultaneously with the anti-PD-1 or anti-CTLA-4 antibody.

In certain embodiments, when administered on the same day, the anti-OX40 antibody is administered about 15 to 45 minutes (e.g., about 30 minutes) before the anti-PD-1 or anti-CTLA-4 antibody. In certain embodiments, when administered on the same day, the anti-OX40 antibody is administered about 15 to 45 minutes (e.g., about 30 minutes) after the anti-PD-1 or anti-CTLA-4 antibody.

Alternatively, anti-OX40 antibodies provided herein can be administered at a flat dose (flat dose regimen).

In some cases, two or more monoclonal antibodies with different binding specificities are administered simultaneously, such that the dosage of each antibody administered falls within the ranges above. In addition, the antibodies usually are administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Anti-OX40 antibodies described herein may be administered with another antibody at the dosage regimen of the other antibody. For example, the anti-OX40 antibody may be administered with an anti-PD-1 antibody, such as nivolumab (OPDIVO), every two weeks as an i.v. infusion over 60 minutes until disease progression or unacceptable toxicity occurs. Alternatively, the anti-OX40 antibody may be administered with pembrolizumab (KEYTRUDA) every 3 weeks as an i.v. infusion over 30 minutes until disease progression or unacceptable toxicity occurs.

Antibodies can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

"Therapeutically effective dosages" of the antibodies described herein preferably results in a decrease in severity of disease symptoms, an increase in frequency and duration of disease symptom-free periods, or a prevention of impairment or disability due to the disease affliction. In the context of cancer, a therapeutically effective dose preferably results in increased survival, and/or prevention of further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

A therapeutically effective dose may prevent or delay onset of cancer, such as may be desired when early or preliminary signs of the disease are present. Laboratory tests utilized in the diagnosis of cancer include chemistries (including the measurement of OX40 levels), hematology, serology and radiology. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

Antibodies and compositions described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, the antibody can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Antibody compositions can be administered with medical devices known in the art. For example, in one embodiment, the composition is administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use in administering the antibodies include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-OX40 antibodies are formulated to ensure proper distribution in vivo. For example, the blood-brain barrier (BBB) excludes many highly hydrophilic compounds. To ensure the antibodies cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; I. J. Killion; I. J. Fidler (1994) *Immunomethods* 4:273.

XVI. Uses and Methods

Anti-OX40 antibodies and compositions described herein have numerous in vitro and in vivo applications involving, for example, enhancement of immune response by activating OX40 signaling, or detection of OX40. In a preferred embodiment, the antibodies are human antibodies. For example, anti-OX40 antibodies described herein can be contacted with cells in culture, in vitro or ex vivo, or administered to human subjects, e.g., in vivo, to enhance immunity in a variety of diseases. Accordingly, provided herein are methods of modifying an immune response in a subject comprising administering to the subject an antibody, or antigen-binding portion thereof, described herein such that the immune response in the subject is modified. Preferably, the response is enhanced, stimulated or up-regulated.

Preferred subjects include human patients in whom enhancement of an immune response would be desirable. The methods are particularly suitable for treating human patients having a disorder that can be treated by augmenting an immune response (e.g., a T-cell mediated immune response, e.g., an antigen specific T cell response). In a particular embodiment, the methods are particularly suitable for treatment of cancer in vivo. To achieve antigen-specific enhancement of immunity, anti-OX40 antibodies described herein can be administered together with an antigen of interest or the antigen may already be present in the subject to be treated (e.g., a tumor-bearing or virus-bearing subject).

When anti-OX40 antibodies are administered together with another agent, the two can be administered separately or simultaneously.

Also encompassed are methods for detecting the presence of human OX40 antigen in a sample, or measuring the amount of human OX40 antigen, comprising contacting the sample, and a control sample, with anti-OX40 antibodies (or antigen binding portions thereof) described herein, under conditions that allow for formation of a complex between the antibody and human OX40. The formation of a complex is then detected, wherein a difference complex formation between the sample compared to the control sample is indicative the presence of human OX40 antigen in the sample. The anti-OX40 antibodies described herein also can be used to purify human OX40 via immunoaffinity purification.

Given the ability of anti-OX40 antibodies described herein to stimulate or co-stimulate T cell responses, e.g., antigen-specific T cell responses, also provided herein are in vitro and in vivo methods of using the antibodies to stimulate, enhance or upregulate antigen-specific T cell responses, e.g., anti-tumor T cell responses. In certain embodiments, CD3 stimulation is also included (e.g., by coincubation with a cell expressing membrane CD3), which stimulation can be provided at the same time, before, or after stimulation with an anti-OX40 antibody. In one embodiment, the method comprises contacting T cells with an anti-OX40 antibody described herein, and optionally with an anti-CD3 antibody, such that an antigen-specific T cell response is stimulated. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 and/or interferon-γ production by the antigen-specific T cell is stimulated.

T cells that can be enhanced or co-stimulated with anti-OX40 antibodies include CD4+ T cells and CD8+ T cells. The T cells can be $T_{eff}$ cells, e.g., CD4+ $T_{eff}$ cells, CD8+ $T_{eff}$ cells, Thelper $(T_h)$ cells and T cytotoxic $(T_a)$ cells.

Also provided are methods of stimulating an immune response (e.g., an antigen-specific T cell response) in a subject comprising administering a therapeutically effective amount of an anti-OX40 antibody described herein to the subject such that an immune response (e.g., an antigen-specific T cell response) in the subject is stimulated. In a preferred embodiment, the subject is a tumor-bearing subject and an immune response against the tumor is stimulated. A tumor may be a solid tumor or a liquid tumor, e.g., a hematological malignancy. In certain embodiments, a tumor is an immunogenic tumor. In certain embodiments, a tumor is non-immunogenic. In certain embodiments, a tumor is PD-L1 positive. In certain embodiments a tumor is PD-L1 negative. A subject may also be a virus-bearing subject and an immune response against the virus is stimulated.

Further provided are methods for inhibiting growth of tumor cells in a subject comprising administering to the subject a therapeutically effective amount of an anti-OX40 antibody described herein such that growth of the tumor is inhibited in the subject. Also provided are methods of treating viral infection in a subject comprising administering to the subject an anti-OX40 antibody described herein such that the viral infection is treated in the subject.

Also encompassed herein are methods for depleting Treg cells from the tumor microenvironment of a subject having a tumor, e.g., cancerous tumor, comprising administering to the subject a therapeutically effective amount of an anti-OX40 antibody described herein that comprises an Fc that stimulates depletion of $T_{reg}$ cells in the tumor microenvironment. An Fc may, e.g., be an Fc with effector function or enhanced effector function, such as binding or having enhanced binding to one or more activating Fc receptors. In a preferred embodiment, $T_{reg}$ depletion occurs without significant depletion or inhibition of $T_{eff}$ in the tumor microenvironment, and without significant depletion or inhibition of $T_{eff}$ cells and $T_{reg}$ cells outside of the tumor microenvironment, e.g., in the periphery. In certain embodiments, the subject has higher levels of OX40 on $T_{reg}$ cells than on $T_{eff}$ cells, e.g., in the tumor microenvironment.

In certain embodiments, the subject is treated with an anti-OX40 antibody having an Fc that enhances agonism, e.g., binds to or has enhanced binding to the inhibitory FcRIIb. Anti-OX40 antibodies may deplete Tregs in tumors and/or Tregs in tumor infiltrating lymphocytes (TILs).

In certain embodiments, the anti-OX40 antibody is given to a subject as an adjunctive therapy. Treatments of subjects having cancer with the anti-OX40 antibody may lead to prolonged survival, e.g., long-term durable response relative to the current standard of care; long term survival of at least 3 months, 6 months, 9 months, 1, 2, 3, 4, 5, 10 or more years, or recurrence-free survival of at least 3 months, 6 months, 9 months, 1, 2, 3, 4, 5, or 10 or more years. In certain embodiments, treatment of a subject having cancer with the anti-OX40 antibody prevents recurrence of cancer or delays recurrence of cancer by, e.g., 3 months, 6 months, 9 months, 1, 2, 3, 4, 5, or 10 or more years. The anti-OX40 antibody treatment can be used as a first-, second-, or third-line treatment.

In preferred embodiments, the anti-OX40 antibody is not significantly toxic. For example, the antibody is not significantly toxic to an organ of a human, e.g., one or more of the liver, kidney, brain, lungs, and heart, as determined, e.g., in clinical trials. In certain embodiments, the antibody does not significantly trigger an undesirable immune response, e.g., autoimmunity or inflammation.

In certain embodiments, treatment of a subject with the anti-OX40 antibody does not result in overstimulation of the immune system to the extent that the subject's immune system then attacks the subject itself (e.g., autoimmune response) or results in, e.g., anaphylaxis. Thus, the antibodies preferably do not cause anaphylaxis.

In certain embodiments, treatment of a subject with the anti-OX40 antibody does not cause significant inflammatory reactions, e.g., immune-mediated pneumonitis, immune-mediated colitis, immune mediated hepatitis, immune-mediated nephritis or renal dysfunction, immune-mediated hypophysitis, immune-mediated hypothyroidism and hyperthyroidism, or other immune-mediated adverse reactions.

In certain embodiments, the anti-OX40 antibody provides synergistic anti-tumor effects in combination with another cancer therapy, such as a compound that stimulates the immune system (e.g., an immune-oncology agent), e.g., a compound described herein or a compound modulating a target described herein.

These and other methods described herein are discussed in further detail below.

Cancer

Activation of OX40 by anti-OX40 antibodies can enhance the immune response to cancerous cells in the patient. Accordingly, provided herein are methods for treating a subject having cancer, comprising administering to the subject the anti-OX40 antibodies described herein, such that the subject is treated, e.g., such that growth of cancerous tumors is inhibited or reduced and/or that the tumors regress and/or that prolonged survival is achieved. The anti-OX40 antibody can be used alone to inhibit the growth of cancerous tumors. Alternatively, the anti-OX40 antibody can be used in conjunction with another agent, e.g., another immunogenic agent, a standard cancer treatment, or another antibody, as described below.

Accordingly, provided herein are methods of treating cancer, e.g., by inhibiting growth of tumor cells, in a subject, comprising administering to the subject a therapeutically effective amount of anti-OX40 antibodies described herein. The antibody may be a human antibody. Additionally or alternatively, the antibody can be a chimeric or humanized antibody.

Also provided herein are combination therapies comprising administration of an anti-OX40 antibody and an anti-PD-1 or anti-CTLA-4 antibody to treat subjects having tumors (e.g., advanced solid tumors).

In certain embodiments, provided herein are methods of treating cancer wherein an anti-OX40 antibody and an anti-PD-1 antibody or anti-CTLA-4 antibody are administered to a patient with a tumor (e.g., advanced solid tumor) according to a defined clinical dosage regimen. In certain embodiments, the anti-OX40 antibody is OX40.21. In certain embodiments, the anti-PD-1 antibody is BMS-936558 (nivolumab). In certain embodiments, the anti-CTLA-4 antibody is ipilimumab (Yervoy®). In certain embodiments, dosage regimens are adjusted to provide the optimum desired response (e.g., an effective response).

As used herein, adjunctive or combined administration (coadministration) includes simultaneous administration of the compounds in the same or different dosage form, or separate administration of the compounds (e.g., sequential administration). Thus, the anti-OX40 and anti-PD-1 antibody or anti-CTLA-4 antibody can be simultaneously administered in a single formulation. Alternatively, the anti-OX40 and anti-PD-1 antibody or anti-CTLA-4 antibody can be formulated for separate administration and are administered concurrently or sequentially (e.g., one antibody is administered within about 30 minutes prior to administration of the second antibody).

For example, the anti-PD1 antibody or anti-CTLA-4 antibody can be administered first and followed by (e.g., immediately followed by) the administration of the anti-OX40 antibody, or vice versa. In certain embodiments, the anti-PD-1 antibody or anti-CTLA-4 antibody is administered prior to administration of the anti-OX40 antibody. In another embodiment, the anti-PD-1 antibody or anti-CTLA-4 antibody is administered after administration of the anti-OX40 antibody. In another embodiment, the anti-OX40 antibody and anti-PD-1 antibody or anti-CTLA-4 antibody are administered concurrently. Such concurrent or sequential administration preferably results in both antibodies being simultaneously present in treated patients.

Cancers whose growth may be inhibited with anti-OX40 antibodies, or combination therapy with an anti-OX40 and an anti-PD-1 or anti-CTLA-4 antibody, include cancers typically responsive to immunotherapy and those that are not typically responsive to immunotherapy. Cancers may be cancers with solid tumors or blood malignancies (liquid tumors). Non-limiting examples of cancers for treatment include squamous cell carcinoma, small-cell lung cancer, non-small cell lung cancer, squamous non-small cell lung cancer (NSCLC), non squamous NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angioimmunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmacytoma, and multiple myelomas, chronic lymphocytic leukemia (CLL), hairy cell lymphoma;

hematopoietic tumors of myeloid lineage, tumors of mesenchymal origin, including fibrosarcoma and rhabdomyosarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, unresectable and/or refractory cancers (e.g., cancers refractory to previous immunotherapy, e.g., with a blocking CTLA-4 or PD-1 antibody), and recurrent cancers.

In certain embodiments, the patient being treated with the anti-OX40 antibody, or combination of anti-OX40 antibody and anti-PD-1 or anti-CTLA-4 antibody, has an advanced solid tumor. For example, in one embodiment, the patient to be treated has cervical cancer. In another embodiment, the patient to be treated has colorectal (CRC) cancer. In another embodiment, the patient to be treated has bladder cancer (e.g., unresectable locally advanced or metastatic bladder cancer). In another embodiment, the patient to be treated has ovarian cancer (e.g., unresectable locally advanced or metastatic ovarian cancer).

In one embodiment, the patient being treated with the anti-OX40 antibody, or combination of anti-OX40 antibody and anti-PD-1 or anti-CTLA-4 antibody, has non-small cell lung cancer (NSCLC). In another embodiment, the patient to be treated has squamous cell carcinoma of the head and neck (SCCHN). In another embodiment, the patient to be treated has B-cell non-Hodgkin's lymphoma (B-NHL). In another embodiment, the patient to be treated has myeloma. In another embodiment, the patient has melanoma. In another embodiment, the patient to be treated has diffuse large B-cell lymphoma (DLBCL).

In certain embodiments, the anti-OX40 antibody is administered to patients having a cancer that exhibited an inadequate response to a prior treatment, e.g., a prior treatment with an immuno-oncology drug, or patients having a cancer that is refractory or resistant, either intrinsically refractory or resistant (e.g., refractory to a PD-1 pathway antagonist), or a wherein the resistance or refractory state is acquired. For example, subjects who are not responsive or not sufficiently responsive to a first therapy or who see disease progression following treatment, e.g., anti-PD-1 treatment, may be treated by administration of the anti-OX40 antibody alone or in combination with another therapy (e.g., with an anti-PD-1 therapy).

In certain embodiments, the anti-OX40 antibody is administered to patients who have not previously received (i.e., been treated with) an immuno-oncology agent, e.g., a PD-1 pathway antagonist.

In certain embodiments, the anti-OX40 antibody may be administered with a standard of care treatment (e.g., surgery, radiation, and chemotherapy). In other embodiments, the anti-OX40 antibody may be administered as a maintenance therapy, e.g., a therapy that is intended to prevent the occurrence or recurrence of tumors.

In certain embodiments, the anti-OX40 antibody may be administered with another treatment, e.g., radiation, surgery, or chemotherapy. For example, anti-OX40 antibody adjunctive therapy may be administered when there is a risk that micrometastases may be present and/or in order to reduce the risk of a relapse.

In certain embodiments, the anti-OX40 antibody can be administered as a monotherapy, or as the only immunostimulating therapy. In other embodiments, the anti-OX40 antibody can also be combined with an immunogenic agent, such as cancerous cells, purified tumor antigens (including recombinant proteins, peptides, and carbohydrate molecules), cells, and cells transfected with genes encoding immune stimulating cytokines (He et al (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. By lowering the threshold of T cell activation via OX40 activation, the tumor responses in the host can be activated, allowing treatment of non-immunogenic tumors or those having limited immunogenicity.

In some embodiments, the anti-OX40 antibody can be used in conjunction with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one such strategy, of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. OX40 activation can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with OX40 activation is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with OX40 activation to activate more potent anti-tumor responses.

Anti-OX40 antibodies described herein can also be combined with chemotherapeutic regimes. In these instances, it may be possible to reduce the dose of chemotherapeutic reagent administered (Mokyr et al. (1998) *Cancer Research* 58: 5301-5304). For example, the anti-OX40 antibody can be used in combination with decarbazine to treat melanoma. In another example, the anti-OX40 antibody can be used in combination with interleukin-2 (IL-2) to treat melanoma. The scientific rationale behind the combined use of anti-OX40 antibodies and chemotherapy is that cell death, a consequence of the cytotoxic action of most chemotherapeutic compounds, should result in increased levels of tumor antigen in the antigen presentation pathway. Other combination therapies that may result in synergy with anti-OX40 antibodies through cell death are radiation, surgery, and hormone deprivation. Each of these protocols creates a source of tumor antigen in the host. Angiogenesis inhibitors can also be used in combination with the anti-OX40 antibody. Inhibition of angiogenesis leads to tumor cell death which may feed tumor antigen into host antigen presentation pathways.

Anti-OX40 antibodies described herein can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the activation of OX40. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-OX40 antibodies to counteract the effects of the immunosuppressive agent and favor tumor immune responses by the host.

Other antibodies which activate host immune responsiveness can be used in combination with the anti-OX40 antibodies described herein. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with anti-OX40 antibodies. Activating antibodies to T cell costimulatory molecules such as CTLA-4 (e.g., U.S. Pat. No. 5,811,097), OX-40 (Weinberg et al. (2000) *Immunol* 164: 2160-2169), 4-1BB (Melero et al. (1997) *Nature Medicine* 3: 682-685 (1997), and ICOS (Hutloff et al. (1999) *Nature* 397: 262-266) may also provide for increased levels of T cell activation. Inhibitors of PD1 or PD-L1 may also be used in conjunction with anti-OX40 antibodies.

Bone marrow transplantation is currently being used to treat a variety of tumors of hematopoietic origin. While graft versus host disease is a consequence of this treatment, therapeutic benefit may be obtained from graft vs. tumor responses. Anti-OX40 antibodies can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-OX40 antibodies can increase the frequency and activity of the adoptively transferred T cells.

Infectious Diseases

Also provided herein are methods to treat patients who have been exposed to particular toxins or pathogens. Accordingly, provided herein are methods of treating an infectious disease in a subject comprising administering to the subject anti-OX40 antibodies described herein, such that the subject is treated for the infectious disease. In certain embodiments, the anti-OX40 antibody is a chimeric or humanized antibody.

Similar to its application to tumors as discussed above, anti-OX40 antibodies can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa*. Anti-OX40 antibodies may be useful against established infections by agents such as HIV that present altered antigens over the course of the infections. These novel epitopes are recognized as foreign at the time of anti-OX40 antibody administration, thus provoking a strong T cell response. Some examples of pathogenic viruses causing infections treatable by the methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by the methods described herein include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by the methods described herein include *Candida* (*albicans, krusei, glabrata, tropicalis*, etc.), *Cryptococcus neoformans, Aspergillus* (*fumigatus, niger,* etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum.*

Some examples of pathogenic parasites causing infections treatable by the methods described herein include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis.*

In all of the above methods, anti-OX40 antibodies can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Autoimmune Reactions

Anti-OX40 antibodies may provoke and amplify autoimmune responses. Indeed, induction of anti-tumor responses using tumor cell and peptide vaccines reveals that many anti-tumor responses involve anti-self reactivities (van Elsas et al. (2001) *J. Exp. Med.* 194:481-489; Overwijk, et al. (1999) *Proc. Natl. Acad. Sci. U.S.A.* 96: 2982-2987; Hurwitz, (2000) supra; Rosenberg & White (1996) *J. Immunother Emphasis Tumor Immunol* 19 (1): 81-4). Therefore, anti-OX40 antibodies can be used in conjunction with various self proteins in order to devise vaccination protocols to efficiently generate immune responses against these self proteins for disease treatment. For example, Alzheimer's disease involves inappropriate accumulation of Aβ peptide in amyloid deposits in the brain; antibody responses against amyloid are able to clear these amyloid deposits (Schenk et al., (1999) *Nature* 400: 173-177).

Other self proteins can also be used as targets such as IgE for the treatment of allergy and asthma, and TNFc for rheumatoid arthritis. Finally, antibody responses to various hormones may be induced by the use of anti-OX40 antibodies. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-OX40 antibodies can be used for induction of therapeutic autoimmune responses to treat patients having an inappropriate accumulation of other self-antigens, such as amyloid deposits, including Aβ in Alzheimer's disease, cytokines such as TNFα, and IgE.

Vaccines

The anti-OX40 antibodies described herein can be used to stimulate antigen-specific immune responses by coadministration of the antibodies with an antigen of interest (e.g., a vaccine). Accordingly, provided herein are methods of enhancing an immune response to an antigen in a subject, comprising administering to the subject: (i) the antigen; and (ii) an anti-OX40 antibody such that an immune response to the antigen in the subject is enhanced. The antibody may be a human anti-OX40 antibody (such as any of the human anti-OX40 antibodies described herein). In other embodiments, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

In certain embodiments, a peptide or fusion protein comprising the epitope to which the anti-OX40 antibody binds is used as a vaccine instead of, or in addition to, the anti-OX40 antibody.

Suitable routes of administering the antibody compositions (e.g., human monoclonal antibodies, multispecific and bispecific molecules and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, anti-OX40 antibodies described herein can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of anti-OX40 antibodies, or antigen binding fragments thereof, described herein with chemotherapeutic agents provides two anti-cancer agents which operate via different mechanisms which yield a cytotoxic effect to human tumor cells. Such co-administration can address problems related to the development of resistance to drugs or a change in the antigenicity of the tumor cells which would render them unreactive with the antibody.

Also provided herein are kits comprising the anti-OX40 antibody compositions described herein (e.g., human antibodies, bispecific or multispecific molecules, or immunoconjugates) and instructions for use. The kit can further contain at least one additional reagent, or one or more additional human antibodies described herein (e.g., a human antibody having a complementary activity which binds to an epitope in OX40 distinct from the first human antibody). Kits typically include a label indicating the intended use of the contents of the kit. The term label includes any writing, or recorded material supplied on or with the kit, or which otherwise accompanies the kit.

Treatment Protocols

Suitable protocols for treating a solid tumor (e.g., an advanced solid tumor) in a human patient include, for example, administering to the patient an effective amount of an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94, wherein the method comprises at least one administration cycle, wherein the cycle is a period of two weeks (Q2W), wherein for each of the at least one cycles, at least one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg.

Another suitable protocol for treating a solid tumor in a human patient includes, for example, administering to the patient an effective amount of each of:

(a) an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94, and (b) an anti-PD-1 antibody comprising CDR1, CDR2 and CDR3 domains of the heavy chain variable region having the sequence set forth in SEQ ID NO: 301, and CDR1, CDR2 and CDR3 domains of the light chain variable region having the sequence set forth in SEQ ID NO: 302, wherein the method comprises at least one administration cycle, wherein the cycle is a period of two weeks, wherein for each of the at least one cycles, at least one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg, and at least one dose of the anti-PD-1 antibody is administered at flat dose of 240 mg or a flat dose of about 240 mg. In some embodiments, the anti-PD-1 antibody is administered once every three weeks (q3w) at a fixed dose of 360 mg, or once every four weeks (q4w) at a dose of 480 mg.

Another suitable protocol for treating a solid tumor in a human patient includes, for example, administering to the patient an effective amount of each of:

(a) an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94, and (b) an anti-CTLA-4 antibody comprising CDR1, CDR2 and CDR3 domains of the heavy chain variable region having the sequence set forth in SEQ ID NO: 309, and CDR1, CDR2 and CDR3 domains of the light chain variable region having the sequence set forth in SEQ ID NO: 310, wherein the method comprises at least one administration cycle, wherein the cycle is a period of three weeks (q3w), wherein for each of the at least one cycles, at least one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg, and at least one dose of the anti-CTLA-4 antibody is administered at flat dose of 1 mg/kg body weight or a flat dose of about 1 mg/kg body weight. In one embodiment, the anti-OX40 antibody is administered together with the anti-CTLA-4 antibody for at least one cycle, followed by anti-OX40 antibody monotherapy for at least one cycle. In certain embodiments, the anti-OX40 antibody is administered together with ipilimumab for the initial four cycles, followed by anti-OX40 antibody monotherapy for subsequent cycles.

In some embodiments, the anti-OX40 antibody and anti-PD-1 antibody are administered at the following doses:

(a) 1 mg/kg anti-OX40 antibody and 240 mg, 360 mg, or 480 mg of anti-PD-1 antibody;

(b) 20 mg anti-OX40 antibody and 240 mg, 360 mg, or 480 mg of anti-PD-1 antibody;

(c) 40 mg anti-OX40 antibody and 240 mg, 360 mg, or 480 mg of anti-PD-1 antibody;

(d) 80 mg anti-OX40 antibody and 240 mg, 360 mg, or 480 mg of anti-PD-1 antibody;

(e) 160 mg anti-OX40 antibody and 240 mg, 360 mg, or 480 mg of anti-PD-1 antibody; or (f) 320 mg anti-OX40 antibody and 240 mg, 360 mg, or 480 mg of anti-PD-1 antibody.

In some embodiments, the anti-OX40 antibody and anti-CTLA-4 antibody are administered at the following doses:

(a) 1 mg/kg anti-OX40 antibody and 1 mg/kg anti-CTLA-4 antibody;

(b) 20 mg anti-OX40 antibody and 1 mg/kg anti-CTLA-4 antibody;

(c) 40 mg anti-OX40 antibody and 1 mg/kg anti-CTLA-4 antibody;

(d) 80 mg anti-OX40 antibody and 1 mg/kg anti-CTLA-4 antibody;

(e) 160 mg anti-OX40 antibody and 1 mg/kg anti-CTLA-4 antibody; or (f) 320 mg anti-OX40 antibody and 1 mg/kg anti-CTLA-4 antibody.

In one embodiment, the dose of the anti-OX40 and/or anti-PD-1 or anti-CTLA-4 antibody is calculated per body weight, e.g., mg/kg body weight. In another embodiment, the dose of the anti-OX40 and/or anti-PD-1 or anti-CTLA-4 antibody is a flat-fixed dose. In another embodiment, the dose of the anti-OX40 and/or anti-PD-1 or anti-CTLA-4 antibody is varied over time. For example, the anti-OX40 and/or anti-PD-1 or anti-CTLA-4 antibody may be initially administered at a high dose and may be lowered over time. In another embodiment, the anti-OX40 and/or anti-PD-1 or anti-CTLA-4 antibody is initially administered at a low dose and increased over time.

In another embodiment, the amount of the anti-OX40 and/or anti-PD-1 or anti-CTLA-4 antibody administered is constant for each dose. In another embodiment, the amount of antibody administered varies with each dose. For example, the maintenance (or follow-on) dose of the antibody can be higher or the same as the loading dose which is first administered. In another embodiment, the maintenance dose of the antibody can be lower or the same as the loading dose.

In some embodiments, the anti-OX40 and/or anti-PD-1 or anti-CTLA-4 antibody are formulated for intravenous administration. In some embodiments, the anti-OX40 antibody, or anti-OX40 antibody and anti-PD-1 or CTLA-4 antibody, are administered on Day 1 of each cycle.

In some embodiments, the anti-OX40 and/or anti-PD-1 or anti-CTLA-4 antibody are administered once per week, once every two weeks, once every three weeks, or once every four weeks, or as long as a clinical benefit is observed or until there is a complete response, confirmed progressive disease or unmanageable toxicity.

In one embodiment, a cycle of administration is two weeks, which can be repeated, as necessary. In another embodiment, the cycle is three weeks. In some embodiments, the treatment consists of up to eight cycles. In other embodiments, the treatment consists of up to 12 cycles.

In one embodiment, one dose each of an anti-OX40 antibody and an anti-PD-1 antibody is administered per two week cycle. In another embodiment, one dose each of the anti-PD-1 antibody and anti-OX40 antibody is administered per three week cycle. In another embodiment, one dose each of the anti-PD-1 antibody and anti-OX40 antibody is administered per four week cycle.

In one embodiment, one dose each of the anti-OX40 antibody and anti-CTLA-4 antibody is administered per three week cycle. In some embodiments, one dose each of the anti-OX40 antibody and anti-CTLA-4 antibody is administered per three week cycle for the first four cycles, followed by anti-OX40 antibody monotherapy for the fifth through eighth cycles.

In another embodiment, the anti-OX40 antibody and anti-PD-1 or anti-CTLA-4 antibody are administered as a first line of treatment (e.g., the initial or first treatment). In another embodiment, the anti-OX40 antibody and anti-PD-1 or anti-CTLA-4 antibody are administered as a second line of treatment (e.g., after the initial or first treatment, including after relapse and/or where the first treatment has failed).

In another aspect, the invention features any of the aforementioned embodiments, wherein the anti-PD-1 antibody is replaced by, or combined with, an anti-PD-L1 or anti-PD-L2 antibody.

In some embodiments, the human patient has a cancer selected from the group consisting of cervical cancer, bladder cancer, colorectal cancer, and ovarian cancer.

In certain embodiments, the anti-OX40 antibody comprises a heavy chain variable region CDR1 comprising the sequence set forth in SEQ ID NO: 87, a heavy chain variable region CDR2 comprising the sequence set forth in SEQ ID NO: 317, a heavy chain variable region CDR3 comprising the sequence set forth in SEQ ID NO: 89, a light chain variable region CDR1 comprising the sequence set forth in SEQ ID NO: 90, a light chain variable region CDR2 comprising the sequence set forth in SEQ ID NO: 91, and a light chain variable region CDR3 comprising the sequence set forth in SEQ ID NO: 92. In certain embodiments, the anti-OX40 antibody comprises heavy and light chain variable regions comprising the sequences set forth in SEQ ID NOs: 318 and 94, respectively. In certain embodiments, the anti-OX40 antibody comprises heavy and light chain sequences comprising the sequences set forth in SEQ ID NOs: 124 and 116, respectively.

In certain embodiments, the anti-PD-1 antibody comprises a heavy chain variable region CDR1, CDR2, and CDR3 comprising the sequences set forth in SEQ ID NOs: 303-305, respectively, and light chain variable region CDR1, CDR2, and CDR3 comprising the sequences set forth in SEQ ID NOs: 306-308, respectively. In certain embodiments, the anti-PD-1 antibody comprises heavy and light chain variable regions sequences set forth in SEQ ID NOs: 301 and 302, respectively. In certain embodiments, the anti-PD-1 antibody comprises heavy and light chain sequences set forth in SEQ ID NOs: 299 and 300, respectively.

In certain embodiments, the anti-CTLA-4 antibody comprises a heavy chain variable region CDR1, CDR2, and CDR3 comprising the sequences set forth in SEQ ID NOs: 311-313, respectively, and light chain variable region CDR1, CDR2, and CDR3 comprising the sequences set forth in SEQ ID NOs: 314-316, respectively. In certain embodiments, the anti-CTLA-4 antibody comprises heavy and light chain variable regions sequences set forth in SEQ ID NOs: 309 and 310, respectively.

Outcomes

With respect to target lesions, responses to therapy may include:

| | |
|---|---|
| Complete Response (CR) (RECIST V1.1) | Disappearance of all target lesions. Any pathological lymph nodes (whether target or non-target) must have reduction in short axis to <10 mm. |
| Partial Response (PR) (RECIST V1.1) | At least a 30% decrease in the sum of the diameters of target lesions, taking as reference the baseline sum diameters. |
| Progressive Disease (PD) (RECIST V1.1) | At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) (RECIST V1.1) | Neither sufficient shrinkage to qualify for PR nor sufficient increase to qualify for PD, taking as reference the smallest sum diameters while on study. |
| Immune-related Complete Response (irCR) (irRECIST) | Disappearance of all target lesions. Any pathological lymph nodes (whether target or non-target) must have reduction in short axis to <10 mm. |
| Immune-related Partial Response (irPR) (irRECIST) | At least a 30% decrease in the sum of diameters of target lesions and all new measurable lesions (ie Percentage Change in Tumor Burden), taking as reference the baseline sum diameters. Note: the appearance of new measurable lesions is factored into the overall Tumor Burden, but does not automatically qualify as progressive disease until the sum of the diameters increases by ≥20% when compared to nadir. |
| Immune-related Progressive Disease (irPD) (irRECIST) | At least a 20% increase in Tumor Burden (ie the sum of diameters of target lesions, and any new measurable lesions) taking as reference the smallest sum on study (this includes the baseline sum if that is the smallest on study). In addition to the relative increase of 20%, the sum must also demonstrate an absolute increase of at least 5 mm. Tumor assessments using immune-related criteria for progressive disease incorporates the contribution of new measurable lesions. Each net percentage change in tumor burden per assessment accounts for the size and growth kinetics of both old and new lesions as they appear. |
| Immune-related Stable Disease (irSD) (irRECIST) | Neither sufficient shrinkage to qualify for irPR nor sufficient increase to qualify for irPD, taking as reference the smallest sum diameters while on study. |

With respect to non-target lesions, responses to therapy may include:

| | |
|---|---|
| Complete Response (CR) (RECIST V1.1) | Disappearance of all non-target lesions. All lymph nodes must be non-pathological in size (<10 mm short axis). |
| Non-CR/Non-PD (RECIST V1.1) | Persistence of one or more non-target lesion(s). |
| Progressive Disease (PD) (RECIST V1.1) | Unequivocal progression of existing non-target lesions. The appearance of one or more new lesions is also considered progression. |

| | |
|---|---|
| Immune-related Complete Response (irCR) (irRECIST) | Disappearance of all non-target lesions. All lymph nodes must be non-pathological in size (<10 mm short axis). |
| Immune-related Progressive Disease (irPD) (irRECIST) | Increases in number or size of non-target lesion(s) does not constitute progressive disease unless/until Tumor Burden increases by 20% (ie the sum of the diameters at nadir of target lesions and any new measurable lesions increases by the required amount). Non-target lesions are not considered in the definition of Stable Disease and Partial Response. |

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, administration of effective amounts of the anti-OX40 antibody and anti-PD-1 or anti-CTLA-4 antibody according to any of the methods provided herein produces at least one therapeutic effect selected from the group consisting of reduction in size of a tumor, reduction in number of metastatic lesions appearing over time, complete remission, partial remission, or stable disease. In still other embodiments, the methods of treatment produce a comparable clinical benefit rate (CBR=CR+ PR+ SD≥6 months) better than that achieved by an anti-OX40 antibody or anti-PD-1 or anti-CTLA-4 antibody alone. In other embodiments, the improvement of clinical benefit rate is about 20% 20%, 30%, 40%, 50%, 60%, 70%, 80% or more compared to an anti-OX40 antibody or anti-PD-1 or anti-CTLA-4 antibody alone.

Combination Therapies

In addition to the combinations therapies provided above, anti-OX40 antibodies described herein can be used in combination therapy, as described below.

Methods of combination therapy include those in which an anti-OX40 antibody, or a combination of anti-OX40 antibody and anti-PD-1 or anti-CTLA-4 antibody, is coadministered with one or more additional agents, e.g., small molecule drugs, antibodies or antigen binding portions thereof, and which are effective in stimulating immune responses to thereby further enhance, stimulate or upregulate immune responses in a subject. For instance, as shown in the Examples, the administration of an anti-OX40 antibody and an antagonist anti-PD-1 antibody to mice can result in a synergic effect in inhibiting tumor growth.

The anti-OX40 antibody can be combined with (i) an agonist of a stimulatory (e.g., co-stimulatory) molecule (e.g., receptor or ligand) and/or (ii) an antagonist of an inhibitory signal or molecule (e.g., receptor or ligand) on immune cells, such as T cells, both of which result in amplifying immune responses, such as antigen-specific T cell responses. In certain aspects, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells involved in innate immunity, e.g., NK cells, and wherein the immuno-oncology agent enhances innate immunity. Such immuno-oncology agents are often referred to as immune checkpoint regulators, e.g., immune checkpoint inhibitor or immune checkpoint stimulator.

In certain embodiments, the anti-OX40 antibody is administered with an agent that targets a stimulatory or inhibitory molecule that is a member of the immunoglobulin super family (IgSF). For example, the anti-OX40 antibody may be administered to a subject with an agent that targets a member of the IgSF family to increase an immune response. In other embodiments, the anti-OX40 antibody may be administered with an agent that targets (or binds specifically to) a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6 or a co-stimulatory or co-inhibitory receptor binding specifically to a B7 family member.

The anti-OX40 antibody may also be administered with an agent that targets a member of the TNF and TNFR family of molecules (ligands or receptors), such as CD40 and CD40L, GITR, GITR-L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDA1, EDA2, TNFR1, Lymphotoxin a/TNFβ, TNFR2, TNFα, LTβR, Lymphotoxin a 1(32, FAS, FASL, RELT, DR6, TROY, and NGFR (see, e.g., Tansey (2009) Drug Discovery Today 00:1).

T cell responses can be stimulated by a combination of anti-OX40 antibodies and one or more of the following agents:

(1) An antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, GPR56, VISTA, B7-H3, B7-H4, 2B4, CD48, GARP, PD1H, LAIR1, TIM-1, and TIM-4; and/or (2) An agonist of a protein that stimulates T cell activation, such as B7-1, B7-2, CD28, 4-1BB (CD137), 4-1BBL, ICOS, ICOS-L, GITR, GITR-L, CD70, CD27, CD40, DR3 and CD28H.

Exemplary agents that modulate one of the above proteins and may be combined with the anti-OX40 antibody for treating cancer, include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), Atacicept (to TACI), CP-870893 (to CD40), Lucatumumab (to CD40), Dacetuzumab (to CD40), Muromonab-CD3 (to CD3), Ipilumumab (to CTLA-4).

Anti-OX40 antibodies may also be administered with pidilizumab (CT-011).

Other molecules that can be combined with the anti-OX40 antibody for the treatment of cancer include antagonists of inhibitory receptors on NK cells or agonists of activating receptors on NK cells. For example, the anti-OX40 antibody can be combined with antagonists of KIR (e.g., lirilumab).

T cell activation is also regulated by soluble cytokines, and anti-OX40 antibodies may be administered to a subject, e.g., having cancer, with antagonists of cytokines that inhibit T cell activation or agonists of cytokines that stimulate T cell activation.

In certain embodiments, anti-OX40 antibodies can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

The anti-OX40 antibodies may also be administered with agents that inhibit TGF-β signaling.

Additional agents that may be combined with the anti-OX40 antibodies described herein include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies that may be combined with the anti-OX40 antibodies include therapies that deplete or block Treg cells, e.g., an agent that specifically binds to CD25.

Another therapy that may be combined with the anti-OX40 antibodies is a therapy that inhibits a metabolic enzyme such as indoleamine dioxygenase (IDO), dioxigenase, arginase, or nitric oxide synthetase.

Another class of agents that may be used with the anti-OX40 antibodies includes agents that inhibit the formation of adenosine or inhibit the adenosine A2A receptor.

Other therapies that may be combined with anti-OX40 antibodies for treating cancer include therapies that reverse/prevent T cell anergy or exhaustion and therapies that trigger an innate immune activation and/or inflammation at a tumor site.

The anti-OX40 antibody may be combined with more than one immuno-oncology agent, and may be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137 and/or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

Anti-OX40 antibodies can be used together with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In certain embodiments, the anti-OX40 antibody is administered to a subject together with a BRAF inhibitor if the subject is BRAF V600 mutation positive.

In certain embodiments, the anti-OX40 antibody is administered together with another immunostimulatory antibody.

Provided herein are methods for stimulating an immune response in a subject comprising administering to the subject the anti-OX40 antibody, and one or more additional immunostimulatory antibodies, such as an anti-PD-1 antagonist, e.g., antagonist antibody, an anti-PD-L1 antagonist, e.g., antagonist antibody, an antagonist anti-CTLA-4 antagonist, e.g., antagonist antibody and/or an anti-LAG3 antagonist, e.g., an antagonist antibody, such that an immune response is stimulated in the subject, for example to inhibit tumor growth or to stimulate an anti-viral response. In one embodiment, the subject is administered the anti-OX40 antibody and an antagonist anti-PD-1 antibody. In one embodiment, the subject is administered the anti-OX40 antibody and an antagonist anti-PD-L1 antibody. In one embodiment, the subject is administered the anti-OX40 antibody and an antagonist anti-CTLA-4 antibody. In one embodiment, the anti-OX40 antibody is a human antibody. Alternatively, the anti-OX40 antibody can be, for example, a chimeric or humanized antibody. In one embodiment, the at least one additional immunostimulatory antibody (e.g., an antagonist anti-PD-1, an antagonist anti-PD-L1, an antagonist anti-CTLA-4 and/or an antagonist anti-LAG3 antibody) is a human antibody. Alternatively, the at least one additional immunostimulatory antibody can be, for example, a chimeric or humanized antibody (e.g., prepared from a mouse anti-PD-1, anti-PD-L1, anti-CTLA-4 and/or anti-LAG3 antibody).

Provided herein are methods for treating a hyperproliferative disease (e.g., cancer), comprising administering the anti-OX40 antibody with an antagonist PD-1 antibody, an antagonist PD-L1 antibody, an anti-CTLA-4 antibody, or an anti-LAG3 antibody to a subject. In certain embodiments, one or both antibodies are administered at a subtherapeutic dose. Also provided herein are methods for altering an adverse event associated with treatment of a hyperproliferative disease with an immunostimulatory agent, comprising administering the anti-OX40 antibody and a subtherapeutic dose of an anti-PD-1, anti-PD-L1, anti-CTLA-4, or anti-LAG3 antibody to a subject (e.g., a human). In certain embodiments, the anti-OX40 antibody comprises the CDRs or variable regions of 3F4, 14B6-1, 14B6-2, 23H3, 6E1-1, 6E1-2, 18E9, 8B11, 20B3, 14A2-1, 14A2-2, and 20C1, or is another agonist anti-OX40 antibody described herein.

Suitable PD-1 antagonists for use in the methods described herein, include, without limitation, ligands, antibodies (e.g., monoclonal antibodies and bispecific antibodies), and multivalent agents. In one embodiment, the PD-1 antagonist is a fusion protein, e.g., an Fc fusion protein, such as AMP-244. In one embodiment, the PD-1 antagonist is an anti-PD-1 or anti-PD-L1 antibody.

An exemplary anti-PD-1 antibody is nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD1 antibody is MK-3475 (Lambrolizumab) described in WO2012/145493; and AMP-514 described in WO 2012/145493. Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 may also be used. An anti-PD-1 antibody that competes for binding with, and/or binds to the same epitope on PD-1 as, as one of these antibodies may also be used in combination treatments. Another approach to target the PD-1 receptor is the recombinant protein composed of the extracellular domain of PD-L2 (B7-DC) fused to the Fc portion of IgG1, called AMP-224. In certain embodiments, the antibody has at least about 90% variable region amino acid sequence identity with the above-mentioned antibodies.

In certain embodiments, the anti-OX40 antibody is used in combination with nivolumab, which comprises heavy and light chains comprising the sequences shown in SEQ ID NOs: 299 and 300, respectively, or antigen binding fragments and variants thereof. In certain embodiments, the antibody has heavy and light chain CDRs or variable regions of nivolumab. Accordingly, in one embodiment, the antibody comprises CDR1, CDR2, and CDR3 domains of the VH of nivolumab having the sequence set forth in SEQ ID NO: 301, and CDR1, CDR2 and CDR3 domains of the VL of nivolumab having the sequence set forth in SEQ ID NO: 302. In certain embodiments, the antibody comprises CDR1, CDR2 and CDR3 domains comprising the sequences set forth in SEQ ID NOs: 303-305, respectively, and CDR1, CDR2 and CDR3 domains comprising the sequences set forth in SEQ ID NOs: 306-308, respectively. In certain embodiments, the antibody comprises VH and/or VL regions comprising the amino acid sequences set forth in SEQ ID NO: 301 and/or SEQ ID NO: 302, respectively. In certain embodiments, the antibody has at least about 90%, e.g., at least about 90%, 95%, or 99% variable region identity with SEQ ID NO: 301 or SEQ ID NO: 302.

Exemplary anti-PD-L1 antibodies include BMS-936559 (referred to as 12A4 in WO 2007/005874 and U.S. Pat. No. 7,943,743), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiments, the anti-PD-L1 antibody is MEDI4736 (also known as Anti-B7-H1), MPDL3280A (also known as RG7446), MSB0010718C (WO2013/79174), or rHigM12B7. Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 may also be used.

Exemplary anti-CTLA-4 antibodies include Yervoy™ (ipilimumab or antibody 10D1, described in PCT Publication WO 01/14424), tremelimumab (formerly ticilimumab, CP-675,206), or an anti-CTLA-4 antibody described in any of the following publications: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. Any of the anti-CTLA-4 antibodies disclosed in WO2013/173223 may also be used.

Exemplary anti-LAGS antibodies include antibodies comprising the CDRs or variable regions of antibodies 25F7, 26H10, 25E3, 8B7, 11F2 or 17E5, which are described in U.S. Patent Publication No. US2011/0150892, WO10/19570 and WO2014/008218. In one embodiment, an anti-LAG-3 antibody is BMS-986016. Other art recognized anti-LAG-3 antibodies that can be used include IMP731 and IMP-321, described in US 2011/007023, WO08/132601, and WO09/44273.

In certain embodiments, the anti-OX40 antibody is used in combination with ipilimumab. In certain embodiments, the antibody has heavy and light chain CDRs or variable regions of ipilimumab. Accordingly, in one embodiment, the antibody comprises CDR1, CDR2, and CDR3 domains of the VH of ipilimumab having the sequence set forth in SEQ ID NO: 309, and CDR1, CDR2 and CDR3 domains of the VL of ipilimumab having the sequence set forth in SEQ ID NO: 310. In certain embodiments, the antibody comprises CDR1, CDR2 and CDR3 domains comprising the sequences set forth in SEQ ID NOs: 311-313, respectively, and CDR1, CDR2 and CDR3 domains comprising the sequences set forth in SEQ ID NOs: 314-316, respectively. In certain embodiments, the antibody comprises VH and/or VL regions comprising the amino acid sequences set forth in SEQ ID NO: 309 and/or SEQ ID NO: 310, respectively. In certain embodiments, the antibody has at least about 90%, e.g., at least about 90%, 95%, or 99% variable region identity with SEQ ID NO: 309 or SEQ ID NO: 310.

Administration anti-OX40 antibodies and antagonists, e.g., antagonist antibodies, to one or more second target antigens such as LAG-3 and/or CTLA-4 and/or PD-1 and/or PD-L1 can enhance the immune response to cancerous cells in the patient. Cancers whose growth may be inhibited using anti-OX40 antibodies include cancers typically responsive to immunotherapy and those that are not typically responsive to immunotherapy. Representative examples of cancers for treatment with the combination therapy of the instant disclosure include those cancers listed herein.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. Furthermore, if more than one dose of the combination therapy is administered sequentially, the order of the sequential administration can be reversed or kept in the same order at each time point of administration, and sequential administrations can be combined with concurrent administrations, or any combination thereof. For example, the first administration of a combination of anti-OX40 antibody and anti-PD1 antibody (and/or anti-CTLA-4 antibody and/or anti-PD-L1 antibody and/or anti-LAG-3 antibody) can be concurrent, the second administration can be sequential with anti-PD1 antibody first and the anti-OX40 antibody second, and the third administration can be sequential with the anti-OX40 antibody first and anti-PD1 antibody second, etc. Another representative dosing scheme involves a first administration that is sequential with the anti-OX40 first and anti-PD1 antibody (and/or anti-CTLA-4 antibody and/or anti-PD-L1 antibody and/or anti-LAG-3 antibody) second, and subsequent administrations may be concurrent.

In certain embodiment, a subject having a disease that may benefit from stimulation of the immune system, e.g., cancer or an infectious disease, is treated by administration to the subject of the anti-OX40 antibody and an immuno-oncology agent. Exemplary immune-oncology agents include CD137 (4-1BB) agonists (e.g., an agonistic CD137 antibody such as urelumab or PF-05082566 (WO12/32433)); GITR agonists (e.g., an agonistic anti-GITR antibody), CD40 agonists (e.g., an agonistic CD40 antibody); CD40 antagonists (e.g., an antagonistic CD40 antibody such as lucatumumab (HCD122), dacetuzumab (SGN-40), CP-870,893 or Chi Lob 7/4); CD27 agonists (e.g., an agonistic CD27 antibody such as varlilumab (CDX-1127)), MGA271 (to B7H3) (WO11/109400)); KIR antagonists (e.g., lirilumab); IDO antagonists (e.g., INCB-024360 (WO2006/122150, WO07/75598, WO08/36653, WO08/36642), indoximod, NLG-919 (WO09/73620, WO09/1156652, WO11/56652, WO12/142237) or F001287); Toll-like receptor agonists (e.g., TLR2/4 agonists (e.g., *Bacillus* Calmette-Guerin); TLR7 agonists (e.g., Hiltonol or Imiquimod); TLR7/8 agonists (e.g., Resiquimod); or TLR9 agonists (e.g., CpG7909)); and TGF-β inhibitors (e.g., GC1008, LY2157299, TEW7197, or IMC-TR1).

In one embodiment, the anti-OX40 antibody is administered prior to administration of a second agent, e.g., an immuno-oncology agent. In another embodiment, the anti-OX40 antibody is administered concurrently with the second agent, e.g., an immunology-oncology agent. In yet another embodiment, the anti-OX40 antibody is administered after administration of the second agent. The administration of the two agents may start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent may start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In certain embodiments, the anti-OX40 antibody and a second agent, e.g., an immuno-oncology agent, are administered simultaneously, e.g., are infused simultaneously, e.g., over a period of 30 or 60 minutes, to a patient. The anti-OX40 antibody may be co-formulated with the second agent, e.g., an immuno-oncology agent.

Optionally, the anti-OX40 antibody as sole immunotherapeutic agent, or a combination of the anti-OX40 antibody and one or more additional immunotherapeutic antibodies (e.g., anti-CTLA-4 and/or anti-PD-1 and/or anti-PD-L1 and/or anti-LAG-3 blockade), can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). A combination of the anti-OX40 antibody and one or more additional antibodies (e.g., CTLA-4 and/or PD-1 and/or PD-L1 and/or LAG-3 blockade) can also be further combined with standard cancer treatments. For example, a combination of the anti-OX40 antibody and one or more additional antibodies (e.g., CTLA-4 and/or PD-1 and/or PD-L1 and/or LAG-3 blockade) can be effectively combined with chemotherapeutic regimes. In these instances, the dose of other chemotherapeutic reagent administered with the combination can be reduced (Mokyr et al. (1998) *Cancer Research* 58: 5301-5304). For example, such a combination may include the anti-OX40 antibody with or without and an additional antibody (e.g., anti-CTLA-4 antibodies and/or anti-PD-1 antibodies and/or anti-PD-L1 antibodies and/or anti-LAG-3 antibodies), further in combination with decarbazine or interleukin-2 (IL-2) for the treatment of melanoma. The scientific rationale behind combining an agonistic anti-OX40 antibody with CTLA-4 and/or PD-1 and/or PD-L1 and/or LAG-3 blockade with chemotherapy is that cell death, which is a consequence of the cytotoxic action of most chemotherapeutic compounds, should result in increased levels of tumor antigen in the antigen presentation pathway. Other combination therapies that may result in synergy with a combination of the anti-OX40 antibody with or without and CTLA-4 and/or PD-1 and/or PD-L1 and/or LAG-3 blockade through cell death include radiation, surgery, or hormone deprivation. Each of these protocols creates a source of tumor antigen in the host. Angiogenesis inhibitors can also be combined with a combination of the anti-OX40 antibody and CTLA-4 and/or PD-1 and/or PD-L1 and/or LAG-3 blockade. Inhibition of angiogenesis leads to tumor cell death, which can be a source of tumor antigen fed into host antigen presentation pathways.

In certain embodiments, the anti-OX40 antibody can be used as the sole immunotherapeutic agent, or a combination of the anti-OX40 antibody and CTLA-4 and/or PD-1 and/or PD-L1 and/or LAG-3 blocking antibodies, can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combination of the anti-OX40 antibody and CTLA-4 and/or PD-1 and/or PD-L1 and/or LAG-3 blockade.

In another example, the anti-OX40 antibody can be used as the sole immunotherapeutic agent, or a combination of the anti-OX40 antibody and additional immunostimulating agent, e.g., anti-CTLA-4 antibody and/or anti-PD-1 antibody and/or anti-PD-L1 antibody and/or LAG-3 agent (e.g., antibody) can be used in conjunction with an anti-neoplastic antibody, such as Rituxan® (rituximab), Herceptin® (trastuzumab), Bexxar® (tositumomab), Zevalin® (ibritumomab), Campath® (alemtuzumab), Lymphocide® (epratuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by the immunostimulating agent (e.g., OX40, CTLA-4, PD-1, PD-L1 or LAG-3 agent, e.g., antibody). In an exemplary embodiment, a treatment of a hyperproliferative disease (e.g., a cancer tumor) can include an anti-cancer agent (e.g., antibody) in combination with the anti-OX40 antibody and optionally an additional immunostimulating agent, e.g., anti-CTLA-4 and/or anti-PD-1 and/or anti-PD-L1 and/or anti-LAG-3 agent (e.g., antibody), concurrently or sequentially or any combination thereof, which can potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be further combined with the anti-OX40 antibody with or without an additional immunostimulating agent, e.g., an anti-CTLA-4 and/or anti-PD-1 and/or anti-PD-L1 and/or anti-LAG-3 agent, such as antibody, to counteract the effects of immunosuppressive agents and favor anti-tumor immune responses by the host.

Other agents (e.g., antibodies) that can be used to activate host immune responsiveness can be further used in combination with the anti-OX40 antibody with or without an additional immunostimulating agent, such as anti-CTLA-4 and/or anti-PD-1 and/or anti-PD-L1 and/or anti-LAG-3 antibody. These include molecules on the surface of dendritic cells that activate DC function and antigen presentation. Anti-CD40 antibodies (Ridge et al., supra) can be used in conjunction with the anti-OX40 antibody and optionally an additional immunostimulating agent, e.g., an anti-CTLA-4 and/or anti-PD-1 and/or anti-PD-L1 and/or anti-LAG-3 agent, e.g., antibody. Other activating antibodies to T cell costimulatory molecules Weinberg et al., supra, Melero et al. supra, Hutloff et al., supra, may also provide for increased levels of T cell activation.

As discussed above, bone marrow transplantation is currently being used to treat a variety of tumors of hematopoietic origin. Anti-OX40 immunotherapy alone or combined with CTLA-4 and/or PD-1 and/or PD-L1 and/or LAG-3 blockade can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of the anti-OX40 antibody with or without an additional immunostimulating therapy, e.g., anti-CTLA-4 and/or anti-PD-1 and/or anti-PD-L1 and/or anti-LAG-3 antibodies can be expected to increase the frequency and activity of the adoptively transferred T cells.

Provided herein are methods for altering an adverse event associated with the treatment of a hyperproliferative disease (e.g., cancer) with an immunostimulatory agent, comprising administering the anti-OX40 antibody with or without an anti-CTLA-4 and/or anti-PD-1 and/or anti-PD-L1 and/or anti-LAG-3 agent (e.g., antibody), to a subject. For example, the methods described herein provide for a method of reducing the incidence of immunostimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In one embodiment, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58$^{th}$ ed. 2004; 608-610.

In still further embodiments, the anti-OX40 antibody with or without CTLA-4 and/or PD-1 and/or PD-L1 and/or LAG-3 blockade (i.e., anti-CTLA-4 and/or anti-PD-1 and/or anti-PD-L1 and/or anti-LAG-3 antibodies) in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods described herein, a salicylate administered in combination with the anti-OX40 antibody with or without anti-CTLA-4 and/or anti-PD-1 and/or anti-PD-L1 and/or LAG-3 antibodies and a non-absorbable steroid can include any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies described herein encompass administering a salicylate and a non-absorbable concurrently or sequentially (e.g., a salicylate is administered 6 hours after a non-absorbable steroid), or any combination thereof. Further, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-OX40 antibody and anti-CTLA-4 and/or anti-PD-1 and/or anti-PD-L1 and/or anti-LAG-3 antibodies.

Anti-OX40 antibodies and combination antibody therapies described herein may also be used in conjunction with other well-known therapies that are selected for their particular usefulness against the indication being treated (e.g., cancer). Combinations with anti-OX40 antibodies may be used sequentially with known pharmaceutically acceptable agent(s).

For example, anti-OX40 antibodies and combination antibody therapies described herein can be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo21/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 inhibitor (e.g., INCB24360, indoximod, NLG-919, or F001287), AT-101 (R-(-)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., $Nat$ $Med$ 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al., Cancer Research 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3f3 inhibitors, IAP inhibitors and/or genotoxic drugs.

Anti-OX40 antibodies and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with anti-OX40 antibodies, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with the anti-OX40 antibody, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions described herein, other agents used in the modulation of tumor growth or metastasis in a clinical setting, such as antimimetics, can also be administered as desired.

In certain embodiments, the anti-OX40 antibody is administered in combination (concurrently or separately) with nivolumab to treat a patient with cancer, for example, colorectal or bladder cancer.

In certain embodiments, the anti-OX40 antibody is administered in combination (concurrently or separately) with ipilimumab to treat a patient with cancer, for example, ovarian, bladder, or prostate cancer.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto. The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The present disclosure is further illustrated by the following examples, which should not be construed as further limiting. The contents of all figures and all references, Genbank sequences, patents, and published patent applications cited throughout this application are expressly incorporated herein by reference.

XVII. Kits and Unit Dosage Forms

Also provided herein are kits which include a pharmaceutical composition containing an anti-OX40 antibody (e.g., OX40.21) and an anti-PD-1 (e.g., nivolumab) or anti-CTLA-4 (ipilimumab) antibody, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the kits include multiple packages of the single-dose pharmaceutical compositions each containing an effective amount of the anti-OX40 antibody or anti-PD-1 or anti-CTLA-4 antibody for a single administration in accordance with the methods provided above. Instruments or devices necessary for administering the pharmaceutical composition(s) also may be included in the kits. For instance, a kit may provide one or more pre-filled syringes containing an amount of the anti-OX40 antibody or anti-PD-1 or anti-CTLA-4 antibody.

In one embodiment, the present invention provides a kit for treating a solid tumor in a human patient, the kit comprising a dose of an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94, and instructions for use in the methods described herein. In certain embodiments, the kit further comprises (a) a dose of an anti-PD-1 antibody comprising CDR1, CDR2 and CDR3 domains of the heavy chain variable region having the sequence set forth in SEQ ID NO: 301, and CDR1, CDR2 and CDR3 domains of the light chain variable region having the sequence set forth in SEQ ID NO: 302, or (b) a dose of an anti-CTLA-4 antibody comprising CDR1, CDR2 and CDR3 domains of the heavy chain variable region having the sequence set forth in SEQ ID NO: 309, and CDR1, CDR2 and CDR3 domains of the light chain variable region having the sequence set forth in SEQ ID NO: 310.

Embodiments

1. An isolated antibody, or antigen binding portion thereof, which binds to human OX40 and exhibits the following properties:
    (a) binds to membrane-bound human OX40;
    (b) binds to cynomolgus OX40;
    (c) binds to soluble human OX40;
    (d) induces or enhances T cell activation;
    (e) inhibits the binding of OX40 ligand to OX40;
    (f) competes for binding to human OX40 with one or more of antibodies 3F4, 14B6-1, 14B6-2, 23H3, 6E1-1, 6E1-2, 18E9, 8B11, 20B3, 14A2-1, 14A2-2, and 20C1.
2. The antibody of embodiment 1, wherein the antibody does not bind to mouse and/or rat OX40.
3. The antibody, or antigen binding portion thereof, of embodiment 1 or 2, wherein the antibody stimulates an anti-tumor immune response.
4. The antibody, or antigen binding portion thereof, of any one of the preceding embodiments, wherein the antibody stimulates an antigen-specific T cell response.
5. The antibody, or antigen binding portion thereof, of any one of the preceding embodiments, wherein the antibody increases IL-2 and/or IFN-γ production in OX40-expressing T cells.
6. The antibody, or antigen binding portion thereof, of any one of the preceding embodiments, wherein the antibody increases T cell proliferation.
7. The antibody, or antigen binding portion thereof, of any one of the preceding embodiments, wherein the antibody binds to Fc receptors.
8. The antibody, or antigen binding portion thereof, of embodiment 7, wherein the antibody binds to one or more activating FcγRs.
9. The antibody, or antigen binding portion thereof, of any one of the preceding embodiments, wherein the antibody binds to soluble human OX40 with a $K_D$ of about 1 nM or less, such as 0.5 nM or less or 0.1 nM or less, as measured by Biacore.
10. The antibody, or antigen binding portion thereof, of any one of the preceding embodiments, wherein the antibody binds to membrane bound human OX40 with an $EC_{50}$ of 50 nM or less, such as 10 nM or less or 1 nM or less, as measured by FACS.
11. The antibody, or antigen binding portion thereof, of any one of the preceding embodiments, wherein the antibody binds to membrane bound cynomolgus OX40 with an $EC_{50}$ of 50 nM or less, such as 10 nM or less or 1 nM or less as measured by FACS.
12. The antibody, or antigen binding portion thereof, of any one of the preceding embodiments, wherein the antibody induces or enhances T cell activation through multivalent cross-linking.
13. The antibody, or antigen binding portion thereof, of any one of the preceding embodiments, wherein the antibody binds the C1q component of human complement.
14. The antibody, or antigen binding portion thereof, of any one of the preceding embodiments, wherein the antibody induces NK cell-mediated lysis of activated CD4+ T cells.
15. The antibody, or antigen binding portion thereof, of any one of the preceding embodiments, wherein the antibody promotes macrophage-mediated phagocytosis of OX40 expressing cells.
16. The antibody, or antigen binding portion thereof, of any one of the preceding embodiments, wherein the antibody inhibits regulatory T cell-mediated suppression of CD4+ T cell proliferation.
17. The antibody, or antigen binding portion thereof, of any one of the preceding embodiments, wherein the antibody binds to the sequence DVVSSKPCKPCTWCNLR (SEQ ID NO: 178) of human OX40 (SEQ ID NO: 2).
18. The antibody, or antigen binding portion thereof, of any one of embodiments 1-16, wherein the antibody binds to the sequence DSYKPGVDCAPCPPGHFSPGDNQACKP-WTNCTLAGK (SEQ ID NO: 179) of human OX40 (SEQ ID NO: 2).
19. An isolated monoclonal antibody, or antigen binding portion thereof, which specifically binds to OX40 and comprises the three variable heavy chain CDRs and the three variable light chain CDRs that are in the variable heavy chain and variable light chain pairs selected from the group consisting of:
    (a) SEQ ID NOs: 318 and 94;
    (b) SEQ ID NOs: 17 and 18;
    (c) SEQ ID NOs: 28 and 29;
    (d) SEQ ID NOs: 28 and 30;
    (e) SEQ ID NOs: 37 and 38;
    (f) SEQ ID NOs: 48 and 49;
    (g) SEQ ID NOs: 48 and 50;
    (h) SEQ ID NOs: 57 and 58;
    (i) SEQ ID NOs: 65 and 66;
    (j) SEQ ID NOs: 73 and 74;
    (k) SEQ ID NOs: 84 and 85;
    (l) SEQ ID NOs: 84 and 86; and
    (m) SEQ ID NOs: 93 and 94.
20. An isolated monoclonal antibody, or antigen binding portion thereof, which binds to OX40, comprising:
    (a) heavy chain CDR1, CDR2, and CDR3 sequences comprising SEQ ID NOs: 87, 317, and 89, respectively, and/or light chain CDR1, CDR2, and CDR3 sequences comprising SEQ ID NOs: 90-92, respectively;

(b) heavy chain CDR1, CDR2, and CDR3 sequences comprising SEQ ID NOs: 11-13, respectively, and/or light chain CDR1, CDR2, and CDR3 sequences comprising SEQ ID NOs: 14-16, respectively;

(c) heavy chain CDR1, CDR2, and CDR3 sequences comprising SEQ ID NOs: 19-21, respectively, and/or light chain CDR1, CDR2, and CDR3 sequences comprising SEQ ID NOs: 22-24, respectively;

(d) heavy chain CDR1, CDR2, and CDR3 sequences comprising SEQ ID NOs: 19-21, respectively, and/or light chain CDR1, CDR2, and CDR3 sequences comprising SEQ ID NOs: 25-27, respectively;

(e) heavy chain CDR1, CDR2, and CDR3 sequences comprising SEQ ID NOs: 31-33, respectively, and/or light chain CDR1, CDR2, and CDR3 sequences comprising SEQ ID NOs: 34-36, respectively;

(f) heavy chain CDR1, CDR2, and CDR3 sequences comprising SEQ ID NOs: 39-41, respectively, and/or light chain CDR1, CDR2, and CDR3 sequences comprising SEQ ID NOs: 42-44, respectively;

(g) heavy chain CDR1, CDR2, and CDR3 sequences comprising SEQ ID NOs: 39-41, respectively, and/or light chain CDR1, CDR2, and CDR3 sequences comprising SEQ ID NOs: 45-47, respectively;

(h) heavy chain CDR1, CDR2, and CDR3 sequences comprising SEQ ID NOs: 51-53, respectively, and/or light chain CDR1, CDR2, and CDR3 sequences comprising SEQ ID NOs: 54-56, respectively;

(i) heavy chain CDR1, CDR2, and CDR3 sequences comprising SEQ ID NOs: 59-61, respectively, and/or light chain CDR1, CDR2, and CDR3 sequences comprising SEQ ID NOs: 62-64, respectively;

(j) heavy chain CDR1, CDR2, and CDR3 sequences comprising SEQ ID NOs: 67-69, respectively, and/or light chain CDR1, CDR2, and CDR3 sequences comprising SEQ ID NOs: 70-72, respectively;

(k) heavy chain CDR1, CDR2, and CDR3 sequences comprising SEQ ID NOs: 75-77, respectively, and/or light chain CDR1, CDR2, and CDR3 sequences comprising SEQ ID NOs: 78-80, respectively;

(l) heavy chain CDR1, CDR2, and CDR3 sequences comprising SEQ ID NOs: 75-77, respectively, and/or light chain CDR1, CDR2, and CDR3 sequences comprising SEQ ID NOs: 81-83, respectively; or (m) heavy chain CDR1, CDR2, and CDR3 sequences comprising SEQ ID NOs: 87-89, respectively, and/or light chain CDR1, CDR2, and CDR3 sequences comprising SEQ ID NOs: 90-92, respectively.

21. An isolated monoclonal antibody, or antigen binding portion thereof, which binds to OX40, comprising:

(a) heavy chain CDR1, CDR2, and CDR3 sequences consisting of SEQ ID NOs: 87, 317, and 89, respectively, and/or light chain CDR1, CDR2, and CDR3 sequences consisting of SEQ ID NOs: 90-92, respectively;

(b) heavy chain CDR1, CDR2, and CDR3 sequences consisting of SEQ ID NOs: 11-13, respectively, and/or light chain CDR1, CDR2, and CDR3 sequences consisting of SEQ ID NOs: 14-16, respectively;

(c) heavy chain CDR1, CDR2, and CDR3 sequences consisting of SEQ ID NOs: 19-21, respectively, and/or light chain CDR1, CDR2, and CDR3 sequences consisting of SEQ ID NOs: 22-24, respectively;

(d) heavy chain CDR1, CDR2, and CDR3 sequences consisting of SEQ ID NOs: 19-21, respectively, and/or light chain CDR1, CDR2, and CDR3 sequences consisting of SEQ ID NOs: 25-27, respectively;

(e) heavy chain CDR1, CDR2, and CDR3 sequences consisting of SEQ ID NOs: 31-33, respectively, and/or light chain CDR1, CDR2, and CDR3 sequences consisting of SEQ ID NOs: 34-36, respectively;

(f) heavy chain CDR1, CDR2, and CDR3 sequences consisting of SEQ ID NOs: 39-41, respectively, and/or light chain CDR1, CDR2, and CDR3 sequences consisting of SEQ ID NOs: 42-44, respectively;

(g) heavy chain CDR1, CDR2, and CDR3 sequences consisting of SEQ ID NOs: 39-41, respectively, and/or light chain CDR1, CDR2, and CDR3 sequences consisting of SEQ ID NOs: 45-47, respectively;

(h) heavy chain CDR1, CDR2, and CDR3 sequences consisting of SEQ ID NOs: 51-53, respectively, and/or light chain CDR1, CDR2, and CDR3 sequences consisting of SEQ ID NOs: 54-56, respectively;

(i) heavy chain CDR1, CDR2, and CDR3 sequences consisting of SEQ ID NOs: 59-61, respectively, and/or light chain CDR1, CDR2, and CDR3 sequences consisting of SEQ ID NOs: 62-64, respectively;

(j) heavy chain CDR1, CDR2, and CDR3 sequences consisting of SEQ ID NOs: 67-69, respectively, and/or light chain CDR1, CDR2, and CDR3 sequences consisting of SEQ ID NOs: 70-72, respectively;

(k) heavy chain CDR1, CDR2, and CDR3 sequences consisting of SEQ ID NOs: 75-77, respectively, and/or light chain CDR1, CDR2, and CDR3 sequences consisting of SEQ ID NOs: 78-80, respectively;

(l) heavy chain CDR1, CDR2, and CDR3 sequences consisting of SEQ ID NOs: 75-77, respectively, and/or light chain CDR1, CDR2, and CDR3 sequences consisting of SEQ ID NOs: 81-83, respectively; or (m) heavy chain CDR1, CDR2, and CDR3 sequences consisting of SEQ ID NOs: 87-89, respectively, and/or light chain CDR1, CDR2, and CDR3 sequences consisting of SEQ ID NOs: 90-92, respectively.

22. An isolated monoclonal antibody, or antigen binding portion thereof, which binds to OX40 and comprises heavy and light chain variable regions, wherein the heavy chain variable region comprises an amino acid sequence which is at least 90% identical to the amino acid sequence selected from the group consisting of SEQ ID NOs: 17, 28, 37, 48, 57, 65, 73, 84, and 93.

23. An isolated monoclonal antibody, or antigen binding portion thereof, which binds to OX40 and comprises heavy and light chain variable regions, wherein the light chain variable region comprises an amino acid sequence which is at least 90% identical to the amino acid sequence selected from the group consisting of SEQ ID NOs: 18, 29, 30, 38, 49, 50, 58, 66, 74, 85, 86, and 94.

24. An isolated monoclonal antibody, or antigen binding portion thereof, which binds to OX40 and comprises heavy and light chain variable region sequences at least 85% identical to the amino acid sequences selected from the group consisting of:

(a) SEQ ID NOs: 318 and 94;
(b) SEQ ID NOs: 17 and 18;
(c) SEQ ID NOs: 28 and 29;
(d) SEQ ID NOs: 28 and 30;
(e) SEQ ID NOs: 37 and 38;
(f) SEQ ID NOs: 48 and 49;
(g) SEQ ID NOs: 48 and 50;
(h) SEQ ID NOs: 57 and 58;
(i) SEQ ID NOs: 65 and 66;
(j) SEQ ID NOs: 73 and 74;
(k) SEQ ID NOs: 84 and 85;
(l) SEQ ID NOs: 84 and 86; and
(m) SEQ ID NOs: 93 and 94.

25. The antibody, or antigen binding portion thereof, of embodiment 24, wherein the heavy and light chain variable regions comprise an amino acid sequence at least 90% identical to the heavy and light chain variable regions selected from the group consisting of (a)-(l) of embodiment 24.

26. The antibody, or antigen binding portion thereof, of embodiment 25, wherein the heavy and light chain variable region comprises an amino acid sequence at least 95% identical to the heavy and light chain variable regions selected from the group consisting of (a)-(l) of embodiment 24.

27. The antibody, or antigen binding portion thereof, of embodiment 26, wherein the heavy and light chain variable region comprises the heavy and light chain variable regions selected from the group consisting of (a)-(l) of embodiment 24.

28. An isolated monoclonal antibody, or antigen binding portion thereof, which binds to OX40 and comprises heavy chain and light chain sequences at least 80%, 85%, 90%, 95%, 96%, 97%, 98% or 99% identical to the amino acid sequences selected from the group consisting of:
  (a) SEQ ID NOs: 124 and 116, respectively;
  (b) SEQ ID NOs: 95 and 96, respectively;
  (c) SEQ ID NOs: 97 and 98, respectively;
  (d) SEQ ID NOs: 99 and 100, respectively;
  (e) SEQ ID NOs: 101 and 102, respectively;
  (f) SEQ ID NOs: 103 and 104, respectively;
  (g) SEQ ID NOs: 105 and 106, respectively;
  (h) SEQ ID NOs: 107 and 108, respectively;
  (i) SEQ ID NOs: 109 and 110, respectively;
  (j) SEQ ID NOs: 111 and 112, respectively;
  (k) SEQ ID NOs: 113 and 114, respectively;
  (l) SEQ ID NOs: 115 and 116, respectively;
  (m) SEQ ID NOs: 117 and 118, respectively;
  (n) SEQ ID NOs: 119 and 120, respectively;
  (o) SEQ ID NOs: 121 and 122, respectively;
  (p) SEQ ID NOs: 123 and 116, respectively; and
  (q) SEQ ID NOs: 125 and 116, respectively.

29. The antibody, or antigen binding portion thereof, of embodiment 28, wherein the heavy and light chains comprises the heavy and light chains selected from the group consisting of (a)-(r) of embodiment 28.

30. An isolated monoclonal antibody, or antigen binding portion thereof, which (a) binds to the same epitope on OX40 as the antibody of embodiment 27, and/or (b) inhibits binding of the antibody of embodiment 27 to OX40 on activated T cells by at least 95% as measured by FACS.

31. The antibody, or antigen binding portion thereof, of any one of embodiments 19-30, wherein the antibody binds to the sequence DVVSSKPCKPCTWCNLR (SEQ ID NO: 178) of human OX40 (SEQ ID NO: 2).

32. The antibody, or antigen binding portion thereof, of any one of embodiments 19-30, wherein the antibody binds to the sequence DSYKPGVDCAPCPPGHFSPGDNQACKPWTNCTLAGK (SEQ ID NO: 179) of human OX40 (SEQ ID NO: 2).

33. The antibody, or antigen binding portion thereof, of any one of embodiments 19-31, wherein the antibody binds to both human and cynomolgus OX40.

34. The antibody, or antigen binding portion thereof, of any one of the preceding embodiments, wherein the antibody is selected from the group consisting of an IgG1, an IgG2, an IgG3, an IgG4, or a variant thereof.

35. The antibody, or antigen binding portion thereof, of embodiment 34, wherein the antibody is an IgG1 antibody.

36. The antibody of embodiment 35, wherein the antibody, or antigen binding portion thereof, comprises an Fc having enhanced binding to an activating FcγR.

37. The antibody, or antigen binding portion thereof, of any one of the preceding embodiments, wherein one or more methionine residues in the CDR regions are substituted for amino acid residues that do not undergo oxidation.

38. The antibody, or antigen binding portion thereof, of any one of the preceding embodiments, wherein the antibody, or antigen binding portion thereof, is a human or humanized antibody.

39. The antibody, or antigen binding portion thereof, of any one of the preceding embodiments, wherein the antibody is not immunogenic, as assessed according to Example 21.

40. The antibody, or antigen binding portion thereof, of any one of the preceding embodiments, wherein the amino acid sequence Asp-Gly, if present in the heavy and/or light chain CDR sequences, is substituted with an amino acid sequence that does not undergo isomerization.

41. The antibody, or antigen binding portion thereof, of embodiment 40, wherein the antibody comprises the heavy chain variable region CDR2 sequence set forth in SEQ ID NO: 76, but wherein the Asp-Gly sequence is replaced an amino acid sequence that does not undergo isomerization.

42. The antibody of embodiment 41, wherein the Asp or Gly in the Asp-Gly sequence is replaced with Ser.

43. A bispecific molecule comprising the antibody of any one of the preceding embodiments linked to a molecule having a second binding specificity.

44. A nucleic acid encoding the heavy and/or light chain variable region of the antibody, or antigen binding portion thereof, of any one of embodiments 1-42.

45. An expression vector comprising the nucleic acid molecule of embodiment 44.

46. A cell transformed with an expression vector of embodiment 45.

47. An immunoconjugate comprising the antibody according to any one of embodiments 1-42, linked to an agent.

48. A composition comprising the antibody, or antigen binding portion thereof, bispecific molecule or immunoconjugate, of any one of embodiments 1-43 and 47, and a carrier.

49. A kit comprising the antibody, or antigen binding portion thereof, or bispecific molecule, or immunoconjugate of any one of embodiments 1-43 and 47 and instructions for use.

50. A method of preparing an OX40 antibody, or antigen binding portion thereof, comprising expressing the antibody, or antigen binding portion thereof, in the cell of embodiment 46 and isolating the antibody, or antigen binding portion thereof, from the cell.

51. A method of stimulating an antigen-specific T cell response comprising contacting the T cell with the antibody, or antigen binding portion thereof, bispecific molecule or immunoconjugate, of any one of embodiments 1-43 and 47 such that an antigen-specific T cell response is stimulated.

52. A method of activating or co-stimulating an effector T cell, comprising contacting an effector T cell with an anti-OX40 antibody, or antigen binding portion thereof, bispecific molecule or immunoconjugate, of any one of embodiments 1-43 and 47 and CD3, wherein the effector T cell is activated or co-stimulated.

53. A method of increasing IL-2 and/or IFN-γ production in a T cell comprising contacting the T cell with an effective amount of the antibody, or antigen binding portion thereof, bispecific molecule or immunoconjugate, of any one of embodiments 1-43 and 47.

54. A method of increasing T cell proliferation comprising contacting the cell with an effective amount of the antibody, or antigen binding portion thereof, bispecific molecule or immunoconjugate, of any one of embodiments 1-43 and 47.

55. A method of increasing IL-2 and/or IFN-γ production in T cells in a subject comprising administering an effective amount of the antibody, or antigen binding portion thereof, bispecific molecule or immunoconjugate, of any one of embodiments 1-43 and 47, to increase IL-2 and/or IFN-γ production from the T cells.

56. A method of reducing or depleting the number of T regulatory cells in a tumor of a subject in need thereof comprising administering an effective amount of an antibody, or antigen binding portion thereof, bispecific molecule or immunoconjugate, of any one of embodiments 1-43 and 47, wherein the antibody, or antigen binding portion thereof, has effector or enhanced effector function, to reduce the number of T regulatory cells in the tumor.

57. A method of stimulating an immune response in a subject comprising administering the antibody, or antigen binding portion thereof, bispecific molecule or immunoconjugate, of any one of embodiments 1-43 and 47 to the subject such that an immune response in the subject is stimulated.

58. The method of embodiment 57, wherein the subject has a tumor and an immune response against the tumor is stimulated.

59. A method for inhibiting the growth of tumor cells in a subject comprising administering to the subject the antibody, or antigen binding portion thereof, bispecific molecule or immunoconjugate, of any one of embodiments 1-43 and 47, such that growth of the tumor is inhibited.

60. A method of treating cancer comprising administering to a subject in need thereof a therapeutically effective amount of the antibody, or antigen binding portion thereof, bispecific molecule or immunoconjugate, of any one of embodiments 1-43 and 47, to treat the cancer.

61. The method of embodiment 60, wherein the cancer is selected from the group consisting of: bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer.

62. The method of embodiment 60 or 61 wherein the cancer is a metastatic cancer, refractory cancer, or recurrent cancer.

63. The method of any one of embodiments 56-62, further comprising administering one or more additional therapeutics.

64. The method of embodiment 63, wherein the one or more additional therapeutics is an antibody or a small molecule.

65. The method of embodiment 64, wherein the additional therapy is an anti-PD1 antibody, a LAG-3 antibody, a CTLA-4 antibody, a PD-L1 antibody, or an anti-TGFβ antibody.

66. A method of treating a solid tumor in a human subject, the method comprising administering to the subject an effective amount of an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94, wherein the method comprises at least one administration cycle, wherein the cycle is a period of two weeks, wherein for each of the at least one cycles, one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg.

67. A method of treating a solid tumor in a human subject, the method comprising administering to the subject an effective amount of each of:
  (a) an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94,
  (b) an anti-PD-1 antibody comprising CDR1, CDR2 and CDR3 domains of the heavy chain variable region having the sequence set forth in SEQ ID NO: 301, and CDR1, CDR2 and CDR3 domains of the light chain variable region having the sequence set forth in SEQ ID NO: 302,
  wherein the method comprises at least one administration cycle, wherein the cycle is a period of two, three, or four weeks, wherein for each of the at least one cycles, one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg, and one dose of the anti-PD-1 antibody is administered at a dose of 240, 360, or 480 mg or a dose of about 240, 360, or 480 mg.

68. The method of embodiment 67, wherein the anti-OX40 antibody and anti-PD-1 antibody are administered at the following doses:
  (a) 1 mg/kg body weight anti-OX40 antibody and 240 mg, 360 mg, or 480 mg of anti-PD-1 antibody;
  (b) 20 mg anti-OX40 antibody and 240 mg, 360 mg, or 480 mg of anti-PD-1 antibody;
  (c) 40 mg anti-OX40 antibody and 240 mg, 360 mg, or 480 mg of anti-PD-1 antibody;
  (d) 80 mg anti-OX40 antibody and 240 mg, 360 mg, or 480 mg of anti-PD-1 antibody;
  (e) 160 mg anti-OX40 antibody and 240 mg, 360 mg, or 480 mg of anti-PD-1 antibody; or
  (f) 320 mg anti-OX40 antibody and 240 mg, 360 mg, or 480 mg of anti-PD-1 antibody.

69. A method of treating a solid tumor in a human subject, the method comprising administering to the subject an effective amount of each of:
  (a) an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94,
  (b) an anti-CTLA-4 antibody comprising CDR1, CDR2 and CDR3 domains of the heavy chain variable region having the sequence set forth in SEQ ID NO: 309, and CDR1, CDR2 and CDR3 domains of the light chain variable region having the sequence set forth in SEQ ID NO: 310,
  wherein the method comprises at least one administration cycle, wherein the cycle is a period of three weeks, wherein for each of the at least one cycles, one dose of the anti-OX40 antibody is administered at a dose of 1 mg/kg body weight; a fixed dose of 20, 40, 80, 160, or 320 mg; a dose of about 1 mg/kg body weight; or a fixed dose of about 20, 40, 80, 160, or 320 mg, and one dose of the anti-CTLA-4 antibody is administered at a dose of 1 mg/kg or a dose of about 1 mg/kg,
  wherein the anti-OX40 antibody is administered together with the anti-CTLA-4 antibody for at least one cycle, followed by anti-OX40 antibody monotherapy for at least one cycle.

70. The method of embodiment 67, wherein the anti-OX40 antibody and anti-CTLA-4 antibody are administered at the following doses:
    (a) 1 mg/kg body weight anti-OX40 antibody and 1 mg/kg anti-CTLA-4 antibody;
    (b) 20 mg anti-OX40 antibody and 1 mg/kg anti-CTLA-4 antibody;
    (c) 40 mg anti-OX40 antibody and 1 mg/kg anti-CTLA-4 antibody;
    (d) 80 mg anti-OX40 antibody and 1 mg/kg anti-CTLA-4 antibody;
    (e) 160 mg anti-OX40 antibody and 1 mg/kg anti-CTLA-4 antibody; or
    (f) 320 mg anti-OX40 antibody and 1 mg/kg anti-CTLA-4 antibody.
71. The method of any one of embodiments 66-70, wherein the anti-OX40 antibody, or anti-OX40 antibody and anti-PD-1 or anti-CTLA-4 antibody, are formulated for intravenous administration.
72. The method of any one of embodiments 67-71, wherein the anti-OX40 and anti-PD-1 or anti-CTLA-4 antibody are formulated together.
73. The method of any one of embodiments 67-71, wherein the anti-OX40 and anti-PD-1 or anti-CTLA-4 antibody are formulated separately.
74. The method of any one of embodiments 66-68, and 71-73, wherein the treatment consists of up to 12 cycles.
75. The method of any one of embodiments 69-73, wherein the treatment consists of 8 cycles.
76. The method of embodiment 75, wherein the anti-OX40 antibody is administered together with the anti-CTLA-4 antibody for the first 4 cycles, followed by anti-OX40 antibody monotherapy for the last 4 cycles.
77. The method of any one of embodiments 66-76, wherein the anti-OX40 antibody, or anti-OX40 antibody and anti-PD-1 or anti-CTLA-4 antibody, are administered on Day 1 of each cycle.
78. The method of any one of embodiments 67-77, wherein the anti-OX40 antibody is administered prior to administration of the anti-PD-1 or anti-CTLA-4 antibody.
79. The method of embodiment 78, wherein the anti-OX40 antibody is administered within about 30 minutes prior to administration of the anti-PD-1 or anti-CTLA-4 antibody.
80. The method of any one of embodiments 67-77, wherein the anti-OX40 antibody is administered after administration of the anti-PD-1 or anti-CTLA-4 antibody.
81. The method of any one of embodiments 67-77, wherein the anti-OX40 antibody is administered concurrently with the anti-PD-1 or anti-CTLA-4 antibody.
82. The method of any one of embodiments 66-81, wherein the treatment produces at least one therapeutic effect chosen from a reduction in size of a tumor, reduction in number of metastatic lesions over time, complete response, partial response, and stable disease.
83. The method of any one of embodiments 66-82, wherein the solid tumor is associated with a cancer selected from the group consisting of: cervical cancer, bladder cancer, colorectal cancer, and ovarian cancer.
84. The method of any one of embodiments 66-83, wherein the anti-OX40 antibody comprises heavy chain and light chain variable region CDRs comprising the amino acid sequences set forth in SEQ ID NOs: 87, 317 and 89, and 90-92, respectively.
85. The method of any one of embodiments 66-84, wherein the anti-OX40 antibody comprises heavy and light chain variable region sequences set forth in SEQ ID NOs: 318 and 94, respectively.
86. The method of any one of embodiments 66-85, wherein the anti-OX40 antibody comprises heavy and light chain sequences set forth in SEQ ID NOs: 124 and 116, respectively.
87. The method of any one of embodiments 67, 68, and 71-86, wherein the anti-PD-1 antibody comprises heavy chain and light chain variable region CDRs comprising the amino acid sequences set forth in SEQ ID NOs: 303-305 and 306-308, respectively.
88. The method of any one of embodiments 67, 68, and 71-87, wherein the anti-PD-1 antibody comprises heavy and light chain variable region sequences set forth in SEQ ID NOs: 301 and 302, respectively.
89. The method of any one of embodiments 69-86, wherein the anti-CTLA-4 antibody comprises heavy chain and light chain variable region CDRs comprising the amino acid sequences set forth in SEQ ID NOs: 311-313 and 314-316, respectively.
90. The method of any one of embodiments 69-86 and 89, wherein the anti-CTLA-4 antibody comprises heavy and light chain variable region sequences set forth in SEQ ID NOs: 309 and 310, respectively.
91. A kit for treating a solid tumor in a human subject, the kit comprising a dose of an anti-OX40 antibody comprising CDR1, CDR2 and CDR3 domains of the heavy chain variable region having the sequence set forth in SEQ ID NO: 318, and CDR1, CDR2 and CDR3 domains of the light chain variable region having the sequence set forth in SEQ ID NO: 94, and instructions for use.
92. The kit of embodiment 91, further comprising (a) a dose of an anti-PD-1 antibody comprising CDR1, CDR2 and CDR3 domains of the heavy chain variable region having the sequence set forth in SEQ ID NO: 301, and CDR1, CDR2 and CDR3 domains of the light chain variable region having the sequence set forth in SEQ ID NO: 302, or (b) a dose of an anti-CTLA-4 antibody comprising CDR1, CDR2 and CDR3 domains of the heavy chain variable region having the sequence set forth in SEQ ID NO: 309, and CDR1, CDR2 and CDR3 domains of the light chain variable region having the sequence set forth in SEQ ID NO: 310.
93. A method of detecting the presence of OX40 in a sample comprising contacting the sample with the antibody, or antigen binding portion thereof, of any one of embodiments 1-38, under conditions that allow for formation of a complex between the antibody, or antigen binding.
94. An antibody which binds to OX40 comprising an amino acid sequence selected from the group consisting of SEQ ID NOs: 282-296.
95. The antibody of embodiment 94, wherein the antibody comprises a heavy chain consisting of an amino acid sequence selected from the group consisting of SEQ ID NOs: 282-296.
96. An isolated monoclonal antibody which binds to OX40, comprising heavy chain CDR1, CDR2, and CDR3 sequences comprising SEQ ID NOs: 87, 317, and 89, respectively, and light chain CDR1, CDR2, and CDR3 sequences comprising SEQ ID NOs: 90-92, respectively.
97. An isolated monoclonal antibody which binds to OX40, comprising heavy and light chain variable regions comprising the amino acid sequences of SEQ ID NOs: 318 and 94, respectively.
98. An isolated monoclonal antibody which binds to OX40, comprising heavy and light chains comprising the amino acid sequences of SEQ ID NOs: 124 and 116, respectively.

99. An isolated monoclonal antibody which binds to OX40, wherein the antibody binds to all or a portion of the sequence DVVSSKPCKPCTWCNLR (SEQ ID NO: 178) of human OX40 (SEQ ID NO: 2).
100. A composition comprising an isolated monoclonal antibody according to any one of embodiments 96-99 and a carrier.
101. A nucleic acid encoding the heavy and/or light chain variable region of the antibody of embodiment 96 or 97, or the heavy and/or light chain of embodiment 98.
102. A kit comprising the antibody of any one of embodiments 96-99.
103. A method of stimulating an antigen-specific T cell response comprising contacting the T cell with an antibody according to any one of embodiments 96-99.
104. A method of treating cancer comprising administering to a subject in need thereof a therapeutically effective amount of an antibody according to any one of embodiments 96-99, to treat the cancer.
105. The method of embodiment 104, wherein the cancer or solid tumor is selected from the group consisting of: cervical cancer, bladder cancer, colorectal cancer, ovarian cancer, non-small cell lung cancer, and squamous cell carcinoma of the head and neck.

EXAMPLES

Example 1: Generation of Anti-OX40 Antibodies

Human anti-OX40 monoclonal antibodies were generated in Hco7, Hco12, Hco17, and Hco38 strains of HuMAb® transgenic mice ("HuMAb" is a Trade Mark of Medarex, Inc., Princeton, N.J.) and KM mice (the KM Mouse® strain contains the SC20 transchromosome as described in PCT Publication WO 02/43478) using recombinant hexahistidine-OX40 antigen.

A total of 52 mice, including 5 genotypes of transgenic mice (KM, Hco7, Hco12, Hco17, and Hco38), were immunized with different immunization strategies. The immunogen was huOX40-6× his prepared in-house and used at 2.0 mg/mL for a total dose of 20 µg per mouse. Routes of administration included: base of tail injection, Hock immunization, intraperitoneal (ip) and subcutaneous (sc) injection, and adjuvant (Ribi, Cat #56322, Sigma). 27 fusions from 30 mice were performed and screened. 541 ELISA antigen positive antibodies were identified from these 27 fusions, and further characterization led to the isolation of antibodies of particular interest, including the antibodies designated as 3F4, 14B6-1, 14B6-2, 23H3, 6E1-1, 6E1-2, 18E9, 8B11, 20B3 (also referred to as OX40.17), 14A2-1, 14A2-2, and 20C1. Their variable region amino acid sequences and isotype are set forth in FIGS. 1-9. The heavy and light chain variable regions of 3F4 consist of amino acid sequences SEQ ID NOs: 17 and 18. The heavy and light chain variable regions of 14B6-1 consist of amino acid sequences SEQ ID NOs: 28 and 29. The heavy and light chain variable regions of 14B6-2 consist of amino acid sequences SEQ ID NOs: 28 and 30. The heavy and light chain variable regions of 23H3 consist of amino acid sequences SEQ ID NOs: 37 and 38. The heavy and light chain variable regions of 6E1-1 consist of amino acid sequences SEQ ID NOs: 48 and 49. The heavy and light chain variable regions of 6E1-2 consist of amino acid sequences SEQ ID NOs: 48 and 50. The heavy and light chain variable regions of 18E9 consist of amino acid sequences SEQ ID NOs: 57 and 58. The heavy and light chain variable regions of 8B11 consist of amino acid sequences SEQ ID NOs: 65 and 66. The heavy and light chain variable regions of 20B3 consist of amino acid sequences SEQ ID NOs: 73 and 74. The heavy and light chain variable regions of 14A2-1 consist of amino acid sequences SEQ ID NOs: 84 and 85. The heavy and light chain variable regions of 14A2-2 consist of amino acid sequences SEQ ID NOs: 84 and 86. The heavy and light chain variable regions of 20C1 consist of amino acid sequences SEQ ID NOs: 93 and 94.

cDNA sequencing identified one heavy and one light chain for each of the antibodies 3F4, 23H3, 18E9, 8B11, 20B3 (also referred to as OX40.17) and 20C1, and one heavy chain and two light chains (light chain 1 or "L1" and light chain 2 or "L2") for each of the antibodies 14B6, 14A2 and 6E1. By protein analysis, a single light chain was identified for antibodies 14B6, 6E1 and 14A2, and N-terminal sequencing and molecular weight determination indicated that it was light chain L1 for 14B6 and 14A2 and light chain L2 for 6E1. Antibodies 14B6-1 and 14B6-2 correspond to antibody 14B6 with a light chain L1 and L2, respectively. Antibodies 14A2-1 and 14A2-2 correspond to antibody 14A2 with a light chain L1 and L2, respectively. Antibodies 6E1-1 and 6E1-2 correspond to antibody 6E1 with a light chain L1 and L2, respectively. The amino acid and nucleotide sequences of each of the light chains of the 3 antibodies are provided in Table 23.

For some of the antibodies above, substitutions in the parental antibody were made in HCDR2 in order to remove the presence of an isomerization site (DG), and framework substitutions (due to derivation from the DP44 germline) were introduced to make the framework more like a commonly expressed antibody. For 20C1-based antibodies, three additional unusual framework residues were reverted to germline (A2V, D24G, and G82bS). The G82bS framework reversion also eliminates a deamidation site (NG). A summary of the various substitutions introduced into the parental hybrid clone sequences is provided in Table 6.

TABLE 6

| Name | Parental hybridoma clone | Isotype | Variable region substitutions |
|---|---|---|---|
| OX40.6 | 23H3 | g1f | Anti-OX40 23H3 with VH-H13Q/M87T |
| OX40.7 | 23H3 | g1f | Anti-OX40 23H3 with VH-M87T/M95Y |
| OX40.8 | 14A2 | g1f | Anti-OX40 14A2 with VH-G103W |
| OX40.9 | 14A2 | g1f | Anti-OX40 14A2 with VH-M97Y/G103W |
| OX40.10 | 14A2 | g1f | Anti-OX40 14A2 with VH-D53S |
| OX40.11 | 14A2 | g1f | Anti-OX40 14A2 with VH-G54S |
| OX40.12 | 14A2 | g1f | Anti-OX40 14A2 with VH-D53S/G103W |
| OX40.13 | 14A2 | g1f | Anti-OX40 14A2 with VH-G54S/G103W |
| OX40.14 | 14A2 | g1f | Anti-OX40 14A2 with VH-D53S/M97Y/G103W |
| OX40.15 | 14A2 | g1f | Anti-OX40 14A2 with VH-G54S/M97Y/G103W |

TABLE 6-continued

| Name | Parental hybridoma clone | Isotype | Variable region substitutions |
|---|---|---|---|
| OX40.16 | 20C1 | g1f | Anti-OX40 20C1 with VH-A2V/H13Q/D24G/M87T/G82bS |
| OX40.17 | 20B3 | g1f | Anti-OX40 20B3 (no substitutions) |
| OX40.18 | 3F4 | g1f | Anti-OX40 3F4 with VH-N27Y/N72D/P102Y |
| OX40.19 | 14A2 | g1f | Anti-OX40 14A2 with VH-M97L/G103W |
| OX40.20 | 20C1 | g1f | Anti-OX40 20C1 with VH-A2V/H13Q/D24G/D54S/M87T/G82bS |
| OX40.21 | 20C1 | g1f | Anti-OX40 201 with VH-A2V/H13Q/D24G/G55A/M87T/G82bS |
| OX40.22 | 20C1 | g1f | Anti-OX40 201 with VH-A2V/H13Q/D24G/D54S/G55T/M87T/G82bS |

*Depending on the germline, there may be a D53 and G54 or a D54 and G55 present, as a potential isomerization site

Example 2: Binding of Anti-OX40 Antibodies to Activated Primary Human T Cells The human monoclonal anti-OX40 antibodies generated in Example 1 were tested for the ability to bind to activated primary human T cells.

Cells were activated for several days before the binding assay in order to induce OX40 expression. Briefly, PBMCs were cultured for three or four days with magnetic beads coated with anti-human CD3 plus anti-human CD28, in the presence of recombinant human IL-2. On the day of the assay, the beads were removed and the cells stained with a titration of each anti-OX40 antibody. Bound antibodies were detected with a fluorescently conjugated anti-human IgG polyclonal secondary antibody, and the cells were co-stained for CD4 and CD25 to detect activated CD4 T cells. The fluorescence intensity of the staining was measured using a FACSCanto II flow cytometer (Becton Dickinson). The geometric mean fluorescence intensity (GMFI) or median fluorescence intensity (MedFI) of anti-OX40 antibody staining was calculated for the CD4+CD25+ population (FACSDiva software). $EC_{50}$s for antibody binding were calculated using GraphPad Prism software.

Figure 11B:
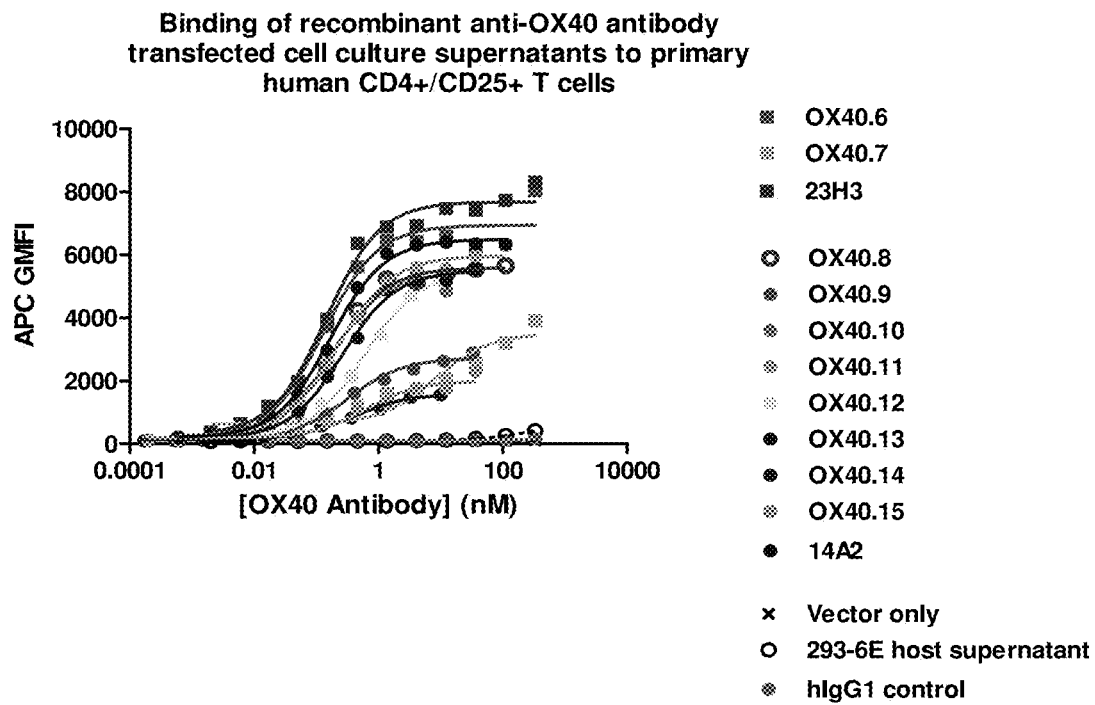

As shown in FIG. 11A, the anti-OX40 antibodies bound to activated primary human T cells with subnanomolar $EC_{50}$s. Notably, OX40.5 showed lowest binding of the anti-OX40 antibodies tested. The same experiment was performed with anti-OX40 antibodies with variable region substitutions. Initial experiments were carried out using antibodies in the form of supernatants from cultures of host cells transfected with recombinant antibody expression vectors. As shown in FIG. 11B, certain substitutions caused a significant loss of binding, namely for antibodies OX40.7, OX40.9, OX40.14 and OX40.15. A set of antibodies with variable region substitutions was analyzed further using purified antibody material.

Figure 11C:
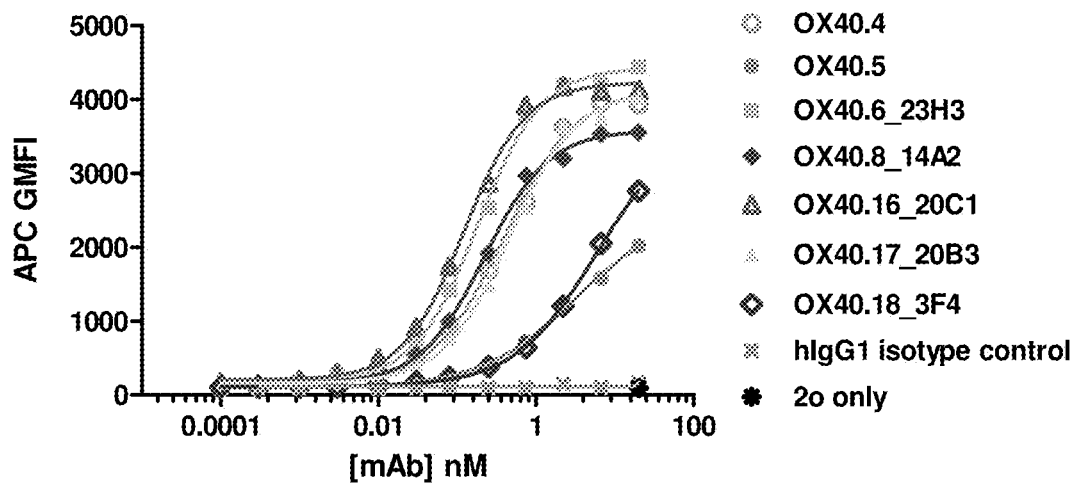
Figure 11D:
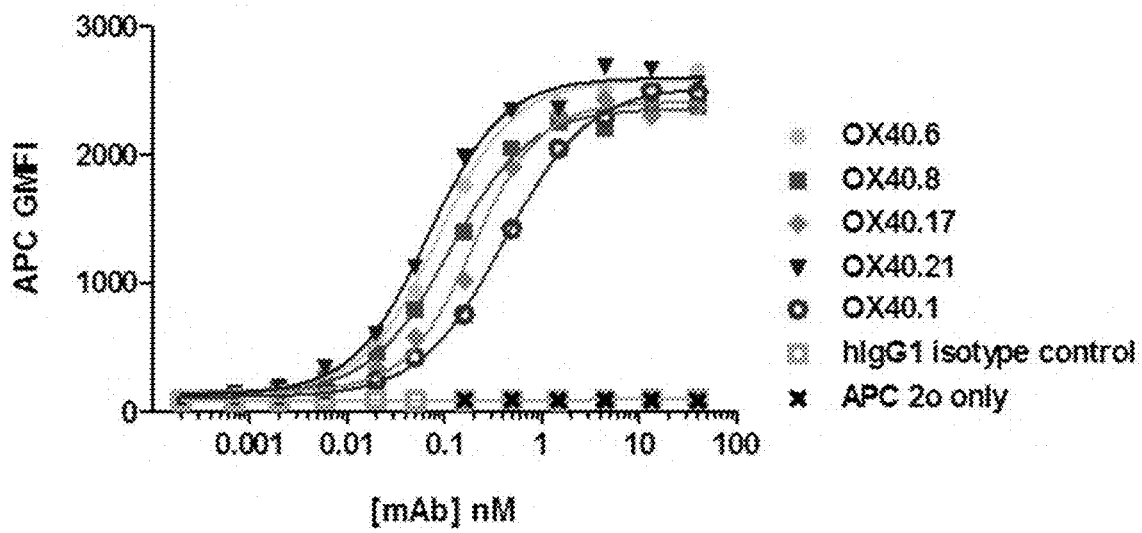

As shown in FIGS. 11C and 11D, all tested antibodies bound with subnanomolar EC50s to OX40, except for OX40.18, which showed lower binding than the 3F4 hybridoma parent clone. OX40.5 showed the lowest binding among the panel of antibodies tested in FIG. 11B, whereas OX40.1 showed the lowest binding among the panel of antibodies tested in FIG. 11C. A summary of the $EC_{50}$ values is presented in Table 7 below.

TABLE 7

$EC_{50}$s for binding of OX40 antibodies to activated human primary T cells.

| Name | Human T Cell Binding EC50 (nM) (mean ± SD) | n |
|---|---|---|
| 3F4 | 0.19 ± 0.15 | 3 |
| 8B11 | 0.14 ± 0.07 | 2 |
| 18E9 | 0.22 ± 0.12 | 2 |
| 20B3 | 0.34 ± 0.23 | 3 |
| 20C1 | 0.10 ± 0.06 | 3 |
| 23H3 | 0.15 ± 0.09 | 3 |
| 6E1 | 0.97 ± 0.05 | 2 |
| 14A2 | 0.33 ± 0.30 | 3 |
| 14B6 | 0.18 ± 0.16 | 2 |
| OX40.6 | 0.13 ± 0.06 | 7 |
| OX40.8 | 0.14 ± 0.07 | 7 |
| OX40.16 | 0.06 ± 0.03 | 5 |
| OX40.17 | 0.26 ± 0.17 | 3 |
| OX40.18 | 3.15 ± 3.9 | 2 |
| OX40.21 | 0.07 ± 0.02 | 5 |
| OX40.1 | 0.35 ± 0.09 | 2 |
| OX40.4 | 0.36 ± 0.06 | 2 |
| OX40.5 | 3.20 ± 0.00 | 2 |

Example 3: Binding of Anti-OX-40 Antibodies to Activated Primary Cynomolgus Macaque T Cells The human monoclonal anti-OX-40 antibodies that were tested for binding to activated primary human T cells in Example 1 were tested for the ability to bind activated primary cynomolgus macaque T cells.

Briefly, cells were activated for several days before the binding assay in order to induce OX40 expression. Total leukocytes were isolated from cynomolgus macaque peripheral blood by lysis of red blood cells using an ammonium chloride buffer. The leukocytes were then cultured for four to five days with in flasks pre-coated with anti-human CD3 plus anti-human CD28 antibodies that cross-react with cynomolgus macaque, in the presence of recombinant human IL-2, in order to expand and activate T cells. On the day of the assay, the cells were harvested and stained with a titration of each anti-OX40 antibody. Bound antibodies were detected with a fluorescently conjugated anti-human IgG polyclonal secondary antibody, and the cells were co-stained for CD4 and CD25 to detect activated CD4 T cells. The fluorescence intensity of the staining was measured using a FACSCanto II flow cytometer (Becton Dickinson). The geometric mean fluorescence intensity (GMFI) or median fluorescence intensity (MedFI) of anti-OX40 antibody staining was calculated for the CD4+CD25+ population (FACSDiva software). Dose-response curves were generated and $EC_{50}$s for antibody binding were calculated using GraphPad Prism software.

As shown in FIGS. 12A and 12B, the anti-OX40 antibodies tested bound with high potency to activated cynomolgus macaque CD4 T cells, with $EC_{50}$s ranging from 0.068 nM (20C1) to 1.4 nM (20B3). 18E9 and 20B3 bound with $EC_{50}$s between 1 and 1.5 nM, while the remaining antibodies bound with $EC_{50}$s below 1 nM. OX40.1 showed the lowest binding among the anti-OX40 antibodies tested in FIG. 12A, and OX40.5 showed the lowest binding among the anti-OX40 antibodies tested in FIG. 12B. The same experiment was performed with anti-OX40 antibodies with variable region substitutions. As shown in FIG. 12C, OX40.6, OX40.8 and OX40.21 antibodies showed the highest potency of binding, with $EC_{50}$s of 0.12 nM or lower. OX40.1 showed much lower binding to cynomolgous macaque CD4 T cells. No binding of the OX40.21 antibody was detected on activated mouse or rat CD4+ T cells. A summary of the $EC_{50}$ values is presented in Table 8 below.

TABLE 8

| Name | Cyno T Cell Binding EC50 (nM) (mean ± SD) | n |
|---|---|---|
| 3F4 | 0.37 ± 0.13 | 4 |
| 8B11 | 0.20 ± 0.08 | 4 |
| 18E9 | 41.70 ± 37.78 | 4 |
| 20B3 | 1.18 ± 0.27 | 4 |
| 20C1 * | 0.17 ± 0.07 | 4 |
| 23H3 | 0.18 ± 0.10 | 4 |
| 6E1 | 0.77 ± 0.14 | 4 |
| 14A2 | 0.27 ± 0.02 | 4 |
| 14B6 | 0.31 | 1 |
| OX40.6 | 0.11 ± 0.01 | 5 |
| OX40.8 | 0.10 ± 0.02 | 4 |
| OX40.16 | 0.06 ± 0.01 | 3 |
| OX40.17 | 0.52 ± 0.12 | 3 |
| OX40.18 | | |
| OX40.21 | 0.07 ± 0.01 | 5 |
| OX40.1 | 23.40 ± 37.75 | 4 |
| OX40.4 | 1.3 | 1 |
| OX40.5 | ~2.2e+012 | 1 |

Example 4: Scatchard Analysis of Binding of Anti-OX40 Antibodies to Activated Primary T Cells and Cells Overexpressing Human and Cynomolgus Monkey OX40

The binding of OX40.21 (IgG1 isotype) to activated human T cells was further assessed using Scatchard analysis. Briefly, OX40.21 was radioiodinated with $^{125}$I—Na (1 mCi; PerkinElmer Catalog NEZ033H001 MC) using IODO-GEN® solid phase iodination reagent (1,3,4,6-tetrachloro-3a-6a-diphenylglycouril; Pierce Catalog 28601). Activated human CD4+ T cells were isolated from peripheral blood mononuclear cells (PBMC), Donor W-326470, purchased from the Stanford Blood Bank. CD4+ T cells were isolated by negative selection (RosetteSep™ Human CD4+ T cell enrichment cocktail, StemCell Technologies Catalog 15062) and frozen. The isolated CD4+ T cells were activated for four days before the binding assay in order to induce OX40 expression, as follows. Thawed cells were cultured for four days with magnetic beads coated with anti-human CD3 plus anti-human CD28 (human T-Expander CD3/CD28 Dynabeads, Invitrogen Catalog 111.41D), at a 1:1 bead cell ratio, in the presence of 200 IU/mL recombinant human IL-2 (Peprotech Catalog 200-02).

Radioiodinated OX40.21 IgG1 binding to activated human T cells was demonstrated by incubating activated human T cells with a titration of $^{125}$I-OX40.21 IgG1. Nonspecific binding was determined by binding in the presence of a titration of a 100 fold molar excess of unlabeled antibody and was subtracted from total CPM to calculate specific binding. A linear standard curve of $^{125}$I-OX40.21 IgG1 concentration versus CPM was used to extrapolate specific activity, maximal nM bound $^{125}$I-OX40.21 IgG1 and thereby calculate receptor number per cell.

As shown in Table 9 and FIG. 13A, saturable binding of OX40.21 IgG1 was observed on activated human T cells endogenously expressing OX40, with a $K_D$ of 0.05 nM for each of two T cell donors.

TABLE 9

Binding of $^{125}$I-OX40.21 to Activated Human T Cells

| Ab Conc. (nM) | Total Binding $^{125}$I-labeled Antibody (nM) | | Non-Specific Binding $^{125}$I-labeled Antibody (nM) | | Specific Binding $^{125}$I-labeled Antibody (nM) | |
|---|---|---|---|---|---|---|
| 10 | 0.0317 | 0.0292 | 0.0120 | 0.0117 | 0.0197 | 0.0175 |
| 5 | 0.0283 | 0.0275 | 0.0073 | 0.0072 | 0.0210 | 0.0204 |
| 2.5 | 0.0230 | 0.0256 | 0.0036 | 0.0030 | 0.0195 | 0.0226 |
| 1.25 | 0.0205 | 0.0221 | 0.0029 | 0.0025 | 0.0176 | 0.0196 |
| 0.625 | 0.0197 | 0.0223 | 0.0014 | 0.0017 | 0.0183 | 0.0207 |
| 0.3125 | 0.0197 | 0.0229 | 0.0013 | 0.0012 | 0.0184 | 0.0217 |
| 0.15625 | 0.0177 | 0.0201 | 0.0012 | 0.0011 | 0.0165 | 0.0190 |
| 0.078125 | 0.0140 | 0.0152 | 0.0010 | 0.0011 | 0.0129 | 0.0141 |
| 0.039063 | 0.0083 | 0.0091 | 0.0007 | 0.0010 | 0.0076 | 0.0081 |
| 0.019531 | 0.0057 | 0.0057 | 0.0009 | 0.0010 | 0.0049 | 0.0047 |
| 0.009766 | 0.0024 | 0.0030 | 0.0007 | 0.0008 | 0.0017 | 0.0022 |

The same assay was performed using HEK293 cells overexpressing human OX40 ("hOX40-293"). Briefly, radioiodinated OX40.21 binding to overexpressed human OX40 was demonstrated by incubating hOX40-293 cells with a titration of $^{125}$I-OX40.21. Nonspecific binding was determined by binding in the presence of a titration of a 100 fold molar excess of unlabeled antibody and was subtracted from total CPM to calculate specific binding. A linear standard curve of $^{125}$I-OX40.21 concentration versus CPM was used to extrapolate maximal nM bound $^{125}$I-OX40.21 and thereby calculate receptor numbers per cell. As shown in FIG. 13B and Table 10, saturable binding of OX40.21 IgG1 was observed for binding to OX40 expressed on hOX40-293 cells. The average $K_D$ for binding from two test conditions using different numbers of hOX40-293 cells per sample was 0.22 nM.

TABLE 10

OX40.21 Binding to hOX40-293 Cells

| Ab Conc. (nM) | Total Binding $^{125}$I-labeled Antibody (nM) | | Non-Specific Binding $^{125}$I-labeled Antibody (nM) | | Specific Binding $^{125}$I-labeled Antibody (nM) | |
|---|---|---|---|---|---|---|
| 10 | 0.1866 | 0.1712 | 0.0129 | 0.0137 | 0.1737 | 0.1575 |
| 5 | 0.1800 | 0.1710 | 0.0080 | 0.0099 | 0.1720 | 0.1611 |
| 2.5 | 0.1799 | 0.1643 | 0.0065 | 0.0065 | 0.1734 | 0.1578 |
| 1.25 | 0.1722 | 0.1628 | 0.0057 | 0.0054 | 0.1665 | 0.1574 |
| 0.625 | 0.1583 | 0.1436 | 0.0067 | 0.0048 | 0.1515 | 0.1388 |
| 0.3125 | 0.0986 | 0.0936 | 0.0038 | 0.0044 | 0.0948 | 0.0891 |
| 0.15625 | 0.0624 | 0.0501 | 0.0035 | 0.0048 | 0.0589 | 0.0453 |
| 0.078125 | 0.0351 | 0.0289 | 0.0035 | 0.0033 | 0.0316 | 0.0255 |
| 0.039063 | 0.0211 | 0.0162 | 0.0038 | 0.0027 | 0.0173 | 0.0136 |
| 0.019531 | 0.0117 | 0.0091 | 0.0029 | 0.0028 | 0.0088 | 0.0063 |
| 0.009766 | 0.0075 | 0.0056 | 0.0027 | 0.0028 | 0.0048 | 0.0028 |

The same assay was performed using CHO cells overexpressing cynomolgus monkey OX40 ("cynoOX40-CHO").

Briefly, radioiodinated OX40.21 binding to cynomologus OX40 was demonstrated by incubating cynoOX40-CHO cells with a titration of $^{125}$I-OX40.21. Nonspecific binding was determined by binding in the presence of a titration of a 100 fold molar excess of unlabeled antibody and was subtracted from total CPM to calculate specific binding. A linear standard curve of $^{125}$I-OX40.21 concentration versus CPM was used to extrapolate maximal nM bound $^{125}$I-OX40.21 and thereby calculate receptor numbers per cell. As shown in FIG. 13C and Table 11, saturable binding of OX40.21 IgG1 was observed for binding to cynomologus OX40 expressed on cynoOX40-CHO cells. The average $K_D$ for binding from two test conditions using different numbers of cells per sample was 0.63 nM.

TABLE 11

OX40.21 Binding to cynoOX40-CHO Cells

| Ab Conc. (nM) | Total Binding $^{125}$I-labeled antibody (nM) | | Non-Specific Binding $^{125}$I-labeled antibody (nM) | | Specific Binding $^{125}$I-labeled antibody (nM) | |
|---|---|---|---|---|---|---|
| 20 | 0.1781 | 0.1814 | 0.0266 | 0.0414 | 0.1515 | 0.1400 |
| 10 | 0.1768 | 0.1651 | 0.0161 | 0.0197 | 0.1607 | 0.1454 |
| 5 | 0.1629 | 0.1820 | 0.0109 | 0.0171 | 0.1520 | 0.1649 |
| 2.5 | 0.1665 | 0.1659 | 0.0080 | 0.0092 | 0.1586 | 0.1567 |
| 1.25 | 0.1197 | 0.1839 | 0.0079 | 0.0084 | 0.1117 | 0.1755 |
| 0.625 | 0.0892 | 0.1197 | 0.0060 | 0.0074 | 0.0832 | 0.1123 |
| 0.3125 | 0.0630 | 0.0754 | 0.0057 | 0.0053 | 0.0573 | 0.0701 |
| 0.15625 | 0.0318 | 0.0437 | 0.0049 | 0.0050 | 0.0269 | 0.0386 |
| 0.078125 | 0.0158 | 0.0212 | 0.0030 | 0.0034 | 0.0128 | 0.0179 |
| 0.039063 | 0.0082 | 0.0110 | 0.0027 | 0.0029 | 0.0055 | 0.0082 |
| 0.019531 | 0.0058 | 0.0058 | 0.0026 | 0.0023 | 0.0032 | 0.0035 |
| 0.009766 | 0.0030 | 0.0032 | 0.0022 | 0.0021 | 0.0009 | 0.0011 |

Example 5: Specific Binding of Anti-OX40 Antibodies to Lymphocytes

The specificity of various OX40 antibodies was tested on a panel of 22 normal human tissue types, including spleen, tonsil, thymus, cerebrum, cerebellum, heart, liver, lung, kidney, pancreas, pituitary, peripheral nerves, stomach, colon, small intestine, thyroid, skin, skeletal muscle, prostate, uterus, testes, and placenta by immunohistochemistry.

Fresh, frozen and/or OCT-embedded human tissues were purchased from multiple commercial tissue networks/vendors (Asterand Inc. Detroit, Mich.; Cooperative Human Tissue Network, Philadelphia, Pa.; ProteoGenex Inc, Culver City, Calif.). To detect tissue binding, a series of anti-OX40 antibodies (OX40.6-FITC, OX40.8-FITC, 6E1-FITC, OX40.16-FITC, OX40.17-FITC, OX40.20-FITC, and OX40.21-FITC) were fluoresceinated and applied to acetone fixed cryostat sections, followed by an anti-FITC bridging antibody and visualization by the EnVision+ System. A nonspecific fluoresceinated human IgG1 was used as isotype control antibody. HT1080 cells stably expressing human OX40 (HT1080/huOX40) and hyperplasic human tonsil tissue sections were used as positive control cells and tissues. To determine if FITC conjugation has any impact on binding properties, both FITC-conjugated and un-conjugated anti-OX40 antibodies were compared in HT1080/huOX40 cells using anti-huIgG as bridging antibody. Stained slides were evaluated under a light microscope.

Initial tests revealed that both un-conjugated and FITC-conjugated anti-OX40 antibodies specifically stained the cytoplasm and membrane of human OX40 transfected cells but not parent HT1080 cells. There was no difference between unconjugated and FITC-conjugated anti-OX40 antibodies. These results suggest that the antibodies were suitable for immunohistochemistry analyses, and that FITC conjugation has no impact on tissue binding properties.

All anti-OX40 antibodies tested exhibited positive staining in a small subset, either as scattered or small clusters, of mononuclear cells (MNC) in lymphoid tissues (tonsil, spleen, and thymus) and lymphoid-rich tissues (colon, stomach, and small intestine), as well as a few scattered MNC in multiple tissues (lung, skin, and thyroid). Based on morphology, these positive cells are primarily lymphocytes.

In addition to staining a subset of lymphocytes, the OX40.6 antibody, a ligand blocker, displayed strong staining in subsets of endothelium/subendothelial matrix and interstitial elements, more often associated with small arteries and adventitia of vessel and its surrounding connective tissues, in virtually all tissues examined (FIG. 14A), as well as specialized interstitial tissue elements such as sheath-like interstitium surrounding the seminiferous tubule in the testis. The OX40.8 antibody, a ligand non-blocker, positively labeled myofilament-like structures in cardiac muscles of the heart (FIG. 14A) and mesangial-like cells in glomerulus of the kidney. Staining with another ligand non-blocker, i.e., the 6E1 antibody, also revealed staining in cardiac muscle cells, as well as in neurons and neuropils of cerebrum and cerebellum and a subset of tubule epithelial cells in kidney. In general, the staining of non-lymphocytes was detected only when the antibodies were used at relatively high concentrations (3 or 5 μg/ml), but not at lower concentrations (1 μg/ml), suggesting low affinity binding or potential off-target binding.

Further testing of other ligand blocking antibodies, OX40.16 (FIG. 14A) and OX40.17, revealed clean staining of a subset of lymphocyte, with no specific staining of other tissue elements for all tissues examined. The OX40.21 antibody, a variant of the OX40.16 antibody, had a similar binding pattern as the OX40.16 antibody (FIG. 14B). Immunohistochemistry in a similar panel of normal cynomolgus tissues revealed very similar staining pattern to human, demonstrating the utility of cynomolgus monkey as a relevant preclinical species.

Example 6: Expression of OX40 in Cancers

FFPE (formalin fixed paraffin embedded) tumor tissue samples were purchased from commercial tissue venders (n=12-20 for each tumor type). To detect binding to tissues, an automated IHC assay with a commercial anti-human OX40 antibody was developed using the Leica BondRX platform. Briefly, heat-induced antigen retrieval (HIER) was performed in pH9 ER2 buffer (Leica) for 20 min at 95° C. The mouse anti-human OX40 monoclonal antibody clone ACT35 (BD Pharmingen) was incubated at 5 μg/ml for 60 minutes, followed by Novolink Max polymer (Leica) for 30 minutes. Finally, slides were reacted with DAB substrate-chromogen solution for 6 minutes, counterstained with Mayer's hematoxylin, dehydrated, cleared, and coverslipped with Permount. Dako protein block was used as diluent for the primary antibody.

To profile TILs, commercially available anti-CD3 (T cell marker) and anti-FoxP3 (Treg marker) monoclonal antibodies were used to stain adjacent sections. Commercial mouse IgG1 was used as a negative control and hyperplasic human tonsil tissue was used as a positive control. After immunostaining, slides were manually evaluated and scored under a light microscope.

In the four tumor types examined, CD3+ TILs were present in all samples examined, with the amount of TILs varying across samples and the distribution within the same tissue heterogeneous. In some cases, TILs were more heavily distributed in the tumor and host interface, as expected. Most TILs were localized in the tumor stroma in the vast majority tissue samples. However, they were readily found in intratumoral nests in many cases. Positive OX40 staining was observed in a small fraction of TILs and primarily distributed in the tumor stroma. In general, the abundance of OX40+ TILs was in proportion to that of CD3+ TILs. Among the four tumor types examined, OX40+ TILs were more abundant in HCC and CRC (FIGS. 15A-15C).

Example 7: Human Monoclonal Anti-OX40 Antibodies that Block the Binding of OX-40L to OX-40

Several anti-OX40 antibodies were tested for their ability to block the binding of recombinant soluble OX40L to human OX40-transfected 293 cells. Briefly, 293 cells stably transfected with human OX40 were first pre-incubated with varying concentrations of anti-OX40 antibodies. A fixed concentration (0.2 μg/mL) of recombinant soluble his-tagged human OX40L (OX40L-His, R & D Systems) was then added and the samples incubated further. After washing the cells, bound OX40L-His was detected using an in-house APC-labeled anti-His tag antibody. The fluorescence intensity of the staining was measured using a FACSCanto II flow cytometer (Becton Dickinson). The geometric mean fluorescence intensity (GMFI) of APC-anti-His tag antibody/OX40L-His staining for the cell population was calculated (FACSDiva software). Dose-response curves were generated and $EC_{50}$s for antibody blocking of OX40L binding were calculated using GraphPad Prism software; the $EC_{50}$s are shown in Table 12.

TABLE 12

| EC50 values for blocking of OX40L/OX40 interaction as measured by FACS. | |
|---|---|
| Antibody Clone | EC50 (nM) |
| 14B6.C5.C8 | 1.0 |
| 3F4.G11.D2 | 0.54 |
| 8B11.H9.C1 | 0.45 |
| 18E9.G5.H4 | 0.48 |
| 20B3.G12.A2 | 0.93 |
| 20C1.F2.D1 | 0.34 |
| 6E1.A12.A2 | no blocking |
| 23H3.C6 | 0.38 |
| OX40.4 | no blocking |
| OX40.5 | ~1.2e+013 |

As shown in FIG. 16, most of the anti-OX40 antibodies tested fully blocked the binding of soluble human OX40L to human OX40 on the surface of transfected cells, with the exception of 6E1, OX40.4, and OX40.5. The incomplete blocking by OX40.5 may be due to a lower potency of binding to human OX40 than the other antibodies tested or binding to an overlapping but different epitope. In contrast, 6E1 and OX40.4 did not block the binding of human OX-40L to OX40. This lack of blocking is likely due to binding to a different epitope than the remaining antibodies.

Example 8: Antibody Competition/Binning

Antibody binning experiments were carried out as follows. One or more anti-OX40 antibodies were coated directly onto a Biacore CM5 chip using amine coupling chemistry. Anti-OX40 antibodies, serially diluted (1:3) from a starting concentration of 60 μg/mL, were incubated with 20 nM of OX40-6×-His antigen for at least 1 hour. The incubated complex was flowed over the antibody coupled surfaces and observed for cross-blocking. The exercise was repeated with several antibodies on the surface to create the epitope map based on mutual cross-blocking of all the antibodies. OX40L was also coated on the surface to identify and bin the antibodies that were able block OX40-OX40L interaction. Experiments were carried out on Biacore T200 or Biacore 3000 SPR instruments.

As summarized in FIG. 17, antibodies 20C1, 20B3, 8B11, 23H3, 18E9, 14B6, OX40.1, and OX40.2 were ligand blockers; antibody 3F4 was a partial ligand blocker; and 14A2, 6E1, and OX40.5 were ligand non-blockers.

Example 9: Biophysical Properties of OX40 Antibodies

The affinity of several OX40 antibodies for soluble human OX40 was tested by SPR analysis. Briefly, affinity measurements were carried out by capturing 1-10 μg/mL of the respective antibody on a CM5 chip coated with anti-human-CH1. Human-OX40-6×HIS antigen in either a single concentration of 400 nM or a 1:2 serial dilution from 400 nM was used. Experiments were carried out on BIACORE® T200 or BIACORE® 3000 SPR instruments. Data was fit to a 1:1 model.

As shown in Table 13, the anti-OX40 antibodies tested had dissociation constants ($K_D$s) in the range of $10^{-8}$ M to $10^{-9}$ M.

TABLE 13

| $K_D$ values for OX-40 antibodies | | | |
|---|---|---|---|
| Clone | $K_D$ (M) | k-on (1/Ms) | k-off (1/s) |
| 3F4 | 7.13e-9 | 5.31e4 | 3.79e-4 |
| 8B11 | 1.05e-8 | 4.8e4 | 5.1e-4 |
| 14B6 | 8.84e-9 | 7.4E4 | 6.54e-4 |
| 6E1 | 1.1e-8 | 1.28e5 | 1.41e-3 |
| 14A2 | 1.51e-9 | 1.46e5 | 2.2e-4 |
| 18E9 | 2.04e-9 | 6.83E4 | 1.39e-4 |
| 20B3 | 3.71e-9 | 5.42e4 | 2.01e-4 |
| 23H3 | 3.6e-9 | 1.1E5 | 3.95e-4 |
| 20C1 | 3.22e-9 | 6.48E4 | 2.09e-4 |
| OX40.21 | 1.49e-9 | 9.41e+5 | 0.0014 |

The thermal stability of the OX40.21 antibody was also tested, with results summarized in Table 14. Thermal stabilities were determined using GE Healthcare CAP-DSC. Samples were run at 250 μg/mL concentration in PBS. The scan rate was 60° C./hr. Data was fit to a non-2-state model. The OX40.21 antibody was determined to be one of the more stable antibodies tested when considered together with other attributes (e.g., low off-target effects, immunogenicity, etc).

TABLE 14

| Clone | Tm1 | Tm2 | Tm3 | % reversibility |
|---|---|---|---|---|
| 3F4 | | 68 | 83 | |
| 8B11 | | 72.7 | 82.9 | |
| 14B6 | | 66.3 | 70.5 | |
| 18E9 | | 65.8 | 71.2 | |
| 23H3 | | 72.3 | 82.7 | |

TABLE 14-continued

| Clone | Tm1 | Tm2 | Tm3 | % reversibility |
|---|---|---|---|---|
| 20C1 | | 68.0 | 83.0 | |
| OX40.21 | 72.2 | | 79.5 | 48% at 80° C. |

The pharmacokinetics of the OX40.21 antibody after single intravenous dosing to cynomolgus monkeys also was tested. The OX40.21 antibody exhibited acceptable pharmacokinetic (PK) properties after single intravenous (IV) dosing to cynomolgus monkeys with linear PK (0.4 to 4 mg/kg) and a long terminal half-life (6 days).

TABLE 15

Pharmacokinetic parameters of OX40.1 after intravenous administration in cynomolgus monkeys (N = 3)

| Dose (mg/kg) | AUC(INF)* (µg/mL × day) | $t_{1/2}$ (day) | CLT (mL/h/kg) | Vss (mL/kg) |
|---|---|---|---|---|
| 0.4 | 86 ± 5 | 5.6 ± 0.5 | 0.20 ± 0.01 | 36 ± 2 |
| 4 | 785 ± 138 | 6.2 ± 0.6 | 0.22 ± 0.04 | 49 ± 12 |

PK parameters were calculated by a non-compartmental method. Values are mean ± SD.
*PK parameters were calculated using plasma conc. up to 10 days, except monkey 2 at 0.4 mg/kg up to 7 days
*% AUCextra ranged between 24% and 42%

The human PK parameters of OX40.21 were projected from cynomolgus monkey PK data using allometric scaling (assuming power exponent=0.85 for CLT and 1 for $V_{SS}$). The projected human $t_{1/2}$ was 10 days (Table 16). PK parameters were calculated by a two-compartment method.

TABLE 16

Projected Human Pharmacokinetic Parameters of OX40.21

| Ab | Dose (mg/kg) | AUC(INF) (µg/mL × day) | $t_{1/2}$ (day) | CLT (mL/h/kg) | Vss (mL/kg) |
|---|---|---|---|---|---|
| OX40.21 | 1 | 303 | 10 | 0.14 | 47 |

Example 10: FACS Cross-Blocking of PE-Labeled Anti-OX40 Antibody Clone L106 by a Panel of Unlabeled Anti-OX40 Antibodies Several anti-OX40 antibodies were tested for their ability to block the binding of PE-labeled anti-OX40 antibody clone L106 to human OX40-transfected 293 cells. Briefly, 293 cells stably transfected with human OX40 were first incubated with varying concentrations of unlabeled anti-OX40 antibodies. The cells were then washed and incubated with a fixed concentration of 2.5 µg/mL of PE-labeled L106 antibody (BD Biosciences). The fluorescence intensity of the staining was measured using a FACSCanto II flow cytometer (Becton Dickinson). The geometric mean fluorescence intensity (GMFI) of PE-L106 antibody staining for the cell population was calculated (FACSDiva software). Dose-response curves for blocking of L106 binding were generated using GraphPad Prism software.

As shown in FIG. 18, the 18E9 and OX40.1 antibodies fully blocked L106 binding to human OX40-transfected cells, while 20B3 showed partial blocking. The remaining antibodies showed little or no blocking, indicating that 18E9 and OX40.1 bind to a different epitope on OX40 than the other antibodies tested.

Example 11: Cross-Block Analysis of Anti-OX40 Antibodies

This experiment was performed to test the cross-blocking properties of various anti-OX40 antibodies to assess binding specificities. In brief, the OX40 antibody OX40.1 was conjugated to allophycocyanin (APC), and human OX40 antibodies OX40.4 and OX40.5 were biotinylated. A panel of unconjugated human OX40 antibodies were applied in dose to engineered 293 or HT1080 cell lines that overexpress human OX40 protein on their surface and were permitted to bind at 4° C. for 30 min. Without washout of the unconjugated Ab, APC-OX40.1 (1 µg/mL), biotin-OX40.4 (0.4 µg/mL), or biotin-OX40.5 (0.4 µg/mL) was applied to the assay wells and allowed to bind at 4° C. for 30 min. Cells were washed and if necessary further incubated in the presence of streptavidin-APC conjugate under the same conditions. After the final wash, cells were analyzed on a FACSCanto flow cytometer (BD Bioscience, San Jose, Calif.). Mean fluorescence intensity (MFI) signal was proportional to bound conjugated antibody.

As shown in FIGS. 19A-19C, binding of APC-OX40.1 to cells overexpressing human OX-40 protein was blocked by OX40.2 and OX40.5, but only modestly, if at all, by OX40.4. Binding of APC-OX40.1 was blocked by 8B11.H9, 3F4.G11, 20B3.G2, and 14B6.C5, but not by 6E1.A12 and 14A2.B9. A diagram of the observed binding relationships between the antibodies evaluated in FIGS. 19A-19C is shown in FIG. 19H.

FIGS. 19D-19E show that binding of biotin-OX40.4 was strongly blocked by 20B3.G2, moderately blocked by 20C1.F2, weakly blocked, if at all, by 3F4.G11 and 23H3.C6, and was not blocked by 14A2.B9. Binding of biotin-OX40.5 was strongly blocked by 20B3.G2, 23H3.C6, and 20C1.F2, moderately blocked by 3F4.G11, and weakly blocked by 14A2.B9.

FIGS. 19F-19G show that binding of biotin-OX40.4 was not blocked by OX40.1 or OX40.8, and was only weakly blocked, if at all, by OX40.5 or OX40.6. Binding of biotin-OX40.5 was blocked by OX40.1, moderately blocked by OX40.6, and was only very weakly blocked, if at all, by OX40.4 or OX40.6.

A diagram of the observed binding relationships between the Abs evaluated in FIGS. 19D-19G is shown in FIG. 19I.

Example 12: Anti-OX40 Antibodies Bind to a Conformation Epitope/Epitope Mapping This example shows that OX40.21 binds to non-denatured human OX40, but not to denatured human OX40, and that binding is not affected by N-glycosylation.

Binding of OX40.21 to native or denatured OX40 that has N-linked glycosylation or not was determined as follows. Samples of native (i.e., non-denatured) and denatured human OX40 were incubated with or without the enzyme N-glycanase PNGase F to remove N-glycosylation. Samples of native human OX40 with or without N-linked glycosylation were subjected to SDS gel electrophoresis, and samples of denatured human OX40 with or without N-linked glycosylation were subjected to denaturing SDS gel electrophoresis.

As shown in FIG. 20A, OX40.21 binds only to native OX40, and not to the denatured form, and the presence or absence of glycosylation does not affect binding to OX40. FIGS. 20B and 20C show that two N-glycopeptides were identified by peptide mapping after deglycosylation (60% occupancy for both AspN118 and AspN12).

These data suggest that OX40.21 binds to an epitope that is conformational and independent of N-linked glycosylation.

Epitope mapping studies were also conducted using mass spectrometry. Peptide fragments of his-tagged human OX40 ("hOX40") were generated by enzymatic digestion with endoproteinases. LC-MS was peformed using AB Sciex 5600 Triple-TOF.

As shown in FIGS. 20D and 20E, binding experiments from native hOX40 by limited proteolysis revealed that OX40.16 and OX40.21 bound predominantly to the peptide DVVSSKPCKPCTWCNLR (SEQ ID NO: 178), which corresponds to amino acids 46-62 of the extracellular portion of mature human OX-40 (SEQ ID NO: 2). OX40.8 bound to the peptide DSYKPGVDCAPCPPGHFSPGDNQACKP-WTNCTLAGK (SEQ ID NO: 179), which corresponds to amino acids 89-124 of the extracellular portion of mature human OX40 (SEQ ID NO: 2). The location of the epitope bound by OX40.21 overlaps part of the binding site of OX40 ligand as determined by crystal structure of the human OX40/OX40L complex (Protein Data Bank (PDB) ID code 2HEV). Additional peptides identified by mass spectrometry for OX40.21 are shown in the upper panel of FIG. 20E, and include QLCTATQDTVCR (SEQ ID NO: 184), SQNTVCRPCGPGFYN (SEQ ID NO: 185), SQNTVCRPCGPG-FYNDVVSSKPCKPCTWCNLR (SEQ ID NO: 182), and PCKPCTWCNLR (SEQ ID NO: 183).

Example 13: Anti-OX-40 Antibodies Promote T Cell Proliferation and Induce IFN-γ and IL-2 Secretion from T Cells Anti-OX-40 antibodies were tested for their ability to induce T cell activity in vitro by measuring the proliferation of and amount of IL-2 and IFN-γ secreted by T cells incubated with the antibodies.

A transfected CHO cell line was generated for use as artificial antigen-presenting cells in a primary T cell activation assay. The CHO-CD3-CD32A cell line expresses anti-human CD3 antibody in a single-chain Fv format, along with the human Fc receptor CD32A to present anti-OX40 antibodies on the CHO cell surface. Briefly, human primary CD4 T cells were isolated by negative selection (RosetteSep™, StemCell Technologies) and co-cultured with irradiated CHO-CD3-CD32A cells at an 8:1 T:CHO ratio, in the presence of graded doses of anti-OX40 antibodies or isotype control antibody. After 3 to 4 days in culture at 37° C., supernatants were harvested for assessment of T cell activation by means of measurement of secreted human IFNγ either by ELISA (BD Biosciences) or HTRF assay (Cisbio), following the manufacturers' recommendations. Afterwards, tritiated thymidine was added for the final approximately 18 hours of culture to measure T proliferation by tritiated thymidine incorporation, as an additional assessment of T cell activation.

As shown in FIGS. 21A-21D and 22A-22D (and summarized in Table 17 below), most tested anti-OX40 antibodies strongly potentiated human CD4 T cell activation stimulated by CHO-CD3-CD32 cells, in a dose-dependent manner, as measured by proliferation and IFNγ secretion. The panel of antibodies tested in this assay co-stimulated T cell activation at least as well as, or better than, OX40.1, OX40.4, and OX40.5.

TABLE 17

| Name | Proliferation $EC_{50}$ (nM) (mean ± SD) | n | IFNγ $EC_{50}$ (nM) (mean ± SD) | n |
|---|---|---|---|---|
| 3F4 | 0.016 ± 0.008 | 5 | | |
| 8B11 | 0.022 ± 0.027 | 3 | | |
| 18E9 | 0.010 ± 0.005 | 3 | | |
| 20B3 | 0.008 ± 0.003 | 3 | | |
| 20C1 | 0.008 ± 0.006 | 4 | | |
| 23H3 | 0.028 ± 0.017 | 3 | | |
| 6E1 | 0.014 ± 0.008 | 2 | | |
| 14A2 | 0.037 ± 0.044 | 4 | | |
| 14B6 | 0.012 ± 0.008 | 3 | | |
| OX40.6 | 0.032 ± 0.028 | 2 | 0.033 ± 0.004 | 2 |
| OX40.8 | 0.043 ± 0.037 | 2 | 0.024 | 1 |
| OX40.16 | 0.017 | 1 | 0.044 | 1 |
| OX40.17 | 0.009± | 1 | 0.044 | 1 |
| OX40.18 | 0.230± | 1 | 0.490 | 1 |
| OX40.21 | 0.011 ± 0.006 | 9 | 0.043 ± 0.023 | 9 |
| OX40.1 | 0.024 ± 0.012 | 4 | | |
| OX40.4 | 0.094 | 1 | ⁻2.3 e+009 | 1 |
| OX40.5 | 1.900 | 1 | ⁻37 | 1 |

The anti-human OX40 antibodies were also tested for their effects on stimulating primary T cells in cultures of staphyloccus enterotoxin B (SEB)-activated human peripheral blood mononuclear cells (PBMCs). Human whole blood was obtained from AllCells, Inc. (Berkeley, Calif.) or from donors at Bristol-Myers Squibb, Redwood City, Calif. under the auspices of an in-house phlebotomy program. PBMCs were isolated by gradient purification on a Ficoll-Hypaque cushion and cultured for 3 days in culture medium supplemented with fixed, suboptimal (85 ng/mL) of superantigen staphylococcus enterotoxin B (SEB; Toxin Technologies, Sarasota, Fla.) in the presence of graded doses of OX40 antibodies or isotype control antibody together with 2-5 μg/mL of soluble cross-linking antibody, F(ab')2 goat anti-human Fcγ. After culturing for 3 days at 37° C., supernatants were harvested for assessment of T cell activation by means of ELISA measurement of secreted human IL-2. Briefly, culture supernatants were diluted 1:10 in sample diluent and tested for the presence of human IL-2 by ELISA (BD Bioscience) per the manufacturer's recommended protocol. Following the addition of TMB substrate, assay plates were read on a Spectramax 340PC reader using Softmax operating software at a wavelength of 650 nm. Measured optical densities of the chromogenic substrate were proportional to bound detecting antibody.

Figure 23A:
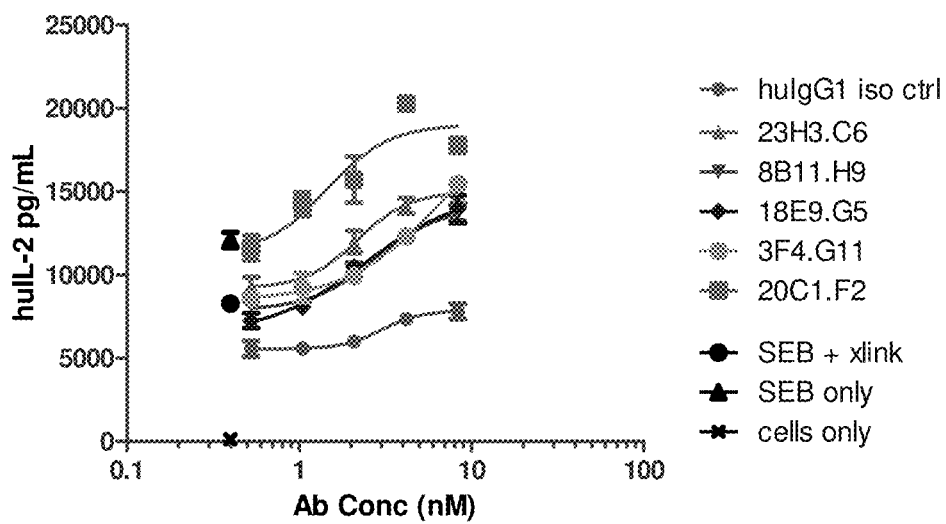
Figure 23B:
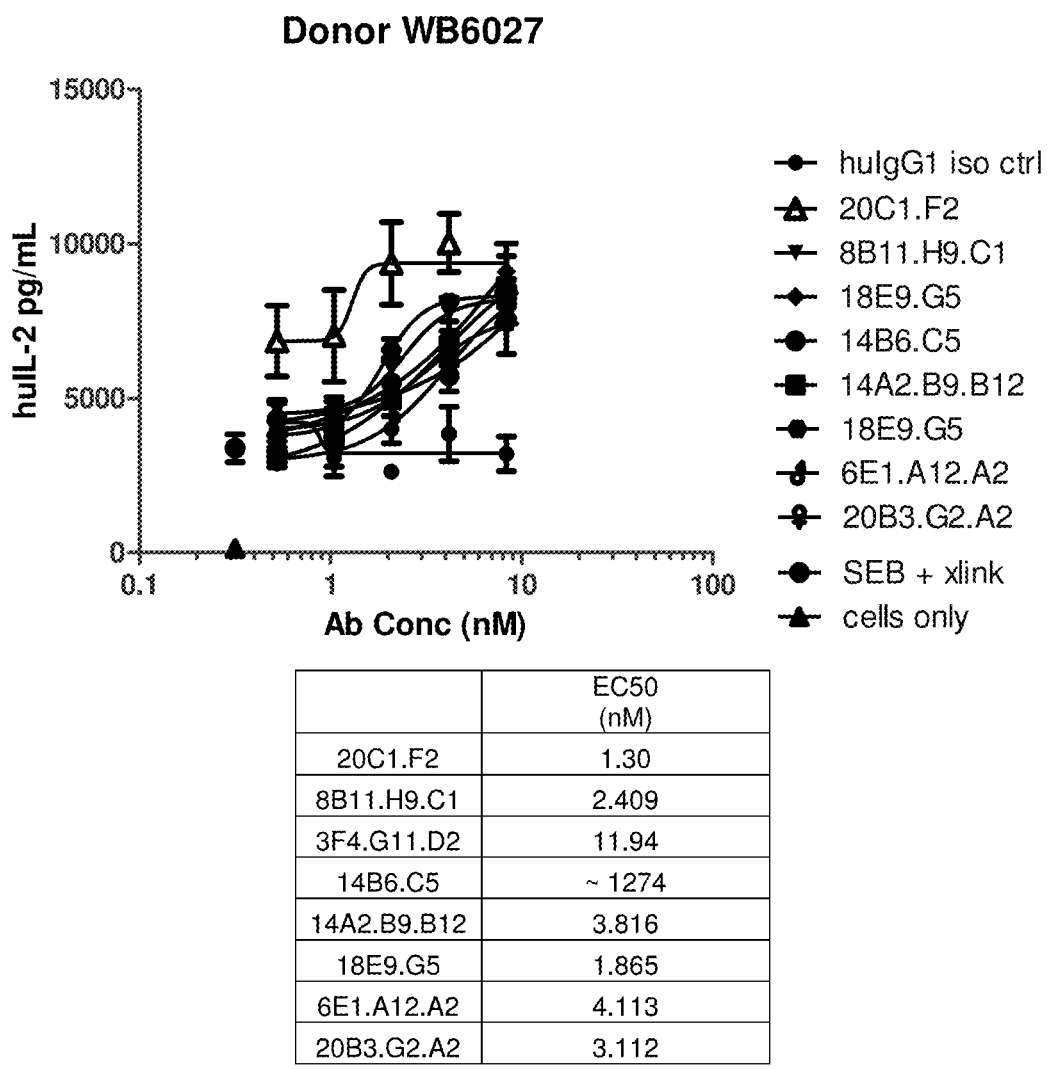
Figure 23C:
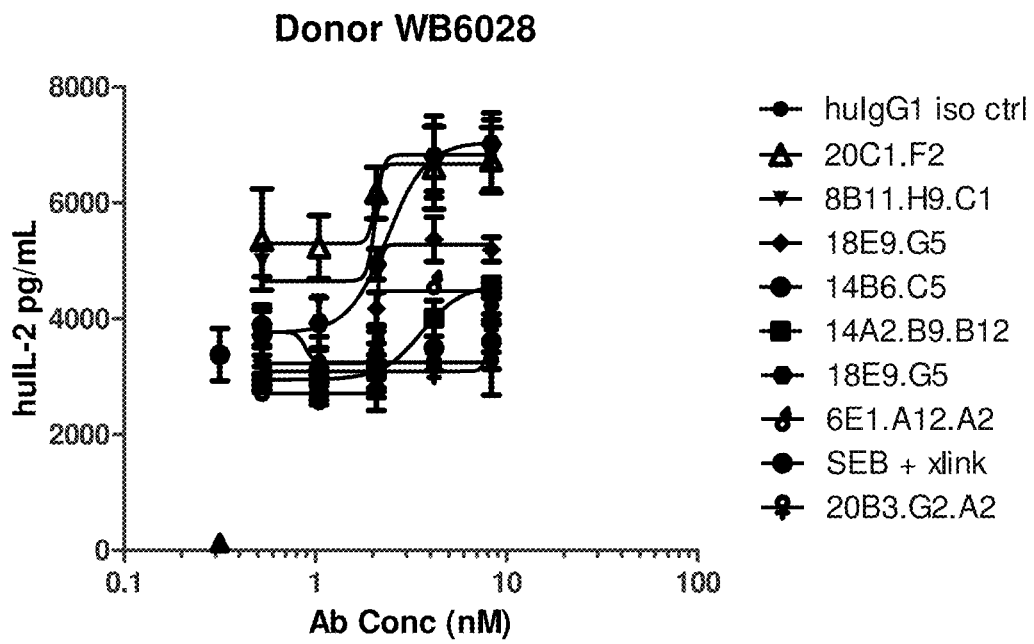
Figure 23D:
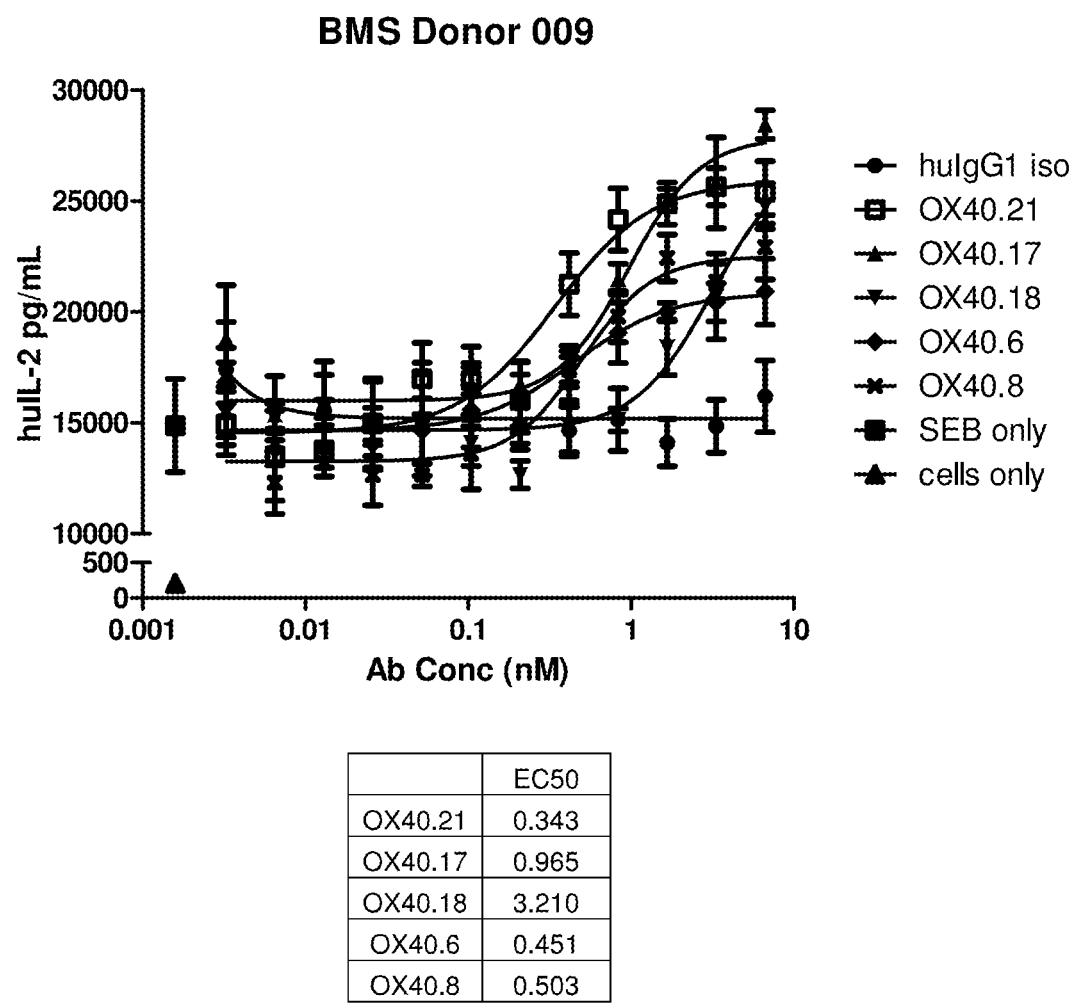
Figure 23E:
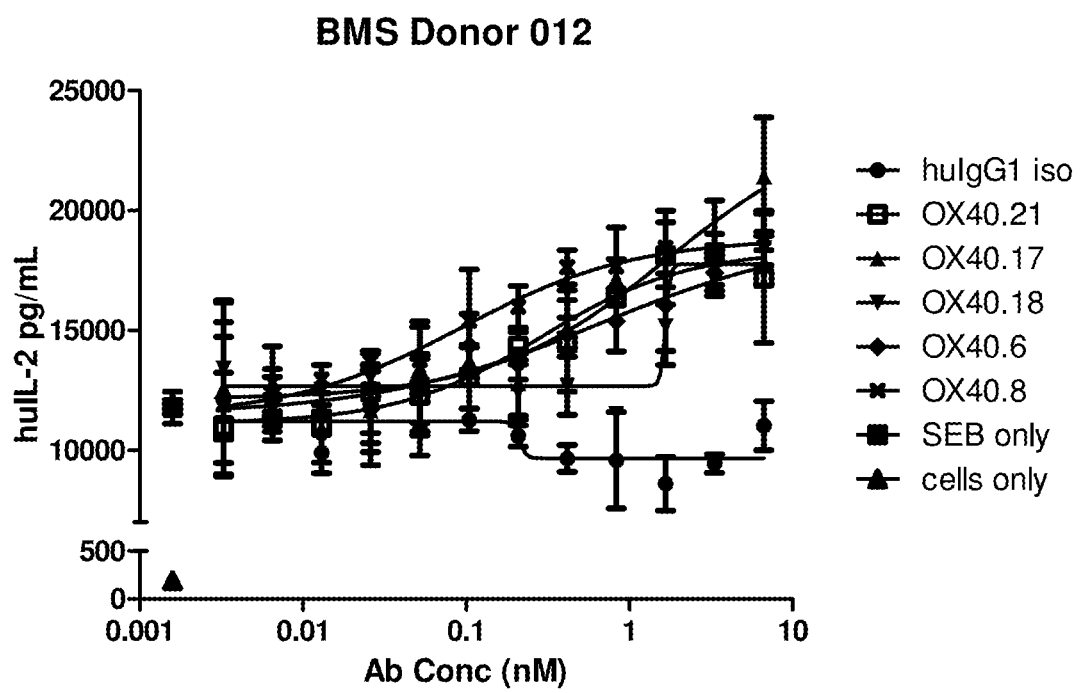
Figure 23F:
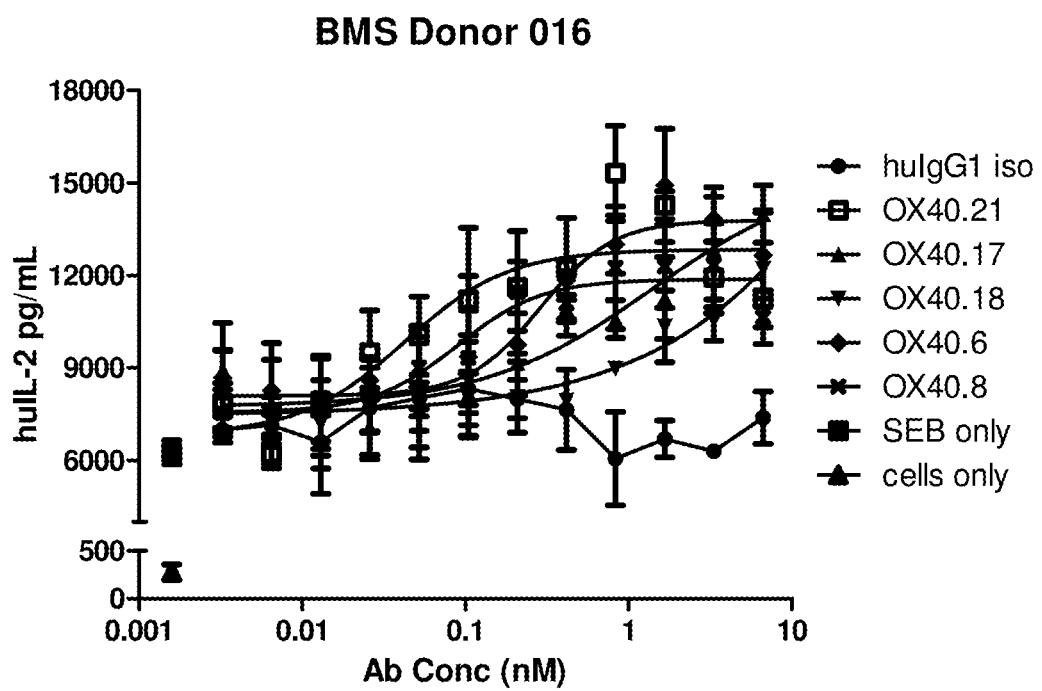

Data from PBMCs isolated from different donors are shown in FIGS. 23A-23F. In general, solubly-crosslinked clone 20C1.F2 elicited a more robust cytokine response ($EC_{50}$ of 1.3-2.0 nM) compared to solubly-crosslinked clones 23H3.C6, 8B11.H9, 3F4.G11, 18E9.G5, 6E1.A12, and 20B3.G2 (FIGS. 23A-23C). With respect to antibodies with variable region mutations, OX-40.21, in general, elicited a more robust cytokine response compared to solubly-crosslinked antibodies OX-40.17, OX40.18, OX40.6, and OX40.8 (FIGS. 23D-23F). Data from these donors together with data from 8 additional donors, in which additional anti-OX40 antibodies were tested, collectively demonstrate that on average, OX40.21 exhibited superior potency in enhancing T cell responses compared to OX40.1, OX40.2, OX40.4, OX40.5, OX40.17, and OX40.18. These results further demonstrate that OX40.21 elicits responses that are comparable to those elicited by OX40.6 and OX40.8 (Table 18).

TABLE 18

| Donor # | | OX40.21 | OX40.17 | OX40.18 | OX40.6 | OX40.8 | | | |
|---|---|---|---|---|---|---|---|---|---|
| BMS-009 | EC50 (nM) | 0.34 | 0.97 | 3.21 | 0.45 | 0.50 | | | |
| BMS-012 | EC50 (nM) | 0.29 | 1.74 | ~1.67 | 0.66 | 0.09 | | | |
| BMS-016 | EC50 (nM) | 0.04 | 1.40 | >100 | 0.29 | 0.09 | | | |

| Donor # | | OX40.21 | OX40.17 | OX40.18 | OX40.6 | OX40.8 | OX40.1 | OX40.2 | OX40.4 | OX40.5 |
|---|---|---|---|---|---|---|---|---|---|---|
| WB10024 | EC50 (nM) | 0.82 | 1.06 | ~3.17 | ~0.42 | ~0.44 | 1.87 | 2.53 | 1.25 | ~1.83 |
| WB10025 | EC50 (nM) | 1.31 | 1.35 | ~1.14 | ~0.85 | 0.79 | 2.08 | ~3.26 | 1.08 | 3.07 |
| WB10026 | EC50 (nM) | 0.79 | 1.68 | 3.02 | 0.28 | 0.63 | 2.24 | 3.16 | 1.14 | 2.59 |
| WB10027 | EC50 (nM) | 1.08 | 1.15 | ~3.27 | 0.45 | ~0.46 | 1.26 | 2.26 | 0.93 | ~3.09 |
| WB10137 | EC50 (nM) | 0.56 | 0.92 | >100 | 0.56 | 0.42 | ~1.824 | >100 | 1.37 | >100 |
| BMS-001 | EC50 (nM) | 0.41 | 0.41 | ~84.76 | 0.49 | ~0.42 | 0.64 | 4.95 | ~0.89 | ~0.43 |
| BMS-004 | EC50 (nM) | ~0.84 | 1.03 | 2.43 | 0.48 | 0.55 | 2.52 | 13.89 | 0.84 | 1.94 |
| BMS-015 | EC50 (nM) | 0.76 | 1.16 | >100 | ~0.46 | ~0.42 | 2.41 | >100 | 0.91 | 1.92 |
| | Mean EC50 (nM) | 0.64 | 1.17 | 2.89 | 0.46 | 0.44 | 1.86 | 5.36 | 1.07 | 2.38 |

*Each set of experiments was performed on different days.

Example 14: Anti-OX40 Antibody Promotion of NK92-Mediated Cell Lysis Using Cell Lines Several anti-human OX40 antibodies were tested for their ability to promote NK92 cell-mediated lysis of activated CD4+ T cells using calcein release as a read-out. Briefly, CD4+ T cells for use as target cells were separated by negative selection using magnetic beads and activated for 72 hours with beads coated with anti-CD3 and anti-CD28. After three days, NK92 cells were plated with calcein AM-labeled activated CD4+ cells at a ratio of 5 to 1. A titration of each anti-OX40 antibody was added and cells were incubated for two hours. Calcein release was measured by reading the fluorescence intensity of the media using an Envision plate reader (Perkin Elmer). The percentage of antibody-dependent cell lysis was calculated based on mean fluorescence intensity (MFI) with the following formula: [(test MFI−mean background)/(mean maximum−mean background)]×100.

As shown in FIG. 24, OX40.8 and OX40.16 induced the highest amount of specific lysis of target cells (60% and 30%, respectively). The $EC_{50}$ of OX40.8 was 16 ng/mL and that for OX40.16 was 4 ng/mL. All other antibodies tested induced ADCC at levels too low for accurate quantitation.

Example 15: Anti-OX40 Antibody Promotion of NK-Mediated Cell Lysis of Primary Human CD4+ T Cells Several anti-human OX40 antibodies were tested for their ability to promote primary NK cell-mediated lysis of activated CD4+ T cells. Briefly, CD4+ T cells for use as target cells were separated from PBMCs from two donors by magnetic selection and activated for 72 hours with beads coated with anti-CD3 and anti-CD28. NK cells, for use as effectors, were separated from a separate donor by negative selection using magnetic beads and activated with IL-2 for 24 hrs. Following the activation period, NK effector cells were mixed with calcein-labeled target T cells at 20:1, 10:1, or 5:1 ratios in the presence of antibody at 1 μg/ml for 2 hours. The level of calcein released by lysed target cells was measured by reading the fluorescence intensity of the media using an Envision plate reader (Perkin Elmer). The percentage of antibody-dependent cell lysis was calculated based on mean fluorescence intensity (MFI) with the following formula: [(test MFI−mean background)/(mean maximum−mean background)]×100.

As shown in FIGS. 25A and 25B, activated CD4+ T cell targets from two donors were lysed most effectively by OX40.8. Lower levels of ADCC activity were seen with both OX40.21 and OX40.1.

Example 16: OX40 Antibody Promotion of Macrophage-Mediated Cell Phagocytosis of OX40-Expressing HEK293 Cells To determine the antibody-mediated phagocytic activity of several OX40 antibodies, primary human macrophages were cultured for four hours with CellTrace Violet-labeled HEK293/OX40 cells and a titration of anti-OX40 antibodies. After four hours, cells were harvested, stained with anti-CD64-APC, and run on a flow cytometer. Cells that stained double positive for CD64 and CellTrace Violet were considered to have been phagocytosed. The percentage of target cells phagocytosed was calculated using the formula: 100×(Number of double positive cells/Total number of CellTrace Violet positive cells).

As shown in FIG. 26, all tested anti-OX40 antibodies induced the phagocytosis of OX40-expressing target cells in a dose-dependent manner. OX40.8 had the highest overall level of phagocytosis and the lowest $EC_{50}$ concentration of 6.2 ng/mL. This demonstrates that human IgG1 anti-OX40 antibodies induce FcR-mediated phagocytosis in a dose-dependent manner.

Example 17: Anti-OX40 Antibodies Bind the C1q Component of Human Complement

A colorimetric ELISA assay was developed to evaluate whether the C1q component of human serum complement binds to the OX40.21 antibody. All tested antibodies were coated on a high binding immunoassay plate at 10 μg/mL. After blocking unoccupied protein binding sites, graded doses of human C1q (3.125-200 μM) were added to the wells, including blocked empty wells that served as controls for non-specific background C1q binding to the assay plate. Binding of C1q to the immobilized antibodies was detected using a combination of biotinylated mouse anti-C1q antibody and streptavidin-poly-HRP, together with tetramethylbenzidine substrate. The results are reported as the optical density read at 450 nm minus 630 nm.

As shown in FIG. 27, C1q bound to OX40.21 (solid squares) and the human IgG1 isotype control (open circles) in a dose dependent manner. The level of C1q binding to OX40.21 however, was lower than to the human IgG1 isotype control antibody. As expected, there was little background signal (gray circles) and no evident C1q binding to an IgG1.1 isotype control (solid black circles). The IgG1.1 antibody contains five mutations in the Fc portion designed to eliminate C1q binding and FcR interaction. This result demonstrates that the C1q component of human serum complement can bind to OX40.21 and indicates that OX40.21 may induce complement mediated lysis of OX40-expressing cells in vivo.

Example 18: OX40 is Expressed in Tumor Infiltrating Lymphocytes

OX-40 is expressed in tumor infiltrating lymphocytes, with a pattern that is generally limited to CD4+ cells (FIG. 28A) with minimal expression on CD8+ T cells (FIG. 28B) in colorectal, lung, and ovarian cancer (FIG. 28C).

Similarly, OX40 is expressed by CD4+ T cells and Tregs in mouse Sa1N tumors (FIG. 28D) and mouse MC38 tumors (FIG. 28E). To test expression of mouse OX-40 in tumors, $2 \times 10^6$ SA1N sarcoma cells or $2 \times 10^6$ MC38 cells were implanted subcutaneously into AJ or B6 mice respectively. On day 15 post-implantation, tumors were harvested, dissociated into single cell suspensions, and stained for flow cytometry. T cell populations were identified based on their expression of CD8, CD4 and Foxp3. For Sa1N tumors, CD4+ Foxp3+ cells from the tumor are shown in the red histogram, CD4+ Foxp4-cells are in the blue histogram and CD8+ cells are in the orange histogram (FIG. 28D). Isotype control stained cells are in the green histogram. For MC38 tumors, Tregs are shown in the blue histogram, CD4+ cells are shown in the green histogram and CD8+ cells in the red histogram (FIG. 28E).

Example 19: Anti-OX40 Antibody Reversal of Treg Cell-Mediated Suppression

Several anti-human OX40 antibodies were tested for their ability to reverse regulatory T (Treg) cell-mediated suppression of human CD4+ T cell proliferation. Briefly, Treg and T responder (Tresp) cells were isolated by enriching PBMCs for CD4+ cells by magnetic bead separation and then sorting $CD4^+CD25^{hi}CD127^{lo}$ Treg and $CD4^+CD25^{lo}CD127^{hi}CD45RO^+$ Tresp cells. Tresp cells were then labeled with proliferation dye and plated with titrating numbers of Treg cells, beginning at a 1:1 ratio. Cultures were stimulated with 3 µg/mL plate-bound anti-CD3, 1 µg/mL soluble anti-CD28, and 2 µg/mL plate-bound anti-OX40 or isotype control. After 96 hours, Tresp cell proliferation was measured by assessing dye dilution using flow cytometry.

As shown in FIG. 29, in both the presence and absence of Treg cells, the anti-OX40 antibodies increased Tresp cell proliferation compared to the isotype control. This suggests that the anti-OX40 antibodies tested reversed the suppressive effects of Treg cells on Tresp cell proliferation.

Example 20: Toxicity Studies

OX40.6 (2 mg/kg) was administered intravenously to monkeys on Days 1 (FIG. 30A) and 29 (FIG. 30B) to evaluate any associated toxicities. No evidence of tolerability issues or clinical pathology abnormalities was observed. OX40.6 stimulated an enhanced immune response to KLH as characterized by a trend towards enhanced CD69 expression in CD4+ T cells in an ex vivo KLH recall assay. Two of 4 monkeys exhibited accelerated clearance, which correlated with the formation of anti-drug antibodies.

The concentration of OX40.6 in cynomolgus monkey serum samples for the experiment above was analyzed by a chemiluminescence (CL) immunoassay. OX40.6 antibody was used to prepare calibrators and quality control (QC) samples. Biotinylated-human-OX40-his was immobilized on streptavidin-coated microplates (Greiner Bio-one) as a capture molecule for OX40.6. Samples, standards, and quality control samples brought up to a final matrix of 10% cyno serum were incubated on the plates. Samples were analyzed at 10% minimum required dilution in 1% BSA/PBS/0.05% Tween 20 (PTB) containing 2% mouse serum. The unbound material was washed away and the captured OX40.6 antibody was detected using an HRP-labeled mouse monoclonal anti-human IgG antibody as the detection molecule. Following addition of SuperSignal ELISA Pico Chemiluminescent Substrate (Thermo Scientific), the concentration of OX40.6 in cyno serum samples was calculated from luminescence intensity as measured by a M5 plate reader using a 4-parameter logistic (4-PL) calibration curve generated from OX40.6 antibody calibrators. The range of the OX40.6 antibody calibration curve was from 5 to 5,000 ng/mL in cyno serum. The upper and lower limits of quantification were 5,000 and 10 ng/mL, respectively (i.e., ULOQ 5000 ng/mL, LLOQ 10 ng/mL). Quality control samples were prepared at 3750, 400, and 20 ng/mL in cynomolgus monkey serum and analyzed on each plate to ensure acceptable assay performance. Calibrators, QCs, and samples were diluted 5-fold in PTB containing 2% mouse serum. Four streptavidin plates were used to analyze the samples. Assay performance was within an acceptable range: interplate % CV of standards was below 25%, and QC recovery was within ±30% nominal values.

The presence of anti-drug antibodies to OX40.6 in cynomolgus monkey serum in the experiment described above was determined by electrochemiluminescence (ECL) bridging immunoassay. Specifically, mouse monoclonal anti-human IgG Fc antibody was used to prepare the positive control. Biotinylated-anti-OX40: anti-hOX40-his was used at 25 ng/mL as the capture molecule and ruthenylated-anti-OX40:anti-hOX40-his was used at 25 ng/mL as the detection molecule. Samples were analyzed at 100-fold dilution in 1% BSA/PBS/0.05% Tween 20 (PTB) containing capture and detection molecules. After 2 hours of incubation in polypropylene plates, the sample mix was transferred to streptavidin-coated MSD plates. Following a one hour incubation, unbound material was washed away, MSD read buffer was added, and ECL was measured with the MSD plate reader S16000. The positive control (Mouse anti-human IgG Fc) was prepared at 1000 (HPC), 100 (MPC), and 10 ng/mL (LPC) in cynomolgus serum. Pooled cynomolgus serum was used as a negative control (NC). The signal ratio for HPC, MPC, and LPC versus NC was 102, 10, and 2, respectively. One streptavidin plate was used to analyze the samples. Assay performance was within the acceptable range: % CV of the PC was below 10%, and the raw signal for the negative control (54 RLU) was comparable to the raw signal for predose samples (48-55 RLU).

Example 21: Immunogenicity Risk Assessment Study

In vitro T cell proliferation assays were conducted for several of the anti-human OX40 antibodies to assess their human immunogenicity potential. Briefly, peripheral blood mononuclear cells (PBMC) from healthy volunteers were isolated by Ficoll (GE Healthcare) and gradient centrifugation, and human lymphocyte antigen (HLA) Class II was characterized by polymerase chain reaction (PCR) amplification and hybridization with oligonucleotide probes (ProImmune).

A panel of 40 PBMC donors having HLA Class II types closely matching world population frequencies was used for an assay run. PBMCs were labeled with CFSE (Invitrogen) to monitor proliferation and plated on 96 well plates in 6 replicates at 200,000 cells per well in RPMI (Lonzo) containing 10% human AB (Bioreclamation), non essential amino acids (Gibco), and pen-strep (Gibco). Anti-human OX40 antibodies, controls proteins, reference antibodies, and ConA were cultured with PBMCs at 1 µM for 7 days, after which media was washed away and cells were labeled with an anti-human CD4 APC (BD science) monoclonal antibody. After removal of unbound anti-CD4 antibody with a wash step, cells were fixed with 3.7% formalin (Sigma) in PBS, and analyzed by flow cytometry to determine the percentage of proliferating CD4+ cells.

The percentage of 40 donors that showed a positive response (defined as a significant increase in proliferating CD4+ T cells relative to media-incubated PBMCs) for the different anti-human OX40 antibodies is shown in FIG. 31. All variants of the anti-human OX40 antibodies showed low potential to activate CD4+ cells in this assay, comparable to the low QC protein, with the exception of OX40.16 and OX40.21, which did not show a positive CD4 proliferation response in any of the 40 donors. These results suggest that these anti-human OX40 antibodies have low potential to elicit an anti-drug antibody response in humans.

Example 22: Binding to Activated Fc Receptors Enhances Anti-mOX40 Activity in a Colon Carcinoma Model To test the role of FcR binding in the activity of anti-mouse OX40 antibodies in mouse tumor models, anti-OX40 antibodies of different isotypes were tested. C57BL/6 mice were subcutaneously injected with 2 million MC38 tumor cells. After 7 days, tumor volumes were determined and mice were randomized into treatment groups so as to have comparable mean tumor volumes. Antibodies formulated in PBS were administered intraperitoneally on days 7, 10, and 14 at 200 µg per dose in a volume of 200 µl.

In syngeneic mouse tumor models, anti-murine OX40 antibodies (e.g., OX86, rat IgG1) exhibit anti-tumor activity. Since varying the isotype of many antibodies specific for T cell surface receptors (both co-stimulatory and co-inhibitory) can alter the anti-tumor activity of these antibodies, mouse Fc isotype variants of OX86, an antibody which does not block the OX40/OX40L interaction, were generated. As shown in FIGS. 32A-32C, OX86 formatted as a mouse IgG2a Fc (FIG. 32C) results in superior anti-tumor activity compared to OX86 formatted as a mouse IgG1 (FIG. 32B). This is likely due both to depletion of Treg cells at the tumor site and to T effector cell expansion from antibody-mediated agonism of OX40.

To confirm the effects of different antibody isotypes on tumor infiltrating T cell populations, tumors from MC38 mice that were treated with the different isotypes were assessed by flow cytometry. Selected mice were sacrificed and tumors and spleens were harvested for analysis on day 15 after tumor implantation. Single cell suspensions were prepared by dissociating tumor and lymph node with the back of a syringe in a 24 well plate. Cell suspensions were passed through 70 µm filters, pelleted, resuspended, and counted. Cells were then plated in 96 well plates with 1×10⁶ cells per well for staining. Samples were then analyzed on a FACS Canto flow cytometer (BD). Analysis of the spleens and tumors of tumor bearing mice treated with anti-OX40 antibodies show that the IgG2a isotype can deplete CD4+ Tregs in tumors (FIG. 33A), and that IgG1 and IgG2a isotypes can activate T cell expansion in the periphery (FIG. 33B) and result in increased cell numbers in the spleen (FIG. 33C). These results suggest that agonism of OX40 (but not necessarily blocking the OX40/OX40L interaction) and Fc receptor binding of the OX86 antibody promotes anti-tumor activity.

The role of human Fc and FcRs were tested using mice where mouse FcRs have been knocked out and replaced with the human FcRs. These experiments were performed using a bone marrow chimera system where CD45.1 congenic hosts were irradiated then reconstituted with human FcR transgenic bone marrow cells. These mice were then allowed to reconstitute for 8 weeks before being inoculated with 2×10⁶ MC38 tumor cells. After 7 days, tumor volumes were determined and mice were randomized into treatment groups so as to have comparable mean tumor volumes. Antibodies formulated in PBS were administered intraperitoneally on days 7, 10, and 14 at 200 µg per dose in a volume of 200 µl. Mice were treated with either a control human IgG1 (FIG. 34A), a chimeric OX-86 human G1 hybrid Ab (FIG. 34B), or the OX-86 human G1 hybrid with a S267E mutation (FIG. 34C). The results were similar to what was observed with the mouse isotypes, i.e., the human IgG1 antibody had a significant anti-tumor effect as it can bind to activating FcRs, while the S267E mutation which increases binding to both CD32B and CD32A had higher activity (FIGS. 34A-34C). This higher level of activity is likely due to increased agonism on effector T cells as well as increased depletion of Tregs at the tumor site.

Figure 35A:
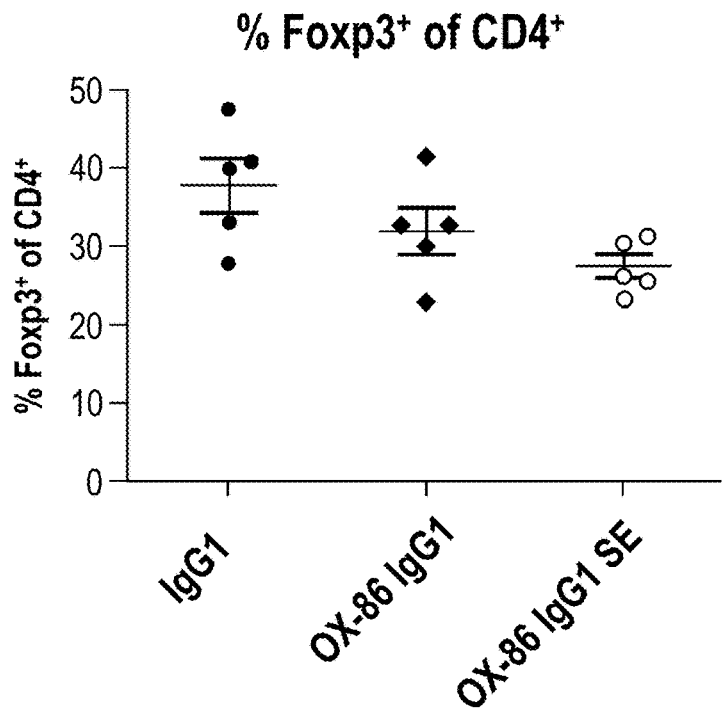
Figure 35B:
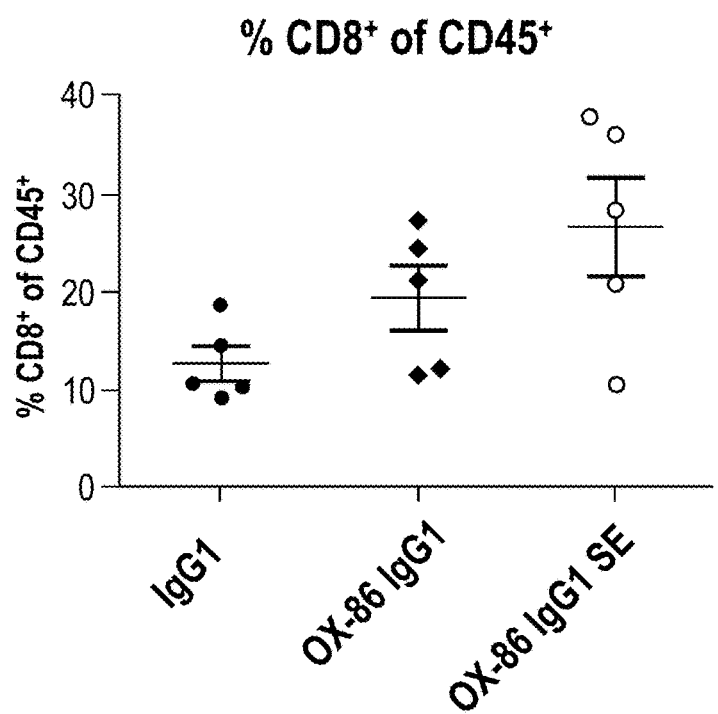
Figure 35C:
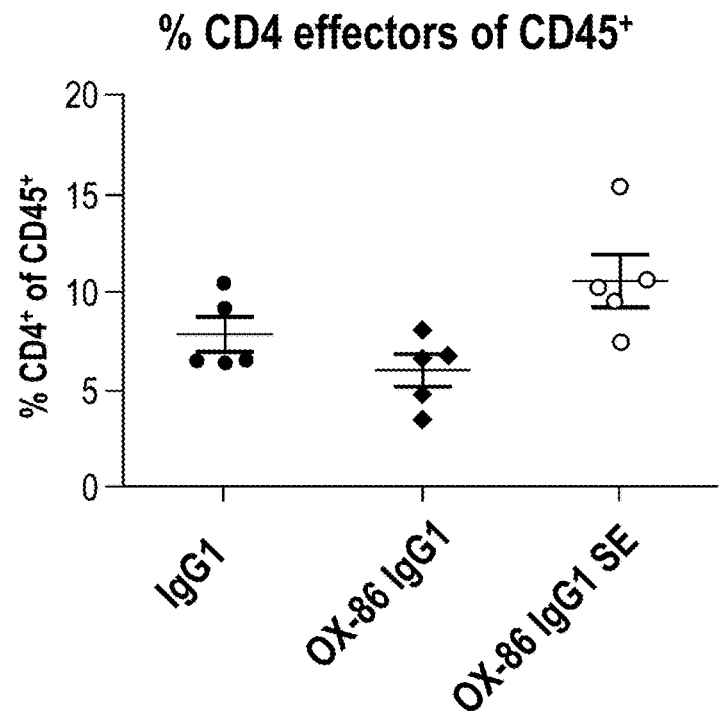
Figure 35D:
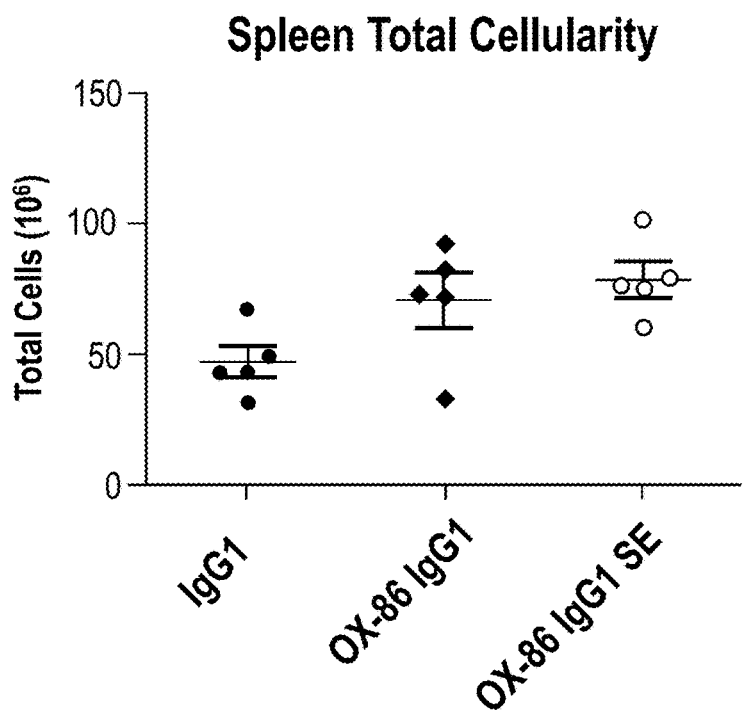

T cell populations at the tumor site and spleens of tumor bearing mice were examined as described earlier. Tregs were less prevalent in mice treated with either the G1 or G1 S267E antibody, with a larger effect seen with the S267E isotype (FIG. 35A). Increases in the percentages of CD8+ T cells (FIG. 35B) and CD4+ effector (FIG. 35C) and at the tumor site were also evident, and these increases were greater with the G1 S267E antibody. Increased cellularity in the spleens of mice treated with the anti-OX-40 antibodies was also noted (FIG. 35D). These results suggest that the OX86-hIgG1 antibody exhibited potent anti-tumor activity (FIGS. 34A-34C) and measurable Treg depletion (FIGS. 35A-35D).

Example 23: A Blocking Anti-OX40 Antibody Exhibits Anti-Tumor Activity in a Mouse Tumor Model The following experiment was conducted to determine whether an antibody which blocks the interaction between OX40/OX40L exhibits potent anti-tumor activity. To this end, a hamster anti-mouse OX40 antibody which blocks the OX40/OX40L interaction (hamster IgG1 8E5 antibody) was generated and tested for its anti-tumor activity in a subcutaneous mouse CT-26 tumor model. CT-26 is a mouse colon adenocarcinoma tumor cell line whose solid tumor growth can be monitored in BALB/c mice when the cells are transplanted subcutaneously.

Female BALB/c mice (Charles River Laboratories, Hollister, Calif.) were acclimated for a minimum of three days prior to the start of the studies. Mice were housed 5 animals per cage, and the cages were placed in microisolator ventilated racks. Housing was at 18-26° C. and 50+20% relative humidity with at least twelve room air changes per hour. A 12 h light/dark cycle was maintained. Animals were provided with sanitized laboratory rodent diet and municipal water ad libitum.

CT-26 cells were maintained in RPMI-1640 medium (Hyclone, Cat. No. SH30096.01) supplemented with 10% fetal bovine serum (FBS; Hyclone, Cat. No. SH30071.03). Approximately twice a week, cells contained in a single T175 flask were divided and expanded to four T175 flasks at a 1:5 dilution until sufficient number of cells were obtained for tumor implantation. The cells were harvested near 80% confluence, washed and resuspended in PBS.

On Day 0, $1 \times 10^6$ CT-26 cells were implanted into the mice using a 1 cc syringe (Becton Dickinson, Franklin Lakes, N.J.) and 27 gauge ⅝ inch needle. Tumors were then measured two times weekly in 3 dimensions with an electronic caliper (Mitutoyo, Aurora, Ill.) and recorded. Tumor volumes ($mm^3$) were calculated using the formula: width×length×height×0.5. Following tumor volume measurements on Day 6 post implantation, mice were staged according to tumor volume. Mice with a mean tumor volume of 26 $mm^3$ were randomized into groups and treated as shown in Table 19.

The hamster isotype control antibody is an inert Armenian hamster IgG monoclonal antibody (mAb) to GST (clone PIP, catalog # BE0260; BioXcell, West Lebanon, N.H.). It was prepared in PBS immediately prior to administration to provide doses of 10 mg/kg per mouse via intraperitoneal (IP) injection on Days 6, 10 and 14 as shown in Table 19.

The monoclonal antibody against mouse OX40 (clone 8E5) was prepared in PBS immediately prior to administration to provide doses of 10, 3, 1 or 0.3 mg/kg per mouse via IP injection on Days 6, 10 and 13 as shown in Table 19.

TABLE 19

| Treatment | Dose | N | Route | Treatment schedule |
|---|---|---|---|---|
| Hamster IgG Istoype Control mAb | 10 mg/kg | 12 | IP | Days 6, 10, 14 |
| Hamster anti-mouse OX40 (clone 8E5) mAb | 10 mg/kg | 12 | IP | Days 6, 10, 14 |
| Hamster anti-mouse OX40 (clone 8E5) mAb | 3 mg/kg | 12 | IP | Days 6, 10, 14 |
| Hamster anti-mouse OX40 (clone 8E5) mAb | 1 mg/kg | 12 | IP | Days 6, 10, 14 |
| Hamster anti-mouse OX40 (clone 8E5) mAb | 0.3 mg/kg | 12 | IP | Days 6, 10, 14 |

Animals were checked daily for postural, grooming, and respiratory changes, as well as lethargy. Animals were weighed two times weekly and euthanized if weight loss was ≥20%. Mice were checked for the presence and size of tumors twice weekly until death or euthanasia. Tumors were measured in 3 dimensions with an electronic caliper (Mitutoyo, Aurora, Ill.) and recorded. Response to treatment compounds was measured as a function of tumor growth. If the tumor reached a volume of ≥1500 $mm^3$ or appeared ulcerated, animals were euthanized.

Figure 36A:
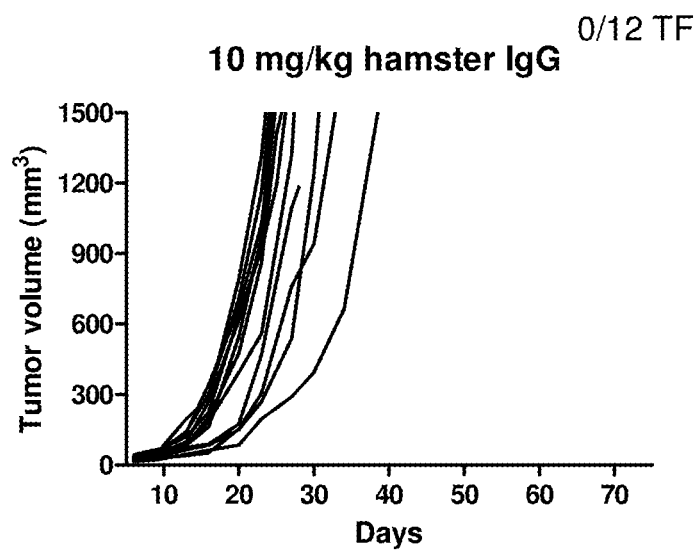
Figure 36B:
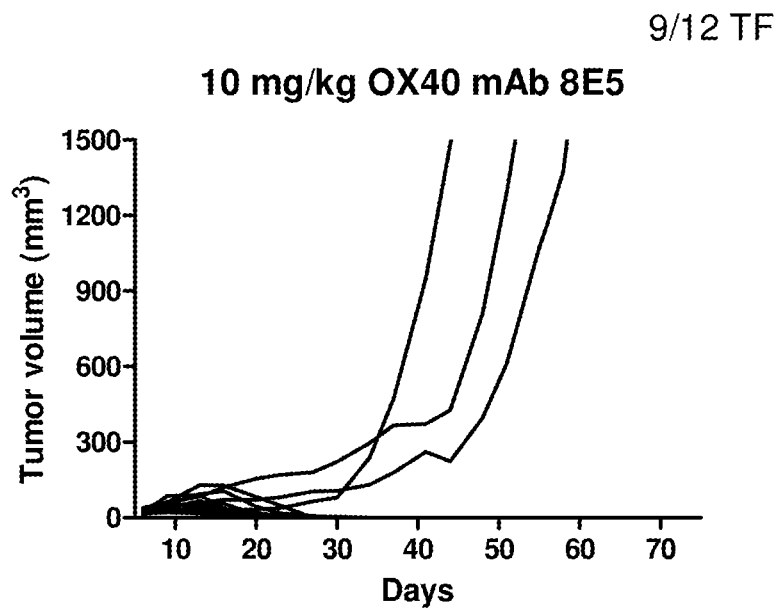
Figure 36C:
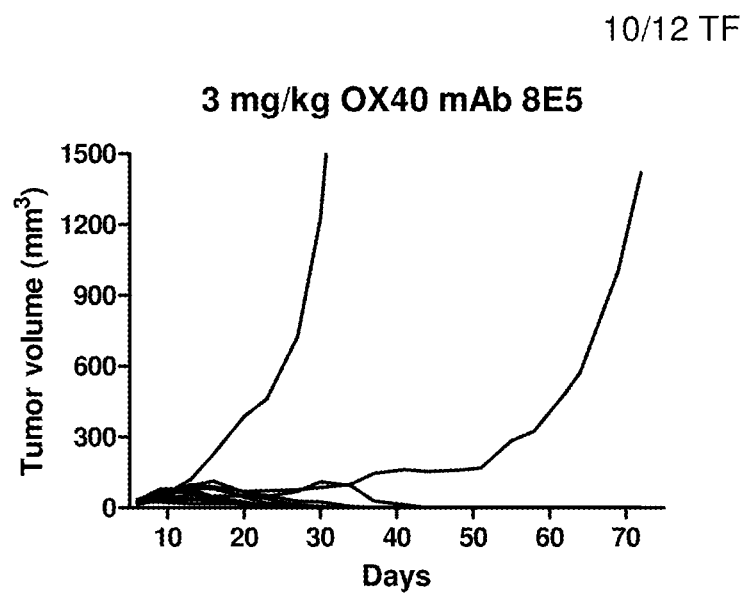
Figure 36D:
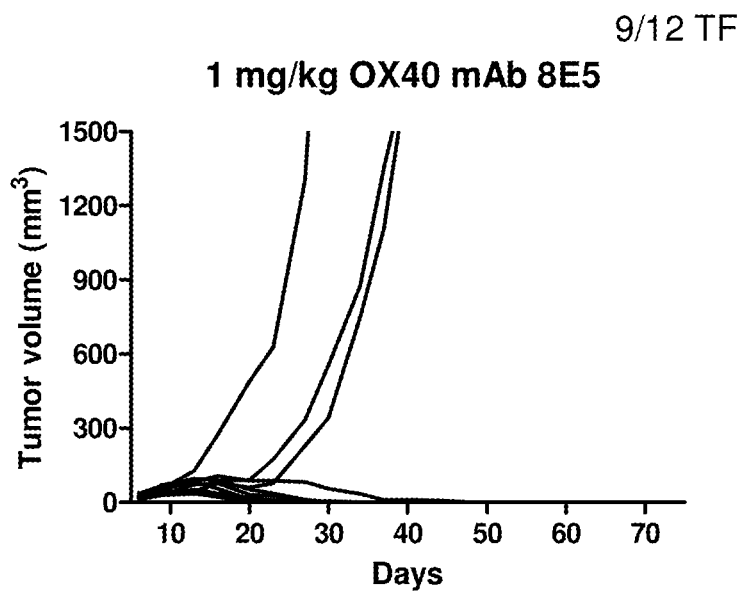
Figure 36E:
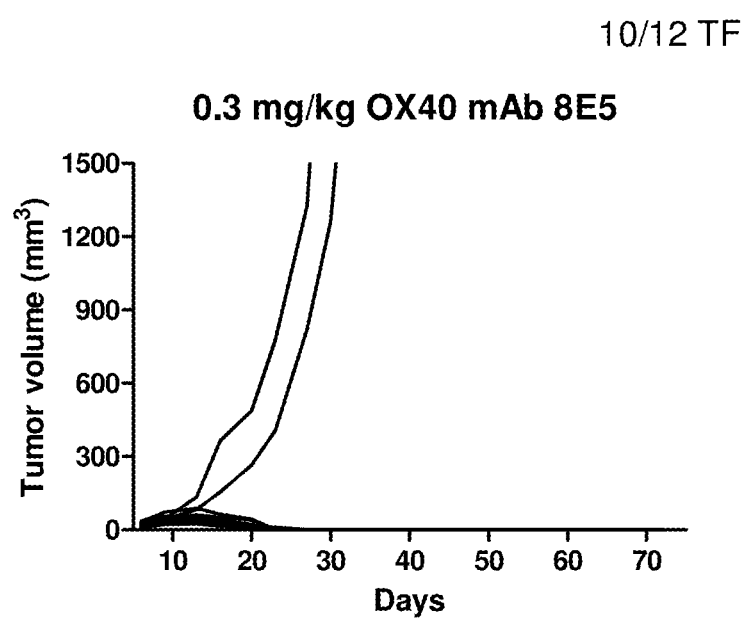
Figure 37A:
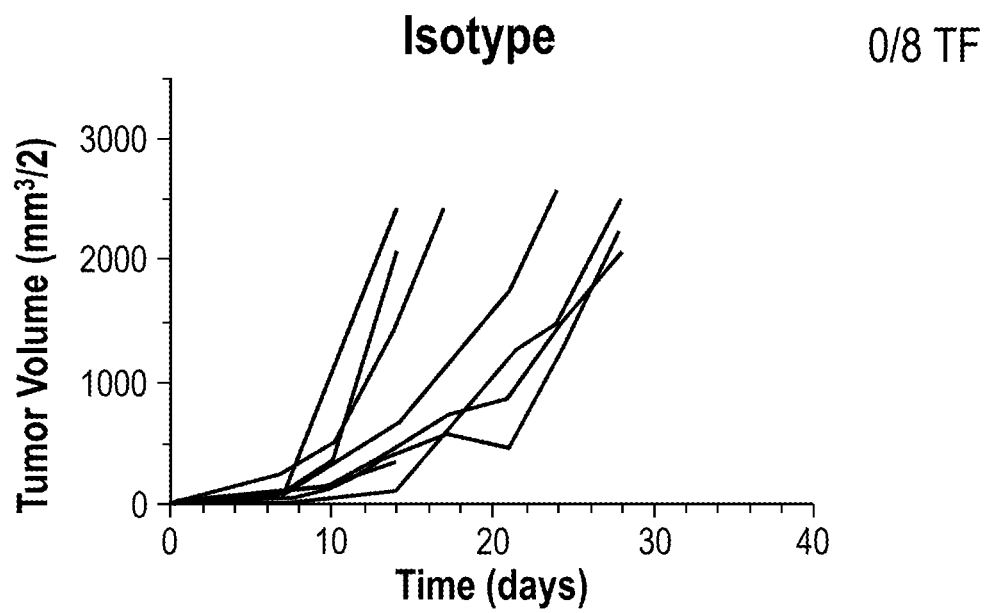
Figure 37B:
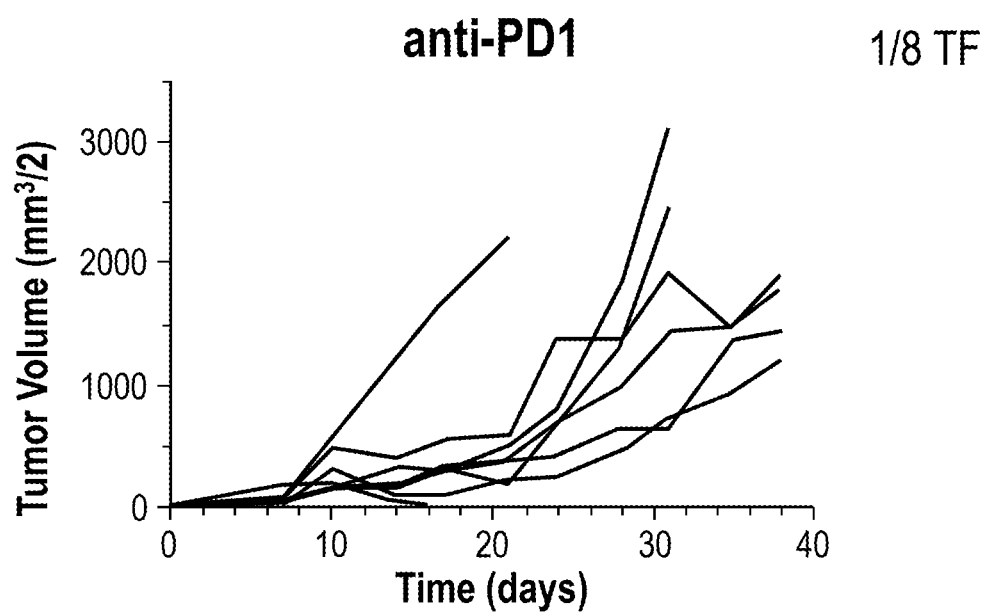
Figure 37C:
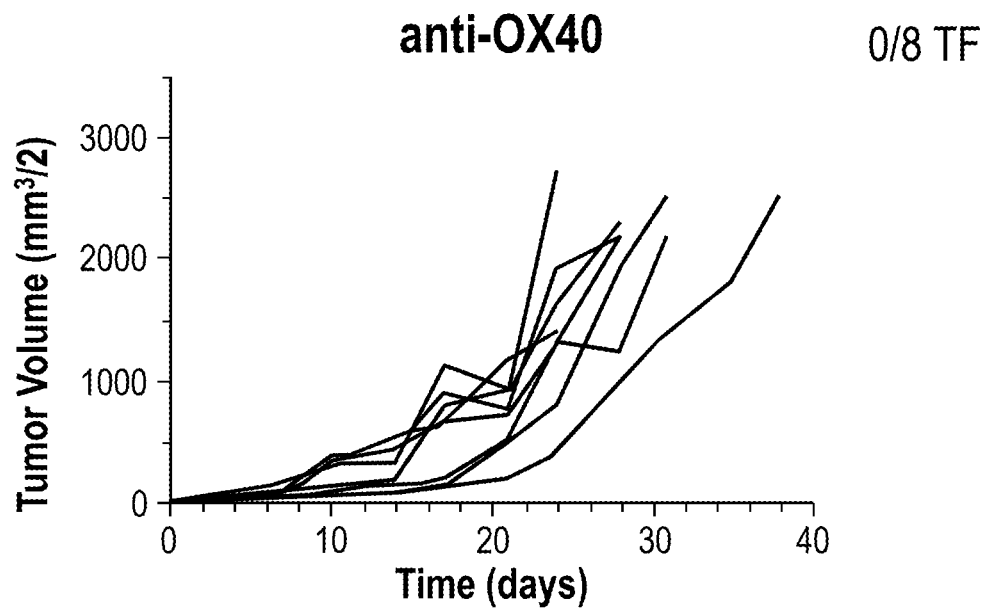
Figure 37D:
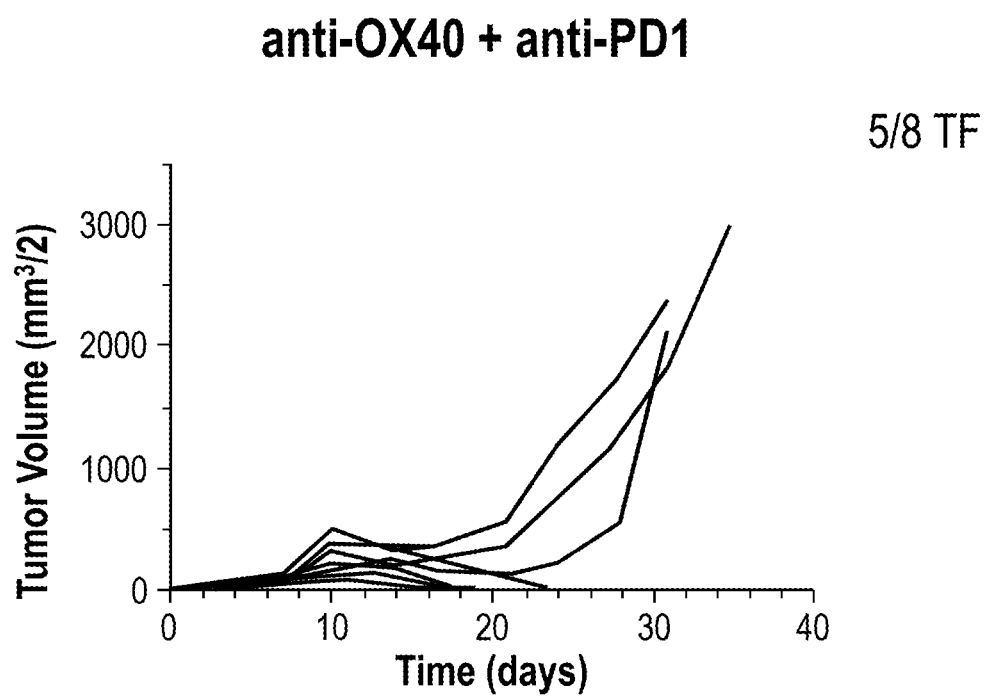

As shown in FIGS. 36A-36E, the hamster anti-mouse OX40 mAb (clone 8E5; FIGS. 36B-36E showing treatment with different doses of 8E5) demonstrated potent anti-tumor activity in the subcutaneous CT-26 model as compared to the hamster IgG isotype control group (FIG. 36A). The 8E5 antibody was administered at doses ranging from 0.3 to 10 mg/kg, and even at the lowest dose evaluated (0.3 mg/kg), 10 of 12 mice were tumor-free (TF) at the end of the study period (Day 72). Although the number of tumor-free mice did not differ significantly amongst each dose group, with each group having 9 or 10 tumor-free mice by the end of the study period, mice treated with either of the two highest doses (3 or 10 mg/kg) showed more tumor growth delays as compared to mice treated with the two lowest doses (0.3 or 1 mg/kg). There were no tumor-free mice in the isotype control-treated group; all mice in that group had been sacrificed by Day 39 as a result of ulceration or tumor burden (>1500 $mm^3$).

These data indicate that an anti-OX40 antibody that blocks the interaction between OX40 and OX40-L demonstrates potent anti-tumor activity in a subcutaneous mouse CT-26 tumor model when administered to mice with established tumors.

Example 24: OX40 Agonism Synergizes with PD-1 Blockage in a Murine MC38 Colon Carcinoma Model To test for synergy between anti-OX-40 antibody and anti-PD-1 antibody treatments, combinations of these antibodies were tested in the MC38 mouse tumor model. C57BL/6 mice were subcutaneously injected with 2 million MC38 tumor cells. After 7 days, tumor volumes were determined and mice were randomized into treatment groups so as to have comparable mean tumor volumes. Antibodies formulated in PBS were administered intraperitoneally on days 7, 10, and 14 at 200 μg per dose in a volume of 200 μl.

As shown in FIGS. 37A-37D, both the anti-PD-1 antibody (FIG. 37B) and anti-OX40 antibody (FIG. 37C) showed minimal activity when used alone, but had significant anti-tumor activity when combined (FIG. 37D), with 5 of 8 mice rendered tumor free.

Example 25: OX40 Agonism Enhances the Response to Vaccines in Cynomolgus Monkey

Enhancement of immune responses to vaccines was measured to evaluate the ability of the OX40.6 antibody to stimulate immune responses in cynomolgus monkeys. This approach was selected because the desired effect, i.e., enhancement of immune responses to tumors, cannot be evaluated in healthy non-human primates, as they lack tumors.

Monkeys were immunized with keyhole limpet hemocyanin (KLH) on Day 1 (10 mg, intramuscularly) and with hepatitis B virus surface antigen (HBsAg) (ENGERIX-B) (20 μg intramuscularly on Days 1 and 29). Following administration of the vaccines, the monkeys were dosed intravenously with 0 or 2 mg/kg of OX40.6 antibody on Days 1 and 29. Immune responses were measured on Days 22 and 41 by ex vivo T cell response to KLH and by T-cell-dependent antibody responses to KLH and HBsAg. As shown in FIGS. 38A and 38B, OX40.6-related findings at 2 mg/kg at Days 22 (FIG. 38A) and 41 (FIG. 38B) included an increase in the ex vivo recall response to KLH, characterized by increases in the mean percent of CD69+, IFN-gamma+, and TNF-alpha+ expressing CD4+CD8− T cells.

Example 26: Fc Receptor Binding for Antibodies with Engineered Constant Domains

This Example demonstrates that antibodies having modified heavy chain constant regions comprising the CH1 and hinge of IgG2 bind to FcγRs when they contain CH2 and CH3 domains of IgG1.

In addition to antigen binding by the variable domains, antibodies can engage Fc-gamma receptors (FcgRs) through interaction with the constant domains. These interactions mediate effector functions such as antibody-dependent cellular cytotoxicity (ADCC) and antibody-dependent cellular phagocytosis (ADCP). Effector function activity is high for the IgG1 isotype, but very low or absent for IgG2 and IgG4 due to these isotypes having lower affinity for FcgRs. In addition, the effector function of IgG1 can be modified through mutation of amino acid residues within the constant regions to alter FcgR affinity and selectivity.

The binding of antibodies to Fc gamma receptors (FcγRs or FcgRs) was studied using biosensor technologies including Biacore surface plasmon resonance (SPR) and Fortebio Biolayer Interferometry (BLI). SPR studies were performed on a Biacore T100 instrument (GE Healthcare) at 25° C. The Fab fragment from a murine anti-6×His antibody was immobilized on a CM5 sensor chip using EDC/NHS to a density of ~3000 RU. Various his-tagged FcgRs (7 ug/ml) were captured via the C-terminal his-tag using a contact time of 30 s at 10 ul/min, and the binding of 1.0 uM antibody was evaluated in a running buffer of 10 mM NaPO4, 130 mM NaCl, 0.05% p20 (PBS-T) pH 7.1. FcgRs used for these experiments included CD64 (FcgRI), CD32a-H131 (FcgRIIa-H131), CD32a-R131 (FcgRIIa-R131), CD32b (FcgRIIb), CD16a-V158 (FcgRIIIa-V158), CD16b-NA1 (FcgRIIIb-NA1), and CD16B-NA2 (FcgRIIIb-NA2). BLI experiments were performed on a Fortebio Octet RED instrument (Pall, Fortebio) at 25° C. in 10 mM NaPO4, 130 mM NaCl, 0.05% p20 (PBS-T) pH 7.1. Antibodies were captured out of undiluted expression supernatants on protein A coated sensors, followed by the binding of 1 µM hCD32a-H131, hCD32a-R131, hCD32b, hCD16a-V158, or 0.1 µM hCD64 analytes.

First, antibodies were made that contain modified IgG1 Fc domains including the substitutions S267E (SE) and S267E/L328F (SELF), as well as various combinations of the mutations P238D, P271G, H268D, A330R, G237D, E233D, referred to as V4, V7, V8, V9 and V12. The binding of these antibodies was studied by Biacore SPR with comparison to IgG1f, IgG2.3 (IgG2-C219S) and IgG4.1 (IgG4-S228P) antibodies, as well as an IgG1.1f antibody which has been engineered to reduce binding to all FcgRs. The results, which are shown in FIG. 70, demonstrate the expected FcgR binding properties for IgG1f, IgG2.3 and IgG4.1 and the mutated IgG1 antibodies, including increased CD32a-H131, CD32a-R131 and CD32b binding for SE and SELF, as well as increased selectivity of the V4, V7, V8, V9 and V12 mutants for CD32b over CD32a-H131 and CD32a-R131 (FIG. 39).

The next set of constructs was used to engineer effector function into the otherwise effector function negative IgG2 isotype. For this study, the mutations described above were introduced in the context of IgG2.3 constant region, or an IgG2.3/IgG1f hybrid termed IgG2.3G1-AY (Table 20). Antibodies were expressed at small scale as supernatants, and tested for binding to FcgRs using Fortebio Octet BioLayer Interferometry biosensor technology. Since the antibodies were present at low concentration in the supernatants, the experiment was performed by capturing antibodies out of the supernatants using protein A coated sensors, followed by binding of FcgR analytes in solution. Purified and supernatant control IgG1f including wild type IgG1, SE, P238D, V4 and V12 antibodies were also included for comparison, and each of these control antibodies demonstrated expected FcgR binding properties (FIG. 40). The IgG2.3 antibody also demonstrated the expected binding profile, with appreciable binding to only CD32a-H131. However, all mutations to introduce S267E, L328F, P238D, P271G, H268D, A330R, G237D, or E233D mutations into IgG2.3 failed to recapitulate the FcgR affinity of the corresponding engineered IgG1 mAbs (FIG. 40). In contrast, the IgG2.3G1-AY construct was able to fully preserve the FcgR binding properties of wild type IgG1, while retaining the CH1 and hinge regions of IgG2.3. In addition, all IgG2.3G1-AY mutants containing S267E, L328F, P238D, P271G, H268D, A330R, G237D, and E233D demonstrated FcgR binding properties comparable to the IgG1 version mAbs containing the same mutations (FIG. 40). This demonstrates the successful engineering of antibodies with CH1 and hinge regions of IgG2 combined with effector function of wild type or mutant IgG1.

TABLE 20

Engineered IgG2 constructs

| Set | ID | Construct | Seq ID# |
|---|---|---|---|
| 1 | IgG2.3 | hHC-IgG2-C219S | 258 |
| | IgG2.3-V13 | hHC-IgG2-C219S-P238D | 267 |
| | IgG2.3-V14 | hHC-IgG2-C219S-P238D, P271G | 268 |
| | IgG2.3-V15 | hHC-IgG2-C219S-P238D, H268D, P271G | 269 |
| | IgG2.3-V16 | hHC-IgG2-C219S-P238D, P271G, A330R | 270 |
| | IgG2.3-V17 | hHC-IgG2-C219S-P238D, H268D, P271G, A330R | 271 |
| | IgG2.3-V18 | hHC-IgG2-C219S-S267E | 272 |
| | IgG2.3-V19 | hHC-IgG2-C219S-S267E, L328F | 273 |
| 2 | IgG2.3G1 | hHC-IgG2-C219S/hHC-IgG1f | 262 |
| | IgG2.3G1-AY-V20 | hHC-IgG2-C219S/hHC-IgG1f-P238D | 274 |
| | IgG2.3G1-AY-V21 | hHC-IgG2-C219S/hHC-IgG1f-P238D, P271G | 275 |
| | IgG2.3G1-AY-V22 | hHC-IgG2-C219S/hHC-IgG1f-P238D, H268D, P271G | 276 |
| | IgG2.3G1-AY-V23 | hHC-IgG2-C219S/hHC-IgG1f-P238D, P271G, A330R | 277 |
| | IgG2.3G1-AY-V24 | hHC-IgG2-C219S/hHC-IgG1f-P238D, H268D, P271G, A330R | 278 |
| | IgG2.3G1-AY-V25 | hHC-IgG2-C219S/hHC-IgG1f-G237D, P238D, H268D, P271G, A330R | 279 |
| | IgG2.3G1-AY-V26 | hHC-IgG2-C219S/hHC-IgG1f-E233D, G237D, P238D, H268D, P271G, A330R | 280 |
| | IgG2.3G1-AY-V27 | hHC-IgG2-C219S/hHC-IgG1f-S267E | 266 |
| | IgG2.3G1-AY-V28 | hHC-IgG2-C219S/hHC-IgG1f-S267E, L328F | 281 |

This engineering strategy was further explored by producing other antibodies formatted with IgG2.3G1-AY, IgG2.3G1-AY-S267E (IgG2.3G1-AY-V27), as well as IgG2-B-form variants (IgG2.5G1-AY and IgG2.5G1-AY-V27), and other hybrid antibodies containing different combinations of IgG1 and IgG2 constant domains, and testing the binding of these antibodies to anti-his Fab captured his-tagged FcgRs using Biacore SPR technology. In agreement with the Octet supernatant data, the SPR data showed that the IgG2.3G1-AY and IgG2.3G1-AY-V27 antibodies had comparable FcgR binding properties to IgG1f and IgG1f-S267E respectively, despite containing the CH1 and hinge regions of an A-form IgG2 antibody (IgG2.3) (Table 21). Similar data was also obtained using IgG2.5G1-AY and IgG2.5G1-AY-V27 antibodies, demonstrating the successful engineering of B-form IgG2 antibodies (containing C131S mutation termed IgG2.5) having IgG1f or modified IgG1f like effector functions. Data for several other antibodies with IgG2.3G1-AY, IgG2.3G1-AY-V27, IgG2.5G1-AY, or IgG2.5G1-AY-V27 constant regions but different variable regions shows that this engineering strategy is broadly applicable to other antibodies independent of the variable domains (Table 21).

TABLE 21

% Rmax values for 1 uM antibodies binding to anti-his Fab captured FcgR-his proteins

| mAb | hCD64 | hCD32a-H131 | hCD32a-R131 | hCD32b | hCD16a-V158 | hCD16B-NA2 |
|---|---|---|---|---|---|---|
| mAb8-IgG1f | 80% | 82% | 51% | 27% | 51% | 21% |
| mAb9-IgG1f | 70% | 33% | 19% | 4% | 28% | 10% |
| mAb11-IgG2.3 | 2% | 44% | 17% | 5% | 1% | 0% |
| mAb6-IgG2.3 | 3% | 66% | 14% | 3% | 1% | 0% |
| mAb4-IgG2.3 | 1% | 39% | 6% | 1% | 1% | 0% |
| mAb5-IgG2.3 | 6% | 100% | 30% | 4% | 3% | 0% |
| mAb12-IgG2.3 | 2% | 39% | 7% | 1% | 1% | 0% |
| mAb13-IgG2.3 | 2% | 40% | 7% | 1% | 1% | 0% |
| mAb11-IgG2.5 | 0% | 40% | 13% | 3% | 0% | −1% |
| mAb7-IgG2.5 | 4% | 72% | 19% | 2% | 2% | 0% |
| mAb8-IgG2.5 | 3% | 59% | 14% | 3% | 2% | 0% |
| mAb10-IgG2.5 | 1% | 29% | 5% | 1% | 1% | 0% |
| mAb6-IgG2.5 | 3% | 75% | 17% | 4% | 2% | 0% |
| mAb4-IgG2.5 | 2% | 46% | 8% | 1% | 1% | 0% |
| mAb5-IgG2.5 | 6% | 89% | 26% | 5% | 4% | 1% |
| mAb12-IgG2.5 | 1% | 36% | 6% | 1% | 1% | 0% |
| mAb13-IgG2.5 | −2% | 39% | 4% | −2% | 0% | −2% |
| mAb8-IgG2.3G1-AY | 77% | 61% | 38% | 10% | 38% | 13% |
| mAb10-IgG2.3G1-AY | 67% | 23% | 14% | 4% | 24% | 8% |
| mAb7-IgG2.5G1-AY | 80% | 73% | 45% | 12% | 47% | 19% |
| mAb8-IgG2.5G1-AY | 77% | 70% | 45% | 17% | 48% | 22% |
| mAb7-IgG2.3G1-AY-V27 | 84% | 68% | 92% | 76% | 26% | 7% |
| mAb8-IgG2.3G1-AY-V27 | 78% | 67% | 80% | 67% | 24% | 7% |
| mAb10-IgG2.3G1-AY-V27 | 69% | 24% | 57% | 40% | 12% | 3% |
| mAb7-IgG2.5G1-AY-V27 | 81% | 74% | 89% | 84% | 32% | 9% |
| mAb8-IgG2.5G1-AY-V27 | 77% | 76% | 79% | 77% | 33% | 10% |

Example 27: Effects of Anti-OX40 Antibodies with Modified Heavy Chain Constant Regions on T Cell Proliferation and IFN-γ and IL-2 Secretion from T Cells with or without Cross-Linking Anti-OX40 antibodies with modified IgG2 CH1/hinge regions may have the ability to promote T cell activation in the absence of cross-linking, and thus may be able to promote T cell activation in vivo in the absence or low expression of cell types expressing FcγRs, and possibly to promote anti-tumor activity in a wider range of tumor types than IgG1 isotype antibodies.

Alternatively, modified CH1/hinge region antibodies may still require cross-linking in order to promote T cell activation, but may have increased agonist activity when bound to FcγRs compared to IgG1 isotype antibodies, and thus be more potent in promoting T cell activation and anti-tumor activity.

Anti-OX40 antibodies having modified heavy chain constant regions comprising the sequences shown in Table 22 are generated and tested for their effects on T cell proliferation and IFN-γ and IL-2 secretion from T cells with or without cross-linking using the assays described below. The light chain sequences for antibodies OX40.6, 40.8, 40.16, and 40.21 correspond to SEQ ID NOs: 96, 110, and 116 (for both OX40.16 and 40.21), respectively.

TABLE 22

| Constructs | SEQ ID NO |
|---|---|
| OX40.6-Vh-hHC-IgG2.3 | 282 |
| OX40.8-Vh-hHC-IgG2.3 | 283 |

TABLE 22-continued

| Constructs | SEQ ID NO |
|---|---|
| OX40.16-Vh-hHC-IgG2.3 | 284 |
| OX40.6-Vh-hHC-IgG2.3G1 | 285 |
| OX40.8-Vh-hHC-IgG2.3G1 | 286 |
| OX40.16-Vh-hHC-IgG2.3G1 | 287 |
| OX40. 6-Vh-hHC-IgG2.3G1-V27 | 288 |
| OX40. 8-Vh-hHC-IgG2.3G1-V27 | 289 |
| OX40.16-Vh-hHC-IgG2.3G1-V27 | 290 |
| OX40.6-Vh-hHC-IgG2.5 | 291 |
| OX40.8-Vh-hHC-IgG2.5 | 292 |
| OX40.16-Vh-hHC-IgG2.5 | 293 |
| OX40.21-Vh-hHC-IgG2.5 | 294 |
| OX40.21-Vh-hHC-IgG2.5G1 | 295 |
| OX40.21-Vh-hHC-IgG2.5G1-V27 | 296 |

CHO-CD3+/−CD32 Assay

Anti-OX-40 antibodies with the sequences shown in Table 22 are tested for their ability to induce T cell activity in vitro by measuring the proliferation of and amount of IL-2 and IFN-γ secreted by T cells incubated with the antibodies.

Transfected CHO cell lines are generated for use as artificial antigen-presenting cells in a primary T cell activation assay. The CHO-CD3-CD32A cell line expresses anti-human CD3 antibody in a single-chain Fv format, along with the human Fc receptor (FcR) CD32A to present anti-OX40 antibodies on the CHO cell surface. The CHO-CD3 cell line expresses anti-human CD3 antibody in a single-chain Fv format without FcR.

Briefly, human primary CD4 T cells are isolated by negative selection (RosetteSep™, StemCell Technologies) and co-cultured with either irradiated CHO-CD3-CD32A cells, or irradiated CHO-CD3 cells, at an 8:1 T:CHO ratio, in the presence of graded doses of anti-OX40 antibodies or isotype control antibody. After 3 to 4 days in culture at 37° C., supernatants are harvested for assessment of T cell activation by means of measurement of secreted human IFN-γ either by ELISA (BD Biosciences) or HTRF assay (Cisbio), following the manufacturers' recommendations. Afterwards, tritiated thymidine is added for the final approximately 18 hours of culture to measure T proliferation by tritiated thymidine incorporation, as an additional assessment of T cell activation.

SEB PBMC Assay

Anti-OX-40 antibodies with the sequences shown in Table 22 are tested for their effects on stimulating primary T cells in cultures of staphyloccus enterotoxin B (SEB)-activated human peripheral blood mononuclear cells (PBMCs). Human whole blood samples are obtained from AllCells, Inc. (Berkeley, Calif.) or from donors at Bristol-Myers Squibb, Redwood City, Calif. under the auspices of an in-house phlebotomy program. PBMCs are isolated by gradient purification on a Ficoll-Hypaque cushion and cultured for 3 days in culture medium supplemented with fixed, suboptimal (85 ng/mL) of superantigen staphylococcus enterotoxin B (SEB; Toxin Technologies, Sarasota, Fla.) in the presence of graded doses of OX40 antibodies or isotype control antibody. In some cases, 2-5 μg/mL of soluble cross-linking antibody, F(ab')2 goat anti-human Fcγ, is also added to the cultures. After culturing for 3 days at 37° C., supernatants are harvested for assessment of T cell activation by means of ELISA measurement of secreted human IL-2. Briefly, culture supernatants are diluted 1:10 in sample diluent and tested for the presence of human IL-2 by ELISA (BD Bioscience) per the manufacturer's recommended protocol. Following the addition of TMB substrate, assay plates are read on a Spectramax 340PC reader using Softmax operating software at a wavelength of 650 nm. Measured optical densities of the chromogenic substrate were proportional to bound detecting antibody.

MLR Assay

Anti-OX-40 antibodies with the sequences shown in Table 22 tested for their ability to potentiate primary human T cell proliferation and IFN-γ secretion in a T cell: Dendritic Cell Allogeneic Mixed Lymphocyte Reaction (T:DC AlloMLR). Total T cells are isolated from peripheral blood from healthy human donors by negative selection (RosetteSep, Stemcell Technologies). Monocytes are isolated from peripheral blood from healthy human donors using CD14 microbeads (Miltenyi), and cultured for six days in the presence of GM-CSF and IL-4 to derive immature dendritic cells (DCs). DCs and T cells are co-cultured in the presence of graded doses of OX40 antibodies or isotype control antibody. In some cases, 2-5 μg/mL of soluble cross-linking antibody, such as F(ab')2 goat anti-human Fcγ, is also added to the cultures. Supernatant from each sample is harvested between Day 4 and Day 7 for measurement of secreted IFN-γ by ELISA (BD Biosciences) or HTRF assay (Cisbio), following the manufacturers' recommendations. After supernatant harvest, the cell cultures are pulsed with 1 μCi/well of $^3$[H]-thymidine for the last 16-18 hours of the culture. The cells are harvested onto filter plates, and $^3$[H] counts per minute of cell-incorporated $^3$[H]-thymidine are read as a measure of T cell proliferation.

Example 28: Anti-Tumor Activity of OX40 Agonist mAb with CTLA-4 Blockade in a CT26 Model To test for synergy between anti-OX-40 antibody and anti-CTLA-4 antibody treatments, combinations of these antibodies were tested in the CT26 mouse tumor model. Mice were inoculated with CT26 tumors and mAb dosing was initiated at Day +3 following inoculation (dosed on Days 3, 7, and 10) with 200 μg/mouse of the antibodies indicated in FIGS. 41A-41D.

As shown in FIGS. 41A-41D, both the anti-CTLA-4 antibody (FIG. 41B) and anti-OX40 antibody (FIG. 41C) showed minimal activity when used alone (1 of 8 mice tumor free for both treatments), but had significant anti-tumor activity when combined (FIG. 41D), with 4 of 8 mice rendered tumor free.

Example 29: Phase 1/2a Trial in Subject Having Solid Tumors

A Phase 1/2a study of OX40.21 administered alone or in combination with nivolumab or ipilimumab is conducted in subjects having advanced solid tumors to demonstrate the efficacy of administering OX40.21 alone or in combination with nivolumab or ipilimumab.

I. Objective

The primary objective of the study is to assess the safety, tolerability, dose-limiting toxicities (DLTs), and maximum tolerated dose (MTD)/recommended phase 2 dose (RP2D) of OX40.21 administered alone or in combination with nivolumab or ipilimumab in subjects with advanced malignant tumors.

Secondary objectives include investigating the preliminary anti-tumor activity of OX40.21 administered alone or in combination with nivolumab or ipilimumab in subjects with advanced malignant tumors; characterizing the PK of OX40.21 administered alone and in combination with nivolumab or ipilimumab; and characterizing the immunogenicity of OX40.21 administered alone or in combination with nivolumab or ipilimumab and the immunogenicity of nivolumab or ipilimumab administered with OX40.21. Additional exploratory objectives include exploring potential associations between anti-tumor activity and select biomarker measures in tumor biopsy specimens and peripheral blood prior to treatment and following administration of OX40.21 alone or in combination with nivolumab or ipilimumab; assessing the potential effect of OX40.21 monotherapy and combination therapy on QTc interval; characterizing nivolumab PK in subjects receiving the combination of nivolumab and OX40.21; characterizing ipilimumab PK in subjects receiving the combination of ipilimumab and OX40.21; assessing the overall survival (OS) in subjects treated with OX40.21 alone and in combination with nivolumab or ipilimumab; and exploring potential relationships between dose/exposure and anti-tumor activity, pharmacodynamic (PD) effects (selected biomarkers in the peripheral blood and tumor biopsy specimens), and key safety measures in subjects treated with OX40.21 alone and in combination with nivolumab or ipilimumab.

2. Study Design and Duration

This is a Phase 1/2a, open label study of OX40.21 in subjects with advanced solid tumors that integrates initial OX40.21 monotherapy with subsequent nivolumab or ipilimumab combination therapy.

Study sections (dose escalation and dose expansion) proceed in a phased approach based on study-emergent safety, PK, and PD data. The first section of the study begins with OX40.21 monotherapy dose escalation cohorts. Clinical data from the first 3 monotherapy dose cohorts serve as a foundation for initiating dose escalation of OX40.21 in combination with nivolumab. Clinical data from the first 3 monotherapy dose cohorts in addition to the clinical data from the first cohort of OX40.21 in combination with nivolumab serve as a foundation for initiating dose escalation of OX40.21 in combination with ipilimumab. After establishment of a tolerable and pharmacologically active RP2D of OX40.21 in the dose escalation section, dose expansion in specific tumor cohorts is initiated.

3. Dose Escalation

A schematic of the study design for Part 1A is shown in FIG. 42.

The dose escalation phase of the study evaluates the safety and tolerability of OX40.21, alone or in combination with nivolumab or ipilimumab, in subjects with advanced solid tumors.

The initial dose level of OX40.21 is 20 mg. Dose escalation decisions for subsequent doses are based on DLTs using a BLRM model (for OX40.21 monotherapy) or a BLRM (-Copula) model (for OX40.21 in combination with nivolumab or ipilimumab). The DLT period is 28 days for both monotherapy and combination therapy dose escalation parts. The DLT rate is determined based on the incidence, severity, and duration of AEs that occur within the DLT period and for which no alternative cause can be identified. Dose selection for the next monotherapy cohort/dose level takes into account the BLRM (-Copula) recommendation in conjunction with all available PK, PD, and clinical and laboratory safety data from all treated subjects. Starting dose selection of OX40.21 for Part 2A is determined using data available from Part 1A, including clinical and laboratory safety assessments, PK/PD data, and modeling recommendation within Bayesian hierarchical modeling framework by incorporating single-agent toxicity profiles of both OX40.21 (Part 1A) and nivolumab (CA209-003). Starting dose selection of OX40.21 for Part 3A is determined using data available from Parts 1A and 2A, including clinical and laboratory safety assessments, PK/PD data, and modeling recommendation within Bayesian modeling framework by incorporating single-agent toxicity profiles of both OX40.21 (Part 1A) and ipilimumab (CA184-022). Actual doses can be modified per the BLRM (-Copula), but do not exceed doubling of the previously tested dose.

During dose escalation for all dose cohorts, the initial subject (sentinel subject) is observed for 5 days before additional subjects in that cohort are treated with study drug.

Approximately 30 subjects are enrolled in each dose escalation part. The number of subjects in each dose escalation cohort varies depending on BLRM (-Copula) recommendations. Initially, approximately 3 subjects are treated at the starting dose levels of OX40.21 or OX40.21 in combination with nivolumab or ipilimumab. Additional cohorts of approximately 3 evaluable subjects are treated at recommended dose levels per BLRM (-Copula) during the dose escalation phase. At least 6 DLT-evaluable subjects are treated at the MTD.

Part 1A: Enrollment begins in Part 1A, OX40.21 monotherapy dose escalation. The initial dose of OX40.21 for Part 1A is 20 mg, with expected subsequent doses of 40, 80, 160, and 320 mg. Actual doses can be modified per the BLRM but do not exceed doubling of the previously tested dose.

Part 2A: Part 2A is the combination arm of OX40.21 with nivolumab that is initiated after at least 3 dose levels in the monotherapy dose escalation are found to be tolerated or an MTD has been determined in the monotherapy dose escalation (Part 1A). The starting dose of OX40.21 in Part 2A is at least 1 dose level below a dose demonstrated to be tolerated in Part 1A to ensure further safety of the combination. At no time does the dose for OX40.21 in Part 2A exceed the highest tolerated dose in Part 1A. Nivolumab is administered at a flat dose of 240 mg. Each treatment cycle is 2 weeks in length and study drugs are administered every 2 weeks starting on Day 1 of each cycle for up to 12 cycles.

Part 3A: Part 3A is the combination arm of OX40.21 with ipilimumab that is initiated only after at least 3 dose levels in the monotherapy dose escalation are found to be tolerated or an MTD is determined in the monotherapy dose escalation (Part 1A) and at least 1 dose cohort is found to be tolerated in the OX40.21 with nivolumab dose escalation part. The starting dose of OX40.21 in Part 3A is at least 1 dose level below a dose demonstrated to be tolerated in Part 1A. At no time does the dose for OX40.21 in Part 3A exceed the highest tolerated dose in Part 1A to further ensure safety of the combination doses in treated subjects. Ipilimumab is administered at a dose of 1 mg/kg. Each treatment cycle is 3 weeks in length. OX40.21 is administered every 3 weeks starting on Cycle 1 Day 1, up to and including 8 cycles, and ipilimumab is administered every 3 weeks starting on Day 1 for 4 cycles. Only OX40.21 is administered in the last 4 cycles.

Dose Expansion:

Treatment in the dose expansion cohorts is initiated when the MTD/RP2D has been determined based on the evaluation of totality of available clinical safety (DLTs, significant AEs occurring after the DLT period), PK, PD, and modeling data from the dose escalation (Parts 1A, 2A, and 3A). Approximately 110 subjects are treated in all dose expansion cohorts.

Part 1B is the OX40.21 monotherapy dose expansion cohort in subjects with cervical cancer at the MTD/RP2D determined in Part 1A. Dosing of OX40.21 begins on Day 1 of each cycle and is administered every 2 weeks for up to 12 cycles. Approximately 12 subjects are treated in this expansion cohort.

Parts 2B is the combination therapy (OX40.21 with nivolumab) dose expansion part in subjects with CRC at the MTD/RP2D determined in Part 2A. Nivolumab is administered at a flat dose of 240 mg. Each treatment cycle is 2 weeks in length and study drugs are administered every 2 weeks starting on Day 1 of each cycle for up to 12 cycles. Approximately 35 subjects are treated in this expansion cohort.

Part 2C is the combination therapy (OX40.21 with nivolumab) dose expansion part in subjects with BC at the MTD/RP2D determined in Part 2A. Each treatment cycle is 2 weeks in length and study drugs are administered every 2 weeks starting on Day 1 of each cycle for up to 12 cycles. Approximately 27 subjects are treated in this expansion cohort.

Part 3B is the combination therapy (OX40.21 with ipilimumab) dose expansion part in subjects with OC at the MTD/RP2D determined in Part 3A. Each treatment cycle is 3 weeks in length. Ipilimumab is administered in the initial 4 cycles in combination with OX40.21. Then the subject continues on OX40.21 monotherapy for up to an additional 4 cycles for a total of up to 24 weeks (8 cycles) of treatment. Approximately 35 subjects with OC are treated in this expansion cohort.

Summary of Study Periods:

Subjects complete up to 5 periods in the study: Screening (up to 28 days), Treatment (up to 24 weeks), Safety Follow-up (minimum 100 days), Response Follow-up, and Survival Long-term Follow-up (up to approximately 2 years from the first dose) as described below. The study visit schematic is presented in FIG. 43.

Screening Period:

The Screening period lasts for up to 28 days. The screening period begins by establishing the subject's initial eligibility and signing of the informed consent form. Subjects are enrolled using an Interactive Response Technology (IRT).

Treatment Period:

The Treatment period consists of up to 24 weeks of dosing. Following each treatment cycle, the decision to treat a subject with the next cycle of study therapy, up to 24 weeks of treatment, is based on risk/benefit and tumor assessments. Tumor assessments are performed every 8 weeks for every 2-week (q2w) dosing regimen and every 9 weeks for every 3-week (q3w) dosing regimen. Assessments of partial response (PR) and complete response (CR) mare confirmed at least 4 weeks following initial assessment. Tumor progression or response endpoints are assessed using Response Evaluation Criteria In Solid Tumors (RECIST) v1.1.

Subjects with a response of stable disease (SD), PR, or CR at the end of a given cycle continue to the next treatment cycle. Subjects are generally allowed to continue study therapy until the first occurrence of one of the following: 1) completion of the maximum number of cycles; 2) progressive disease; 3) clinical deterioration suggesting that no further benefit from treatment is likely; 4) intolerability to therapy; or 5) meeting the criteria for discontinuation of study therapy.

Safety Follow-Up:

Upon completion of study therapy, subjects enter the Safety Follow-up period. After the end of treatment (EOT) visit, subjects are evaluated for any new adverse events (AEs) for at least 100 days after the last dose of therapy. Follow-up visits occur at Days 30, 60 and 100 after the last dose or the date of discontinuation. Subjects (except those who withdraw consent for study participation) complete 3 clinical Safety Follow-up visits regardless of whether they start new anti-cancer therapy.

Survival Follow-Up:

After completion of the Safety Follow-up period, subjects enter the Survival Follow-up period. Subjects are followed approximately every 3 months (12 weeks) until death, lost to follow-up, withdrawal of consent, or conclusion of the study, whichever comes first. The duration of this phase is up to 2 years following the first dose of study drug.

Response Follow-Up:

After completion of the Safety Follow-up period, all subjects with ongoing SD, PR, or CR at the EOT visit enter the Response Follow-up period, which occurs simultaneously with the Survival Follow-up period. These subjects continue to have radiological and clinical tumor assessments every 3 months (12 weeks) during the Response Follow-up period or until disease progression or withdrawal of study consent. Radiological tumor assessments for subjects who have ongoing clinical benefit continue to be collected after subjects complete the survival phase of the study. Subjects who have disease progression following initial course of study therapy are not evaluated for response beyond the EOT visit and are allowed to receive other tumor directed therapy as required.

Duration of Study:

The total duration of study time for any individual subject is approximately 2 years. The study ends when the last subject completes their last study visit, which is approximately 4 years after the start of the study.

Number of Subjects:

Approximately 225 subjects will be enrolled, and approximately 200 subjects will be treated in the study.

Study Population:

Subjects are at least 18 years old and have histologic or cytologic confirmation of a malignancy that is advanced (metastatic, recurrent, refractory and/or unresectable) with measurable disease per RECIST v1.1.

Dose Escalation and Stopping Rules

In Parts 1A, 2A, and 3A, the BLRM and BLRM (-Copula) models are utilized for dose escalation recommendations after DLT information becomes available for each cohort of subjects. OX40.21 dose selection for the next cohort/dose level takes into account the BLRM (-Copula) recommendation in conjunction with clinical recommendation and all available PK, PD, and clinical and laboratory safety data from all treated subjects.

Dose-Limiting Toxicities

To guide dose escalation, DLTs are defined based on the incidence, intensity, and duration of AEs for which no clear alternative cause is identified. The DLT period is 28 days of initiation of the study drug(s). For subject management, an AE that meets DLT criteria, regardless of the cycle in which it occurs, leads to discontinuation of study drug. Subjects who withdraw from the study during the DLT evaluation interval for reasons other than a DLT may be replaced with a new subject at the same dose level. The incidence of DLT(s) during the DLT evaluation period is used in dose escalation decisions and to define the MTD. AEs occurring after the DLT period are considered for the purposes of defining the MTD, if they are determined to have no clear alternative cause and are not related to disease progression. Subjects experiencing a DLT are not retreated with study drug and enter the safety follow-up period of the study. AEs are graded according to the National Cancer Institute (NCI) Common Terminology Criteria for Adverse Events (CTCAE) v4.03.

Non-Hematologic DLT:

A. Hepatic DLT

Any ≥Grade 3 elevation of AST, ALT, or total bilirubin AST, ALT, or total bilirubin, Grade 2 AST or ALT with symptomatic liver inflammation (e.g., right upper quadrant tenderness, jaundice, pruritis)

AST or ALT >3×ULN and concurrent total bilirubin >2×ULN without initial findings of cholestasis (elevated serum alkaline phosphatase [ALP]) (e.g., findings consistent with Hy's law or FDA definition of potential drug-induced liver injury or pDILI)

B. Non-Hepatic DLT

Grade 2 or greater uveitis, episcleritis, or iritis

Any other Grade 2 eye pain or blurred vision that does not respond to topical therapy and does not improve to Grade 1 severity within 2 weeks OR requires systemic treatment Grade 3 or greater pneumonitis, bronchospasm, neurologic toxicity, hypersensitivity reaction, or infusion reaction Any Grade 3 or greater non-dermatologic, non-hepatic toxicity will be considered a DLT with the following specific exceptions:

Grade 3 or Grade 4 electrolyte abnormalities that are not complicated by associated clinical adverse experiences, last less than 72 hours, and either resolve spontaneously or respond to conventional medical intervention Grade 3 nausea, vomiting, or diarrhea that lasts less than 72 hours, and either resolves spontaneously or responds to conventional medical intervention Grade 3 or 4 elevation of amylase or lipase not associated with clinical or radiographic evidence of pancreatitis Isolated Grade 3 fever not associated with hemodynamic compromise (e.g., hypotension, clinical, or laboratory evidence of impaired end-organ perfusion)

Grade 3 endocrinopathy that is well controlled by hormone replacement

Grade 3 tumor flare (defined as pain, irritation, or rash that localizes to sites of known or suspected tumor)

Grade 3 fatigue for less than 7 days

Grade 3 infusion reaction that returns to Grade 1 in less than 6 hours

Dermatologic DLT

Grade 4 rash

Grade 3 rash if no improvement (i.e., resolution to ≤Grade 1) after a 1- to 2-week infusion delay. Subjects who have not experienced a Grade 3 skin AE may resume treatment in the presence of Grade 2 skin toxicity.

Hematologic DLT

Grade 4 neutropenia ≥5 days in duration

Grade 4 thrombocytopenia or Grade 3 thrombocytopenia with clinically significant bleeding, or any requirement for platelet transfusion Grade 4 anemia not explained by underlying disease Grade 4 febrile neutropenia Grade 3 febrile neutropenia that lasts >48 hours Grade ≥3 hemolysis (i.e., requiring transfusion or medical intervention such as steroids)

Treatment with Additional Cycles Beyond 24 Weeks

Subjects are treated for 24 weeks unless criteria for study drug discontinuation are met earlier. Subjects completing approximately 24 weeks of treatment with ongoing disease control (CR, PR, or SD) are eligible for an additional 24 weeks of study therapy in monotherapy (Part 1) and combination therapy (Parts 2 and 3) beyond the initial 24 weeks when the risk/benefit assessment favors continued administration of study therapy. Upon completion of the additional 24 weeks of study therapy, subjects enter the Safety Follow-up period.

Treatment Beyond Progression

Treatment beyond progression is allowed in select subjects with initial RECIST v1.1-defined progressive disease after determining that the benefit/risk assessment favors continued administration of study therapy (e.g., subjects are continuing to experience clinical benefit, tolerating treatment, and meeting other criteria).

Retreatment

Retreatment is allowed if confirmed disease progression occurs during the response follow-up period. Subjects completing approximately 24 weeks (or additional cycles of treatment, if appropriate) of therapy who enter the response follow-up period with ongoing disease control (CR, PR, or SD) without any significant toxicity are eligible for retreatment. Such subjects are eligible for retreatment on a case-by-case basis after evaluation and determining whether the risk/benefit ratio supports administration of further study therapy, and the subject continues to meet eligibility criteria for treatment with study therapy. Subjects meeting criteria for retreatment are treated with the originally assigned monotherapy or combination therapy regimen (e.g., the same dose and dose schedule as administered during the first 24 weeks), unless that dose and schedule were subsequently found to exceed the MTD, in which case the subject is treated at the next lower dose deemed tolerable/safe.

Inclusion Criteria

1) Signed Written Informed Consent
  a) The subject must sign the informed consent form prior to the performance of any study-related procedures that are not considered part of SOC.
  b) Consent for tumor biopsy samples (mandatory pre- and on-treatment biopsies are required for the dose expansion cohorts, and for additional subjects added to any of the previously completed dose escalation cohorts and optional for dose escalation cohorts).

2) Target Population

Subjects must be at least 18 years old and have histologic or cytologic confirmation of a malignancy that is advanced (metastatic, recurrent, refractory, and/or unresectable) with measurable disease per RECIST v1.1.

A. Dose Escalation:

Subjects must have received, and then progressed, or have been refractory or intolerant to, at least 1 standard treatment regimen in the advanced or metastatic setting, if such a therapy exists. Subjects who are ineligible for any standard therapy are allowed to enroll provided their ineligibility is documented in medical records. The following tumor histologies are permitted except for subjects with primary central nervous system (CNS) tumors, or with CNS metastases as the only site of active disease.

(i) Melanoma: BRAF mutation status must be documented if known.
(ii) NSCLC: EGFR, ALK, KRAS, and ROS1 mutational status must be documented if known
(iii) Head and neck cancer restricted to squamous cell carcinoma. HPV status must be documented if known
(iv) Transitional cell carcinoma of the genitourinary tract
(v) Renal cell carcinoma
(vi) Pancreatic adenocarcinoma
(vii) CRC: MSI, KRAS, and BRAF status must be documented if known.
(viii) Cervical cancer: HPV status must be documented if known.
(ix) Triple negative breast cancer HER2, ER and PR status must be documented
(x) Adenocarcinoma of the endometrium
(xi) Ovarian cancer
(xii) Prostate adenocarcinoma
(xiii) Hepatocellular cancer-Child Pugh A only
(xiv) Small cell lung cancer
(xv) Gastric and gastric esophageal junction cancer: HER2 Status must be documented if known.

B. Dose Expansion: Parts 1B, 2B, 2C, and 3B

The following tumor types will be permitted:

(a) Cervical Cancer—Part 1B
  (i) Histologically confirmed cervical cancer that is unresectable, metastatic, or recurrent with documented disease progression
  (ii) Document tumor HPV status if known. If unknown, subjects must consent to allow their submitted archived tumor tissue sample (block or unstained slides) to be tested.
  (iii) Prior therapy requirement:
    1. Must have received and then progressed or have been intolerant or refractory to at least 1 standard systemic therapy, for metastatic and/or unresectable disease (e.g., paclitaxel/cisplatin, paclitaxel/cisplatin/bevacizumab). Concurrent chemotherapy administered with primary radiation and adjuvant chemotherapy given following completion of radiation therapy do not count as systemic chemotherapy regimens.

(b) Colorectal Cancer—Part 2B
  (i) Histologically confirmed CRC that is metastatic or recurrent with documented disease progression
  (ii) Document MSI, MMR, KRAS, and BRAF status if known. If unknown, subjects must consent to allow their submitted archived tumor tissue sample (block or unstained slides) to be tested.
(iii) Prior therapy requirement:
Subjects must have received and then progressed or have been intolerant or refractory to at least 1 standard systemic therapy, for metastatic and/or unresectable disease (or have progressed within 6 months of adjuvant therapy).
(c) Bladder Cancer—Part 2C
(i) Histologically or cytologically confirmed urothelial carcinoma (including mixed histologies of urothelial carcinoma with elements of other subtypes) of the renal pelvis, ureter, bladder, or urethra with progression or refractory disease
(ii) Prior therapy requirement:
Subjects must have received and then progressed or have been intolerant or refractory to at least 1 standard systemic therapy (e.g., platinum based chemotherapy) regimen for the treatment of metastatic (Stage IV) or locally advanced unresectable disease.
(d) Ovarian—Part 3B
(i) Histologically or cytologically confirmed ovarian carcinoma (including epithelial OC, primary peritoneal, or fallopian tube carcinoma) with documented disease progression
(ii) Documented germline BRCA mutation status, if known. If unknown, subjects must consent to allow their submitted archived tumor tissue sample (block or unstained slides) to be tested.
(iii) Prior therapy requirement:
Subjects must have received and then progressed or have been intolerant or refractory to at least 1 standard systemic therapy (e.g., platinum-based chemotherapy), for metastatic and/or unresectable disease.

3) Eastern Cooperative Oncology Group (ECOG) performance status of ≤1.

4) Presence of at least 1 lesion with measurable disease as defined by RECIST v1.1 for response assessment. Subjects with lesions in a previously irradiated field as the sole site of measurable disease are permitted to enroll provided the lesion(s) have demonstrated clear progression and can be measured accurately.

5) For subjects requiring fresh tumor biopsy, subjects must have at least one lesion accessible for pre- and on-treatment biopsy, in addition to the minimum one RECIST v1.1 measurable lesion required for response assessment. This lesion needs to be distinct from index lesion(s) being evaluated for radiological response.

6) Subjects with prior exposure to therapy with any agent specifically targeting checkpoint pathway inhibition (such as anti-PD-1, anti-PD-L1, anti-PD-L2, anti-LAG-3, and anti-CTLA-4 antibody) are permitted after a washout period of any time greater than 4 weeks from the last treatment
Note: (i) Subjects who experienced prior Grade 1 to 2 checkpoint therapy-related immune-mediated AEs must have confirmed recovery from these events at the time of study entry, other than endocrinopathies treated with supplementation, as documented by resolution of all related clinical symptoms, abnormal findings on physical examination, and/or associated laboratory abnormalities. Where applicable, these subjects must also have completed steroid tapers for treatment of these AEs by a minimum of 14 days prior to commencing treatment with study therapy. (ii) Eligibility of subjects with prior ≥Grade 3 checkpoint therapy-related immune AEs, will be considered on a case-by-case basis after discussion with the Medical Monitor (e.g., asymptomatic isolated Grade 3 lipase elevations without clinical or radiological features of pancreatitis are permitted to enroll).

7) Subjects with prior therapy with any agent specifically targeting T-cell co-stimulation pathways except anti-OX40 antibody, anti-CD137, anti-GITR antibody, and anti-CD27 are permitted after a washout period of any time greater than 4 weeks from the last treatment.

8) Prior palliative radiotherapy must have been completed at least 2 weeks prior to first dose of study drug. Subjects with symptomatic tumor lesions at baseline that may require palliative radiotherapy within 4 weeks of first dose of study drug are strongly encouraged to receive palliative radiotherapy prior to enrollment.

9) Subjects enrolled into dose escalation and expansion cohorts must consent to the acquisition of existing formalin-fixed, paraffin-embedded (FFPE) tumor tissue, either a block or a minimum of 15 unstained slides (25 slides preferred), for performance of correlative studies. If an archived sample is not available, subject must consent to a pre-treatment tumor biopsy. Subjects unable to provide an archived tumor sample and who either do not consent to a pre-treatment tumor biopsy or do not have accessible lesions are not eligible. (However, subjects whose pre-treatment biopsy yields inadequate tissue quantity or quality will not be ineligible on this basis alone). For any additional subjects added to any of the previously completed dose escalation cohorts, mandatory pre- and on-treatment biopsies are required.

10) Subjects enrolled into dose expansion, or added to any previously completed dose escalation cohort, are required to undergo mandatory pre- and ontreatment biopsies at acceptable clinical risk. (a) The solid tumor tissue specimen must be a core needle, excisional, or incisional biopsy. Fine needle biopsies, drainage of pleural effusions with cytospins, or punch biopsies are not considered adequate for biomarker review. Biopsies of bone lesions that do not have a soft tissue component or decalcified bone tumor samples are also not acceptable. (b) Biopsied lesions should be distinct from index lesion(s) being evaluated for radiological response 11) Adequate organ function for subjects as defined by the following:
(a) Neutrophils ≥1500/μL (stable off any growth factor within 4 weeks of first study drug administration)
(b) Platelets ≥80×103/μL (transfusion to achieve this level is not permitted within 2 weeks of first study drug administration)
(c) Hemoglobin ≥8 g/dL (transfusion to achieve this level is not permitted within 2 weeks of first study drug administration)
(d) ALT and AST ≤3× upper limit of normal (ULN)
(e) Total bilirubin ≤1.5×ULN (except subjects with Gilbert's Syndrome who must have normal direct bilirubin)
(f) Normal thyroid function or stable on hormone supplementation per investigator assessment
(g) Albumin >2 mg/dl
(h) Serum creatinine <1.5×ULN or creatinine clearance (CrCl)≥40 ml/min (measured using the Cockcroft-Gault formula below):

Female CrCl=(140−age in years)×weight in kg×0.85

72×serum creatinine in mg/dL

Male CrCl=(140−age in years)×weight in kg×1.00v

72×serum creatinine in mg/dL

12) Ability to comply with treatment, PK and PD sample collection, and required study follow-up Age and Reproductive Status a) Men and women, ages ≥18 years at the time of informed consent.

b) Women of childbearing potential (WOCBP) must have a negative serum or urine pregnancy test (minimum sensitivity 25 IU/L or equivalent units of human chorionic gonadotrophin [hCG]) within 24 hours prior to the start of study drug.

c) Women must not be breastfeeding.

d) WOCBP must agree to follow instructions for method(s) of contraception for the duration of treatment with study drug OX40.21 plus 5 half-lives of study drug plus 30 days. This duration should be 12 weeks for Parts 1 and 3 subjects (50 days plus 30 days) or 23 weeks for Part 2 subjects (130 days plus 30 days [duration of ovulatory cycle]), for a total of up to 160 days post-treatment completion.

e) Men who are sexually active with WOCBP must agree to follow instructions for method(s) of contraception for the duration of treatment with study drug OX40.21 plus 5 half-lives of the study drug plus 90 days. The duration should be 20 weeks for Parts 1 and 3 subjects (50 days plus 90 days) or 31 weeks for Part 2 subjects (130 days completion. In addition, male subjects must be willing to refrain from sperm donation during this time.

f) Azoospermic males are exempt from contraceptive requirements. WOCBP who are continuously not heterosexually active are also exempt from contraceptive requirements, but still undergo pregnancy testing.

Exclusion Criteria

1) Target Disease Exceptions a) Subjects with known or suspected CNS metastases or untreated CNS metastases, or with the CNS as the only site of disease, are excluded. However, subjects with controlled brain metastases are allowed to enroll. Controlled brain metastases are defined as no radiographic progression for at least 4 weeks following radiation and/or surgical treatment (or 4 weeks of observation if no intervention is clinically indicated), and off of steroids for at least 2 weeks, and no new or progressive neurological signs and symptoms.

b) Subjects with carcinomatous meningitis c) For ovarian cancer:

i) ovarian cancer subjects with history of bowel obstruction in the prior 6 months or with Tenckhoff catheter are excluded.

ii) up to 4 prior anti-cancer treatments are permitted (i.e., chemotherapy, radiotherapy, hormonal, or immunotherapy). Restarting the same regimen after a drug holiday may be considered one regimen; however it would be counted as two regimens if there was any other regimen used in between.

2) Medical History and Concurrent Diseases a) Subjects with a prior malignancy, different from the one used for enrollment in this study, diagnosed within less than 2 years prior to study entry are excluded (except non-melanoma skin cancers and in situ cancers such as bladder, colon, cervical/dysplasia, melanoma, or breast). In addition, subjects with other second malignancies diagnosed more than 2 years ago who have received therapy with curative intent with no evidence of disease during the interval who are considered to present a low risk for recurrence are eligible.

b) Other active malignancy requiring concurrent intervention c) Prior organ allograft d) Previous treatment:

i) Prior anti-cancer treatments are permitted (i.e., chemotherapy, radiotherapy, hormonal, or immunotherapy)

ii) Toxicity (except for alopecia) related to prior anti-cancer therapy and/or surgery must either have resolved, returned to baseline or Grade 1 or have been deemed irreversible iii) For cytotoxic agents at least 4 weeks must have elapsed between the last dose of prior to anti-cancer therapy and initiation of study therapy iv) For non-cytotoxic agents at least 4 weeks or 5 half-lives (whichever is shorter) must have elapsed from last dose of prior anti-cancer therapy and the initiation of study therapy.

e) Prior therapy with anti-OX40 antibody f) Subjects with active, known, or suspected autoimmune disease are excluded. Subjects with vitiligo, type 1 diabetes mellitus, residual hypothyroidism due to autoimmune condition only requiring hormone replacement, euthyroid subjects with a history of Grave's disease (subjects with suspected autoimmune thyroid disorders must be negative for thyroglobulin and thyroid peroxidase antibodies and thyroid stimulating immunoglobulin prior to first dose of study drug), psoriasis not requiring systemic treatment, or conditions not expected to recur in the absence of an external trigger are permitted to enroll. Subjects with well controlled asthma and/or mild allergic rhinitis (seasonal allergies) are eligible.

g) Subjects with history of life-threatening toxicity related to prior immune therapy (e.g., anti-CTLA-4 or anti-PD-1/PD-L1 treatment or any other antibody or drug specifically targeting T-cell co-stimulation or immune checkpoint pathways) except those that are unlikely to re-occur with standard countermeasures (e.g., hormone replacement after adrenal crisis)

h) Subjects with interstitial lung disease that is symptomatic or that may interfere with the detection or management of suspected drug-related pulmonary toxicity i) Chronic obstructive pulmonary disease requiring recurrent steroid bursts or chronic steroids at doses greater than 10 mg/day of prednisone or the equivalent j) Subjects with a condition requiring systemic treatment with either corticosteroids (>10 mg daily prednisone equivalents) or other immunosuppressive medications within 14 days of study drug administration except for adrenal replacement steroid doses >10 mg daily prednisone equivalent in the absence of active autoimmune disease. Note: Treatment with a short course of steroids (<5 days) up to 7 days prior to initiating study drug is permitted.

k) Uncontrolled or significant cardiovascular disease, including but not limited to any of the following:

i) Myocardial infarction or stroke/transient ischemic attack within the past 6 months ii) Uncontrolled angina within the past 3 months iii) Any history of clinically significant arrhythmias (such as ventricular tachycardia, ventricular fibrillation, or torsades de pointes)

iv) History of other clinically significant heart disease (e.g., cardiomyopathy, congestive heart failure with New York Heart Association functional classification III-IV, pericarditis, significant pericardial effusion)

v) Cardiovascular disease-related requirement for daily supplemental oxygen therapy vi) QT interval corrected for heart rate using Fridericia's formula (QTcF) prolongation >480 msec l) History of any chronic hepatitis as evidenced by the following:
  i) Positive test for hepatitis B surface antigen
  ii) Positive test for qualitative hepatitis C viral load (by PCR)
  Note: Subjects with positive hepatitis C antibody and negative quantitative hepatitis C by PCR are eligible. History of resolved hepatitis A virus infection is not an exclusion criterion. Additional testing or substitute testing per institutional guidelines to rule out infection is permitted.
m) Evidence of active infection that requires systemic antibacterial, antiviral, or antifungal therapy ≤7 days prior to initiation of study drug therapy (does not apply to viral infections that are presumed to be associated with the underlying tumor type required for study entry)
n) Known history of testing positive for HIV or known acquired immunodeficiency syndrome.
o) Evidence or history of active or latent tuberculosis infection including PPD recently converted to positive; chest x-ray with evidence of infectious infiltrate; recent unexplained changes in fever/chill patterns.
p) Any major surgery within 4 weeks of study drug administration. Subjects must have recovered from the effects of major surgery or significant traumatic injury at least 14 days before the first dose of study drug.
q) Use of non-oncology vaccines containing live virus for prevention of infectious diseases within 4 weeks prior to study drug. The use of inactivated seasonal influenza vaccines, e.g., Fluzone®, is permitted.
r) Use of pRBC or platelet transfusion within 2 weeks prior to the first dose of study drug
s) A known or underlying medical or psychiatric condition and/or social reason that could make the administration of study drug hazardous to the subjects or could adversely affect the ability of the subject to comply with or tolerate the study.

3) Allergies and Adverse Drug Reaction
  a) History of allergy to nivolumab or ipilimumab (Parts 2 and 3 only, respectively)
  b) History of any significant drug allergy (such as anaphylaxis or hepatotoxicity) to prior anti-cancer immune modulating therapies (e.g., checkpoint inhibitors, T-cell co-stimulatory antibodies)

Study Assessments:
  Physical examinations, vital sign measurements, 12-lead electrocardiograms (ECGs), and clinical laboratory evaluations are performed at selected times throughout the dosing interval. Subjects are closely monitored for AEs throughout the study.
  Safety Assessments: AEs are assessed during the study and for 100 days after the last treatment. AEs are evaluated according to NCI CTCAE v4.03. Subjects are followed until all treatment-related AEs have recovered to baseline or are deemed irreversible.
  Efficacy Assessments: Disease assessment with CT and/or MRI as appropriate are performed at baseline and every 8 weeks (±1 week) for q2w dosing regimens and every 9 weeks (±1 week) for q3w dosing regimens, then every 12 weeks during the treatment and response follow-up phases until discontinuation of treatment or withdrawal from study. Tumor assessments at other time points are performed if there are concerns about tumor progression. Assessment of tumor response is made according to RECIST v1.1 for subjects with malignant tumors.
  Pharmacokinetic and Immunogenicity Assessments: Samples for PK and immunogenicity assessments are collected for subjects receiving OX40.21 alone or in combination with nivolumab or ipilimumab. The PK of OX40.21 is characterized by non-compartmental analysis (NCA) method. Immunogenicity samples are analyzed for anti-OX40.21 antibodies and/or anti-nivolumab antibodies and/or anti-ipilimumab antibodies by validated immunoassays.
  Exploratory Biomarker Assessments: To explore potential predictive markers for clinical response to OX40.21 in relation to dose and PK, 3 types of specimens are obtained from all subjects for biomarker testing: (i) whole blood, (ii) serum/plasma, and (iii) tumor tissue.

Statistical Considerations
Sample Size Determination
Dose Escalation:
  As a Phase 1 dose escalation trial, the sample size for each dose escalation cohort depends on observed toxicity and posterior inference. Approximately 30 subjects are treated during each dose escalation part (OX40.21 monotherapy [Part 1A], OX40.21 in combination with nivolumab [Part 2A], and OX40.21 in combination with ipilimumab [Part 3A]) for a combined total of about 90 subjects in Parts 1A, 2A, and 3A. Initially, approximately 3 subjects are treated at the starting dose levels of OX40.21 or OX40.21 in combination with nivolumab or ipilimumab. Additional cohorts of approximately 3 evaluable subjects are treated at recommended dose levels per BLRM (-Copula) recommendations during the dose escalation phase. At least 6 DLT-evaluable subjects are treated at the MTD.

Dose Expansion:
  In general terms, the expansion phase sizing is based on target response rates (target overall response rate) and the ability to identify a signal for such clinical response that is above the standard of care (historical overall response rate).
  Approximately 12 subjects are treated in the Part 1B dose expansion cohort. Approximately 35 subjects are treated in the Part 2B dose expansion cohort. Approximately 27 subjects are treated in the Part 2C dose expansion cohort. Approximately 35 subjects are treated in the Part 3B dose expansion cohort.

Endpoints
Primary Endpoints
  The assessment of safety is based on the incidence of AEs, serious AEs, AEs leading to discontinuation, and deaths. In addition, clinical laboratory test abnormalities are examined.

Secondary Endpoints
Efficacy:
  The anti-tumor activity of OX40.21 alone and OX40.21 in combination with nivolumab or ipilimumab is measured by ORR, duration of response, and progression free survival rate (PFSR) at 24 weeks based on RECIST v1.1. The above are determined based on tumor measurements occurring at baseline, every 8 weeks (±1 week) for q2w dosing regimens and every 9 weeks (±1 week) for q3w dosing regimens during the treatment period, and every 3 months (12 weeks) during the survival follow-up period.
  Best overall response (BOR) is assessed per RECIST 1.1 criteria.
  ORR is the proportion of all treated subjects whose BOR is either CR or PR.
  Duration of response, computed for all treated subjects with a BOR of CR or PR, is the time between the date of first response and the date of disease progression or death, whichever occurs first.

PFSR at 24 weeks is defined as the proportion of treated subjects remaining progression free and surviving at 24 weeks. The proportion is calculated by the Kaplan-Meier estimate, which takes into account censored data.

Pharmacokinetics

Selected parameters, such as Cmax, Tmax, AUC(0-t), and AUC(TAU), are assessed in 2 cycles depending on the schedule for monotherapy or in combination with nivolumab or ipilimumab. Parameters such as Ctau, CLT, Css-avg, accumulation index (AI), and effective elimination half-life (T-HALFeff) are assessed in the second cycle when intensive PK is collected.

Immunogenicity

The secondary objective of immunogenicity is assessed by the frequency of positive ADA to OX40.21 or nivolumab or ipilimumab.

Exploratory Endpoints:

Exploratory objectives related to OS are assessed by OS rate at a certain time point (e.g., 2 years). OS rate is the proportion of subjects alive at that time point. OS for a subject is defined the time from the date of first dose of study medication to the date of death from any cause. Exploratory objectives related to biomarkers are assessed by the change from baseline or baseline level biomarker measurements in peripheral blood (e.g., soluble factors including, but not limited to, cytokine and chemokines) or tumor tissue (e.g., tumor-infiltrating lymphocytes).

For subjects with multiple ECG measurements, the following parameters are optionally assessed: changes in the ECG intervals QT, QTc, QRS, and P-R interval from baseline.

Analyses

Safety analyses: All recorded AEs are listed and tabulated by system organ class, preferred term, and treatment. Vital signs and clinical laboratory test results are listed and summarized by treatment. Any significant physical examination findings and clinical laboratory results are also noted. ECG readings are evaluated, and abnormalities, if present, are noted.

Efficacy analyses: Listing of tumor measurements are provided by subject and study day in each arm and dose level. Individual subject's BOR is listed based on RECIST 1.1. To describe the anti-tumor activity of OX40.21 alone or in combination with nivolumab or ipilimumab, ORR is calculated. ORR and corresponding 2-sided 95% CI by the Clopper-Pearson method are provided by treatment and/or dose level and tumor type. Median duration of response and corresponding 2-sided 95% CI are reported by treatment and/or dose level and tumor type. Duration of response is analyzed using the Kaplan-Meier method. In addition, PFSR, the probability of a subject remaining progression free or surviving to 24 weeks, is estimated by the Kaplan-Meier methodology by treatment, tumor type, and dose level. The corresponding 95% CI is derived based on Greenwood formula. OS is plotted using the Kaplan-Meier method. Median OS and corresponding 2-sided 95% CI are reported.

Pharmacokinetic analyses: All individual PK parameters are listed for each analyte, including any exclusions and reasons for exclusion from summaries. Summary statistics are tabulated for each PK parameter by treatment. Geometric means and coefficients of variation are presented for Cmax, AUC(0-t), AUC(TAU), Ctau, CLT, Cssavg, and AI. Medians and ranges are presented for Tmax. Means and standard deviations are presented for all other PK parameters (e.g., T-HALFeff).

OX40.21 dose dependency is assessed in dose escalation monotherapy. To describe the dependency on dose of OX40.21, scatter plots of Cmax, AUC(0-t), and AUC(TAU) versus dose are provided for each day measured. An exploratory assessment of dose proportionality based on a power model and a CI around the power coefficient is performed. Nivolumab and ipilimumab end of infusion and trough (Ctrough) concentrations and OX40.21 trough concentration are tabulated by treatment and study day using summary statistics. These data may also be pooled with other datasets for population PK analysis.

Immunogenicity analysis: All available immunogenicity data are provided by treatment, dose, and immunogenicity status. The frequency of subjects with positive ADA assessment of OX40.21, nivolumab, and ipilimumab are determined.

Exploratory biomarker analyses: Summary statistics for biomarkers and their corresponding changes (or percent changes) from baseline are tabulated by planned study day and dose in each arm. The time course of biomarker measures are represented graphically. If there is indication of meaningful pattern over time, further analysis (e.g., by linear mixed model) is performed to characterize the relationship. Methods such as, but not limited to, logistic regression are used to explore possible associations between biomarker measures from peripheral blood or tumor biopsy and clinical outcomes.

TABLE 23

SUMMARY OF SEQUENCES

| SEQ ID | Description | Sequence |
|---|---|---|
| 1 | Human OX40 precursor | MCVGARRLGRGPCAALLLLGLGLSTVTGLHCVGDTYPSNDRCCHECRPGNGMVS RCSRSQNTVCRPCGPGFYNDVVSSKPCKPCTWCNLRSGSERKQLCTATQDTVCR CRAGTQPLDSYKPGVDCAPCPPGHFSPGDNQACKPWTNCTLAGKHTLQPASNSS DAICEDRDPPATQPQETQGPPARPITVQPTEAWPRTSQGPSTRPVEVPGGRAVA AILGLGLVLGLLGPLAILLALYLLRRDQRLPPDAHKPPGGGSFRTPIQEEQADA HSTLAKI |
| 2 | Extracellular domain of mature human OX40 | LHCVGDTYPSNDRCCHECRPGNGMVSRCSRSQNTVCRPCGPGFYNDVVSSKPCK PCTWCNLRSGSERKQLCTATQDTVCRCRAGTQPLDSYKPGVDCAPCPPGHFSPG DNQACKPWTNCTLAGKHTLQPASNSSDAICEDRDPPATQPQETQGPPARPITVQ PTEAWPRTSQGPSTRPVEVPGGRAVAA |
| 3 | Cynomolgus OX40 | MCVGARRLGRGPCAALLLLGLGLSTTAKLHCVGDTYPSNDRCCQECRPGNGMVS RCNRSQNTVCRPCGPGFYNDVVSAKPCKACTWCNLRSGSERKQPCTATQDTVCR CRAGTQPLDSYKPGVDCAPCPPGHFSPGDNQACKPWTNCTLAGKHTLQPASNSS DAICEDRDPPPTQPQETQGPPARPTTVQPTEAWPRTSQRPSTRPVEVPRGPAVA |

TABLE 23-continued

SUMMARY OF SEQUENCES

| SEQ ID | Description | Sequence |
|---|---|---|
| | | AILGLGLALGLLGPLAMLLALLLLRRDQRLPPDAPKAPGGGSFRTPIQEEQADA HSALAKI |
| 4 | Human OX40-L | HERVQPLEEN VGNAARPRFE RNKLLLVASV IQGLGLLLCF TYICLHFSTL QVSHRYPRIQ SIKVQFTEYK KEKGFILTSQ KEDEINKVQN NSVIINCDGF YLISLKGYFS QEVNISLHYQ KDEEPLFQLK KVRSVHSLMV ASLTYKDKVY LNVTTDNTSL DDFHVNGGEL ILIHQNPGEF CVL* |
| 5 | human IgG1 constant domain | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPG |
| 6 | human IgG1 constant domain (allotypic variant) | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| 7 | human IgG1 kappa light chain | RTVAAPSVFIFPPSDEQLKSGTASVVCLLNNFYPREAKVQWKVDNA LQSGNSQESVTEQDSKDSTYSLSSTLTLSKADYEKHKVYACEVTHQ GLSSPVTKSFNRGEC |
| 8 | heavy chain constant region alternative C-terminus | LSPGK |
| 9 | heavy chain constant region alternative C-terminus | LSPG |
| 10 | Human IgG1 kappa light chain constant region (CL) | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC |
| 11 | 3F4 VH CDR1 | SYDVN |
| 12 | 3F4 VH CDR2 | WMNPNSGNTGYAPKFQG |
| 13 | 3F4 VH CDR3 | IYSSSYNWFDP |
| 14 | 3F4 VL CDR1 | RASQSVSSYLA |
| 15 | 3F4 VL CDR2 | DASNRAT |
| 16 | 3F4 VL CDR3 | QQRSNWPLT |
| 17 | 3F4 VH | QVQLVQSGAEVKKPGASVKVSCKASGNTFTSYDVNWVRQATGQGLEWMG WMNPNSGNTGYAPKFQGRVTMTRNTSISTAYMELSSLRSEDTAVYYCAR IYSSSYNWFDPWGQGTLVTVSS |
| 18 | 3F4 VL | EIVLTQSPATLSLSPGERATLSCRASQSVSSYLAWYQQKPGQAPRLLIY DASNRATGIPARFSGSGSGTDFTLTISSLEPEDFAVYYCQQRSNWPLTF GGGTKVEIK |
| 19 | 14B6 VH CDR1 | SNWIG |
| 20 | 14B6 VH CDR2 | FIYPGDSDTRYSPSFQG |
| 21 | 14B6 VH CDR3 | YGDDWYFDL |
| 22 | 14B6 VL1 CDR1 | RASQSVSSYLA |
| 23 | 14B6 VL1 CDR2 | DASNRAT |
| 24 | 14B6 VL1 CDR3 | QQRGDWPIT |
| 25 | 14B6 VL2 CDR1 | RASQGISSWLA |

TABLE 23-continued

SUMMARY OF SEQUENCES

| SEQ ID | Description | Sequence |
|---|---|---|
| 26 | 14B6 VL2 CDR2 | AASSLQS |
| 27 | 14B6 VL2 CDR3 | QQYNSYPRIT |
| 28 | 14B6 VH | EVQLEQSGAEVKKPGESLKISCKGSGYSFTSNWIGWVRQMPGKGLEWMG FIYPGDSDTRYSPSFQGQVTISADKSISTAYLQWSSLKASDIAMYYCAR YGDDWYFDLWGRGTLVTVSS |
| 29 | 14B6 VL1 | EIVLTQSPATLSLSPGERATLSCRASQSVSSYLAWFQQRPGQAPRLLIY DASNRATGIPARFSGSGSGTDFSLTISSLEPEDFAVYYCQQRGDWPITF GQGTRLEIK |
| 30 | 14B6 VL2 | DIQMTQSPSSLSASVGDRVTITCRASQGISSWLAWYQQKPEKAPKSLIY AASSLQSGVPSRFSGSGSGTDFTLTISSLQPEDFATYYCQQYNSYPRIT FGQGTRLEIK |
| 31 | 23H3 VH CDR1 | NYAMY |
| 32 | 23H3 VH CDR2 | AIGIGGDTFYTDSVKG |
| 33 | 23H3 VH CDR3 | MGTGYFFDY |
| 34 | 23H3 VL CDR1 | RASQSVSSYLA |
| 35 | 23H3 VL CDR2 | DASNRAT |
| 36 | 23H3 VL CDR3 | QQRSNWPLT |
| 37 | 23H3 VH | EVQLVQSGGGLVHPGGSLRLSCAGSGFTFSNYAMYWVRQAPGKGLEWVS AIGIGGDTFYTDSVKGRFTISRDNAKNSLSLQMNSLRAEDMAVYYCARM GTGYFFDYWGQGTLVTVSS |
| 38 | 23H3 VL | EIVLTQSPATLSLSPGERATLSCRASQSVSSYLAWYQQKPGQAPRLLIY DASNRATGIPARFSGSGSGTDFTLTISSLEPEDFAVYYCQQRSNWPLTF GPGTKVDIK |
| 39 | 6E1 VH CDR1 | SFAMH |
| 40 | 6E1 VH CDR2 | VISYDGSIKYYTDSVKG |
| 41 | 6E1 VH CDR3 | DGNYGSARYFQH |
| 42 | 6E1 VL1 CDR1 | RASQGISSWLA |
| 43 | 6E1 VL1 CDR2 | AASSLQS |
| 44 | 6E1 VL1 CDR3 | QQYNSYPRT |
| 45 | 6E1 VL2 CDR1 | RASQSVSSYLA |
| 46 | 6E1 VL2 CDR2 | DASNRAT |
| 47 | 6E1 VL2 CDR3 | QQRSNWPYT |
| 48 | 6E1 VH | QVQLVESGGGVVQPGRSLRLSCAASGFTFSSFAMHWVRQAPGKGLEWVT VISYDGSIKYYTDSVKGRFTFSRDNSKNTLYLQMNSLRAEDTAVYYCTR DGNYGSARYFQHWGQGTLVTVSS |
| 49 | 6E1 VL1 | DIQMTQSPSSLSASVGDRVTITCRASQGISSWLAWYQQKPEKAPKSLIY AASSLQSGVPSRFSGSGSGTDFTLTISSLQPEDFATYYCQQYNSYPRTF GQGTKVEIK |
| 50 | 6E1 VL2 | EIVLTQSPATLSLSPGERATLSCRASQSVSSYLAWYQQKPGQAPRLLIY DASNRATGIPARFSGSGSGTDFTLTISSLEPEDFAVYYCQQRSNWPYTF GQGTKLEIK |
| 51 | 18E9 VH CDR1 | SSAMH |
| 52 | 18E9 VH CDR2 | AIGTGGDTYYADSVKG |
| 53 | 18E9 VH CDR3 | DFYDILTGIFDY |
| 54 | 18E9 VL CDR1 | RASQGISSWLA |

TABLE 23-continued

SUMMARY OF SEQUENCES

| SEQ ID | Description | Sequence |
|---|---|---|
| 55 | 18E9 VL CDR2 | AASSLQS |
| 56 | 18E9 VL CDR3 | QQANSFPST |
| 57 | 18E9 VH | EVQLVQSGGGLVHPGGSLRLSCAHSGFTFTSSAMHWVRQAPGKGLEWIS AIGTGGDTYYADSVKGRFTISRDNAKNSLYLQINSLRAEDMAVYYCARD FYDILTGIFDYWGQGTLVTVSS |
| 58 | 18E9 VL | DIQMTQSPSSVSASVGDRVTITCRASQGISSWLAWYQHKPGKAPKLLIY AASSLQSGVPSRFSGSGSGTDFTLTISSLQPEDFATYYCQQANSFPSTF GQGTKVEIK |
| 59 | 8B11 VH CDR1 | SDAMY |
| 60 | 8B11 VH CDR2 | AIGIGGDTYYTDSVMG |
| 61 | 8B11 VH CDR3 | LGMGYYFDY |
| 62 | 8B11 VL CDR1 | RASQSVSSYLA |
| 63 | 8B11 VL CDR2 | DASNRAT |
| 64 | 8B11 VL CDR3 | QQRSNWPPT |
| 65 | 8B11 VH | MEFVLSWVFLVAILKGVQCEIQLVQSGGGLVHPGGSLRLSCAGSGFTFS SDAMYWVRQAPGKGLEWVSAIGIGGDTYYTDSVMGRFTISRDNAKNSLY LQMNSLRAEDMAVYYCARLGMGYYFDYWGQGTLVTVSS |
| 66 | 8B11 VL | EIVLTQSPATLSLSPGERATLSCRASQSVSSYLAWYQQKPGQAPRLLIY DASNRATGIPARFSGSGSGTDFTLTISSLEPEDFAVYYCQQRSNWPPTF GQGTKVEIK |
| 67 | 20B3 VH CDR1 | SYDMH |
| 68 | 20B3 VH CDR2 | VIGTAGDTYYPGSVKG |
| 69 | 20B3 VH CDR3 | GGMGNYFDY |
| 70 | 20B3 VL CDR1 | RASQSVSSYLA |
| 71 | 20B3 VL CDR2 | DASNRAT |
| 72 | 20B3 VL CDR3 | QQRSNWPLT |
| 73 | 20B3 VH | EVQLVESGGGLVQPGGSLRLSCAASGFTFSSYDMHWVRQTTGKGLEWVS VIGTAGDTYYPGSVKGRFTISRENAKNSLYLQMNSLRAGDTAVYYCARG GMGNYFDYWGQGTLVTVSS |
| 74 | 20B3 VL | EIVLTQSPATLSLSPGERATLSCRASQSVSSYLAWYQQKPGQAPRLLIY DASNRATGIPARFSGSGSGTDFTLTISSLEPEDFAVYYCQQRSNWPLTF GGGTKVEIK |
| 75 | 14A2 VH CDR1 | NYALH |
| 76 | 14A2 VH CDR2 | LISYDGSRKHYADSVKG |
| 77 | 14A2 VH CDR3 | LTMVREGG |
| 78 | 14A2 VL1 CDR1 | RASQSVSSSYLA |
| 79 | 14A2 VL1 CDR2 | GASSRAT |
| 80 | 14A2 VL1 CDR3 | QQYGSSPFT |
| 81 | 14A2 VL2 CDR1 | RVSQGISSYLN |
| 82 | 14A2 VL2 CDR2 | SASNLQS |
| 83 | 14A2 VL2 CDR3 | QRTYNAPYT |
| 84 | 14A2 VH | QVQLVESGGGVVQPGRSLRLSCAASGFTFSNYALHWVRQAPGKGLEWVA LISYDGSRKHYADSVKGRFSISRDNSKNTLYLQMNSLRAEDTAVYYCAS LTMVREGGQGTLVTVSS |

TABLE 23-continued

SUMMARY OF SEQUENCES

| SEQ ID | Description | Sequence |
|---|---|---|
| 85 | 14A2 VL1 | EIVLTQSPGTLSLSPGERATLSCRASQSVSSSYLAWYQQKPGQAPRLLI YGASSRATGIPDRFSGSGSGTDFTLTISRLEPEDFAVYYCQQYGSSPFT FGPGTKVDIK |
| 86 | 14A2 VL2 | DIQLTQSPSSLSASVGDRVTITCRVSQGISSYLNWYRQKPGKVPKLLIY SASNLQSGVPSRFSGSGSGTDFTLTISSLQPEDVATYYGQRTYNAPYTF GGGTKVEIK |
| 87 | 20C1 VH CDR1 | SYAMY |
| 88 | 20C1 VH CDR2 | AIDTDGGTFYADSVRG |
| 89 | 20C1 VH CDR3 | LGEGYFFDY |
| 90 | 20C1 VL CDR1 | RASQSVSSYLA |
| 91 | 20C1 VL CDR2 | DASNRAT |
| 92 | 20C1 VL CDR3 | QQRSNWPPT |
| 93 | 20C1 VH | EAQLVQSGGGLVHPGGSLRLSCADSGFTFSSYAMYWVRQAPGKGLEWVS AIDTDGGTFYADSVRGRFTISRDNAKNSLYLQMNGLRAEDMAVYFCARL GEGYFFDYWGQGTLVTVSS |
| 94 | 20C1 VL | EIVLTQSPATLSLSPGERATLSCRASQSVSSYLAWYQQKPGQAPRLLIY DASNRATGIPARFSGSGSGTDFTLTISSLEPEDFAVYYCQQRSNWPPTF GGGTKVEIK |
| 95 | OX40.6 heavy chain | EVQLVQSGGGLVQPGGSLRLSCAGSGFTFSNYAMYWVRQAPGKGLE WVSAIGIGGDTFYTDSVKGRFTISRDNAKNSLSLQMNSLRAEDTAV YYCARMGTGYFFDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKRVEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPG |
| 96 | OX40.6 light chain | EIVLTQSPATLSLSPGERATLSCRASQSVSSYLAWYQQKPGQAPRL LIYDASNRATGIPARFSGSGSGTDFTLTISSLEPEDFAVYYCQQRS NWPLTFGPGTKVDIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 97 | OX40.7 heavy chain | EVQLVQSGGGLVHPGGSLRLSCAGSGFTFSNYAMYWVRQAPGKGLE WVSAIGIGGDTFYTDSVKGRFTISRDNAKNSLSLQMNSLRAEDTAV YYCARYGTGYFFDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKRVEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPG |
| 98 | OX40.7 light chain | EIVLTQSPATLSLSPGERATLSCRASQSVSSYLAWYQQKPGQAPRL LIYDASNRATGIPARFSGSGSGTDFTLTISSLEPEDFAVYYCQQRS NWPLTFGPGTKVDIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 99 | OX40.8 heavy chain | QVQLVESGGGVVQPGRSLRLSCAASGFTFSNYALHWVRQAPGKGLE WVALISYDGSRKHYADSVKGRFSISRDNSKNTLYLQMNSLRAEDTA VYYCASLTMVREWGQGTLVTVSSASTKGPSVFPLAPSSKSTSGGTA ALGCLVKDYFPEPVTVSWNSGALTSGVHTFPAVLQSSGLYSLSSVV TVPSSSLGTQTYICNVNHKPSNTKVDKRVEPKSCDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVK GFYPSDIAVEWESNGQPENNYKTTPPVLDSDGSFFLYSKLTVDKSR WQQGNVFSCSVMHEALHNHYTQKSLSLSPG |

TABLE 23-continued

SUMMARY OF SEQUENCES

| SEQ ID | Description | Sequence |
|---|---|---|
| 100 | OX40.8 light chain | EIVLTQSPGTLSLSPGERATLSCRASQSVSSSYLAWYQQKPGQAPR<br>LLIYGASSRATGIPDRFSGSGSGTDFTLTISRLEPEDFAVYYCQQY<br>GSSPFTFGPGTKVDIKRTVAAPSVFIFPPSDEQLKSGTASVVCLLN<br>NFYPREAKVQWKVDNALQSGNSQESVTEQDSKDSTYSLSSTLTLSK<br>ADYEKHKVYACEVTHQGLSSPVTKSFNRGEC |
| 101 | OX40.9 heavy chain | QVQLVESGGGVVQPGRSLRLSCAASGFTFSNYALHWVRQAPGKGLE<br>WVALISYDGSRKHYADSVKGRFSISRDNSKNTLYLQMNSLRAEDTA<br>VYYCASLTYVREWGQGTLVTVSSASTKGPSVFPLAPSSKSTSGGTA<br>ALGCLVKDYFPEPVTVSWNSGALTSGVHTFPAVLQSSGLYSLSSVV<br>TVPSSSLGTQTYICNVNHKPSNTKVDKRVEPKSCDKTHTCPPCPAP<br>ELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVK<br>GFYPSDIAVEWESNGQPENNYKTTPPVLDSDGSFFLYSKLTVDKSR<br>WQQGNVFSCSVMHEALHNHYTQKSLSLSPG |
| 102 | OX40.9 light chain | EIVLTQSPGTLSLSPGERATLSCRASQSVSSSYLAWYQQKPGQAPR<br>LLIYGASSRATGIPDRFSGSGSGTDFTLTISRLEPEDFAVYYCQQY<br>GSSPFTFGPGTKVDIKRTVAAPSVFIFPPSDEQLKSGTASVVCLLN<br>NFYPREAKVQWKVDNALQSGNSQESVTEQDSKDSTYSLSSTLTLSK<br>ADYEKHKVYACEVTHQGLSSPVTKSFNRGEC |
| 103 | OX40.10 heavy chain | QVQLVESGGGVVQPGRSLRLSCAASGFTFSNYALHWVRQAPGKGLE<br>WVALISYSGSRKHYADSVKGRFSISRDNSKNTLYLQMNSLRAEDTA<br>VYYCASLTMVREGGQGTLVTVSSASTKGPSVFPLAPSSKSTSGGTA<br>ALGCLVKDYFPEPVTVSWNSGALTSGVHTFPAVLQSSGLYSLSSVV<br>TVPSSSLGTQTYICNVNHKPSNTKVDKRVEPKSCDKTHTCPPCPAP<br>ELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVK<br>GFYPSDIAVEWESNGQPENNYKTTPPVLDSDGSFFLYSKLTVDKSR<br>WQQGNVFSCSVMHEALHNHYTQKSLSLSPG |
| 104 | OX40.10 light chain | EIVLTQSPGTLSLSPGERATLSCRASQSVSSSYLAWYQQKPGQAPR<br>LLIYGASSRATGIPDRFSGSGSGTDFTLTISRLEPEDFAVYYCQQY<br>GSSPFTFGPGTKVDIKRTVAAPSVFIFPPSDEQLKSGTASVVCLLN<br>NFYPREAKVQWKVDNALQSGNSQESVTEQDSKDSTYSLSSTLTLSK<br>ADYEKHKVYACEVTHQGLSSPVTKSFNRGEC |
| 105 | OX40.11 heavy chain | QVQLVESGGGVVQPGRSLRLSCAASGFTFSNYALHWVRQAPGKGLE<br>WVALISYDSSRKHYADSVKGRFSISRDNSKNTLYLQMNSLRAEDTA<br>VYYCASLTMVREGGQGTLVTVSSASTKGPSVFPLAPSSKSTSGGTA<br>ALGCLVKDYFPEPVTVSWNSGALTSGVHTFPAVLQSSGLYSLSSVV<br>TVPSSSLGTQTYICNVNHKPSNTKVDKRVEPKSCDKTHTCPPCPAP<br>ELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVK<br>GFYPSDIAVEWESNGQPENNYKTTPPVLDSDGSFFLYSKLTVDKSR<br>WQQGNVFSCSVMHEALHNHYTQKSLSLSPG |
| 106 | OX40.11 light chain | EIVLTQSPGTLSLSPGERATLSCRASQSVSSSYLAWYQQKPGQAPR<br>LLIYGASSRATGIPDRFSGSGSGTDFTLTISRLEPEDFAVYYCQQY<br>GSSPFTFGPGTKVDIKRTVAAPSVFIFPPSDEQLKSGTASVVCLLN<br>NFYPREAKVQWKVDNALQSGNSQESVTEQDSKDSTYSLSSTLTLSK<br>ADYEKHKVYACEVTHQGLSSPVTKSFNRGEC |
| 107 | OX40.12 heavy chain | QVQLVESGGGVVQPGRSLRLSCAASGFTFSNYALHWVRQAPGKGLE<br>WVALISYSGSRKHYADSVKGRFSISRDNSKNTLYLQMNSLRAEDTA<br>VYYCASLTMVREWGQGTLVTVSSASTKGPSVFPLAPSSKSTSGGTA<br>ALGCLVKDYFPEPVTVSWNSGALTSGVHTFPAVLQSSGLYSLSSVV<br>TVPSSSLGTQTYICNVNHKPSNTKVDKRVEPKSCDKTHTCPPCPAP<br>ELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVS<br>NKALPAPIEKTISKAKGQPREPQVYTLPPSREEMTKNQVSLTCLVK<br>GFYPSDIAVEWESNGQPENNYKTTPPVLDSDGSFFLYSKLTVDKSR<br>WQQGNVFSCSVMHEALHNHYTQKSLSLSPG |
| 108 | OX40.12 light chain | EIVLTQSPGTLSLSPGERATLSCRASQSVSSSYLAWYQQKPGQAPR<br>LLIYGASSRATGIPDRFSGSGSGTDFTLTISRLEPEDFAVYYCQQY<br>GSSPFTFGPGTKVDIKRTVAAPSVFIFPPSDEQLKSGTASVVCLLN<br>NFYPREAKVQWKVDNALQSGNSQESVTEQDSKDSTYSLSSTLTLSK<br>ADYEKHKVYACEVTHQGLSSPVTKSFNRGEC |

TABLE 23-continued

SUMMARY OF SEQUENCES

| SEQ ID | Description | Sequence |
|---|---|---|
| 109 | OX40.13 heavy chain | QVQLVESGGGVVQPGRSLRLSCAASGFTFSNYALHWVRQAPGKGLE WVALISYDSSRKHYADSVKGRFSISRDNSKNTLYLQMNSLRAEDTA VYYCASLTMVREWGQGTLVTVSSASTKGPSVFPLAPSSKSTSGGTA ALGCLVKDYFPEPVTVSWNSGALTSGVHTFPAVLQSSGLYSLSSVV TVPSSSLGTQTYICNVNHKPSNTKVDKRVEPKSCDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVK GFYPSDIAVEWESNGQPENNYKTTPPVLDSDGSFFLYSKLTVDKSR WQQGNVFSCSVMHEALHNHYTQKSLSLSPG |
| 110 | OX40.13 light chain | EIVLTQSPGTLSLSPGERATLSCRASQSVSSSYLAWYQQKPGQAPR LLIYGASSRATGIPDRFSGSGSGTDFTLTISRLEPEDFAVYYCQQY GSSPFTFGPGTKVDIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC |
| 111 | OX40.14 heavy chain | QVQLVESGGGVVQPGRSLRLSCAASGFTFSNYALHWVRQAPGKGLE WVALISYSGSRKHYADSVKGRFSISRDNSKNTLYLQMNSLRAEDTA VYYCASLTYVREWGQGTLVTVSSASTKGPSVFPLAPSSKSTSGGTA ALGCLVKDYFPEPVTVSWNSGALTSGVHTFPAVLQSSGLYSLSSVV TVPSSSLGTQTYICNVNHKPSNTKVDKRVEPKSCDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVK GFYPSDIAVEWESNGQPENNYKTTPPVLDSDGSFFLYSKLTVDKSR WQQGNVFSCSVMHEALHNHYTQKSLSLSPG |
| 112 | OX40.14 light chain | EIVLTQSPGTLSLSPGERATLSCRASQSVSSSYLAWYQQKPGQAPR LLIYGASSRATGIPDRFSGSGSGTDFTLTISRLEPEDFAVYYCQQY GSSPFTFGPGTKVDIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC |
| 113 | OX40.15 heavy chain | QVQLVESGGGVVQPGRSLRLSCAASGFTFSNYALHWVRQAPGKGLE WVALISYDSSRKHYADSVKGRFSISRDNSKNTLYLQMNSLRAEDTA VYYCASLTYVREWGQGTLVTVSSASTKGPSVFPLAPSSKSTSGGTA ALGCLVKDYFPEPVTVSWNSGALTSGVHTFPAVLQSSGLYSLSSVV TVPSSSLGTQTYICNVNHKPSNTKVDKRVEPKSCDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVK GFYPSDIAVEWESNGQPENNYKTTPPVLDSDGSFFLYSKLTVDKSR WQQGNVFSCSVMHEALHNHYTQKSLSLSPG |
| 114 | OX40.15 light chain | EIVLTQSPGTLSLSPGERATLSCRASQSVSSSYLAWYQQKPGQAPR LLIYGASSRATGIPDRFSGSGSGTDFTLTISRLEPEDFAVYYCQQY GSSPFTFGPGTKVDIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC |
| 115 | OX40.16 heavy chain | EVQLVQSGGGLVQPGGSLRLSCAGSGFTFSSYAMYWVRQAPGKGLE WVSAIDTDGGTFYADSVRGRFTISRDNAKNSLYLQMNSLRAEDTAV YFCARLGEGYFFDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKRVEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPG |
| 116 | OX40.16 light chain (shared by OX40.20, OX40.21, OX40.22) | EIVLTQSPATLSLSPGERATLSCRASQSVSSYLAWYQQKPGQAPRL LIYDASNRATGIPARFSGSGSGTDFTLTISSLEPEDFAVYYCQQRS NWPPTFGGGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 117 | OX40.17 heavy chain | EVQLVESGGGLVQPGGSLRLSCAASGFTFSSYDMHWVRQTTGKGLE WVSVIGTAGDTYYPGSVKGRFTISRENAKNSLYLQMNSLRAGDTAV YYCARGGMGNYFDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKRVEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEYKCK |

TABLE 23-continued

SUMMARY OF SEQUENCES

| SEQ ID | Description | Sequence |
|---|---|---|
| | | VSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPG |
| 118 | OX40.17 light chain | EIVLTQSPATLSLSPGERATLSCRASQSVSSYLAWYQQKPGQAPRL LIYDASNRATGIPARFSGSGSGTDFTLTISSLEPEDFAVYYCQQRS NWPLTFGGGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 119 | OX40.18 heavy chain | QVQLVQSGAEVKKPGASVKVSCKASGYTFTSYDVNWVRQATGQGLE WMGWMNPNSGNTGYAPKFQGRVTMTRDTSISTAYMELSSLRSEDTA VYYCARIYSSSYNWFDYWGQGTLVTVSSASTKGPSVFPLAPSSKST SGGTAALGCLVKDYFPEPVTVSWNSGALTSGVHTFPAVLQSSGLYS LSSVVTVPSSSLGTQTYICNVNHKPSNTKVDKRVEPKSCDKTHTCP PCPAPELLGGPSVFLFPPKPKDTLMISRTPEVTCVVVDVSHEDPEV KFNWYVDGVEVHNAKTKPREEQYNSTYRVVSVLTVLHQDWLNGKEY KCKVSNKALPAPIEKTISKAKGQPREPQVYTLPPSREEMTKNQVSL TCLVKGFYPSDIAVEWESNGQPENNYKTTPPVLDSDGSFFLYSKLT VDKSRWQQGNVFSCSVMHEALHNHYTQKSLSLSPG |
| 120 | OX40.18 light chain | EIVLTQSPATLSLSPGERATLSCRASQSVSSYLAWYQQKPGQAPRL LIYDASNRATGIPARFSGSGSGTDFTLTISSLEPEDFAVYYCQQRS NWPLTFGGGTKVEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSFNRGEC |
| 121 | OX40.19 heavy chain | QVQLVESGGGVVQPGRSLRLSCAASGFTFSNYALHWVRQAPGKGLE WVALISYDGSRKHYADSVKGRFSISRDNSKNTLYLQMNSLRAEDTA VYYCASLTLVREWGQGTLVTVSSASTKGPSVFPLAPSSKSTSGGTA ALGCLVKDYFPEPVTVSWNSGALTSGVHTFPAVLQSSGLYSLSSVV TVPSSSLGTQTYICNVNHKPSNTKVDKRVEPKSCDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSREEMTKNQVSLTCLVK GFYPSDIAVEWESNGQPENNYKTTPPVLDSDGSFFLYSKLTVDKSR WQQGNVFSCSVMHEALHNHYTQKSLSLSPG |
| 122 | OX40.19 light chain | EIVLTQSPGTLSLSPGERATLSCRASQSVSSSYLAWYQQKPGQAPR LLIYGASSRATGIPDRFSGSGSGTDFTLTISRLEPEDFAVYYCQQY GSSPFTFGPGTKVDIKRTVAAPSVFIFPPSDEQLKSGTASVVCLLN NFYPREAKVQWKVDNALQSGNSQESVTEQDSKDSTYSLSSTLTLSK ADYEKHKVYACEVTHQGLSSPVTKSFNRGEC |
| 123 | OX40.20 heavy chain | EVQLVQSGGGLVQPGGSLRLSCAGSGFTFSSYAMYWVRQAPGKGLE WVSAIDTSGGTFYADSVRGRFTISRDNAKNSLYLQMNSLRAEDTAV YFCARLGEGYFFDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKRVEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPG |
| — | OX40.20 light chain | SEQ ID NO: 116 |
| 124 | OX40.21 heavy chain | EVQLVQSGGGLVQPGGSLRLSCAGSGFTFSSYAMYWVRQAPGKGLE WVSAIDTDAGTFYADSVRGRFTISRDNAKNSLYLQMNSLRAEDTAV YFCARLGEGYFFDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKRVEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPG |
| — | OX40.21 light chain | SEQ ID NO: 116 |
| 125 | OX40.22 heavy chain | EVQLVQSGGGLVQPGGSLRLSCAGSGFTFSSYAMYWVRQAPGKGLE WVSAIDTSTGTFYADSVRGRFTISRDNAKNSLYLQMNSLRAEDTAV YFCARLGEGYFFDYWGQGTLVTVSSASTKGPSVFPLAPSSKSTSGG TAALGCLVKDYFPEPVTVSWNSGALTSGVHTFPAVLQSSGLYSLSS VVTVPSSSLGTQTYICNVNHKPSNTKVDKRVEPKSCDKTHTCPPCP |

TABLE 23-continued

SUMMARY OF SEQUENCES

| SEQ ID | Description | Sequence |
|---|---|---|
| | | APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSREEMTKNQVSLTCL VKGFYPSDIAVEWESNGQPENNYKTTPPVLDSDGSFFLYSKLTVDK SRWQQGNVFSCSVMHEALHNHYTQKSLSLSPG |
| — | OX40.22 light chain | SEQ ID NO: 116 |
| 126 | 3F4 VH (nucleotide sequence) | CAGGTGCAGCTGGTGCAGTCTGGGGCTGAGGTGAAGAAGCCTGGGGCCT CAGTGAAGGTCTCCTGCAAGGCTTCTGGAAACACCTTCACCAGTTATGA TGTCAACTGGGTGCGACAGGCCACTGGACAAGGGCTTGAGTGGATGGGA TGGATGAACCCTAACAGTGGTAACACAGGCTATGCACCGAAGTTCCAGG GCAGAGTCACCATGACCAGGAACACCTCCATAAGCACAGCCTACATGGA GCTGAGCAGCCTGAGATCTGAGGACACGGCCGTTTATTACTGTGCGAGA ATATATAGCAGCTCGTACAACTGGTTCGACCCCTGGGGCCAGGGAACCC TGGTCACCGTCTCCTCA |
| 127 | 3F4 VL | GAAATTGTGTTGACACAGTCTCCAGCCACCCTGTCTTTGTCTCCAGGGG AAAGAGCCACCCTCTCCTGCAGGGCCAGTCAGAGTGTTAGCAGCTACTT AGCCTGGTACCAACAGAAACCTGGCCAGGCTCCCAGGCTCCTCATCTAT GATGCATCCAACAGGGCCACTGGCATCCCAGCCAGGTTCAGTGGCAGTG GGTCTGGGACAGACTTCACTCTCACCATCAGCAGCCTAGAGCCTGAAGA TTTTGCAGTTTATTACTGTCAGCAGCGTAGCAACTGGCCTCTCACTTTC GGCGGAGGGACCAAGGTGGAGATCAAA |
| 128 | 14B6 VH | GAGGTGCAGCTGGAGCAGTCTGGAGCAGAGGTGAAAAAGCCCGGGGAGT CTCTGAAGATCTCCTGTAAGGGTTCTGGATACAGCTTTACCAGCAACTG GATCGGCTGGGTGCGCCAGATGCCCGGGAAAGGCCTGGAGTGGATGGGG TTCATCTATCCTGGTGACTCTGATACCAGGTACAGCCCGTCCTTCCAAG GCCAGGTCACCATCTCAGCCGACAAGTCCATCAGCACCGCCTACCTGCA GTGGAGCAGCCTCAAGGCCTCGGACATCGCCATGTATTACTGTGCGAGA TATGGGGATGACTGGTACTTCGATCTCTGGGGCCGTGGCACCCTGGTCA CTGTCTCCTCA |
| 129 | 14B6 VL1 | GAAATTGTGTTGACACAGTCTCCAGCCACCCTGTCTTTGTCTCCAGGGG AAAGAGCCACCCTCTCCTGCAGGGCCAGTCAGAGTGTTAGCAGCTACTT AGCCTGGTTCCAACAGAGACCTGGCCAGGCTCCCAGGCTCCTCATCTAT GATGCATCCAACAGGGCCACTGGCATCCCAGCCAGGTTCAGTGGCAGTG GGTCTGGGACAGACTTCTCTCTCACCATCAGCAGCCTAGAGCCTGAAGA TTTTGCAGTTTATTACTGTCAGCAGCGTGGCGACTGGCCCATCACCTTC GGCCAAGGGACACGACTGGAGATTAAA |
| 130 | 14B6 VL2 | GACATCCAGATGACCCAGTCTCCATCCTCACTGTCTGCATCTGTAGGAG ACAGAGTCACCATCACTTGTCGGGCGAGTCAGGGTATTAGCAGCTGGTT AGCCTGGTATCAGCAGAAACCAGAGAAAGCCCCTAAGTCCCTGATCTAT GCTGCATCCAGTTTGCAAAGTGGGGTCCCATCAAGGTTCAGCGGCAGTG GATCTGGGACAGATTTCACTCTCACCATCAGCAGCCTGCAGCCTGAAGA TTTTGCAACTTATTACTGCCAACAGTATAATAGTTACCCTCGGATCACC TTCGGCCAAGGGACACGACTGGAGATTAAA |
| 131 | 23H3 VH | GAGGTTCAGCTGGTGCAGTCTGGGGGAGGCTTGGTACATCCTGGGGGGT CCCTGAGACTCTCCTGTGCAGGCTCTGGATTCACCTTCAGTAACTATGC TATGTACTGGGTTCGCCAGGCTCCAGGGAAAAGGTCTGGAGTGGGTATCA GCCATTGGTATTGGTGGTGACACATTCTATACAGACTCCGTGAAGGGCC GATTCACCATCTCCAGAGACAATGCCAAGAACTCCTTGTCTCTTCAAAT GAACAGCCTGAGAGCCGAGGACATGGCTGTGTATTACTGTGCAAGAATG GGAACTGGGTACTTCTTTGACTACTGGGGCCAGGGAACCCTGGTCACCG TCTCCTCA |
| 132 | 23H3 VL | GAAATTGTGTTGACACAGTCTCCAGCCACCCTGTCTTTGTCTCCAGGGG AAAGAGCCACCCTCTCCTGCAGGGCCAGTCAGAGTGTTAGCAGCTACTT AGCCTGGTACCAACAGAAACCTGGCCAGGCTCCCAGGCTCCTCATCTAT GATGCATCCAACAGGGCCACTGGCATCCCAGCCAGGTTCAGTGGCAGTG GGTCTGGGACAGACTTCACTCTCACCATCAGCAGCCTAGAGCCTGAAGA TTTTGCAGTTTATTACTGTCAGCAGCGTAGCAACTGGCCTCTCACTTTC GGCCCTGGGACCAAAGTGGATATCAAA |
| 133 | 6E1 VH | CAGGTGCAGCTGGTGGAGTCTGGGGGAGGCGTGGTCCAGCCTGGGAGGT CCCTGAGACTCTCCTGTGCAGCCTCTGGATTCACCTTCAGTAGCTTTGC TATGCACTGGGTCCGCCAGGCTCCAGGCAAGGGGCTGGAGTGGGTGACA GTTATTTCATATGATGGAAGCATTAAATACTACACAGACTCCGTGAAGG GCCGATTCACCTTCTCCAGAGACAATTCCAAGAACACTCTGTATCTGCA AATGAACAGCCTGAGAGCTGAGGACACGGCTGTGTATTACTGTACGAGA GATGGAAACTATGGTTCGGCGAGATACTTCCAGCACTGGGGCCAGGGCA CCCTGGTCACCGTCTCCTCA |

TABLE 23-continued

SUMMARY OF SEQUENCES

| SEQ ID | Description | Sequence |
|---|---|---|
| 134 | 6E1 VL1 | GACATCCAGATGACCCAGTCTCCATCCTCACTGTCTGCATCTGTAGGAG<br>ACAGAGTCACCATCACTTGTCGGGCGAGTCAGGGTATTAGCAGCTGGTT<br>AGCCTGGTATCAGCAGAAACCAGAGAAAGCCCCTAAGTCCCTGATCTAT<br>GCTGCATCCAGTTTGCAAAGTGGGGTCCCATCAAGGTTCAGCGGCAGTG<br>GATCTGGGACAGATTTCACTCTCACCATCAGCAGCCTGCAGCCTGAAGA<br>TTTTGCAACTTATTACTGCCAACAGTATAATAGTTACCCTCGGACGTTC<br>GGCCAAGGGACCAAGGTGGAAATCAAA |
| 135 | 6E1 VL2 | GAAATTGTGTTGACACAGTCTCCAGCCACCCTGTCTTTGTCTCCAGGGG<br>AAAGAGCCACCCTCTCCTGCAGGGCCAGTCAGAGTGTTAGCAGCTACTT<br>AGCCTGGTACCAACAGAAACCTGGCCAGGCTCCCAGGCTCCTCATCTAT<br>GATGCATCCAACAGGGCCACTGGCATCCCAGCCAGGTTCAGTGGCAGTG<br>GGTCTGGGACAGACTTCACTCTCACCATCAGCAGCCTAGAGCCTGAAGA<br>TTTTGCAGTTTATTACTGTCAGCAGCGTAGCAACTGGCCGTACACTTTT<br>GGCCAGGGGACCAAGCTGGAGATCAAA |
| 136 | 18E9 VH | GAGGTTCAGCTGGTGCAGTCTGGGGGAGGCTTGGTTCATCCTGGGGGGT<br>CCCTGAGACTCTCCTGTGCACACTCTGGATTCACCTTCACTAGCTCTGC<br>TATGCACTGGGTTCGCCAGGCTCCAGGAAAAGGTCTGGAATGGATATCA<br>GCTATTGGTACTGGTGGTGACACATACTATGCAGACTCCGTGAAGGGCC<br>GATTCACCATCTCCAGAGACAATGCCAAGAACTCCTTGTATCTTCAAAT<br>AAACAGCCTGAGAGCCGAGGACATGGCTGTATATTACTGTGCAAGAGAC<br>TTTTACGATATTTTGACTGGTATCTTTGACTACTGGGGCCAGGGAACCC<br>TGGTCACCGTCTCCTCA |
| 137 | 18E9 VL | GACATCCAGATGACCCAGTCTCCATCTTCCGTGTCTGCATCTGTAGGAG<br>ACAGAGTCACCATCACTTGTCGGGCGAGTCAGGGTATTAGCAGCTGGTT<br>AGCCTGGTATCAGCATAAACCAGGGAAAGCCCCTAAGTCCTGATCTAT<br>GCTGCATCCAGTTTGCAAAGTGGGGTCCCATCAAGGTTCAGCGGCAGTG<br>GATCTGGGACAGATTTCACTCTCACCATCAGCAGCCTGCAGCCTGAAGA<br>TTTTGCAACTTACTATTGTCAACAGGCTAATAGTTTCCCTTCGACGTTC<br>GGCCAAGGGACCAAGGTGGAAATCAAA |
| 138 | 8B11 VH | ATGGAGTTTGTGCTGAGCTGGGTTTTCCTTGTTGCTATATTAAAAGGTG<br>TCCAGTGTGAAATTCAGCTGGTGCAGTCTGGGGGAGGCTTGGTACATCC<br>TGGGGGGTCCCTGAGACTCTCCTGTGCAGGCTCTGGATTCACCTTCAGT<br>AGCGATGCTATGTACTGGGTTCGCCAGGCTCCAGGAAAAGGTCTGGAGT<br>GGGTATCAGCTATTGGTATTGGTGGTGACACATACTATACAGACTCCGT<br>GATGGGCCGATTCACCATCTCCAGAGACAATGCCAAGAACTCCTTGTAT<br>CTTCAAATGAACAGCCTGAGAGCCGAGGACATGGCTGTGTATTACTGTG<br>CAAGGCTGGGGATGGGGTACTACTTTGACTACTGGGGCCAGGGAACCCT<br>GGTCACCGTCTCCTCA |
| 139 | 8B11 VL | GAAATTGTGTTGACACAGTCTCCAGCCACCCTGTCTTTGTCTCCAGGGG<br>AAAGAGCCACCCTCTCCTGCAGGGCCAGTCAGAGTGTTAGCAGCTACTT<br>AGCCTGGTACCAACAGAAACCTGGCCAGGCTCCCAGGCTCCTCATCTAT<br>GATGCATCCAACAGGGCCACTGGCATCCCAGCCAGGTTCAGTGGCAGTG<br>GGTCTGGGACAGACTTCACTCTCACCATCAGCAGCCTAGAGCCTGAAGA<br>TTTTGCAGTTTATTACTGTCAGCAGCGTAGCAACTGGCCTCCGACGTTC<br>GGCCAAGGGACCAAGGTGGAAATCAAA |
| 140 | 20B3 VH | GAGGTGCAGCTGGTGGAGTCTGGGGGAGGCTTGGTACAGCCTGGGGGGT<br>CCCTGAGACTCTCCTGTGCAGCCTCTGGATTCACCTTCAGTAGCTACGA<br>CATGCACTGGGTCCGCCAAACTACAGGAAAAGGTCTGGAGTGGGTCTCA<br>GTTATTGGTACTGCTGGTGACACATACTATCCAGGCTCCGTGAAGGGCC<br>GATTCACCATCTCCAGAGAAAATGCCAAGAACTCCTTGTATCTTCAAAT<br>GAACAGCCTGAGAGCCGGGGACACGGCTGTGTATTACTGTGCAAGAGGG<br>GGGATGGGGAACTACTTTGACTACTGGGGCCAGGGAACCCTGGTCACCG<br>TCTCCTCA |
| 141 | 20B3 VL | GAAATTGTGTTGACACAGTCTCCAGCCACCCTGTCTTTGTCTCCAGGGG<br>AAAGAGCCACCCTCTCCTGCAGGGCCAGTCAGAGTGTTAGCAGCTACTT<br>AGCCTGGTACCAACAGAAACCTGGCCAGGCTCCCAGGCTCCTCATCTAT<br>GATGCATCCAACAGGGCCACTGGCATCCCAGCCAGGTTCAGTGGCAGTG<br>GGTCTGGGACAGACTTCACTCTCACCATCAGCAGCCTAGAGCCTGAAGA<br>TTTTGCAGTTTATTACTGTCAGCAGCGTAGCAACTGGCCGCTCACTTTC<br>GGCGGAGGGACCAAGGTGGAGATCAAA |
| 142 | 14A2 VH | CAGGTGCAGCTGGTGGAGTCTGGGGGAGGCGTGGTCCAGCCTGGGAGGT<br>CCCTGAGACTCTCCTGTGCAGCCTCTGGATTCACCTTCAGTAACTATGC<br>TCTGCACTGGGTCCGCCAGGCTCCAGGCAAGGGGCTGGAGTGGGTGGCA<br>CTTATATCATATGATGGAAGCAGGAAACACTACGCAGACTCCGTGAAGG<br>GCCGATTCAGTATCTCCAGAGACAATTCCAAGAACACACTGTATCTGCA<br>AATGAACAGCCTGAGAGCTGAGGACACGGCTGTGTATTACTGTGCGAGT |

TABLE 23-continued

SUMMARY OF SEQUENCES

| SEQ ID | Description | Sequence |
|---|---|---|
| | | CTTACTATGGTTCGGGAGGGGGGCCAGGGAACCCTGGTCACCGTCTCCT<br>CA |
| 143 | 14A2 VL1 | GAAATTGTGTTGACGCAGTCTCCAGGCACCCTGTCTTTGTCTCCAGGGG<br>AAAGAGCCACCCTCTCCTGCAGGGCCAGTCAGAGTGTTAGCAGCAGCTA<br>CTTAGCCTGGTACCAGCAGAAACCTGGCCAGGCTCCCAGGCTCCTCATC<br>TATGGTGCATCCAGCAGGGCCACTGGCATCCCAGACAGGTTCAGTGGCA<br>GTGGGTCTGGGACAGACTTCACTCTCACCATCAGCAGACTGGAGCCTGA<br>AGATTTTGCAGTGTATTACTGTCAGCAGTATGGTAGCTCACCATTCACT<br>TTCGGCCCTGGGACCAAAGTGGATATCAAA |
| 144 | 14A2 VL2 | GACATCCAGTTGACCCAGTCTCCATCCTCCCTGTCTGCATCTGTAGGAG<br>ACAGAGTCACCATCACTTGCCGGGTGAGTCAGGGCATTAGCAGTTATTT<br>AAATTGGTATCGGCAGAAACCAGGGAAAGTTCCTAAGCTCCTGATCTAT<br>AGTGCATCCAATTTGCAATCTGGAGTCCCATCTCGGTTCAGTGGCAGTG<br>GATCTGGGACAGATTTCACTCTCACTATCAGCAGCCTGCAGCCTGAAGA<br>TGTTGCAACTTATTACGGTCAACGGACTTACAATGCCCCTTACACTTTC<br>GGCGGAGGGACCAAGGTGGAGATCAAA |
| 145 | 20C1 VH | GAGGCTCAGCTGGTGCAGTCTGGGGGAGGCTTGGTTCATCCTGGGGGGT<br>CCCTGAGACTCTCCTGTGCAGACTCTGGATTCACCTTCAGTAGCTATGC<br>TATGTACTGGGTTCGCCAGGCTCCAGGAAAAGGTCTGGAGTGGGTATCA<br>GCTATTGATACTGATGGTGGCACATTCTATGCAGACTCCGTGCGGGGCC<br>GATTCACCATCTCCAGAGACAATGCCAAGAACTCCTTGTATCTTCAAAT<br>GAACGGCCTGAGAGCCGAGGACATGGCTGTGTATTTCTGTGCAAGACTT<br>GGGGAAGGGTACTTCTTTGACTACTGGGGCCAGGGAACCCTGGTCACCG<br>TCTCCTCA |
| 146 | 20C1 VL | GAAATTGTGTTGACACAGTCTCCAGCCACCCTGTCTTTGTCTCCAGGGG<br>AAAGAGCCACCCTCTCCTGCAGGGCCAGTCAGAGTGTTAGCAGCTACTT<br>AGCCTGGTACCAACAGAAACCTGGCCAGGCTCCCAGGCTCCTCATCTAT<br>GATGCATCCAACAGGGCCACTGGCATCCCAGCCAGGTTCAGTGGCAGTG<br>GGTCTGGGACAGACTTCACTCTCACCATCAGCAGCCTAGAGCCTGAAGA<br>TTTTGCAGTTTATTACTGTCAGCAGCGTAGCAACTGGCCTCCCACTTTC<br>GGCGGAGGGACCAAGGTGGAGATCAAA |
| 147 | OX40.6 heavy chain | GAGGTTCAGCTGGTGCAGTCTGGGGGAGGCTTGGTACAGCCTGGGG<br>GGTCCCTGAGACTCTCCTGTGCAGGCTCTGGATTCACCTTCAGTAA<br>CTATGCTATGTACTGGGTTCGCCAGGCTCCAGGAAAAGGTCTGGAG<br>TGGGTATCAGCCATTGGTATTGGTGGTGACACATTCTATACAGACT<br>CCGTGAAGGGCCGATTCACCATCTCCAGAGACAATGCCAAGAACTC<br>CTTGTCTCTTCAAATGAACAGCCTGAGAGCCGAGGACACGGCTGTG<br>TATTACTGTGCAAGAATGGGAACTGGGTACTTCTTTGACTACTGGG<br>GCCAGGGAACCCTGGTCACCGTCTCCTCAGCTAGCACCAAGGGCCC<br>ATCGGTCTTCCCCCTGGCACCCTCCTCCAAGAGCACCTCTGGGGGC<br>ACAGCGGCCCTGGGCTGCCTGGTCAAGGACTACTTCCCCGAACCGG<br>TGACGGTGTCGTGGAACTCAGGCGCCCTGACCAGCGGCGTGCACAC<br>CTTCCCGGCTGTCCTACAGTCCTCAGGACTCTACTCCCTCAGCAGC<br>GTGGTGACCGTGCCCTCCAGCAGCTTGGGCACCCAGACCTACATCT<br>GCAACGTGAATCACAAGCCCAGCAACACCAAGGTGGACAAGAGAGT<br>TGAGCCCAAATCTTGTGACAAAACTCACACATGCCCACCGTGCCCA<br>GCACCTGAACTCCTGGGGGGACCGTCAGTCTTCCTCTTCCCCCCAA<br>AACCCAAGGACACCCTCATGATCTCCCGGACCCCTGAGGTCACATG<br>CGTGGTGGTGGACGTGAGCCACGAAGACCCTGAGGTCAAGTTCAAC<br>TGGTACGTGGACGGCGTGGAGGTGCATAATGCCAAGACAAAGCCGC<br>GGGAGGAGCAGTACAACAGCACGTACCGTGTGGTCAGCGTCCTCAC<br>CGTCCTGCACCAGGACTGGCTGAATGGCAAGGAGTACAAGTGCAAG<br>GTCTCCAACAAAGCCCTCCCAGCCCCCATCGAGAAAACCATCTCCA<br>AAGCCAAAGGGCAGCCCCGAGAACCACAGGTGTACACCCTGCCCCC<br>ATCCCGGGAGGAGATGACCAAGAACCAGGTCAGCCTGACCTGCCTG<br>GTCAAAGGCTTCTATCCCAGCGACATCGCCGTGGAGTGGGAGAGCA<br>ATGGGCAGCCGGAGAACAACTACAAGACCACGCCTCCCGTGCTGGA<br>CTCCGACGGCTCCTTCTTCCTCTATAGCAAGCTCACCGTGGACAAG<br>AGCAGGTGGCAGCAGGGGAACGTCTTCTCATGCTCCGTGATGCATG<br>AGGCTCTGCACAACCACTACACGCAGAAGAGCCTCTCCCTGTCCCC<br>GGGT |
| 148 | OX40.6 light chain | GAAATTGTGTTGACACAGTCTCCAGCCACCCTGTCTTTGTCTCCAG<br>GGGAAAGAGCCACCCTCTCCTGCAGGGCCAGTCAGAGTGTTAGCAG<br>CTACTTAGCCTGGTACCAACAGAAACCTGGCCAGGCTCCCAGGCTC<br>CTCATCTATGATGCATCCAACAGGGCCACTGGCATCCCAGCCAGGT<br>TCAGTGGCAGTGGGTCTGGGACAGACTTCACTCTCACCATCAGCAG<br>CCTAGAGCCTGAAGATTTTGCAGTTTATTACTGTCAGCAGCGTAGC<br>AACTGGCCTCTCACTTTCGGCCCTGGGACCAAAGTGGATATCAAAC<br>GTACGGTGGCTGCACCATCTGTCTTCATCTTCCCGCCATCTGATGA |

TABLE 23-continued

SUMMARY OF SEQUENCES

| SEQ ID | Description | Sequence |
|---|---|---|
| | | GCAGTTGAAATCTGGAACTGCCTCTGTTGTGTGCCTGCTGAATAAC<br>TTCTATCCCAGAGAGGCCAAAGTACAGTGGAAGGTGGATAACGCCC<br>TCCAATCGGGTAACTCCCAGGAGAGTGTCACAGAGCAGGACAGCAA<br>GGACAGCACCTACAGCCTCAGCAGCACCCTGACGCTGAGCAAAGCA<br>GACTACGAGAAACACAAAGTCTACGCCTGCGAAGTCACCCATCAGG<br>GCCTGAGCTCGCCCGTCACAAAGAGCTTCAACAGGGGAGAGTGT |
| 149 | OX40.7 heavy chain | GAGGTTCAGCTGGTGCAGTCTGGGGGAGGCTTGGTACATCCTGGGG<br>GGTCCCTGAGACTCTCCTGTGCAGGCTCTGGATTCACCTTCAGTAA<br>CTATGCTATGTACTGGGTTCGCCAGGCTCCAGGAAAAGGTCTGGAG<br>TGGGTATCAGCCATTGGTATTGGTGGTGACACATTCTATACAGACT<br>CCGTGAAGGGCCGATTCACCATCTCCAGAGACAATGCCAAGAACTC<br>CTTGTCTCTTCAAATGAACAGCCTGAGAGCCGAGGACACGGCTGTG<br>TATTACTGTGCAAGATATGGAACTGGGTACTTCTTTGACTACTGGG<br>GCCAGGGAACCCTGGTCACCGTCTCCTCAGCTAGCACCAAGGGCCC<br>ATCGGTCTTCCCCCTGGCACCCTCCTCCAAGAGCACCTCTGGGGGC<br>ACAGCGGCCCTGGGCTGCCTGGTCAAGGACTACTTCCCCGAACCGG<br>TGACGGTGTCGTGGAACTCAGGCGCCCTGACCAGCGGCGTGCACAC<br>CTTCCCGGCTGTCCTACAGTCCTCAGGACTCTACTCCCTCAGCAGC<br>GTGGTGACCGTGCCCTCCAGCAGCTTGGGCACCCAGACCTACATCT<br>GCAACGTGAATCACAAGCCCAGCAACACCAAGGTGGACAAGAGAGT<br>TGAGCCCAAATCTTGTGACAAAACTCACACATGCCCACCGTGCCCA<br>GCACCTGAACTCCTGGGGGGACCGTCAGTCTTCCTCTTCCCCCCAA<br>AACCCAAGGACACCCTCATGATCTCCCGGACCCCTGAGGTCACATG<br>CGTGGTGGTGGACGTGAGCCACGAAGACCCTGAGGTCAAGTTCAAC<br>TGGTACGTGGACGGCGTGGAGGTGCATAATGCCAAGACAAAGCCGC<br>GGGAGGAGCAGTACAACAGCACGTACCGTGTGGTCAGCGTCCTCAC<br>CGTCCTGCACCAGGACTGGCTGAATGGCAAGGAGTACAAGTGCAAG<br>GTCTCCAACAAAGCCCTCCCAGCCCCCATCGAGAAAACCATCTCCA<br>AAGCCAAAGGGCAGCCCCGAGAACCACAGGTGTACACCCTGCCCCC<br>ATCCCGGGAGGAGATGACCAAGAACCAGGTCAGCCTGACCTGCCTG<br>GTCAAAGGCTTCTATCCCAGCGACATCGCCGTGGAGTGGGAGAGCA<br>ATGGGCAGCCGGAGAACAACTACAAGACCACGCCTCCCGTGCTGGA<br>CTCCGACGGCTCCTTCTTCCTCTATAGCAAGCTCACCGTGGACAAG<br>AGCAGGTGGCAGCAGGGGAACGTCTTCTCATGCTCCGTGATGCATG<br>AGGCTCTGCACAACCACTACACGCAGAAGAGCCTCTCCCTGTCCCC<br>GGGT |
| 150 | OX40.7 light chain | GAAATTGTGTTGACACAGTCTCCAGCCACCCTGTCTTTGTCTCCAG<br>GGGAAAGAGCCACCCTCTCCTGCAGGGCCAGTCAGAGTGTTAGCAG<br>CTACTTAGCCTGGTACCAACAGAAACCTGGCCAGGCTCCCAGGCTC<br>CTCATCTATGATGCATCCAACAGGGCCACTGGCATCCCAGCCAGGT<br>TCAGTGGCAGTGGGTCTGGGACAGACTTCACTCTCACCATCAGCAG<br>CCTAGAGCCTGAAGATTTTGCAGTTTATTACTGTCAGCAGCGTAGC<br>AACTGGCCTCTCACTTTCGGCCCTGGGACCAAAGTGGATATCAAAC<br>GTACGGTGGCTGCACCATCTGTCTTCATCTTCCCGCCATCTGATGA<br>GCAGTTGAAATCTGGAACTGCCTCTGTTGTGTGCCTGCTGAATAAC<br>TTCTATCCCAGAGAGGCCAAAGTACAGTGGAAGGTGGATAACGCCC<br>TCCAATCGGGTAACTCCCAGGAGAGTGTCACAGAGCAGGACAGCAA<br>GGACAGCACCTACAGCCTCAGCAGCACCCTGACGCTGAGCAAAGCA<br>GACTACGAGAAACACAAAGTCTACGCCTGCGAAGTCACCCATCAGG<br>GCCTGAGCTCGCCCGTCACAAAGAGCTTCAACAGGGGAGAGTGT |
| 151 | OX40.8 heavy chain | CAGGTGCAGCTGGTGGAGTCTGGGGGAGGCGTGGTCCAGCCTGGGA<br>GGTCCCTGAGACTCTCCTGTGCAGCCTCTGGATTCACCTTCAGTAA<br>CTATGCTCTGCACTGGGTCCGCCAGGCTCCAGGCAAGGGGCTGGAG<br>TGGGTGGCACTTATATCATATGATGGAAGCAGGAAACACTACGCAG<br>ACTCCGTGAAGGGCCGATTCAGTATCTCCAGAGACAATTCCAAGAA<br>CACACTGTATCTGCAAATGAACAGCCTGAGAGCTGAGGACACGGCT<br>GTGTATTACTGTGCGAGTCTTACTATGGTTCGGGAGTGGGGCCAGG<br>GAACCCTGGTCACCGTCTCCTCAGCTAGCACCAAGGGCCCATCGGT<br>CTTCCCCCTGGCACCCTCCTCCAAGAGCACCTCTGGGGGCACAGCG<br>GCCCTGGGCTGCCTGGTCAAGGACTACTTCCCCGAACCGGTGACGG<br>TGTCGTGGAACTCAGGCGCCCTGACCAGCGGCGTGCACACCTTCCC<br>GGCTGTCCTACAGTCCTCAGGACTCTACTCCCTCAGCAGCGTGGTG<br>ACCGTGCCCTCCAGCAGCTTGGGCACCCAGACCTACATCTGCAACG<br>TGAATCACAAGCCCAGCAACACCAAGGTGGACAAGAGAGTTGAGCC<br>CAAATCTTGTGACAAAACTCACACATGCCCACCGTGCCCAGCACCT<br>GAACTCCTGGGGGGACCGTCAGTCTTCCTCTTCCCCCCAAAACCCA<br>AGGACACCCTCATGATCTCCCGGACCCCTGAGGTCACATGCGTGGT<br>GGTGGACGTGAGCCACGAAGACCCTGAGGTCAAGTTCAACTGGTAC<br>GTGGACGGCGTGGAGGTGCATAATGCCAAGACAAAGCCGCGGGAGG<br>AGCAGTACAACAGCACGTACCGTGTGGTCAGCGTCCTCACCGTCCT<br>GCACCAGGACTGGCTGAATGGCAAGGAGTACAAGTGCAAGGTCTCC<br>AACAAAGCCCTCCCAGCCCCCATCGAGAAAACCATCTCCAAAGCCA |

TABLE 23-continued

SUMMARY OF SEQUENCES

| SEQ ID | Description | Sequence |
|---|---|---|
| | | AAGGGCAGCCCCGAGAACCACAGGTGTACACCCTGCCCCCATCCCG<br>GGAGGAGATGACCAAGAACCAGGTCAGCCTGACCTGCCTGGTCAAA<br>GGCTTCTATCCCAGCGACATCGCCGTGGAGTGGGAGAGCAATGGGC<br>AGCCGGAGAACAACTACAAGACCACGCCTCCCGTGCTGGACTCCGA<br>CGGCTCCTTCTTCCTCTATAGCAAGCTCACCGTGGACAAGAGCAGG<br>TGGCAGCAGGGGAACGTCTTCTCATGCTCCGTGATGCATGAGGCTC<br>TGCACAACCACTACACGCAGAAGAGCCTCTCCCTGTCCCCGGGT |
| 152 | OX40.8 light chain | GAAATTGTGTTGACGCAGTCTCCAGGCACCCTGTCTTTGTCTCCAG<br>GGGAAAGAGCCACCCTCTCCTGCAGGGCCAGTCAGAGTGTTAGCAG<br>CAGCTACTTAGCCTGGTACCAGCAGAAACCTGGCCAGGCTCCCAGG<br>CTCCTCATCTATGGTGCATCCAGCAGGGCCACTGGCATCCCAGACA<br>GGTTCAGTGGCAGTGGGTCTGGGACAGACTTCACTCTCACCATCAG<br>CAGACTGGAGCCTGAAGATTTTGCAGTGTATTACTGTCAGCAGTAT<br>GGTAGCTCACCATTCACTTTCGGCCCTGGGACCAAAGTGGATATCA<br>AACGTACGGTGGCTGCACCATCTGTCTTCATCTTCCCGCCATCTGA<br>TGAGCAGTTGAAATCTGGAACTGCCTCTGTTGTGTGCCTGCTGAAT<br>AACTTCTATCCCAGAGAGGCCAAAGTACAGTGGAAGGTGGATAACG<br>CCCTCCAATCGGGTAACTCCCAGGAGAGTGTCACAGAGCAGGACAG<br>CAAGGACAGCACCTACAGCCTCAGCAGCACCCTGACGCTGAGCAAA<br>GCAGACTACGAGAAACACAAAGTCTACGCCTGCGAAGTCACCCATC<br>AGGGCCTGAGCTCGCCCGTCACAAAGAGCTTCAACAGGGGAGAGTG<br>T |
| 153 | OX40.9 heavy chain | CAGGTGCAGCTGGTGGAGTCTGGGGGAGGCGTGGTCCAGCCTGGGA<br>GGTCCCTGAGACTCTCCTGTGCAGCCTCTGGATTCACCTTCAGTAA<br>CTATGCTCTGCACTGGGTCCGCCAGGCTCCAGGCAAGGGGCTGGAG<br>TGGGTGGCACTTATATCATATGATGGAAGCAGGAAACACTACGCAG<br>ACTCCGTGAAGGGCCGATTCAGTATCTCCAGAGACAATTCCAAGAA<br>CACACTGTATCTGCAAATGAACAGCCTGAGAGCTGAGGACACGGCT<br>GTGTATTACTGTGCGAGTCTTACTTACGTTCGGGAGTGGGGCCAGG<br>GAACCCTGGTCACCGTCTCCTCAGCTAGCACCAAGGGCCCATCGGT<br>CTTCCCCCTGGCACCCTCCTCCAAGAGCACCTCTGGGGGCACAGCG<br>GCCCTGGGCTGCCTGGTCAAGGACTACTTCCCCGAACCGGTGACGG<br>TGTCGTGGAACTCAGGCGCCCTGACCAGCGGCGTGCACACCTTCCC<br>GGCTGTCCTACAGTCCTCAGGACTCTACTCCCTCAGCAGCGTGGTG<br>ACCGTGCCCTCCAGCAGCTTGGGCACCCAGACCTACATCTGCAACG<br>TGAATCACAAGCCCAGCAACACCAAGGTGGACAAGAGAGTTGAGCC<br>CAAATCTTGTGACAAAACTCACACATGCCCACCGTGCCCAGCACCT<br>GAACTCCTGGGGGGACCGTCAGTCTTCCTCTTCCCCCCAAAACCCA<br>AGGACACCCTCATGATCTCCCGGACCCCTGAGGTCACATGCGTGGT<br>GGTGGACGTGAGCCACGAAGACCCTGAGGTCAAGTTCAACTGGTAC<br>GTGGACGGCGTGGAGGTGCATAATGCCAAGACAAAGCCGCGGGAGG<br>AGCAGTACAACAGCACGTACCGTGTGGTCAGCGTCCTCACCGTCCT<br>GCACCAGGACTGGCTGAATGGCAAGGAGTACAAGTGCAAGGTCTCC<br>AACAAAGCCCTCCCAGCCCCCATCGAGAAAACCATCTCCAAAGCCA<br>AAGGGCAGCCCCGAGAACCACAGGTGTACACCCTGCCCCCATCCCG<br>GGAGGAGATGACCAAGAACCAGGTCAGCCTGACCTGCCTGGTCAAA<br>GGCTTCTATCCCAGCGACATCGCCGTGGAGTGGGAGAGCAATGGGC<br>AGCCGGAGAACAACTACAAGACCACGCCTCCCGTGCTGGACTCCGA<br>CGGCTCCTTCTTCCTCTATAGCAAGCTCACCGTGGACAAGAGCAGG<br>TGGCAGCAGGGGAACGTCTTCTCATGCTCCGTGATGCATGAGGCTC<br>TGCACAACCACTACACGCAGAAGAGCCTCTCCCTGTCCCCGGGT |
| 154 | OX40.9 light chain | GAAATTGTGTTGACGCAGTCTCCAGGCACCCTGTCTTTGTCTCCAG<br>GGGAAAGAGCCACCCTCTCCTGCAGGGCCAGTCAGAGTGTTAGCAG<br>CAGCTACTTAGCCTGGTACCAGCAGAAACCTGGCCAGGCTCCCAGG<br>CTCCTCATCTATGGTGCATCCAGCAGGGCCACTGGCATCCCAGACA<br>GGTTCAGTGGCAGTGGGTCTGGGACAGACTTCACTCTCACCATCAG<br>CAGACTGGAGCCTGAAGATTTTGCAGTGTATTACTGTCAGCAGTAT<br>GGTAGCTCACCATTCACTTTCGGCCCTGGGACCAAAGTGGATATCA<br>AACGTACGGTGGCTGCACCATCTGTCTTCATCTTCCCGCCATCTGA<br>TGAGCAGTTGAAATCTGGAACTGCCTCTGTTGTGTGCCTGCTGAAT<br>AACTTCTATCCCAGAGAGGCCAAAGTACAGTGGAAGGTGGATAACG<br>CCCTCCAATCGGGTAACTCCCAGGAGAGTGTCACAGAGCAGGACAG<br>CAAGGACAGCACCTACAGCCTCAGCAGCACCCTGACGCTGAGCAAA<br>GCAGACTACGAGAAACACAAAGTCTACGCCTGCGAAGTCACCCATC<br>AGGGCCTGAGCTCGCCCGTCACAAAGAGCTTCAACAGGGGAGAGTG<br>T |
| 155 | OX40.10 heavy chain | CAGGTGCAGCTGGTGGAGTCTGGGGGAGGCGTGGTCCAGCCTGGGA<br>GGTCCCTGAGACTCTCCTGTGCAGCCTCTGGATTCACCTTCAGTAA<br>CTATGCTCTGCACTGGGTCCGCCAGGCTCCAGGCAAGGGGCTGGAG<br>TGGGTGGCACTTATATCATATAGTGGAAGCAGGAAACACTACGCAG<br>ACTCCGTGAAGGGCCGATTCAGTATCTCCAGAGACAATTCCAAGAA |

TABLE 23-continued

SUMMARY OF SEQUENCES

| SEQ ID | Description | Sequence |
|---|---|---|
| | | CACACTGTATCTGCAAATGAACAGCCTGAGAGCTGAGGACACGGCT GTGTATTACTGTGCGAGTCTTACTATGGTTCGGGAGGGGGCCAGG GAACCCTGGTCACCGTCTCCTCAGCTAGCACCAAGGGCCCATCGGT CTTCCCCCTGGCACCCTCCTCCAAGAGCACCTCTGGGGGCACAGCG GCCCTGGGCTGCCTGGTCAAGGACTACTTCCCCGAACCGGTGACGG TGTCGTGGAACTCAGGCGCCCTGACCAGCGGCGTGCACACCTTCCC GGCTGTCCTACAGTCCTCAGGACTCTACTCCCTCAGCAGCGTGGTG ACCGTGCCCTCCAGCAGCTTGGGCACCCAGACCTACATCTGCAACG TGAATCACAAGCCCAGCAACACCAAGGTGGACAAGAGAGTTGAGCC CAAATCTTGTGACAAAACTCACACATGCCCACCGTGCCCAGCACCT GAACTCCTGGGGGGACCGTCAGTCTTCCTCTTCCCCCCAAAACCCA AGGACACCCTCATGATCTCCCGGACCCCTGAGGTCACATGCGTGGT GGTGGACGTGAGCCACGAAGACCCTGAGGTCAAGTTCAACTGGTAC GTGGACGGCGTGGAGGTGCATAATGCCAAGACAAAGCCGCGGGAGG AGCAGTACAACAGCACGTACCGTGTGGTCAGCGTCCTCACCGTCCT GCACCAGGACTGGCTGAATGGCAAGGAGTACAAGTGCAAGGTCTCC AACAAAGCCCTCCCAGCCCCCATCGAGAAAACCATCTCCAAAGCCA AAGGGCAGCCCCGAGAACCACAGGTGTACACCCTGCCCCCATCCCG GGAGGAGATGACCAAGAACCAGGTCAGCCTGACCTGCCTGGTCAAA GGCTTCTATCCCAGCGACATCGCCGTGGAGTGGGAGAGCAATGGGC AGCCGGAGAACAACTACAAGACCACGCCTCCCGTGCTGGACTCCGA CGGCTCCTTCTTCCTCTATAGCAAGCTCACCGTGGACAAGAGCAGG TGGCAGCAGGGGAACGTCTTCTCATGCTCCGTGATGCATGAGGCTC TGCACAACCACTACACGCAGAAGAGCCTCTCCCTGTCCCCGGGT |
| 156 | OX40.10 light chain | GAAATTGTGTTGACGCAGTCTCCAGGCACCCTGTCTTTGTCTCCAG GGGAAAGAGCCACCCTCTCCTGCAGGGCCAGTCAGAGTGTTAGCAG CAGCTACTTAGCCTGGTACCAGCAGAAACCTGGCCAGGCTCCCAGG CTCCTCATCTATGGTGCATCCAGCAGGGCCACTGGCATCCCAGACA GGTTCAGTGGCAGTGGGTCTGGGACAGACTTCACTCTCACCATCAG CAGACTGGAGCCTGAAGATTTTGCAGTGTATTACTGTCAGCAGTAT GGTAGCTCACCATTCACTTTCGGCCCTGGGACCAAAGTGGATATCA AACGTACGGTGGCTGCACCATCTGTCTTCATCTTCCCGCCATCTGA TGAGCAGTTGAAATCTGGAACTGCCTCTGTTGTGTGCCTGCTGAAT AACTTCTATCCCAGAGAGGCCAAAGTACAGTGGAAGGTGGATAACG CCCTCCAATCGGGTAACTCCCAGGAGAGTGTCACAGAGCAGGACAG CAAGGACAGCACCTACAGCCTCAGCAGCACCCTGACGCTGAGCAAA GCAGACTACGAGAAACACAAAGTCTACGCCTGCGAAGTCACCCATC AGGGCCTGAGCTCGCCCGTCACAAAGAGCTTCAACAGGGGAGAGTG T |
| 157 | OX40.11 heavy chain | CAGGTGCAGCTGGTGGAGTCTGGGGGAGGCGTGGTCCAGCCTGGGA GGTCCCTGAGACTCTCCTGTGCAGCCTCTGGATTCACCTTCAGTAA CTATGCTCTGCACTGGGTCCGCCAGGCTCCAGGCAAGGGGCTGGAG TGGGTGGCACTTATATCATATGATAGTAGCAGGAAACACTACGCAG ACTCCGTGAAGGGCCGATTCAGTATCTCCAGAGACAATTCCAAGAA CACACTGTATCTGCAAATGAACAGCCTGAGAGCTGAGGACACGGCT GTGTATTACTGTGCGAGTCTTACTATGGTTCGGGAGGGGGCCAGG GAACCCTGGTCACCGTCTCCTCAGCTAGCACCAAGGGCCCATCGGT CTTCCCCCTGGCACCCTCCTCCAAGAGCACCTCTGGGGGCACAGCG GCCCTGGGCTGCCTGGTCAAGGACTACTTCCCCGAACCGGTGACGG TGTCGTGGAACTCAGGCGCCCTGACCAGCGGCGTGCACACCTTCCC GGCTGTCCTACAGTCCTCAGGACTCTACTCCCTCAGCAGCGTGGTG ACCGTGCCCTCCAGCAGCTTGGGCACCCAGACCTACATCTGCAACG TGAATCACAAGCCCAGCAACACCAAGGTGGACAAGAGAGTTGAGCC CAAATCTTGTGACAAAACTCACACATGCCCACCGTGCCCAGCACCT GAACTCCTGGGGGGACCGTCAGTCTTCCTCTTCCCCCCAAAACCCA AGGACACCCTCATGATCTCCCGGACCCCTGAGGTCACATGCGTGGT GGTGGACGTGAGCCACGAAGACCCTGAGGTCAAGTTCAACTGGTAC GTGGACGGCGTGGAGGTGCATAATGCCAAGACAAAGCCGCGGGAGG AGCAGTACAACAGCACGTACCGTGTGGTCAGCGTCCTCACCGTCCT GCACCAGGACTGGCTGAATGGCAAGGAGTACAAGTGCAAGGTCTCC AACAAAGCCCTCCCAGCCCCCATCGAGAAAACCATCTCCAAAGCCA AAGGGCAGCCCCGAGAACCACAGGTGTACACCCTGCCCCCATCCCG GGAGGAGATGACCAAGAACCAGGTCAGCCTGACCTGCCTGGTCAAA GGCTTCTATCCCAGCGACATCGCCGTGGAGTGGGAGAGCAATGGGC AGCCGGAGAACAACTACAAGACCACGCCTCCCGTGCTGGACTCCGA CGGCTCCTTCTTCCTCTATAGCAAGCTCACCGTGGACAAGAGCAGG TGGCAGCAGGGGAACGTCTTCTCATGCTCCGTGATGCATGAGGCTC TGCACAACCACTACACGCAGAAGAGCCTCTCCCTGTCCCCGGGT |
| 158 | OX40.11 light chain | GAAATTGTGTTGACGCAGTCTCCAGGCACCCTGTCTTTGTCTCCAG GGGAAAGAGCCACCCTCTCCTGCAGGGCCAGTCAGAGTGTTAGCAG CAGCTACTTAGCCTGGTACCAGCAGAAACCTGGCCAGGCTCCCAGG CTCCTCATCTATGGTGCATCCAGCAGGGCCACTGGCATCCCAGACA |

TABLE 23-continued

SUMMARY OF SEQUENCES

| SEQ ID | Description | Sequence |
|---|---|---|
| | | GGTTCAGTGGCAGTGGGTCTGGGACAGACTTCACTCTCACCATCAG<br>CAGACTGGAGCCTGAAGATTTTGCAGTGTATTACTGTCAGCAGTAT<br>GGTAGCTCACCATTCACTTTCGGCCCTGGGACCAAAGTGGATATCA<br>AACGTACGGTGGCTGCACCATCTGTCTTCATCTTCCCGCCATCTGA<br>TGAGCAGTTGAAATCTGGAACTGCCTCTGTTGTGTGCCTGCTGAAT<br>AACTTCTATCCCAGAGAGGCCAAAGTACAGTGGAAGGTGGATAACG<br>CCCTCCAATCGGGTAACTCCCAGGAGAGTGTCACAGAGCAGGACAG<br>CAAGGACAGCACCTACAGCCTCAGCAGCACCCTGACGCTGAGCAAA<br>GCAGACTACGAGAAACACAAAGTCTACGCCTGCGAAGTCACCCATC<br>AGGGCCTGAGCTCGCCCGTCACAAAGAGCTTCAACAGGGGAGAGTG<br>T |
| 159 | OX40.12 heavy chain | CAGGTGCAGCTGGTGGAGTCTGGGGGAGGCGTGGTCCAGCCTGGGA<br>GGTCCCTGAGACTCTCCTGTGCAGCCTCTGGATTCACCTTCAGTAA<br>CTATGCTCTGCACTGGGTCCGCCAGGCTCCAGGCAAGGGGCTGGAG<br>TGGGTGGCACTTATATCATATAGTGGAAGCAGGAAACACTACGCAG<br>ACTCCGTGAAGGGCCGATTCAGTATCTCCAGAGACAATTCCAAGAA<br>CACACTGTATCTGCAAATGAACAGCCTGAGAGCTGAGGACACGGCT<br>GTGTATTACTGTGCGAGTCTTACTATGGTTCGGGAGTGGGGCCAGG<br>GAACCCTGGTCACCGTCTCCTCAGCTAGCACCAAGGGCCCATCGGT<br>CTTCCCCCTGGCACCCTCCTCCAAGAGCACCTCTGGGGGCACAGCG<br>GCCCTGGGCTGCCTGGTCAAGGACTACTTCCCCGAACCGGTGACGG<br>TGTCGTGGAACTCAGGCGCCCTGACCAGCGGCGTGCACACCTTCCC<br>GGCTGTCCTACAGTCCTCAGGACTCTACTCCCTCAGCAGCGTGGTG<br>ACCGTGCCCTCCAGCAGCTTGGGCACCCAGACCTACATCTGCAACG<br>TGAATCACAAGCCCAGCAACACCAAGGTGGACAAGAGAGTTGAGCC<br>CAAATCTTGTGACAAAACTCACACATGCCCACCGTGCCCAGCACCT<br>GAACTCCTGGGGGGACCGTCAGTCTTCCTCTTCCCCCCAAAACCCA<br>AGGACACCCTCATGATCTCCCGGACCCCTGAGGTCACATGCGTGGT<br>GGTGGACGTGAGCCACGAAGACCCTGAGGTCAAGTTCAACTGGTAC<br>GTGGACGGCGTGGAGGTGCATAATGCCAAGACAAAGCCGCGGGAGG<br>AGCAGTACAACAGCACGTACCGTGTGGTCAGCGTCCTCACCGTCCT<br>GCACCAGGACTGGCTGAATGGCAAGGAGTACAAGTGCAAGGTCTCC<br>AACAAAGCCCTCCCAGCCCCCATCGAGAAAACCATCTCCAAAGCCA<br>AAGGGCAGCCCCGAGAACCACAGGTGTACACCCTGCCCCCATCCCG<br>GGAGGAGATGACCAAGAACCAGGTCAGCCTGACCTGCCTGGTCAAA<br>GGCTTCTATCCCAGCGACATCGCCGTGGAGTGGGAGAGCAATGGGC<br>AGCCGGAGAACAACTACAAGACCACGCCTCCCGTGCTGGACTCCGA<br>CGGCTCCTTCTTCCTCTATAGCAAGCTCACCGTGGACAAGAGCAGG<br>TGGCAGCAGGGGAACGTCTTCTCATGCTCCGTGATGCATGAGGCTC<br>TGCACAACCACTACACGCAGAAGAGCCTCTCCCTGTCCCCGGGT |
| 160 | OX40.12 light chain | GAAATTGTGTTGACGCAGTCTCCAGGCACCCTGTCTTTGTCTCCAG<br>GGGAAAGAGCCACCCTCTCCTGCAGGGCCAGTCAGAGTGTTAGCAG<br>CAGCTACTTAGCCTGGTACCAGCAGAAACCTGGCCAGGCTCCCAGG<br>CTCCTCATCTATGGTGCATCCAGCAGGGCCACTGGCATCCCAGACA<br>GGTTCAGTGGCAGTGGGTCTGGGACAGACTTCACTCTCACCATCAG<br>CAGACTGGAGCCTGAAGATTTTGCAGTGTATTACTGTCAGCAGTAT<br>GGTAGCTCACCATTCACTTTCGGCCCTGGGACCAAAGTGGATATCA<br>AACGTACGGTGGCTGCACCATCTGTCTTCATCTTCCCGCCATCTGA<br>TGAGCAGTTGAAATCTGGAACTGCCTCTGTTGTGTGCCTGCTGAAT<br>AACTTCTATCCCAGAGAGGCCAAAGTACAGTGGAAGGTGGATAACG<br>CCCTCCAATCGGGTAACTCCCAGGAGAGTGTCACAGAGCAGGACAG<br>CAAGGACAGCACCTACAGCCTCAGCAGCACCCTGACGCTGAGCAAA<br>GCAGACTACGAGAAACACAAAGTCTACGCCTGCGAAGTCACCCATC<br>AGGGCCTGAGCTCGCCCGTCACAAAGAGCTTCAACAGGGGAGAGTG<br>T |
| 161 | OX40.13 heavy chain | CAGGTGCAGCTGGTGGAGTCTGGGGGAGGCGTGGTCCAGCCTGGGA<br>GGTCCCTGAGACTCTCCTGTGCAGCCTCTGGATTCACCTTCAGTAA<br>CTATGCTCTGCACTGGGTCCGCCAGGCTCCAGGCAAGGGGCTGGAG<br>TGGGTGGCACTTATATCATATGATAGTAGCAGGAAACACTACGCAG<br>ACTCCGTGAAGGGCCGATTCAGTATCTCCAGAGACAATTCCAAGAA<br>CACACTGTATCTGCAAATGAACAGCCTGAGAGCTGAGGACACGGCT<br>GTGTATTACTGTGCGAGTCTTACTATGGTTCGGGAGTGGGGCCAGG<br>GAACCCTGGTCACCGTCTCCTCAGCTAGCACCAAGGGCCCATCGGT<br>CTTCCCCCTGGCACCCTCCTCCAAGAGCACCTCTGGGGGCACAGCG<br>GCCCTGGGCTGCCTGGTCAAGGACTACTTCCCCGAACCGGTGACGG<br>TGTCGTGGAACTCAGGCGCCCTGACCAGCGGCGTGCACACCTTCCC<br>GGCTGTCCTACAGTCCTCAGGACTCTACTCCCTCAGCAGCGTGGTG<br>ACCGTGCCCTCCAGCAGCTTGGGCACCCAGACCTACATCTGCAACG<br>TGAATCACAAGCCCAGCAACACCAAGGTGGACAAGAGAGTTGAGCC<br>CAAATCTTGTGACAAAACTCACACATGCCCACCGTGCCCAGCACCT<br>GAACTCCTGGGGGGACCGTCAGTCTTCCTCTTCCCCCCAAAACCCA<br>AGGACACCCTCATGATCTCCCGGACCCCTGAGGTCACATGCGTGGT |

TABLE 23-continued

SUMMARY OF SEQUENCES

| SEQ ID | Description | Sequence |
|---|---|---|
| | | GGTGGACGTGAGCCACGAAGACCCTGAGGTCAAGTTCAACTGGTAC GTGGACGGCGTGGAGGTGCATAATGCCAAGACAAAGCCGCGGGAGG AGCAGTACAACAGCACGTACCGTGTGGTCAGCGTCCTCACCGTCCT GCACCAGGACTGGCTGAATGGCAAGGAGTACAAGTGCAAGGTCTCC AACAAAGCCCTCCCAGCCCCCATCGAGAAAACCATCTCCAAAGCCA AAGGGCAGCCCCGAGAACCACAGGTGTACACCCTGCCCCCATCCCG GGAGGAGATGACCAAGAACCAGGTCAGCCTGACCTGCCTGGTCAAA GGCTTCTATCCCAGCGACATCGCCGTGGAGTGGGAGAGCAATGGGC AGCCGGAGAACAACTACAAGACCACGCCTCCCGTGCTGGACTCCGA CGGCTCCTTCTTCCTCTATAGCAAGCTCACCGTGGACAAGAGCAGG TGGCAGCAGGGGAACGTCTTCTCATGCTCCGTGATGCATGAGGCTC TGCACAACCACTACACGCAGAAGAGCCTCTCCCTGTCCCCGGGT |
| 162 | OX40.13 light chain | GAAATTGTGTTGACGCAGTCTCCAGGCACCCTGTCTTTGTCTCCAG GGGAAAGAGCCACCCTCTCCTGCAGGGCCAGTCAGAGTGTTAGCAG CAGCTACTTAGCCTGGTACCAGCAGAAACCTGGCCAGGCTCCCAGG CTCCTCATCTATGGTGCATCCAGCAGGGCCACTGGCATCCCAGACA GGTTCAGTGGCAGTGGGTCTGGGACAGACTTCACTCTCACCATCAG CAGACTGGAGCCTGAAGATTTTGCAGTGTATTACTGTCAGCAGTAT GGTAGCTCACCATTCACTTTCGGCCCTGGGACCAAAGTGGATATCA AACGTACGGTGGCTGCACCATCTGTCTTCATCTTCCCGCCATCTGA TGAGCAGTTGAAATCTGGAACTGCCTCTGTTGTGTGCCTGCTGAAT AACTTCTATCCCAGAGAGGCCAAAGTACAGTGGAAGGTGGATAACG CCCTCCAATCGGGTAACTCCCAGGAGAGTGTCACAGAGCAGGACAG CAAGGACAGCACCTACAGCCTCAGCAGCACCCTGACGCTGAGCAAA GCAGACTACGAGAAACACAAAGTCTACGCCTGCGAAGTCACCCATC AGGGCCTGAGCTCGCCCGTCACAAAGAGCTTCAACAGGGGAGAGTG T |
| 163 | OX40.14 heavy chain | CAGGTGCAGCTGGTGGAGTCTGGGGGAGGCGTGGTCCAGCCTGGGA GGTCCCTGAGACTCTCCTGTGCAGCCTCTGGATTCACCTTCAGTAA CTATGCTCTGCACTGGGTCCGCCAGGCTCCAGGCAAGGGGCTGGAG TGGGTGGCACTTATATCATATAGTGGAAGCAGGAAACACTACGCAG ACTCCGTGAAGGGCCGATTCAGTATCTCCAGAGACAATTCCAAGAA CACACTGTATCTGCAAATGAACAGCCTGAGAGCTGAGGACACGGCT GTGTATTACTGTGCGAGTCTTACTTACGTTCGGGAGTGGGGCCAGG GAACCCTGGTCACCGTCTCCTCAGCTAGCACCAAGGGCCCATCGGT CTTCCCCCTGGCACCCTCCTCCAAGAGCACCTCTGGGGGCACAGCG GCCCTGGGCTGCCTGGTCAAGGACTACTTCCCCGAACCGGTGACGG TGTCGTGGAACTCAGGCGCCCTGACCAGCGGCGTGCACACCTTCCC GGCTGTCCTACAGTCCTCAGGACTCTACTCCCTCAGCAGCGTGGTG ACCGTGCCCTCCAGCAGCTTGGGCACCCAGACCTACATCTGCAACG TGAATCACAAGCCCAGCAACACCAAGGTGGACAAGAGAGTTGAGCC CAAATCTTGTGACAAAACTCACACATGCCCACCGTGCCCAGCACCT GAACTCCTGGGGGGACCGTCAGTCTTCCTCTTCCCCCCAAAACCCA AGGACACCCTCATGATCTCCCGGACCCCTGAGGTCACATGCGTGGT GGTGGACGTGAGCCACGAAGACCCTGAGGTCAAGTTCAACTGGTAC GTGGACGGCGTGGAGGTGCATAATGCCAAGACAAAGCCGCGGGAGG AGCAGTACAACAGCACGTACCGTGTGGTCAGCGTCCTCACCGTCCT GCACCAGGACTGGCTGAATGGCAAGGAGTACAAGTGCAAGGTCTCC AACAAAGCCCTCCCAGCCCCCATCGAGAAAACCATCTCCAAAGCCA AAGGGCAGCCCCGAGAACCACAGGTGTACACCCTGCCCCCATCCCG GGAGGAGATGACCAAGAACCAGGTCAGCCTGACCTGCCTGGTCAAA GGCTTCTATCCCAGCGACATCGCCGTGGAGTGGGAGAGCAATGGGC AGCCGGAGAACAACTACAAGACCACGCCTCCCGTGCTGGACTCCGA CGGCTCCTTCTTCCTCTATAGCAAGCTCACCGTGGACAAGAGCAGG TGGCAGCAGGGGAACGTCTTCTCATGCTCCGTGATGCATGAGGCTC TGCACAACCACTACACGCAGAAGAGCCTCTCCCTGTCCCCGGGT |
| 164 | OX40.14 light chain | GAAATTGTGTTGACGCAGTCTCCAGGCACCCTGTCTTTGTCTCCAG GGGAAAGAGCCACCCTCTCCTGCAGGGCCAGTCAGAGTGTTAGCAG CAGCTACTTAGCCTGGTACCAGCAGAAACCTGGCCAGGCTCCCAGG CTCCTCATCTATGGTGCATCCAGCAGGGCCACTGGCATCCCAGACA GGTTCAGTGGCAGTGGGTCTGGGACAGACTTCACTCTCACCATCAG CAGACTGGAGCCTGAAGATTTTGCAGTGTATTACTGTCAGCAGTAT GGTAGCTCACCATTCACTTTCGGCCCTGGGACCAAAGTGGATATCA AACGTACGGTGGCTGCACCATCTGTCTTCATCTTCCCGCCATCTGA TGAGCAGTTGAAATCTGGAACTGCCTCTGTTGTGTGCCTGCTGAAT AACTTCTATCCCAGAGAGGCCAAAGTACAGTGGAAGGTGGATAACG CCCTCCAATCGGGTAACTCCCAGGAGAGTGTCACAGAGCAGGACAG CAAGGACAGCACCTACAGCCTCAGCAGCACCCTGACGCTGAGCAAA GCAGACTACGAGAAACACAAAGTCTACGCCTGCGAAGTCACCCATC AGGGCCTGAGCTCGCCCGTCACAAAGAGCTTCAACAGGGGAGAGTG T |

TABLE 23-continued

SUMMARY OF SEQUENCES

| SEQ ID | Description | Sequence |
|---|---|---|
| 165 | OX40.15 heavy chain | CAGGTGCAGCTGGTGGAGTCTGGGGGAGGCGTGGTCCAGCCTGGGA
GGTCCCTGAGACTCTCCTGTGCAGCCTCTGGATTCACCTTCAGTAA
CTATGCTCTGCACTGGGTCCGCCAGGCTCCAGGCAAGGGGCTGGAG
TGGGTGGCACTTATATCATATGATAGTAGCAGGAAACACTACGCAG
ACTCCGTGAAGGGCCGATTCAGTATCTCCAGAGACAATTCCAAGAA
CACACTGTATCTGCAAATGAACAGCCTGAGAGCTGAGGACACGGCT
GTGTATTACTGTGCGAGTCTTACTTACGTTCGGGAGTGGGGCCAGG
GAACCCTGGTCACCGTCTCCTCAGCTAGCACCAAGGGCCCATCGGT
CTTCCCCCTGGCACCCTCCTCCAAGAGCACCTCTGGGGGCACAGCG
GCCCTGGGCTGCCTGGTCAAGGACTACTTCCCCGAACCGGTGACGG
TGTCGTGGAACTCAGGCGCCCTGACCAGCGGCGTGCACACCTTCCC
GGCTGTCCTACAGTCCTCAGGACTCTACTCCCTCAGCAGCGTGGTG
ACCGTGCCCTCCAGCAGCTTGGGCACCCAGACCTACATCTGCAACG
TGAATCACAAGCCCAGCAACACCAAGGTGGACAAGAGAGTTGAGCC
CAAATCTTGTGACAAAACTCACACATGCCCACCGTGCCCAGCACCT
GAACTCCTGGGGGACCGTCAGTCTTCCTCTTCCCCCCAAAACCCA
AGGACACCCTCATGATCTCCCGGACCCCTGAGGTCACATGCGTGGT
GGTGGACGTGAGCCACGAAGACCCTGAGGTCAAGTTCAACTGGTAC
GTGGACGGCGTGGAGGTGCATAATGCCAAGACAAAGCCGCGGGAGG
AGCAGTACAACAGCACGTACCGTGTGGTCAGCGTCCTCACCGTCCT
GCACCAGGACTGGCTGAATGGCAAGGAGTACAAGTGCAAGGTCTCC
AACAAAGCCCTCCCAGCCCCCATCGAGAAAACCATCTCCAAAGCCA
AAGGGCAGCCCCGAGAACCACAGGTGTACACCCTGCCCCCATCCCG
GGAGGAGATGACCAAGAACCAGGTCAGCCTGACCTGCCTGGTCAAA
GGCTTCTATCCCAGCGACATCGCCGTGGAGTGGGAGAGCAATGGGC
AGCCGGAGAACAACTACAAGACCACGCCTCCCGTGCTGGACTCCGA
CGGCTCCTTCTTCCTCTATAGCAAGCTCACCGTGGACAAGAGCAGG
TGGCAGCAGGGGAACGTCTTCTCATGCTCCGTGATGCATGAGGCTC
TGCACAACCACTACACGCAGAAGAGCCTCTCCCTGTCCCCGGGT |
| 166 | OX40.15 light chain | GAAATTGTGTTGACGCAGTCTCCAGGCACCCTGTCTTTGTCTCCAG
GGGAAAGAGCCACCCTCTCCTGCAGGGCCAGTCAGAGTGTTAGCAG
CAGCTACTTAGCCTGGTACCAGCAGAAACCTGGCCAGGCTCCCAGG
CTCCTCATCTATGGTGCATCCAGCAGGGCCACTGGCATCCCAGACA
GGTTCAGTGGCAGTGGGTCTGGGACAGACTTCACTCTCACCATCAG
CAGACTGGAGCCTGAAGATTTTGCAGTGTATTACTGTCAGCAGTAT
GGTAGCTCACCATTCACTTTCGGCCCTGGGACCAAAGTGGATATCA
AACGTACGGTGGCTGCACCATCTGTCTTCATCTTCCCGCCATCTGA
TGAGCAGTTGAAATCTGGAACTGCCTCTGTTGTGTGCCTGCTGAAT
AACTTCTATCCCAGAGAGGCCAAAGTACAGTGGAAGGTGGATAACG
CCCTCCAATCGGGTAACTCCCAGGAGAGTGTCACAGAGCAGGACAG
CAAGGACAGCACCTACAGCCTCAGCAGCACCCTGACGCTGAGCAAA
GCAGACTACGAGAAACACAAAGTCTACGCCTGCGAAGTCACCCATC
AGGGCCTGAGCTCGCCCGTCACAAAGAGCTTCAACAGGGGAGAGTG
T |
| 167 | OX40.16 heavy chain | GAGGTTCAGCTGGTGCAGTCTGGGGGAGGCTTGGTTCAGCCTGGGG
GGTCCCTGAGACTCTCCTGTGCAGGCTCTGGATTCACCTTCAGTAG
CTATGCTATGTACTGGGTTCGCCAGGCTCCAGGAAAAGGTCTGGAG
TGGGTATCAGCTATTGATACTGATGGTGGCACATTCTATGCAGACT
CCGTGCGGGGCCGATTCACCATCTCCAGAGACAATGCCAAGAACTC
CTTGTATCTTCAAATGAACAGCCTGAGAGCCGAGGACACGGCTGTG
TATTTCTGTGCAAGACTTGGGGAAGGGTACTTCTTTGACTACTGGG
GCCAGGGAACCCTGGTCACCGTCTCCTCAGCTAGCACCAAGGGCCC
ATCGGTCTTCCCCCTGGCACCCTCCTCCAAGAGCACCTCTGGGGGC
ACAGCGGCCCTGGGCTGCCTGGTCAAGGACTACTTCCCCGAACCGG
TGACGGTGTCGTGGAACTCAGGCGCCCTGACCAGCGGCGTGCACAC
CTTCCCGGCTGTCCTACAGTCCTCAGGACTCTACTCCCTCAGCAGC
GTGGTGACCGTGCCCTCCAGCAGCTTGGGCACCCAGACCTACATCT
GCAACGTGAATCACAAGCCCAGCAACACCAAGGTGGACAAGAGAGT
TGAGCCCAAATCTTGTGACAAAACTCACACATGCCCACCGTGCCCA
GCACCTGAACTCCTGGGGGACCGTCAGTCTTCCTCTTCCCCCCAA
AACCCAAGGACACCCTCATGATCTCCCGGACCCCTGAGGTCACATG
CGTGGTGGTGGACGTGAGCCACGAAGACCCTGAGGTCAAGTTCAAC
TGGTACGTGGACGGCGTGGAGGTGCATAATGCCAAGACAAAGCCGC
GGGAGGAGCAGTACAACAGCACGTACCGTGTGGTCAGCGTCCTCAC
CGTCCTGCACCAGGACTGGCTGAATGGCAAGGAGTACAAGTGCAAG
GTCTCCAACAAAGCCCTCCCAGCCCCCATCGAGAAAACCATCTCCA
AAGCCAAAGGGCAGCCCCGAGAACCACAGGTGTACACCCTGCCCCC
ATCCCGGGAGGAGATGACCAAGAACCAGGTCAGCCTGACCTGCCTG
GTCAAAGGCTTCTATCCCAGCGACATCGCCGTGGAGTGGGAGAGCA
ATGGGCAGCCGGAGAACAACTACAAGACCACGCCTCCCGTGCTGGA
CTCCGACGGCTCCTTCTTCCTCTATAGCAAGCTCACCGTGGACAAG
AGCAGGTGGCAGCAGGGGAACGTCTTCTCATGCTCCGTGATGCATG |

TABLE 23-continued

SUMMARY OF SEQUENCES

| SEQ ID | Description | Sequence |
|---|---|---|
| | | AGGCTCTGCACAACCACTACACGCAGAAGAGCCTCTCCCTGTCCCC<br>GGGTTGA |
| 168 | OX40.16 light chain (shared by OX40.20, OX40.21, OX40.22) | GAAATTGTGTTGACACAGTCTCCAGCCACCCTGTCTTTGTCTCCAGGGG<br>AAAGAGCCACCCTCTCCTGCAGGGCCAGTCAGAGTGTTAGCAGCTACTT<br>AGCCTGGTACCAACAGAAACCTGGCCAGGCTCCCAGGCTCCTCATCTAT<br>GATGCATCCAACAGGGCCACTGGCATCCCAGCCAGGTTCAGTGGCAGTG<br>GGTCTGGGACAGACTTCACTCTCACCATCAGCAGCCTAGAGCCTGAAGA<br>TTTTGCAGTTTATTACTGTCAGCAGCGTAGCAACTGGCCTCCCACTTTC<br>GGCGGAGGGACCAAGGTGGAGATCAAACGTACGGTGGCTGCACCATCTG<br>TCTTCATCTTCCCGCCATCTGATGAGCAGTTGAAATCTGGAACTGCCTC<br>TGTTGTGTGCCTGCTGAATAACTTCTATCCCAGAGAGGCCAAAGTACAG<br>TGGAAGGTGGATAACGCCCTCCAATCGGGTAACTCCCAGGAGAGTGTCA<br>CAGAGCAGGACAGCAAGGACAGCACCTACAGCCTCAGCAGCACCCTGAC<br>GCTGAGCAAAGCAGACTACGAGAAACACAAAGTCTACGCCTGCGAAGTC<br>ACCCATCAGGGCCTGAGCTCGCCCGTCACAAAGAGCTTCAACAGGGGAG<br>AGTGTTAG |
| 169 | OX40.17 heavy chain | GAGGTGCAGCTGGTGGAGTCTGGGGGAGGCTTGGTACAGCCTGGGG<br>GGTCCCTGAGACTCTCCTGTGCAGCCTCTGGATTCACCTTCAGTAG<br>CTACGACATGCACTGGGTCCGCCAAACTACAGGAAAAGGTCTGGAG<br>TGGGTCTCAGTTATTGGTACTGCTGGTGACACATACTATCCAGGCT<br>CCGTGAAGGGCCGATTCACCATCTCCAGAGAAAATGCCAAGAACTC<br>CTTGTATCTTCAAATGAACAGCCTGAGAGCCGGGGACACGGCTGTG<br>TATTACTGTGCAAGAGGGGGATGGGGAACTACTTTGACTACTGGG<br>GCCAGGGAACCCTGGTCACCGTCTCCTCAGCTAGCACCAAGGGCCC<br>ATCGGTCTTCCCCCTGGCACCCTCCTCCAAGAGCACCTCTGGGGGC<br>ACAGCGGCCCTGGGCTGCCTGGTCAAGGACTACTTCCCCGAACCGG<br>TGACGGTGTCGTGGAACTCAGGCGCCCTGACCAGCGGCGTGCACAC<br>CTTCCCGGCTGTCCTACAGTCCTCAGGACTCTACTCCCTCAGCAGC<br>GTGGTGACCGTGCCCTCCAGCAGCTTGGGCACCCAGACCTACATCT<br>GCAACGTGAATCACAAGCCCAGCAACACCAAGGTGGACAAGAGAGT<br>TGAGCCCAAATCTTGTGACAAAACTCACACATGCCCACCGTGCCCA<br>GCACCTGAACTCCTGGGGGGACCGTCAGTCTTCCTCTTCCCCCCAA<br>AACCCAAGGACACCCTCATGATCTCCCGGACCCCTGAGGTCACATG<br>CGTGGTGGTGGACGTGAGCCACGAAGACCCTGAGGTCAAGTTCAAC<br>TGGTACGTGGACGGCGTGGAGGTGCATAATGCCAAGACAAAGCCGC<br>GGGAGGAGCAGTACAACAGCACGTACCGTGTGGTCAGCGTCCTCAC<br>CGTCCTGCACCAGGACTGGCTGAATGGCAAGGAGTACAAGTGCAAG<br>GTCTCCAACAAAGCCCTCCCAGCCCCCATCGAGAAAACCATCTCCA<br>AAGCCAAAGGGCAGCCCCGAGAACCACAGGTGTACACCCTGCCCCC<br>ATCCCGGGAGGAGATGACCAAGAACCAGGTCAGCCTGACCTGCCTG<br>GTCAAAGGCTTCTATCCCAGCGACATCGCCGTGGAGTGGGAGAGCA<br>ATGGGCAGCCGGAGAACAACTACAAGACCACGCCTCCCGTGCTGGA<br>CTCCGACGGCTCCTTCTTCCTCTATAGCAAGCTCACCGTGGACAAG<br>AGCAGGTGGCAGCAGGGGAACGTCTTCTCATGCTCCGTGATGCATG<br>AGGCTCTGCACAACCACTACACGCAGAAGAGCCTCTCCCTGTCCCC<br>GGGTTGA |
| 170 | OX40.17 light chain | GAAATTGTGTTGACACAGTCTCCAGCCACCCTGTCTTTGTCTCCAG<br>GGGAAAGAGCCACCCTCTCCTGCAGGGCCAGTCAGAGTGTTAGCAG<br>CTACTTAGCCTGGTACCAACAGAAACCTGGCCAGGCTCCCAGGCTC<br>CTCATCTATGATGCATCCAACAGGGCCACTGGCATCCCAGCCAGGT<br>TCAGTGGCAGTGGGTCTGGGACAGACTTCACTCTCACCATCAGCAG<br>CCTAGAGCCTGAAGATTTTGCAGTTTATTACTGTCAGCAGCGTAGC<br>AACTGGCCGCTCACTTTCGGCGGAGGGACCAAGGTGGAGATCAAAC<br>GTACGGTGGCTGCACCATCTGTCTTCATCTTCCCGCCATCTGATGA<br>GCAGTTGAAATCTGGAACTGCCTCTGTTGTGTGCCTGCTGAATAAC<br>TTCTATCCCAGAGAGGCCAAAGTACAGTGGAAGGTGGATAACGCCC<br>TCCAATCGGGTAACTCCCAGGAGAGTGTCACAGAGCAGGACAGCAA<br>GGACAGCACCTACAGCCTCAGCAGCACCCTGACGCTGAGCAAAGCA<br>GACTACGAGAAACACAAAGTCTACGCCTGCGAAGTCACCCATCAGG<br>GCCTGAGCTCGCCCGTCACAAAGAGCTTCAACAGGGGAGAGTGTTA<br>G |
| 171 | OX40.18 heavy chain | CAGGTGCAGCTGGTGCAGTCTGGGGCTGAGGTGAAGAAGCCTGGGG<br>CCTCAGTGAAGGTCTCCTGCAAGGCTTCTGGATACACCTTCACCAG<br>TTATGATGTCAACTGGGTGCGACAGGCCACTGGACAAGGGCTTGAG<br>TGGATGGGATGGATGAACCCTAACAGTGGTAACACAGGCTATGCAC<br>CGAAGTTCCAGGGCAGAGTCACCATGACCAGGGACACCTCCATAAG<br>CACAGCCTACATGGAGCTGAGCAGCCTGAGATCTGAGGACACGGCC<br>GTTTATTACTGTGCGAGAATATATAGCAGCTCGTACAACTGGTTCG<br>ACTACTGGGGCCAGGGAACCCTGGTCACCGTCTCCTCAGCTAGCAC<br>CAAGGGCCCATCGGTCTTCCCCCTGGCACCCTCCTCCAAGAGCACC<br>TCTGGGGGCACAGCGGCCCTGGGCTGCCTGGTCAAGGACTACTTCC |

TABLE 23-continued

SUMMARY OF SEQUENCES

| SEQ ID | Description | Sequence |
|---|---|---|
| | | CCGAACCGGTGACGGTGTCGTGGAACTCAGGCGCCCTGACCAGCGG<br>CGTGCACACCTTCCCGGCTGTCCTACAGTCCTCAGGACTCTACTCC<br>CTCAGCAGCGTGGTGACCGTGCCCTCCAGCAGCTTGGGCACCCAGA<br>CCTACATCTGCAACGTGAATCACAAGCCCAGCAACACCAAGGTGGA<br>CAAGAGAGTTGAGCCCAAATCTTGTGACAAAACTCACACATGCCCA<br>CCGTGCCCAGCACCTGAACTCCTGGGGGGACCGTCAGTCTTCCTCT<br>TCCCCCCAAAACCCAAGGACACCCTCATGATCTCCCGGACCCCTGA<br>GGTCACATGCGTGGTGGTGGACGTGAGCCACGAAGACCCTGAGGTC<br>AAGTTCAACTGGTACGTGGACGGCGTGGAGGTGCATAATGCCAAGA<br>CAAAGCCGCGGGAGGAGCAGTACAACAGCACGTACCGTGTGGTCAG<br>CGTCCTCACCGTCCTGCACCAGGACTGGCTGAATGGCAAGGAGTAC<br>AAGTGCAAGGTCTCCAACAAAGCCCTCCCAGCCCCCATCGAGAAAA<br>CCATCTCCAAAGCCAAAGGGCAGCCCCGAGAACCACAGGTGTACAC<br>CCTGCCCCCATCCCGGGAGGAGATGACCAAGAACCAGGTCAGCCTG<br>ACCTGCCTGGTCAAAGGCTTCTATCCCAGCGACATCGCCGTGGAGT<br>GGGAGAGCAATGGGCAGCCGGAGAACAACTACAAGACCACGCCTCC<br>CGTGCTGGACTCCGACGGCTCCTTCTTCCTCTATAGCAAGCTCACC<br>GTGGACAAGAGCAGGTGGCAGCAGGGGAACGTCTTCTCATGCTCCG<br>TGATGCATGAGGCTCTGCACAACCACTACACGCAGAAGAGCCTCTC<br>CCTGTCCCCGGGTTGA |
| 172 | OX40.18 light chain | GAAATTGTGTTGACACAGTCTCCAGCCACCCTGTCTTTGTCTCCAG<br>GGGAAAGAGCCACCCTCTCCTGCAGGGCCAGTCAGAGTGTTAGCAG<br>CTACTTAGCCTGGTACCAACAGAAACCTGGCCAGGCTCCCAGGCTC<br>CTCATCTATGATGCATCCAACAGGGCCACTGGCATCCCAGCCAGGT<br>TCAGTGGCAGTGGGTCTGGGACAGACTTCACTCTCACCATCAGCAG<br>CCTAGAGCCTGAAGATTTTGCAGTTTATTACTGTCAGCAGCGTAGC<br>AACTGGCCTCTCACTTTCGGCGGAGGGACCAAGGTGGAGATCAAAC<br>GTACGGTGGCTGCACCATCTGTCTTCATCTTCCCGCCATCTGATGA<br>GCAGTTGAAATCTGGAACTGCCTCTGTTGTGTGCCTGCTGAATAAC<br>TTCTATCCCAGAGAGGCCAAAGTACAGTGGAAGGTGGATAACGCCC<br>TCCAATCGGGTAACTCCCAGGAGAGTGTCACAGAGCAGGACAGCAA<br>GGACAGCACCTACAGCCTCAGCAGCACCCTGACGCTGAGCAAAGCA<br>GACTACGAGAAACACAAAGTCTACGCCTGCGAAGTCACCCATCAGG<br>GCCTGAGCTCGCCCGTCACAAAGAGCTTCAACAGGGGAGAGTGTTA<br>G |
| 173 | OX40.19 heavy chain | CAGGTGCAGCTGGTGGAGTCTGGGGGAGGCGTGGTCCAGCCTGGGA<br>GGTCCCTGAGACTCTCCTGTGCAGCCTCTGGATTCACCTTCAGTAA<br>CTATGCTCTGCACTGGGTCCGCCAGGCTCCAGGCAAGGGGCTGGAG<br>TGGGTGGCACTTATATCATATGATGGAAGCAGGAAACACTACGCAG<br>ACTCCGTGAAGGGCCGATTCAGTATCTCCAGAGACAATTCCAAGAA<br>CACACTGTATCTGCAAATGAACAGCCTGAGAGCTGAGGACACGGCT<br>GTGTATTACTGTGCGAGTCTTACTCTGGTTCGGGAGTGGGGCCAGG<br>GAACCCTGGTCACCGTCTCCTCAGCTAGCACCAAGGGCCCATCGGT<br>CTTCCCCCTGGCACCCTCCTCCAAGAGCACCTCTGGGGGCACAGCG<br>GCCCTGGGCTGCCTGGTCAAGGACTACTTCCCCGAACCGGTGACGG<br>TGTCGTGGAACTCAGGCGCCCTGACCAGCGGCGTGCACACCTTCCC<br>GGCTGTCCTACAGTCCTCAGGACTCTACTCCCTCAGCAGCGTGGTG<br>ACCGTGCCCTCCAGCAGCTTGGGCACCCAGACCTACATCTGCAACG<br>TGAATCACAAGCCCAGCAACACCAAGGTGGACAAGAGAGTTGAGCC<br>CAAATCTTGTGACAAAACTCACACATGCCCACCGTGCCCAGCACCT<br>GAACTCCTGGGGGGACCGTCAGTCTTCCTCTTCCCCCCAAAACCCA<br>AGGACACCCTCATGATCTCCCGGACCCCTGAGGTCACATGCGTGGT<br>GGTGGACGTGAGCCACGAAGACCCTGAGGTCAAGTTCAACTGGTAC<br>GTGGACGGCGTGGAGGTGCATAATGCCAAGACAAAGCCGCGGGAGG<br>AGCAGTACAACAGCACGTACCGTGTGGTCAGCGTCCTCACCGTCCT<br>GCACCAGGACTGGCTGAATGGCAAGGAGTACAAGTGCAAGGTCTCC<br>AACAAAGCCCTCCCAGCCCCCATCGAGAAAACCATCTCCAAAGCCA<br>AAGGGCAGCCCCGAGAACCACAGGTGTACACCCTGCCCCCATCCCG<br>GGAGGAGATGACCAAGAACCAGGTCAGCCTGACCTGCCTGGTCAAA<br>GGCTTCTATCCCAGCGACATCGCCGTGGAGTGGGAGAGCAATGGGC<br>AGCCGGAGAACAACTACAAGACCACGCCTCCCGTGCTGGACTCCGA<br>CGGCTCCTTCTTCCTCTATAGCAAGCTCACCGTGGACAAGAGTAGG<br>TGGCAGCAGGGGAACGTCTTCTCATGCTCCGTGATGCATGAGGCTC<br>TGCACAACCACTACACGCAGAAGAGCCTCTCCCTGTCCCCGGGT |
| 174 | OX40.19 light chain | GAAATTGTGTTGACGCAGTCTCCAGGCACCCTGTCTTTGTCTCCAG<br>GGGAAAGAGCCACCCTCTCCTGCAGGGCCAGTCAGAGTGTTAGCAG<br>CAGCTACTTAGCCTGGTACCAGCAGAAACCTGGCCAGGCTCCCAGG<br>CTCCTCATCTATGGTGCATCCAGCAGGGCCACTGGCATCCCAGACA<br>GGTTCAGTGGCAGTGGGTCTGGGACAGACTTCACTCTCACCATCAG<br>CAGACTGGAGCCTGAAGATTTTGCAGTGTATTACTGTCAGCAGTAT<br>GGTAGCTCACCATTCACTTTCGGCCCTGGGACCAAAGTGGATATCA<br>AACGTACGGTGGCTGCACCATCTGTCTTCATCTTCCCGCCATCTGA |

TABLE 23-continued

SUMMARY OF SEQUENCES

| SEQ ID | Description | Sequence |
|---|---|---|
| | | TGAGCAGTTGAAATCTGGAACTGCCTCTGTTGTGTGCCTGCTGAAT AACTTCTATCCCAGAGAGGCCAAAGTACAGTGGAAGGTGGATAACG CCCTCCAATCGGGTAACTCCCAGGAGAGTGTCACAGAGCAGGACAG CAAGGACAGCACCTACAGCCTCAGCAGCACCCTGACGCTGAGCAAA GCAGACTACGAGAAACACAAAGTCTACGCCTGCGAAGTCACCCATC AGGGCCTGAGCTCGCCCGTCACAAAGAGCTTCAACAGGGGAGAGTG T |
| 175 | OX40.20 heavy chain | GAGGTTCAGCTGGTGCAGTCTGGGGGAGGCTTGGTTCAGCCTGGGG GGTCCCTGAGACTCTCCTGTGCAGGCTCTGGATTCACCTTCAGTAG CTATGCTATGTACTGGGTTCGCCAGGCTCCAGGAAAAGGTCTGGAG TGGGTATCAGCTATTGATACTAGTGGTGGCACATTCTATGCAGACT CCGTGCGGGGCCGATTCACCATCTCCAGAGACAATGCCAAGAACTC CTTGTATCTTCAAATGAACAGCCTGAGAGCCGAGGACACGGCTGTG TATTTCTGTGCAAGACTTGGGGAAGGGTACTTCTTTGACTACTGGG GCCAGGGAACCCTGGTCACCGTCTCCTCAGCTAGCACCAAGGGCCC ATCGGTCTTCCCCCTGGCACCCTCCTCCAAGAGCACCTCTGGGGGC ACAGCGGCCCTGGGCTGCCTGGTCAAGGACTACTTCCCCGAACCGG TGACGGTGTCGTGGAACTCAGGCGCCCTGACCAGCGGCGTGCACAC CTTCCCGGCTGTCCTACAGTCCTCAGGACTCTACTCCCTCAGCAGC GTGGTGACCGTGCCCTCCAGCAGCTTGGGCACCCAGACCTACATCT GCAACGTGAATCACAAGCCCAGCAACACCAAGGTGGACAAGAGAGT TGAGCCCAAATCTTGTGACAAAACTCACACATGCCCACCGTGCCCA GCACCTGAACTCCTGGGGGGACCGTCAGTCTTCCTCTTCCCCCCAA AACCCAAGGACACCCTCATGATCTCCCGGACCCCTGAGGTCACATG CGTGGTGGTGGACGTGAGCCACGAAGACCCTGAGGTCAAGTTCAAC TGGTACGTGGACGGCGTGGAGGTGCATAATGCCAAGACAAAGCCGC GGGAGGAGCAGTACAACAGCACGTACCGTGTGGTCAGCGTCCTCAC CGTCCTGCACCAGGACTGGCTGAATGGCAAGGAGTACAAGTGCAAG GTCTCCAACAAAGCCCTCCCAGCCCCCATCGAGAAAACCATCTCCA AAGCCAAAGGGCAGCCCCGAGAACCACAGGTGTACACCCTGCCCCC ATCCCGGGAGGAGATGACCAAGAACCAGGTCAGCCTGACCTGCCTG GTCAAAGGCTTCTATCCCAGCGACATCGCCGTGGAGTGGGAGAGCA ATGGGCAGCCGGAGAACAACTACAAGACCACGCCTCCCGTGCTGGA CTCCGACGGCTCCTTCTTCCTCTATAGCAAGCTCACCGTGGACAAG AGCAGGTGGCAGCAGGGGAACGTCTTCTCATGCTCCGTGATGCATG AGGCTCTGCACAACCACTACACGCAGAAGAGCCTCTCCCTGTCCCC GGGTTGA |
| — | OX40.20 light chain | SEQ ID NO: 168 |
| 176 | OX40.21 heavy chain | GAGGTTCAGCTGGTGCAGTCTGGGGGAGGCTTGGTTCAGCCTGGGG GGTCCCTGAGACTCTCCTGTGCAGGCTCTGGATTCACCTTCAGTAG CTATGCTATGTACTGGGTTCGCCAGGCTCCAGGAAAAGGTCTGGAG TGGGTATCAGCTATTGATACTGATGCTGGCACATTCTATGCAGACT CCGTGCGGGGCCGATTCACCATCTCCAGAGACAATGCCAAGAACTC CTTGTATCTTCAAATGAACAGCCTGAGAGCCGAGGACACGGCTGTG TATTTCTGTGCAAGACTTGGGGAAGGGTACTTCTTTGACTACTGGG GCCAGGGAACCCTGGTCACCGTCTCCTCAGCTAGCACCAAGGGCCC ATCGGTCTTCCCCCTGGCACCCTCCTCCAAGAGCACCTCTGGGGGC ACAGCGGCCCTGGGCTGCCTGGTCAAGGACTACTTCCCCGAACCGG TGACGGTGTCGTGGAACTCAGGCGCCCTGACCAGCGGCGTGCACAC CTTCCCGGCTGTCCTACAGTCCTCAGGACTCTACTCCCTCAGCAGC GTGGTGACCGTGCCCTCCAGCAGCTTGGGCACCCAGACCTACATCT GCAACGTGAATCACAAGCCCAGCAACACCAAGGTGGACAAGAGAGT TGAGCCCAAATCTTGTGACAAAACTCACACATGCCCACCGTGCCCA GCACCTGAACTCCTGGGGGGACCGTCAGTCTTCCTCTTCCCCCCAA AACCCAAGGACACCCTCATGATCTCCCGGACCCCTGAGGTCACATG CGTGGTGGTGGACGTGAGCCACGAAGACCCTGAGGTCAAGTTCAAC TGGTACGTGGACGGCGTGGAGGTGCATAATGCCAAGACAAAGCCGC GGGAGGAGCAGTACAACAGCACGTACCGTGTGGTCAGCGTCCTCAC CGTCCTGCACCAGGACTGGCTGAATGGCAAGGAGTACAAGTGCAAG GTCTCCAACAAAGCCCTCCCAGCCCCCATCGAGAAAACCATCTCCA AAGCCAAAGGGCAGCCCCGAGAACCACAGGTGTACACCCTGCCCCC ATCCCGGGAGGAGATGACCAAGAACCAGGTCAGCCTGACCTGCCTG GTCAAAGGCTTCTATCCCAGCGACATCGCCGTGGAGTGGGAGAGCA ATGGGCAGCCGGAGAACAACTACAAGACCACGCCTCCCGTGCTGGA CTCCGACGGCTCCTTCTTCCTCTATAGCAAGCTCACCGTGGACAAG AGCAGGTGGCAGCAGGGGAACGTCTTCTCATGCTCCGTGATGCATG AGGCTCTGCACAACCACTACACGCAGAAGAGCCTCTCCCTGTCCCC GGGTTGA |
| — | OX40.21 light chain | SEQ ID NO: 168 |

TABLE 23-continued

SUMMARY OF SEQUENCES

| SEQ ID | Description | Sequence |
|---|---|---|
| 177 | OX40.22 heavy chain | GAGGTTCAGCTGGTGCAGTCTGGGGGAGGCTTGGTTCAGCCTGGGG GGTCCCTGAGACTCTCCTGTGCAGGCTCTGGATTCACCTTCAGTAG CTATGCTATGTACTGGGTTCGCCAGGCTCCAGGAAAAGGTCTGGAG TGGGTATCAGCTATTGATACTAGTACTGGCACATTCTATGCAGACT CCGTGCGGGGCCGATTCACCATCTCCAGAGACAATGCCAAGAACTC CTTGTATCTTCAAATGAACAGCCTGAGAGCCGAGGACACGGCTGTG TATTTCTGTGCAAGACTTGGGGAAGGGTACTTCTTTGACTACTGGG GCCAGGGAACCCTGGTCACCGTCTCCTCAGCTAGCACCAAGGGCCC ATCGGTCTTCCCCCTGGCACCCTCCTCCAAGAGCACCTCTGGGGGC ACAGCGGCCCTGGGCTGCCTGGTCAAGGACTACTTCCCCGAACCGG TGACGGTGTCGTGGAACTCAGGCGCCCTGACCAGCGGCGTGCACAC CTTCCCGGCTGTCCTACAGTCCTCAGGACTCTACTCCCTCAGCAGC GTGGTGACCGTGCCCTCCAGCAGCTTGGGCACCCAGACCTACATCT GCAACGTGAATCACAAGCCCAGCAACACCAAGGTGGACAAGAGAGT TGAGCCCAAATCTTGTGACAAAACTCACACATGCCCACCGTGCCCA GCACCTGAACTCCTGGGGGGACCGTCAGTCTTCCTCTTCCCCCCAA AACCCAAGGACACCCTCATGATCTCCCGGACCCCTGAGGTCACATG CGTGGTGGTGGACGTGAGCCACGAAGACCCTGAGGTCAAGTTCAAC TGGTACGTGGACGGCGTGGAGGTGCATAATGCCAAGACAAAGCCGC GGGAGGAGCAGTACAACAGCACGTACCGTGTGGTCAGCGTCCTCAC CGTCCTGCACCAGGACTGGCTGAATGGCAAGGAGTACAAGTGCAAG GTCTCCAACAAAGCCCTCCCAGCCCCCATCGAGAAAACCATCTCCA AAGCCAAAGGGCAGCCCCGAGAACCACAGGTGTACACCCTGCCCCC ATCCCGGGAGGAGATGACCAAGAACCAGGTCAGCCTGACCTGCCTG GTCAAAGGCTTCTATCCCAGCGACATCGCCGTGGAGTGGGAGAGCA ATGGGCAGCCGGAGAACAACTACAAGACCACGCCTCCCGTGCTGGA CTCCGACGGCTCCTTCTTCCTCTATAGCAAGCTCACCGTGGACAAG AGCAGGTGGCAGCAGGGGAACGTCTTCTCATGCTCCGTGATGCATG AGGCTCTGCACAACCACTACACGCAGAAGAGCCTCTCCCTGTCCCC GGGTTGA |
| — | OX40.22 light chain | SEQ ID NO: 168 |
| 178 | hOX40 epitope | DVVSSKPCKPCTWCNLR |
| 179 | hOX40 epitope | DSYKPGVDCAPCPPGHFSPGDNQACKPWTNCTLAGK |
| 180 | peptide linker | PVGVV |
| 181 | sortase A recognition motif | LPXTG, where in X is any amino acid |
| 182 | hOX40 epitope | QNTVCRPCGPGFYNDVVSSKPCKPCTWCNLR |
| 183 | hOX40 epitope | PCKPCTWCNLR |
| 184 | hOX40 epitope | QLCTATQDTVCR |
| 185 | hOX40 epitope | SQNTVCRPCGPGFYN |
| 186 | IgG1 C-termianl $C_H1$ (same for IgG3 (17-15-15-15), igG3 (17-15-15), IgG3 (17-15), IgG3 (15-15-15), IgG3 (15), and IgG4 | VDKRV |
| 187 | IgG2 C-terminal $C_H1$ | VDKTV |
| 188 | IgG1 upper hinge | EPKSCDKTHT |
| 189 | IgG3 (17-15-15-15) upper hinge (same for IgG3 (17-15-15) and IgG3 (17-15)) | ELKTPLGDTTHT |
| 190 | IgG3 (15-15-15) upper hinge (same for IgG3(15)) | EPKS |
| 191 | IgG4 upper hinge | ESKYGPP |
| 192 | IgG1 middle hinge | CPPCP |
| 193 | IgG2 middle hinge | CCVECPPCP |

TABLE 23-continued

SUMMARY OF SEQUENCES

| SEQ ID | Description | Sequence |
|---|---|---|
| 194 | IgG3 (17-15-15-15) middle hinge | CPRCP(EPKSCDTPPPCPRCP)$_3$ |
| 195 | IgG3 (17-15-15) middle hinge | CPRCP(EPKSCDTPPPCPRCP)$_2$ |
| 196 | IgG3 (17-15) middle hinge | CPRCP(EPKSCDTPPPCPRCP)$_1$ |
| 197 | IgG3 (15-15-15) middle hinge | CDTPPPCPRCP(EPKSCDTPPPCPRCP)$_2$ |
| 198 | IgG3 (15) middle hinge | CDTPPPCPRCP |
| 199 | IgG4 middle hinge | CPSCP |
| 200 | IgG1 lower hinge (same for IgG3 (17-15-15-15), IgG3 (17-15-15), IgG3 (17-15), IgG3 (15-15-15), IgG3 (15), and IgG4) | APELLGG |
| 201 | IgG2 lower hinge | APPVAG |
| 202 | Wildtype human IgG1 CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| 203 | Wildtype human IgG2 CH1 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| 204 | Wildtype human IgG1 CH2 | PSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK |
| 205 | Wildtype human IgG2 CH2 | PSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK |
| 206 | Wildtype human IgG1 CH3 | GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 207 | Wildtype human IgG2 CH3 | GQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 208 | Alternative hinge | ERKCCVECPPCPAPPVAG |
| 209 | Alternative hinge | ERKSCVECPPCPAPPVAG |
| 210 | Alternative hinge | ERKCSVECPPCPAPPVAG |
| 211 | Alternative hinge | ERKXCVECPPCPAPPVAG |
| 212 | Alternative hinge | ERKCXVECPPCPAPPVAG |
| 213 | Alternative hinge | ERKCCVECPPCPAPPVAGX |
| 214 | Alternative hinge | ERKSCVECPPCPAPPVAGX |
| 215 | Alternative hinge | ERKCSVECPPCPAPPVAGX |
| 216 | Alternative hinge | ERKXCVECPPCPAPPVAGX |
| 217 | Alternative hinge | ERKCXVECPPCPAPPVAGX |
| 218 | Alternative hinge | ERKCCVECPPCPAPELLGG |
| 219 | Alternative hinge | ERKSCVECPPCPAPELLGG |
| 220 | Alternative hinge | ERKCCSVECPPCPAPELLGG |
| 221 | Alternative hinge | ERKXCVECPPCPAPELLGG |
| 222 | Alternative hinge | ERKCXVECPPCPAPELLGG |

TABLE 23-continued

SUMMARY OF SEQUENCES

| SEQ ID | Description | Sequence |
|---|---|---|
| 223 | Alternative hinge | ERKCCVECPPCPAPELLG |
| 224 | Alternative hinge | ERKSCVECPPCPAPELLG |
| 225 | Alternative hinge | ERKCCSVECPPCPAPELLG |
| 226 | Alternative hinge | ERKXCVECPPCPAPELLG |
| 227 | Alternative hinge | ERKCXVECPPCPAPELLG |
| 228 | Alternative hinge | ERKCCVECPPCPAP |
| 229 | Alternative hinge | ERKSCVECPPCPAP |
| 230 | Alternative hinge | ERKCSVECPPCPAP |
| 231 | Alternative hinge | ERKXCVECPPCPAP |
| 232 | Alternative hinge | ERKCXVECPPCPAP |
| 233 | Portion of hinge | PVAG |
| 234 | Portion of hinge | ELLG |
| 235 | Portion of hinge | ELLGG |
| 236 | Portion of hinge | SCDKTHT |
| 237 | Portion of hinge | CCVE |
| 238 | WT human IgG2 hinge | ERKCCVECPPCPAPPVAG |
| 239 | Human IgG2 hinge with C219S | ERKSCVECPPCPAPPVAG |
| 240 | IgG2/IgG1 hinge | ERKCCVECPPCPAP<u>ELLGG</u> |
| 241 | IgG2 (C219S)/IgG1 hinge | ERKSCVECPPCPAP<u>ELLGG</u> |
| 242 | Wild type human IgG1 hinge | EPKSCDKTHTCPPCPAPELLGG |
| 243 | Human IgG1 CH2 with A330S/P331S | PSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALP<u>SS</u>IEKT<br>ISKAK |
| 244 | IgG1-IgG2-IgG1f | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br><u>ERKCCVECPPCPAPELLGG</u>PSVFLFPPKPKDTLMISRTPEVTCVVVDVS<br>HEDPEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPG |
| 245 | IgG1-IgG2-1gG1f2 | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br><u>ERKCCVECPPCPAPPVAG</u>PSVFLFPPKPKDTLMISRTPEVTCVVVDVS<br>EDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 246 | IgG1-IgG2CS-IgG1f | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br><u>ERKSCVECPPCPAPPVAG</u>PSVFLFPPKPKDTLMISRTPEVTCVVVDVSH<br>EDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 247 | IgG1-IgG2CS-IgG1f2 | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br><u>ERKSCVECPPCPAPPVAG</u>PSVFLFPPKPKDTLMISRTPEVTCVVVDVSH<br>EDPEVKFNWYVDGVEVHNAKTKPREEQYNSTYRVVSVLTVLHQDWLNGK |

TABLE 23-continued

SUMMARY OF SEQUENCES

| SEQ ID | Description | Sequence |
| --- | --- | --- |
| | | EYKCKVSNKALPAPIEKTISKAKGQPREPQVYTLPPSREEMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 248 | IgG2-IgG1f | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPELLGGPSVFLFPPKPKDTLMISRTPEVTCVVVDVS<br>HEDPEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSL<br>TCLVKGFYPSDIAVEWESNGQPENNYKTTVDKTPPVLDSDGSFFLYSKL<br>SRWQQGNVFSCSVMHEALHNHYTQKSLSLSPG |
| 249 | IgG2-IgG1f2 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPPVAGPSVFLFPPKPKDTLMISRTPEVTCVVVDVSH<br>EDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 250 | IgG2C5-IgG1f | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGPSVFLFPPKPKDTLMISRTPEVTCVVVDVS<br>HEDPEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPG |
| 251 | IgG2CS-IgG1f2 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGPSVFLFPPKPKDTLMISRTPEVTCVVVDVSH<br>EDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 252 | IgG1-IgG2-IgG1.1f | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br>ERKCCVECPPCPAPPVAGPSVFLFPPKPKDTLMISRTPEVTCVVVDVSH<br>EDPEVKFNWYVDGVEVHNAKTKPREEQYNSTYRVVSVLTVLHQDWLNGK<br>EYKCKVSNKALPSSIEKTISKAKGQPREPQVYTLPPSRREMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 253 | IgG1-IgG2CS-IgG1.1f | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKKV<br>ERKSCVECPPCPAPPVAGPSVFLFPPKPKDTLMISRTPEVTCVVVDVSH<br>EDPEVKFNWYVDGVEVHNAKTKPREEQYNSTYRVVSVLTVLHQDWLNGK<br>EYKCKVSNKALPSSIEKTISKAKGQPREPQVYTLPPSREEMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 254 | IgG2-IgG1.1f | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPPVAGPSVFLFPPKPKDTLMISRTPEVTCVVVDVSH<br>EDPEVKFNWYVDGVEVHNAKTKPREEQYNSTYRVVSVLTVLHQDWLNGK<br>EYKCKVSNKALPSSIEKTISKAKGQPREPQVYTLPPSREEMTKNQVSLT<br>CLVKGFYPSDIAVEWESNGQPENNYKTTPPVLDSDGSFFLYSKLTVDKS<br>RWQQGNVFSCSVMHEALHNHYTQKSLSLSPG |
| 255 | IgG2CS-IgG1.1f | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGPSVFLFPPKPKDTLMISRTPEVTCVVVDVS<br>HEDPEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPG |
| 256 | IgG1f | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKRV<br>EPKSCDKTHTCPPCPAPELLGGPSVFLFPPKPKDTLMISRTPEVTCVVV<br>DVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLT<br>VDKSRWQQGNVFSCSVMHEALHNHYTQKSLSLSPGK |

TABLE 23-continued

SUMMARY OF SEQUENCES

| SEQ ID | Description | Sequence |
|---|---|---|
| 257 | IgG1.1f | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRV EPKSCDKTHTCPPCPAPEAEGAPSVFLFPPKPKDTLMISRTPEVTCVVV DVSHEDPEVKFNWYVDGVEVHNAKTKPREEQYNSTYRVVSVLTVLHQDW LNGKEYKCKVSNKALPSSIEKTISKAKGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK |
| 258 | IgG2.3 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKSCVECPPCPAPPVAGPSVFLFPPKPKDTLMISRTPEV TCVVVDVSHEDPEVQFNWYVDGVEVHNAKTKPREEQFNSTFRVVSV LTVVHQDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHNHYTQKSLSL SPGK |
| 259 | IgG2.5 | ASTKGPSVFPLAPSSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTFRVVSV LTVVHQDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHNHYTQKSLSL SPGK |
| 260 | IgG2.3G1-KH | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKSCVECPPCPAPPVAGPSVFLFPPKPKDTLMISRTPEV TCVVVDVSHEDPEVKFNWYVDGVEVHNAKTKPREEQYNSTYRVVSV LTVLHQDWLNGKEYKCKVSNKALPAPIEKTISKAKGQPREPQVYTL PPSREEMTKNQVSLTCLVKGFYPSDIAVEWESNGQPENNYKTTPPV LDSDGSFFLYSKLTVDKSRWQQGNVFSCSVMHEALHNHYTQKSLSL SPGK |
| 261 | IgG2.5G1-KH | ASTKGPSVFPLAPSSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVKFNWYVDGVEVHNAKTKPREEQYNSTYRVVSV LTVLHQDWLNGKEYKCKVSNKALPAPIEKTISKAKGQPREPQVYTL PPSREEMTKNQVSLTCLVKGFYPSDIAVEWESNGQPENNYKTTPPV LDSDGSFFLYSKLTVDKSRWQQGNVFSCSVMHEALHNHYTQKSLSL SPGK |
| 262 | IgG2.3G1-AY | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKSCVECPPCPAPELLGGPSVFLFPPKPKDTLMISRTPE VTCVVVDVSHEDPEVKFNWYVDGVEVHNAKTKPREEQYNSTYRVVS VLTVLHQDWLNGKEYKCKVSNKALPAPIEKTISKAKGQPREPQVYT LPPSREEMTKNQVSLTCLVKGFYPSDIAVEWESNGQPENNYKTTPP VLDSDGSFFLYSKLTVDKSRWQQGNVFSCSVMHEALHNHYTQKSLS LSPGK |
| 263 | IgG2.5G1-AY | ASTKGPSVFPLAPSSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPELLGGPSVFLFPPKPKDTLMISRTPE VTCVVVDVSHEDPEVKFNWYVDGVEVHNAKTKPREEQYNSTYRVVS VLTVLHQDWLNGKEYKCKVSNKALPAPIEKTISKAKGQPREPQVYT LPPSREEMTKNQVSLTCLVKGFYPSDIAVEWESNGQPENNYKTTPP VLDSDGSFFLYSKLTVDKSRWQQGNVFSCSVMHEALHNHYTQKSLS LSPGK |
| 264 | IgG2.3G1.1f-KH | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKSCVECPPCPAPPVAGPSVFLFPPKPKDTLMISRTPEV TCVVVDVSHEDPEVKFNWYVDGVEVHNAKTKPREEQYNSTYRVVSV LTVLHQDWLNGKEYKCKVSNKALPSSIEKTISKAKGQPREPQVYTL PPSREEMTKNQVSLTCLVKGFYPSDIAVEWESNGQPENNYKTTPPV LDSDGSFFLYSKLTVDKSRWQQGNVFSCSVMHEALHNHYTQKSLSL SPGK |
| 265 | IgG2.5G1.1f-KH | ASTKGPSVFPLAPSSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV |

TABLE 23-continued

SUMMARY OF SEQUENCES

| SEQ ID | Description | Sequence |
|---|---|---|
| | | TCVVVDVSHEDPEVKFNWYVDGVEVHNAKTKPREEQYNSTYRVVSV<br>LTVLHQDWLNGKEYKCKVSNKALPSSIEKTISKAKGQPREPQVYTL<br>PPSREEMTKNQVSLTCLVKGFYPSDIAVEWESNGQPENNYKTTPPV<br>LDSDGSFFLYSKLTVDKSRWQQGNVFSCSVMHEALHNYTQKSLSL<br>SPGK |
| 266 | IgG2.5G1-V27 | ASTKGPSVFPLAPSSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPELLGGPSVFLF<br>PPKPKDTLMISRTPEVTCVVVDVEHEDPEVKFNWYVDGVEVHNAKTKPR<br>EEQYNSTYRVVSVLTVLHQDWLNGKEYKCKVSNKALPAPIEKTISKAKG<br>QPREPQVYTLPPSREEMTKNQVSLTCLVKGFYPSDIAVEWESNGQPENN<br>YKTTPPVLDSDGSFFLYSKLTVDKSRWQQGNVFSCSVMHEALHNHYTQK<br>SLSLSPGK |
| 267 | IgG2.3-V13 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGDSVFLFPPKPKDTLMISRTPEVTCVVVDVSH<br>EDPEVQFNWYVDGVEVHNAKTKPREEQFNSTFRVVSVLTVVHQDWLNGK<br>EYKCKVSNKGLPAPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 268 | IgG2.3-V14 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGDSVFLFPPKPKDTLMISRTPEVTCVVVDVSH<br>EDGEVQFNWYVDGVEVHNAKTKPREEQFNSTFRVVSVLTVVHQDWLNGK<br>EYKCKVSNKGLPAPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 269 | IgG2.3-V15 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGDSVFLFPPKPKDTLMISRTPEVTCVVVDVSD<br>EDGEVQFNWYVDGVEVHNAKTKPREEQFNSTFRVVSVLTVVHQDWLNGK<br>EYKCKVSNKGLPAPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 270 | IgG2.3-V16 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGDSVFLFPPKPKDTLMISRTPEVTCVVVDVSH<br>EDDEVQFNWYVDGVEVHNAKTKPREEQFNSTFRVVSVLTVVHQDWLNGK<br>EYKCKVSNKGLPRPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 271 | IgG2.3-V17 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGDSVFLFPPKPKDTLMISRTPEVTCVVVDVSD<br>EDGEVQFNWYVDGVEVHNAKTKPREEQFNSTFRVVSVLTVVHQDWLNGK<br>EYKCKVSNKGLPRPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 272 | IgG2.3-V18 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGDSVFLFPPKPKDTLMISRTPEVTCVVVDVEH<br>EDPEVQFNWYVDGVEVHNAKTKPREEQFNSTFRVVSVLTVVHQDWLNGK<br>EYKCKVSNKGLPAPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 273 | IgG2.3-V19 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPPVAGDSVFLFPPKPKDTLMISRTPEVTCVVVDVEH<br>EDPEVQFNWYVDGVEVHNAKTKPREEQFNSTFRVVSVLTVVHQDWLNGK<br>EYKCKVSNKGEPAPIEKTISKTKGQPREPQVYTLPPSREEMTKNQVSLT<br>CLVKGFYPSDIAVEWESNGQPENNYKTTPPMLDSDGSFFLYSKLTVDKS<br>RWQQGNVFSCSVMHEALHNHYTQKSLSLSPGK |
| 274 | IgG2.3G1-AY-V20 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGPSVFLFPPKPKDTLMISRTPEVTCVVVDVS<br>HEDPEVKFNWYVDGVEVHNAKTKPREEQYNSTYRVVSVLTVLHQDWLNG |

TABLE 23-continued

SUMMARY OF SEQUENCES

| SEQ ID | Description | Sequence |
|---|---|---|
| | | KEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 275 | IgG2.3G1-AY-V21 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGDSVFLFPPKPKDTLMISRTPEVTCVVVDVS<br>HEDGEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 276 | IgG2.3G1-AY-V22 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGDSVFLFPPKPKDTLMISRTPEVTCVVVDVS<br>DEDGEVKFNWYVDGVEVHNAKTKPREEQYNSTYRVVSVLTVLHQDWLNG<br>KEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 277 | IgG2.3G1-AY-V23 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGDSVFLFPPKPKDTLMISRTPEVTCVVVDVS<br>HEDGEVKFNWYVDGVEVHNAKTKPREEQYNSTYRVVSVLTVLHQDWLNG<br>KEYKCKVSNKALPRPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 278 | IgG2.3G1-AY-V24 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGDSVFLFPPKPKDTLMISRTPEVTCVVVDVS<br>DEDGEVKFNWYVDGVEVHNAKTKPREEQYNSTYRVVSVLTVLHQDWLNG<br>KEYKCKVSNKALPRPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 279 | IgG2.3G1-AY-V25 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGDDSVFLFPPKPKDTLMISRTPEVTCVVVDVS<br>DEDGEVKFNWYVDGVEVHNAKTKPREEQYNSTYRVVSVLTVLHQDWLNG<br>KEYKCKVSNKALPRPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 280 | IgG2.3G1-AY-V26 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPDLLGDDSVFLFPPKPKDTLMISRTPEVTCVVVDVS<br>DEDGEVKFNWYVDGVEVHNAKTKPREEQYNSTYRVVSVLTVLHQDWLNG<br>KEYKCKVSNKALPRPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 281 | IgG2.3G1-AY-V28 | ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKSCVECPPCPAPELLGGPSVFLFPPKPKDTLMISRTPEVTCVVVDVE<br>HEDPEVKFNWYVDGVEVHNAKTKPREEQYNSTYRVVSVLTVLHQDWLNG<br>KEYKCKVSNKAFPAPIEKTISKAKGQPREPQVYTLPPSREEMTKNQVSL<br>TCLVKGFYPSDIAVEWESNGQPENNYKTTPPVLDSDGSFFLYSKLTVDK<br>SRWQQGNVFSCSVMHEALHNHYTQKSLSLSPGK |
| 282 | OX40.6-Vh-hHC-IgG2.3 | EVQLVQSGGGLVQPGGSLRLSCAGSGFTFSNYAMYWVRQAPGKGLEWVS<br>AIGIGGDTFYTDSVKGRFTISRDNAKNSLSLQMNSLRAEDTAVYYCARM<br>GTGYFFDYWGQGTLVTVSSASTKGPSVFPLAPCSRSTSESTAALGCLVK<br>DYFPEPVTVSWNSGALTSGVHTFPAVLQSSGLYSLSSVVTVPSSNFGTQ<br>TYTCNVDHKPSNTKVDKTVERKSCVECPPCPAPPVAGPSVFLFPPKPKD<br>TLMISRTPEVTCVVVDVSHEDPEVQFNWYVDGVEVHNAKTKPREEQFNS<br>TFRVVSVLTVVHQDWLNGKEYKCKVSNKGLPAPIEKTISKTKGQPREPQ<br>VYTLPPSREEMTKNQVSLTCLVKGFYPSDIAVEWESNGQPENNYKTTPP<br>MLDSDGSFFLYSKLTVDKSRWQQGNVFSCSVMHEALHNHYTQKSLSLSP<br>GK |
| 283 | OX40.8-Vh-hHC-IgG2.3 | QVQLVESGGGVVQPGRSLRLSCAASGFTFSNYALHWVRQAPGKGLEWVA<br>LISYDGSRKHYADSVKGRFSISRDNSKNTLYLQMNSLRAEDTAVYYCAS<br>LTMVREWGQGTLVTVSSASTKGPSVFPLAPCSRSTSESTAALGCLVKDY<br>FPEPVTVSWNSGALTSGVHTFPAVLQSSGLYSLSSVVTVPSSNFGTQTY |

TABLE 23-continued

SUMMARY OF SEQUENCES

| SEQ ID | Description | Sequence |
|---|---|---|
| | | TCNVDHKPSNTKVDKTVERKSCVECPPCPAPPVAGPSVFLFPPKPKDTL<br>MISRTPEVTCVVVDVSHEDPEVQFNWYVDGVEVHNAKTKPREEQFNSTF<br>RVVSVLTVVHQDWLNGKEYKCKVSNKGLPAPIEKTISKTKGQPREPQVY<br>TLPPSREEMTKNQVSLTCLVKGFYPSDIAVEWESNGQPENNYKTTPPML<br>DSDGSFFLYSKLTVDKSRWQQGNVFSCSVMHEALHNHYTQKSLSLSPGK |
| 284 | OX40.16-Vh-hHC-IgG2.3 | EVQLVQSGGGLVQPGGSLRLSCAGSGFTFSSYAMYWVRQAPGKGLEWVS<br>AIDTDGGTFYADSVRGRFTISRDNAKNSLYLQMNSLRAEDTAVYFCARL<br>GEGYFFDYWGQGTLVTVSSASTKGPSVFPLAPCSRSTSESTAALGCLVK<br>DYFPEPVTVSWNSGALTSGVHTFPAVLQSSGLYSLSSVVTVPSSNFGTQ<br>TYTCNVDHKPSNTKVDKTVERKSCVECPPCPAPPVAGPSVFLFPPKPKD<br>TLMISRTPEVTCVVVDVSHEDPEVQFNWYVDGVEVHNAKTKPREEQFNS<br>TFRVVSVLTVVHQDWLNGKEYKCKVSNKGLPAPIEKTISKTKGQPREPQ<br>VYTLPPSREEMTKNQVSLTCLVKGFYPSDIAVEWESNGQPENNYKTTPP<br>MLDSDGSFFLYSKLTVDKSRWQQGNVFSCSVMHEALHNHYTQKSLSLSP<br>GK |
| 285 | OX40.6-Vh-hHC-IgG2.3G1 | EVQLVQSGGGLVQPGGSLRLSCAGSGFTFSNYAMYWVRQAPGKGLEWVS<br>AIGIGGDTFYTDSVKGRFTISRDNAKNSLSLQMNSLRAEDTAVYYCARM<br>GTGYFFDYWGQGTLVTVSSASTKGPSVFPLAPCSRSTSESTAALGCLVK<br>DYFPEPVTVSWNSGALTSGVHTFPAVLQSSGLYSLSSVVTVPSSNFGTQ<br>TYTCNVDHKPSNTKVDKTVERKSCVECPPCPAPELLGGPSVFLFPPKPK<br>DTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLS<br>PGK |
| 286 | OX40.8-Vh-hHC-IgG2.3G1 | QVQLVESGGGVVQPGRSLRLSCAASGFTFSNYALHWVRQAPGKGLEWVA<br>LISYDGSRKHYADSVKGRFSISRDNSKNTLYLQMNSLRAEDTAVYYCAS<br>LTMVREWGQGTLVTVSSASTKGPSVFPLAPCSRSTSESTAALGCLVKDY<br>FPEPVTVSWNSGALTSGVHTFPAVLQSSGLYSLSSVVTVPSSNFGTQTY<br>TCNVDHKPSNTKVDKTVERKSCVECPPCPAPELLGGPSVFLFPPKPKDT<br>LMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPG<br>K |
| 287 | OX40.16-Vh-hHC-IgG2.3G1 | EVQLVQSGGGLVQPGGSLRLSCAGSGFTFSSYAMYWVRQAPGKGLEWVS<br>AIDTDGGTFYADSVRGRFTISRDNAKNSLYLQMNSLRAEDTAVYFCARL<br>GEGYFFDYWGQGTLVTVSSASTKGPSVFPLAPCSRSTSESTAALGCLVK<br>DYFPEPVTVSWNSGALTSGVHTFPAVLQSSGLYSLSSVVTVPSSNFGTQ<br>TYTCNVDHKPSNTKVDKTVERKSCVECPPCPAPELLGGPSVFLFPPKPK<br>DTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLS<br>PGK |
| 288 | OX40.6-Vh-hHC-IgG2.3G1-V27 | EVQLVQSGGGLVQPGGSLRLSCAGSGFTFSNYAMYWVRQAPGKGLEWVS<br>AIGIGGDTFYTDSVKGRFTISRDNAKNSLSLQMNSLRAEDTAVYYCARM<br>GTGYFFDYWGQGTLVTVSSASTKGPSVFPLAPCSRSTSESTAALGCLVK<br>DYFPEPVTVSWNSGALTSGVHTFPAVLQSSGLYSLSSVVTVPSSNFGTQ<br>TYTCNVDHKPSNTKVDKTVERKSCVECPPCPAPELLGGPSVFLFPPKPK<br>DTLMISRTPEVTCVVVDVEHEDPEVKFNWYVDGVEVHNAKTKPREEQYN<br>STYRVVSVLTVLHQDWLNGKEYKCKVSNKALPAPIEKTISKAKGQPREP<br>QVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLS<br>PGK |
| 289 | OX40.8-Vh-hHC-IgG2.3G1-V27 | QVQLVESGGGVVQPGRSLRLSCAASGFTFSNYALHWVRQAPGKGLEWVA<br>LISYDGSRKHYADSVKGRFSISRDNSKNTLYLQMNSLRAEDTAVYYCAS<br>LTMVREWGQGTLVTVSSASTKGPSVFPLAPCSRSTSESTAALGCLVKDY<br>FPEPVTVSWNSGALTSGVHTFPAVLQSSGLYSLSSVVTVPSSNFGTQTY<br>TCNVDHKPSNTKVDKTVERKSCVECPPCPAPELLGGPSVFLFPPKPKDT<br>LMISRTPEVTCVVVDVEHEDPEVKFNWYVDGVEVHNAKTKPREEQYNST<br>YRVVSVLTVLHQDWLNGKEYKCKVSNKALPAPIEKTISKAKGQPREPQV<br>YTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPG<br>K |
| 290 | OX40.16-Vh-hHC-IgG2.3G1-V27 | EVQLVQSGGGLVQPGGSLRLSCAGSGFTFSSYAMYWVRQAPGKGLEWVS<br>AIDTDGGTFYADSVRGRFTISRDNAKNSLYLQMNSLRAEDTAVYFCARL<br>GEGYFFDYWGQGTLVTVSSASTKGPSVFPLAPCSRSTSESTAALGCLVK |

TABLE 23-continued

SUMMARY OF SEQUENCES

| SEQ ID | Description | Sequence |
|---|---|---|
| | | DYFPEPVTVSWNSGALTSGVHTFPAVLQSSGLYSLSSVVTVPSSNFGTQ TYTCNVDHKPSNTKVDKTVERKSCVECPPCPAPELLGGPSVFLFPPKPK DTLMISRTPEVTCVVVDVEHEDPEVKFNWYVDGVEVHNAKTKPREEQYN STYRVVSVLTVLHQDWLNGKEYKCKVSNKALPAPIEKTISKAKGQPREP QVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLS PGK |
| 291 | OX40.6-Vh-hHC-IgG2.5 | EVQLVQSGGGLVQPGGSLRLSCAGSGFTFSNYAMYWVRQAPGKGLEWVS AIGIGGDTFYTDSVKGRFTISRDNAKNSLSLQMNSLRAEDTAVYYCARM GTGYFFDYWGQGTLVTVSSASTKGPSVFPLAPSSRSTSESTAALGCLVK DYFPEPVTVSWNSGALTSGVHTFPAVLQSSGLYSLSSVVTVPSSNFGTQ TYTCNVDHKPSNTKVDKTVERKCCVECPPCPAPPVAGPSVFLFPPKPKD TLMISRTPEVTCVVVDVSHEDPEVQFNWYVDGVEVHNAKTKPREEQFNS TFRVVSVLTVVHQDWLNGKEYKCKVSNKGLPAPIEKTISKTKGQPREPQ VYTLPPSREEMTKNQVSLTCLVKGFYPSDIAVEWESNGQPENNYKTTPP MLDSDGSFFLYSKLTVDKSRWQQGNVFSCSVMHEALHNHYTQKSLSLSP GK |
| 292 | OX40.8-Vh-hHC-IgG2.5 | QVQLVESGGGVVQPGRSLRLSCAASGFTFSNYALHWVRQAPGKGLEWVA LISYDGSRKHYADSVKGRFSISRDNSKNTLYLQMNSLRAEDTAVYYCAS LTMVREWGQGTLVTVSSASTKGPSVFPLAPSSRSTSESTAALGCLVKDY FPEPVTVSWNSGALTSGVHTFPAVLQSSGLYSLSSVVTVPSSNFGTQTY TCNVDHKPSNTKVDKTVERKCCVECPPCPAPPVAGPSVFLFPPKPKDTL MISRTPEVTCVVVDVSHEDPEVQFNWYVDGVEVHNAKTKPREEQFNSTF RVVSVLTVVHQDWLNGKEYKCKVSNKGLPAPIEKTISKTKGQPREPQVY TLPPSREEMTKNQVSLTCLVKGFYPSDIAVEWESNGQPENNYKTTPPML DSDGSFFLYSKLTVDKSRWQQGNVFSCSVMHEALHNHYTQKSLSLSPGK |
| 293 | OX40.16-Vh-hHC-IgG2.5 | EVQLVQSGGGLVQPGGSLRLSCAGSGFTFSSYAMYWVRQAPGKGLEWVS AIDTDGGTFYADSVRGRFTISRDNAKNSLYLQMNSLRAEDTAVYFCARL GEGYFFDYWGQGTLVTVSSASTKGPSVFPLAPSSRSTSESTAALGCLVK DYFPEPVTVSWNSGALTSGVHTFPAVLQSSGLYSLSSVVTVPSSNFGTQ TYTCNVDHKPSNTKVDKTVERKCCVECPPCPAPPVAGPSVFLFPPKPKD TLMISRTPEVTCVVVDVSHEDPEVQFNWYVDGVEVHNAKTKPREEQFNS TFRVVSVLTVVHQDWLNGKEYKCKVSNKGLPAPIEKTISKTKGQPREPQ VYTLPPSREEMTKNQVSLTCLVKGFYPSDIAVEWESNGQPENNYKTTPP MLDSDGSFFLYSKLTVDKSRWQQGNVFSCSVMHEALHNHYTQKSLSLSP GK |
| 294 | OX40.21-Vh-hHC-IgG2.5 | EVQLVQSGGGLVQPGGSLRLSCAGSGFTFSSYAMYWVRQAPGKGLEWVS AIDTDAGTFYADSVRGRFTISRDNAKNSLYLQMNSLRAEDTAVYFCARL GEGYFFDYWGQGTLVTVSSASTKGPSVFPLAPSSRSTSESTAALGCLVK DYFPEPVTVSWNSGALTSGVHTFPAVLQSSGLYSLSSVVTVPSSNFGTQ TYTCNVDHKPSNTKVDKTVERKCCVECPPCPAPPVAGPSVFLFPPKPKD TLMISRTPEVTCVVVDVSHEDPEVQFNWYVDGVEVHNAKTKPREEQFNS TFRVVSVLTVVHQDWLNGKEYKCKVSNKGLPAPIEKTISKTKGQPREPQ VYTLPPSREEMTKNQVSLTCLVKGFYPSDIAVEWESNGQPENNYKTTPP MLDSDGSFFLYSKLTVDKSRWQQGNVFSCSVMHEALHNHYTQKSLSLSP GK |
| 295 | OX40.21-Vh-hHC-IgG2.5G1 | EVQLVQSGGGLVQPGGSLRLSCAGSGFTFSSYAMYWVRQAPGKGLEWVS AIDTDAGTFYADSVRGRFTISRDNAKNSLYLQMNSLRAEDTAVYFCARL GEGYFFDYWGQGTLVTVSSASTKGPSVFPLAPSSRSTSESTAALGCLVK DYFPEPVTVSWNSGALTSGVHTFPAVLQSSGLYSLSSVVTVPSSNFGTQ TYTCNVDHKPSNTKVDKTVERKCCVECPPCPAPELLGGPSVFLFPPKPK DTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREP QVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLS PGK |
| 296 | OX40.21-Vh-hHC-IgG2.5G1-V27 | EVQLVQSGGGLVQPGGSLRLSCAGSGFTFSSYAMYWVRQAPGKGLEWVS AIDTDAGTFYADSVRGRFTISRDNAKNSLYLQMNSLRAEDTAVYFCARL GEGYFFDYWGQGTLVTVSSASTKGPSVFPLAPSSRSTSESTAALGCLVK DYFPEPVTVSWNSGALTSGVHTFPAVLQSSGLYSLSSVVTVPSSNFGTQ TYTCNVDHKPSNTKVDKTVERKCCVECPPCPAPELLGGPSVFLFPPKPK DTLMISRTPEVTCVVVDVEHEDPEVKFNWYVDGVEVHNAKTKPREEQYN STYRVVSVLTVLHQDWLNGKEYKCKVSNKALPAPIEKTISKAKGQPREP QVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLS PGK |
| 297 | IgG2.3G1-V27 | ASTKGPSVFPPLAPCSRSTSESTAALGCLVKDYFPEPVTVSWNSGALTSG VHTFPAVLQSSGLYSLSSVVTVPSSNFGTQTYTCNVDHKPSNTKVDKTV |

TABLE 23-continued

SUMMARY OF SEQUENCES

| SEQ ID | Description | Sequence |
|---|---|---|
| | | ERKSCVECPPCPAPELLGGPSVFLFPPKPKDTLMISRTPEVTCVVVDVEHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 298 | Human IgG1 CH2 with A330S/P331S | PSVFLFPPKPKDTLMISRTPEVTCVVVDVSHEDPEVKFNWYVDGVEVHNAKTKPREEQYNSTYRVVSVLTVLHQDWLNGKEYKCKVSNKALP<u>SS</u>IEKTISKAK |
| 299 | Heavy chain- nivolumab | <u>QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS</u>ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 300 | Light chain- nivolumab | <u>EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK</u>RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 301 | Heavy chain variable region- nivolumab | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| 302 | Light chain variable region- nivolumab | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK |
| 303 | HCDR1- nivolumab | NSGMH |
| 304 | HCDR2- nivolumab | VIWYDGSKRYYADSVKG |
| 305 | HCDR3- nivolumab | NDDY |
| 306 | LCDR1- nivolumab | RASQSVSSYLA |
| 307 | LCDR2- nivolumab | DASNRAT |
| 308 | LCDR3- nivolumab | QQSSNWPRT |
| 309 | Heavy chain variable region- ipilimumab (from WO01/014424) | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS |
| 310 | Light chain variable region- ipilimumab (from WO01/014424) | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK |
| 311 | HCDR1- ipilimumab (from WO01/014424) | SYTMH |
| 312 | HCDR2- ipilimumab (from WO01/014424) | FISYDGNNKYYADSVKG |
| 313 | HCDR3- ipilimumab (from WO01/014424) | TGWLGPFDY |
| 314 | LCDR1- ipilimumab (from WO01/014424) | RASQSVGSSYLA |
| 315 | LCDR2- ipilimumab (from WO01/014424) | GAFSRAT |
| 316 | LCDR3- ipilimumab (from WO01/014424) | QQYGSSPWT |
| 317 | HCDR2 of OX40.21 | AIDTDAGTFYADSVRG |

TABLE 23-continued

SUMMARY OF SEQUENCES

| SEQ ID | Description | Sequence |
|---|---|---|
| 318 | VH of OX40.21 | EVQLVQSGGGLVQPGGSLRLSCAGSGFTFSSYAMYWVRQAPGKGLE WVSAIDTDAGTFYADSVRGRFTISRDNAKNSLYLQMNSLRAEDTAV YFCARLGEGYFFDYWGQGTLVTVSS |

Table 23 provides the sequences of the mature variable regions and heavy and light chains and where indicated, sequences with signal peptides.

EQUIVALENTS

Those skilled in the art will recognize, or be able to ascertain using no more than routine experimentation, many equivalents of the specific embodiments disclosed herein. Such equivalents are intended to be encompassed by the following claims.

---

The invention claimed is:

1. A nucleic acid encoding a heavy and/or light chain variable region of an antibody which binds to OX40, wherein the antibody comprises the heavy chain variable region sequence of SEQ ID NO: 318 and the light chain variable region sequence of
SEQ ID NO: 94.

2. The nucleic acid of claim 1, wherein the antibody comprises the heavy chain sequence of SEQ ID NO: 124 and the light chain sequence of
SEQ ID NO: 116.

3. The nucleic acid of claim 1, wherein the antibody comprises heavy and light chain constant regions.

4. The nucleic acid of claim 1, wherein the antibody stimulates an antigen-specific T cell response.

5. The nucleic acid of claim 1, wherein the antibody binds to soluble human OX40 with a KD of 1 nM or less, as measured by Biacore.

6. The nucleic acid of claim 3, wherein the heavy chain constant region either lacks a C-terminal lysine or comprises an amino acid other than lysine at the C-terminus.

7. The nucleic acid of claim 1, wherein the antibody is an IgG1 isotype.

8. The nucleic acid of claim 1, wherein the antibody is a human antibody.

9. A nucleic acid comprising a nucleotide sequence of SEQ ID NO: 176 and/or SEQ ID NO: 168.

10. A nucleic acid encoding a heavy chain variable region of an antibody which binds to OX40, wherein the heavy chain variable region comprises
CDR1, CDR2, and CDR3 sequences comprising SEQ ID NOs: 87, 317, and 89, respectively.

11. The nucleic acid of claim 10, which further encodes a light chain variable region comprising CDR1, CDR2, and CDR3 sequences comprising SEQ ID NOs: 90-92, respectively.

12. An expression vector comprising the nucleic acid molecule of claim 1.

13. A cell transformed with the expression vector of claim 12.

14. An expression vector comprising the nucleic acid molecule of claim 2.

15. An expression vector comprising the nucleic acid molecule of claim 10.

16. An expression vector comprising the nucleic acid molecule of claim 11.

17. A cell transformed with the expression vector of claim 14.

18. A cell transformed with the expression vector of claim 15.

19. A cell transformed with the expression vector of claim 16.

* * * * *